US012674185B2

(12) United States Patent
Smolke et al.

(10) Patent No.: US 12,674,185 B2
(45) **Date of Patent: *Jul. 7, 2026**

(54) METHODS OF PRODUCING MORPHINAN ALKALOIDS AND DERIVATIVES

(71) Applicant: Antheia, Inc., Menlo Park, CA (US)

(72) Inventors: Christina D. Smolke, Menlo Park, CA (US); Isis Trenchard, Redwood City, CA (US); Kristy M. Hawkins, Menlo Park, CA (US); Catherine Thodey, Menlo Park, CA (US)

(73) Assignee: Antheia Inc., Menlo Park, CA (US)

( * ) Notice: Subject to any disclaimer, the term of this patent is extended or adjusted under 35 U.S.C. 154(b) by 92 days.

This patent is subject to a terminal disclaimer.

(21) Appl. No.: 18/511,394

(22) Filed: Nov. 16, 2023

(65) Prior Publication Data

US 2024/0209403 A1 Jun. 27, 2024

Related U.S. Application Data

(63) Continuation of application No. 16/984,900, filed on Aug. 4, 2020, now Pat. No. 11,884,949, which is a continuation of application No. PCT/US2019/017357, filed on Feb. 8, 2019.

(60) Provisional application No. 62/628,264, filed on Feb. 8, 2018.

(51) Int. Cl.

*C12P 17/12* (2006.01)
*C12N 9/88* (2006.01)
*C12N 9/90* (2006.01)
*C12N 15/52* (2006.01)

(52) U.S. Cl.

CPC ................ *C12P 17/12* (2013.01); *C12N 9/88* (2013.01); *C12N 9/90* (2013.01); *C12N 15/52* (2013.01); *C12Y 402/99* (2013.01)

(58) Field of Classification Search

CPC .......... C12P 17/12; C12P 17/188; C12N 9/88; C12N 9/90; C12N 15/52; C12Y 402/99; C07D 217/16; C07D 221/28

See application file for complete search history.

(56) References Cited

U.S. PATENT DOCUMENTS

| | | | |
|---|---|---|---|
| 6,573,428 B1 | 6/2003 | Vodkin et al. | |
| 10,544,420 B2 * | 1/2020 | Smolke | C12P 17/18 |
| 11,142,780 B2 | 10/2021 | Facchini et al. | |
| 11,427,827 B2 * | 8/2022 | Smolke | C12N 15/52 |
| 11,479,586 B2 | 10/2022 | Facchini et al. | |
| 11,884,949 B2 * | 1/2024 | Smolke | C07D 217/16 |
| 2009/0156815 A1 * | 6/2009 | Wang | A61P 25/04 546/44 |
| 2016/0208269 A1 | 7/2016 | Smolke et al. | |
| 2020/0325509 A1 | 10/2020 | Enquist-Newman et al. | |
| 2021/0062235 A1 | 3/2021 | Smolke et al. | |
| 2022/0205004 A1 | 6/2022 | Facchini et al. | |

FOREIGN PATENT DOCUMENTS

| | | | |
|---|---|---|---|
| WO | WO-2011/058446 A2 | 5/2011 | |
| WO | WO-2015/081437 A1 | 6/2015 | |
| WO | WO-2015/173590 A1 | 11/2015 | |
| WO | WO 201/005553 A1 * | 1/2018 | C12N 9/00 |
| WO | WO-2018/000089 A1 | 1/2018 | |
| WO | WO-2018/005553 A1 | 1/2018 | |

OTHER PUBLICATIONS

Facchini, P.J., "GenBank Accession No. FE967184" Mar. 31, 2008, [online] [retrieved on Sep. 19, 2017]. Retrieved from the internet: <https://www.ncbi.nlm.nih.gov/nucest/FE967184>.

Shitan et al., "Alkaloid Transporters in Plants", Plant Biotechnology, 31:453-463 (2014), DOI 10.5511/ Plantbiotechnology. 14.1002a.

Fossati et al., "Synthesis of Morphinan Alkaloids in *Saccharomyces cerevisiae*", PLOS ONE, DOI: 10.1371/journal.pone.0124453 (2015).

Sabarna, "Approaches to isolating a cDNA encoding thebaine synthase or morphine biosynthesis from opium poppy *Papaver somniferum* L.", Internet Citation, [Online], Retrieved from the Internet: URL:http://sundoc.bibliothek.uni-halle.de/ Jun. 22, 2007 (Jun. 22, 2007).

Fisinger et al., "Thebaine synthase: A new enzyme in the morphone pathway in Papaver somniferum", Natural Product Communications, 2: 249-253 (2007).

Beaudoin et al., "Benzylisoquinoline alkaloid biosynthesis in opium poppy", Planta, 240: 19-32 (2014).

Database EMBL [Online] Jul. 2, 2015 (Jul. 2, 2015), "*Papaver somniferum* (opium poppy) reticuline epimerase ID-AKO60181 ; SV 1 ; linearl; genomic DNA; STD; PLN; 2703 BP.", retrieved from EBI accession No. EM_CDS: AKO60181.

DATABASE Geneseq [Online] Apr. 9, 2015 (Apr. 9, 2015), "Papaver somniferum OMT protein, SEQ ID 543.", retrieved from EBI accession No. GSP:BBU80692 Database accession No. BBU80692.

Winzer et al, "A Papaver somniferum 10-Gene Cluster for Synthesis of the Anticancer Alkaloid Noscapine", Science, 336:1704-1708 (2012.

Hagel et al., "Dioxygenases catalyze the O-demethylation steps of morphine biosynthesis in opium poppy", Nature Chemical Biology, 6:273-275 (2010).

(Continued)

*Primary Examiner* — Ganapathirama Raghu

(74) *Attorney, Agent, or Firm* — Mintz, Levin, Cohn, Ferris, Glovsky and Popeo, P.C.

(57) ABSTRACT

A method of producing promorphinan, morphinan, nal-opioid, and nor-opioid alkaloid products through the increased conversion of a promorphinan alkaloid to a morphinan alkaloid. The method comprises contacting the promorphinan alkaloid with at least one enzyme. Contacting the promorphinan alkaloid with the at least one enzyme converts the promorphinan alkaloid to a morphinan alkaloid.

20 Claims, 40 Drawing Sheets

Specification includes a Sequence Listing.

(56) References Cited

OTHER PUBLICATIONS

Morris et al., "Plug-and-Play Benzylisoquinoline Alkaloid Biosynthetic Gene Discovery in Engineered Yeast" in Methods in Enzymology, 144-178 (Elsevier 2016).
Galanie et al., "Complete biosynthesis of opioids in yeast", Science, 349:1095-1100 (2015).
Glenn, W.S. et al., "Recent progress in the metabolic engineering of alkaloids in plant 1-49 systems" (Apr. 2013). Curr. Opin. Biotechnol 24(2):354-365.
Chen et al, "A pathogenesis-related 10 protein catalyzes the final step in thebaine biosynthesis", 2018, Nature Chemical Biology, 14:738-743.
Zulak et al, "Gene transcript and metabolite profiling of elicitor-induced opium poppy cell cultures reveals the coordinate regulation of primary and secondary metabolism", 2007, Planta, 225:1085-1106.
Dastmalchi et al, "Purine Permease-Type Benzylisoquinoline Alkaloid Transporters in Opium Poppy", 2019, Plant Psychology, 181:916-933.
Grothe, T. et al. (2001). "Molecular characterization of the salutaridinol 7-O-acetyltransferase involved in morphine biosynthesis in opium poppy *Papaver somniferum,*" The Journal of Biological Chemistry 276:30717-30723.
Choe et al., "Genetic and chemical components analysis of Papaver setigerum naturalized in Korea", Forensic Science International, 222:387-393 (2012).
Samanani et al., "The role of phloem sieve elements and laticifers in the biosynthesis and accumulation of alkaloids in opium poppy", Plant Journal, 47:547-563 (2006).
Facchini et al., "Developmental and inducible accumulation of gene transcripts involved in alkaloid biosynthesis in opium poppy", Phytochemistry, 64:177-186 (2003).
Kisselev L., "Polypeptide Release Factors in Prokaryotes and Eukaryotes: Same Function, Different Structure", Structure, 2002, vol. 10: 8-9.
Witkowski et al., "Conversion of a B-Ketoacyl Synthase to a Malonyl Decazrboxylase by Replacement of the Active-Site Cysteine with Glutamine", Biochemistry 38:11643-11650, 1999.
Whisstock et al., Quarterly Reviews of Biophysics 2003, vol. 36 (3):307-340.
Devos et al., "Practical Limits of Function Prediction", Proteins: Structure, Function and Genetics, 2000, vol. 41:98-107.
U.S. Non-Final Office Action dated May 20, 2020 in U.S. Appl. No. 16/312,895.
U.S. Final Office Action dated Nov. 25, 2020 in U.S. Appl. No. 16/312,895.
U.S. Non-Final Office Action dated Aug. 28, 2020 in U.S. Appl. No. 16/312,776.
U.S. Notice of Allowance dated Mar. 15, 2021 in U.S. Appl. No. 16/312,776.
Farrow et at "Stereochemical inversion of (S)-reticuline by a cytochrome P450 fusion in opium poppy" Nature Chemical Biology, vol. 11, Sep. 2015, p. 728-732; abstract.
U.S. Office Action dated Apr. 23, 2021 in U.S. Appl. No. 16/312,895.

* cited by examiner 5,6,7,8-Tetrahydrobiopterin

Tetrahydrobiopterin 4a-carbinolamine

Quinonoid dihydrobiopterin 7,8-Dihydrobiopterin

Biopterin

SEQ ID No. 16

MELQYISYFQPTSSVVALLLALVSILSSVVVLRKTFLNNYSSSPAS
STKTAVLSHQRQQSCALPISGLLH
IFMNKNGLIHVTLGNMADKYGPIFSFPTGSHRTLVVSSWEMV
KECFTGNNDTAFSNRPIPLAFKTIFYAC
GGIDSYGLSSVPYGKYWRELRKVCVHNLLSNQQLLKFRHLIIS
QVDTSFNKLYELCKNSEDNQGNYPTTT
TAAGMVRIDDWLAELSFNVIGRIVCGFQSGPKTGAPSRVEQF
KEAINEASYFMSTSPVSDNVPMLGWIDQ
LTGLTRNMKHCGKKLDLVVESIINDHRQKRRFSRTKGGDEKD
DEQDDFIDICLSIMEQPQLPGNNNPSQI
PIKSIVLDMIGGGTDTTKLTTIWTLSLLLNNPHVLDKAKQEVD
AHFRTKRRSTNDAAAAVVDFDDIRNLV
YIQAIIKESMRLYPASPVVERLSGEDCVVGGFHVPAGTRLWAN
VWKMQRDPKVWDDPLVFRPDRFLSDEQ
KMVDVRGQNYELLPFGAGRRVCPGVSFSLDLMQLVLTRLILE
FEMKSPSGKVDMTATPGLMSYKVIPLDI
LLTHRRIKPCVQSAASERDMESSGVPVITLGSGKVMPVLGMG
TFEKVGKGSERERLAILKAIEVGYRYFD
TAAAYETEEVLGEAIAEALQLGLVKSRDELFISSMLWCTDAHA
DRVLLALQNSLRNLKLEYVDLYMLPFP
ASLKPGKITMDIPEEDICRMDYRSVWAAMEECQNLGFTKSIG
VSNFSCKKLQELMATANIPPAVNQVEMS
PAFQQKKLREYCNANNILVSAISVLGSNGTPWGSNAVLGSEVL
KKIAMAKGKSVAQVSMRWVYEQGASLV
VKSFSEERLRENLNIFDWELTKEDHEKIGEIPQCRILSAYFLVSP
NGPFKSQEELWDDEA

FIG. 4

Split Enzymes originating from SEQ ID No. 16

DRS enzyme (SEQ ID No. 17):

MELQYFSYFQPTSSVVALLLALVSILFSVVVLRKTFSNNYSSPASSTETAVLCHQRQQSC
ALPISGLLHVFMNKNGLIHVTLGNMADKYGPIFSFPTGSHRTLVVSSWEMVKECFTGN
NDTAFSNRPIPLAFQTIFYACGGIDSYGLSSVPYGKYWRELRKVCVHNLLSNQQLLKFR
HLIISQVDTSFNKLYELCKNSEDNQGMVRMDDWLAQLSFNVIGRIVCGFQSDPKTGA
PSRVEQFKEVINEASYFMSTSPVSDNVPMLGWIDQLTGLTRNMKHCGKKLDLVVESII
KDHRQKRRFSRTKGGDEKDDEQDDFIDICLSIMEQPQLPGNNSPPQIPIKSIVLDMIG
GGTDTTKLTTIWTLSLLLNNPHVLDKAKQEVDAHFRKKRRSTDDAAAAVVDFDDIRNL
VYIQAIIKESMRLYPASPVVERLSGEDCVVGGFHVPAGTRLWANVWKMQRDPKVWD
DPLVFRPERFLSDEQKMVDVRGQNYELLPFGAGRRICPGVSFSLDLMQLVLTRLILEFE
MKSPSGKVDMTATPGLMSYKVVPLDILLTHRRIKSCVQLASSERD*

DRR enzyme (SEQ ID No. 18):

MESSGVPVITLSSGKVMPVLGMGTFEKVGKGSERERLAILKAIEVGYRYFDTAAAYETE
EVLGEAIAEALQLGLIESRDELFISSMLWCTDAHPDRVLLALQNSLRNLKLEYLDLYMLP
FPASLKPGKITMDIPEEDICRMDYRSVWSAMEECQNLGFTKSIGVSNFSCKKLQELMA
TANIPPAVNQVEMSPAFQQKKLREYCNANNILVSAVSILGSNGTPWGSNAVLGSEVLK
QIAMAKGKSVAQVSMRWVYEQGASLVVKSFSEERLRENLNIFDWELTKEDNEKIGEIP
QCRILTAYFLVSPNGPFKSQEELWDDKA*

FIG. 5

*3-O-demethylase (ODM):*
SUBSTRATE PRODUCT
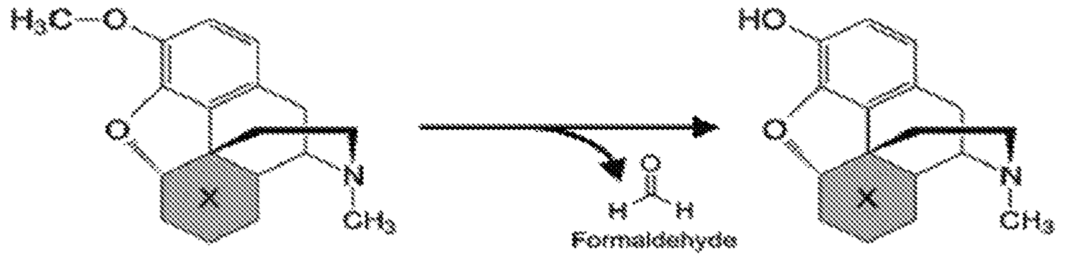
|  | **Substrate** | **Product** |
|---|---|---|
|  | Codeine | Morphine |
|  | Oxycodone | Oxymorphone |
|  | Thebaine | Oripavine |
|  | Hydrocodone | Hydromorphone |
| 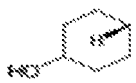 | Dihydrocodeine | Dihydromorphine |
|  | 14-hydroxycodeine | 14-hydroxymorphine |
|  | Codeinone | Morphinone |
|  | 14-hydroxycodeinone | 14-hydroxymorphinone |
FIG. 6

*N-demethylase (NDM):*

|  | Substrate | | Product | |
|---|---|---|---|---|
| | $R = CH_3$ | $R = H$ | $R = CH_3$ | $R = H$ |
|  | Codeine | Morphine | Norcodeine | Normorphine |
|  | Oxycodone | Oxymorphone | Noroxycodone | Noroxymorphone |
| 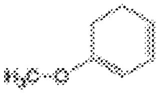 | Thebaine | Oripavine | Northebaine | Nororipavine |
|  | Hydrocodone | Hydromorphone | Norhydrocodone | Norhydro-morphone |
|  | Dihydrocodeine | Dihydromorphine | Nordihydro-codeine | Nordihydro-morphine |
|  | 14-hydroxy-codeine | 14-hydroxy-morphine | Nor-14-hydroxy-codeine | Nor-14-hydroxy-morphine |
|  | Codeinone | Morphinone | Norcodeinone | Normorphinone |
|  | 14-hydroxy-codeinone | 14-hydroxy-morphinone | Nor-14-hydroxy-codeinone | Nor-14-hydroxy-morphinone |

FIG. 7 cont.

*N-methyltransferase (NMT):*

*Example reaction scheme:*

Expression plasmids

Expression plasmids
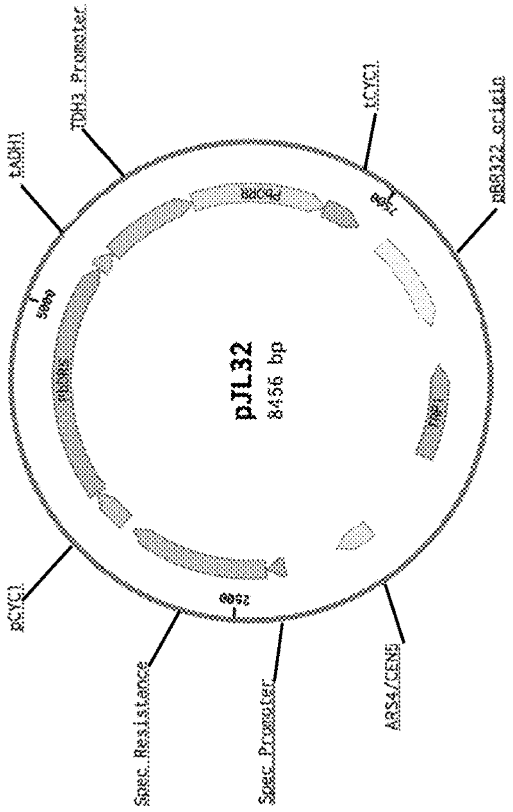
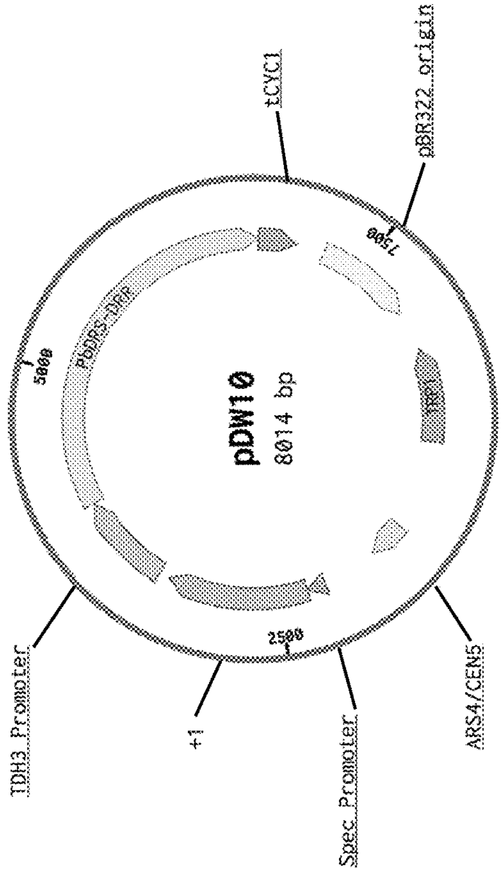
FIG. 11 cont.

Expression plasmids

3'hydroxy-N-methylcoclaurine

Reticuline

Downstream BIAs

Salutaridinol

Salutaridinol 7-O-acetate

Neopinone

Thebaine

FIG. 15
T6ODM
COR
morA
CODM
morB
morA
morB
morA
morA
morB
COR
morA
CODM
morA

L-Tyrosine
Thebaine
Neopinone
Neopine
Neomorphine
Codeinone
Codeine
Morphine
Hydrocodone
Dihydrocodeine
14-Hydroxycodeinone
Oxycodone
14-hydroxycodeine
Morphinone
Hydromorphone
Dihydromorphine

*Route (iii)* *Route (i)* *Route (ii)*

Alignment between PbDRS-DRR, PrDRS, and PrDRR

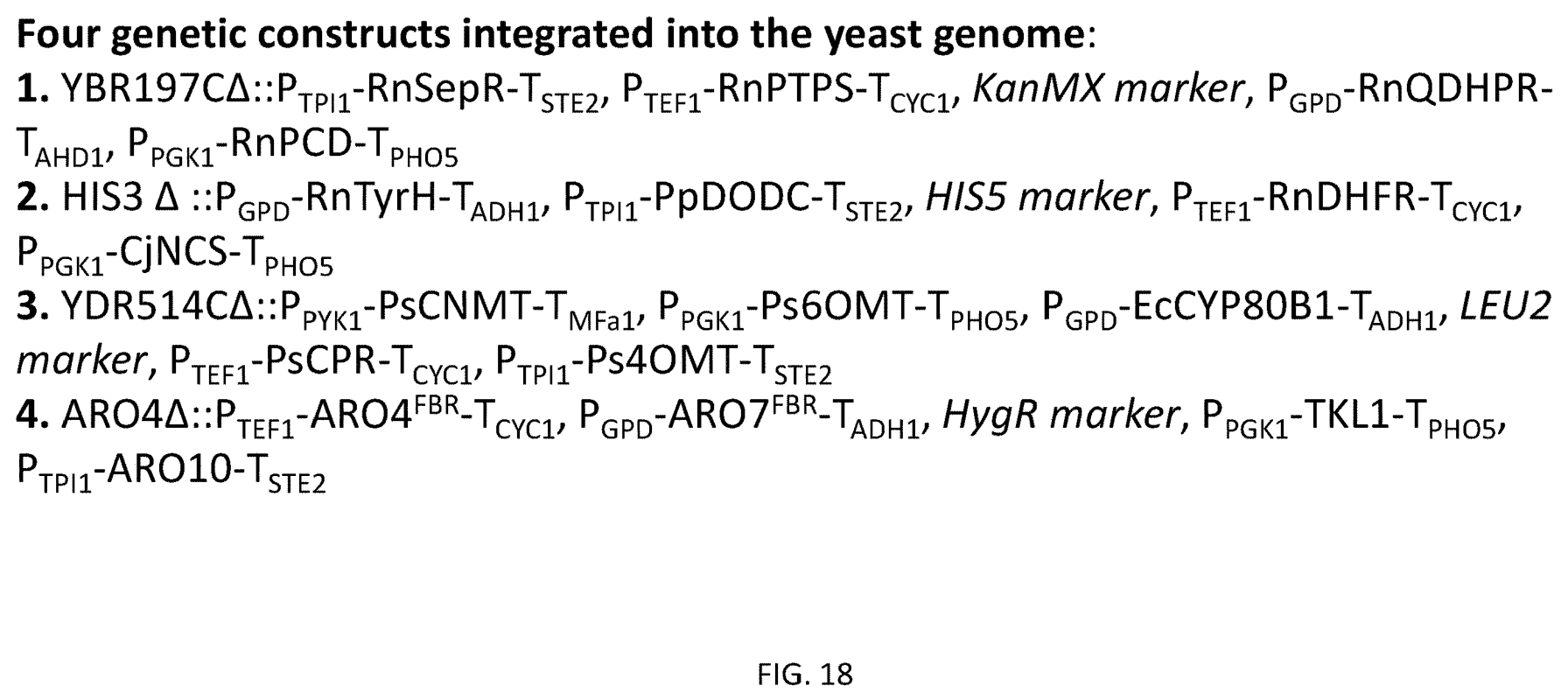

Four genetic constructs integrated into the yeast genome:

1. YBR197CΔ::$P_{TPI1}$-RnSepR-$T_{STE2}$, $P_{TEF1}$-RnPTPS-$T_{CYC1}$, *KanMX marker*, $P_{GPD}$-RnQDHPR-$T_{AHD1}$, $P_{PGK1}$-RnPCD-$T_{PHO5}$

2. HIS3 Δ ::$P_{GPD}$-RnTyrH-$T_{ADH1}$, $P_{TPI1}$-PpDODC-$T_{STE2}$, *HIS5 marker*, $P_{TEF1}$-RnDHFR-$T_{CYC1}$, $P_{PGK1}$-CjNCS-$T_{PHO5}$

3. YDR514CΔ::$P_{PYK1}$-PsCNMT-$T_{MFa1}$, $P_{PGK1}$-Ps6OMT-$T_{PHO5}$, $P_{GPD}$-EcCYP80B1-$T_{ADH1}$, *LEU2 marker*, $P_{TEF1}$-PsCPR-$T_{CYC1}$, $P_{TPI1}$-Ps4OMT-$T_{STE2}$

4. ARO4Δ::$P_{TEF1}$-ARO4$^{FBR}$-$T_{CYC1}$, $P_{GPD}$-ARO7$^{FBR}$-$T_{ADH1}$, *HygR marker*, $P_{PGK1}$-TKL1-$T_{PHO5}$, $P_{TPI1}$-ARO10-$T_{STE2}$

FIG. 18

Schematic of the integrated constructs indicating the orientation of each expression cassette:

Construct: Product: Locus:

1    BH₄    YBR197CΔ::

2    (S)-Norcoclaurine    HIS3Δ::

3    (S)-Reticuline    YDR514CΔ::

4    Tyrosine and    ARO4Δ ::
     4HPA
     overproduction

Example genetic constructs:

5. YPL250CΔ::$P_{GPD}$-RnTyrH-$T_{ADH1}$, $P_{TEF1}$-Ps4OMT-$T_{CYC1}$, $P_{PGK1}$-CjNCS-$T_{PHO5}$, bleR marker
6. TRP1::$P_{PGK1}$-PsSalAT-$T_{PHOS5}$, $P_{TPI1}$-PbSalR-$T_{STE2}$, URA3 marker, $P_{GPD}$-EcCFS$^{1\text{-}83}$-PbSalSyn$^{92\text{-}504}$-$T_{ADH1}$, $P_{HXT7}$-PbCYP-COR-$T_{CYC1}$
7. HOΔ::$P_{GPD}$-PsT6ODM-$T_{ADH1}$, $P_{PGK1}$-PbmorB-$T_{PHO5}$

FIG. 19

Tetracyclic scaffold

Pentacyclic scaffold

SEQUENCE LISTING

```
Sequence total quantity: 153
SEQ ID NO: 1            moltype = AA  length = 901
FEATURE                 Location/Qualifiers
source                  1..901
                        mol_type = protein
                        organism = Papaver somniferum
SEQUENCE: 1
MELQYISYFQ PTSSVVALLL ALVSILSSVV VLRKTFLNNY SSSPASSTKT AVLSHQRQQS  60
CALPISGLLH IFMNKNGLIH VTLGNMADKY GPIFSFPTGS HRTLVVSSWE MVKECFTGNN  120
DTAFSNRPIP LAFKTIFYAC GGIDSYGLSS VPYGKYWREL RKVCVHNLLS NQQLLKFRHL  180
IISQVDTSFN KLYELCKNSE DNHGNYTTTT TTAAGMVRID DWLAELSFNV IGRIVCGFQS  240
GPKTGAPSRV EQFKEAINEA SYFMSTSPVS DNVPMLGWID QLTGLTRNMK HCGKKLDLVV  300
ESIINDHRQK RRFSRTKGGD EKDDEQDDFI DICLSIMEQP QLPGNNNPSQ IPIKSIVLDM  360
IGGGTDTTKL TTIWTLSLLL NNPHVLDKAK QEVDAHFRTK RRSTNDAAAA VVDFDDIRNL  420
VYIQAIIKES MRLYPASPVV ERLSGEDCVV GGFHVPAGTR LWANVWKMQR DPKVWDDPLV  480
FRPDRFLSDE QKMVDVRGQN YELLPFGAGR RVCPGVSFSL DLMQLVLTRL ILEFEMKSPS  540
GKVDMTATPG LMSYKVIPLD ILLTHRRIKP CVQSAASERD MESSGVPVIT LGSGKVMPVL  600
GMGTFEKVGK GSERERLAIL KAIEVGYRYF DTAAAYETEE VLGEAIAEAL QLGLVKSRDE  660
LFISSMLWCT DAHADRVLLA LQNSLRNLKL EYVDLYMLPF PASLKPGKIT MDIPEEDICR  720
MDYRSVWAAM EECQNLGFTK SIGVSNFSCK KLQELMATAN IPPAVNQVEM SPAFQQKKLR  780
EYCNANNILV SAISVLGSNG TPWGSNAVLG SEVLKKIAMA KGKSVAQVSM RWVYEQGASL  840
VVKSFSEERL RENLNIFDWE LTKEDHEKIG EIPQCRILSA YFLVSPNGPF KSQEELWDDE  900
A                                                                  901

SEQ ID NO: 2            moltype = AA  length = 919
FEATURE                 Location/Qualifiers
VARIANT                 209
                        note = Any amino acid
VARIANT                 226
                        note = Any amino acid
source                  1..919
                        mol_type = protein
                        organism = Papaver somniferum
SEQUENCE: 2
MELQYISYFQ PTSSVVALLL ALVSILSSVV VLRKTFLNNY SSSPASSTKT AVLSHQRQQS  60
CALPISGLLH IFMNKNGLIH VTLGNMADKY GPIFSFPTGS HRTLVVSSWE MVKECFTGNN  120
DTAFSNRPIP LAFKTIFYAC GGIDSYGLSS VPYGKYWREL RKVCVHNLLS NQQLLKFRHL  180
```

-continued

```
IISQVDTSFN KLYELCKNSE DNHGNYTTXL LLPQLAWRQP WKLYYXTTTT AAGMVRIDDW  240
LAELSFNVIG RIVCGFQSGP KTGAPSRVEQ FKEAINEASY FMSTSPVSDN VPMLGWIDQL  300
TGLTRNMKHC GKKLDLVVES IINDHRQKRR FSRTKGGDEK DDEQDDFIDI CLSIMEQPQL  360
PGNNNPSQIP IKSIVLDMIG GGTDTTKLTT IWTLSLLLNN PHVLDKAKQE VDAHFRTKRR  420
STNDAAAAVV DFDDIRNLVY IQAIIKESMR LYPASPVVER LSGEDCVVGG FHVPAGTRLW  480
ANVWKMQRDP KVWDDPLVFR PDRFLSDEQK MVDVRGQNYE LLPFGAGRRV CPGVSFSLDL  540
MQLVLTRLIL EFEMKSPSGK VDMTATPGLM SYKVIPLDIL LTHRRIKPCV QSAASERDME  600
SSGVPVITLG SGKVMPVLGM GTFEKVGKGS ERERLAILKA IEVGYRYFDT AAAYETEEVL  660
GEAIAEALQL GLVKSRDELF ISSMLWCTDA HADRVLLALQ NSLRNLKLEY VDLYMLPFPA  720
SLKPGKITMD IPEEDICRMD YRSVWAAMEE CQNLGFTKSI GVSNFSCKKL QELMATANIP  780
PAVNQVEMSP AFQQKKLREY CNANNILVSA ISVLGSNGTP WGSNAVLGSE VLKKIAMAKG  840
KSVAQVSMRW VYEQGASLVV KSFSEERLRE NLNIFDWELT KEDHEKIGEI PQCRILSAYF  900
LVSPNGPFKS QEELWDDEA                                               919

SEQ ID NO: 3           moltype = AA  length = 732
FEATURE                Location/Qualifiers
VARIANT                725
                       note = Any amino acid
source                 1..732
                       mol_type = protein
                       organism = Papaver somniferum
SEQUENCE: 3
MELQYISYFQ PTSSVVALLL ALVSILSSVV VLRKTFLNNY SSSPASSTKT AVLSHQRQQS  60
CALPISGLLH IFMNKNGLIH VTLGNMADKY GPIFSFPTGS HRTLVVSSWE MVKECFTGNN  120
DTAFSNRPIP LAFKTIFYAC GGIDSYGLSS VPYGKYWREL RKVCVHNLLS NQQLLKFRHL  180
IISQVDTSFN KLYELCKNSE DNHGNYTTTT TTAAGMVRID DWLAELSFNV IGRIVCGFQS  240
GPKTGAPSRV EQFKEAINEA SYFMSTSPVS DNVPMLGWID QLTGLTRNMK HCGKKLDLVV  300
ESIINDHRQK RRFSRTKGGD EKDDEQDDFI DICLSIMEQP QLPGNNNPSQ IPIKSIVLDM  360
IGGGTDTTKL TTIWTLSLLL NNPHVLDKAK QEVDAHFRTK RRSTNDAAAA VVDFDDIRNL  420
VYIQAIIKES MRLYPASPVV ERLSGEDCVV GGFHVPAGTR LWANVWKMQR DPKVWDDPLV  480
FRPDRFLSDE QKMVDVRGQN YELLPFGAGR RVCPGVSFSL DLMQLVLTRL ILEFEMKSPS  540
GKVDMTATPG LMSYKVIPLD ILLTHRRIKP CVQSAASERD MESSGVPVIT LGSGKVMPVL  600
GMGTFEKVGK GSERERLAIL KAIEVGYRYF DTAAAYETEE VLGEAIAEAL QLGLVKSRDE  660
LFISSMLWCT DAHADRVLLA LQNSLRNLKL EYVDLYMLPF PASLKPGKIT MDIPEEDICR  720
MDYRXVSKPW LH                                                     732

SEQ ID NO: 4           moltype = AA  length = 764
FEATURE                Location/Qualifiers
VARIANT                6
                       note = Any amino acid
source                 1..764
                       mol_type = protein
                       organism = Papaver somniferum
SEQUENCE: 4
MRWHRXIDSY GLSSVPYGKY WRELRKVCVH NLLSNQQLLK FRHLIISQVD TSFNKLYELC  60
KNSEDNQGNY PTTTTAAGMV RIDDWLAELS FNVIGRIVCG FQSGPKTGAP SRVEQFKEAI  120
NEASYFMSTS PVSDNVPMLG WIDQLTGLTR NMKHCGKKLD LVVESIINDH RQKRRFSRTK  180
GGDEKDDEQD DFIDICLSIM EQPQLPGNNN PSQIPIKSIV LDMIGGGTDT TKLTTIWTLS  240
LLLNNPHVLD KAKQEVDAHF RTKRRSTNDA AAVVDFDDI RNLVYIQAII KESMRLYPAS  300
PVVERLSGED CVVGGFHVPA GTRLWANVWK MQRDPKVWDD PLVFRPDRFL SDEQKMVDVR  360
GQNYELLPFG AGRRVCPGVS FSLDLMQLVL TRLILEFEMK SPSGKVDMTA TPGLMSYKVI  420
PLDILLTHRR IKPCVQSAAS ERDMESSGVP VITLGSGKVM PVLGMGTFEK VGKGSERERL  480
AILKAIEVGY RYFDTAAAYE TEEVLGEAIA EALQLGLVKS RDELFISSML WCTDAHADRV  540
LLALQNSLRN LKLEYVDLYM LPFPASLKPG KITMDIPEED ICRMDYRSVW AAMEECQNLG  600
FTKSIGVSNF SCKKLQELMA TANIPPAVNQ VEMSPAFQQK KLREYCNANN ILVSAISVLG  660
SNGTPWGSNA VLGSEVLKKI AMAKGKSVAQ VSMRWVYEQG ASLVVKSFSE ERLRENLNIF  720
DWELTKEDHE KIGEIPQCRI LSAYFLVSPN GPFKSQEELW DDEA                   764

SEQ ID NO: 5           moltype = AA  length = 900
FEATURE                Location/Qualifiers
source                 1..900
                       mol_type = protein
                       note = subspecies: setigerum
                       organism = Papaver somniferum
SEQUENCE: 5
MELQYISYFQ PTSSVVALLL ALVSILSSVV VLRKTFLNNY SSSPASSTKT AVLSHQRQQS  60
CALPISGLLH IFMNKNGLIH VTLGNMADKY GPIFSFPTGS HRTLVVSSWE MVKECFTGNN  120
DTAFSNRPIP LAFKTIFYAC GGIDSYGLSS VPYGKYWREL RKVCVHNLLS NQQLLKFRHL  180
IISQVDTSFN KLYELCKNSE DNQGNYTTTT TAAGMVRIDD WLAELSFNVI GRIVCGFQSG  240
PKTGAPSRVE QFKEAINEAS YFMSTSPVSD NVPMLGWIDQ LTGLTRNMKH CGKKLDLVVE  300
SIINDHRQKR RFSRTKGGDE KDDEQDDFID ICLSIMEQPQ LPGNNNPSQI PIKSIVLDMI  360
GGGTDTTKLT TIWTLSLLLN NPHVLDKAKQ EVDAHFRTKR RSTNDAAAAV VDFDDIRNLV  420
YIQAIIKESM RLYPASPVVE RLSGEDCVVG GFHVPAGTRL WANVWKMQRD PKVWDDPLVF  480
RPDRFLSDEQ KMVDVRGQNY ELLPFGAGRR VCPGVSFSLD LMQLVLTRLI LEFEMKSPSG  540
KVDMTATPGL MSYKVIPLDI LLTHRRIKPC VQSAASERDM ESSGVPVITL GSGKVMPVLG  600
MGTFEKVGKG SERERLAILK AIEVGYRYFD TAAAYETEEV LGEAIAEALQ LGLVKSRDEL  660
FISSMLWCTD AHADRVLLAL QNSLRNLKLE YVDLYMLPFP ASLKPGKITM DIPEEDICRM  720
DYRSVWAAME ECQNLGFTKS IGVSNFSCKK LQELMATANI PPAVNQVEMS PAFQQKKLRE  780
YCNANNILVS AISVLGSNGT PWGSNAVLGS EVLKKIAMAK GKSVAQVSMR WVYEQGASLV  840
```

-continued

```
VKSFSEERLR ENLNIFDWEL TKEDHEKIGE IPQCRILSAY FLVSPNGPFK SQEELWDDEA  900

SEQ ID NO: 6           moltype = AA  length = 724
FEATURE                Location/Qualifiers
source                 1..724
                       mol_type = protein
                       note = subspecies: setigerum
                       organism = Papaver somniferum
SEQUENCE: 6
MELQYISYFQ PTSSVVALLL ALVSILSSVV VLRKTFLNNY SSSPASSTKT AVLSHQRQQS  60
CALPISGLLH IFMNKNGLIH VTLGNMADKY GPIFSFPTGS HRTLVVSSWE MVKECFTGNN  120
DTAFSNRPIP LAFKTIFYAC GGIDSYGLSS VPYGKYWREL RKVCVHNLLS NQQLLKFRHL  180
IISQVDTSFN KLYELCKNSE DNQGNYTTTT TAAGMVRIDD WLAELSFNVI GRIVCGFQSG  240
PKTGAPSRVE QFKEAINEAS YFMSTSPVSD NVPMLGWIDQ LTGLTRNMKH CGKKLDLVVE  300
SIINDHRQKR RFSRTKGGDE KDDEQDDFID ICLSIMEQPQ LPGNNNPSQI PIKSIVLDMI  360
GGGTDTTKLT TIWTLSLLLN NPHVLDKAKQ EVDAHFRTKR RSTNDAAAAV VDFDDIRNLV  420
YIQALYPASP VVERLSGEDC VVGGFHVPAG TRLWANVWKM QRDPKVWDDP LVFRPDRFLS  480
DEQKMVDVRG QNYELLPFGA GRRVCPGVSF SLDLMQLVLT RLILEFEMKS PSGKVDMTAT  540
PGLMSYKVIP LDILLTHRRI KPCVQSAASE RDMESSGVPV ITLGSGKVMP VLGMGTFEKV  600
GKGSERERLA ILKAIEVGYR YFDTAAAYET EEVLGEAIAE ALQLGLVKSR DELFISSMLW  660
CTDAHADRVL LALQNSLRNL KLEYVDLYML PFPASLKPGK ITMDIPEEDI CRMDYRSVWA  720
AMEE                                                              724

SEQ ID NO: 7           moltype = AA  length = 889
FEATURE                Location/Qualifiers
source                 1..889
                       mol_type = protein
                       organism = Papaver bracteatum
SEQUENCE: 7
MELQYFSYFQ PTSSVVALLL ALVSILFSVV VLRKTFSNNY SSPASSTETA VLCHQRQQSC  60
ALPISGLLHV FMNKNGLIHV TLGNMADKYG PIFSFPTGSH RTLVVSSWEM VKECFTGNND  120
TAFSNRPIPL AFQTIFYACG GIDSYGLSSV PYGKYWRELR KVCVHNLLSN QQLLKFRHLI  180
ISQVDTSFNK LYELCKNSED NQGMVRMDDW LAQLSFNVIG RIVCGFQSDP KTGAPSRVEQ  240
FKEVINEASY FMSTSPVSDN VPMLGWIDQL TGLTRNMKHC GKKLDLVVES IIKDHRQKRR  300
FSRTKGGDEK DDEQDDFIDI CLSIMEQPQL PGNNSPPQIP IKSIVLDMIG GGTDTTKLTT  360
IWTLSLLLNN PHVLDKAKQE VDAHFRKKRR STDDAAAAVV DFDDIRNLVY IQAIIKESMR  420
LYPASPVVER LSGEDCVVGG FHVPAGTRLW ANVWKMQRDP KVWDDPLVFR PERFLSDEQK  480
MVDVRGQNYE LLPFGAGRRI CPGVSFSLDL MQLVLTRLIL EFEMKSPSGK VDMTATPGLM  540
SYKVVPLDIL LTHRRIKSCV QLASSERDME SSGVPVITLS SGKVMPVLGM GTFEKVGKGS  600
ERERLAILKA IEVGYRYFDT AAAYETEEVL GEAIAEALQL GLIESRDELF ISSMLWCTDA  660
HPDRVLLALQ NSLRNLKLEY LDLYMLPFPA SLKPGKITMD IPEEDICRMD YRSVWSAMEE  720
CQNLGFTKSI GVSNFSSKKL QELMATANIP PAVNQVEMSP AFQQKKLREY CNANNILVSA  780
VSILGSNGTP WGSNAVLGSE VLKQIAMAKG KSVAQVSMRW VYEQGASLVV KSFSEERLRE  840
NLNIFDWELT KEDNEKIGEI PQCRILTAYF LVSPNGPFKS QEELWDDKA             889

SEQ ID NO: 8           moltype = AA  length = 889
FEATURE                Location/Qualifiers
source                 1..889
                       mol_type = protein
                       organism = Papaver bracteatum
SEQUENCE: 8
MELQYFSYFQ PTSSVVALLL ALVSILFSVV VLRKTFSNNY SSPASSTETA VLCHQRQQSC  60
ALPISGLLHV FMNKNGLIHV TLGNMADKYG PIFSFPTGSH RTLVVSSWEM VKECFTGNND  120
TAFSNRPIPL AFQTIFYACG GIDSYGLSSV PYGKYWRELR KVCVHNLLSN QQLLKFRHLI  180
ISQVDTSFNK LYELCKNSED NQGMVRMDDW LAQLSFNVIG RIVCGFQSDP KTGAPSRVEQ  240
FKEVINEASY FMSTSPVSDN VPMLGWIDQL TGLTRNMKHC GKKLDLVVES IIKDHRQKRR  300
FSRTKGGDEK DDEQDDFIDI CLSIMEQPQL PGNNSPPQIP IKSIVLDMIG GGTDTTKLTT  360
IWTLSLLLNN PHVLDKAKQE VDAHFRKKRR STDDAAAAVV DFDDIRNLVY IQAIIKESMR  420
LYPASPVVER LSGEDCVVGG FHVPAGTRLW ANVWKMQRDP KVWDDPLVFR PERFLSDEQK  480
MVDVRGQNYE LLPFGAGRRI CPGVSFSLDL MQLVLTRLIL EFEMKSPSGK VDMTATPGLM  540
SYKVVPLDIL LTHRRIKSCV QLASSERDME SSGVPVITLS SGKVMPVLGM GTFEKVGKGS  600
ERERLAILKA IEVGYRYFDT AAAYETEEVL GEAIAEALQL GLIESRDELF ISSMLWCTDA  660
HPDRVLLALQ NSLRNLKLEY LDLYMLPFPA SLKPGKITMD IPEEDICRMD YRSVWSAMEE  720
CQNLGFTKSI GVSNFSCKKL QELMATANIP PAVNQVEMSP AFQQKKLREY CNANNILVSA  780
VSILGSNGTP WGSNAVLGSE VLKQIAMAKG KSVAQVSMRW VYEQGASLVV KSFSEERLRE  840
NLNIFDWELT KEDNEKIGEI PQCRILTAYF LVSPNGPFKS QEELWDDKA             889

SEQ ID NO: 9           moltype = AA  length = 848
FEATURE                Location/Qualifiers
source                 1..848
                       mol_type = protein
                       organism = Papaver bracteatum
SEQUENCE: 9
SSPASSTETA VLCHQRQQSC ALPISGLLHI FMNKNGLIHV TLGNMADKYG PIFSFPTGSH  60
RILVVSSWEM VKECFTGNND TAFSNRPIPL AFKTIFYACR GIDSYGLSSV PYGKYWRELR  120
KVCVHNLLSN QQLLKFRHLI ISQVDTSFNK LYELCKNSED NQGMVRMDDW LAQLSFSVIG  180
RIVCGFQSDP KTGAPSRVEQ FKEAINEASY FMSTSPVSDN VPMLGWIDQL TGLTRNMTHC  240
GKKLDLVVES IINDHRQKRR FSRTKGGDEK DDEQDDFIDI CLSIMEQPQL PGNNNPPKIP  300
IKSIVLDMIG AGTDTTKLTI IWTLSLLLNN PNVLAKAKQE VDAHFETKKR STNEASVVVD  360
```

-continued

```
FDDIGNLVYI QAIIKESMRL YPVSPVVERL SSEDCVVGGF HVPAGTRLWA NVWKMQRDPK  420
VWDDPLVFRP ERFLSDEQKM VDVRGQNYEL LPFGAGRRIC PGVSFSLDLM QLVLTRLILE  480
FEMKSPSGKV DMTATPGLMS YKVVPLDILL THRRIKSCVQ LASSERDMES SGVPVITLRS  540
GKVMPVLGMG TFEKAGKGSE RERLAILKAI EVGYRYFDTA AAYETEEVLG EAIAEALQLG  600
LIKSRDELFI SSMLWCTDAH PDRVLLALQN SLRNLKLEYV DLYMLPFPAS LKPGKITMDI  660
PEEDICPMDY RSVWSAMEEC QNLGLTKSIG VSNFSCKKLE ELMATANIPP AVNQVEMSPA  720
FQQKKLREYC NANNILVSAV SILGSNGTPW GSNAVLGSEV LKKIAMAKGK SVAQVSMRWV  780
YEQGASLVVK SFSEERLREN LNIFDWQLTK EDNEKIGEIP QCRILSAYFL VSPKGPFKSQ  840
EELWDDKA                                                          848

SEQ ID NO: 10          moltype = AA  length = 847
FEATURE                Location/Qualifiers
source                 1..847
                       mol_type = protein
                       organism = Papaver bracteatum
SEQUENCE: 10
SSPASSTETA VLCHQRQQSC ALPISGLLHI FMNKNGLIHV TLGNMADKYG PIFSFPTGSH  60
RILVVSSWEM VKECFTGNND TFFSNRPIPL AFKIIFYAGG VDSYGLALVP YGKYWRELRK  120
ICVHNLLSNQ QLLKFRHLII SQVDTSFNKL YELCKNSEDN QGMVRMDDWL AQLSFSVIGR  180
IVCGFQSDPK TGAPSRVEQF KEAINEASYF MSTSPVSDNV PMLGWIDQLT GLTRNMTHCG  240
KKLDLVVESI INDHRQKRRF SRTKGGDEKD DEQDDFIDIC LSIMEQPQLP GNNNPPKIPI  300
KSIVLDMIGG GTDTTKLTTI WTLSLLLNNP HVLDKAKQEV DAHFLTKRRS TNDAAVVDFD  360
DIRNLVYIQA IIKESMRLYP ASPVVERLSG EDCVVGGFHV PAGTRLWVNV WKMQRDPNVW  420
ADPMVFRPER FLSHGQKKMV DVRGKNYELL PFGAGRRICP GISFSLDLMQ LVLTRLILEF  480
EMKSPSGKVD MTATPGLMSY KVVPLDILLT HRRIKSCVQL ASSERDMESS GVPVITLRSG  540
KVMPVLGMGT FEKAGKGSER ERLAILKAIE VGYRYFDTAA AYETEEVLGE AIAEALQLGL  600
IKSRDELFIS SMLWCTDAHP DRVLLALQNS LRNLKLEYVD LYMLPFPASL KPGKITMDIP  660
EEDICPMDYR SVWSAMEECQ NLGLTKSIGV SNFSCKKLEE LMATANIPPA VNQVEMSPAF  720
QQKKLREYCN ANNILVSAVS ILGSNGTPWG SNAVLGSEVL KKIAMAKGKS VAQVSMRWVY  780
EQGASLVVKS FSEERLRENL NIFDWQLTKE DNEKIGEIPQ CRILSAYFLV SPKGPFKSQE  840
ELWDDKA                                                           847

SEQ ID NO: 11          moltype = AA  length = 845
FEATURE                Location/Qualifiers
source                 1..845
                       mol_type = protein
                       organism = Papaver bracteatum
SEQUENCE: 11
SSPASSTETA VLCHQRQQSC ALPISGLLHI FMNKNGLIHV TLGNMADKYG PIFSFPTGSH  60
RILVVSSWEM VKECFTGNND TFFSNRPIPL AFKIIFYAGG VDSYGLALVP YGKYWRELRK  120
ICVHNLLSNQ QLLNFRHLII SQVDTSFNKL YDLSNKKKNT TTDSGTVRMD DWLAQLSFNV  180
IGRIVCGFQT HTETSATSSV ERFTEAIDEA SRFMSIATVS DTFPWLGWID QLTGLTRKMK  240
HYGKKLDLVV ESIIEDHRQN RRISGTKQGD DFIDICLSIM EQPQIIPGNN DPPRQIPIKS  300
IVLDMIGGGT DTTKLTTTWT LSLLLNNPHV LEKAREEVDA HFGTKRRPTN DDAVMVEFDD  360
IRNLVYIQAI IKESMRLYPA SPVVERLSGE DCVVGGFHVP AGTRLWVNVW KMQRDPNVWA  420
DPMVFRPERF LSDEQKMVDV RGQNYELLPF GAGRRICPGV SFSLDLMQLV LTRLILEFEM  480
KSPSGKVDMT ATPGLMSYKV VPLDILLTHR RIKSCVQLAS SERDMESSGV PVITLRSGKV  540
MPVLGMGTFE KAGKGSERER LAILKAIEVG YRYFDTAAAY ETEEVLGEAI AEALQLGLIK  600
SRDELFISSM LWCTDAHPDR VLLALQNSLR NLKLEYVDLY MLPFPASLKP GKITMDIPEE  660
DICPMDYRSV WSAMEECQNL GLTKSIGVSN FSCKKLEELM ATANIPPAVN QVEMSPAFQQ  720
KKLREYCNAN NILVSAVSIL GSNGTPWGSN AVLGSEVLKK IAMAKGKSVA QVSMRWVYEQ  780
GASLVVKSFS EERLRENLNI FDWQLTKEDN EKIGEIPQCR ILSAYFLVSP KGPFKSQEEL  840
WDDKA                                                             845

SEQ ID NO: 12          moltype = AA  length = 869
FEATURE                Location/Qualifiers
source                 1..869
                       mol_type = protein
                       organism = Papaver bracteatum
SEQUENCE: 12
VALRKKILKN YYSSSSSTAT AVSHQWPKAS RALPLIDLLH VFFNKTDLMH VTLGNMADKF  60
GPIFSFPTGS HRTLVVSSWE KAKECFTGNN DIVFSGRPLP LAFKLIFYAG GIDSYGISQV  120
PYGKKWRELR NICVHNILSN QQLLKFRHLM ISQVDNSFNK LYEVCNSNKD EGDSATSTTA  180
AGIVRMDDWL GKLAFDVIAR IVCGFQSQTE TSTTSSMERF TEAMDEASRF MSVTAVSDTV  240
PWLGWIDQLT GLKRNMKHCG KKLNLVVKSI IEDHRQKRRL SSTKKGDENI IDEDEQDDFI  300
DICLSIMEQP QLPGNNNPPK IPIKSIVLDM IGGGTDTTKL TTIWTLSLLL NNPHVLDKAK  360
QEVDAHFLTK RRSTNDAAVV DFDDIRNLVY IQAIIKESMR LYPASPVVER LSGEDCVVGG  420
FHVPAGTRLW VNVWKMQRDP NVWADPMVFR PERFLSDEQK MVDVRGQNYE LLPFGAGRRI  480
CPGVSFSLDL MQLVLTRLIL EFEMKSPSGK VDMTATPGLM SYKVVPLDIL LTHRRIKSCV  540
QLASSERDME SSGVPVITLR SGKVMPVLGM GTFEKAGKGS ERERLAILKA IEVGYRYFDT  600
AAAYETEEVL GEAIAEALQL GLIKSRDELF ISSMLWCTDA HPDRVLLALQ NSLRNLKLEY  660
VDLYMLPFPA SLKPGKITMD IPEEDICPMD YRSVWSAMEE CQNLGLTKSI GVSNFSCKKL  720
EELMATANIP PAVNQVEMSP AFQQKKLREY CNANNILVSA VSILGSNGTP WGSNAVLGSE  780
VLKKIAMAKG KSVAQVSMRW VYEQGASLVV KSFSEERLRE NLNIFDWQLT KEDNEKIGEI  840
PQCRILSAYF LVSPKGPFKS QEELWDDKA                                   869

SEQ ID NO: 13          moltype = AA  length = 858
FEATURE                Location/Qualifiers
VARIANT                822
```

```
                         note = Any amino acid
source                   1..858
                         mol_type = protein
                         organism = Papaver bracteatum
SEQUENCE: 13
MELQYFSYFQ PTSSVVALLL ALVSILFSVV VLRKTFSNNY SSPASSTETA VLCHQRQQSC  60
ALPISGLLHV FMNKNGLIHV TLGNMADKYG PIFSFPTGSH RTLVVSSWEM VKECFTGNND  120
TAFSNRPIPL AFQTIFYACG GIDSYGLSSV PYGKYWRELR KVCVHNLLSN QQLLKFRHLI  180
ISQVDTSFNK LYELCKNSED NQGMVRMDDW LAQLSFNVIG RIVCGFQSDP KTGAPSRVEQ  240
FKEVINEASY FMSTSPVSDN VPMLGWIDQL TGLTRNMKHC GKKLDLVVES IIKDHRQKRR  300
FSRTKGGDEK DDEQDDFIDI CLSIMEQPQL PGNNSPPQIP IKSIVLDMIG GGTDTTKLTT  360
IWTLSLLLNN PHVLDKAKQE VDAHFRKKRR STDDAAAAVV DFDDIRNLVY IQAIIKESMR  420
LYPASPVVER LSGEDCVVGG FHVPAGTRLW ANVWKMQRDP KVWDDPLVFR PERFLSDEQK  480
MVDVRGQNYE LLPFGAGRRI CPGVSFSLDL MQLVLTRLIL EFEMKSPSGK VDMTATPGLM  540
SYKVVPLDIL LTHRRIKSCV QLASSERDME SSGVPVITLS SGKVMPVLGM GTFEKVGKGS  600
ERERLAILKA IEVGYRYFDT AAAYETEEVL GEAIAEALQL GLIESRDELF ISSMLWCTDA  660
HPDRVLLALQ NSLRNLKLEY LDLYMLPFPA SLKPGKITMD IPEEDICRMD YRSVWSAMEE  720
CQNLGFTKSI GVSNFSSKKL QELMATANIP PAVNQVEMSP AFQQKKLREY CNANNILVSA  780
VSILGSNGTP WGSNAVLGSE VLKQIAMAKG KSVAQVSMRW VXKFSAYAIV WSLFFGHRIC  840
ITLYSFLIRN VAYICITY                                                858

SEQ ID NO: 14            moltype = AA  length = 716
FEATURE                  Location/Qualifiers
source                   1..716
                         mol_type = protein
                         organism = Papaver bracteatum
SEQUENCE: 14
MELQYFSYFQ PTSSVVALLL ALVSILFSVV VLRKTFSNNY SSPASSTETA VLCHQRQQSC  60
ALPISGLLHV FMNKNGLIHV TLGNMADKYG PIFSFPTGSH RTLVVSSWEM VKECFTGNND  120
TAFSNRPIPL AFQTIFYACG GIDSYGLSSV PYGKYWRELR KVCVHNLLSN QQLLKFRHLI  180
ISQVDTSFNK LYELCKNSED NQGMVRMDDW LAQLSFNVIG RIVCGFQSDP KTGAPSRVEQ  240
FKEVINEASY FMSTSPVSDN VPMLGWIDQL TGLTRNMKHC GKKLDLVVES IIKDHRQKRR  300
FSRTKGGDEK DDEQDDFIDI CLSIMEQPQL PGNNSPPQIP IKSIVLDMIG GGTDTTKLTT  360
IWTLSLLLNN PHVLDKAKQE VDAHFRKKRR STDDAAAAVV DFDDIRNLVY IQAIIKESMR  420
LYPASPVVER LSGEDCVVGG FHVPAGTRLW ANVWKMQRDP KVWDDPLVFR PERFLSDEQK  480
MVDVRGQNYE LLPFGAGRRI CPGVSFSLDL MQLVLTRLIL EFEMKSPSGK VDMTATPGLM  540
SYKVVPLDIL LTHRRIKSCV QLASSERDME SSGVPVITLS SGKVMPVLGM GTFEKVGKGS  600
ERERLAILKA IEVGYRYFDT AAAYETEEVL GEAIAEALQL GLIESRDELF ISSMLWCTDA  660
HPDRVLLALQ NSLRQVFLMQ IRLIYICTYQ QVHLNIYFQI NEFVLCDMYR NLKLEY      716

SEQ ID NO: 15            moltype = AA  length = 864
FEATURE                  Location/Qualifiers
source                   1..864
                         mol_type = protein
                         organism = Chelidonium majus
SEQUENCE: 15
LNNYSSSPAS STKTAVLSHQ RQQSCALPIS GLLHIFMNKN GLIHVTLGNM ADKYGPIFSF  60
PTGSHRTLVV SSWEMVKECF TGNNDTAFSN RPIPLAFKTI FYACGGIDSY GLSSVPYGKY  120
WRELRKVCVH NLLSNQQLLK FRHLIISQVD TSFNKLYELC KNSEDNQGNY PTTTTAAGMV  180
RIDDWLAELS FNVIGRIVCG FQSGPKTGAP SRVEQFKEAI NEASYFMSTS PVSDNVPMLG  240
WIDQLTGLTR NMKHCGKKLD LVVESIINDH RQKRRFSRTK GGDEKDDEQD DFIDICLSIM  300
EQPQLPGNNN PSQIPIKSIV LDMIGGGTDT TKLTTIWTLS LLLNNPHVLD KAKQEVDAHF  360
RTKRRSTNDA AAAVVDFDDI RNLVYIQAII KESMRLYPAS PVVERLSGED CVVGGFHVPA  420
GTRLWANVWK MQRDPKVWDD PLVFRPDRFL SDEQKMVDVR GQNYELLPFG AGRRVCPGVS  480
FSLDLMQLVL TRLILEFEMK SPSGKVDMTA TPGLMSYKVI PLDILLTHRR IKPCVQSAAS  540
ERDMESSGVP VITLGSGKVM PVLGMGTFEK VGKGSERERL AFLKAIEVGY RYFDTAAAYE  600
TEEFLGEAIA EALQLGLIKS RDELFITSKL WPCDAHPDLV VPALQNSLRN LKLEYVDLYM  660
LPFPASLKPG KITMDIPEED ICRMDYRSVW AAMEECQNLG FTKSIGVSNF SCKKLQELMA  720
TANIPPAVNQ VEMSPAFQQK KLREYCNANN ILVSAISVLG SNGTPWGSNA VLGSEVLKKI  780
AMAKGKSVAQ VSMRWVYEQG ASLVVKSFSE ERLRENLNIF DWELTKEDHE KIGEIPQCRI  840
LSAYFLVSPN GPFKSQEELW DDEA                                         864

SEQ ID NO: 16            moltype = AA  length = 889
FEATURE                  Location/Qualifiers
REGION                   1..889
                         note = Description of Artificial Sequence: Synthetic
                          polypeptide
source                   1..889
                         mol_type = protein
                         organism = synthetic construct
SEQUENCE: 16
MELQYFSYFQ PTSSVVALLL ALVSILFSVV VLRKTFSNNY SSPASSTETA VLCHQRQQSC  60
ALPISGLLHV FMNKNGLIHV TLGNMADKYG PIFSFPTGSH RTLVVSSWEM VKECFTGNND  120
TAFSNRPIPL AFQTIFYACG GIDSYGLSSV PYGKYWRELR KVCVHNLLSN QQLLKFRHLI  180
ISQVDTSFNK LYELCKNSED NQGMVRMDDW LAQLSFNVIG RIVCGFQSDP KTGAPSRVEQ  240
FKEVINEASY FMSTSPVSDN VPMLGWIDQL TGLTRNMKHC GKKLDLVVES IIKDHRQKRR  300
FSRTKGGDEK DDEQDDFIDI CLSIMEQPQL PGNNSPPQIP IKSIVLDMIG GGTDTTKLTT  360
IWTLSLLLNN PHVLDKAKQE VDAHFRKKRR STDDAAAAVV DFDDIRNLVY IQAIIKESMR  420
LYPASPVVER LSGEDCVVGG FHVPAGTRLW ANVWKMQRDP KVWDDPLVFR PERFLSDEQK  480
```

-continued

```
MVDVRGQNYE LLPFGAGRRI CPGVSFSLDL MQLVLTRLIL EFEMKSPSGK VDMTATPGLM  540
SYKVVPLDIL LTHRRIKSCV QLASSERDME SSGVPVITLS SGKVMPVLGM GTFEKVGKGS  600
ERERLAILKA IEVGYRYFDT AAAYETEEVL GEAIAEALQL GLIESRDELF ISSMLWCTDA  660
HPDRVLLALQ NSLRNLKLEY LDLYMLPFPA SLKPGKITMD IPEEDICRMD YRSVWSAMEE  720
CQNLGFTKSI GVSNFSCKKL QELMATANIP PAVNQVEMSP AFQQKKLREY CNANNILVSA  780
VSILGSNGTP WGSNAVLGSE VLKQIAMAKG KSVAQVSMRW VYEQGASLVV KSFSEERLRE  840
NLNIFDWELT KEDNEKIGEI PQCRILTAYF LVSPNGPFKS QEELWDDKA             889

SEQ ID NO: 17           moltype = AA  length = 568
FEATURE                 Location/Qualifiers
REGION                  1..568
                        note = Description of Artificial Sequence: Synthetic
                         polypeptide
source                  1..568
                        mol_type = protein
                        organism = synthetic construct
SEQUENCE: 17
MELQYFSYFQ PTSSVVALLL ALVSILFSVV VLRKTFSNNY SSPASSTETA VLCHQRQQSC  60
ALPISGLLHV FMNKNGLIHV TLGNMADKYG PIFSFPTGSH RTLVVSSWEM VKECFTGNND  120
TAFSNRPIPL AFQTIFYACG GIDSYGLSSV PYGKYWRELR KVCVHNLLSN QQLLKFRHLI  180
ISQVDTSFNK LYELCKNSED NQGMVRMDDW LAQLSFNVIG RIVCGFQSDP KTGAPSRVEQ  240
FKEVINEASY FMSTSPVSDN VPMLGWIDQL TGLTRNMKHC GKKLDLVVES IIKDHRQKRR  300
FSRTKGGDEK DDEQDDFIDI CLSIMEQPQL PGNNSPPQIP IKSIVLDMIG GGTDTTKLTT  360
IWTLSLLLNN PHVLDKAKQE VDAHFRKKRR STDDAAAAVV DFDDIRNLVY IQAIIKESMR  420
LYPASPVVER LSGEDCVVGG FHVPAGTRLW ANVWKMQRDP KVWDDPLVFR PERFLSDEQK  480
MVDVRGQNYE LLPFGAGRRI CPGVSFSLDL MQLVLTRLIL EFEMKSPSGK VDMTATPGLM  540
SYKVVPLDIL LTHRRIKSCV QLASSERD                                    568

SEQ ID NO: 18           moltype = AA  length = 321
FEATURE                 Location/Qualifiers
REGION                  1..321
                        note = Description of Artificial Sequence: Synthetic
                         polypeptide
source                  1..321
                        mol_type = protein
                        organism = synthetic construct
SEQUENCE: 18
MESSGVPVIT LSSGKVMPVL GMGTFEKVGK GSERERLAIL KAIEVGYRYF DTAAAYETEE  60
VLGEAIAEAL QLGLIESRDE LFISSMLWCT DAHPDRVLLA LQNSLRNLKL EYLDLYMLPF  120
PASLKPGKIT MDIPEEDICR MDYRSVWSAM EECQNLGFTK SIGVSNFSCK KLQELMATAN  180
IPPAVNQVEM SPAFQQKKLR EYCNANNILV SAVSILGSNG TPWGSNAVLG SEVLKQIAMA  240
KGKSVAQVSM RWVYEQGASL VVKSFSEERL RENLNIFDWE LTKEDNEKIG EIPQCRILTA  300
YFLVSPNGPF KSQEELWDDK A                                           321

SEQ ID NO: 19           moltype = DNA  length = 682
FEATURE                 Location/Qualifiers
source                  1..682
                        mol_type = genomic DNA
                        organism = Saccharomyces cerevisiae
SEQUENCE: 19
ttcagttcga gtttatcatt atcaatactg ccatttcaaa gaatacgtaa ataattaata  60
gtagtgattt tcctaacttt atttagtcaa aaaattagcc ttttaattct gctgtaaccc  120
gtacatgccc aaaatagggg gcgggttaca cagaatatat aacatcgtag gtgtctgggt  180
gaacagttta ttcctggcat ccactaaata taatggagcc cgctttttaa gctggcatcc  240
agaaaaaaaa agaatcccag caccaaaata ttgttttctt caccaaccat cagttcatag  300
gtccattctc ttagcgcaac tacagagaac aggggcacaa acaggcaaaa aacgggcaca  360
acctcaatgg agtgatgcaa cctgcctgga gtaaatgatg acacaaggca attgacccac  420
gcatgtatct atctcatttt cttacacctt ctattacctt ctgctctctc tgatttggaa  480
aaagctgaaa aaaaaggttg aaaccagttc cctgaaatta ttcccctact tgactaataa  540
gtatataaag acggtaggta ttgattgtaa ttctgtaaat ctatttctta aacttcttaa  600
attctacttt tatagttagt cttttttta gttttaaaac accaagaact tagtttcgaa   660
taaacacaca taaacaaaca aa                                           682

SEQ ID NO: 20           moltype = DNA  length = 289
FEATURE                 Location/Qualifiers
source                  1..289
                        mol_type = genomic DNA
                        organism = Saccharomyces cerevisiae
SEQUENCE: 20
gagcgttggt tggtggatca agcccacgcg taggcaatcc tcgagcagat ccgccaggcg  60
tgtatatata gcgtggatgg ccaggcaact ttagtgctga cacatacagg catatatata  120
tgtgtgcgac gacacatgat catatggcat gcatgtgctc tgtatgtata taaaactctt  180
gttttcttct tttctctaaa tattctttcc ttatacatta ggacctttgc agcataaatt  240
actatacttc tatagacaca caaacacaaa tacacacact aaattaata             289

SEQ ID NO: 21           moltype = DNA  length = 413
FEATURE                 Location/Qualifiers
source                  1..413
                        mol_type = genomic DNA
```

```
                         organism = Saccharomyces cerevisiae
SEQUENCE: 21
catagcttca aaatgtttct actccttttt tactcttcca gattttctcg gactccgcgc  60
atcgccgtac cacttcaaaa cacccaagca cagcatacta aatttcccct ctttcttcct  120
ctagggtgtc gttaattacc cgtactaaag gtttggaaaa gaaaaaagag accgcctcgt  180
ttcttttttct tcgtcgaaaa aggcaataaa aatttttatc acgtttcttt ttcttgaaaa  240
tttttttttt tgattttttt ctctttcgat gacctcccat tgatatttaa gttaataaac  300
ggtcttcaat ttctcaagtt tcagtttcat ttttcttgtt ctattacaac ttttttttact  360
tcttgctcat tagaaagaaa gcatagcaat ctaatctaag ttttaattac aaa         413

SEQ ID NO: 22            moltype = DNA  length = 274
FEATURE                  Location/Qualifiers
source                   1..274
                         mol_type = genomic DNA
                         organism = Saccharomyces cerevisiae
SEQUENCE: 22
acaggcccct tttcctttgt cgatatcatg taattagtta tgtcacgctt acattcacgc  60
cctcctccca catccgctct aaccgaaaag gaaggagtta gacaacctga agtctaggtc  120
cctatttatt ttttttaata gttatgttag tattaagaac gttatttata tttcaaattt  180
ttcttttttt tctgtacaaa cgcgtgtacg catgtaacat tatactgaaa accttgcttg  240
agaaggtttt gggacgctcg aaggctttaa tttg                              274

SEQ ID NO: 23            moltype = DNA  length = 150
FEATURE                  Location/Qualifiers
source                   1..150
                         mol_type = genomic DNA
                         organism = Saccharomyces cerevisiae
SEQUENCE: 23
gcgaatttct tatgatttat gatttttatt attaaataag ttataaaaaa aataagtgta  60
tacaaatttt aaagtgactc ttaggtttta aaacgaaaat tcttattctt gagtaactct  120
ttcctgtagg tcaggttgct ttctcaggta                                   150

SEQ ID NO: 24            moltype = DNA  length = 8014
FEATURE                  Location/Qualifiers
misc_feature             1..8014
                         note = Description of Artificial Sequence: Synthetic
                          polynucleotide
source                   1..8014
                         mol_type = other DNA
                         organism = synthetic construct
SEQUENCE: 24
cctcgccgca gttaattaaa gtcagtgagc gaggaagcgc gtaactataa cggtcctaag  60
gtagcgaatc ctgatgcggt attttctcct tacgcatctg tgcggtattt cacaccgcat  120
agatcggcaa gtgcacaaac aatacttaaa taaatactac tcagtaataa cctatttctt  180
agcatttttg acgaaatttg ctattttgtt agagtctttt acaccatttg tctccacacc  240
tccgcttaca tcaacaccaa taacgccatt taatctaagc gcatcaccaa cattttctgg  300
cgtcagtcca ccagctaaca taaaatgtaa gctttcgggg ctctcttgcc ttccaaccca  360
gtcagaaatc gagttccaat ccaaaagttc acctgtccca cctgcttctg aatcaaacaa  420
gggaataaac gaatgaggtt tctgtgaagc tgcactgagt agtatgttgc agtcttttgg  480
aaatacgagt cttttaataa ctggcaaacc gaggaactct tggtattctt gccacgactc  540
atctccatgc agttggacga tatcaatgcc gtaatcattg accagagcca aaacatcctc  600
cttaagttga ttacgaaaca cgccaaccaa gtatttcgga gtgcctgaac tatttttata  660
tgcttttaca agacttgaaa ttttccttgc aataaccggg tcaattgttc tctttctatt  720
gggcacacat ataataccca gcaagtcagc atcggaatct agagcacatt ctgcggcctc  780
tgtgctctgc aagccgcaaa ctttcaccaa tggaccagaa ctacctgtga aattaataac  840
agacatactc caagctgcct ttgtgtgctt aatcacgtat actcacgtgc tcaatagtca  900
ccaatgccct ccctcttggc cctctccttt tcttttttcg accgaattaa ttcttaatcg  960
gcaaaaaaag aaaagctccg gatcaagatt gtacgtaagg tgacaagcta tttttcaata  1020
aagaatatct tccactactg ccatctggcg tcataactgc aaagtacaca tatattacga  1080
tgctgttcta ttaaatgctt cctatattat atatatagta atgtcgtgat ctatggtgca  1140
ctctcagtac aatctgctct gatgccgcat agttaagcca gccccgacac ccgccaacac  1200
ccgctgacgc gccctgacgg gcttgtctgc tcccggcatc cgcttacaga caagctgtga  1260
ccgtctccgg gagctgcatg tgtcagaggt tttcaccgtc atcaccgaaa cgcgcgagac  1320
gaaagggcct cgtgatacgc ctatttttat aggttaatgt catgataata atggtttctt  1380
agacggatcg cttgcctgta acttacacgc gcctcgtatc ttttaatgat ggaataattt  1440
gggaatttac tctgtgttta tttattttta tgttttgtat ttggatttta gaaagtaaat  1500
aaagaaggta gaagagttac ggaatgaaga aaaaaaaata aacaaaggtt taaaaaattt  1560
caacaaaaag cgtactttac atatatattt attagacaag aaaagcagat taaatagata  1620
tacattcgat taacgataag taaaatgtaa aatcacagga ttttcgtgtg tggtcttcta  1680
cacagacaag gtgaaacaat tcggcattaa tacctgagag caggaagagc aagataaaag  1740
gtagtatttg ttggcgatcc ccctagagtc ttttacatct tcggaaaaca aaaactattt  1800
tttctttaat ttcttttttt actttctatt tttaatttat atatttatat taaaaaattt  1860
aaattataat tatttttata gcacgtgatg aaaaggaccc aggtggcact tttcggggaa  1920
atgtgcgcgg aacccctatt tgtttatttt tctaaataca ttcaaatatg tatccgctca  1980
tgagacaata accctgataa atgcttcaat aatattgaaa aaggaagagt atgagtattc  2040
aacatttccg tgtcgccctt attccctttt ttgcggcatt ttgccttcct gtttttgctc  2100
acccagaaac gctggtgaaa gtaaaagatg ctgaagatca gttgggacgc gtagtctaga  2160
ccagccagga cagaaatgcc tcgacttcgc tgctacccaa ggttgccggg tgacgcacac  2220
cgtggaaacg gatgaaggca cgaacccagt ggacataagc ctgttcggtt cgtaagctgt  2280
```

-continued

```
aatgcaagta gcgtatgcgc tcacgcaact ggtccagaac cttgaccgaa cgcagcggtg  2340
gtaacggcgc agtggcggtt ttcatggctt gttatgactg tttttttggg gtacagtcta  2400
tgcctcgggc atccaagcag caagcgcgtt acgccgtggg tcgatgtttg atgttatgga  2460
gcagcaacga tgttacgcag cagggcagtc gccctaaaac aaagttaaac attatgaggg  2520
aagcggtgat cgccgaagta tcgactcaac tatcagaggt agttggcgcc atcgagcgcc  2580
atctcgaacc gacgttgctg gccgtacatt tgtacggctc cgcagtggat ggcggcctga  2640
agccacacag tgatattgat ttgctggtta cggtgaccgt aaggcttgat gaaacaacgc  2700
ggcgagcttt gatcaacgac cttttggaaa cttcggcttc ccctggagag agcgagattc  2760
tccgcgctgt agaagtcacc attgttgtgc acgacgacat cattccgtgg cgttatccag  2820
ctaagcgcga actgcaattt ggagaatggc agcgcaatga cattcttgca ggtatcttcg  2880
agccagccac gatcgacatt gatctggcta tcttgctgac aaaagcaaga gaacatagcg  2940
ttgccttggt aggtccagcg gcggaggaac tctttgatcc ggttcctgaa caggatctat  3000
ttgaggcgct aaatgaaacc ttaacgctat ggaactcgcc gcccgactgg gctggcgatg  3060
agcgaaatgt agtgcttacg ttgtcccgca tttggtacag cgcagtaacc ggcaaaatcg  3120
cgccgaagga tgtcgctgcc ggctgggcaa tggagcgcct gccggcccag tatcagcccg  3180
tcatacttga agctagacag gcttatcttg gacaagaaga agatcgcttg gcctcgcgcg  3240
cagatcagtt ggaagaattt gtccactacg tgaaaggcga gatcaccaag gtagtcggca  3300
aataaccctc gagcattcaa ggcgccttga ttatttgacg tggtttgatg gcctccacgc  3360
acgttgtgat atgtagatga ttcagttcga gtttatcatt atcaatactg ccatttcaaa  3420
gaatacgtaa ataattaata gtagtgattt tcctaacttt atttagtcaa aaaattagcc  3480
ttttaattct gctgtaaccc gtacatgccc aaaatagggg gcgggttaca cagaatatat  3540
aacatcgtag gtgtctgggt gaacagttta ttcctggcat ccactaaata taatggagcc  3600
cgctttttaa gctggcatcc agaaaaaaaa agaatcccag caccaaaata ttgttttctt  3660
caccaaccat cagttcatag gtccattctc ttagcgcaac tacagagaac aggggcacaa  3720
acaggcaaaa aacgggcaca acctcaatgg agtgatgcaa cctgcctgga gtaaatgatg  3780
acacaaggca attgacccac gcatgtatct atctcatttt cttacacctt ctattacctt  3840
ctgctctctc tgatttggaa aaagctgaaa aaaaaggttg aaaccagttc cctgaaatta  3900
ttcccctact tgactaataa gtatataaag acggtaggta ttgattgtaa ttctgtaaat  3960
ctatttctta aacttcttaa attctacttt tatagttagt cttttttttta gttttaaaac  4020
accaagaact tagtttcgaa taaacacaca taaacaaaca aaatggaact tcagtacttc  4080
tcctattttc aacccacttc atctgtcgta gccctactac tagcactagt gagtatttta  4140
tttagcgtag ttgttttgag gaagactttc agtaacaatt actccagccc cgcgtcaagt  4200
acggaaaccg ctgtgctgtg tcatcagagg caacagagtt gcgccctacc tatcagcggc  4260
cttcttcacg tgttcatgaa taagaacggc ctgattcatg tcaccttggg aaatatggct  4320
gacaaatatg gccctatctt cagttttccg acaggcagcc accgtacttt agtagtcagt  4380
tcctgggaaa tggtgaaaga gtgtttcacc ggtaataacg acacggcatt ctccaacaga  4440
ccaatccctt tggcttttca aaccatattc tacgcctgtg gcggcattga ttcttacggt  4500
ttaagtagtg tcccgtatgg taaatactgg agggagttga gaaaggtgtg tgttcacaac  4560
ctgctgagta atcagcaatt gctgaagttc agacatctta taatctccca agtggatacg  4620
tcttttaaca agttgtatga gctgtgtaag aactctgaag ataatcaagg tatggtaagg  4680
atggatgatt ggctagctca actttccttt aacgtcatcg gtaggatcgt ttgcggattc  4740
cagtctgacc caaagacggg tgcaccttca agggtagaac agtttaagga agtcataaat  4800
gaggcgtcat attttatgtc aacaagtcca gtctccgata acgtaccaat gttgggatgg  4860
atcgaccaat tgaccggtct gacgaggaac atgaagcatt gtgggaagaa gcttgactta  4920
gtagtggagt caattatcaa ggaccatagg caaaagagac gtttttcacg tacaaaaggt  4980
ggcgatgaga aggatgacga acaggacgac tttattgata tttgcttgag catcatggag  5040
cagccacagt tgcccgggaa caattctccc cctcaaattc cgatcaaatc tatcgtgcta  5100
gacatgattg ggggtggtac cgacactacg aaacttacaa ccatatggac cctatcactt  5160
ttgttgaaca atcctcacgt gttagataaa gctaaacaag aggtcgacgc tcactttcgt  5220
aaaaagagaa gatcaacaga tgacgcagca gcggcagtcg ttgattttga cgacataaga  5280
aatttagtat acatccaagc catcattaaa gaaagtatga ggctttatcc agccagcccg  5340
gtggttgagc gtctttccgg cgaggattgc gttgttggag gttttcacgt gcctgctggt  5400
acgagactat gggctaacgt ttggaagatg caaagagatc ccaaagtttg ggacgatcct  5460
ctagtattca gacctgaaag gtttttgagc gacgagcaaa agatggtaga cgttcgtggc  5520
caaaactatg aacttctgcc attcggcgca ggaagaagaa tctgtccagg cgtttccttt  5580
agtcttgacc ttatgcaact tgtcctaacc aggttaatcc tagagttcga aatgaagtcc  5640
ccgtccggca aggtagatat gaccgcaact ccaggactaa tgtcttacaa ggtggttcca  5700
ttggacatat tgctgactca ccgtcgtatc aagtcatgcg ttcaattggc gtcttctgaa  5760
cgtgatatgg aaagttctgg ggtgcctgtg atcacattgt cctcaggtaa agtaatgccc  5820
gtactgggca tgggaacctt cgaaaaggtg ggtaaggggt ctgaacgtga gcgtttagcc  5880
attcttaaag cgatcgaagt tggttaccgt tactttgata ccgcagcggc atatgaaacg  5940
gaagaagttc taggggaagc cattgctgaa gctttacaat tgggtctgat agagagccgt  6000
gacgagctgt tcatcagctc aatgctttgg tgcaccgacg cacatccaga ccgtgtgcta  6060
cttgctctgc aaaacagtct gagaaatcta aaacttgaat atctagacct atatatgttg  6120
ccgtttcctg ccagccttaa gccgggcaaa attacgatgg atattcctga ggaggatatt  6180
tgccgtatgg attatcgttc agtctggagc gccatggaag agtgtcaaaa cttaggattt  6240
actaaaagta ttggtgtaag caacttttct tgcaagaaat tacaagaatt aatggccact  6300
gcaaatatcc cgcccgcggt aaatcaagta gagatgtcac cagctttcca acagaaaaaa  6360
ctgagggaat attgtaacgc aaacaacata ttggtatccg cagtaagcat tctgggatca  6420
aacgggacgc cctggggtag taatgctgtt cttggaagcg aagttttgaa acagatcgcg  6480
atggcgaaag gcaaaagcgt tgcgcaagtc agtatgaggt gggtctatga gcagggcgcg  6540
tctttagtag tcaagagttt ctctgaagaa cgtttaagag aaaacctgaa tatttttgac  6600
tgggagctta cgaaagaaga caatgagaag ataggcgaaa tcccgcaatg tagaatcctt  6660
actgcgtact tccttgtctc cccgaacggc ccgtttaaat ctcaggaaga gctttgggat  6720
gacaaggcat aaacaggccc cttttccttt gtcgatatca tgtaattagt tatgtcacgc  6780
ttacattcac gccctcctcc cacatccgct ctaaccgaaa aggaaggagt tagacaacct  6840
gaagtctagg tccctattta ttttttttaa tagttatgtt agtattaaga acgttattta  6900
tatttcaaat ttttcttttt tttctgtaca aacgcgtgta cgcatgtaac attatactga  6960
aaaccttgct tgagaaggtt ttgggacgct cgaaggcttt aatttgtaat cattatcact  7020
```

```
ttacgggtcc tttccggtga tccgacaggt tacggggcgg cgacctcgcg ggttttcgct  7080
atttatgaaa attttccggt ttaaggcgtt tccgttcttc ttcgtcataa cttaatgttt  7140
ttatttaaaa tacctcgcga gtggcaacac tgaaaatacc catggagcgg cgtaaccgtc  7200
gcacaggatc taggtgaaga tcctttttga taatctcatg accaaaatcc cttaacgtga  7260
gttttcgttc cactgagcgt cagaccccgt agaaaagatc aaaggatctt cttgagatcc  7320
tttttttctg cgcgtaatct gctgcttgca aacaaaaaaa ccaccgctac cagcggtggt  7380
ttgtttgccg gatcaagagc taccaactct ttttccgaag gtaactggct tcagcagagc  7440
gcagatacca aatactgtcc ttctagtgta gccgtagtta ggccaccact tcaagaactc  7500
tgtagcaccg cctacatacc tcgctctgct aatcctgtta ccagtggctg ctgccagtgg  7560
cgataagtcg tgtcttaccg ggttggactc aagacgatag ttaccggata aggcgcagcg  7620
gtcgggctga acggggggtt cgtgcacaca gcccagcttg gagcgaacga cctacaccga  7680
actgagatac ctacagcgtg agctatgaga aagcgccacg cttcccgaag ggagaaaggc  7740
ggacaggtat ccggtaagcg gcagggtcgg aacaggagag cgcacgaggg agcttccagg  7800
gggaaacgcc tggtatcttt atagtcctgt cgggtttcgc cacctctgac ttgagcgtcg  7860
atttttgtga tgctcgtcag gggggcggag cctatggaaa aacgccagca acgcggcagt  7920
ggaacgtgca ttatgaatta gttacgctag ggataacagg gtaatataga acccgaacga  7980
ccgagcgcag cggcggccgc gctgataccg ccgc                              8014

SEQ ID NO: 25           moltype = DNA  length = 7621
FEATURE                 Location/Qualifiers
misc_feature            1..7621
                        note = Description of Artificial Sequence: Synthetic
                         polynucleotide
source                  1..7621
                        mol_type = other DNA
                        organism = synthetic construct
SEQUENCE: 25
cctcgccgca gttaattaaa gtcagtgagc gaggaagcgc gtaactataa cggtcctaag  60
gtagcgaatc ctgatgcggt attttctcct tacgcatctg tgcggtattt cacaccgcat  120
agatcggcaa gtgcacaaac aatacttaaa taaatactac tcagtaataa cctatttctt  180
agcatttttg acgaaatttg ctattttgtt agagtctttt acaccatttg tctccacacc  240
tccgcttaca tcaacaccaa taacgccatt taatctaagc gcatcaccaa cattttctgg  300
cgtcagtcca ccagctaaca taaaatgtaa gctttcgggg ctctcttgcc ttccaaccca  360
gtcagaaatc gagttccaat ccaaaagttc acctgtccca cctgcttctg aatcaaacaa  420
gggaataaac gaatgaggtt tctgtgaagc tgcactgagt agtatgttgc agtcttttgg  480
aaatacgagt cttttaataa ctggcaaacc gaggaactct tggtattctt gccacgactc  540
atctccatgc agttggacga tatcaatgcc gtaatcattg accagagcca aaacatcctc  600
cttaagttga ttacgaaaca cgccaaccaa gtatttcgga gtgcctgaac tatttttata  660
tgcttttaca agacttgaaa ttttccttgc aataaccggg tcaattgttc tctttctatt  720
gggcacacat ataataccca gcaagtcagc atcggaatct agagcacatt ctgcggcctc  780
tgtgctctgc aagccgcaaa ctttcaccaa tggaccagaa ctacctgtga aattaataac  840
agacatactc caagctgcct ttgtgtgctt aatcacgtat actcacgtgc tcaatagtca  900
ccaatgccct ccctcttggc cctctccttt tctttttcg accgaattaa ttcttaatcg  960
gcaaaaaaag aaaagctccg gatcaagatt gtacgtaagg tgacaagcta tttttcaata  1020
aagaatatct tccactactg ccatctggcg tcataactgc aaagtacaca tatattacga  1080
tgctgttcta ttaaatgctt cctatattat atatatagta atgtcgtgat ctatggtgca  1140
ctctcagtac aatctgctct gatgccgcat agttaagcca gccccgacac ccgccaacac  1200
ccgctgacgc gccctgacgg gcttgtctgc tcccggcatc cgcttacaga caagctgtga  1260
ccgtctccgg gagctgcatg tgtcagaggt tttcaccgtc atcaccgaaa cgcgcgagac  1320
gaaagggcct cgtgatacgc ctatttttat aggttaatgt catgataata atggtttctt  1380
agacggatcg cttgcctgta acttacacgc gcctcgtatc ttttaatgat ggaataattt  1440
gggaatttac tctgtgttta tttattttta tgttttgtat ttggatttta gaaagtaaat  1500
aaagaaggta gaagagttac ggaatgaaga aaaaaaaata aacaaaggtt taaaaaattt  1560
caacaaaaag cgtactttac atatatattt attagacaag aaaagcagat taaatagata  1620
tacattcgat taacgataag taaaatgtaa aatcacagga ttttcgtgtg tggtcttcta  1680
cacagacaag gtgaaacaat tcggcattaa tacctgagag caggaagagc aagataaaag  1740
gtagtatttg ttggcgatcc ccctagagtc ttttacatct tcggaaaaca aaaactattt  1800
tttctttaat ttcttttttt actttctatt tttaatttat atatttatat taaaaaattt  1860
aaattataat tatttttata gcacgtgatg aaaaggaccc aggtggcact tttcggggaa  1920
atgtgcgcgg aacccctatt tgtttatttt tctaaataca ttcaaatatg tatccgctca  1980
tgagacaata accctgataa atgcttcaat aatattgaaa aaggaagagt atgagtattc  2040
aacatttccg tgtcgccctt attccctttt ttgcggcatt ttgccttcct gtttttgctc  2100
acccagaaac gctggtgaaa gtaaaagatg ctgaagatca gttgggacgc gtagtctaga  2160
ccagccagga cagaaatgcc tcgacttcgc tgctacccaa ggttgccggg tgacgcacac  2220
cgtggaaacg gatgaaggca cgaacccagt ggacataagc ctgttcggtt cgtaagctgt  2280
aatgcaagta gcgtatgcgc tcacgcaact ggtccagaac cttgaccgaa cgcagcggtg  2340
gtaacggcgc agtggcggtt ttcatggctt gttatgactg tttttttggg gtacagtcta  2400
tgcctcgggc atccaagcag caagcgcgtt acgccgtggg tcgatgtttg atgttatgga  2460
gcagcaacga tgttacgcag cagggcagtc gccctaaaac aaagttaaac attatgaggg  2520
aagcggtgat cgccgaagta tcgactcaac tatcagaggt agttggcgcc atcgagcgcc  2580
atctcgaacc gacgttgctg gccgtacatt tgtacggctc cgcagtggat ggcggcctga  2640
agccacacag tgatattgat ttgctggtta cggtgaccgt aaggcttgat gaaacaacgc  2700
ggcgagcttt gatcaacgac cttttggaaa cttcggcttc ccctggagag agcgagattc  2760
tccgcgctgt agaagtcacc attgttgtgc acgacgacat cattccgtgg cgttatccag  2820
ctaagcgcga actgcaattt ggagaatggc agcgcaatga cattcttgca ggtatcttcg  2880
agccagccac gatcgacatt gatctggcta tcttgctgac aaaagcaaga gaacatagcg  2940
ttgccttggt aggtccagcg gcggaggaac tctttgatcc ggttcctgaa caggatctat  3000
ttgaggcgct aaatgaaacc ttaacgctat ggaactcgcc gcccgactgg gctggcgatg  3060
agcgaaatgt agtgcttacg ttgtcccgca tttggtacag cgcagtaacc ggcaaaatcg  3120
```

-continued

```
cgccgaagga tgtcgctgcc ggctgggcaa tggagcgcct gccggcccag tatcagcccg  3180
tcatacttga agctagacag gcttatcttg gacaagaaga agatcgcttg gcctcgcgcg  3240
cagatcagtt ggaagaattt gtccactacg tgaaaggcga gatcaccaag gtagtcggca  3300
aataaccctc gagcattcaa ggcgccttga ttatttgacg tggtttgatg gcctccacgc  3360
acgttgtgat atgtagatga gagcgttggt tggtggatca agcccacgcg taggcaatcc  3420
tcgagcagat ccgccaggcg tgtatatata gcgtggatgg ccaggcaact ttagtgctga  3480
cacatacagg catatatata tgtgtgcgac gacacatgat catatggcat gcatgtgctc  3540
tgtatgtata taaaactctt gttttcttct tttctctaaa tattctttcc ttatacatta  3600
ggacctttgc agcataaatt actatacttc tatagacaca caaacacaaa tacacacact  3660
aaattaataa tggaacttca gtacttctcc tattttcaac ccacttcatc tgtcgtagcc  3720
ctactactag cactagtgag tattttattt agcgtagttg ttttgaggaa gactttcagt  3780
aacaattact ccagccccgc gtcaagtacg gaaaccgctg tgctgtgtca tcagaggcaa  3840
cagagttgcg ccctacctat cagcggcctt cttcacgtgt tcatgaataa gaacggcctg  3900
attcatgtca ccttgggaaa tatggctgac aaatatggcc ctatcttcag ttttccgaca  3960
ggcagccacc gtactttagt agtcagttcc tgggaaatgg tgaaagagtg tttcaccggt  4020
aataacgaca cggcattctc caacagacca atccctttgg cttttcaaac catattctac  4080
gcctgtggcg gcattgattc ttacggttta agtagtgtcc cgtatggtaa atactggagg  4140
gagttgagaa aggtgtgtgt tcacaacctg ctgagtaatc agcaattgct gaagttcaga  4200
catcttataa tctcccaagt ggatacgtct tttaacaagt tgtatgagct gtgtaagaac  4260
tctgaagata atcaaggtat ggtaaggatg gatgattggc tagctcaact ttcctttaac  4320
gtcatcggta ggatcgtttg cggattccag tctgacccaa agacgggtgc accttcaagg  4380
gtagaacagt ttaaggaagt cataaatgag gcgtcatatt ttatgtcaac aagtccagtc  4440
tccgataacg taccaatgtt gggatggatc gaccaattga ccggtctgac gaggaacatg  4500
aagcattgtg ggaagaagct tgacttagta gtggagtcaa ttatcaagga ccataggcaa  4560
aagagacgtt tttcacgtac aaaaggtggc gatgagaagg atgacgaaca ggacgacttt  4620
attgatattt gcttgagcat catggagcag ccacagttgc ccgggaacaa ttctccccct  4680
caaattccga tcaaatctat cgtgctagac atgattgggg gtggtaccga cactacgaaa  4740
cttacaacca tatggaccct atcacttttg ttgaacaatc ctcacgtgtt agataaagct  4800
aaacaagagg tcgacgctca ctttcgtaaa aagagaagat caacagatga cgcagcagcg  4860
gcagtcgttg attttgacga cataagaaat ttagtataca tccaagccat cattaaagaa  4920
agtatgaggc tttatccagc cagcccggtg gttgagcgtc tttccggcga ggattgcgtt  4980
gttggaggtt ttcacgtgcc tgctggtacg agactatggg ctaacgtttg gaagatgcaa  5040
agagatccca aagtttggga cgatcctcta gtattcagac ctgaaaggtt tttgagcgac  5100
gagcaaaaga tggtagacgt tcgtggccaa aactatgaac ttctgccatt cggcgcagga  5160
agaagaatct gtccaggcgt ttcctttagt cttgacctta tgcaacttgt cctaaccagg  5220
ttaatcctag agttcgaaat gaagtccccg tccggcaagg tagatatgac cgcaactcca  5280
ggactaatgt cttacaaggt ggttccattg gacatattgc tgactcaccg tcgtatcaag  5340
tcatgcgttc aattggcgtc ttctgaacgt gatatggaaa gttctggggt gcctgtgatc  5400
acattgtcct caggtaaagt aatgcccgta ctgggcatgg gaaccttcga aaaggtgggt  5460
aaggggtctg aacgtgagcg tttagccatt cttaaagcga tcgaagttgg ttaccgttac  5520
tttgataccg cagcggcata tgaaacggaa gaagttctag ggaagccat tgctgaagct  5580
ttacaattgg gtctgataga gagccgtgac gagctgttca tcagctcaat gctttggtgc  5640
accgacgcac atccagaccg tgtgctactt gctctgcaaa acagtctgag aaatctaaaa  5700
cttgaatatc tagacctata tatgttgccg tttcctgcca gccttaagcc gggcaaaatt  5760
acgatggata ttcctgagga ggatatttgc cgtatggatt atcgttcagt ctggagcgcc  5820
atggaagagt gtcaaaactt aggatttact aaaagtattg gtgtaagcaa cttttcttgc  5880
aagaaattac aagaattaat ggccactgca aatatcccgc ccgcggtaaa tcaagtagag  5940
atgtcaccag ctttccaaca gaaaaaactg agggaatatt gtaacgcaaa caacatattg  6000
gtatccgcag taagcattct gggatcaaac gggacgccct ggggtagtaa tgctgttctt  6060
ggaagcgaag ttttgaaaca gatcgcgatg gcgaaaggca aaagcgttgc gcaagtcagt  6120
atgaggtggg tctatgagca gggcgcgtct ttagtagtca agagtttctc tgaagaacgt  6180
ttaagagaaa acctgaatat ttttgactgg gagcttacga aagaagacaa tgagaagata  6240
ggcgaaatcc cgcaatgtag aatccttact gcgtacttcc ttgtctcccc gaacggcccg  6300
tttaaatctc aggaagagct ttgggatgac aaggcataaa caggcccctt ttcctttgtc  6360
gatatcatgt aattagttat gtcacgctta cattcacgcc ctcctcccac atccgctcta  6420
accgaaaagg aaggagttag acaacctgaa gtctaggtcc ctatttattt tttttaatag  6480
ttatgttagt attaagaacg ttatttatat ttcaaatttt tctttttttt ctgtacaaac  6540
gcgtgtacgc atgtaacatt atactgaaaa ccttgcttga gaaggttttg ggacgctcga  6600
aggctttaat ttgtaatcat tatcacttta cgggtccttt ccggtgatcc gacaggttac  6660
ggggcggcga cctcgcgggt tttcgctatt tatgaaaatt ttccggttta aggcgtttcc  6720
gttcttcttc gtcataactt aatgttttta tttaaaatac ctcgcgagtg gcaacactga  6780
aaatacccat ggagcggcgt aaccgtcgca caggatctag gtgaagatcc tttttgataa  6840
tctcatgacc aaaatccctt aacgtgagtt ttcgttccac tgagcgtcag accccgtaga  6900
aaagatcaaa ggatcttctt gagatccttt ttttctgcgc gtaatctgct gcttgcaaac  6960
aaaaaaacca ccgctaccag cggtggtttg tttgccggat caagagctac caactctttt  7020
tccgaaggta actggcttca gcagagcgca gataccaaat actgtccttc tagtgtagcc  7080
gtagttaggc caccacttca agaactctgt agcaccgcct acatacctcg ctctgctaat  7140
cctgttacca gtggctgctg ccagtggcga taagtcgtgt cttaccgggt tggactcaag  7200
acgatagtta ccggataagg cgcagcggtc gggctgaacg gggggttcgt gcacacagcc  7260
cagcttggag cgaacgacct acaccgaact gagataccta cagcgtgagc tatgagaaag  7320
cgccacgctt cccgaaggga gaaaggcgga caggtatccg gtaagcggca gggtcggaac  7380
aggagagcgc acgagggagc ttccaggggg aaacgcctgg tatctttata gtcctgtcgg  7440
gtttcgccac ctctgacttg agcgtcgatt tttgtgatgc tcgtcagggg ggcggagcct  7500
atggaaaaac gccagcaacg cggcagtgga acgtgcatta tgaattagtt acgctaggga  7560
taacagggta atatagaacc cgaacgaccg agcgcagcgg cggccgcgct gataccgccg  7620
c                                                                  7621
```

SEQ ID NO: 26          moltype = DNA  length = 8187
FEATURE                Location/Qualifiers

```
misc_feature            1..8187
                        note = Description of Artificial Sequence: Synthetic
                         polynucleotide
source                  1..8187
                        mol_type = other DNA
                        organism = synthetic construct
SEQUENCE: 26
cctcgccgca gttaattaaa gtcagtgagc gaggaagcgc gtaactataa cggtcctaag  60
gtagcgaatc ctgatgcggt attttctcct tacgcatctg tgcggtattt cacaccgcat  120
agatcggcaa gtgcacaaac aatacttaaa taaatactac tcagtaataa cctatttctt  180
agcatttttg acgaaatttg ctattttgtt agagtctttt acaccatttg tctccacacc  240
tccgcttaca tcaacaccaa taacgccatt taatctaagc gcatcaccaa cattttctgg  300
cgtcagtcca ccagctaaca taaaatgtaa gctttcgggg ctctcttgcc ttccaaccca  360
gtcagaaatc gagttccaat ccaaaagttc acctgtccca cctgcttctg aatcaaacaa  420
gggaataaac gaatgaggtt tctgtgaagc tgcactgagt agtatgttgc agtcttttgg  480
aaatacgagt cttttaataa ctggcaaacc gaggaactct tggtattctt gccacgactc  540
atctccatgc agttggacga tatcaatgcc gtaatcattg accagagcca aaacatcctc  600
cttaagttga ttacgaaaca cgccaaccaa gtatttcgga gtgcctgaac tatttttata  660
tgcttttaca agacttgaaa ttttccttgc aataaccggg tcaattgttc tctttctatt  720
gggcacacat ataataccca gcaagtcagc atcggaatct agagcacatt ctgcggcctc  780
tgtgctctgc aagccgcaaa ctttcaccaa tggaccagaa ctacctgtga aattaataac  840
agacatactc caagctgcct ttgtgtgctt aatcacgtat actcacgtgc tcaatagtca  900
ccaatgccct ccctcttggc cctctccttt tcttttttcg accgaattaa ttcttaatcg  960
gcaaaaaaag aaaagctccg gatcaagatt gtacgtaagg tgacaagcta tttttcaata  1020
aagaatatct tccactactg ccatctggcg tcataactgc aaagtacaca tatattacga  1080
tgctgttcta ttaaatgctt cctatattat atatatagta atgtcgtgat ctatggtgca  1140
ctctcagtac aatctgctct gatgccgcat agttaagcca gccccgacac ccgccaacac  1200
ccgctgacgc gccctgacgg gcttgtctgc tcccggcatc cgcttacaga caagctgtga  1260
ccgtctccgg gagctgcatg tgtcagaggt tttcaccgtc atcaccgaaa cgcgcgagac  1320
gaaagggcct cgtgatacgc ctatttttat aggttaatgt catgataata atggtttctt  1380
agacggatcg cttgcctgta acttacacgc gcctcgtatc ttttaatgat ggaataattt  1440
gggaatttac tctgtgttta tttattttta tgttttgtat ttggatttta gaaagtaaat  1500
aaagaaggta gaagagttac ggaatgaaga aaaaaaaata aacaaaggtt taaaaaattt  1560
caacaaaaag cgtactttac atatatattt attagacaag aaaagcagat taaatagata  1620
tacattcgat taacgataag taaaatgtaa aatcacagga ttttcgtgtg tggtcttcta  1680
cacagacaag gtgaaacaat tcggcattaa tacctgagag caggaagagc aagataaaag  1740
gtagtatttg ttggcgatcc ccctagagtc ttttacatct tcggaaaaca aaaactattt  1800
tttctttaat ttcttttttt actttctatt tttaatttat atatttatat taaaaaattt  1860
aaattataat tatttttata gcacgtgatg aaaaggaccc aggtggcact tttcggggaa  1920
atgtgcgcgg aacccctatt tgtttatttt tctaaataca ttcaaatatg tatccgctca  1980
tgagacaata accctgataa atgcttcaat aatattgaaa aaggaagagt atgagtattc  2040
aacatttccg tgtcgccctt attccctttt ttgcggcatt ttgccttcct gtttttgctc  2100
acccagaaac gctggtgaaa gtaaaagatg ctgaagatca gttgggacgc gtagtctaga  2160
ccagccagga cagaaatgcc tcgacttcgc tgctacccaa ggttgccggg tgacgcacac  2220
cgtggaaacg gatgaaggca cgaacccagt ggacataagc ctgttcggtt cgtaagctgt  2280
aatgcaagta gcgtatgcgc tcacgcaact ggtccagaac cttgaccgaa cgcagcggtg  2340
gtaacggcgc agtggcggtt ttcatggctt gttatgactg tttttttggg gtacagtcta  2400
tgcctcgggc atccaagcag caagcgcgtt acgccgtggg tcgatgtttg atgttatgga  2460
gcagcaacga tgttacgcag cagggcagtc gccctaaaac aaagttaaac attatgaggg  2520
aagcggtgat cgccgaagta tcgactcaac tatcagaggt agttggcgcc atcgagcgcc  2580
atctcgaacc gacgttgctg gccgtacatt tgtacggctc cgcagtggat ggcggcctga  2640
agccacacag tgatattgat ttgctggtta cggtgaccgt aaggcttgat gaaacaacgc  2700
ggcgagcttt gatcaacgac cttttggaaa cttcggcttc ccctggagag agcgagattc  2760
tccgcgctgt agaagtcacc attgttgtgc acgacgacat cattccgtgg cgttatccag  2820
ctaagcgcga actgcaattt ggagaatggc agcgcaatga cattcttgca ggtatcttcg  2880
agccagccac gatcgacatt gatctggcta tcttgctgac aaaagcaaga gaacatagcg  2940
ttgccttggt aggtccagcg gcggaggaac tctttgatcc ggttcctgaa caggatctat  3000
ttgaggcgct aaatgaaacc ttaacgctat ggaactcgcc gcccgactgg gctggcgatg  3060
agcgaaatgt agtgcttacg ttgtcccgca tttggtacag cgcagtaacc ggcaaaatcg  3120
cgccgaagga tgtcgctgcc ggctgggcaa tggagcgcct gccggcccag tatcagcccg  3180
tcatacttga agctagacag gcttatcttg gacaagaaga agatcgcttg gcctcgcgcg  3240
cagatcagtt ggaagaattt gtccactacg tgaaaggcga gatcaccaag gtagtcggca  3300
aataaccctc gagcattcaa ggcgccttga ttatttgacg tggtttgatg gcctccacgc  3360
acgttgtgat atgtagatga gagcgttggt tggtggatca agcccacgcg taggcaatcc  3420
tcgagcagat ccgccaggcg tgtatatata gcgtggatgg ccaggcaact ttagtgctga  3480
cacatacagg catatatata tgtgtgcgac gacacatgat catatggcat gcatgtgctc  3540
tgtatgtata taaaactctt gttttcttct tttctctaaa tattctttcc ttatacatta  3600
ggacctttgc agcataaatt actatacttc tatagacaca caaacacaaa tacacacact  3660
aaattaataa tggaacttca gtacttctcc tattttcaac ccacttcatc tgtcgtagcc  3720
ctactactag cactagtgag tattttattt agcgtagttg ttttgaggaa gactttcagt  3780
aacaattact ccagccccgc gtcaagtacg gaaaccgctg tgctgtgtca tcagaggcaa  3840
cagagttgcg ccctacctat cagcggcctt cttcacgtgt tcatgaataa gaacggcctg  3900
attcatgtca ccttgggaaa tatggctgac aaatatggcc ctatcttcag ttttccgaca  3960
ggcagccacc gtactttagt agtcagttcc tgggaaatgg tgaaagagtg tttcaccggt  4020
aataacgaca cggcattctc caacagacca atccctttgg cttttcaaac catattctac  4080
gcctgtggcg gcattgattc ttacggttta agtagtgtcc cgtatggtaa atactggagg  4140
gagttgagaa aggtgtgtgt tcacaacctg ctgagtaatc agcaattgct gaagttcaga  4200
catcttataa tctcccaagt ggatacgtct tttaacaagt tgtatgagct gtgtaagaac  4260
tctgaagata atcaaggtat ggtaaggatg gatgattggc tagctcaact ttcctttaac  4320
```

-continued

```
gtcatcggta ggatcgtttg cggattccag tctgacccaa agacgggtgc accttcaagg  4380
gtagaacagt ttaaggaagt cataaatgag gcgtcatatt ttatgtcaac aagtccagtc  4440
tccgataacg taccaatgtt gggatggatc gaccaattga ccggtctgac gaggaacatg  4500
aagcattgtg ggaagaagct tgacttagta gtggagtcaa ttatcaagga ccataggcaa  4560
aagagacgtt tttcacgtac aaaaggtggc gatgagaagg atgacgaaca ggacgacttt  4620
attgatattt gcttgagcat catggagcag ccacagttgc ccgggaacaa ttctccccct  4680
caaattccga tcaaatctat cgtgctagac atgattgggg gtggtaccga cactacgaaa  4740
cttacaacca tatggaccct atcactttg ttgaacaatc ctcacgtgtt agataaagct  4800
aaacaagagg tcgacgctca ctttcgtaaa aagagaagat caacagatga cgcagcagcg  4860
gcagtcgttg attttgacga cataagaaat ttagtataca tccaagccat cattaaagaa  4920
agtatgaggc tttatccagc cagcccggtg gttgagcgtc tttccggcga ggattgcgtt  4980
gttggaggtt ttcacgtgcc tgctggtacg agactatggg ctaacgtttg gaagatgcaa  5040
agagatccca aagtttggga cgatcctcta gtattcagac ctgaaaggtt tttgagcgac  5100
gagcaaaaga tggtagacgt tcgtggccaa aactatgaac ttctgccatt cggcgcagga  5160
agaagaatct gtccaggcgt ttcctttagt cttgacctta tgcaacttgt cctaaccagg  5220
ttaatcctag agttcgaaat gaagtccccg tccggcaagg tagatatgac cgcaactcca  5280
ggactaatgt cttacaaggt ggttccattg gacatattgc tgactcaccg tcgtatcaag  5340
tcatgcgttc aattggcgtc ttctgaacgt gattaagcga atttcttatg atttatgatt  5400
tttattatta aataagttat aaaaaaaata agtgtataca aattttaaag tgactcttag  5460
gttttaaaac gaaaattctt attcttgagt aactctttcc tgtaggtcag gttgctttct  5520
caggtacata gcttcaaaat gtttctactc cttttttact cttccagatt ttctcggact  5580
ccgcgcatcg ccgtaccact tcaaaacacc caagcacagc atactaaatt tcccctcttt  5640
cttcctctag ggtgtcgtta attacccgta ctaaaggttt ggaaaagaaa aaagagaccg  5700
cctcgtttct ttttcttcgt cgaaaaaggc aataaaaatt tttatcacgt ttcttttttct  5760
tgaaaatttt ttttttttgat ttttttctct ttcgatgacc tcccattgat atttaagtta  5820
ataaacggtc ttcaatttct caagtttcag tttcattttt cttgttctat tacaactttt  5880
tttacttctt gctcattaga aagaaaagcat agcaatctaa tctaagtttt aattacaaaa  5940
tggaaagttc tggggtgcct gtgatcacat tgtcctcagg taaagtaatg cccgtactgg  6000
gcatgggaac cttcgaaaag gtgggtaagg ggtctgaacg tgagcgttta gccattctta  6060
aagcgatcga agttggttac cgttactttg ataccgcagc ggcatatgaa acggaagaag  6120
ttctagggga agccattgct gaagctttac aattgggtct gatagagagc cgtgacgagc  6180
tgttcatcag ctcaatgctt tggtgcaccg acgcacatcc agaccgtgtg ctacttgctc  6240
tgcaaaacag tctgagaaat ctaaaacttg aatatctaga cctatatatg ttgccgtttc  6300
ctgccagcct taagccgggc aaaattacga tggatattcc tgaggaggat atttgccgta  6360
tggattatcg ttcagtctgg agcgccatgg aagagtgtca aaacttagga tttactaaaa  6420
gtattggtgt aagcaacttt tcttgcaaga aattacaaga attaatggcc actgcaaata  6480
tcccgcccgc ggtaaatcaa gtagagatgt caccagcttt ccaacagaaa aaactgaggg  6540
aatattgtaa cgcaaacaac atattggtat ccgcagtaag cattctggga tcaaacggga  6600
cgccctgggg tagtaatgct gttcttggaa gcgaagtttt gaaacagatc gcgatggcga  6660
aaggcaaaag cgttgcgcaa gtcagtatga ggtgggtcta tgagcagggc gcgtctttag  6720
tagtcaagag tttctctgaa gaacgtttaa gagaaaacct gaatattttt gactgggagc  6780
ttacgaaaga agacaatgag aagataggcg aaatcccgca atgtagaatc cttactgcgt  6840
acttccttgt ctccccgaac ggcccgttta aatctcagga agagctttgg gatgacaagg  6900
cataaacagg cccctttcc tttgtcgata tcatgtaatt agttatgtca cgcttacatt  6960
cacgccctcc tcccacatcc gctctaaccg aaaaggaagg agttagacaa cctgaagtct  7020
aggtccctat ttattttttt taatagttat gttagtatta agaacgttat ttatatttca  7080
aatttttctt tttttctgt acaaacgcgt gtacgcatgt aacattatac tgaaaacctt  7140
gcttgagaag gttttgggac gctcgaaggc tttaatttgt aatcattatc actttacggg  7200
tcctttccgg tgatccgaca ggttacgggg cggcgacctc gcgggttttc gctatttatg  7260
aaaatttcc ggtttaaggc gtttccgttc ttcttcgtca taacttaatg tttttattta  7320
aaatacctcg cgagtggcaa cactgaaaat acccatggag cggcgtaacc gtcgcacagg  7380
atctaggtga agatcctttt tgataatctc atgaccaaaa tcccttaacg tgagttttcg  7440
ttccactgag cgtcagaccc cgtagaaaag atcaaaggat cttcttgaga tcctttttt  7500
ctgcgcgtaa tctgctgctt gcaaacaaaa aaaccaccgc taccagcggt ggtttgtttg  7560
ccggatcaag agctaccaac tctttttccg aaggtaactg gcttcagcag agcgcagata  7620
ccaaatactg tccttctagt gtagccgtag ttaggccacc acttcaagaa ctctgtagca  7680
ccgcctacat acctcgctct gctaatcctg ttaccagtgg ctgctgccag tggcgataag  7740
tcgtgtctta ccgggttgga ctcaagacga tagttaccgg ataaggcgca gcggtcgggc  7800
tgaacggggg gttcgtgcac acagcccagc ttggagcgaa cgacctacac cgaactgaga  7860
tacctacagc gtgagctatg agaaagcgcc acgcttcccg aagggagaaa ggcggacagg  7920
tatccggtaa gcggcagggt cggaacagga gagcgcacga gggagcttcc agggggaaac  7980
gcctggtatc tttatagtcc tgtcgggttt cgccacctct gacttgagcg tcgatttttg  8040
tgatgctcgt caggggggcg gagcctatgg aaaaacgcca gcaacgcggc agtggaacgt  8100
gcattatgaa ttagttacgc tagggataac agggtaatat agaacccgaa cgaccgagcg  8160
cagcggcggc cgcgctgata ccgccgc                                    8187
```

```
SEQ ID NO: 27          moltype = DNA  length = 8580
FEATURE                Location/Qualifiers
misc_feature           1..8580
                       note = Description of Artificial Sequence: Synthetic
                        polynucleotide
source                 1..8580
                       mol_type = other DNA
                       organism = synthetic construct
SEQUENCE: 27
cctcgccgca gttaattaaa gtcagtgagc gaggaagcgc gtaactataa cggtcctaag  60
gtagcgaatc ctgatgcggt attttctcct tacgcatctg tgcggtattt cacaccgcat  120
agatcggcaa gtgcacaaac aatacttaaa taaatactac tcagtaataa cctatttctt  180
agcattttg acgaaatttg ctattttgtt agagtctttt acaccatttg tctccacacc  240
```

-continued tccgcttaca tcaacaccaa taacgccatt taatctaagc gcatcaccaa cattttctgg 300
cgtcagtcca ccagctaaca taaaatgtaa gctttcgggg ctctcttgcc ttccaaccca 360
gtcagaaatc gagttccaat ccaaaagttc acctgtccca cctgcttctg aatcaaacaa 420
gggaataaac gaatgaggtt tctgtgaagc tgcactgagt agtatgttgc agtcttttgg 480
aaatacgagt cttttaataa ctggcaaacc gaggaactct tggtattctt gccacgactc 540
atctccatgc agttggacga tatcaatgcc gtaatcattg accagagcca aaacatcctc 600
cttaagttga ttacgaaaca cgccaaccaa gtatttcgga gtgcctgaac tatttttata 660
tgcttttaca agacttgaaa ttttccttgc aataaccggg tcaattgttc tctttctatt 720
gggcacacat ataataccca gcaagtcagc atcggaatct agagcacatt ctgcggcctc 780
tgtgctctgc aagccgcaaa ctttcaccaa tggaccagaa ctacctgtga aattaataac 840
agacatactc caagctgcct ttgtgtgctt aatcacgtat actcacgtgc tcaatagtca 900
ccaatgccct ccctcttggc cctctccttt tctttttcg accgaattaa ttcttaatcg 960
gcaaaaaaag aaaagctccg gatcaagatt gtacgtaagg tgacaagcta tttttcaata 1020
aagaatatct tccactactg ccatctggcg tcataactgc aaagtacaca tatattacga 1080
tgctgttcta ttaaatgctt cctatattat atatatagta atgtcgtgat ctatggtgca 1140
ctctcagtac aatctgctct gatgccgcat agttaagcca gccccgacac ccgccaacac 1200
ccgctgacgc gccctgacgg gcttgtctgc tcccggcatc cgcttacaga caagctgtga 1260
ccgtctccgg gagctgcatg tgtcagaggt tttcaccgtc atcaccgaaa cgcgcgagac 1320
gaaagggcct cgtgatacgc ctatttttat aggttaatgt catgataata atggtttctt 1380
agacggatcg cttgcctgta acttacacgc gcctcgtatc ttttaatgat ggaataattt 1440
gggaatttac tctgtgttta tttattttta tgttttgtat ttggatttta gaaagtaaat 1500
aaagaaggta gaagagttac ggaatgaaga aaaaaaaata aacaaaggtt taaaaaattt 1560
caacaaaaag cgtactttac atatatattt attagacaag aaaagcagat taaatagata 1620
tacattcgat taacgataag taaaatgtaa aatcacagga ttttcgtgtg tggtcttcta 1680
cacagacaag gtgaaacaat tcggcattaa tacctgagag caggaagagc aagataaaag 1740
gtagtatttg ttggcgatcc ccctagagtc ttttacatct tcggaaaaca aaaactattt 1800
tttctttaat ttcttttttt actttctatt tttaatttat atatttatat taaaaaattt 1860
aaattataat tatttttata gcacgtgatg aaaaggaccc aggtggcact tttcggggaa 1920
atgtgcgcgg aacccctatt tgtttatttt tctaaataca ttcaaatatg tatccgctca 1980
tgagacaata accctgataa atgcttcaat aatattgaaa aaggaagagt atgagtattc 2040
aacatttccg tgtcgccctt attccctttt ttgcggcatt ttgccttcct gtttttgctc 2100
acccagaaac gctggtgaaa gtaaaagatg ctgaagatca gttgggacgc gtagtctaga 2160
ccagccagga cagaaatgcc tcgacttcgc tgctacccaa ggttgccggg tgacgcacac 2220
cgtggaaacg gatgaaggca cgaacccagt ggacataagc ctgttcggtt cgtaagctgt 2280
aatgcaagta gcgtatgcgc tcacgcaact ggtccagaac cttgaccgaa cgcagcggtg 2340
gtaacggcgc agtggcggtt ttcatggctt gttatgactg tttttttggg gtacagtcta 2400
tgcctcgggc atccaagcag caagcgcgtt acgccgtggg tcgatgtttg atgttatgga 2460
gcagcaacga tgttacgcag cagggcagtc gccctaaaac aaagttaaac attatgaggg 2520
aagcggtgat cgccgaagta tcgactcaac tatcagaggt agttggcgcc atcgagcgcc 2580
atctcgaacc gacgttgctg gccgtacatt tgtacggctc cgcagtggat ggcggcctga 2640
agccacacag tgatattgat ttgctggtta cggtgaccgt aaggcttgat gaaacaacgc 2700
ggcgagcttt gatcaacgac cttttggaaa cttcggcttc ccctggagag agcgagattc 2760
tccgcgctgt agaagtcacc attgttgtgc acgacgacat cattccgtgg cgttatccag 2820
ctaagcgcga actgcaattt ggagaatggc agcgcaatga cattcttgca ggtatcttcg 2880
agccagccac gatcgacatt gatctggcta tcttgctgac aaaagcaaga gaacatagcg 2940
ttgccttggt aggtccagcg gcggaggaac tctttgatcc ggttcctgaa caggatctat 3000
ttgaggcgct aaatgaaacc ttaacgctat ggaactcgcc gcccgactgg gctggcgatg 3060
agcgaaatgt agtgcttacg ttgtcccgca tttggtacag cgcagtaacc ggcaaaatcg 3120
cgccgaagga tgtcgctgcc ggctgggcaa tggagcgcct gccggcccag tatcagcccg 3180
tcatacttga agctagacag gcttatcttg gacaagaaga agatcgcttg gcctcgcgcg 3240
cagatcagtt ggaagaattt gtccactacg tgaaaggcga gatcaccaag gtagtcggca 3300
aataaccctc gagcattcaa ggcgccttga ttatttgacg tggtttgatg gcctccacgc 3360
acgttgtgat atgtagatga ttcagttcga gtttatcatt atcaatactg ccatttcaaa 3420
gaatacgtaa ataattaata gtagtgattt tcctaacttt atttagtcaa aaaattagcc 3480
ttttaattct gctgtaaccc gtacatgccc aaaatagggg gcgggttaca cagaatatat 3540
aacatcgtag gtgtctgggt gaacagttta ttcctggcat ccactaaata taatggagcc 3600
cgctttttaa gctggcatcc agaaaaaaaa agaatcccag caccaaaata ttgttttctt 3660
caccaaccat cagttcatag gtccattctc ttagcgcaac tacagagaac aggggcacaa 3720
acaggcaaaa aacgggcaca acctcaatgg agtgatgcaa cctgcctgga gtaaatgatg 3780
acacaaggca attgacccac gcatgtatct atctcatttt cttacacctt ctattacctt 3840
ctgctctctc tgatttggaa aaagctgaaa aaaaaggttg aaaccagttc cctgaaatta 3900
ttcccctact tgactaataa gtatataaag acggtaggta ttgattgtaa ttctgtaaat 3960
ctatttctta aacttcttaa attctacttt tatagttagt ctttttttta gttttaaaac 4020
accaagaact tagtttcgaa taaacacaca taaacaaaca aaatggaact tcagtacttc 4080
tcctattttc aacccacttc atctgtcgta gccctactac tagcactagt gagtatttta 4140
tttagcgtag ttgttttgag gaagactttc agtaacaatt actccagccc cgcgtcaagt 4200
acggaaaccg ctgtgctgtg tcatcagagg caacagagtt gcgccctacc tatcagcggc 4260
cttcttcacg tgttcatgaa taagaacggc ctgattcatg tcaccttggg aaatatggct 4320
gacaaatatg gccctatctt cagttttccg acaggcagcc accgtacttt agtagtcagt 4380
tcctgggaaa tggtgaaaga gtgtttcacc ggtaataacg acacggcatt ctccaacaga 4440
ccaatccctt tggcttttca aaccatattc tacgcctgtg gcggcattga ttcttacggt 4500
ttaagtagtg tcccgtatgg taaatactgg agggagttga gaaaggtgtg tgttcacaac 4560
ctgctgagta atcagcaatt gctgaagttc agacatctta taatctccca agtggatacg 4620
tcttttaaca agttgtatga gctgtgtaag aactctgaag ataatcaagg tatggtaagg 4680
atggatgatt ggctagctca actttccttt aacgtcatcg gtaggatcgt ttgcggattc 4740
cagtctgacc caaagacggg tgcaccttca agggtagaac agtttaagga agtcataaat 4800
gaggcgtcat attttatgtc aacaagtcca gtctccgata acgtaccaat gttgggatgg 4860
atcgaccaat tgaccggtct gacgaggaac atgaagcatt gtgggaagaa gcttgactta 4920
gtagtggagt caattatcaa ggaccatagg caaaagagac gtttttcacg tacaaaaggt 4980

-continued

```
ggcgatgaga aggatgacga acaggacgac tttattgata tttgcttgag catcatggag  5040
cagccacagt tgcccgggaa caattctccc cctcaaattc cgatcaaatc tatcgtgcta  5100
gacatgattg ggggtggtac cgacactacg aaacttacaa ccatatggac cctatcactt  5160
ttgttgaaca atcctcacgt gttagataaa gctaaacaag aggtcgacgc tcactttcgt  5220
aaaaagagaa gatcaacaga tgacgcagca gcggcagtcg ttgattttga cgacataaga  5280
aatttagtat acatccaagc catcattaaa gaaagtatga ggctttatcc agccagcccg  5340
gtggttgagc gtctttccgg cgaggattgc gttgttggag gttttcacgt gcctgctggt  5400
acgagactat gggctaacgt ttggaagatg caaagagatc ccaaagtttg ggacgatcct  5460
ctagtattca gacctgaaag gtttttgagc gacgagcaaa agatggtaga cgttcgtggc  5520
caaaactatg aacttctgcc attcggcgca ggaagaagaa tctgtccagg cgtttccttt  5580
agtcttgacc ttatgcaact tgtcctaacc aggttaatcc tagagttcga aatgaagtcc  5640
ccgtccggca aggtagatat gaccgcaact ccaggactaa tgtcttacaa ggtggttcca  5700
ttggacatat tgctgactca ccgtcgtatc aagtcatgcg ttcaattggc gtcttctgaa  5760
cgtgattaag cgaatttctt atgatttatg atttttatta ttaaataagt tataaaaaaa  5820
ataagtgtat acaaatttta aagtgactct taggttttaa aacgaaaatt cttattcttg  5880
agtaactctt tcctgtaggt caggttgctt tctcaggtac atagcttcaa aatgtttcta  5940
ctcctttttt actcttccag attttctcgg actccgcgca tcgccgtacc acttcaaaac  6000
acccaagcac agcatactaa atttcccctc tttcttcctc tagggtgtcg ttaattaccc  6060
gtactaaagg tttggaaaag aaaaaagaga ccgcctcgtt tctttttctt cgtcgaaaaa  6120
ggcaataaaa atttttatca cgtttctttt tcttgaaaat ttttttttt gattttttc  6180
tctttcgatg acctcccatt gatatttaag ttaataaacg gtcttcaatt tctcaagttt  6240
cagtttcatt tttcttgttc tattacaact ttttttactt cttgctcatt agaaagaaag  6300
catagcaatc taatctaagt tttaattaca aaatggaaag ttctggggtg cctgtgatca  6360
cattgtcctc aggtaaagta atgcccgtac tgggcatggg aaccttcgaa aaggtgggta  6420
aggggtctga acgtgagcgt ttagccattc ttaaagcgat cgaagttggt taccgttact  6480
ttgataccgc agcggcatat gaaacggaag aagttctagg ggaagccatt gctgaagctt  6540
tacaattggg tctgatagag agccgtgacg agctgttcat cagctcaatg ctttggtgca  6600
ccgacgcaca tccagaccgt gtgctacttg ctctgcaaaa cagtctgaga aatctaaaac  6660
ttgaatatct agacctatat atgttgccgt ttcctgccag ccttaagccg ggcaaaatta  6720
cgatggatat tcctgaggag gatatttgcc gtatggatta tcgttcagtc tggagcgcca  6780
tggaagagtg tcaaaactta ggatttacta aaagtattgg tgtaagcaac ttttcttgca  6840
agaaattaca agaattaatg gccactgcaa atatcccgcc cgcggtaaat caagtagaga  6900
tgtcaccagc tttccaacag aaaaaactga gggaatattg taacgcaaac aacatattgg  6960
tatccgcagt aagcattctg ggatcaaacg ggacgccctg gggtagtaat gctgttcttg  7020
gaagcgaagt tttgaaacag atcgcgatgg cgaaaggcaa aagcgttgcg caagtcagta  7080
tgaggtgggt ctatgagcag ggcgcgtctt tagtagtcaa gagtttctct gaagaacgtt  7140
taagagaaaa cctgaatatt tttgactggg agcttacgaa agaagacaat gagaagatag  7200
gcgaaatccc gcaatgtaga atccttactg cgtacttcct tgtctccccg aacggcccgt  7260
ttaaatctca ggaagagctt tgggatgaca aggcataaac aggccccttt tcctttgtcg  7320
atatcatgta attagttatg tcacgcttac attcacgccc tcctcccaca tccgctctaa  7380
ccgaaaagga aggagttaga caacctgaag tctaggtccc tatttatttt ttttaatagt  7440
tatgttagta ttaagaacgt tatttatatt tcaaattttt cttttttttc tgtacaaacg  7500
cgtgtacgca tgtaacatta tactgaaaac cttgcttgag aaggttttgg gacgctcgaa  7560
ggctttaatt tgtaatcatt atcactttac gggtcctttc cggtgatccg acaggttacg  7620
gggcggcgac ctcgcgggtt ttcgctattt atgaaaattt tccggtttaa ggcgtttccg  7680
ttcttcttcg tcataactta atgtttttat ttaaaatacc tcgcgagtgg caacactgaa  7740
aatacccatg gagcggcgta accgtcgcac aggatctagg tgaagatcct ttttgataat  7800
ctcatgacca aaatccctta acgtgagttt tcgttccact gagcgtcaga ccccgtagaa  7860
aagatcaaag gatcttcttg agatcctttt tttctgcgcg taatctgctg cttgcaaaca  7920
aaaaaaccac cgctaccagc ggtggtttgt ttgccggatc aagagctacc aactcttttt  7980
ccgaaggtaa ctggcttcag cagagcgcag ataccaaata ctgtccttct agtgtagccg  8040
tagttaggcc accacttcaa gaactctgta gcaccgccta catacctcgc tctgctaatc  8100
ctgttaccag tggctgctgc cagtggcgat aagtcgtgtc ttaccgggtt ggactcaaga  8160
cgatagttac cggataaggc gcagcggtcg ggctgaacgg ggggttcgtg cacacagccc  8220
agcttggagc gaacgaccta caccgaactg agatacctac agcgtgagct atgagaaagc  8280
gccacgcttc ccgaagggag aaaggcggac aggtatccgg taagcggcag ggtcggaaca  8340
ggagagcgca cgagggagct tccaggggga aacgcctggt atctttatag tcctgtcggg  8400
tttcgccacc tctgacttga gcgtcgattt ttgtgatgct cgtcaggggg gcggagccta  8460
tggaaaaacg ccagcaacgc ggcagtggaa cgtgcattat gaattagtta cgctagggat  8520
aacagggtaa tatagaaccc gaacgaccga gcgcagcggc ggccgcgctg ataccgccgc  8580
```

```
SEQ ID NO: 28          moltype = DNA  length = 8456
FEATURE                Location/Qualifiers
misc_feature           1..8456
                       note = Description of Artificial Sequence: Synthetic
                        polynucleotide
source                 1..8456
                       mol_type = other DNA
                       organism = synthetic construct
SEQUENCE: 28
cctcgccgca gttaattaaa gtcagtgagc gaggaagcgc gtaactataa cggtcctaag  60
gtagcgaatc ctgatgcggt attttctcct tacgcatctg tgcggtattt cacaccgcat  120
agatcggcaa gtgcacaaac aatacttaaa taaatactac tcagtaataa cctatttctt  180
agcatttttg acgaaatttg ctattttgtt agagtctttt acaccatttg tctccacacc  240
tccgcttaca tcaacaccaa taacgccatt taatctaagc gcatcaccaa cattttctgg  300
cgtcagtcca ccagctaaca taaaatgtaa gctttcgggg ctctcttgcc ttccaaccca  360
gtcagaaatc gagttccaat ccaaaagttc acctgtccca cctgcttctg aatcaaacaa  420
gggaataaac gaatgaggtt tctgtgaagc tgcactgagt agtatgttgc agtcttttgg  480
aaatacgagt cttttaataa ctggcaaacc gaggaactct tggtattctt gccacgactc  540
```

-continued atctccatgc agttggacga tatcaatgcc gtaatcattg accagagcca aaacatcctc 600
cttaagttga ttacgaaaca cgccaaccaa gtatttcgga gtgcctgaac tatttttata 660
tgcttttaca agacttgaaa ttttccttgc aataaccggg tcaattgttc tctttctatt 720
gggcacacat ataataccca gcaagtcagc atcggaatct agagcacatt ctgcggcctc 780
tgtgctctgc aagccgcaaa ctttcaccaa tggaccagaa ctacctgtga aattaataac 840
agacatactc caagctgcct ttgtgtgctt aatcacgtat actcacgtgc tcaatagtca 900
ccaatgccct ccctcttggc cctctccttt tcttttttcg accgaattaa ttcttaatcg 960
gcaaaaaaag aaaagctccg gatcaagatt gtacgtaagg tgacaagcta tttttcaata 1020
aagaatatct tccactactg ccatctggcg tcataactgc aaagtacaca tatattacga 1080
tgctgttcta ttaaatgctt cctatattat atatatagta atgtcgtgat ctatggtgca 1140
ctctcagtac aatctgctct gatgccgcat agttaagcca gccccgacac ccgccaacac 1200
ccgctgacgc gccctgacgg gcttgtctgc tcccggcatc cgcttacaga caagctgtga 1260
ccgtctccgg gagctgcatg tgtcagaggt tttcaccgtc atcaccgaaa cgcgcgagac 1320
gaaagggcct cgtgatacgc ctatttttat aggttaatgt catgataata atggtttctt 1380
agacggatcg cttgcctgta acttacacgc gcctcgtatc ttttaatgat ggaataattt 1440
gggaatttac tctgtgttta tttattttta tgttttgtat ttggatttta gaaagtaaat 1500
aaagaaggta gaagagttac ggaatgaaga aaaaaaaata aacaaaggtt taaaaaattt 1560
caacaaaaag cgtactttac atatatattt attagacaag aaaagcagat taaatagata 1620
tacattcgat taacgataag taaaatgtaa aatcacagga ttttcgtgtg tggtcttcta 1680
cacagacaag gtgaaacaat tcggcattaa tacctgagag caggaagagc aagataaaag 1740
gtagtatttg ttggcgatcc ccctagagtc ttttacatct tcggaaaaca aaaactattt 1800
tttctttaat ttcttttttt actttctatt tttaatttat atatttatat taaaaaattt 1860
aaattataat tatttttata gcacgtgatg aaaaggaccc aggtggcact tttcggggaa 1920
atgtgcgcgg aacccctatt tgtttatttt tctaaataca ttcaaatatg tatccgctca 1980
tgagacaata accctgataa atgcttcaat aatattgaaa aaggaagagt atgagtattc 2040
aacatttccg tgtcgccctt attccctttt ttgcggcatt ttgccttcct gtttttgctc 2100
acccagaaac gctggtgaaa gtaaaagatg ctgaagatca gttgggacgc gtagtctaga 2160
ccagccagga cagaaatgcc tcgacttcgc tgctacccaa ggttgccggg tgacgcacac 2220
cgtggaaacg gatgaaggca cgaacccagt ggacataagc ctgttcggtt cgtaagctgt 2280
aatgcaagta gcgtatgcgc tcacgcaact ggtccagaac cttgaccgaa cgcagcggtg 2340
gtaacggcgc agtggcggtt ttcatggctt gttatgactg tttttttggg gtacagtcta 2400
tgcctcgggc atccaagcag caagcgcgtt acgccgtggg tcgatgtttg atgttatgga 2460
gcagcaacga tgttacgcag cagggcagtc gccctaaaac aaagttaaac attatgaggg 2520
aagcggtgat cgccgaagta tcgactcaac tatcagaggt agttggcgcc atcgagcgcc 2580
atctcgaacc gacgttgctg gccgtacatt tgtacggctc cgcagtggat ggcggcctga 2640
agccacacag tgatattgat ttgctggtta cggtgaccgt aaggcttgat gaaacaacgc 2700
ggcgagcttt gatcaacgac cttttggaaa cttcggcttc ccctggagag agcgagattc 2760
tccgcgctgt agaagtcacc attgttgtgc acgacgacat cattccgtgg cgttatccag 2820
ctaagcgcga actgcaattt ggagaatggc agcgcaatga cattcttgca ggtatcttcg 2880
agccagccac gatcgacatt gatctggcta tcttgctgac aaaagcaaga gaacatagcg 2940
ttgccttggt aggtccagcg gcggaggaac tctttgatcc ggttcctgaa caggatctat 3000
ttgaggcgct aaatgaaacc ttaacgctat ggaactcgcc gcccgactgg gctggcgatg 3060
agcgaaatgt agtgcttacg ttgtcccgca tttggtacag cgcagtaacc ggcaaaatcg 3120
cgccgaagga tgtcgctgcc ggctgggcaa tggagcgcct gccggcccag tatcagcccg 3180
tcatacttga agctagacag gcttatcttg gacaagaaga agatcgcttg gcctcgcgcg 3240
cagatcagtt ggaagaattt gtccactacg tgaaaggcga gatcaccaag gtagtcggca 3300
aataaccctc gagcattcaa ggcgccttga ttatttgacg tggtttgatg gcctccacgc 3360
acgttgtgat atgtagatga gagcgttggt tggtggatca agcccacgcg taggcaatcc 3420
tcgagcagat ccgccaggcg tgtatatata gcgtggatgg ccaggcaact ttagtgctga 3480
cacatacagg catatatata tgtgtgcgac gacacatgat catatggcat gcatgtgctc 3540
tgtatgtata taaaactctt gttttcttct tttctctaaa tattctttcc ttatacatta 3600
ggacctttgc agcataaatt actatacttc tatagacaca caaacacaaa tacacacact 3660
aaattaataa tggaacttca gtacttctcc tattttcaac ccacttcatc tgtcgtagcc 3720
ctactactag cactagtgag tattttattt agcgtagttg ttttgaggaa gactttcagt 3780
aacaattact ccagccccgc gtcaagtacg gaaaccgctg tgctgtgtca tcagaggcaa 3840
cagagttgcg ccctacctat cagcggcctt cttcacgtgt tcatgaataa gaacggcctg 3900
attcatgtca ccttgggaaa tatggctgac aaatatggcc ctatcttcag ttttccgaca 3960
ggcagccacc gtactttagt agtcagttcc tgggaaatgg tgaaagagtg tttcaccggt 4020
aataacgaca cggcattctc caacagacca atccctttgg cttttcaaac catattctac 4080
gcctgtggcg gcattgattc ttacggttta agtagtgtcc cgtatggtaa atactggagg 4140
gagttgagaa aggtgtgtgt tcacaacctg ctgagtaatc agcaattgct gaagttcaga 4200
catcttataa tctcccaagt ggatacgtct tttaacaagt tgtatgagct gtgtaagaac 4260
tctgaagata atcaaggtat ggtaaggatg gatgattggc tagctcaact ttcctttaac 4320
gtcatcggta ggatcgtttg cggattccag tctgacccaa agacgggtgc accttcaagg 4380
gtagaacagt ttaaggaagt cataaatgag gcgtcatatt ttatgtcaac aagtccagtc 4440
tccgataacg taccaatgtt gggatggatc gaccaattga ccggtctgac gaggaacatg 4500
aagcattgtg ggaagaagct tgacttagta gtggagtcaa ttatcaagga ccataggcaa 4560
aagagacgtt tttcacgtac aaaaggtggc gatgagaagg atgacgaaca ggacgacttt 4620
attgatattt gcttgagcat catggagcag ccacagttgc ccgggaacaa ttctccccct 4680
caaattccga tcaaatctat cgtgctagac atgattgggg gtggtaccga cactacgaaa 4740
cttacaacca tatggaccct atcacttttg ttgaacaatc ctcacgtgtt agataaagct 4800
aaacaagagg tcgacgctca ctttcgtaaa aagagaagat caacagatga cgcagcagcg 4860
gcagtcgttg attttgacga cataagaaat ttagtataca tccaagccat cattaaagaa 4920
agtatgaggc tttatccagc cagcccggtg gttgagcgtc tttccggcga ggattgcgtt 4980
gttggaggtt ttcacgtgcc tgctggtacg agactatggg ctaacgtttg gaagatgcaa 5040
agagatccca aagtttggga cgatcctcta gtattcagac ctgaaaggtt tttgagcgac 5100
gagcaaaaga tggtagacgt tcgtggccaa aactatgaac ttctgccatt cggcgcagga 5160
agaagaatct gtccaggcgt ttcctttagt cttgacctta tgcaacttgt cctaaccagg 5220
ttaatcctag agttcgaaat gaagtccccg tccggcaagg tagatatgac cgcaactcca 5280

```
ggactaatgt cttacaaggt ggttccattg gacatattgc tgactcaccg tcgtatcaag  5340
tcatgcgttc aattggcgtc ttctgaacgt gattaagcga atttcttatg atttatgatt  5400
tttattatta aataagttat aaaaaaaata agtgtataca aattttaaag tgactcttag  5460
gttttaaaac gaaaattctt attcttgagt aactctttcc tgtaggtcag gttgctttct  5520
caggtattca gttcgagttt atcattatca atactgccat ttcaaagaat acgtaaataa  5580
ttaatagtag tgattttcct aactttattt agtcaaaaaa ttagcctttt aattctgctg  5640
taacccgtac atgcccaaaa tagggggcgg gttacacaga atatataaca tcgtaggtgt  5700
ctgggtgaac agtttattcc tggcatccac taaatataat ggagcccgct ttttaagctg  5760
gcatccagaa aaaaaaagaa tcccagcacc aaaatattgt tttcttcacc aaccatcagt  5820
tcataggtcc attctcttag cgcaactaca gagaacaggg gcacaaacag gcaaaaaacg  5880
ggcacaacct caatggagtg atgcaacctg cctggagtaa atgatgacac aaggcaattg  5940
acccacgcat gtatctatct cattttctta caccttctat taccttctgc tctctctgat  6000
ttggaaaaag ctgaaaaaaa aggttgaaac cagttccctg aaattattcc cctacttgac  6060
taataagtat ataaagacgg taggtattga ttgtaattct gtaaatctat ttcttaaact  6120
tcttaaattc tacttttata gttagtcttt tttttagttt taaaacacca agaacttagt  6180
ttcgaataaa cacacataaa caaacaaaat ggaaagttct ggggtgcctg tgatcacatt  6240
gtcctcaggt aaagtaatgc ccgtactggg catgggaacc ttcgaaaagg tgggtaaggg  6300
gtctgaacgt gagcgtttag ccattcttaa agcgatcgaa gttggttacc gttactttga  6360
taccgcagcg gcatatgaaa cggaagaagt tctaggggaa gccattgctg aagctttaca  6420
attgggtctg atagagagcc gtgacgagct gttcatcagc tcaatgcttt ggtgcaccga  6480
cgcacatcca gaccgtgtgc tacttgctct gcaaaacagt ctgagaaatc taaaacttga  6540
atatctagac ctatatatgt tgccgtttcc tgccagcctt aagccgggca aaattacgat  6600
ggatattcct gaggaggata tttgccgtat ggattatcgt tcagtctgga gcgccatgga  6660
agagtgtcaa aacttaggat ttactaaaag tattggtgta agcaactttt cttgcaagaa  6720
attacaagaa ttaatggcca ctgcaaatat cccgcccgcg gtaaatcaag tagagatgtc  6780
accagctttc caacagaaaa aactgaggga atattgtaac gcaaacaaca tattggtatc  6840
cgcagtaagc attctgggat caaacgggac gccctggggt agtaatgctg ttcttggaag  6900
cgaagttttg aaacagatcg cgatggcgaa aggcaaaagc gttgcgcaag tcagtatgag  6960
gtgggtctat gagcagggcg cgtctttagt agtcaagagt ttctctgaag aacgtttaag  7020
agaaaacctg aatatttttg actgggagct tacgaaagaa gacaatgaga agataggcga  7080
aatcccgcaa tgtagaatcc ttactgcgta cttccttgtc tccccgaacg gcccgtttaa  7140
atctcaggaa gagctttggg atgacaaggc ataaacaggc cccttttcct ttgtcgatat  7200
catgtaatta gttatgtcac gcttacattc acgccctcct cccacatccg ctctaaccga  7260
aaaggaagga gttagacaac ctgaagtcta ggtccctatt tattttttt aatagttatg  7320
ttagtattaa gaacgttatt tatatttcaa atttttcttt tttttctgta caaacgcgtg  7380
tacgcatgta acattatact gaaaaccttg cttgagaagg ttttgggacg ctcgaaggct  7440
ttaatttgta atcattatca ctttacgggt cctttccggt gatccgacag gttacggggc  7500
ggcgacctcg cgggttttcg ctatttatga aaattttccg gtttaaggcg tttccgttct  7560
tcttcgtcat aacttaatgt tttatttaa aatacctcgc gagtggcaac actgaaaata  7620
cccatggagc ggcgtaaccg tcgcacagga tctaggtgaa gatccttttt gataatctca  7680
tgaccaaaat cccttaacgt gagttttcgt tccactgagc gtcagacccc gtagaaaaga  7740
tcaaaggatc ttcttgagat cctttttttc tgcgcgtaat ctgctgcttg caaacaaaaa  7800
aaccaccgct accagcggtg gtttgtttgc cggatcaaga gctaccaact ctttttccga  7860
aggtaactgg cttcagcaga gcgcagatac caaatactgt ccttctagtg tagccgtagt  7920
taggccacca cttcaagaac tctgtagcac cgcctacata cctcgctctg ctaatcctgt  7980
taccagtggc tgctgccagt ggcgataagt cgtgtcttac cgggttggac tcaagacgat  8040
agttaccgga taaggcgcag cggtcgggct gaacgggggg ttcgtgcaca cagcccagct  8100
tggagcgaac gacctacacc gaactgagat acctacagcg tgagctatga gaaagcgcca  8160
cgcttcccga agggagaaag gcggacaggt atccggtaag cggcagggtc ggaacaggag  8220
agcgcacgag ggagcttcca gggggaaacg cctggtatct ttatagtcct gtcgggtttc  8280
gccacctctg acttgagcgt cgatttttgt gatgctcgtc aggggggcgg agcctatgga  8340
aaaacgccag caacgcggca gtggaacgtg cattatgaat tagttacgct agggataaca  8400
gggtaatata gaacccgaac gaccgagcgc agcggcggcc gcgctgatac cgccgc      8456

SEQ ID NO: 29          moltype = DNA  length = 8456
FEATURE                Location/Qualifiers
misc_feature           1..8456
                       note = Description of Artificial Sequence: Synthetic
                        polynucleotide
source                 1..8456
                       mol_type = other DNA
                       organism = synthetic construct
SEQUENCE: 29
cctcgccgca gttaattaaa gtcagtgagc gaggaagcgc gtaactataa cggtcctaag  60
gtagcgaatc ctgatgcggt attttctcct tacgcatctg tgcggtattt cacaccgcat  120
agatcggcaa gtgcacaaac aatacttaaa taaatactac tcagtaataa cctatttctt  180
agcatttttg acgaaatttg ctattttgtt agagtctttt acaccatttg tctccacacc  240
tccgcttaca tcaacaccaa taacgccatt taatctaagc gcatcaccaa cattttctgg  300
cgtcagtcca ccagctaaca taaaatgtaa gctttcgggg ctctcttgcc ttccaaccca  360
gtcagaaatc gagttccaat ccaaaagttc acctgtccca cctgcttctg aatcaaacaa  420
gggaataaac gaatgaggtt tctgtgaagc tgcactgagt agtatgttgc agtcttttgg  480
aaatacgagt cttttaataa ctggcaaacc gaggaactct tggtattctt gccacgactc  540
atctccatgc agttggacga tatcaatgcc gtaatcattg accagagcca aaacatcctc  600
cttaagttga ttacgaaaca cgccaaccaa gtatttcgga gtgcctgaac tatttttata  660
tgcttttaca agacttgaaa ttttccttgc aataaccggg tcaattgttc tctttctatt  720
gggcacacat ataataccca gcaagtcagc atcggaatct agagcacatt ctgcggcctc  780
tgtgctctgc aagccgcaaa ctttcaccaa tggaccagaa ctacctgtga aattaataac  840
agacatactc caagctgcct ttgtgtgctt aatcacgtat actcacgtgc tcaatagtca  900
ccaatgccct ccctcttggc cctctccttt tctttttcg accgaattaa ttcttaatcg  960
```

-continued

```
gcaaaaaaag aaaagctccg gatcaagatt gtacgtaagg tgacaagcta tttttcaata  1020
aagaatatct tccactactg ccatctggcg tcataactgc aaagtacaca tatattacga  1080
tgctgttcta ttaaatgctt cctatattat atatatagta atgtcgtgat ctatggtgca  1140
ctctcagtac aatctgctct gatgccgcat agttaagcca gccccgacac ccgccaacac  1200
ccgctgacgc gccctgacgg gcttgtctgc tcccggcatc cgcttacaga caagctgtga  1260
ccgtctccgg gagctgcatg tgtcagaggt tttcaccgtc atcaccgaaa cgcgcgagac  1320
gaaagggcct cgtgatacgc ctatttttat aggttaatgt catgataata atggtttctt  1380
agacggatcg cttgcctgta acttacacgc gcctcgtatc ttttaatgat ggaataattt  1440
gggaatttac tctgtgttta tttatttta tgttttgtat ttggatttta gaaagtaaat  1500
aaagaaggta gaagagttac ggaatgaaga aaaaaaaata aacaaaggtt taaaaaattt  1560
caacaaaaag cgtactttac atatatattt attagacaag aaaagcagat taaatagata  1620
tacattcgat taacgataag taaaatgtaa aatcacagga ttttcgtgtg tggtcttcta  1680
cacagacaag gtgaaacaat tcggcattaa tacctgagag caggaagagc aagataaaag  1740
gtagtatttg ttggcgatcc ccctagagtc ttttacatct tcggaaaaca aaaactattt  1800
tttctttaat ttcttttttt actttctatt tttaatttat atatttatat taaaaaattt  1860
aaattataat tatttttata gcacgtgatg aaaaggaccc aggtggcact tttcggggaa  1920
atgtgcgcgg aacccctatt tgtttatttt tctaaataca ttcaaatatg tatccgctca  1980
tgagacaata accctgataa atgcttcaat aatattgaaa aaggaagagt atgagtattc  2040
aacatttccg tgtcgccctt attccctttt ttgcggcatt ttgccttcct gtttttgctc  2100
acccagaaac gctggtgaaa gtaaaagatg ctgaagatca gttgggacgc gtagtctaga  2160
ccagccagga cagaaatgcc tcgacttcgc tgctacccaa ggttgccggg tgacgcacac  2220
cgtggaaacg gatgaaggca cgaacccagt ggacataagc ctgttcggtt cgtaagctgt  2280
aatgcaagta gcgtatgcgc tcacgcaact ggtccagaac cttgaccgaa cgcagcggtg  2340
gtaacggcgc agtggcggtt ttcatggctt gttatgactg tttttttggg gtacagtcta  2400
tgcctcgggc atccaagcag caagcgcgtt acgccgtggg tcgatgtttg atgttatgga  2460
gcagcaacga tgttacgcag cagggcagtc gccctaaaac aaagttaaac attatgaggg  2520
aagcggtgat cgccgaagta tcgactcaac tatcagaggt agttggcgcc atcgagcgcc  2580
atctcgaacc gacgttgctg gccgtacatt tgtacggctc cgcagtggat ggcggcctga  2640
agccacacag tgatattgat ttgctggtta cggtgaccgt aaggcttgat gaaacaacgc  2700
ggcgagcttt gatcaacgac cttttggaaa cttcggcttc ccctggagag agcgagattc  2760
tccgcgctgt agaagtcacc attgttgtgc acgacgacat cattccgtgg cgttatccag  2820
ctaagcgcga actgcaattt ggagaatggc agcgcaatga cattcttgca ggtatcttcg  2880
agccagccac gatcgacatt gatctggcta tcttgctgac aaaagcaaga gaacatagcg  2940
ttgccttggt aggtccagcg gcggaggaac tctttgatcc ggttcctgaa caggatctat  3000
ttgaggcgct aaatgaaacc ttaacgctat ggaactcgcc gcccgactgg gctggcgatg  3060
agcgaaatgt agtgcttacg ttgtcccgca tttggtacag cgcagtaacc ggcaaaatcg  3120
cgccgaagga tgtcgctgcc ggctgggcaa tggagcgcct gccggcccag tatcagcccg  3180
tcatacttga agctagacag gcttatcttg gacaagaaga agatcgcttg gcctcgcgcg  3240
cagatcagtt ggaagaattt gtccactacg tgaaaggcga gatcaccaag gtagtcggca  3300
aataaccctc gagcattcaa ggcgccttga ttatttgacg tggtttgatg gcctccacgc  3360
acgttgtgat atgtagatga ttcagttcga gtttatcatt atcaatactg ccatttcaaa  3420
gaatacgtaa ataattaata gtagtgattt tcctaacttt atttagtcaa aaaattagcc  3480
ttttaattct gctgtaaccc gtacatgccc aaaatagggg gcgggttaca cagaatatat  3540
aacatcgtag gtgtctgggt gaacagttta ttcctggcat ccactaaata taatggagcc  3600
cgctttttaa gctggcatcc agaaaaaaaa agaatcccag caccaaaata ttgttttctt  3660
caccaaccat cagttcatag gtccattctc ttagcgcaac tacagagaac aggggcacaa  3720
acaggcaaaa aacgggcaca acctcaatgg agtgatgcaa cctgcctgga gtaaatgatg  3780
acacaaggca attgacccac gcatgtatct atctcatttt cttacacctt ctattacctt  3840
ctgctctctc tgatttggaa aaagctgaaa aaaaaggttg aaaccagttc cctgaaatta  3900
ttcccctact tgactaataa gtatataaag acggtaggta ttgattgtaa ttctgtaaat  3960
ctatttctta aacttcttaa attctacttt tatagttagt cttttttttta gttttaaaac  4020
accaagaact tagtttcgaa taaacacaca taaacaaaca aaatggaact tcagtacttc  4080
tcctattttc aacccacttc atctgtcgta gccctactac tagcactagt gagtatttta  4140
tttagcgtag ttgttttgag gaagactttc agtaacaatt actccagccc cgcgtcaagt  4200
acggaaaccg ctgtgctgtg tcatcagagg caacagagtt gcgccctacc tatcagcggc  4260
cttcttcacg tgttcatgaa taagaacggc ctgattcatg tcaccttggg aaatatggct  4320
gacaaatatg gccctatctt cagttttccg acaggcagcc accgtacttt agtagtcagt  4380
tcctgggaaa tggtgaaaga gtgtttcacc ggtaataacg acacggcatt ctccaacaga  4440
ccaatcccctt tggcttttca aaccatattc tacgcctgtg gcggcattga ttcttacggt  4500
ttaagtagtg tcccgtatgg taaatactgg agggagttga gaaaggtgtg tgttcacaac  4560
ctgctgagta atcagcaatt gctgaagttc agacatctta taatctccca agtggatacg  4620
tcttttaaca agttgtatga gctgtgtaag aactctgaag ataatcaagg tatggtaagg  4680
atggatgatt ggctagctca actttccttt aacgtcatcg gtaggatcgt ttgcggattc  4740
cagtctgacc caaagacggg tgcaccttca agggtagaac agtttaagga agtcataaat  4800
gaggcgtcat attttatgtc aacaagtcca gtctccgata acgtaccaat gttgggatgg  4860
atcgaccaat tgaccggtct gacgaggaac atgaagcatt gtgggaagaa gcttgactta  4920
gtagtggagt caattatcaa ggaccatagg caaaagagac gtttttcacg tacaaaaggt  4980
ggcgatgaga aggatgacga acaggacgac tttattgata tttgcttgag catcatggag  5040
cagccacagt tgcccgggaa caattctccc cctcaaattc cgatcaaatc tatcgtgcta  5100
gacatgattg ggggtggtac cgacactacg aaacttacaa ccatatggac cctatcactt  5160
ttgttgaaca atcctcacgt gttagataaa gctaaacaag aggtcgacgc tcactttcgt  5220
aaaaagagaa gatcaacaga tgacgcagca gcggcagtcg ttgattttga cgacataaga  5280
aatttagtat acatccaagc catcattaaa gaaagtatga ggctttatcc agccagcccg  5340
gtggttgagc gtctttccgg cgaggattgc gttgttggag gttttcacgt gcctgctggt  5400
acgagactat gggctaacgt ttggaagatg caaagagatc ccaaagtttg ggacgatcct  5460
ctagtattca gacctgaaag gtttttgagc gacgagcaaa agatggtaga cgttcgtggc  5520
caaaactatg aacttctgcc attcggcgca ggaagaagaa tctgtccagg cgtttccttt  5580
agtcttgacc ttatgcaact tgtcctaacc aggttaatcc tagagttcga aatgaagtcc  5640
ccgtccggca aggtagatat gaccgcaact ccaggactaa tgtcttacaa ggtggttcca  5700
```

-continued

```
ttggacatat tgctgactca ccgtcgtatc aagtcatgcg ttcaattggc gtcttctgaa  5760
cgtgattaag cgaatttctt atgatttatg atttttatta ttaaataagt tataaaaaaa  5820
ataagtgtat acaaatttta aagtgactct taggttttaa aacgaaaatt cttattcttg  5880
agtaactctt tcctgtaggt caggttgctt tctcaggtag agcgttggtt ggtggatcaa  5940
gcccacgcgt aggcaatcct cgagcagatc cgccaggcgt gtatatatag cgtggatggc  6000
caggcaactt tagtgctgac acatacaggc atatatatat gtgtgcgaca acacatgatc  6060
atatggcatg catgtgctct gtatgtatat aaaactcttg ttttcttctt ttctctaaat  6120
attctttcct tatacattag gacctttgca gcataaatta ctatacttct atagacacac  6180
aaacacaaat acacacacta aattaataat ggaaagttct ggggtgcctg tgatcacatt  6240
gtcctcaggt aaagtaatgc ccgtactggg catgggaacc ttcgaaaagg tgggtaaggg  6300
gtctgaacgt gagcgtttag ccattcttaa agcgatcgaa gttggttacc gttactttga  6360
taccgcagcg gcatatgaaa cggaagaagt tctaggggaa gccattgctg aagctttaca  6420
attgggtctg atagagagcc gtgacgagct gttcatcagc tcaatgcttt ggtgcaccga  6480
cgcacatcca gaccgtgtgc tacttgctct gcaaaacagt ctgagaaatc taaaacttga  6540
atatctagac ctatatatgt tgccgtttcc tgccagcctt aagccgggca aaattacgat  6600
ggatattcct gaggaggata tttgccgtat ggattatcgt tcagtctgga gcgccatgga  6660
agagtgtcaa aacttaggat ttactaaaag tattggtgta agcaactttt cttgcaagaa  6720
attacaagaa ttaatggcca ctgcaaatat cccgcccgcg gtaaatcaag tagagatgtc  6780
accagctttc caacagaaaa aactgaggga atattgtaac gcaaacaaca tattggtatc  6840
cgcagtaagc attctgggat caaacgggac gccctggggt agtaatgctg ttcttggaag  6900
cgaagttttg aaacagatcg cgatggcgaa aggcaaaagc gttgcgcaag tcagtatgag  6960
gtgggtctat gagcagggcg cgtctttagt agtcaagagt ttctctgaag aacgtttaag  7020
agaaaacctg aatattttg actgggagct tacgaaagaa gacaatgaga agataggcga  7080
aatcccgcaa tgtagaatcc ttactgcgta cttccttgtc tccccgaacg gcccgtttaa  7140
atctcaggaa gagctttggg atgacaaggc ataaacaggc cccttttcct ttgtcgatat  7200
catgtaatta gttatgtcac gcttacattc acgccctcct cccacatccg ctctaaccga  7260
aaaggaagga gttagacaac ctgaagtcta ggtccctatt tattttttt aatagttatg  7320
ttagtattaa gaacgttatt tatatttcaa atttttcttt tttttctgta caaacgcgtg  7380
tacgcatgta acattatact gaaaaccttg cttgagaagg ttttgggacg ctcgaaggct  7440
ttaatttgta atcattatca ctttacgggt cctttccggt gatccgacag gttacggggc  7500
ggcgacctcg cgggttttcg ctatttatga aaattttccg gtttaaggcg tttccgttct  7560
tcttcgtcat aacttaatgt ttttatttaa aatacctcgc gagtggcaac actgaaaata  7620
cccatggagc ggcgtaaccg tcgcacagga tctaggtgaa gatccttttt gataatctca  7680
tgaccaaaat cccttaacgt gagttttcgt tccactgagc gtcagacccc gtagaaaaga  7740
tcaaaggatc ttcttgagat ccttttttc tgcgcgtaat ctgctgcttg caaacaaaaa  7800
aaccaccgct accagcggtg gtttgtttgc cggatcaaga gctaccaact ctttttccga  7860
aggtaactgg cttcagcaga gcgcagatac caaatactgt ccttctagtg tagccgtagt  7920
taggccacca cttcaagaac tctgtagcac cgcctacata cctcgctctg ctaatcctgt  7980
taccagtggc tgctgccagt ggcgataagt cgtgtcttac cgggttggac tcaagacgat  8040
agttaccgga taaggcgcag cggtcgggct gaacgggggg ttcgtgcaca cagcccagct  8100
tggagcgaac gacctacacc gaactgagat acctacagcg tgagctatga gaaagcgcca  8160
cgcttcccga agggagaaag gcggacaggt atccggtaag cggcagggtc ggaacaggag  8220
agcgcacgag ggagcttcca gggggaaacg cctggtatct ttatagtcct gtcgggtttc  8280
gccacctctg acttgagcgt cgatttttgt gatgctcgtc aggggggcgg agcctatgga  8340
aaaacgccag caacgcggca gtggaacgtg cattatgaat tagttacgct agggataaca  8400
gggtaatata gaacccgaac gaccgagcgc agcggcggcc gcgctgatac cgccgc      8456
```

```
SEQ ID NO: 30          moltype = AA  length = 153
FEATURE                Location/Qualifiers
source                 1..153
                       mol_type = protein
                       organism = Papaver bracteatum
SEQUENCE: 30
MAPRGVSGLV GKLSTELDVN CDAEKYYNMY KNGEDVQKAV PHLCMDVKVI SGDATRSGCI  60
KEWNVNIDGK TIRSVEETTH NDETKTLRHR VFEGDMMKDY KKFDTIMEVN PKPDGNGCVV  120
TRSIEYEKVN ENSPTPFDYL QFGHQAMEDM NKY                             153

SEQ ID NO: 31          moltype = AA  length = 144
FEATURE                Location/Qualifiers
source                 1..144
                       mol_type = protein
                       note = subspecies: setigerum
                       organism = Papaver somniferum
SEQUENCE: 31
MLVGKLSTEL EVDCDAEKYY NMYKHGEDVK KALCVDVKVI SGDPTRSGCI KEWNVNIDGK  60
TIRSVEETTH NDETKTLRHR VFEGDMMKDF KKFDTIMVVN PKPDGNGCVV TRSIEYEKTN  120
ENSPTPFDYL QFGHQAIEDM NKYL                                       144

SEQ ID NO: 32          moltype = AA  length = 141
FEATURE                Location/Qualifiers
source                 1..141
                       mol_type = protein
                       note = subspecies: setigerum
                       organism = Papaver somniferum
SEQUENCE: 32
MLVGKLSTEL EVDCDAEKYY NMYKHGEDKR QCVDVKVISG DPTRSGCIKE WNVNIDGKTI  60
RSVEETTHND ETKTLRHRVF EGDMMKDFKK FDTIMVVNPK PDGNGCVVTR SIEYEKTNEN  120
SPTPFDYLQF GHQAIEDMNK Y                                          141
```

-continued

```
SEQ ID NO: 33          moltype = AA  length = 147
FEATURE                Location/Qualifiers
source                 1..147
                       mol_type = protein
                       note = subspecies: setigerum
                       organism = Papaver somniferum
SEQUENCE: 33
MLVGKLSTEL EVDCDAEKYY NMYKHGEDVK KAVPHLCVDV KIISGDPTSS GCIKEWNVNI  60
DGKTIRSVEE TTHDDETKTL RHRVFEGDVM KDFKKFDTIM VVNPKPDGNG CVVTRSIEYE  120
KTNENSPTPF DYLQFGHQAI EDMNKYL                                      147

SEQ ID NO: 34          moltype = AA  length = 109
FEATURE                Location/Qualifiers
source                 1..109
                       mol_type = protein
                       note = subspecies: setigerum
                       organism = Papaver somniferum
SEQUENCE: 34
MVKIISGDPT SSGCIKEWNV NIDGKTIRSV EETTHDDETK TLRHRVFEGD VMKDFKKFDT  60
IMVVNPKPDG NGCVVTRSIE YEKTNENSPT PFDYLQFGHQ AIEDMNKYL              109

SEQ ID NO: 35          moltype = AA  length = 180
FEATURE                Location/Qualifiers
source                 1..180
                       mol_type = protein
                       organism = Papaver somniferum
SEQUENCE: 35
MDSINSSIYF CAYFRELIIK LLMAPPGVSG LVGKLSTELE VNCDAEKYYN MYKHGEDVQK  60
AVPHLCVDVK VISGDPTRSG CIKEWNVNID GKTIRSVEET THNDETKTLR HRVFEGDVMK  120
DFKKFDTIMV VNPKPDGNGC VVTRSIEYEK TNDNSPTPFD YLQFGHQAIE DMNKYLRDSE  180

SEQ ID NO: 36          moltype = AA  length = 164
FEATURE                Location/Qualifiers
source                 1..164
                       mol_type = protein
                       organism = Papaver somniferum
SEQUENCE: 36
MNFFIKDHLY ICLVGKLSTE LEVDCDAEKY YNMYKHGEDV KKAVPHLCVD VKIISGDPTS  60
SGCIKEWNVN IDGKTIRSVE ETTHDDETKT LRHRVFEGDV MKDFKKFDTI MVVNPKPDGN  120
GCVVTRSIEY EKTNENSPTP FDYLQFGHQA IEDMNKYLRD SESN                   164

SEQ ID NO: 37          moltype = AA  length = 160
FEATURE                Location/Qualifiers
source                 1..160
                       mol_type = protein
                       organism = Papaver somniferum
SEQUENCE: 37
MAPLGVSGLV GKLSTELEVD CDAEKYYNMY KHGEDVKKAV PHLCVDVKII SGDPTSSGCI  60
KEWNVNIDGK TIRSVEETTH DDETKTLRHR VFEGDVMKDF KKFDTIMVVN PKPDGNGCVV  120
TRSIEYEKTN ENSPTPFDYL QFGHQAIEDM NKYLRDSESN                        160

SEQ ID NO: 38          moltype = AA  length = 400
FEATURE                Location/Qualifiers
source                 1..400
                       mol_type = protein
                       organism = Papaver somniferum
SEQUENCE: 38
MMKVCVSSRE KIKPSRPTPG HLKTHKLSFL DQVAARIYVP LLLYYAGNKE NVDTDTRCNI  60
IKKSLAETLT KFYILAGKIV NDEIERFVNC NDDGVDFCVT KVSNCQLFQV IKRPDIFDQV  120
TLFLPFDPCD NEITASGDFL LSVQVNVFED CRGMVIGLCI NHKVADASSI TTFVNYWATI  180
ARGLVLNVDD RQIQDPCFQV QSIFPQKEKG IGFKISSSSI DGTLVTKKFG FEASKLAELK  240
ERCKFAGATE DIRGGYKPNR VEALSTFLWK CFIDIDQAKT KAAAPARVYL ASNAVNIRSR  300
IVPQLPTSSF GNMVAITDAI FTVNSNENNG INDPYYPKLV QKFRDAVKRV DGEYIEALQS  360
TDLLLNNVTK LFKHILNGQT LSISFTSWCR FPFYDTDLLD                        400

SEQ ID NO: 39          moltype = AA  length = 386
FEATURE                Location/Qualifiers
source                 1..386
                       mol_type = protein
                       organism = Papaver somniferum
SEQUENCE: 39
MKVQVISKEL IKPSTPTPPR LRNFKLSLLD QLLPPFYVPI IIFYPANDDH ESNNNDQCIK  60
ANILKKSLSE TLTRFYPIAG RIRDKILVEC NDEGVHYIEA KVNAVMSDFM SLDVIHQLHP  120
SYITLDDLAE EAQLAVQVTM FDCGGIALSI CSSHKIIDGC TSTTFLNSWA ATARAPSNPE  180
IVYPTFDAAA IFPAQPSGVQ VSTLESDDRL QGENVVTKRF LFSASKITAL RARIAESRSS  240
NILSKYPSRS EAVSALVWKS FMETSRVKVT REHTFSAEAS TKPIVRSIAN FVVNLRTRLN  300
PPLPNVSFGN IIMDATAESL IIDNGENTLG FVETLDGLIS QLRLGVTKMD DEYVRKLRED  360
DVEFLKSLDE ASHPSNGEGD GNGERV                                       386
```

-continued

```
SEQ ID NO: 40          moltype = AA  length = 525
FEATURE                Location/Qualifiers
source                 1..525
                       mol_type = protein
                       note = subspecies: setigerum
                       organism = Papaver somniferum
SEQUENCE: 40
MNDTMKIEVV SKESIKPSYP TPNNLKIHNL SNLDQLIPAF YMDHILYYPS LDSNDSSLGD  60
DEEDKKMIFS ASSRHRCDVV KKSLAETLTR YYPLAGRIKD EKSVECNDEG VDYIEARVVG  120
ITVSQVIQLA SSDIEVMEPF LPYEPYGGTG SAFRRAGIHS NSKPLLKIQV NVFDCGGMVI  180
CLSGSHKVID ATSILNFVND WAATARGGFD THDDELKVAV VDKPCYIFSS MFPPTSFGNQ  240
EEKDTADQAQ LVPDRIEIVT KRFVFKDSSI AKLKKKCIHV NTNNGSDHQV DKQEHNMQQM  300
PSRIEALTSL IWMCFMDVDR RFRVKQIDDA VSPVNTVNEV SLPKQVQYVA GFAINLRTRT  360
IQPLPTNSFG NMTDTAIAEV TLNLTGSDHF NNEKGIRDQS QNYPELVSKI KDSIKLVDNK  420
HIEAMKRNLA ISCNNIKMHQ MMKESTFDQN TRELLMFSSW CRFPIYEADF GWGKPSWASI  480
TKLLYKNCVM FLDTSSGDGI EAWVSLKEED MVEFERHEEL VALAS                 525

SEQ ID NO: 41          moltype = AA  length = 459
FEATURE                Location/Qualifiers
source                 1..459
                       mol_type = protein
                       organism = Papaver somniferum
SEQUENCE: 41
MKVQVISKEI IKPSSPTPPH LRNFKLSLLD QILPPFYVPI VMFYPAGDDY VTNNNIHDQS  60
SKSEFLKKSL SETLTRFYPI AGRIKDNILI DCNNEGVDYI EAKVNGIMSD FMSVDVVHQL  120
HPSHIMLDDV AKEAQLAVQV NLFDCGGIAI SISMSHKIVD ACTAITFING WAATARAAPK  180
QEIVCPTFDS AAIFPALPPG VQVSSLESDD SVQGVNVVTK MFAFTAPKIA SLRARIAELR  240
SSSDGLSKYP TRTEALSALV WKSFIRTSRV KAARKYSLSP ASTKPVIKSV ANYAVNLRTR  300
LNPPLPQVSF GNILMDATAE STTTIDDDDS HEFADTLAGL IGQLRLGVSR INGDYIRKLQ  360
EGDLAFLKSL DEASHDSNGE KVQICWISSL CRFPFYEADF GWGKPSWVAL NTNAEYKNSL  420
FLMDTKCGTG IEAWVSLEED DMAIFEEDQD LLQCVKSIN                        459

SEQ ID NO: 42          moltype = AA  length = 477
FEATURE                Location/Qualifiers
source                 1..477
                       mol_type = protein
                       note = subspecies: setigerum
                       organism = Papaver somniferum
SEQUENCE: 42
MENMKVEVVL KQTIKPSTQT PLHSKTFNLS FLDQHLGPPI YIPFTLYYES GDVNNKNNHC  60
DGYKNNLEEA CEHRVSVIKQ SLSETLARYY PLAGRMKEDN LAVECNDEGV EYFETRVSDV  120
RLSQVIKRSP NHNSVLRKFL PPCISSCDNS MSIPFDYGFK SKTLLAIQVN IFECGGIVIG  180
MCMAHRLADA STMFTFITDW AATARGAIED IKGPSFDFSY TLFPQKDVIN NFKPFDPMLT  240
REEDLVTKYF VFPASKIVEL KRRNVNNIVC QDTSQQNTSP CTRVEAVTSF MWKRYMDSVR  300
AKNQTQATSV EKYGALYTVN LRSRITPPLP ANSFGNIYTF TIALSTPSDE NDIDDGLRKD  360
VSSPNDLNLV GKVRDAIKKI DDKYTRKLQS SEDELVNDVK PLTSGEAIFL GFSSWCRFPI  420
YEADFGWGKP TWVSIGTMAL RNTVFLMDTK SGDGIEAFVN MAKEDMDNFE VKLLADQ     477

SEQ ID NO: 43          moltype = AA  length = 485
FEATURE                Location/Qualifiers
source                 1..485
                       mol_type = protein
                       note = subspecies: setigerum
                       organism = Papaver somniferum
SEQUENCE: 43
MENMKVEVVL EQTIKPSTQT PLHSKTFNLS FLDQHLGPPI YIPFTLYYES GDVNNKNNHC  60
DGYKNNLEEV CEHRVSVIKQ SLSETLARYY PLAGRMKEDN LAVECNDEGV EYFETRVSDV  120
RLSQVIKRSP NHNSVLRKFL PPCISSCDNS MSIPFDYGFK SKTLLAIQVN IFECGGIVIG  180
MCMAHRLADA STMFTFITDW AATARGAIED IKGPSFDFSY TLFPQKDVIN NFKPFDPMLT  240
REEDLVTKYF VFPASKIVEL KRRNVNNIVC QDTSQQNTSP CTRVEAVTSF MWKRYMDSVR  300
AKNQTQATSV EKYGALYTVN LRSRITPPLP ANSFGNIYTF TIALSTPSDE NDIDDGLRKD  360
VSSPNDLNLV GKVRDAIKKI DDKYTRKLQS SEDELVNDVK PLTSGEAIFL GFSSWCRFPI  420
YEADFGWGKP TWVSIGTMAL RNTVFLMDTK SGDGIEAFVN MAKEDMDNFE VKLLADQLLH  480
VHPTV                                                             485

SEQ ID NO: 44          moltype = AA  length = 452
FEATURE                Location/Qualifiers
source                 1..452
                       mol_type = protein
                       note = subspecies: setigerum
                       organism = Papaver somniferum
SEQUENCE: 44
MSSTVEVISK QTIKPSTPTP IQRKNHSLSL IDQHFAPIYI PIVLFYPAAA VNDTGNVQHG  60
DNTCVLKRSL SETLVHFYPL AGRMKDNIVV DCNDQGVEFT EVKVSGTMCD FLMKPDEQLS  120
GLLPSEAVCM NFVREAQVMI QVNTFDCGSK AISLCVSHKI ADASTITTFS RCWAETTIAV  180
SKSTSAVTPI VSSKFHPTFD AASLFPPIKQ LISPSGVTPA LPELIPSEES KFGKIISKRF  240
LFSATTINSV REKLSALMAD KLKYRRLTRV EVVSALIWNS FDKLATTGSV AVMVKHAVNL  300
RKRIDPPLPD VSFGNILEFT KAVVGEAAAN TTTQGTVGSS SKLLEELSEF AGQLREPVSK  360
MNKGDHDFDM ENTDYEERDL WMSSWCNYGL YDIDFGCGKP VWVTTVATMY PYSDGFFMND  420
```

-continued

```
TRCGQGIEVW GNLVEEDMAN FQLNLSELLD RI                              452

SEQ ID NO: 45          moltype = AA  length = 451
FEATURE                Location/Qualifiers
source                 1..451
                       mol_type = protein
                       organism = Papaver somniferum
SEQUENCE: 45
MMKVCVSSRE KIKPSRPTPG HLKTHKLSFL DQVAARIYVP LLLYYAGNKE NVDTDTRCNI  60
IKKSLAETLT KFYILAGKIV NDEIERFVNC NDDGVDFCVT KVSNCQLFQV IKRPDIFDQV  120
TLFLPFDPCD NEITASGDFL LSVQVNVFED CRGMVIGLCI NHKVADASSI TTFVNYWATI  180
ARGLVLNVDD RQIQDPCFQV QSIFPQKEKG IGFKISSSSI DGTLVTKKFG FEASKLAELK  240
ERCKFTTEPE DGYKPTRVEA LSAFLWKCFI DIDQAKLKGV ARTKVYLATN AVNMRSRMVP  300
QLPTSSFGNI ISITDAVFSI NNDDSTGIND PYYPKLVRKF RDAIKKIDRD YIEALRSTDL  360
LLNNMMKLIE HVLSGHTLSI YFSSWCRFPL YETDFGWGKP IWVSTCTIPQ KNVIVLMDSN  420
SSADGIEAYV TLAKEDMGEL EHHEELLALI S                               451

SEQ ID NO: 46          moltype = AA  length = 232
FEATURE                Location/Qualifiers
source                 1..232
                       mol_type = protein
                       organism = Papaver somniferum
SEQUENCE: 46
MGAMKFFSFL AVAMVLSLAH IQAQQGNWGD ETVPYTMGPE KITKLRFYFH DIVTGNNPTA  60
VQIAQATGTN SSSTLFGALF MIDDPLTEGP DPDSRLVGRA QGFYGSAGQN EAALILGMSL  120
VFTGNEKFNG STISVLSRNP VTHTEREFAI VGGTGYFQFA RGFISAKTYS LVGPNAVVEY  180
NCTIVHPSSV SESGKSNSSP GKSDSNSGSQ ISLGSNLVFV SVIAYVTIIL SL         232

SEQ ID NO: 47          moltype = AA  length = 224
FEATURE                Location/Qualifiers
source                 1..224
                       mol_type = protein
                       note = subspecies: setigerum
                       organism = Papaver somniferum
SEQUENCE: 47
MVLSMSHSQA QEGNWGDESV PYTMGPEKMT KLRFYFHDII TGNSPTAVQI AQATGTNTSA  60
TMFGALMMID DPLTEGPDPN SRLVGRAQGF YGSAGQNELA LILGMSLVFT GNEKFNGSTI  120
SVLSRNPVMH TEREFAIVGG TGYFQFARGF ISAKTYSLVG PNAVVEYNCT IVHPSSVSES  180
GKSDSSSGKS DSSSGSQISL GTNLVFLSVI AFVTIIVSPQ HFSW                 224

SEQ ID NO: 48          moltype = AA  length = 210
FEATURE                Location/Qualifiers
source                 1..210
                       mol_type = protein
                       organism = Papaver somniferum
SEQUENCE: 48
MTKTVLVDDI PFPQNITTVT TEKQLPLLGQ GITDMEIHFL QIKFTAIGTA IGVYLEPEIA  60
SHLQQWKGKT GAELSQDDEF FAAVVSASVE KYVRVVVIKE IKGSQYMLQL ESWVRDELAA  120
ADKYEDEEEE SLDKVIEFFQ SKYLKQLSFI PSHFSATTPA VAEIGLEIEG QKDLKIKVEN  180
GNVIEMIQKW YLGGTRGVSP STTQSLATSL                                 210

SEQ ID NO: 49          moltype = AA  length = 210
FEATURE                Location/Qualifiers
source                 1..210
                       mol_type = protein
                       organism = Papaver somniferum
SEQUENCE: 49
MPFLKAIEIE GCKFRPFVTP PGSTQILFLA GSGVKEEFGD SKSMKYSSCA IYLQPTCILY  60
LAKAWAQKSV VDITQSLNFF MDIATGPFEK YCRITMLETA KGEDYAAMIT KNCEEMLTNS  120
KRYSETAKAA LTKFSEAFNG RTLASGSSIH VTVSTSNSVT LAFTEDGSTP KQGDVTLDCK  180
EVGEAFLMST ISLHTTIRES MGSRISGLYK                                 210

SEQ ID NO: 50          moltype = AA  length = 166
FEATURE                Location/Qualifiers
source                 1..166
                       mol_type = protein
                       note = subspecies: setigerum
                       organism = Papaver somniferum
SEQUENCE: 50
MAPMAQLSEI QVEQFVFPPT MTPPSSTESL FLGGAGVRGL QIQDRFIKFT AIGVYLAEEA  60
IPSLSPKWKS KSPEELTDDV EFFMDIVTGP FEKFVKITMI LPLTGDQYAE KVTENCIQYL  120
KSKDMYTDAE AKAVERFIEI FKNEMFPPAS SILFTISPAG SLTVGF               166

SEQ ID NO: 51          moltype = AA  length = 160
FEATURE                Location/Qualifiers
source                 1..160
                       mol_type = protein
                       organism = Papaver rhoeas
SEQUENCE: 51
```

-continued

```
MVYLEPEIAT HLKQWKGKTG AELSQDDDFF SAVVSAPVEK YVRVVVIKEI KGSQYMLQLE  60
SWVRDELAAA DKYEDEEEES LDKVIEFFQS KYLKQHSVII TFHFSATTPA VAEIGLEIEG  120
QKDLKIKVEN GNVVEMIQKW YLGGTRGVSP STTQSLATSL                        160

SEQ ID NO: 52          moltype = AA  length = 206
FEATURE                Location/Qualifiers
source                 1..206
                       mol_type = protein
                       organism = Papaver bracteatum
SEQUENCE: 52
MTKMVLVDDI PFPQNITTAT TAKQLPLLGQ GITDMEIHFL QIKFTAIGVY LEPEIASHLK  60
QWKGKTGAEL SQDDEFFSAI VSAPVEKYVR VVVIKEIKGS QYMLQLESWV RDELAAADKY  120
EDEEEESLEK VIEFFQSKYL KQHSVIPFHF SATTPAVAEI GLEIEGHKDL KMKVENGNVV  180
EMIQKWYLAG TRGVSPSTTQ SLATSL                                       206

SEQ ID NO: 53          moltype = AA  length = 216
FEATURE                Location/Qualifiers
source                 1..216
                       mol_type = protein
                       organism = Papaver bracteatum
SEQUENCE: 53
MAPMAQLSEI QVEQFVFPPT MTPPSSTESL FLGGAGVRGL QIQDRFIKFT AIGVYLAEEA  60
IPSLSPKWKS KTPEELTNDV EFFMDIVTGP FEKFVKITMI LPLTGDQYAE KVTENCVEYL  120
KSKDLYTDAE AKAVERFIEI FKNEMFPPAS SILFTISPTG SLTVGFSKDT SIPEARNAVI  180
ENKALSESIL ESIIGKNGVS PAAKQSLAER ISELLK                             216

SEQ ID NO: 54          moltype = AA  length = 151
FEATURE                Location/Qualifiers
source                 1..151
                       mol_type = protein
                       organism = Panax ginseng
SEQUENCE: 54
MGLTGKLICQ TGIKSDGDVF HELFGTRPHH VPNITPANIQ GCDLHEGEFG KVGSVVIWNY  60
SIDGNAMIAK EEIVAIDEED KSVTFKVVEG HLFEEFKSIV FSVHVDTKGE DNLVTWSIDY  120
EKLNESVKDP TSYLDFLLSV TRDIEAHHLP K                                  151

SEQ ID NO: 55          moltype = AA  length = 157
FEATURE                Location/Qualifiers
source                 1..157
                       mol_type = protein
                       organism = Arachis hypogaea
SEQUENCE: 55
MGVFTFEDEI TSTVPPAKLY NAMKDADSIT PKIIDDVKSV EIVEGNGGPG TIKKLTIVED  60
GETKFILHKV ESIDEANYAY NYSVVGGVAL PPTAEKITFE TKLVEGPNGG SIGKLTLKYH  120
TKGDAKPDEE ELKKGKAKGE GLFRAIEGYV LANPTQY                            157

SEQ ID NO: 56          moltype = AA  length = 166
FEATURE                Location/Qualifiers
source                 1..166
                       mol_type = protein
                       organism = Hypericum perforatum
SEQUENCE: 56
MGIDPFTMAA YTIVKEEESP IAPHRLFKAL VLERHQVLVK AQPHVFKSGE IIEGDGGVGT  60
VTKITFVDGH PLTYMLHKFD EIDAANFYCK YTLFEGDVLR DNIEKVVYEV KLEAVGGGSK  120
GKITVTYHPK PGCTVNEEEV KIGEKKAYEF YKQVEEYLAA NPEVFA                  166

SEQ ID NO: 57          moltype = AA  length = 158
FEATURE                Location/Qualifiers
source                 1..158
                       mol_type = protein
                       organism = Lupinus luteus
SEQUENCE: 57
MGVFTFQDEY TSTIAPAKLY KALVTDADII IPKAVETIQS VEIVEGNGGP GTIKKLTFIE  60
GGESKYVLHK IEAIDEANLG YNYSIVGGVG LPDTIEKISF ETKLVEGANG GSIGKVTIKI  120
ETKGDAQPNE EEGKAAKARG DAFFKAIESY LSAHPDYN                           158

SEQ ID NO: 58          moltype = AA  length = 161
FEATURE                Location/Qualifiers
source                 1..161
                       mol_type = protein
                       organism = Fragaria X ananassa
SEQUENCE: 58
MAGVFTYETE FTSVIPPPRL FKAFILDADN LIPKIAPQAV KCAEIIEGDG GVGTIKKITF  60
GEGSQFGSVT HKIDGIDKEN FVYSYSLIEG DALSDKIEKI SYETKLVSSS DGGSIIKSTS  120
NYHTKGDVEI KEEHVKAGKE KFSHLFKLVE GYLLANPNEY C                       161

SEQ ID NO: 59          moltype = AA  length = 150
FEATURE                Location/Qualifiers
source                 1..150
```

```
                         mol_type = protein
                         note = subspecies: deliciosa
                         organism = Actinidia chinensis
SEQUENCE: 59
MDLSGKMVKQ VEILSDGIVF YEIFRYRLYL ISEMSPVNIQ GVDLLEGNWG TVGSVIFFKY  60
TIDGKEKTAK DIVEAIDEET KSVTFKIVEG DLMELYKTFI IIVQVDTKGE HNSVTWTFHY  120
EKLKEDVEEP NTLMNFCIEI TKDIETYHLK                                  150

SEQ ID NO: 60            moltype = AA  length = 164
FEATURE                  Location/Qualifiers
source                   1..164
                         mol_type = protein
                         organism = Thalictrum flavum
SEQUENCE: 60
MGIINQVSTV TKVIHHELEV AASADDIWTV YSWPGLAKHL PDLLPGAFEK LEIIGDGGVG  60
TILDMTFVPG EFPHEYKEKF ILVDNEHRLK KVQMIEGGYL DLGVTYYMDT IHVVPTGKDS  120
CVIKSSTEYH VKPEFVKIVE PLITTGPLAA MADAISKLVL EHKS                  164

SEQ ID NO: 61            moltype = AA  length = 155
FEATURE                  Location/Qualifiers
source                   1..155
                         mol_type = protein
                         organism = Vigna radiata
SEQUENCE: 61
MVKEFNTQTE LSVRLEALWA VLSKDFITVV PKVLPHIVKD VQLIEGDGGV GTILIFNFLP  60
EVSPSYQREE ITEFDESSHE IGLQVIEGGY LSQGLSYYKT TFKLSEIEED KTLVNVKISY  120
DHDSDIEEKV TPTKTSQSTL MYLRRLERYL SNGSA                            155

SEQ ID NO: 62            moltype = AA  length = 364
FEATURE                  Location/Qualifiers
source                   1..364
                         mol_type = protein
                         organism = Papaver sp.
SEQUENCE: 62
MEKAKLMKLG NGMEIPSVQE LAKLTLAEIP SRYVCANENL LLPMGASVIN DHETIPVIDI  60
ENLLSPEPII GKLELDRLHF ACKEWGFFQV VNHGVDASLV DSVKSEIQGF FNLSMDEKTK  120
YEQEDGDVEG FGQGFIESED QTLDWADIFM MFTLPLHLRK PHLFSKLPVP LRETIESYSS  180
EMKKLSMVLF NKMEKALQVQ AAEIKGMSEV FIDGTQAMRM NYYPPCPQPN LAIGLTSHSD  240
FGGLTILLQI NEVEGLQIKR EGTWISVKPL PNAFVVNVGD ILEIMTNGIY HSVDHRAVVN  300
STNERLSIAT FHDPSLESVI GPISSLITPE TPALFKSGST YGDLVEECKT RKLDGKSFLD  360
SMRI                                                              364

SEQ ID NO: 63            moltype = AA  length = 360
FEATURE                  Location/Qualifiers
source                   1..360
                         mol_type = protein
                         organism = Papaver sp.
SEQUENCE: 63
METPILIKLG NGLSIPSVQE LAKLTLAEIP SRYTCTGESP LNNIGASVTD DETVPVIDLQ  60
NLLSPEPVVG KLELDKLHSA CKEWGFFQLV NHGVDALLMD NIKSEIKGFF NLPMNEKTKY  120
GQQDGDFEGF GQPYIESEDQ RLDWTEVFSM LSLPLHLRKP HLFPELPLPF RETLESYLSK  180
MKKLSTVVFE MLEKSLQLVE IKGMTDLFED GLQTMRMNYY PPCPRPELVL GLTSHSDFSG  240
LTILLQLNEV EGLQIRKEER WISIKPLPDA FIVNVGDILE IMTNGIYRSV EHRAVVNSTK  300
ERLSIATFHD SKLESEIGPI SSLVTPETPA LFKRGRYEDI LKENLSRKLD GKSFLDYMRM  360

SEQ ID NO: 64            moltype = AA  length = 364
FEATURE                  Location/Qualifiers
source                   1..364
                         mol_type = protein
                         organism = Papaver somniferum
SEQUENCE: 64
MEKAKLMKLG NGLSIPSVQE LAELTFAEVP SRYVCTNDEN LLLMTMGASE IDDETVPVID  60
LQNLLSPEPA IGKSELDWLH YSCKEWGFFQ LVNHGVDALL VDHVKSEIHS FFNLPLNEKT  120
KYGQRDGDVE GFGQAFLVSE NQKLDWADMF FINTLPLHLR KPHLFPNLPL PLRETIESYS  180
SEMKKLSMVL FEMMGKAIEV IDIKEAITEM FEDGMQSMRM NYYPPCPQPE RVIGITPHSD  240
FDGLTILLQL NEVEGLQIRK EDKWISIKPL PDAFIVNVGD IWEIMTNGVH RSVDHRGVIN  300
STKERLSIAT FHSPKLELEI GPISSLIRPE TPAVFKSAGR FEDLLKEGLS RKLDGKSFLD  360
CMRM                                                              364

SEQ ID NO: 65            moltype = AA  length = 294
FEATURE                  Location/Qualifiers
source                   1..294
                         mol_type = protein
                         organism = Papaver somniferum
SEQUENCE: 65
MEKAKLMKLG NGMEIPSVQE LAKLTLAEIP SRYVCANENL LLPMGASVIN DHETIPVIDI  60
ENLLSPEPII GKLELDRLHF ACKEWGFFQV VNHGVDASLV DSVKSEIQGF FNLSMDEKTK  120
YEQEDGDVEG FGQGFIESED QTLDWADIFM MFTLPLHLRK PHLFSKLPVP LRETIESYSS  180
EMKKLSMVLF NKMEKALQVQ AAEIKGMSEV FIDGTQAMRM NYYPPCPQPN LAIGLTSHSD  240
```

-continued

```
FGGLTILLQI NEVEGLQIKR EGTWISVKPL PNAFVVNVGD ILEIMTNGIY HSVD        294

SEQ ID NO: 66          moltype = AA  length = 364
FEATURE                Location/Qualifiers
source                 1..364
                       mol_type = protein
                       organism = Papaver somniferum
SEQUENCE: 66
METAKLMKLG NGMSIPSVQE LAKLTLAEIP SRYICTVENL QLPVGASVID DHETVPVIDI  60
ENLISSEPVT EKLELDRLHS ACKEWGFFQV VNHGVDTSLV DNVKSDIQGF FNLSMNEKIK  120
YGQKDGDVEG FGQAFVASED QTLDWADIFM ILTLPLHLRK PHLFSKLPLP LRETIESYSS  180
EMKKLSMVLF EKMEKALQVQ AVEIKEISEV FKDMTQVMRM NYYPPCPQPE LAIGLTPHSD  240
FGGLTILLQL NEVEGLQIKN EGRWISVKPL PNAFVVNVGD VLEIMTNGMY RSVDHRAVVN  300
STKERLSIAT FHDPNLESEI GPISSLITPN TPALFRSGST YGELVEEFHS RKLDGKSFLD  360
SMRM                                                              364

SEQ ID NO: 67          moltype = AA  length = 369
FEATURE                Location/Qualifiers
source                 1..369
                       mol_type = protein
                       organism = Papaver bracteatum
SEQUENCE: 67
METPKSIKLG GSLLVPSVQE LAQQSFAEVP ARYVRDDLEP LTDLSGVSMI DQTIPVIDLQ  60
KLQSPVPIIR ELESEKLHSA CKEWGFFQVV NHGVDILLVE KTKSEIKDFF NLPMDEKKKF  120
WQEEGDIQGF GQAFVQSEDQ KLDWADIFLM VTLPRHTRNP RLFPKLPLPL RNTMDSYSSK  180
LSKLASTLIE MMGKALHMET SVLAELFEDG RQTMRINYYP PCPQPKDVIG LTPHSDGGGL  240
TILLQLNEVD GLQIRKEKIW IPIKPLPNAF VVNIGNILEI MTNGIYRSVE HRATIHSTKE  300
RLSVAAFHNP KVGVEIGPIV SMITPESPAL FRTIEYDDYG KKYFSRKLDG KSSLDFMRIG  360
EGDEENKAT                                                         369

SEQ ID NO: 68          moltype = AA  length = 366
FEATURE                Location/Qualifiers
source                 1..366
                       mol_type = protein
                       organism = Papaver bracteatum
SEQUENCE: 68
METPKLIKLG GSLLVPSVLE LTKQSPAEVP ARYIRNDLEP MTDLSSASLT DQTIPVIDLQ  60
NLLSPEPELE LEKLHSGCKE WGFFQVMNHG VDILLVEKVK SEIQGFFNLP IDEKNKFWQE  120
EGDLEGYGKA FVHSEDEKLD WADMFFILTQ PQYMRKPRVF PKLPLRLRET IESYSLELSK  180
LGLTLLDLMG KALQIETGVM SELFEDGRQT MRMNYYPPCP QPEHVIGLTP HSDGGALTIL  240
LQLNQVDGLQ IRKEEIWVPI KPLPNAFVVN IGDILEIMSN GVYRSVEHRA TINSSKERLS  300
VAIFQSPKHG TEIGPILSMI TPEAPALFKT IPYEDYLRKF FSRKLGGKSF VDSMRIGESD  360
EDNNTA                                                            366

SEQ ID NO: 69          moltype = AA  length = 366
FEATURE                Location/Qualifiers
source                 1..366
                       mol_type = protein
                       organism = Papaver bracteatum
SEQUENCE: 69
METQKQENFG ASLSVPNVQE LAKQSPEQVP DRYIRSDQDS STNISCPSMT DQIPVIDLQS  60
LLSPDPIIGE LELERLHSAC KEWGFFQVVN HGVDNLLVEK VKSEIQGFFN LPMDEKKKFW  120
QEEGDFEGFG QAFVFSEDQK LDWGDVFFIL TQPQHMRKPR LFPKLPLPFR KTIESYSLET  180
NKLSMTLLEL MEKALKIETG VMTELFEGGI QRMRMTYYPP CPQPKHVIGL TPHSDPDALT  240
ILLQLNEVDG LQIRKEKIWV PIKPLSNAFV VNIGDILEIM SNGIYRSVEH RATVNSTKER  300
LSVATFHSPR KDTEIGPILI TPETPALFRT SGFEDYFRKF FAHKLNGKSF LSSIRIGETD  360
EGNNAT                                                            366

SEQ ID NO: 70          moltype = AA  length = 379
FEATURE                Location/Qualifiers
source                 1..379
                       mol_type = protein
                       organism = Papaver bracteatum
SEQUENCE: 70
MEAPKLIMLG GSLFVPSVQE LAKQSLAEVP VRYVRDDQDT LGNNINITPM SMIDQSIPVI  60
DLEKLLSPEP IVGELELERL HSACKEWGFF QVVNHGVDSL LVEKVKSEIE GFFKLPMDEK  120
TKFWQEEGDI EGFGQVFVHS QDQKLDWGDM FLMQTLPRHT RKPRLFPNLP LPLRQTIESY  180
SSELSKLVLT LVDLMGKALQ MESGVLTELF ENGIQRMRMN YYPPCPQPEQ VIGLTPHSDV  240
GGLTILLQLN EVDGLQIKKD KVWVPIKPLA NAFVVNVGDA LEIMSNGIYR SVEHRATINS  300
TKERLSIATF HNPRADREIG PIPSMISPET PALFKTTGYE EYFKKFFSRK LEGKSFLDSL  360
RIREGDEHCG RLDVKGPCN                                              379

SEQ ID NO: 71          moltype = AA  length = 365
FEATURE                Location/Qualifiers
source                 1..365
                       mol_type = protein
                       organism = Papaver bracteatum
SEQUENCE: 71
MEIPNPIKIG SSLLVPSVQE LAKQSFAEVP ARYIRNDVDP LITKLSDVSL IDQTVPVIDL  60
```

-continued

```
QKLLSPEPIV GELELERLHS ACKEWGFFQV VNHGVDNLLV EKVKSEIQGF FNLPMEEKKK  120
FWQEEGDFEG FGQMFVQSEE QKLDWGDMFF ILTQPQHMRK PRLFSKLPLP LRETIESYSL  180
ELIKLGLTII KLMEKALQID AGVMAELFED GIHTMRMNYY PPCPQPEHVI GLTPHSDGGG  240
LTILLQLNEV DGLQIRRENI WVPIKPLPNA FVVNIGDILE ILSNGIYRSV EHRSTVNATK  300
ERLSVATFQN PKQESVIGPN MITPERPALF RKIVYKDYMK KLFSRKLDGK SFLDSLRIGE  360
GDERP                                                             365

SEQ ID NO: 72          moltype = AA  length = 349
FEATURE                Location/Qualifiers
source                 1..349
                       mol_type = protein
                       organism = Papaver bracteatum
SEQUENCE: 72
METLKTVKPG GSLFIPNGQE LAKQSLEEVY VGNDQDTMLL IGQTIPVIDL QKLLSPEPIT  60
GDMELDKLHS ACKEWGFFQV VNHGVDILLV EKVKSEVHDF FNIPMDEKKP FWQEEGDLEG  120
FGQVFITSED QQLDWGDMFF MVTLPKHMRK PRLFLKLPLP LRETIESYSL KLSKLGVTLV  180
ELMGKALQME DRIMSELFDD GRQTMRMNYY PPCPQPEQVI GLTPHSDPGG LTILLELNEV  240
NGLIRKENIW VPIIPLPNAF IVNIGDILEI MSNGIYHSVE HRATINSTKE RLSVAMFNSP  300
KVDTEIGPIH SMITPETPAL FRTIGYDEYL KIFFSRKLDG KSLLESMKI              349

SEQ ID NO: 73          moltype = AA  length = 379
FEATURE                Location/Qualifiers
VARIANT                373
                       note = Any amino acid
VARIANT                377
                       note = Any amino acid
source                 1..379
                       mol_type = protein
                       organism = Papaver bracteatum
SEQUENCE: 73
MEAPKLIMLG GSLFVPSVQE LAKQSLAEVP VRYVRDDQDT LGNNINITPM SMIDQSIPVI  60
DLEKLLSPEP IVGELELERL HSACKEWGFF QVVNHGVDSL LVEKVKSEIE GFFELPVDEK  120
KKFWQEEGDI EGFGQIFVHS EDQKLDWADM FYMLTLPPNM RKPRLFPNLP LPLRQTIDSY  180
SSELSKLVLT LVDLMGKALQ MESGVLTELF ENGIQRMRMN YYPPCPQPEQ VIGLTPHSDV  240
GGLTILLQLN EVDGLQIKKD KIWVPIKPLR NAFVVNVGDA LEIMSNGIYR SVEHRATINS  300
TKERLSIATF HNPRADREIG PIPSMISPET PALFKTTGYE EYFKKFFSRK LEGKSFLDSL  360
RIGEGDEHCG RLXVKGXCN                                              379

SEQ ID NO: 74          moltype = AA  length = 362
FEATURE                Location/Qualifiers
source                 1..362
                       mol_type = protein
                       organism = Papaver bracteatum
SEQUENCE: 74
METPKLMKLG GSLFVPSVQE LAKQSLAEVP ARYVRDDRDM VGNIINVTPM SMIDQSIPVI  60
DLEKLLSPDL IVGELELERL HSACKEWGFF QVVNHGVDSL LVEKVKSEIE GFFELPMDEK  120
KKFWQEEGDA EGFAQFFVQS EDQKLDYSGD MFFMLNLPQH MRKPRLFLKL PLPLRETIES  180
YSLKLSKLGV TLVELMGKAL QMEDRIMSEL FDDGRQTMRM NYYPPCPQPE QVIGLTPHSD  240
PGGLTILLEL NEVNGLIRKE NIWVPIIPLP NAFIVNIGDI LEIMSNGIYH SVEHRATINS  300
TKERLSVAMF NSPKVDTEIG PIHSMITPET PALFRTIGYD EYLKIFFSRK LDGKSLLESM  360
KI                                                                362

SEQ ID NO: 75          moltype = AA  length = 365
FEATURE                Location/Qualifiers
source                 1..365
                       mol_type = protein
                       organism = Papaver bracteatum
SEQUENCE: 75
METPKLRDFG SFLPVPSVQE LAKQVLTEIP PRYIRTDLEA LNKLSCASNT DQTVPIIDMQ  60
CLLSAEPEME LEKLHSACKE WGFFRVVNHG VDNLESVKSE IESFLNLPVN AKNKYGQKQG  120
DDQGFGSRFV LSEEQKLDWG DFFYMVTRPL YLRKPHLFPE LPLPLRETIE SYSSEVSKLA  180
MALFEMMGKA LKIETGVMTE IFEGGMQAMR MNYYPPCPRP DLVIGLNAHS DFGGLTILLQ  240
LNEVEGLEIR NKGEWVSVKP LANAFVVNVG DVMEILTNGI YHSVEHRATI NSSKERLSVA  300
TFHYPKLETG IGPLPCMITP KTPALFGRIE RYELLLRKYY ARKLNGKSTL DCMRIGNGFE  360
DDNTA                                                             365

SEQ ID NO: 76          moltype = AA  length = 370
FEATURE                Location/Qualifiers
source                 1..370
                       mol_type = protein
                       organism = Papaver bracteatum
SEQUENCE: 76
MEAPKLIMLG GSLFVPSVQE LAKQSLAEVP ARYVRDDQDT LGNNINITPM SMIDQSIPVI  60
DLEKLLSPEP IVGELELERL HSACKEWGFF QVVNHGVDSL LVEKVKSEIE GFFELPVDEK  120
KKFWQEEGDI EGFGQIFVHS EDQKLDWADM FYMLTLPPNM RKPRLFPNLP LPLRQTIDSY  180
SSELSKLVLT LVDLMGKALQ MESGVLTELF ENGIQRMRMN YYPPCPQPEQ VIGLTPHSEV  240
GGLTILLQLN EVDGLQIRKE KIWVPIKPLS NAFIVNIGDI LEIMSNGIYR SVEHRATVNS  300
TKERLSVATF HSPRKDTEIG PILITPETPA LFRTSGFEDY FRKFFAHKLN GKSFLSSIRI  360
GETDEGNNAT                                                        370
```

-continued

```
SEQ ID NO: 77          moltype = AA  length = 313
FEATURE                Location/Qualifiers
source                 1..313
                       mol_type = protein
                       organism = Papaver bracteatum
SEQUENCE: 77
MSMIDQSIPV IDLEKLLSPE PIVGELELER LHSACKEWGF FQVVNHGVDS LLVEKVKSEI  60
EGFFELPVDE KKKFWQEEGD IEGFGQIFVH SEDQKLDWAD MFYMLTLPPN MRKPRLFPNL  120
PLPLRQTIDS YSSELSKLVL TLVDLMGKAL QMESGVLTEL FENGIQRMRM NYYPPCPQPE  180
QVIGLTPHSD VGGLTILLQL NEVDGLQIRK EKIWVPIKPL SNAFIVNIGD ILEIMSNGIY  240
HSVEHRATIN STKERLSVAM FNSPKVDTEI GPIHSMITPE TPALFRTIGY DEYLKIFFSR  300
KLDGKSLLES MKI                                                      313

SEQ ID NO: 78          moltype = AA  length = 365
FEATURE                Location/Qualifiers
source                 1..365
                       mol_type = protein
                       organism = Papaver bracteatum
SEQUENCE: 78
METPKLVKSS GSSLFLSTSV QELAKQSLPE VPARYIRTNL EPLSNVSGDS QSVPVIDLQK  60
LLSSEPIIGE LELDKLHSAC KEWGFFQVVN HGVDNLVMEK IKTEIQGFFN LSLDEKQKFW  120
KKEGDAEGFG QNFIESEDQK LDWGDTFGMF TLPIHMRNPR LFPELPLPLR ETIESYSLDV  180
RKLALALIGL MEKALKIKTS AMSELFEDGG QAMRMNYYPP CPQPEHVIGL TPHSDAGGLT  240
ILLQLNEVDG LQIKKDKIWV PIKPLPNAFV VNIGDILEIM TNGIYRSVEH RATINSSKER  300
LSVAAFHSPK GDTLIGPMVS LITPETPALF RTIGYQDYMK KFMSRKLDGK SLVNSMRIGE  360
GDEDK                                                               365

SEQ ID NO: 79          moltype = AA  length = 356
FEATURE                Location/Qualifiers
source                 1..356
                       mol_type = protein
                       organism = Papaver bracteatum
SEQUENCE: 79
METPTLMKLG NGLSVPSVQE LAKATLAEIP SRYICTDENL LTMGASTTDN ETVPVIDLQN  60
LLSPEPVIGM LELDRLHSAC KEWGFFQLVN HGVDALLVDN EVQGFFNLPM DEKTKYGQKD  120
GDDEGFGQFF VISEDQKLDW ADVFYMSTLP LHSRKPHLFP ELPLPLRETM ESYSSEMKKL  180
SMVLFDMMGK ALQVVEIKGI TELFEDGAQQ IRMNYYPPCP QPELVFGLTS HSDFDGLTIL  240
LQLGEVEGLQ IKKEERWISI KPLPDAFIVN VGDILEIMTN GIYRSVDHRA VVNSIKERLT  300
IATFHDPRLE AEIGPISSLI TPETPALFKR GVFEDLLKEM FLRKLDGKSF LDCMRM       356

SEQ ID NO: 80          moltype = AA  length = 350
FEATURE                Location/Qualifiers
source                 1..350
                       mol_type = protein
                       organism = Papaver rhoeas
SEQUENCE: 80
GNGLSVPSVQ ELAKQTLAEI PSRYICTDEN PLITGASVVD DETVPVINLQ NLLSPEPVIG  60
KLELDKLHSA CKEWGFFQVV NHGVNDSLVD SVKSEIEGFF NLPANEKLKY GQKDGDVEGF  120
GQHFVVSEDQ KLDWADVFYM VTLPVRLRKP HLFPELPLPL RDTLDSYSSE LNKLSMVLLE  180
MMEKALKLVE CKGITDFFED GFQQMRMNYY PPCPRPELVT GLTSHSDFGG LTILLQLNDV  240
EGLQIKKEER WISIKPLPNA FIVNIGDVLE IMSNGIYRSV DHRAVINSTK VRMSVATFHD  300
PRLEAVIGPI SSLITPETPA LFKRGVFEDL LKEMFLRKLD GKSFLDCMRI             350

SEQ ID NO: 81          moltype = AA  length = 351
FEATURE                Location/Qualifiers
source                 1..351
                       mol_type = protein
                       note = subspecies: setigerum
                       organism = Papaver somniferum
SEQUENCE: 81
LMKLANGMSV PIVQELAKLT VGEIPSRYIC TDGNLLTMGA SVIDYETVPV IDLQNLQSRE  60
PVIEKLELDR LHSACKEWGF FQLLNHGVDA SLMDNVRSEI RGFFNLPISD KMKYGQKDGD  120
EEGFGQHFIV SEDQKLDWVD AFMMFTLPLH SRNPRLTPEF PQPLRETVES YSSEMKKLSV  180
LLFELMEKAL QVKGITEMFE DGLQSIRMNY YPPCPRPELA IGLTSHSDFD GLTILLQLNE  240
VEGLQIKKEE RWISIKPLPN AFIVNVGDVL EVMTNGIYRS VDHRAVVNST KERLSIATFH  300
DPELESEIGP IASLITPETP ALFKRGRFKD LLKENLSTKL DGKSFLDCIR M            351

SEQ ID NO: 82          moltype = AA  length = 497
FEATURE                Location/Qualifiers
source                 1..497
                       mol_type = protein
                       organism = Homo sapiens
SEQUENCE: 82
MGLEALVPLA VIVAIFLLLV DLMHRRQRWA ARYSPGPLPL PGLGNLLHVD FQNTPYCFDQ  60
LRRRFGDVFS LQLAWTPVVV LNGLAAVREA LVTHGEDTAD RPPVPITQIL GFGPRSQGVF  120
LARYGPAWRE QRRFSVSTLR NLGLGKKSLE QWVTEEAACL CAAFANHSGR PFRPNGLLDK  180
AVSNVIASLT CGRRFEYDDP RFLRLLDLAQ EGLKEESGFL REVLNAVPVL LHIPALAGKV  240
LRFQKAFLTQ LDELLTEHRM TWDPAQPPRD LTEAFLAEME KAKGNPESSF NDENLRIVVA  300
```

-continued

```
DLFSAGMVTT STTLAWGLLL MILHPDVQRR VQQEIDDVIG QVRRPEMGDQ AHMPYTTAVI  360
HEVQRFGDIV PLGVTHMTSR DIEVQGFRIP KGTTLITNLS SVLKDEAVWE KPFRFHPEHF  420
LDAQGHFVKP EAFLPFSAGR RACLGEPLAR MELFLFFTSL LQHFSFSVPT GQPRPSHHGV  480
FAFLVTPSPY ELCAVPR                                                 497

SEQ ID NO: 83          moltype = AA  length = 1049
FEATURE                Location/Qualifiers
source                 1..1049
                       mol_type = protein
                       organism = Bacillus megaterium
SEQUENCE: 83
MTIKEMPQPK TFGELKNLPL LNTDKPVQAL MKIADELGEI FKFEAPGRVT RYLSSQRLIK  60
EACDESRFDK NLSQAAKFAR DFAGDGLVTS WTHEKNWKKA HNILLPSFSQ QAMKGYHAMM  120
VDIAVQLVQK WERLNADEHI EVSEDMTRLT LDTIGLCGFN YRFNSFYRDQ PHPFIISMVR  180
AADEVMNKLQ RANPDDPAYD ENKRQFQEDI KVMNDLVDKI IADRKARGEQ SDDLLTQMLN  240
GKDPETGEPL DDGNIRYQII TFLIAGHETT SGLLSFALYF LVKNPHVLQK VAEEAARVLV  300
DPVPSYKQVK QLKYVGMVLN EALRLWPTAP AFSLYAKEDT VLGGEYPLEK GDEVMVLIPQ  360
LHRDKTVWGD DVEEFRPERF ENPSAIPQHA FKPFGNGQRA CIGQQFALHE ATLVLGMMLK  420
HFDFEDHTNY ELDIKETLTL KPKGFVVKAK SKKIPLGGIP SPSTEQSAKK VRKKAENAHN  480
TPLLVLYGSN MGTAEGTARD LADIAMSKGF APQVATLDSH AGNLPREGAV LIVTASYNGH  540
PPDNAKQFVD WLDQASADEV KGVRYSVFGC GDKNWATTYQ KVPAFIDETL AAKGAENIAD  600
RGEADASDDF EGTYEEWREH MWSDVAAYFN LDIENSEDNK STLSLQFVDS AADMPLAKMH  660
GAFSTNVVAS KELQQPGSAR STRHLEIELP KEASYQEGDH LGVIPRNYEG IVNRVTARFG  720
LDASQQIRLE AEEEKLAHLP LAKTVSVEEL LQYVELQDPV TRTQLRAMAA KTVCPPHKVE  780
LEALLEKQAY KEQVLAKRLT MLELLEKYPA CEMKFSEFIA LLPSIRPRYY SISSSPRVDE  840
KQASITVSVV SGEAWSGYGE YKGIASNYLA ELQEGDTITC FISTPQSEFT LPKDPETPLI  900
MVGPGTGVAP FRGFVQARKQ LKEQGQSLGE AHLYFGCRSP HEDYLYQEEL ENAQSEGIIT  960
LHTAFSRMPN QPKTYVQHVM EQDGKKLIEL LDQGAHFYIC GDGSQMAPAV EATLMKSYAD  1020
VHQVSEADAR LWLQQLEEKG RYAKDVWAG                                    1049

SEQ ID NO: 84          moltype = AA  length = 503
FEATURE                Location/Qualifiers
source                 1..503
                       mol_type = protein
                       organism = Homo sapiens
SEQUENCE: 84
MALIPDLAME TWLLLAVSLV LLYLYGTHSH GLFKKLGIPG PTPLPFLGNI LSYHKGFCMF  60
DMECHKKYGK VWGFYDGQQP VLAITDPDMI KTVLVKECYS VFTNRRPFGP VGFMKSAISI  120
AEDEEWKRLR SLLSPTFTSG KLKEMVPIIA QYGDVLVRNL RREAETGKPV TLKDVFGAYS  180
MDVITSTSFG VNIDSLNNPQ DPFVENTKKL LRFDFLDPFF LSITVFPFLI PILEVLNICV  240
FPREVTNFLR KSVKRMKESR LEDTQKHRVD FLQLMIDSQN SKETESHKAL SDLELVAQSI  300
IFIFAGYETT SSVLSFIMYE LATHPDVQQK LQEEIDAVLP NKAPPTYDTV LQMEYLDMVV  360
NETLRLFPIA MRLERVCKKD VEINGMFIPK GVVVMIPSYA LHRDPKYWTE PEKFLPERFS  420
KKNKDNIDPY IYTPFGSGPR NCIGMRFALM NMKLALIRVL QNFSFKPCKE TQIPLKLSLG  480
GLLQPEKPVV LKVESRDGTV SGA                                          503

SEQ ID NO: 85          moltype = AA  length = 502
FEATURE                Location/Qualifiers
source                 1..502
                       mol_type = protein
                       organism = Homo sapiens
SEQUENCE: 85
MALIPDLAME TWLLLAVSLV LLYLYGTHSH GLFKKLGIPG PTPLPFLGNI LSYHKGFCMF  60
DMECHKKYGK VWGFYDGQQP VLAITDPDMI KTVLVKECYS VFTNRRPFGP VGFMKSAISI  120
AEDEEWKRLR SLLSPTFTSG KLKEMVPIIA QYGDVLVRNL RREAETGKPV TLKDVFGAYS  180
MDVITSTSFG VNIDSLNNPQ DPFVENTKKL LRFDFLDPFF LSIIFPFLIP ILEVLNICVF  240
PREVTNFLRK SVKRMKESRL EDTQKHRVDF LQLMIDSQNS KETESHKALS DLELVAQSII  300
FIFAGYETTS SVLSFIMYEL ATHPDVQQKL QEEIDAVLPN KAPPTYDTVL QMEYLDMVVN  360
ETLRLFPIAM RLERVCKKDV EINGMFIPKG VVVMIPSYAL HRDPKYWTEP EKFLPERFSK  420
KNKDNIDPYI YTPFGSGPRN CIGMRFALMN MKLALIRVLQ NFSFKPCKET QIPLKLSLGG  480
LLQPEKPVVL KVESRDGTVS GA                                           502

SEQ ID NO: 86          moltype = AA  length = 534
FEATURE                Location/Qualifiers
source                 1..534
                       mol_type = protein
                       organism = Menispermum canadense
SEQUENCE: 86
MIMMFIDYYS SWLPQTLLLQ SILLAVSLVI FINLFLTRRR SYSSKSHTNI IHPPKAAGAL  60
PVIGHLYTLF RGLSAGVPLY RQLDAMADRY GPAFIIHLGV YPTLVVTCRE LAKECFTTND  120
QTFATRPSTC AGKYIGYNYA FFGFAPYGPY WREARKIATV ELLSNYRLDS LRHVREAEVG  180
RNVDELYALH ASSSTNKQNM MKIDMKQWFD QVTLNVILMM VVGKRCVTTG GNEEEVRVVK  240
VLHEFFKHLG TLSVSDVVPY VEWMDLDGNI GRMKSTAKEL DCILGRWLEE HRRERRSDFM  300
DAMLAMVEGI KIPYYDSDTV IKAICLNLLN AGSDTLGITM TWALSLLLNN RHVLKKVKDE  360
LDVHVGKNRQ VEELDVKNLV YLHAVVKETL RLFPPAPLGV PHEAMEDCVV GGFHVAKGTR  420
LVVNVWKLHR DPSVWSDPLA FKPERFLDNN TVDVRGQHFQ LLPFGSGRRG CPGITFALQV  480
AHLTLARLLH GFEWDTPDGA PVDMSEVSVL TTAKKNPVEV LFTPRLPAEV YTQN        534

SEQ ID NO: 87          moltype = AA  length = 527
```

```
FEATURE                 Location/Qualifiers
source                  1..527
                        mol_type = protein
                        organism = Nigella sativa
SEQUENCE: 87
MLSIHDSTMV FLQLQAICGI FGFIFIITWW TRWKSSNKMK APEVAGAWPV IGHLHLLGGG  60
RPLYQLLGDM SDKYGPAFTL RMGIQKALVV SSWEVAKECL TTNDRALATR PSSAGGKYMG  120
YNNALIPFSP YGPYWRDMRK IATLELLSNH RLEELKHVRE MEINTCISDM YKLCQVEDGV  180
EIKPISVDLS QWFADLTFNV VVMMITGKRY IGSTDAGDMN EIRHFQAALV KFMRLLRISL  240
LVDVFPVLQW INYGGFKGVM KSTARDIDSV LENWLQEHQR KRLSPDFNGN HDFIDVMIST  300
LEGTEFSDYD HNTIIKAISM AMVVGGTDTT TTTLIWAISL LLNNPNAMKK VQEELEIHVG  360
KERNVDGSDI QHLVYLQAVV KETLRLYPPV PLSVMHQAME DCVIGSYNIQ AGTRVLFNLW  420
KLHRDSSVWS DPLEFRPERF LTSHVDVDVR GQHFELIPFG SGRRSCPGIS FALQVIHLTI  480
ARLFHGFNLT TPGNSSVDMS EISGATLSKV TPLEVLVTPR LSSKLYN                527

SEQ ID NO: 88           moltype = AA  length = 525
FEATURE                 Location/Qualifiers
source                  1..525
                        mol_type = protein
                        organism = Hydrastis canadensis
SEQUENCE: 88
MDSLLQLQII GALAALIFTY KLLKVICRSP MTDGMEAPEP PGAWPIIGHL HLLGGQDPIA  60
RTLGVMTDKY GPILKLRLGV HTGLVVSNWE LAKECFTTND RVLASRPMGA AGKYLGYNYA  120
IFGLAPHGPY WSEVRKIVLR ELLSNQSLEK LKHVRISEIN TCLKNLFSLN NGNTPIKVDM  180
KQWFERPMFN VVTMMIAGKR YFSMENDNEA MNFRKVATEF MYLTGVFVVS DALPYLEWLD  240
LQGHVSAMKR TAKELDIHVG KWLEEHRRAK LLGETKNEDD FVDVLLTILP EDLKDNQTYI  300
HDRDTIIKAT ALALFLAASD TTAITLTWAL SLILNNPDVL KRAQDELDKH VGKEKLVKES  360
DIINLVYLQA IIKETLRLYP AAPLLLPHEA MEDCTVGGYH VPKGTRIFVN IWKLQRDPRV  420
WFDPNEFRPE RFLTTHANVD FKGQHFEYIP FSSGRRVCPG ITFSTQIMHL TLAHLLHEFN  480
IVTPTKSNAG VDMTESLGIT MPKATPLEVL LTPRLPSNLY NQYRD                  525

SEQ ID NO: 89           moltype = AA  length = 550
FEATURE                 Location/Qualifiers
source                  1..550
                        mol_type = protein
                        organism = Eschscholzia californica
SEQUENCE: 89
MNLLIFFQFL LQFQVLVGLS VLLAFSYYLW VSKNPKINKF KGKGALLAPQ AAGAWPIVGH  60
LPQLVGPKPL FRILGAMADN YGPIFMLRFG VHPTVVVSSW EMTKECFTTN DRHLASRPSN  120
AASQYLIYEV YALFGFSLYG SSYWRDARKI ATLELLSHRR LELLKHVPYT EIDTCIKQLH  180
RLWTKNNKNQ NNPELKVEMN QFFTDLTMNV ILKLVVGKRF FNVDDAADHE KEEARKIQGT  240
IFEFFKLTEG SVSAGALPLL NWLDLNGQKR AMKRTAKKMD SIAEKLLDEH RQKRLSKEGV  300
KGTHDHNDFM DVLLSILDAD QGDYSHHPFN YSRDHVIKAT TLSMILSSMS ISVSLSWALS  360
LLLNNRHVLK KAQDELDMNV GKDRQVEEGD IKNLVYLQAI VKETFRMYPA NPLLLPHEAI  420
EDCKIGGFNV PAGTRVVVNA WKLQHDPRVW SNPSEFKPER FLNDQAAKVV DVRGQNFEYL  480
PFGSGRRVCP GISFSLQTIH MSLARLVQAF ELGTPSNERI DMTEGSGLTM PKTTPLHVLL  540
NPRLPLPLYE                                                         550

SEQ ID NO: 90           moltype = AA  length = 537
FEATURE                 Location/Qualifiers
source                  1..537
                        mol_type = protein
                        organism = Glaucium flavum
SEQUENCE: 90
MELINSLEIQ PITISILALL TVSILLYKII WNHGSRKNNK SNKNNRKTSS SAGVVEIPGA  60
WPIIGHLHLF NGSEQMFHKL GSLADQYGPA PFFIRFGSRK YVVVSNWELV KTCFTAQSQI  120
FVSRPPMLAM NILFFPKDSL SYIQHGDHWR ELRKISSTKL LSSHRVETQK HLIASEVDYC  180
FKQLYKLSNN GEFTLVRLNT WCEDMALNVH VRMIAGMKNY VAAPGSGEYG GQARRYRKAL  240
EEALDLLNQF TITDVVPWLG WLDHFRDVVG RMKRCGAELD SIFATWVEEH RVKRASGKGG  300
DVEPDFIDLC WESMEQLPGN DPATVIKLMC KEHIFNGSGT SSLTLAWILS LIMNNPYVIK  360
KAREELEKHV GNHRQVEESD LPNLLYIQAI IKEGMRLYTP GPFIDRNTTE DYEINGVHIP  420
AGTCLYVNLW KIHRDPNVYE DPLEFKPERF LKNNSDLDLK GQNYQLLPFG AGRRICPGVS  480
LALPLMYLTV SRLIHGFDMK LPKGVEKADM TAHGGVINQR AYPLEVLLKP RLTFQQA      537

SEQ ID NO: 91           moltype = AA  length = 568
FEATURE                 Location/Qualifiers
source                  1..568
                        mol_type = protein
                        organism = Stylophorum diphyllum
SEQUENCE: 91
MTIGALALLS FIYFLRVSVI KRTKYTNTAV TATNKLENDE DEANHSKRVV APPEVAGAWP  60
ILGHLPQLVG LKQPLFRVLG DMADKYGPIF IVRFGMYPTL VVSSWEMAKE CFTTNDRVLA  120
SRPASASGKY LTYNYAMFGF TNGPYWREIR KISMLELLSH RRVELLKHVP STEIDSSIKQ  180
LYHLWVENQN QNKQGDHQVK VDMSQLLRDL TLNIVLKLVV GKRLFNNNDM DHEQDEAARK  240
LQKTMVELIK VAGASVASDA LPFLGWLDVD GLKRTMKRIA KEIDVIAERW LQEHRQKKLT  300
SNDKGGSNNI QGGGGDNDFM DVMLSILDDD SNFFINYNRD TVIKATSLTM ILAGSDTTTL  360
SLTWALTLLA TNPGALRKAQ DELDTKVGRD RQVDERDIKN LVYLQAIVKE TLRMYPAAPL  420
AIPHEATQDC IVGGYHVTAG TRVWVNLWKL QRDPHAWPNP SEFRPERFLA VENDCKQQGT  480
CDGEAANMDF RGQHFEYMPF GSGRRMCPGI NFAIQIIHMT LARLLHSFEL RVPEEEVIDM  540
```

-continued

```
AEDSGLTISK VTPLELLLTP RLPLPLYI                                   568

SEQ ID NO: 92          moltype = AA  length = 561
FEATURE                Location/Qualifiers
source                 1..561
                       mol_type = protein
                       organism = Stylophorum diphyllum
SEQUENCE: 92
FCQFQGIVGI LLAFLTFLYY LWRASITGLR TKPKHNDFKV TKAAPEADGA WPIVGHFAQF  60
IGPRPLFRIL GDMADKYGSI FMVRFGMYPT LVVSSWEMAK ECFTTNDRFL ASRPASAAGK  120
YLTYDFAMLS FSFYGPYWRE IRKISMLELL SHRRVELLKH VPSTEIDSSI KQLYHLWVEN  180
QNQNKQGDHQ VKVDMSQLLR DLTLNIVLKL VVGKRLFNNN DMDHEQDEAA RKLQKTMVEL  240
IKVAGASVAS DALPFLGWLD VDGLKRTMKR IAKEIDVIAE RWLQEHRQKK LTSNDKGGSN  300
NIQGGGGDND FMDVMLSILD DDSNFFINYN RDTVIKATSL TMILAGSDTT TLSLTWALTL  360
LATYPLCALR KAQDELDTKV GRDRQVDERD IKNLVYLQAI VKETLRMYPA APLAIPHEAT  420
QDCIVGGYHV TAGTRVWVNL WKLQRDPHAW PNPSEFRPER FLAVENDCKQ QGTCDGEAAN  480
MDFRGQHFEY MPFGSGRRMC PGINFAIQII HMTLARLLHS FELRVPEEEV IDMAEDSGLT  540
ISKVTPLELL LTPRLPLPLY I                                          561

SEQ ID NO: 93          moltype = AA  length = 561
FEATURE                Location/Qualifiers
source                 1..561
                       mol_type = protein
                       organism = Chelidonium majus
SEQUENCE: 93
MDLFIFFSRF QYIVGLLAFL TFFYYLWRVS ITGTRIKTNQ NIMNGTNMMA PEAAGAWPIV  60
GHLPQLVGPQ PLFKILGDMA DKYGSIFMVR FGMHPTLVVS SWEMAKECFT TNDKFLASRP  120
TSAGGKYLTY DFAMFGFSFY GPYWREIRKI STLELLSHRR VELLKHVPYT EIGGSIKQLY  180
KLWMETQNQN KQRDDHQVKV DMSQVFGYLT LNTVLKLVVG KGLFNNNDMN HEQEEGRKLH  240
ETVLEFFKLA GVSVASDALP FLGWLDVDGQ KRSMKRIAKE MDLIAERWLQ EHRQKRLTSN  300
NKASSGHDDF MSVLLSILDD DSNFFNYNRD TVIKATSLNL ILAASDTTSV SLTWVLSLLV  360
TNPGALKKVQ DELDTKVGRN RHVEERDIEK LVYLQATVKE TLRMYPAGPL SVPHEATQDC  420
TVGGYQVTAG TRLVVNVWKL QRDPRVWPNP SEFKPERFLP DGCEVGCGEA ANMDFRGQHF  480
EYIPFGSGRR MCPGIDFAIQ IIHMTLACLL HAFEFQVPSS LDKHLVPAVI DMSEGSGLTM  540
PKVTPLEVLL NPRLPLPLYE L                                          561

SEQ ID NO: 94          moltype = AA  length = 561
FEATURE                Location/Qualifiers
source                 1..561
                       mol_type = protein
                       organism = Eschscholzia californica
SEQUENCE: 94
MEKPILLQLQ PGILGLLALM CFLYYVIKVS LSTRNCNQLV RHPPEAAGSW PIVGHLPQLV  60
GSGKPLFRVL GDMADKFGPI FMVRFGVHPT LVVSSWEMAK ECFTSNDKFL ASRPPSAASI  120
YMAYDHAMLG FSSYGPYWRE IRKISTLHLL SHRRLELLKH VPHLEIHNFI KGLYGIWKDH  180
QKQQQQPTAR DDQDSVMLEM SQLFGYLTLN IVLSLVVGKR VCNYHADGHL DDGEEAGQGQ  240
KLHQTITDFF KLSGVSVASD ALPFLGLFDL DGQKKIMKRV AKEMDFVAER WLQDKKSSLL  300
LSSKSNNKQN EAGEGDVDDF MDVLMSTLPD DDDSFFTKYS RDTVIKANSL SMVVAGSDTT  360
SVSLTWALSL LLNNIQVLRK AQDELDTKVG RDRHVEEKDI DNLVYLQAIV KETLRMYPAG  420
PLSVPHEAIE DCNVGGYHIK TGTRLLVNIW KLQRDPRVWS NPSEFRPERF LDNQSNGTLL  480
DFRGQHFEYI PFGSGRRMCP GVNLATPILH MTLARLLQSF DLTTPSSSPV DMTEGSGLTM  540
PKVTPLKVLL TPRLPLPLYD Y                                          561

SEQ ID NO: 95          moltype = AA  length = 567
FEATURE                Location/Qualifiers
source                 1..567
                       mol_type = protein
                       organism = Papaver bracteatum
SEQUENCE: 95
MDVAIIVDHH YLQPFVSIAG LLALLSFFYC IWVFIIRPRI IKSNLDERKL SPSSPPEVAG  60
AWPIVGHLPQ LIGSTPLFKI LADMSNKYGP IFMVRFGMYP TLVVSSWEMS KECFTTNDRL  120
FATRPPSAAG KYLTKALFAF SVYGPYWREI RKISTIHLLS LRRLELLKHG RYLEIDKCMK  180
RLFEYWMEHH KNIISTTSSV KVNMSQVFAE LSLNVVLKII VGKTLFIKNG NEDYTKEEEE  240
GQKLHKTILK FMELAGVSVA SDVLPFLGWL DVDGQKKQMK RVYKEMNLIA SKWLGEHRER  300
KRLQIIQKRG AARGSNYDDG NDFMDVLMSI LDEENDDLFF GYSRDTVIKS TCLQLIVAAS  360
DTTSLAMTWA LSLLLTNPNV LQKAQDELDT KVGRDRIIEE HDIECLVYLQ AIVKETLRLY  420
PPAPLSLPHE AMEDCTVGGY QVKAGTRLVV NLWKLQRDPR VWSNPLEFKP ERFLPQSDGG  480
FGGEEARMDF RGQHFEYTPF GSGRRICPGI DFFLQTVHMA LARLLQAFDF NTAGGLVIDM  540
VEGPGLTMPK VTPLEVHLNP RLPVTLY                                    567

SEQ ID NO: 96          moltype = AA  length = 558
FEATURE                Location/Qualifiers
source                 1..558
                       mol_type = protein
                       organism = Papaver bracteatum
SEQUENCE: 96
MQVDWPNILQ KYYPIITCSL LTLLSFYYIW VSITKPSRNS KTKLPPPEVA GSWPIVGHLP  60
QLVGSTPLFK ILANMSDKYG PIFMVRFGMH PTLVVSSWEM SKECFTTNDK FLASRPPSAS  120
AKYLGYDNAM FVFSDYGPYW REIRKISTLQ LLTHKRLDSL KNIPYLEINS CVKTLYTRWA  180
```

```
KTQSQIKQNV GGAADDFVKV DMTEMFGHLN LNVVLRLVVG KPIFIQKDNA DEDYTKDGHN  240
KEELGQKLHK TIIEFFELAG ASVASDVLPY LGWLDVDGQK KRMKKIAMEM DLFAQKWLEE  300
HRQKGINHDN ENDFMAVLIS VLGEGKDDHI FGYSRDTVIK ATCLTLIVAA TDTTLVSLTW  360
ALSLLLTNPR VLSKAQDELD TVVGKERNVE DRDVNHLVYL QAVIKETLRL YPPSPLAVPH  420
EAIENCNVGG YEVKARTRLL VNLWKIHRDP RVWSNPLEFK PERFLPKLDG GTGEASKLDF  480
KGQDFVYTPF GSGRRMCPGI NFASQTLHMT LARLLHAFDF DIESNGLVID MTEGSGLTMP  540
KVTPLQVHLR PRLPATLY                                               558

SEQ ID NO: 97          moltype = AA  length = 571
FEATURE                Location/Qualifiers
source                 1..571
                       mol_type = protein
                       organism = Papaver bracteatum
SEQUENCE: 97
MMDLAMFIDQ YFSLAKIAGL LALLSFFYYL WISTLWSPRN PKLSSVSPPE VAGAWPILGH  60
LPQLLGSRPL FKILADMSDN YGPIFMVRFG MHPTLVVSSW EMAKECFTTN DRFLAGRPSG  120
AANKYLTFAL FGFSTYGPYW REIRKIATLH LLSHRRLELL KHVPDLEVTN CMKHLHRRWI  180
DSQNQIKQND AAAGSVKVDM GRVFGELTLN VVLKLVAGKS IFFKNDNTRQ YDSKDGHNKE  240
EEEGKKLHKT IIDFYSLAGA SVASDVLPFL GWLDVDGQKK RMKRVAKDMD FIAAKWLEEH  300
RHQKRQTVLS SSATLGSSNH DDAKDFMDVL MSILDGENDD LFFGYSRDTV IKTTCLQLIA  360
AAADTTSVTM TWALALLITN PTILRKAQDE LDTKVGKDRN IEERDINDLV YLQAIVKETL  420
RMYPAGPLNV PHEAIADCNI GGYEVRAGTR LLVNLWKMHR DPRVWSNPSE FKPERFLPQL  480
DGGSGGEAAN LDFRGQDFEY LPFSAGRRMC PGIDFSLQTL HMTLARLLHG FDFNNDSAGI  540
IIDMEEGSGL TMPKLTPLEI YLCPRLPAKL Y                                571

SEQ ID NO: 98          moltype = AA  length = 361
FEATURE                Location/Qualifiers
source                 1..361
                       mol_type = protein
                       organism = Thalictrum flavum
SEQUENCE: 98
MAVEGKQVAP KKAIIVELLK KLELGLVPDD EIKKLIRIQL GRRLQWGCKS TYEEQIAQLV  60
NLTHSLRQMK IATEVETLDD QMYEVPIDFL KIMNGSNLKG SCCYFKNDST TLDEAEIAML  120
ELYCERAQIK DGHSVLDLGC GQGALTLYVA QKYKNSRVTA VTNSVSQKEF IEEESRKRNL  180
SNVEVLLADI TTHKMPDTYD RILVVELFEH MKNYELLLRK IKEWMAKDGL LFVEHICHKT  240
FAYHYEPIDE DDWFTEYVFP AGTMIIPSAS FFLYFQDDVS VVNHWTLSGK HFSRTNEEWL  300
KRLDANVELI KPMFVTITGQ CRQEAMKLIN YWRGFCLSGM EMFGYNNGEE WMASHVLFKK  360
K                                                                 361

SEQ ID NO: 99          moltype = AA  length = 358
FEATURE                Location/Qualifiers
source                 1..358
                       mol_type = protein
                       organism = Coptis japonica
SEQUENCE: 99
MAVEAKQTKK AAIVELLKQL ELGLVPYDDI KQLIRRELAR RLQWGYKPTY EEQIAEIQNL  60
THSLRQMKIA TEVETLDSQL YEIPIEFLKI MNGSNLKGSC CYFKEDSTTL DEAEIAMLDL  120
YCERAQIQDG QSVLDLGCGQ GALTLHVAQK YKNCRVTAVT NSVSQKEYIE EESRRRNLLN  180
VEVKLADITT HEMAETYDRI LVIELFEHMK NYELLLRKIS EWISKDGLLF LEHICHKTFA  240
YHYEPLDDDD WFTEYVFPAG TMIIPSASFF LYFQDDVSVV NHWTLSGKHF SRTNEEWLKR  300
LDANLDVIKP MFETLMGNEE EAVKLINYWR GFCLSGMEMF GYNNGEEWMA SHVLFKKK    358

SEQ ID NO: 100         moltype = AA  length = 351
FEATURE                Location/Qualifiers
source                 1..351
                       mol_type = protein
                       organism = Papaver somniferum
SEQUENCE: 100
MQLKAKEELL RNMELGLIPD QEIRQLIRVE LEKRLQWGYK ETHEEQLSQL LDLVHSLKGM  60
KMATEMENLD LKLYEAPMEF LKIQHGSNMK QSAGYYTDES TTLDEAEIAM LDLYMERAQI  120
KDGQSVLDLG CGLGAVALFG ANKFKKCQFT GVTSSVEQKD YIEGKCKELK LTNVKVLLAD  180
ITTYETEERF DRIFAVELIE HMKNYQLLLK KISEWMKDDG LLFVEHVCHK TLAYHYEPVD  240
AEDWYTNYIF PAGTLTLSSA SMLLYFQDDV SVVNQWTLSG KHYSRSHEEW LKNMDKNIVE  300
FKEIMRSITK TEKEAIKLLN FWRIFCMCGA ELFGYKNGEE WMLTHLLFKK K           351

SEQ ID NO: 101         moltype = AA  length = 358
FEATURE                Location/Qualifiers
source                 1..358
                       mol_type = protein
                       organism = Papaver somniferum
SEQUENCE: 101
MGSIDEVKKE SAGETLGRLL KGEIKDEELK KLIKFQFEKR LQWGYKSSHQ EQLSFNLDFI  60
KSLKKMEMSG EIETMNKETY ELPSEFLEAV FGKTVKQSMC YFTHESATID EAEEAAHELY  120
CERAQIKDGQ TVLDIGCGQG GLVLYIAQKY KNCHVTGLTN SKAQVNYLLK QAEKLGLTNV  180
DAILADVTQY ESDKTYDRLL MIEAIEHMKN LQLFMKKLST WMTKESLLFV DHVCHKTFAH  240
FFEAVDEDDW YSGFIFPPGC ATILAANSLL YFQDDVSVVD HWVVNGMHMA RSVDIWRKAL  300
DKNMEAAKEI LLPGLGGSHE TVNGVVTHIR TFCMGGYEQF SMNNGDEWMV AQLLFKKK    358

SEQ ID NO: 102         moltype = AA  length = 350
```

-continued

```
FEATURE                Location/Qualifiers
source                 1..350
                       mol_type = protein
                       organism = Eschscholzia californica
SEQUENCE: 102
MGSSAGEIMG RLMKGEIEDE ELKKLIRHQW DRRIEWGYKP THEKQLAFNL DFIKGLKEMV  60
MSGEIDTMNK ETYELPTAFL EAVFGKTVKQ SCCYFKDENS TIDEAEEAAH ELYCERAQIK  120
DGQTVLDIGC GQGGLVLYIA EKYKNCHVTG LTNSKAQANY IEQQAEKLEL TNVDVIFADV  180
TKFDTDKTYD RILVVETIEH MKNIQLFMKK LSTWMTEDSL LFVDHISHKT FNHNFEALDE  240
DDWYSGFIFP KGCVTILSSS TLLYFQDDVS ALDHWVVNGM HMARSVEAWR KKLDETIEAA  300
REILEPGLGS KEAVNQVITH IRTFCIGGYE QFSYNNGEEW MITQILFKKK            350

SEQ ID NO: 103         moltype = AA  length = 363
FEATURE                Location/Qualifiers
source                 1..363
                       mol_type = protein
                       organism = Papaver somniferum
SEQUENCE: 103
MSTTMETTKI SQQDDLWKNM ELGQISDEEV RRLMKIGIEK RIKWGTKPTQ QEQLAQLLDF  60
NKSLRGMKMA TEIDTLENHK IYETPESFNQ IIGGKESAGL FTDETTTTME EANTKMMDLY  120
CERAGLKDGH TILDLGCGAG LLVLHLAKKY KKSKITGITN TSSHKEYILK QCKNLNLSNV  180
EIILADVTKV DIESTFDRVF VIGLIEHMKN FELFLRKISK WMKDDGLLLL EHLCHKSFSD  240
HWEPLSEDDW YAKNFFPSGT LVIPSATCLL YFQEDVTVID HWILSGNNFA RSNEVILKRI  300
DGKIEEVKDI FMSFYGIGRE EAVKLINWWR LLCITANELF KYNNGEEWLI SQLLFKKKLM  360
TCI                                                               363

SEQ ID NO: 104         moltype = AA  length = 356
FEATURE                Location/Qualifiers
source                 1..356
                       mol_type = protein
                       organism = Thalictrum flavum
SEQUENCE: 104
METKQTKKEA VANLIKRIEH GEVSDEEIRG MMKIQVQKRL KWGYKPTHEQ QLAQLVTFAQ  60
SLKGMEMAEE VDTLDAELYE IPLPFLHIMC GKTLKFSPGY FKDESTTLDE SEVYMMDLYC  120
ERAQIKDGQS ILDLGCGHGS LTLHVAQKYR GCKVTGITNS VSQKEFIMDQ CKKLDLSNVE  180
IILEDVTKFE TEITYDRIFA VALIEHMKNY ELFLKKVSTW IAQYGLLFVE HHCHKVFAYQ  240
YEPLDEDDWY TEYIFPSGTL VMSSSSILLY FQEDVSVVNH WTLSGKHPSL GFKQWLKRLD  300
DNIDEVKEIF ESFYGSKEKA MKFITYWRVF CIAHSQMYST NNGEEWMLSQ VLFKKK      356

SEQ ID NO: 105         moltype = AA  length = 358
FEATURE                Location/Qualifiers
source                 1..358
                       mol_type = protein
                       organism = Papaver bracteatum
SEQUENCE: 105
MGSIDEVKKE SAGETLGRLL KGEIKDEELK KLIKFQFEKR LQWGYKSSHQ EQLSFNLDFI  60
KSLKKMEMSG EIETMNKETY ELPSEFLEAV FGKTVKQSMC YFKHESATID EAEEAAHELY  120
CERAQIKDGQ TVLDIGCGQG GLVLYIARKY KKCHVTGLTN SKAQVNYLLK QAEKLGLTNV  180
DAILADVTQY ESDKTYDRLL MIEAIEHMKN LQLFMKKLST WMTEESLLFV DHVCHKTFAH  240
FFEAVDEDDW YSGFIFPPGC ATILAANSLL YFQDDVSVVD HWVVNGMHMA RSVDIWRKAL  300
DKNMEAAKEI LLPGLGGSHE AVNGVVTHIR TFCMGGYEQF SMNDGDEWMV AQLLFKKK    358

SEQ ID NO: 106         moltype = AA  length = 358
FEATURE                Location/Qualifiers
source                 1..358
                       mol_type = protein
                       organism = Papaver bracteatum
SEQUENCE: 106
MGSIEEVKKE SAEETLGRLL RGEINDEELK KLIKYQLEKR LQWGYKSSHQ EQLSFNLDFI  60
NSLKKMGMSG QVEAFTNEVY ELPTECFEAA YGKSMKLSGC YFKHESSTID EAEEASHELY  120
CERAQIKDGQ TVLDIGCGQG GLVLYVAQKY KNCHVTGLTN SKEQVNYILK QAEKLGLRNV  180
DVILADVTQY ESDKTYDRIL VIGVVEHMKN MQLFIKKLST WMAEDSLLFV DHSCHKTFNH  240
FFEALDEDDW YSGYIFPPGC ATFLSADSLL YFQDDVSVVD HWVVNGMHFA RTVDAWRKKL  300
DKNMEAVKEI LLPGLGGNHE AVNGVITHIR TCCVGGYVQF SLNDGDEWMN AQLLFKKK    358

SEQ ID NO: 107         moltype = AA  length = 368
FEATURE                Location/Qualifiers
source                 1..368
                       mol_type = protein
                       organism = Argemone mexicana
SEQUENCE: 107
MCLFFAEKMG LMAEANNQQQ LKKEDLLKNM ELGLIPDEEI RKLIRVQLEK RLNWGYKSTH  60
EQQLSQLLHL VHSLKKMKIA TEMENLDLKL YEAPFSFVQI QHGSTIKESS GLFKDESTTL  120
DEAEIAMLDL YTKRAKIEDG QSVLDLGCGL GAVTLYVAQK FKNCYVTGIT SSVEQKDFIE  180
GRCKELKLSN VKVILADITT YETEEKYNRI FAVELIEHMK NYELLLRKIS EWMKQDGLLF  240
IEHVCHKTLA YHYEPLDEED WYTNYIFPAG TLTLSSATLL LYFQDDVAVV DQWTLSGKHY  300
SRSHEEWLKR IDGNIEEVKE IMKSITKSEE EAKKLLNFWR IFCMCGAELF GYKNGEEWMM  360
THILFKKK                                                          368
```

-continued

```
SEQ ID NO: 108         moltype = AA  length = 364
FEATURE                Location/Qualifiers
source                 1..364
                       mol_type = protein
                       organism = Glaucium flavum
SEQUENCE: 108
MDLMATSKQV KKKEELLKNM ELGLVPDEEI RRLIRIELEK RLKWGYKPTH QQQLAQLLDL  60
VHSLKKMKIA TEMESLDLKL YEAPFSFVQI KHGSTIKESS SYFKDESMTL DEAEIAMLDL  120
YVERAQIEDG QSVLDLGCGL GAVTLHVAKK YKNCHVTGLT NSVEQKDFIE GKCKELNLSN  180
VKVILADVTS HEMEDKFDRI FAVELIEHMK NYELLLRRIS KWMKDDGLLF IEHVCHKTFA  240
YHYEPIDEDD WYTEYIFPAG TLTLSSASLL LYFQDDVSVV NHWTLSGKHY SRSHEEWLKR  300
IDGNMDAVKE IMKSITKTEE EAVKLINFWR IFCMCGAELF GYKDGEEWMM SHVLFKKKQL  360
LQQC                                                               364

SEQ ID NO: 109         moltype = AA  length = 353
FEATURE                Location/Qualifiers
source                 1..353
                       mol_type = protein
                       organism = Eschscholzia californica
SEQUENCE: 109
MVDLKVEKEE LLKSMELGLV PDEDIRKHIR SQLEKRLKWG YKPNHEQQLA QLLDVIHSLK  60
KMKISKEYES FDLRLYEAPF DFHKIQLGTH LKESCSYYKD ESTTLDEAEG AMLDLYTQKA  120
KIEDGQSILD LGCGVGAVTL FVANKYKNCK VTGITSCQWQ KDFIENKCKE LNLTNVRVII  180
GDVTAYEMEE TFDRIFAIEL IEHMKNYELL LRKISKWMKD DGLLFIEHVC HKILAYPYEP  240
IDEEDWFTEY IFPGGTLTLS SASLLLYFQD DVSVVEHSSL NGKHYSRSHG EWLKNIDANI  300
DEVKGIMRSI TKTEEEAVRL VNFWRIFCMC GIELFGYNNG EEWMVSHILL KKK         353

SEQ ID NO: 110         moltype = AA  length = 359
FEATURE                Location/Qualifiers
source                 1..359
                       mol_type = protein
                       organism = Eschscholzia californica
SEQUENCE: 110
MAADLVVKKW NNKKELIDEM ELGLVGDEEI RELIRNDLEK RLKWGYKSNH EQQLAQLLHF  60
VHSLRGMKIA ADEVESFNIK VYEAPFSFNK IQLGSSLKES SCYYKHDETT LDEGEIAMME  120
LYTEKAQIKD GQSVLDLGCG LGSLTLYVAN KYPNCKVTGT TASLWHKDFI ESKCKEQELT  180
NVKIVLGDAT THEMEERFDR ILAIGLIEHL KNYGLLLGRI SKWLKDDGFL FIQHVCHKTL  240
AYPLVPVDEE DWIGEYIFPG GTLTMPSASL LLYFQDELSV VDHSTLNGKH FSRTHEEWLK  300
NIDAKIDEVK EILKSVTKTE EEVVRLTNFW RIFCMFGVEM FGYNEGEEWM LSQILFKKK   359

SEQ ID NO: 111         moltype = AA  length = 353
FEATURE                Location/Qualifiers
source                 1..353
                       mol_type = protein
                       organism = Chelidonium majus
SEQUENCE: 111
MASGKVVDLL KRLDSGLVSD EELRRVIRFE LERRLKWGYK PTHEQQLAEL LNLAHATKQM  60
EIATKIDTLN STMYEVPNSF LEIQLGSTLK ESCLYFKDES TTVDEAEIAM MDLYLERAQI  120
KDGQIILDLG CGLGALAFHI AQKYTNCNVT SVTNSVKQKE FIEEKCKILN VSNVKVILTD  180
ICTLEMEATF DRIFAIGLIE HMKNYELLLR KFSAWMKQDG LLFIEHLCHK TLGYHNEPID  240
EDDWYTAYFF PAGTLTFIPS SFLLYFQDDV SVVNHWTLSG KHFSRSNEEW LKRMDNKIDE  300
VKEIYKAAAS ETKDDDIMKL IRLWRFLSIS AAEMFGYKDG EEWMISQVLF KKK         353

SEQ ID NO: 112         moltype = AA  length = 366
FEATURE                Location/Qualifiers
source                 1..366
                       mol_type = protein
                       organism = Eschscholzia californica
SEQUENCE: 112
MASLVEEGSF VNNKESVKER VSELVKRLKN GLVSDEELRK LMRVELEKRL EWGYKSTHEQ  60
QLSQLIDLAH SMKKMEIAME IDALNSTVYE VPLSFLQIIH GTTIKESCLY FKDESTTVDE  120
AEIAMMDLYL ERAQIKDGQS ILDLGCGLGG FSFHIASKFT GCNITAVTNS VKQKEFIEEK  180
CKTLNVPNIK VILADICTTE IENVFDRIIA IGLIEHMKNY ELLLKKFSKW MTQDGLLFIE  240
HLCHKTFGYH NEPLDEDDWY TTYFFPAGTL TFIPSSFLLY FQDDVSVVDH WTLNGKHFAR  300
SNEEWLKRMD EKMDEVKQIF RSNLKSENEV TKTIGEWRFL SMSAAEMFGY NNGEEWMVSQ  360
LLFKKK                                                             366

SEQ ID NO: 113         moltype = AA  length = 362
FEATURE                Location/Qualifiers
source                 1..362
                       mol_type = protein
                       organism = Glaucium flavum
SEQUENCE: 113
MGSNETNGEL KTKEMVPDLL KRLESGLVAD EELRKLIRFE LERRLKWGYK PTHEQQLAEL  60
LKLAHSTKQM KIATETDSLN STMYEVPIPF LQLQFGSAIK ESCCYFKDES TTLDEAEVAM  120
MDLYLERTQI KDGQSILDLG CGLGALAFHI VQKYPNCNVL AITNSVEQKE FIEEKCKIRK  180
VENVKVSLAD ICTLEMKTTF DRIFAIGLLE HMKNYQLLLK KFSNWMKQDG LLFIEHLCHK  240
TLAYHYEPLD EDDWYTEYFF PAGTLTIISS SFLLYFQDDV SIVNHWSLSG KHFSRSNEEW  300
LKRMDMKIDE VKEILEAAFE NKDHDITKLI NHWRFLAINA TEMFGYNNGE EWMVSQVLFK  360
```

```
KK                                                            362

SEQ ID NO: 114         moltype = AA  length = 365
FEATURE                Location/Qualifiers
source                 1..365
                       mol_type = protein
                       organism = Sanguinaria canadensis
SEQUENCE: 114
MASDHEVSNK ELKKKKEVIT ELLKRLESGL VSDEELRGLI RFELERRLRW GYKPTHEQQL  60
AQLLNLAHSM KQMKIATEID ALNSTMYEVP IPFLQIQLGS TLKESCCYFK DESTTVDEAE  120
IAMMDLYLER AQIKDGQSIL DLGCGLGALA FHIAQKYTNC NITAITNSVR QKEFIEEKCK  180
ILNVSNVKVS LADICTLEME ATFDRIFAIG LIEHMKNYEL LLKKFSEWMK QDGLIFIEHL  240
CHKTLAYHYE PLDEDDWYTE YFFPAGTLTL ISSSFLLYFQ DDVSVVDHWT LSGKHFSRSN  300
EEWLKRMDEK IDEVKEIFES VSDSKDDDVT KLINHWRFFC ISSAEMFGYN NGEEWMISQV  360
LFKKK                                                         365

SEQ ID NO: 115         moltype = AA  length = 371
FEATURE                Location/Qualifiers
source                 1..371
                       mol_type = protein
                       organism = Corydalis cheilanthifolia
SEQUENCE: 115
MIKKSKIMAF SDHHHEVVKN HSKKEMIADL LKRLEAGLVP DEEMRNLFRF ELERRLQWGY  60
KSIHQEQLSQ LLKLAHSTKE MTIVAEMDAL NSSMYELPIS FLQIQLGSNL KQSSLYFKDE  120
LTTVDEAEVA IMDLYLERAQ IEDGQSILDL GCGLGAFSFH VARKYTNCNI TAVTNSLTQK  180
EFIEKKSKIL NIQNVKVIFA DVTTVEMETT FDRVFAIGLI EHMQNYELFL KKLSKWMKQD  240
GLLFIEHFCH KTLAYHYKPI DEDDWFTNLL YPNGTVISSS LLLYFQDDVS VVDHWSLSGK  300
HFSRASEESL KRMDAKMDEM KEIFESITDS KEEAMKLINQ WRIFCISCAE MFGYNNGEEW  360
MTSHFLFKKK L                                                  371

SEQ ID NO: 116         moltype = AA  length = 373
FEATURE                Location/Qualifiers
source                 1..373
                       mol_type = protein
                       organism = Corydalis cheilanthifolia
SEQUENCE: 116
MGSSTASDHE MVIMENDSKN KQVVIADLLK RLVGGLVPDE EMRNMFRFEL EKRLKWGYKS  60
THQQQLSQLL NLVELNKGIA KIAPEMDALN SAMYEVPIPY LKLMLGSTLK QSCLYFKDES  120
TTLDEAEIEM MDLYLERADI QDGQSILDLG CGLGGLGFHI AQKYISCNIT ALTNSLTQKE  180
FIEEKCKTLN IPNVKVILAD VTTVEIETTF DRLFAIGLVE HMENYELFLR KLSKWMKQDG  240
LLFIEHLCHK TLAYHYKPID EDDWYSNLLY PTGTLTSASF LLYFQDDLSV VDHWSLSGKH  300
FSRATEEWLK MIDANMDKIR EIYESVTESK EEATRSINQW RIFCISCAEM FGYNDGEEWM  360
ISHFLFKNKK QIE                                                373

SEQ ID NO: 117         moltype = AA  length = 366
FEATURE                Location/Qualifiers
source                 1..366
                       mol_type = protein
                       organism = Corydalis cheilanthifolia
SEQUENCE: 117
MATSDQEVKT SKMEMIADLL KRLEAGLVPD DEIRSLIRVE LERRLKWGYK STHQEQLDQL  60
LNLAHSIKKM KIASTEMDGL TSTMYEVPIS LVQIQLGSHL KESCLYFKDE TTTVDEAEIA  120
MMDLYLERAQ IKDGQSILDL GCGLGAVSFH IAQKYTSCNI TAVTNSVRQK EFIEEKSKTL  180
NVPNVKVLLA DITTLEMEHT FDRLFAISLI EHMENYELLL RKLSEWMKQD GLLFIEHLCH  240
KTLSYHFEPM DEDDWYTNLL FPAGTLTLVS ASFLLYFQDD LSVVNQWVMS GKHFSRANEE  300
WLKNMDAKMD EMREIFESIT DSEEEVVKLI NHWRIFCISS AEMFAYNDGE EWMNSHVLFK  360
KKKQIQ                                                        366

SEQ ID NO: 118         moltype = AA  length = 359
FEATURE                Location/Qualifiers
source                 1..359
                       mol_type = protein
                       organism = Corydalis cheilanthifolia
SEQUENCE: 118
MAGSGANKEM IADLLKRLEV GLVPDEEIRS LIRFQLKRRL KWGYKTTHQE QLEQLLSLAH  60
SIRKMKIATE MDALNSTMYE VPISFMQIVF GSTLKESCLY FKDEATTVNE AEIAMMDLYL  120
ERAQIKDGQS ILDLGCGMGS LCFHIARKYT NCNITAVTNS VSQKEFIEEK SKTLNLPNVK  180
VILADITTLE MDDTYDCLFA IGLIEHMKNY ELLLRKLSNW MKQDSLLFID HVCHKTLAYH  240
YEPIDEDDWY TNLLFPAGTL TLVSASFLLY FQDDLSLVDH WSMSGKHFSR TNKEWLKNID  300
GKMDKIREIV KSITDSEEEV VKLINHWRML CINSSEMFGF NDGEEWMNSH VLFKKKKQI   359

SEQ ID NO: 119         moltype = AA  length = 353
FEATURE                Location/Qualifiers
source                 1..353
                       mol_type = protein
                       organism = Sanguinaria canadensis
SEQUENCE: 119
MEMIADLLKR LEAGLVPDDE IRSLIRVELE RRLKWGYKST HQEQLDQLLN LAHSIKKMKI  60
ASTEMDGLTS TMYEVPISLV QIQLGSHLKE SCLYFKDETT TVDEAEIAMM DLYLERAQIK  120
```

-continued

```
DGQSILDLGC GLGSVCFHIA RKYTSCNITA VTNSVSQKEF IEEKSKTLNV PNVKVLLADI   180
TTLEMDDTFD CLFAIGLIEH MENYELLLRK LSDWMKQDGL LFIDHVCHKT LSYHFEPMDE   240
DDWYTNLLFP AGTLTLVSAS FLLYFQDDLS LVDHWSMSGK HFSRTNKEWL KNIDGKMDKI   300
REIVKSITDS EEEVVKLINH WRMLCINSSE MFGFNDGEEW MNSHVLFKKK KQI          353

SEQ ID NO: 120              moltype = AA   length = 363
FEATURE                     Location/Qualifiers
source                      1..363
                            mol_type = protein
                            organism = Papaver bracteatum
SEQUENCE: 120
MCTTMDTTKI SQQDDLWKNM ELGLISDEEV RRLMKIETEK RIKWGTKPTQ QEQLAQLLDF   60
NKSLRGMKMA TEVHALENHK IYEIPDSFNQ IIGGKESAGL FTDEATTTIE EANTKMMDLY   120
CERAGLKDGQ TILDIGCGAG LLVLHLAKKY KNCKITGVTN TSWHKEHILE QCKNLNLSNV   180
EVILADVTTV DIERTFDRVF VIGLIEHMKN FELFLRKISK WMKDDGLLFL EHLCHKSFSD   240
HWEPLSEDDW YAKNFFPSGT LVIPSATCLL YFQEDVTVKD HWLLSGNNFA RSNEAILKRI   300
DSKIEEVKDI FMSFYGIGEE EAVKLINWWR LLCITANELF KYNNGEEWLI SQLLFKKKLM   360
TCI                                                                 363

SEQ ID NO: 121              moltype = AA   length = 366
FEATURE                     Location/Qualifiers
source                      1..366
                            mol_type = protein
                            organism = Papaver bracteatum
SEQUENCE: 121
MVKGDQFQTT TMEETKISQE NDLWTNMELG LIPDEEVRRL MKIEIEKRIE WGMKPTQHQQ   60
LAQLLDFTKS LRGMKMATEL DKLDSKLYET PHSFNQIVNG STLKESSGLY TDVTTTMDEA   120
SIKMMDLYCE RANIKDGQTI LDLGCGPGPL VLHIAKKYSN CKITGVTNAF SQREYILEEC   180
KKLSLSNVEI ILADVTSLDL ETTFDRVFVI GFIEHMKNFE LFLRKISKWM KDDAVLFLEH   240
FCHKSFSYHG EPLSEDDWYA KNFFAPGTLV IPSATCLLYF QEDLAVIDHW FLSGNHFART   300
NEEMLKGIDG KIEEIKDIFM SFYGINEAEA VKLINWWRLF CITGAEMFSY NNGEEWFISQ   360
LLFKKK                                                              366

SEQ ID NO: 122              moltype = AA   length = 364
FEATURE                     Location/Qualifiers
source                      1..364
                            mol_type = protein
                            organism = Eschscholzia californica
SEQUENCE: 122
MALEQEDSMS VPERNEGVAD LIKRMELGLV NDEEIRRLMR IQIENRLKWG YKPTHDQQLA   60
QHLHFINSLK EMKMATEMDS LDSQVYESPN SFQQIMCGRS MKESAGLFMD DVTTVEEAHI   120
RMMDLYCDKA TFEDGQKILD LGCGHGSVVL HVAQKYKGCQ VTGVTNSSAQ KQYILEQCKK   180
LDLSNVEIIL ADVTTLEMEE KFDRVIIIGL IEHMKNFKLF FQKVSKWMKE GGLLFLENYF   240
HKDFAYHCEK IDEDDWYDGY IFPPGSLLMP SASTLLYFQE DLTVADHWVL PGTHFAKTFE   300
EFLKKIDLRI EEVREIFEAF YGISKEEAMK LSNYWRNFCI SAMEIFNYNN GQEWMISHLL   360
YTKK                                                                364

SEQ ID NO: 123              moltype = AA   length = 368
FEATURE                     Location/Qualifiers
source                      1..368
                            mol_type = protein
                            organism = Chelidonium majus
SEQUENCE: 123
METGKNNQNM KTTIDDLWNQ MMLGIVPDKE IRRLMKIELK KRLDWGYRPT HQQQLSQLLD   60
FAKGLCNYCW TALRCMKMSA EFDTLDSKVY ETPKSFQQIM CGTTIKESSG LFMNESTTLD   120
QAQISMLDLY FDKAKIKDGQ SILDLGCGHG ALILYLAQKY QNCNITGVTN SLSQKEFIVE   180
KCKKLGLSNV EILLADVTKL EMEDMFDRVF VIGLIEHMKN FELFLRKISE WMKPDGLLFL   240
EHYCHKSFAH QWEPIDEEDW FSKYIFPPGT VIIPSASFLL YFQEDVKVID HWTLSGNHFA   300
RTQEEWLKGI DGHIDEVEKT FESFYGISKE EAVKLINFWR VFCLSGVEMF GYNNGEEWMI   360
SHLLFKKK                                                            368

SEQ ID NO: 124              moltype = AA   length = 361
FEATURE                     Location/Qualifiers
source                      1..361
                            mol_type = protein
                            organism = Glaucium flavum
SEQUENCE: 124
MTMEANNAKK EAIENLWEQM MMGLVPDHEI TRLMKSELQK RLNWGYKPTH QQQISQLLDF   60
AKSLRRMEMS LDFDNLELDT KMYETPESFQ LIMSGTTLKE SSGLFTDETA TLDQTQIRMM   120
DLYLEKAKIK DGQSILDLGC GHGALILHVA QKYRNCNVTG VTNSIAQKEF IFKQCKKLGL   180
SNVEMVLADV TKCEMKATFD HIFVIGLIEH MKNFELFLRK VSEWMKSDGL LFMEHYCHKS   240
FAYQWEPMDD DDLFSKYVFP PGSAIIPSAS FLLYFQDDLT VVDHWTLSGN HFARTHQEWL   300
KRIDSQSDEI KGIFESFYGI SKEEAVKLIN YWRVFCLFGV EMFGYNNGEE WMISHLLFKK   360
K                                                                   361

SEQ ID NO: 125              moltype = AA   length = 363
FEATURE                     Location/Qualifiers
source                      1..363
                            mol_type = protein
```

```
                        organism = Corydalis cheilanthifolia
SEQUENCE: 125
MEVVATSSAR NPKKEIVDLW KRMELGLIPD EEIRDLMKIG LEKRLKWGYK PTHEQQLSQL  60
LHFAKSLRSM KMASEMETLD DQMYETPTAF QQLMCGSTIK ESAGFFKDES TTLDEAEIKM  120
LDLYCEKARI EDGQKILDLG CGHGAVMLHI AQKYKNCNVT GVTNSISQQQ FIVQRSKELN  180
LSNVNMILAD VTMLEMDATY DRIFIIGLIE HMKNFELFLR KISKWITKEG LLFLEHYCHK  240
TFAYQCEPVD EDDWYNMFIF PPGTLILPSA SFLLYFQDDL IVVDRWTLNG NHYARTQEEW  300
LKRIDANVDG VKQMFESVCD GNKEEAVKLM NFWRIFCISG AEMLAYNNGE EWMISHYLFK  360
KRN                                                            363

SEQ ID NO: 126          moltype = AA  length = 357
FEATURE                 Location/Qualifiers
source                  1..357
                        mol_type = protein
                        organism = Nigella sativa
SEQUENCE: 126
MEATQITKKQ GVAELIKRIE NGQVPDEEIT RMMKIQIQKR LKLGYKSTHE QQLAQLLHFV  60
HSLQKMEMAE EVDTLDSELY EIPLPFLHIM CGKALKFSPG YFKDESTTLD ESEVNMLDLY  120
CERAQIEDGQ TILDLGCGHG SLTLHVAKKY RGCKVTGITN SVSQKDFIME ECKKLNLSNV  180
EIILEDVTKF ETGTTYDRIF AVALIEHMKN YELFLKKVSA WMAQDGLLFV EHHCHKVFAY  240
KYEPIDDDDW YTEYIFPTGT LVMSSSSILL YFQEDVSVVN HWTLSGKHPS LGFKQWLKRI  300
DDNIDEIKEI FESFYGSKEK ATKFITYWRV FCIAHSEMYA TNGGEEWMLS QVLFKRK     357

SEQ ID NO: 127          moltype = AA  length = 349
FEATURE                 Location/Qualifiers
source                  1..349
                        mol_type = protein
                        organism = Sanguinaria canadensis
SEQUENCE: 127
MGGVADLLKK MELGLVPEEE IRRLMRIIIE KRLEWGYKPT HAEQLDHLTN FIQCLRGMKM  60
ADEIDALDAK MYEIPLPFMQ TICGSTLKFS PGYFKDESTT LDESEIHMMD LYCERAEVKD  120
GHSILDLGCG HGGFVLHVAQ KYKNSIVTGV TNSVAEKEFI MTQCKKLCLS NVEIILADVT  180
KFEPETTYDR VFAIALIEHM KNYELVLEKL SKWVAQDGFL FVEHHCHKVF PYKYEPLDED  240
DWYTEYIFPG GTIVLPSASI LLYFQKDVSV VNHWSLNGKH PARGFKEWLK RLDENMDAVK  300
AIFEPFYGSK EEAMKWITYW RVFCITHSEM YAYNNGEEWM LSQVLFKRK              349

SEQ ID NO: 128          moltype = AA  length = 350
FEATURE                 Location/Qualifiers
source                  1..350
                        mol_type = protein
                        organism = Jeffersonia diphylla
SEQUENCE: 128
MSKGVAKLVE RMELGLVSDD EVRRLMRILI EKRLKWGYKP THEEQLTYLT NFIQGLKGMK  60
IAEEIDALDA KMYEIPIAFM QILCGYSLKF SPGFFEDEST TLDESETIMM DLYCERAQVQ  120
DGQSILDLGC GHGGFVLHVA QKYKNCKVTG VTNSVSETEY IMEQCKKLGL SNVEIIIADV  180
TKFEPEVTYD RVFAIALIEH MKNYELVLQK LSKWVAQDGF LFVDHHCHKV FPYKYEPIDE  240
DDWYTQYIFP GGTLVLPSAS ILLYFQEDVS IVNHWTLSGN HPARGFKEWL KRLDDNMDEI  300
KAIFEPFYGS KEEAMKWITY WRVFCITHSE MYAYNGGEEW MISQVLFKRK             350

SEQ ID NO: 129          moltype = AA  length = 357
FEATURE                 Location/Qualifiers
source                  1..357
                        mol_type = protein
                        organism = Berberis thunbergii
SEQUENCE: 129
MEVKQAGKEG VTELLVKRME LGLVPEEEIR RLMRIQIQKR LDWGYKPTHE EQLAHLTKFI  60
QNIRGMKMAD EIDALDAKMY EIPLPFLQTI CGKTLKFSPG YFKDESTTLD ESETLMMDLY  120
CERAQVKDGQ SILDLGCGHG GFVLHLAQKY RNSVVTGVTN SVSETEYIKE QCKKLGLSNV  180
EIIIADVTKF EPEVTYDRVF AIALIEHMKN YALVLNKISK WVAQDGYLFV EHHCHKVFPY  240
KYEPLDEDDW YTNYIFPGGT LILPSASILL YFQEDVTVLN HWSLSGKHPS RGFIEWLKRL  300
DENIDVIMGI FEPFYGSKEE ATKWINYWRV FCMTHSEMYA YGNGEEWMLS QVLLKRK     357

SEQ ID NO: 130          moltype = AA  length = 339
FEATURE                 Location/Qualifiers
source                  1..339
                        mol_type = protein
                        organism = Berberis aquifolium
SEQUENCE: 130
MELGLVPEKE IRRLMRIQIQ KRLEWGYKPT HEEQLAHLTK FIQNIRGMKM ADEIDALDAK  60
MYEIPLPFLQ TICGKTLKFS PGYFKDESTT LDESETLMMD LYCERAQVKD GQSILDLGCG  120
HGGFVLHLAQ KYRNSIVTGV TNSVSETEYI KEQCKKLGLS NVEIIIADVT KFEPEVTYDR  180
VFAIALIEHM KNYALVLNKI SKWVAQDGYL FVEHHCHKVF PYKYEPLDED DWYTNYIFPG  240
GTLILPSASI LLYFQEDVTV LNHWSLSGKH PSRGFIEWLK RLDENIDVIM GIFEPFYGSK  300
EEATKWINYW RVFCITHSEM YAYGNGEEWM LSQVLLKRK                         339

SEQ ID NO: 131          moltype = AA  length = 355
FEATURE                 Location/Qualifiers
VARIANT                 86
                        note = Any amino acid
```

-continued

```
VARIANT            96
                   note = Any amino acid
VARIANT            127
                   note = Any amino acid
VARIANT            138
                   note = Any amino acid
VARIANT            153
                   note = Any amino acid
VARIANT            292
                   note = Any amino acid
source             1..355
                   mol_type = protein
                   organism = Menispermum canadense
SEQUENCE: 131
MDKANERELK RAELFKKLED DLVTYDEIKQ VMRTELAKRL EWGYKPTHQQ QLAHLLDFAH  60
ALEGMKIANE VETLASEVYE TPLPFXEIVL GPAKKXSSCL FEDESTTLEQ AEIAMLDLYF  120
ERAQIRXGMS VLDLGCGXGS VGLHIARKYK NCXVTCITNS ISQKQYIENQ CKLYNLSNVK  180
IILADIVAHD TDDTFDVVLV IGVIEHMKNY ALLLNKISKW MAKDGLLFVE HLCHKTFPYH  240
FEPLDEDDWY SNFVFPTGTL TMPSVSFLLY FQADVSILNH WILSGKNFSR TXEEFLKRID  300
ANVDAIKDGL KPSLGSEGVA KLISYWRGFC LTGMEMFGYN NGEEWMVSQV LFKNK        355

SEQ ID NO: 132        moltype = AA   length = 366
FEATURE               Location/Qualifiers
source                1..366
                      mol_type = protein
                      organism = Tinospora cordifolia
SEQUENCE: 132
MEDNNNLLQE EMNVVELLQR PELGLVPDEK IRKLTRLQLQ KRLKWGYKPT HEAQLSHLFQ  60
FIHSLPSLNM ESEDENPKSW LYETPTSFLQ LLYGDCIKES DTYYKEDTAT LEEAVINMLE  120
LYCERARITE GLSVLDLGCG YGALTLHVAQ KYKSCKVTGV TSSISQKQYI MEKCKKLNLT  180
NVEIILADVA TIEIEAASYD RIFALGIFEH VNDYKLFLGK LSKWMKQDGL LFVEYLCHKT  240
FPYQNKPLDK GDKWYNEYVF PSGGLIIPSA SFILYFQNDV SVVRQWTQGG QHSARTFEEL  300
LKRIDGNIDK IKEIFIESYG SKEDAVRFIN YWRVFLITGV EMFSYNDGEE WMGAHFLFKK  360
KFIMQE                                                             366

SEQ ID NO: 133        moltype = AA   length = 359
FEATURE               Location/Qualifiers
source                1..359
                      mol_type = protein
                      note = subspecies: mucronata
                      organism = Cissampelos pareira
SEQUENCE: 133
MEVKQSKGDE LRSRVAELLE RPELGLVPDE EIRRLAKARL EKRLKWGYKA THGEQLSSLL  60
QFVESLPSLN MASEDDSPKA WLYETPTSFL QLIYGDIIKE SGSYYKDEST TLEEAMIHNM  120
NLCCERANIK EGQSVVDLGC GYGAFILHVA QKYKTCRVTG ITSSISQKHY IMEQCKKLNL  180
SNVEVILADV ATIKLDATFD RVFAAGMFEH VNDYKSFLRK ITNWMKPDGR LFVEHLCNKT  240
FPYQNKPLDD GDNWGEYVFP SGGLIIPSAS LLLYFQEDVS IVNHWTFSGK HAANKFEELL  300
KRIDAKIDAI KRIFNECYGS KDSIRFINYW RVFLITAAEM FGYNNGEEWM GVHLLFKKK   359

SEQ ID NO: 134        moltype = AA   length = 352
FEATURE               Location/Qualifiers
source                1..352
                      mol_type = protein
                      organism = Cocculus orbiculatus
SEQUENCE: 134
GLKSSVAELL ERPELGLVPD GEIRKLTKTR LAKRLEWGYK ATHEDQLSHL LRFIHSLPSL  60
NMASEDDSPK AWLYETPTSF LQLIYGDIIK ESGTYYKDES STLEEAIIHN MDLCCERARI  120
KEGQSVLDLG CGYGAFTLHV AQKYKSCSVT GITSSISQKD YIMEQCKKLN LSNVEVILAD  180
VATIKMNTTF DRVFALGMFE HINDYKLFLR RISNWMKHDG LLFVEHLCNK TFAYQNKPLD  240
DGDDWFNEYV FPSAGLIIPS ASLLLYFQED VSIVHHWTFS GKHAAYKFEE LLERIDAKIE  300
AIKEIFIECY GSKEDAIRFI NYWRVFLITA AEMFAYRDGE EWMGSHVLFK KK           352

SEQ ID NO: 135        moltype = AA   length = 364
FEATURE               Location/Qualifiers
source                1..364
                      mol_type = protein
                      note = subspecies: mucronata
                      organism = Cissampelos pareira
SEQUENCE: 135
MEAKQHESNN NIDEELKNRV NIGEQEERPG FEDEEIRRLA KAQLAKRLKW GYKPTHEQQL  60
SHLLQFLQSL PSLNMASEDE SSKAWLYETP TSFLQLLFGN VIKFSGYYYK HESSTFEESM  120
IHNMDLCCER ANIKEGQNVI DLGCGYGAFV LHVAQKYKSC SVTGITCSIT QKHHIMEECK  180
KLNLCNVKVI LADVATIELG TAFDRVFAFG MFEEINDYKL ILRKISNWMK PDGLFFVEHL  240
CHKTLAYQNK LIDDQDWYEE YIFPSGGLIV PSASLLLYFQ DDLSVVYHWT YNGKHGARSF  300
EKMLERTDAN IDTIKDMFTE FYGSKEKAIK FINYWRVFFI TAAEMFAYND GEEWMCSQLL  360
FKKK                                                               364

SEQ ID NO: 136        moltype = AA   length = 364
FEATURE               Location/Qualifiers
```

```
source                  1..364
                        mol_type = protein
                        note = subspecies: mucronata
                        organism = Cissampelos pareira
SEQUENCE: 136
MEHKIEDIRK LKSRVEEQLE RPELGLVKDE DIKTLAKAKL EKRLKWGYKP TYAEQLSNLL  60
QFAQSLPSLK MENVDDQGSS KQWLYGVPSE FLQIIYGGII KMSGSYYEDE STTLEESMIK  120
DMDSCCEKAN VKEGHSVLDI GCGYGSLIIH IAKKYRTCNV TGITNFVEQK QYIMEECKKL  180
NLSNVEVIVG DGTTINLNTT TFDRVFVTGM LEEINDYKLF LKSVSDWMKP DGLLLVTHFC  240
HKTFAYQNNK ALDDEDWHNE YIFPSGNLIV PSASLLLYFQ EDLSVVSHWA TNGTHTGRTC  300
KKLVERIDAN IEKIKEIFSE FYGSKEDAIR MINYWRVLCI TGAEMYTCKD GEEWMDVYYL  360
FKKK                                                              364

SEQ ID NO: 137          moltype = AA  length = 1049
FEATURE                 Location/Qualifiers
REGION                  1..1049
                        note = Description of Artificial Sequence: Synthetic
                         polypeptide
source                  1..1049
                        mol_type = protein
                        organism = synthetic construct
SEQUENCE: 137
MTIKEMPQPK TFGELKNLPL LNTDKPVQAL MKIADELGEI FKFEAPGRVT RYLSSQRLIK  60
EACDESRFDK NLSQALKFAR DFAGDGLVTS WTHEKNWKKA HNILLPSFSQ QAMKGYHAMM  120
VDIAVQLVQK WERLNADEHI EVSEDMTRLT LDTIGLCGFN YRFNSFYRDQ PHPFIISMVR  180
ALDEVMNKLQ RANPDDPAYD ENKRQFQEDI KVMNDLVDKI IADRKARGEQ SDDLLTQMLN  240
GKDPETGEPL DDGNIRYQII TFLIAGHETT SGLLSFALYF LVKNPHVLQK VAEEAARVLV  300
DPVPSYKQVK QLKYVGMVLN EALRLWPTAP AFSLYAKEDT VLGGEYPLEK GDEVMVLIPQ  360
LHRDKTVWGD DVEEFRPERF ENPSAIPQHA FKPFGNGQRA CIGQQFALHE ATLVLGMMLK  420
HFDFEDHTNY ELDIKETATL KPKGFVVKAK SKKIPLGGIP SPSTEQSAKK VRKKAENAHN  480
TPLLVLYGSN MGTAEGTARD LADIAMSKGF APQVATLDSH AGNLPREGAV LIVTASYNGH  540
PPDNAKQFVD WLDQASADEV KGVRYSVFGC GDKNWATTYQ KVPAFIDETL AAKGAENIAD  600
RGEADASDDF EGTYEEWREH MWSDVAAYFN LDIENSEDNK STLSLQFVDS AADMPLAKMH  660
GAFSTNVVAS KELQQPGSAR STRHLEIELP KEASYQEGDH LGVIPRNYEG IVNRVTARFG  720
LDASQQIRLE AEEEKLAHLP LAKTVSVEEL LQYVELQDPV TRTQLRAMAA KTVCPPHKVE  780
LEALLEKQAY KEQVLAKRLT MLELLEKYPA CEMKFSEFIA LLPSIRPRYY SISSSPRVDE  840
KQASITVSVV SGEAWSGYGE YKGIASNYLA ELQEGDTITC FISTPQSEFT LPKDPETPLI  900
MVGPGTGVAP FRGFVQARKQ LKEQGQSLGE AHLYFGCRSP HEDYLYQEEL ENAQSEGIIT  960
LHTAFSRMPN QPKTYVQHVM EQDGKKLIEL LDQGAHFYIC GDGSQMAPAV EATLMKSYAD  1020
VHQVSEADAR LWLQQLEEKG RYAKDVWAG                                   1049

SEQ ID NO: 138          moltype = AA  length = 1049
FEATURE                 Location/Qualifiers
REGION                  1..1049
                        note = Description of Artificial Sequence: Synthetic
                         polypeptide
source                  1..1049
                        mol_type = protein
                        organism = synthetic construct
SEQUENCE: 138
MTIKEMPQPK TFGELKNLPL LNTDKPVQAL MKIADELGEI FKFEAPGRVT RYLSSQRLIK  60
EACDESRFDK NLSQALKFAR DFAGDGLVTS WTHEKNWKKA HNILLPSFSQ QAMKGYHAMM  120
VDIAVQLVQK WERLNADEHI EVSEDMTRLT LDTIGLCGFN YRFNSFYRDQ PHPFIISMVR  180
AADEVMNKLQ RANPDDPAYD ENKRQFQEDI KVMNDLVDKI IADRKARGEQ SDDLLTQMLN  240
GKDPETGEPL DDGNIRYQII AFLIAGHETT SGLLSFALYF LVKNPHVLQK VAEEAARVLV  300
DPVPSYKQVK QLKYVGMVLN EALRLWPTAP AFSLYAKEDT VLGGEYPLEK GDEVMVLIPQ  360
LHRDKTVWGD DVEEFRPERF ENPSAIPQHA FKPFGNGQRA CIGQQFALHE ATLVLGMMLK  420
HFDFEDHTNY ELDIKETATL KPKGFVVKAK SKKIPLGGIP SPSTEQSAKK VRKKAENAHN  480
TPLLVLYGSN MGTAEGTARD LADIAMSKGF APQVATLDSH AGNLPREGAV LIVTASYNGH  540
PPDNAKQFVD WLDQASADEV KGVRYSVFGC GDKNWATTYQ KVPAFIDETL AAKGAENIAD  600
RGEADASDDF EGTYEEWREH MWSDVAAYFN LDIENSEDNK STLSLQFVDS AADMPLAKMH  660
GAFSTNVVAS KELQQPGSAR STRHLEIELP KEASYQEGDH LGVIPRNYEG IVNRVTARFG  720
LDASQQIRLE AEEEKLAHLP LAKTVSVEEL LQYVELQDPV TRTQLRAMAA KTVCPPHKVE  780
LEALLEKQAY KEQVLAKRLT MLELLEKYPA CEMKFSEFIA LLPSIRPRYY SISSSPRVDE  840
KQASITVSVV SGEAWSGYGE YKGIASNYLA ELQEGDTITC FISTPQSEFT LPKDPETPLI  900
MVGPGTGVAP FRGFVQARKQ LKEQGQSLGE AHLYFGCRSP HEDYLYQEEL ENAQSEGIIT  960
LHTAFSRMPN QPKTYVQHVM EQDGKKLIEL LDQGAHFYIC GDGSQMAPAV EATLMKSYAD  1020
VHQVSEADAR LWLQQLEEKG RYAKDVWAG                                   1049

SEQ ID NO: 139          moltype = AA  length = 1049
FEATURE                 Location/Qualifiers
REGION                  1..1049
                        note = Description of Artificial Sequence: Synthetic
                         polypeptide
source                  1..1049
                        mol_type = protein
                        organism = synthetic construct
SEQUENCE: 139
MTIKEMPQPK TFGELKNLPL LNTDKPVQAL MKIADELGEI FKFEAPGRVT RYLSSQRLIK  60
```

-continued

```
EACDESRFDK NLSQAAKFAR DFAGDGLVTS WTHEKNWKKA HNILLPSFSQ QAMKGYHAMM  120
VDIAVQLVQK WERLNADEHI EVSEDMTRLT LDTIGLCGFN YRFNSFYRDQ PHPFIISMVR  180
AADEVMNKLQ RANPDDPAYD ENKRQFQEDI KVMNDLVDKI IADRKARGEQ SDDLLTQMLN  240
GKDPETGEPL DDGNIRYQII TFLIAGHETT SGLLSFALYF LVKNPHVLQK VAEEAARVLV  300
DPVPSYKQVK QLKYVGMVLN EALRLWPTAP AFSLYAKEDT VLGGEYPLEK GDEVMVLIPQ  360
LHRDKTVWGD DVEEFRPERF ENPSAIPQHA FKPFGNGQRA CIGQQFALHE ATLVLGMMLK  420
HFDFEDHTNY ELDIKETLTL KPKGFVVKAK SKKIPLGGIP SPSTEQSAKK VRKKAENAHN  480
TPLLVLYGSN MGTAEGTARD LADIAMSKGF APQVATLDSH AGNLPREGAV LIVTASYNGH  540
PPDNAKQFVD WLDQASADEV KGVRYSVFGC GDKNWATTYQ KVPAFIDETL AAKGAENIAD  600
RGEADASDDF EGTYEEWREH MWSDVAAYFN LDIENSEDNK STLSLQFVDS AADMPLAKMH  660
GAFSTNVVAS KELQQPGSAR STRHLEIELP KEASYQEGDH LGVIPRNYEG IVNRVTARFG  720
LDASQQIRLE AEEEKLAHLP LAKTVSVEEL LQYVELQDPV TRTQLRAMAA KTVCPPHKVE  780
LEALLEKQAY KEQVLAKRLT MLELLEKYPA CEMKFSEFIA LLPSIRPRYY SISSSPRVDE  840
KQASITVSVV SGEAWSGYGE YKGIASNYLA ELQEGDTITC FISTPQSEFT LPKDPETPLI  900
MVGPGTGVAP FRGFVQARKQ LKEQGQSLGE AHLYFGCRSP HEDYLYQEEL ENAQSEGIIT  960
LHTAFSRMPN QPKTYVQHVM EQDGKKLIEL LDQGAHFYIC GDGSQMAPAV EATLMKSYAD  1020
VHQVSEADAR LWLQQLEEKG RYAKDVWAG                                  1049

SEQ ID NO: 140         moltype = AA  length = 1049
FEATURE                Location/Qualifiers
REGION                 1..1049
                       note = Description of Artificial Sequence: Synthetic
                        polypeptide
source                 1..1049
                       mol_type = protein
                       organism = synthetic construct
SEQUENCE: 140
MTIKEMPQPK TFGELKNLPL LNTDKPVQAL MKIADELGEI FKFEAPGRVT RYLSSQRLIK  60
EACDESRFDK NLSQAAKFAR DFAGDGLVTS WTHEKNWKKA HNILLPSFSQ QAMKGYHAMM  120
VDIAVQLVQK WERLNADEHI EVSEDMTRLT LDTIGLCGFN YRFNSFYRDQ PHPFIISAVR  180
AADEVMNKLQ RANPDDPAYD ENKRQFQEDI KVMNDLVDKI IADRKARGEQ SDDLLTQMLN  240
GKDPETGEPL DDGNIRYQII TFLIAGHETT SGLLSFALYF LVKNPHVLQK VAEEAARVLV  300
DPVPSYKQVK QLKYVGMVLN EALRLWPTAP AFSLYAKEDT VLGGEYPLEK GDEVMVLIPQ  360
LHRDKTVWGD DVEEFRPERF ENPSAIPQHA FKPFGNGQRA CIGQQFALHE ATLVLGMMLK  420
HFDFEDHTNY ELDIKETLTL KPKGFVVKAK SKKIPLGGIP SPSTEQSAKK VRKKAENAHN  480
TPLLVLYGSN MGTAEGTARD LADIAMSKGF APQVATLDSH AGNLPREGAV LIVTASYNGH  540
PPDNAKQFVD WLDQASADEV KGVRYSVFGC GDKNWATTYQ KVPAFIDETL AAKGAENIAD  600
RGEADASDDF EGTYEEWREH MWSDVAAYFN LDIENSEDNK STLSLQFVDS AADMPLAKMH  660
GAFSTNVVAS KELQQPGSAR STRHLEIELP KEASYQEGDH LGVIPRNYEG IVNRVTARFG  720
LDASQQIRLE AEEEKLAHLP LAKTVSVEEL LQYVELQDPV TRTQLRAMAA KTVCPPHKVE  780
LEALLEKQAY KEQVLAKRLT MLELLEKYPA CEMKFSEFIA LLPSIRPRYY SISSSPRVDE  840
KQASITVSVV SGEAWSGYGE YKGIASNYLA ELQEGDTITC FISTPQSEFT LPKDPETPLI  900
MVGPGTGVAP FRGFVQARKQ LKEQGQSLGE AHLYFGCRSP HEDYLYQEEL ENAQSEGIIT  960
LHTAFSRMPN QPKTYVQHVM EQDGKKLIEL LDQGAHFYIC GDGSQMAPAV EATLMKSYAD  1020
VHQVSEADAR LWLQQLEEKG RYAKDVWAG                                  1049

SEQ ID NO: 141         moltype = AA  length = 1049
FEATURE                Location/Qualifiers
REGION                 1..1049
                       note = Description of Artificial Sequence: Synthetic
                        polypeptide
source                 1..1049
                       mol_type = protein
                       organism = synthetic construct
SEQUENCE: 141
MTIKEMPQPK TFGELKNLPL LNTDKPVQAL MKIADELGEI FKFEAPGRVT RYLSSQRLIK  60
EACDESRFDK NLSQAAKFAR DFAGDGLVTS WTHEKNWKKA HNILLPSFSQ QAMKGYHAMM  120
VDIAVQLVQK WERLNADEHI EVSEDMTRLT LDTIGLCGFN YRFNSFYRDQ PHPFIISAVR  180
AADEVMNKLQ RANPDDPAYD ENKRQFQEDI KVMNDLVDKI IADRKARGEQ SDDLLTQMLN  240
GKDPETGEPL DDGNIRYQII AFLIAGHETT SGLLSFALYF LVKNPHVLQK VAEEAARVLV  300
DPVPSYKQVK QLKYVGMVLN EALRLWPTAP AFSLYAKEDT VLGGEYPLEK GDEVMVLIPQ  360
LHRDKTVWGD DVEEFRPERF ENPSAIPQHA FKPFGNGQRA CIGQQFALHE ATLVLGMMLK  420
HFDFEDHTNY ELDIKETLTL KPKGFVVKAK SKKIPLGGIP SPSTEQSAKK VRKKAENAHN  480
TPLLVLYGSN MGTAEGTARD LADIAMSKGF APQVATLDSH AGNLPREGAV LIVTASYNGH  540
PPDNAKQFVD WLDQASADEV KGVRYSVFGC GDKNWATTYQ KVPAFIDETL AAKGAENIAD  600
RGEADASDDF EGTYEEWREH MWSDVAAYFN LDIENSEDNK STLSLQFVDS AADMPLAKMH  660
GAFSTNVVAS KELQQPGSAR STRHLEIELP KEASYQEGDH LGVIPRNYEG IVNRVTARFG  720
LDASQQIRLE AEEEKLAHLP LAKTVSVEEL LQYVELQDPV TRTQLRAMAA KTVCPPHKVE  780
LEALLEKQAY KEQVLAKRLT MLELLEKYPA CEMKFSEFIA LLPSIRPRYY SISSSPRVDE  840
KQASITVSVV SGEAWSGYGE YKGIASNYLA ELQEGDTITC FISTPQSEFT LPKDPETPLI  900
MVGPGTGVAP FRGFVQARKQ LKEQGQSLGE AHLYFGCRSP HEDYLYQEEL ENAQSEGIIT  960
LHTAFSRMPN QPKTYVQHVM EQDGKKLIEL LDQGAHFYIC GDGSQMAPAV EATLMKSYAD  1020
VHQVSEADAR LWLQQLEEKG RYAKDVWAG                                  1049

SEQ ID NO: 142         moltype = DNA  length = 3150
FEATURE                Location/Qualifiers
misc_feature           1..3150
                       note = Description of Artificial Sequence: Synthetic
                        polynucleotide
```

source 1..3150
mol_type = other DNA
organism = synthetic construct
SEQUENCE: 142
atgaccatca aagaaatgcc acaacctaag actttcggtg aattgaagaa tttgcctttg 60
ttgaacaccg ataagccagt tcaagctttg atgaagattg ctgatgaatt gggtgaaatc 120
ttcaagtttg aagctccagg tagagtcact agatacttgt catctcaaag attgatcaaa 180
gaagcctgcg acgaatccag atttgataag aatttgtctc aagctttgaa gttcgctaga 240
gattttgctg gtgatggttt ggttacttct tggactcacg aaaagaattg gaagaaggcc 300
cataacattt tgttgccatc tttctcacaa caagccatga agggttatca tgctatgatg 360
gttgatatcg ccgttcaatt ggttcaaaag tgggaaagat tgaacgccga tgaacatatc 420
gaagtctctg aagatatgac cagattgacc ttggatacca ttggtttgtg tggtttcaac 480
tacagattca actccttcta cagagatcaa ccacatccat tcatcatctc tatggttaga 540
gctttggatg aagtcatgaa caaattgcaa agagctaatc cagacgatcc agcttatgac 600
gaaaacaaga gacaattcca agaagatatc aaggtcatga acgatttggt cgataagatt 660
atcgctgata gaaaggctag aggtgaacaa tctgatgatt tgttgaccca aatgttgaac 720
ggtaaggatc cagaaactgg tgaaccattg gatgatggta acatcagata ccaaattatc 780
accttcttga ttgctggtca cgaaactaca tctggtttgt tgtcttttgc cttgtacttt 840
ttggttaaga acccacacgt cttgcaaaag gttgctgaag aagctgcaag agttttggtt 900
gatccagttc catcttacaa gcaagtcaag caattgaagt acgttggtat ggttttgaac 960
gaagctttga gattgtggcc aactgctcca gctttttcat tatacgctaa agaagatacc 1020
gtcttgggtg gtgaatatcc attggaaaaa ggtgatgaag ttatggtctt gatcccacaa 1080
ttgcatagag ataagactgt ttggggtgat gatgtcgaag aattcagacc agaaagattc 1140
gaaaacccat ctgctattcc acaacatgct tttaagccat ttggtaacgg tcaaagagct 1200
tgcattggtc aacaattcgc tttacatgaa gctaccttgg ttttgggtat gatgttgaaa 1260
cacttcgact tcgaagatca caccaactac gaattggata tcaaagaaac cgctaccttg 1320
aagccaaagg gttttgttgt taaggctaag tccaaaaaga ttccattggg tggtattcca 1380
tctccatcta ctgaacaatc cgctaagaag gttagaaaga aagctgaaaa cgctcataac 1440
acacctttgt tggtcttgta cggttctaat atgggtactg ctgaaggtac agcaagagat 1500
ttggcagata ttgctatgtc taaaggtttc gctccacaag ttgctacttt ggattctcat 1560
gctggtaatt tgccaagaga aggtgctgtt ttgatagtta ctgcttctta caatggtcac 1620
ccaccagata atgctaagca attcgttgat tggttggatc aagcttcagc tgatgaagta 1680
aaaggtgtta gatactctgt tttcggttgc ggtgacaaaa attgggctac tacttatcaa 1740
aaggttccag cctttattga cgaaactttg gctgctaaag gtgctgaaaa cattgctgac 1800
agaggtgaag ctgatgcctc cgacgacttc gaaggtactt acgaagaatg gagagaacac 1860
atgtggtctg acgttgctgc ttacttcaac ttggacatcg aaaactctga agacaacaag 1920
tccactttgt ctttgcaatt cgttgactcc gctgctgaca tgccattggc taagatgcac 1980
ggtgctttct ctaccaacgt cgttgcctcc aaggaattgc aacaaccagg ttctgctaga 2040
tctactagac acttggaaat cgaattgcca aaggaagctt cctaccaaga aggtgaccac 2100
ttgggcgtta ttccaagaaa ctacgaaggt atcgtcaaca gagttactgc tagattcggt 2160
ttggatgctt ctcaacaaat cagattagaa gctgaagaag aaaagttggc tcacttgcca 2220
ttagctaaga ctgtctccgt tgaagaattg ttgcaatacg tcgaattgca agacccagtt 2280
accagaaccc aattgagagc catggctgcc aagaccgtct gtccaccaca caaggttgaa 2340
ttggaagcct tgttggaaaa gcaagcctac aaggaacaag ttttggctaa gagattgacc 2400
atgttggaat tgttggaaaa gtacccagcc tgcgaaatga agttctctga atttatcgcc 2460
ttgttgccat ctatcagacc acgttactac tctatttctt cctctccacg tgttgacgaa 2520
aagcaagctt ctattactgt ttccgttgtc tccggtgaag cttggtccgg ttacggtgaa 2580
tacaagggta ttgcttctaa ctacttggct gaattgcaag aaggtgacac cattacttgt 2640
ttcatctcta ctccacaatc cgaatttact ttgccaaagg acccagaaac tccattgatc 2700
atggttggtc caggtactgg tgtcgctcca ttcagaggtt tcgttcaagc tagaaaacaa 2760
ttgaaggaac aaggtcaatc tttgggtgaa gctcacttgt acttcggttg tagatctcca 2820
cacgaagact acttatacca agaagaattg gaaaacgctc aatccgaagg tattatcact 2880
ttgcacaccg ctttctccag aatgccaaac caaccaaaga cttacgtcca acacgttatg 2940
gaacaagacg gtaagaagtt gattgaattg ttggaccaag gtgctcactt ctacatttgt 3000
ggtgatggtt ctcaaatggc tccagccgtt gaagccactt tgatgaagtc ttacgctgat 3060
gttcaccaag tttccgaagc cgatgctaga ttatggttgc aacaattgga agaaaaaggt 3120
cgttacgcta aggatgtctg ggccggttga 3150

SEQ ID NO: 143 moltype = DNA length = 3150
FEATURE Location/Qualifiers
misc_feature 1..3150
note = Description of Artificial Sequence: Synthetic
polynucleotide
source 1..3150
mol_type = other DNA
organism = synthetic construct
SEQUENCE: 143
atgaccatca aagaaatgcc acaacctaag actttcggtg aattgaagaa tttgcctttg 60
ttgaacaccg ataagccagt tcaagctttg atgaagattg ctgatgaatt gggtgaaatc 120
ttcaagtttg aagctccagg tagagtcact agatacttgt catctcaaag attgatcaaa 180
gaagcctgcg acgaatccag atttgataag aatttgtctc aagctttgaa gttcgctaga 240
gattttgctg gtgatggttt ggttacttct tggactcacg aaaagaattg gaagaaggcc 300
cataacattt tgttgccatc tttctcacaa caagccatga agggttatca tgctatgatg 360
gttgatatcg ccgttcaatt ggttcaaaag tgggaaagat tgaacgccga tgaacatatc 420
gaagtctctg aagatatgac cagattgacc ttggatacca ttggtttgtg tggtttcaac 480
tacagattca actccttcta cagagatcaa ccacatccat tcatcatctc tatggttaga 540
gctgcagatg aagtcatgaa caaattgcaa agagctaatc cagacgatcc agcttatgac 600
gaaaacaaga gacaattcca agaagatatc aaggtcatga acgatttggt cgataagatt 660
atcgctgata gaaaggctag aggtgaacaa tctgatgatt tgttgaccca aatgttgaac 720

```
ggtaaggatc cagaaactgg tgaaccattg gatgatggta acatcagata ccaaattatc  780
gctttcttga ttgctggtca cgaaactaca tctggtttgt tgtcttttgc cttgtacttt  840
ttggttaaga acccacacgt cttgcaaaag gttgctgaag aagctgcaag agttttggtt  900
gatccagttc catcttacaa gcaagtcaag caattgaagt acgttggtat ggttttgaac  960
gaagctttga gattgtggcc aactgctcca gctttttcat tatacgctaa agaagatacc  1020
gtcttgggtg gtgaatatcc attggaaaaa ggtgatgaag ttatggtctt gatcccacaa  1080
ttgcatagag ataagactgt ttggggtgat gatgtcgaag aattcagacc agaaagattc  1140
gaaaacccat ctgctattcc acaacatgct tttaagccat ttggtaacgg tcaaagagct  1200
tgcattggtc aacaattcgc tttacatgaa gctaccttgg ttttgggtat gatgttgaaa  1260
cacttcgact tcgaagatca caccaactac gaattggata tcaaagaaac cgctaccttg  1320
aagccaaagg gttttgttgt taaggctaag tccaaaaaga ttccattggg tggtattcca  1380
tctccatcta ctgaacaatc cgctaagaag gttagaaaga aagctgaaaa cgctcataac  1440
acacctttgt tggtcttgta cggttctaat atgggtactg ctgaaggtac agcaagagat  1500
ttggcagata ttgctatgtc taaaggtttc gctccacaag ttgctacttt ggattctcat  1560
gctggtaatt tgccaagaga aggtgctgtt ttgatagtta ctgcttctta caatggtcac  1620
ccaccagata atgctaagca attcgttgat tggttggatc aagcttcagc tgatgaagta  1680
aaaggtgtta gatactctgt tttcggttgc ggtgacaaaa attgggctac tacttatcaa  1740
aaggttccag cctttattga cgaaactttg gctgctaaag gtgctgaaaa cattgctgac  1800
agaggtgaag ctgatgcctc cgacgacttc gaaggtactt acgaagaatg gagagaacac  1860
atgtggtctg acgttgctgc ttacttcaac ttggacatcg aaaactctga agacaacaag  1920
tccactttgt ctttgcaatt cgttgactcc gctgctgaca tgccattggc taagatgcac  1980
ggtgctttct ctaccaacgt cgttgcctcc aaggaattgc aacaaccagg ttctgctaga  2040
tctactagac acttggaaat cgaattgcca aaggaagctt cctaccaaga aggtgaccac  2100
ttgggcgtta ttccaagaaa ctacgaaggt atcgtcaaca gagttactgc tagattcggt  2160
ttggatgctt ctcaacaaat cagattagaa gctgaagaag aaaagttggc tcacttgcca  2220
ttagctaaga ctgtctccgt tgaagaattg ttgcaatacg tcgaattgca agacccagtt  2280
accagaaccc aattgagagc catggctgcc aagaccgtct gtccaccaca caaggttgaa  2340
ttggaagcct tgttggaaaa gcaagcctac aaggaacaag ttttggctaa gagattgacc  2400
atgttggaat tgttggaaaa gtacccagcc tgcgaaatga agttctctga atttatcgcc  2460
ttgttgccat ctatcagacc acgttactac tctatttctt cctctccacg tgttgacgaa  2520
aagcaagctt ctattactgt ttccgttgtc tccggtgaag cttggtccgg ttacggtgaa  2580
tacaagggta ttgcttctaa ctacttggct gaattgcaag aaggtgacac cattacttgt  2640
ttcatctcta ctccacaatc cgaatttact ttgccaaagg acccagaaac tccattgatc  2700
atggttggtc caggtactgg tgtcgctcca ttcagaggtt tcgttcaagc tagaaaacaa  2760
ttgaaggaac aaggtcaatc tttgggtgaa gctcacttgt acttcggttg tagatctcca  2820
cacgaagact acttatacca agaagaattg gaaaacgctc aatccgaagg tattatcact  2880
ttgcacaccg ctttctccag aatgccaaac caaccaaaga cttacgtcca acacgttatg  2940
gaacaagacg gtaagaagtt gattgaattg ttggaccaag gtgctcactt ctacatttgt  3000
ggtgatggtt ctcaaatggc tccagccgtt gaagccactt tgatgaagtc ttacgctgat  3060
gttcaccaag tttccgaagc cgatgctaga ttatggttgc aacaattgga agaaaaaggt  3120
cgttacgcta aggatgtctg ggccggttga                                   3150

SEQ ID NO: 144          moltype = DNA  length = 3150
FEATURE                 Location/Qualifiers
misc_feature            1..3150
                        note = Description of Artificial Sequence: Synthetic
                         polynucleotide
source                  1..3150
                        mol_type = other DNA
                        organism = synthetic construct
SEQUENCE: 144
atgaccatca aagaaatgcc acaacctaag actttcggtg aattgaagaa tttgcctttg  60
ttgaacaccg ataagccagt tcaagctttg atgaagattg ctgatgaatt gggtgaaatc  120
ttcaagtttg aagctccagg tagagtcact agatacttgt catctcaaag attgatcaaa  180
gaagcctgcg acgaatccag atttgataag aatttgtctc aagctgctaa gttcgctaga  240
gattttgctg gtgatggttt ggttacttct tggactcacg aaaagaattg gaagaaggcc  300
cataacattt tgttgccatc tttctcacaa caagccatga agggttatca tgctatgatg  360
gttgatatcg ccgttcaatt ggttcaaaag tgggaaagat tgaacgccga tgaacatatc  420
gaagtctctg aagatatgac cagattgacc ttggatacca ttggtttgtg tggtttcaac  480
tacagattca actccttcta cagagatcaa ccacatccat tcatcatctc tatggttaga  540
gctgcagatg aagtcatgaa caaattgcaa agagctaatc cagacgatcc agcttatgac  600
gaaaacaaga gacaattcca agaagatatc aaggtcatga acgatttggt cgataagatt  660
atcgctgata gaaaggctag aggtgaacaa tctgatgatt tgttgaccca aatgttgaac  720
ggtaaggatc cagaaactgg tgaaccattg gatgatggta acatcagata ccaaattatc  780
accttcttga ttgctggtca cgaaactaca tctggtttgt tgtcttttgc cttgtacttt  840
ttggttaaga acccacacgt cttgcaaaag gttgctgaag aagctgcaag agttttggtt  900
gatccagttc catcttacaa gcaagtcaag caattgaagt acgttggtat ggttttgaac  960
gaagctttga gattgtggcc aactgctcca gctttttcat tatacgctaa agaagatacc  1020
gtcttgggtg gtgaatatcc attggaaaaa ggtgatgaag ttatggtctt gatcccacaa  1080
ttgcatagag ataagactgt ttggggtgat gatgtcgaag aattcagacc agaaagattc  1140
gaaaacccat ctgctattcc acaacatgct tttaagccat ttggtaacgg tcaaagagct  1200
tgcattggtc aacaattcgc tttacatgaa gctaccttgg ttttgggtat gatgttgaaa  1260
cacttcgact tcgaagatca caccaactac gaattggata tcaaagaaac cttgaccttg  1320
aagccaaagg gttttgttgt taaggctaag tccaaaaaga ttccattggg tggtattcca  1380
tctccatcta ctgaacaatc cgctaagaag gttagaaaga aagctgaaaa cgctcataac  1440
acacctttgt tggtcttgta cggttctaat atgggtactg ctgaaggtac agcaagagat  1500
ttggcagata ttgctatgtc taaaggtttc gctccacaag ttgctacttt ggattctcat  1560
gctggtaatt tgccaagaga aggtgctgtt ttgatagtta ctgcttctta caatggtcac  1620
ccaccagata atgctaagca attcgttgat tggttggatc aagcttcagc tgatgaagta  1680
```

-continued

```
aaaggtgtta gatactctgt tttcggttgc ggtgacaaaa attgggctac tacttatcaa  1740
aaggttccag cctttattga cgaaactttg gctgctaaag gtgctgaaaa cattgctgac  1800
agaggtgaag ctgatgcctc cgacgacttc gaaggtactt acgaagaatg gagagaacac  1860
atgtggtctg acgttgctgc ttacttcaac ttggacatcg aaaactctga agacaacaag  1920
tccactttgt ctttgcaatt cgttgactcc gctgctgaca tgccattggc taagatgcac  1980
ggtgctttct ctaccaacgt cgttgcctcc aaggaattgc aacaaccagg ttctgctaga  2040
tctactagac acttggaaat cgaattgcca aaggaagctt cctaccaaga aggtgaccac  2100
ttgggcgtta ttccaagaaa ctacgaaggt atcgtcaaca gagttactgc tagattcggt  2160
ttggatgctt ctcaacaaat cagattagaa gctgaagaag aaaagttggc tcacttgcca  2220
ttagctaaga ctgtctccgt tgaagaattg ttgcaatacg tcgaattgca agacccagtt  2280
accagaaccc aattgagagc catggctgcc aagaccgtct gtccaccaca caaggttgaa  2340
ttggaagcct tgttggaaaa gcaagcctac aaggaacaag ttttggctaa gagattgacc  2400
atgttggaat tgttggaaaa gtacccagcc tgcgaaatga agttctctga atttatcgcc  2460
ttgttgccat ctatcagacc acgttactac tctatttctt cctctccacg tgttgacgaa  2520
aagcaagctt ctattactgt ttccgttgtc tccggtgaag cttggtccgg ttacggtgaa  2580
tacaagggta ttgcttctaa ctacttggct gaattgcaag aaggtgacac cattacttgt  2640
ttcatctcta ctccacaatc cgaatttact ttgccaaagg acccagaaac tccattgatc  2700
atggttggtc caggtactgg tgtcgctcca ttcagaggtt tcgttcaagc tagaaaacaa  2760
ttgaaggaac aaggtcaatc tttgggtgaa gctcacttgt acttcggttg tagatctcca  2820
cacgaagact acttatacca agaagaattg gaaaacgctc aatccgaagg tattatcact  2880
ttgcacaccg ctttctccag aatgccaaac caaccaaaga cttacgtcca acacgttatg  2940
gaacaagacg gtaagaagtt gattgaattg ttggaccaag gtgctcactt ctacatttgt  3000
ggtgatggtt ctcaaatggc tccagccgtt gaagccactt tgatgaagtc ttacgctgat  3060
gttcaccaag tttccgaagc cgatgctaga ttatggttgc aacaattgga agaaaaaggt  3120
cgttacgcta aggatgtctg ggccggttga                                    3150

SEQ ID NO: 145          moltype = DNA  length = 3150
FEATURE                 Location/Qualifiers
misc_feature            1..3150
                        note = Description of Artificial Sequence: Synthetic
                         polynucleotide
source                  1..3150
                        mol_type = other DNA
                        organism = synthetic construct
SEQUENCE: 145
atgaccatca aagaaatgcc acaacctaag actttcggtg aattgaagaa tttgcctttg  60
ttgaacaccg ataagccagt tcaagctttg atgaagattg ctgatgaatt gggtgaaatc  120
ttcaagtttg aagctccagg tagagtcact agatacttgt catctcaaag attgatcaaa  180
gaagcctgcg acgaatccag atttgataag aatttgtctc aagctgctaa gttcgctaga  240
gattttgctg gtgatggttt ggttacttct tggactcacg aaaagaattg gaagaaggcc  300
cataacattt tgttgccatc tttctcacaa caagccatga agggttatca tgctatgatg  360
gttgatatcg ccgttcaatt ggttcaaaag tgggaaagat tgaacgccga tgaacatatc  420
gaagtctctg aagatatgac cagattgacc ttggatacca ttggtttgtg tggtttcaac  480
tacagattca actccttcta cagagatcaa ccacatccat tcatcatctc tgctgttaga  540
gctgcagatg aagtcatgaa caaattgcaa agagctaatc cagacgatcc agcttatgac  600
gaaaacaaga gacaattcca agaagatatc aaggtcatga acgatttggt cgataagatt  660
atcgctgata gaaaggctag aggtgaacaa tctgatgatt tgttgaccca aatgttgaac  720
ggtaaggatc cagaaactgg tgaaccattg gatgatggta acatcagata ccaaattatc  780
accttcttga ttgctggtca cgaaactaca tctggtttgt tgtcttttgc cttgtacttt  840
ttggttaaga acccacacgt cttgcaaaag gttgctgaag aagctgcaag agttttggtt  900
gatccagttc catcttacaa gcaagtcaag caattgaagt acgttggtat ggttttgaac  960
gaagctttga gattgtggcc aactgctcca gctttttcat tatacgctaa agaagatacc  1020
gtcttgggtg gtgaatatcc attggaaaaa ggtgatgaag ttatggtctt gatcccacaa  1080
ttgcatagag ataagactgt ttggggtgat gatgtcgaag aattcagacc agaaagattc  1140
gaaaacccat ctgctattcc acaacatgct tttaagccat ttggtaacgg tcaaagagct  1200
tgcattggtc aacaattcgc tttacatgaa gctaccttgg ttttgggtat gatgttgaaa  1260
cacttcgact tcgaagatca caccaactac gaattggata tcaaagaaac cttgaccttg  1320
aagccaaagg gttttgttgt taaggctaag tccaaaaaga ttccattggg tggtattcca  1380
tctccatcta ctgaacaatc cgctaagaag gttagaaaga aagctgaaaa cgctcataac  1440
acacctttgt tggtcttgta cggttctaat atgggtactg ctgaaggtac agcaagagat  1500
ttggcagata ttgctatgtc taaaggtttc gctccacaag ttgctacttt ggattctcat  1560
gctggtaatt tgccaagaga aggtgctgtt ttgatagtta ctgcttctta caatggtcac  1620
ccaccagata atgctaagca attcgttgat tggttggatc aagcttcagc tgatgaagta  1680
aaaggtgtta gatactctgt tttcggttgc ggtgacaaaa attgggctac tacttatcaa  1740
aaggttccag cctttattga cgaaactttg gctgctaaag gtgctgaaaa cattgctgac  1800
agaggtgaag ctgatgcctc cgacgacttc gaaggtactt acgaagaatg gagagaacac  1860
atgtggtctg acgttgctgc ttacttcaac ttggacatcg aaaactctga agacaacaag  1920
tccactttgt ctttgcaatt cgttgactcc gctgctgaca tgccattggc taagatgcac  1980
ggtgctttct ctaccaacgt cgttgcctcc aaggaattgc aacaaccagg ttctgctaga  2040
tctactagac acttggaaat cgaattgcca aaggaagctt cctaccaaga aggtgaccac  2100
ttgggcgtta ttccaagaaa ctacgaaggt atcgtcaaca gagttactgc tagattcggt  2160
ttggatgctt ctcaacaaat cagattagaa gctgaagaag aaaagttggc tcacttgcca  2220
ttagctaaga ctgtctccgt tgaagaattg ttgcaatacg tcgaattgca agacccagtt  2280
accagaaccc aattgagagc catggctgcc aagaccgtct gtccaccaca caaggttgaa  2340
ttggaagcct tgttggaaaa gcaagcctac aaggaacaag ttttggctaa gagattgacc  2400
atgttggaat tgttggaaaa gtacccagcc tgcgaaatga agttctctga atttatcgcc  2460
ttgttgccat ctatcagacc acgttactac tctatttctt cctctccacg tgttgacgaa  2520
aagcaagctt ctattactgt ttccgttgtc tccggtgaag cttggtccgg ttacggtgaa  2580
tacaagggta ttgcttctaa ctacttggct gaattgcaag aaggtgacac cattacttgt  2640
```

```
ttcatctcta ctccacaatc cgaatttact ttgccaaagg acccagaaac tccattgatc  2700
atggttggtc caggtactgg tgtcgctcca ttcagaggtt tcgttcaagc tagaaaacaa  2760
ttgaaggaac aaggtcaatc tttgggtgaa gctcacttgt acttcggttg tagatctcca  2820
cacgaagact acttatacca agaagaattg gaaaacgctc aatccgaagg tattatcact  2880
ttgcacaccg ctttctccag aatgccaaac caaccaaaga cttacgtcca acacgttatg  2940
gaacaagacg gtaagaagtt gattgaattg ttggaccaag gtgctcactt ctacatttgt  3000
ggtgatggtt ctcaaatggc tccagccgtt gaagccactt tgatgaagtc ttacgctgat  3060
gttcaccaag tttccgaagc cgatgctaga ttatggttgc aacaattgga agaaaaaggt  3120
cgttacgcta aggatgtctg ggccggttga                                    3150

SEQ ID NO: 146          moltype = DNA  length = 3150
FEATURE                 Location/Qualifiers
misc_feature            1..3150
                        note = Description of Artificial Sequence: Synthetic
                         polynucleotide
source                  1..3150
                        mol_type = other DNA
                        organism = synthetic construct
SEQUENCE: 146
atgaccatca aagaaatgcc acaacctaag actttcggtg aattgaagaa tttgcctttg  60
ttgaacaccg ataagccagt tcaagctttg atgaagattg ctgatgaatt gggtgaaatc  120
ttcaagtttg aagctccagg tagagtcact agatacttgt catctcaaag attgatcaaa  180
gaagcctgcg acgaatccag atttgataag aatttgtctc aagctgctaa gttcgctaga  240
gattttgctg gtgatggttt ggttacttct tggactcacg aaaagaattg gaagaaggcc  300
cataacattt tgttgccatc tttctcacaa caagccatga agggttatca tgctatgatg  360
gttgatatcg ccgttcaatt ggttcaaaag tgggaaagat tgaacgccga tgaacatatc  420
gaagtctctg aagatatgac cagattgacc ttggatacca ttggtttgtg tggtttcaac  480
tacagattca actccttcta cagagatcaa ccacatccat tcatcatctc tgctgttaga  540
gctgcagatg aagtcatgaa caaattgcaa agagctaatc cagacgatcc agcttatgac  600
gaaaacaaga gacaattcca agaagatatc aaggtcatga acgatttggt cgataagatt  660
atcgctgata gaaaggctag aggtgaacaa tctgatgatt tgttgaccca aatgttgaac  720
ggtaaggatc cagaaactgg tgaaccattg gatgatggta acatcagata ccaaattatc  780
gctttcttga ttgctggtca cgaaactaca tctggtttgt tgtcttttgc cttgtacttt  840
ttggttaaga acccacacgt cttgcaaaag gttgctgaag aagctgcaag agttttggtt  900
gatccagttc catcttacaa gcaagtcaag caattgaagt acgttggtat ggttttgaac  960
gaagctttga gattgtggcc aactgctcca gctttttcat tatacgctaa agaagatacc  1020
gtcttgggtg gtgaatatcc attggaaaaa ggtgatgaag ttatggtctt gatcccacaa  1080
ttgcatagag ataagactgt ttggggtgat gatgtcgaag aattcagacc agaaagattc  1140
gaaaacccat ctgctattcc acaacatgct tttaagccat ttggtaacgg tcaaagagct  1200
tgcattggtc aacaattcgc tttacatgaa gctaccttgg ttttgggtat gatgttgaaa  1260
cacttcgact tcgaagatca caccaactac gaattggata tcaaagaaac cttgaccttg  1320
aagccaaagg gttttgttgt taaggctaag tccaaaaaga ttccattggg tggtattcca  1380
tctccatcta ctgaacaatc cgctaagaag gttagaaaga aagctgaaaa cgctcataac  1440
acacctttgt tggtcttgta cggttctaat atgggtactg ctgaaggtac agcaagagat  1500
ttggcagata ttgctatgtc taaaggtttc gctccacaag ttgctacttt ggattctcat  1560
gctggtaatt tgccaagaga aggtgctgtt ttgatagtta ctgcttctta caatggtcac  1620
ccaccagata atgctaagca attcgttgat tggttggatc aagcttcagc tgatgaagta  1680
aaaggtgtta gatactctgt tttcggttgc ggtgacaaaa attgggctac tacttatcaa  1740
aaggttccag cctttattga cgaaactttg gctgctaaag gtgctgaaaa cattgctgac  1800
agaggtgaag ctgatgcctc cgacgacttc gaaggtactt acgaagaatg gagagaacac  1860
atgtggtctg acgttgctgc ttacttcaac ttggacatcg aaaactctga agacaacaag  1920
tccactttgt ctttgcaatt cgttgactcc gctgctgaca tgccattggc taagatgcac  1980
ggtgctttct ctaccaacgt cgttgcctcc aaggaattgc aacaaccagg ttctgctaga  2040
tctactagac acttggaaat cgaattgcca aaggaagctt cctaccaaga aggtgaccac  2100
ttgggcgtta ttccaagaaa ctacgaaggt atcgtcaaca gagttactgc tagattcggt  2160
ttggatgctt ctcaacaaat cagattagaa gctgaagaag aaaagttggc tcacttgcca  2220
ttagctaaga ctgtctccgt tgaagaattg ttgcaatacg tcgaattgca agacccagtt  2280
accagaaccc aattgagagc catggctgcc aagaccgtct gtccaccaca caaggttgaa  2340
ttggaagcct tgttggaaaa gcaagcctac aaggaacaag ttttggctaa gagattgacc  2400
atgttggaat tgttggaaaa gtacccagcc tgcgaaatga agttctctga atttatcgcc  2460
ttgttgccat ctatcagacc acgttactac tctatttctt cctctccacg tgttgacgaa  2520
aagcaagctt ctattactgt ttccgttgtc tccggtgaag cttggtccgg ttacggtgaa  2580
tacaagggta ttgcttctaa ctacttggct gaattgcaag aaggtgacac cattacttgt  2640
ttcatctcta ctccacaatc cgaatttact ttgccaaagg acccagaaac tccattgatc  2700
atggttggtc caggtactgg tgtcgctcca ttcagaggtt tcgttcaagc tagaaaacaa  2760
ttgaaggaac aaggtcaatc tttgggtgaa gctcacttgt acttcggttg tagatctcca  2820
cacgaagact acttatacca agaagaattg gaaaacgctc aatccgaagg tattatcact  2880
ttgcacaccg ctttctccag aatgccaaac caaccaaaga cttacgtcca acacgttatg  2940
gaacaagacg gtaagaagtt gattgaattg ttggaccaag gtgctcactt ctacatttgt  3000
ggtgatggtt ctcaaatggc tccagccgtt gaagccactt tgatgaagtc ttacgctgat  3060
gttcaccaag tttccgaagc cgatgctaga ttatggttgc aacaattgga agaaaaaggt  3120
cgttacgcta aggatgtctg ggccggttga                                    3150

SEQ ID NO: 147          moltype = DNA  length = 5372
FEATURE                 Location/Qualifiers
misc_feature            1..5372
                        note = Description of Artificial Sequence: Synthetic
                         polynucleotide
source                  1..5372
```

-continued

```
                         mol_type = other DNA
                         organism = synthetic construct
SEQUENCE: 147
cctcgccgca gttaattaaa gtcagtgagc gaggaagcgc gtaactataa cggtcctaag  60
gtagcgaatc ctgatgcggt attttctcct tacgcatctg tgcggtattt cacaccgcat  120
agatcggcaa gtgcacaaac aatacttaaa taaatactac tcagtaataa cctatttctt  180
agcatttttg acgaaatttg ctattttgtt agagtctttt acaccatttg tctccacacc  240
tccgcttaca tcaacaccaa taacgccatt taatctaagc gcatcaccaa cattttctgg  300
cgtcagtcca ccagctaaca taaaatgtaa gctttcgggg ctctcttgcc ttccaaccca  360
gtcagaaatc gagttccaat ccaaaagttc acctgtccca cctgcttctg aatcaaacaa  420
gggaataaac gaatgaggtt tctgtgaagc tgcactgagt agtatgttgc agtcttttgg  480
aaatacgagt cttttaataa ctggcaaacc gaggaactct tggtattctt gccacgactc  540
atctccatgc agtggagcca atcaattctt gcggtcaact ttggacgata tcaatgccgt  600
aatcattgac cagagccaaa acatcctcct taagttgatt acgaaacacg ccaaccaagt  660
atttcggagt gcctgaacta tttttatatg cttttacaag acttgaaatt ttccttgcaa  720
taaccgggtc aattgttctc tttctattgg gcacacatat aatacccagc aagtcagcat  780
cggaatctag agcacattct gcggcctctg tgctctgcaa gccgcaaact ttcaccaatg  840
gaccagaact acctgtgaaa ttaataacag acatactcca agctgccttt gtgtgcttaa  900
tcacgtatac tcacgtgctc aatagtcacc aatgccctcc ctcttggccc tctccttttc  960
tttttttcgac cgaattaatt cttaatcggc aaaaaaagaa aagctccgga tcaagattgt  1020
acgtaaggtg acaagctatt tttcaataaa gaatatcttc cactactgcc atctggcgtc  1080
ataactgcaa agtacacata tattacgatg ctgttctatt aaatgcttcc tatattatat  1140
atatagtaat gtcgtgatct atggtgcact ctcagtacaa tctgctctga tgccgcatag  1200
ttaagccagc cccgacaccc gccaacaccc gctgacgcgc cctgacgggc ttgtctgctc  1260
ccggcatccg cttacagaca agctgtgacc gtctccggga gctgcatgtg tcagaggttt  1320
tcaccgtcat caccgaaacg cgcgagacga aagggcctcg tgatacgcct atttttatag  1380
gttaatgtca tgataataat ggtttcttag acggatcgct tgcctgtaac ttacacgcgc  1440
ctcgtatctt ttaatgatgg aataatttgg gaatttactc tgtgtttatt tatttttatg  1500
ttttgtattt ggattttaga aagtaaataa agaaggtaga agagttacgg aatgaagaaa  1560
aaaaaataaa caaaggttta aaaaatttca acaaaaagcg tactttacat atatatttat  1620
tagacaagaa aagcagatta aatagatata cattcgatta acgataagta aaatgtaaaa  1680
tcacaggatt ttcgtgtgtg gtcttctaca cagacaaggt gaaacaattc ggcattaata  1740
cctgagagca ggaagagcaa gataaaaggt agtatttgtt ggcgatcccc ctagagtctt  1800
ttacatcttc ggaaaacaaa aactattttt tctttaattt cttttttttac tttctatttt  1860
taatttatat atttatatta aaaaatttaa attataatta tttttatagc acgtgatgaa  1920
aaggacccag gtggcacttt tcggggaaat gtgcgcggaa cccctatttg tttatttttc  1980
taaatacatt caaatatgta tccgctcatg agacaataac cctgataaat gcttcaataa  2040
tattgaaaaa ggaagagtat gagtattcaa catttccgtg tcgcccttat tccctttttt  2100
gcggcatttt gccttcctgt ttttgctcac ccagaaacgc tggtgaaagt aaaagatgct  2160
gaagatcagt tgggacgcgt agtctagacc agccaggaca gaaatgcctc gacttcgctg  2220
ctacccaagg ttgccgggtg acgcacaccg tggaaacgga tgaaggcacg aacccagtgg  2280
acataagcct gttcggttcg taagctgtaa tgcaagtagc gtatgcgctc acgcaactgg  2340
tccagaacct tgaccgaacg cagcggtggt aacggcgcag tggcggtttt catggcttgt  2400
tatgactgtt tttttggggt acagtctatg cctcgggcat ccaagcagca agcgcgttac  2460
gccgtgggtc gatgtttgat gttatggagc agcaacgatg ttacgcagca gggcagtcgc  2520
cctaaaacaa agttaaacat tatgagggaa gcggtgatcg ccgaagtatc gactcaacta  2580
tcagaggtag ttggcgccat cgagcgccat ctcgaaccga cgttgctggc cgtacatttg  2640
tacggctccg cagtggatgg cggcctgaag ccacacagtg atattgattt gctggttacg  2700
gtgaccgtaa ggcttgatga aacaacgcgg cgagctttga tcaacgacct tttggaaact  2760
tcggcttccc ctggagagag cgagattctc cgcgctgtag aagtcaccat tgttgtgcac  2820
gacgacatca ttccgtggcg ttatccagct aagcgcgaac tgcaatttgg agaatggcag  2880
cgcaatgaca ttcttgcagg tatcttcgag ccagccacga tcgacattga tctggctatc  2940
ttgctgacaa aagcaagaga acatagcgtt gccttggtag gtccagcggc ggaggaactc  3000
tttgatccgg ttcctgaaca ggatctattt gaggcgctaa atgaaacctt aacgctatgg  3060
aactcgccgc ccgactgggc tggcgatgag cgaaatgtag tgcttacgtt gtcccgcatt  3120
tggtacagcg cagtaaccgg caaaatcgcg ccgaaggatg tcgctgccgg ctgggcaatg  3180
gagcgcctgc cggcccagta tcagcccgtc atacttgaag ctagacaggc ttatcttgga  3240
caagaagaag atcgcttggc ctcgcgcgca gatcagttgg aagaatttgt ccactacgtg  3300
aaaggcgaga tcaccaaggt agtcggcaaa taaccctcga gcattcaagg cgccttgatt  3360
atttgacgtg gtttgatggc ctccacgcac gttgtgatat gtagatgatt cagttcgagt  3420
ttatcattat caatactgcc atttcaaaga atacgtaaat aattaatagt agtgattttc  3480
ctaactttat ttagtcaaaa aattagcctt ttaattctgc tgtaacccgt acatgcccaa  3540
aatagggggc gggttacaca gaatatataa catcgtaggt gtctgggtga acagtttatt  3600
cctggcatcc actaaatata atggagcccg ctttttaagc tggcatccag aaaaaaaaag  3660
aatcccagca ccaaaatatt gttttcttca ccaaccatca gttcataggt ccattctctt  3720
agcgcaacta cagagaacag gggcacaaac aggcaaaaaa cgggcacaac ctcaatggag  3780
tgatgcaacc tgcctggagt aaatgatgac acaaggcaat tgacccacgc atgtatctat  3840
ctcattttct tacaccttct attaccttct gctctctctg atttggaaaa agctgaaaaa  3900
aaaggttgaa accagttccc tgaaattatt cccctacttg actaataagt atataaagac  3960
ggtaggtatt gattgtaatt ctgtaaatct atttcttaaa cttcttaaat tctactttta  4020
tagttagtct tttttttagt tttaaaacac caagaactta gtttcgaata aacacacata  4080
aacaaacaaa acaggcccct tttcctttgt cgatatcatg taattagtta tgtcacgctt  4140
acattcacgc cctcctccca catccgctct aaccgaaaag gaaggagtta gacaacctga  4200
agtctaggtc cctatttatt ttttttaata gttatgttag tattaagaac gttatttata  4260
tttcaaattt ttcttttttt tctgtacaaa cgcgtgtacg catgtaacat tatactgaaa  4320
accttgcttg agaaggtttt gggacgctcg aaggctttaa tttgtaatca ttatcacttt  4380
acgggtcctt tccggtgatc cgacaggtta cggggcggcg acctcgcggg ttttcgctat  4440
ttatgaaaat tttccggttt aaggcgtttc cgttcttctt cgtcataact taatgttttt  4500
atttaaaata cctcgcgagt ggcaacactg aaaataccca tggagcggcg taaccgtcgc  4560
```

-continued

```
acaggatcta ggtgaagatc ctttttgata atctcatgac caaaatccct taacgtgagt  4620
tttcgttcca ctgagcgtca gaccccgtag aaaagatcaa aggatcttct tgagatcctt  4680
tttttctgcg cgtaatctgc tgcttgcaaa caaaaaaacc accgctacca gcggtggttt  4740
gtttgccgga tcaagagcta ccaactcttt ttccgaaggt aactggcttc agcagagcgc  4800
agataccaaa tactgtcctt ctagtgtagc cgtagttagg ccaccacttc aagaactctg  4860
tagcaccgcc tacatacctc gctctgctaa tcctgttacc agtggctgct gccagtggcg  4920
ataagtcgtg tcttaccggg ttggactcaa gacgatagtt accggataag gcgcagcggt  4980
cgggctgaac ggggggttcg tgcacacagc ccagcttgga gcgaacgacc tacaccgaac  5040
tgagatacct acagcgtgag ctatgagaaa gcgccacgct tcccgaaggg agaaaggcgg  5100
acaggtatcc ggtaagcggc agggtcggaa caggagagcg cacgagggag cttccagggg  5160
gaaacgcctg gtatctttat agtcctgtcg ggtttcgcca cctctgactt gagcgtcgat  5220
ttttgtgatg ctcgtcaggg gggcggagcc tatggaaaaa cgccagcaac gcggcagtgg  5280
aacgtgcatt atgaattagt tacgctaggg ataacagggt aatatagaac ccgaacgacc  5340
gagcgcagcg gcggccgcgc tgataccgcc gc                               5372
```

```
SEQ ID NO: 148          moltype = DNA  length = 4977
FEATURE                 Location/Qualifiers
misc_feature            1..4977
                        note = Description of Artificial Sequence: Synthetic
                         polynucleotide
source                  1..4977
                        mol_type = other DNA
                        organism = synthetic construct
SEQUENCE: 148
aacgacctac accgaactga gatacctaca gcgtgagcta tgagaaagcg ccacgcttcc  60
cgaagggaga aaggcggaca ggtatccggt aagcggcagg gtcggaacag gagagcgcac  120
gagggagctt ccagggggaa acgcctggta tctttatagt cctgtcgggt ttcgccacct  180
ctgacttgag cgtcgatttt tgtgatgctc gtcagggggg cggagcctat ggaaaaacgc  240
cagcaacgcg gcagtggaac gtgcattatg aattagttac gctagggata acagggtaat  300
atagaacccg aacgaccgag cgcagcggcg gccgcgctga taccgccgcc ctcgccgcag  360
ttaattaaag tcagtgagcg aggaagcgcg taactataac ggtcctaagg tagcgaatcc  420
tgatgcggta ttttctcctt acgcatctgt gcggtatttc acaccgcata gatcggcaag  480
tgcacaaaca atacttaaat aaatactact cagtaataac ctatttctta gcatttttga  540
cgaaatttgc tattttgtta gagtctttta caccatttgt ctccacacct ccgcttacat  600
caacaccaat aacgccattt aatctaagcg catcaccaac attttctggc gtcagtccac  660
cagctaacat aaaatgtaag ctttcggggc tctcttgcct tccaacccag tcagaaatcg  720
agttccaatc caaaagttca cctgtcccac ctgcttctga atcaaacaag ggaataaacg  780
aatgaggttt ctgtgaagct gcactgagta gtatgttgca gtcttttgga aatacgagtc  840
ttttaataac tggcaaaccg aggaactctt ggtattcttg ccacgactca tctccatgca  900
gtggagccaa tcaattcttg cggtcaactt tggacgatat caatgccgta atcattgacc  960
agagccaaaa catcctcctt aagttgatta cgaaacacgc caaccaagta tttcggagtg  1020
cctgaactat ttttatatgc ttttacaaga cttgaaattt tccttgcaat aaccgggtca  1080
attgttctct ttctattggg cacacatata atacccagca agtcagcatc ggaatctaga  1140
gcacattctg cggcctctgt gctctgcaag ccgcaaactt tcaccaatgg accagaacta  1200
cctgtgaaat taataacaga catactccaa gctgcctttg tgtgcttaat cacgtatact  1260
cacgtgctca atagtcacca atgccctccc tcttggccct ctccttttct tttttcgacc  1320
gaattaattc ttaatcggca aaaaaagaaa agctccggat caagattgta cgtaaggtga  1380
caagctattt ttcaataaag aatatcttcc actactgcca tctggcgtca taactgcaaa  1440
gtacacatat attacgatgc tgttctatta aatgcttcct atattatata tatagtaatg  1500
tcgtgatcta tggtgcactc tcagtacaat ctgctctgat gccgcatagt taagccagcc  1560
ccgacacccg ccaacacccg ctgacgcgcc ctgacgggct tgtctgctcc cggcatccgc  1620
ttacagacaa gctgtgaccg tctccgggag ctgcatgtgt cagaggtttt caccgtcatc  1680
accgaaacgc gcgagacgaa agggcctcgt gatacgccta tttttatagg ttaatgtcat  1740
gataataatg gtttcttaga cggatcgctt gcctgtaact tacacgcgcc tcgtatcttt  1800
taatgatgga ataatttggg aatttactct gtgtttattt atttttatgt tttgtatttg  1860
gattttagaa agtaaataaa gaaggtagaa gagttacgga atgaagaaaa aaaaataaac  1920
aaaggtttaa aaaatttcaa caaaaagcgt actttacata tatatttatt agacaagaaa  1980
agcagattaa atagatatac attcgattaa cgataagtaa aatgtaaaat cacaggattt  2040
tcgtgtgtgg tcttctacac agacaaggtg aaacaattcg gcattaatac ctgagagcag  2100
gaagagcaag ataaaaggta gtatttgttg gcgatccccc tagagtcttt tacatcttcg  2160
gaaaacaaaa actatttttt ctttaatttc tttttttact ttctattttt aatttatata  2220
tttatattaa aaaatttaaa ttataattat ttttatagca cgtgatgaaa aggacccagg  2280
tggcactttt cggggaaatg tgcgcggaac ccctatttgt ttatttttct aaatacattc  2340
aaatatgtat ccgctcatga gacaataacc ctgataaatg cttcaataat attgaaaaag  2400
gaagagtatg agtattcaac atttccgtgt cgcccttatt ccctttttttg cggcattttg  2460
ccttcctgtt tttgctcacc cagaaacgct ggtgaaagta aaagatgctg aagatcagtt  2520
gggacgcgta gtctagacca gccaggacag aaatgcctcg acttcgctgc tacccaaggt  2580
tgccgggtga cgcacaccgt ggaaacggat gaaggcacga acccagtgga cataagcctg  2640
ttcggttcgt aagctgtaat gcaagtagcg tatgcgctca cgcaactggt ccagaacctt  2700
gaccgaacgc agcggtggta acggcgcagt ggcggttttc atggcttgtt atgactgttt  2760
ttttggggta cagtctatgc ctcgggcatc caagcagcaa gcgcgttacg ccgtgggtcg  2820
atgtttgatg ttatggagca gcaacgatgt tacgcagcag ggcagtcgcc ctaaaacaaa  2880
gttaaacatt atgagggaag cggtgatcgc cgaagtatcg actcaactat cagaggtagt  2940
tggcgccatc gagcgccatc tcgaaccgac gttgctggcc gtacatttgt acggctccgc  3000
agtggatggc ggcctgaagc cacacagtga tattgatttg ctggttacgg tgaccgtaag  3060
gcttgatgaa acaacgcggc gagctttgat caacgacctt ttggaaactt cggcttcccc  3120
tggagagagc gagattctcc gcgctgtaga agtcaccatt gttgtgcacg acgacatcat  3180
tccgtggcgt tatccagcta agcgcgaact gcaatttgga gaatggcagc gcaatgacat  3240
tcttgcaggt atcttcgagc cagccacgat cgacattgat ctggctatct tgctgacaaa  3300
```

```
agcaagagaa catagcgttg ccttggtagg tccagcggcg gaggaactct ttgatccggt  3360
tcctgaacag gatctatttg aggcgctaaa tgaaacctta acgctatgga actcgccgcc  3420
cgactgggct ggcgatgagc gaaatgtagt gcttacgttg tcccgcattt ggtacagcgc  3480
agtaaccggc aaaatcgcgc cgaaggatgt cgctgccggc tgggcaatgg agcgcctgcc  3540
ggcccagtat cagcccgtca tacttgaagc tagacaggct tatcttggac aagaagaaga  3600
tcgcttggcc tcgcgcgcag atcagttgga agaatttgtc cactacgtga aaggcgagat  3660
caccaaggta gtcggcaaat aaccctcgag cattcaaggc gccttgatta tttgacgtgg  3720
tttgatggcc tccacgcacg ttgtgatatg tagatgagag cgttggttgg tggatcaagc  3780
ccacgcgtag gcaatcctcg agcagatccg ccaggcgtgt atatatagcg tggatggcca  3840
ggcaacttta gtgctgacac atacaggcat atatatatgt gtgcgacaac acatgatcat  3900
atggcatgca tgtgctctgt atgtatataa aactcttgtt ttcttctttt ctctaaatat  3960
tctttcctta tacattagga cctttgcagc ataaattact atacttctat agacacacaa  4020
acacaaatac acacactaaa ttaataacag gccccttttc ctttgtcgat atcatgtaat  4080
tagttatgtc acgcttacat tcacgccctc cccccacatc cgctctaacc gaaaaggaag  4140
gagttagaca acctgaagtc taggtcccta tttatttttt tatagttatg ttagtattaa  4200
gaacgttatt tatatttcaa atttttcttt tttttctgta caaacgcgtg tacgcatgta  4260
acattatact gaaaaccttg cttgagaagg ttttgggacg ctcgaaggct ttaatttgta  4320
atcattatca ctttacgggt cctttccggt gatccgacag gttacggggc ggcgacctcg  4380
cgggttttcg ctatttatga aaattttccg gtttaaggcg tttccgttct tcttcgtcat  4440
aacttaatgt tttttatttaa aatacctcgc gagtggcaac actgaaaata cccatggagc  4500
ggcgtaaccg tcgcacagga tctaggtgaa gatccttttt gataatctca tgaccaaaat  4560
cccttaacgt gagttttcgt tccactgagc gtcagacccc gtagaaaaga tcaaaggatc  4620
ttcttgagat cctttttttc tgcgcgtaat ctgctgcttg caaacaaaaa aaccaccgct  4680
accagcggtg gtttgtttgc cggatcaaga gctaccaact ctttttccga aggtaactgg  4740
cttcagcaga gcgcagatac caaatactgt ccttctagtg tagccgtagt taggccacca  4800
cttcaagaac tctgtagcac cgcctacata cctcgctctg ctaatcctgt taccagtggc  4860
tgctgccagt ggcgataagt cgtgtcttac cgggttggac tcaagacgat agttaccgga  4920
taaggcgcag cggtcgggct gaacgggggg ttcgtgcaca cagcccagct tggagcg     4977

SEQ ID NO: 149          moltype = DNA  length = 5079
FEATURE                 Location/Qualifiers
misc_feature            1..5079
                        note = Description of Artificial Sequence: Synthetic
                         polynucleotide
source                  1..5079
                        mol_type = other DNA
                        organism = synthetic construct
SEQUENCE: 149
acgacctaca ccgaactgag atacctacag cgtgagctat gagaaagcgc cacgcttccc  60
gaagggagaa aggcggacag gtatccggta agcggcaggg tcggaacagg agagcgcacg  120
agggagcttc caggggggaaa cgcctggtat ctttatagtc ctgtcgggtt tcgccacctc  180
tgacttgagc gtcgattttt gtgatgctcg tcaggggggc ggagcctatg gaaaaacgcc  240
agcaacgcgg cagtggaacg tgcattatga attagttacg ctagggataa cagggtaata  300
tagaacccga acgaccgagc gcagcggcgg ccgcgctgat accgccgccc tcgccgcagt  360
taattaaagt cagtgagcga ggaagcgcgt aactataacg gtcctaaggt agcgaatcct  420
gatgcggtat tttctcctta cgcatctgtg cggtatttca caccgcatag atcggcaagt  480
gcacaaacaa tacttaaata aatactactc agtaataacc tatttcttag catttttgac  540
gaaatttgct attttgttag agtcttttac accatttgtc tccacacctc cgcttacatc  600
aacaccaata acgccattta atctaagcgc atcaccaaca ttttctggcg tcagtccacc  660
agctaacata aaatgtaagc tttcggggct ctcttgcctt ccaacccagt cagaaatcga  720
gttccaatcc aaaagttcac ctgtcccacc tgcttctgaa tcaaacaagg gaataaacga  780
atgaggtttc tgtgaagctg cactgagtag tatgttgcag tcttttggaa atacgagtct  840
tttaataact ggcaaaccga ggaactcttg gtattcttgc cacgactcat ctccatgcag  900
tggagccaat caattcttgc ggtcaacttt ggacgatatc aatgccgtaa tcattgacca  960
gagccaaaac atcctcctta agttgattac gaaacacgcc aaccaagtat ttcggagtgc  1020
ctgaactatt tttatatgct tttacaagac ttgaaatttt ccttgcaata accgggtcaa  1080
ttgttctctt tctattgggc acacatataa tacccagcaa gtcagcatcg gaatctagag  1140
cacattctgc ggcctctgtg ctctgcaagc cgcaaacttt caccaatgga ccagaactac  1200
ctgtgaaatt aataacagac atactccaag ctgcctttgt gtgcttaatc acgtatactc  1260
acgtgctcaa tagtcaccaa tgccctccct cttggccctc tccttttctt ttttcgaccg  1320
aattaattct taatcggcaa aaaaagaaaa gctccggatc aagattgtac gtaaggtgac  1380
aagctatttt tcaataaaga atatcttcca ctactgccat ctggcgtcat aactgcaaag  1440
tacacatata ttacgatgct gttctattaa atgcttccta tattatatat atagtaatgt  1500
cgtgatctat ggtgcactct cagtacaatc tgctctgatg ccgcatagtt aagccagccc  1560
cgacacccgc caacacccgc tgacgcgccc tgacgggctt gtctgctccc ggcatccgct  1620
tacagacaag ctgtgaccgt ctccgggagc tgcatgtgtc agaggttttc accgtcatca  1680
ccgaaacgcg cgagacgaaa gggcctcgtg atacgcctat ttttataggt taatgtcatg  1740
ataataatgg tttcttagac ggatcgcttg cctgtaactt acacgcgcct cgtatctttt  1800
aatgatggaa taatttggga atttactctg tgtttattta ttttatgtt ttgtatttgg  1860
attttagaaa gtaaataaag aaggtagaag agttacggaa tgaagaaaaa aaaataaaca  1920
aaggtttaaa aaatttcaac aaaaagcgta ctttacatat atatttatta gacaagaaaa  1980
gcagattaaa tagatataca ttcgattaac gataagtaaa atgtaaaatc acaggatttt  2040
cgtgtgtggt cttctacaca gacaaggtga aacaattcgg cattaatacc tgagagcagg  2100
aagagcaaga taaaaggtag tatttgttgg cgatccccct agagtctttt acatcttcgg  2160
aaaacaaaaa ctatttttc tttaatttct tttttactt tctattttta atttatatat  2220
ttatattaaa aaatttaaat tataattatt tttatagcac gtgatgaaaa ggacccaggt  2280
ggcacttttc ggggaaatgt gcgcggaacc cctatttgtt tattttcta aatacattca  2340
aatatgtatc cgctcatgag acaataaccc tgataaatgc ttcaataata ttgaaaaagg  2400
aagagtatga gtattcaaca tttccgtgtc gcccttattc ccttttttgc ggcattttgc  2460
```

-continued

```
cttcctgttt ttgctcaccc agaaacgctg gtgaaagtaa aagatgctga agatcagttg  2520
ggacgcgtag tctagaccag ccaggacaga aatgcctcga cttcgctgct acccaaggtt  2580
gccgggtgac gcacaccgtg gaaacggatg aaggcacgaa cccagtggac ataagcctgt  2640
tcggttcgta agctgtaatg caagtagcgt atgcgctcac gcaactggtc cagaaccttg  2700
accgaacgca gcggtggtaa cggcgcagtg gcggttttca tggcttgtta tgactgtttt  2760
tttggggtac agtctatgcc tcgggcatcc aagcagcaag cgcgttacgc cgtgggtcga  2820
tgtttgatgt tatggagcag caacgatgtt acgcagcagg gcagtcgccc taaaacaaag  2880
ttaaacatta tgagggaagc ggtgatcgcc gaagtatcga ctcaactatc agaggtagtt  2940
ggcgccatcg agcgccatct cgaaccgacg ttgctggccg tacatttgta cggctccgca  3000
gtggatggcg gcctgaagcc acacagtgat attgatttgc tggttacggt gaccgtaagg  3060
cttgatgaaa caacgcggcg agctttgatc aacgaccttt tggaaacttc ggcttcccct  3120
ggagagagcg agattctccg cgctgtagaa gtcaccattg ttgtgcacga cgacatcatt  3180
ccgtggcgtt atccagctaa gcgcgaactg caatttggag aatggcagcg caatgacatt  3240
cttgcaggta tcttcgagcc agccacgatc gacattgatc tggctatctt gctgacaaaa  3300
gcaagagaac atagcgttgc cttggtaggt ccagcggcgg aggaactctt tgatccggtt  3360
cctgaacagg atctatttga ggcgctaaat gaaaccttaa cgctatggaa ctcgccgccc  3420
gactgggctg gcgatgagcg aaatgtagtg cttacgttgt cccgcatttg gtacagcgca  3480
gtaaccggca aaatcgcgcc gaaggatgtc gctgccggct gggcaatgga gcgcctgccg  3540
gcccagtatc agcccgtcat acttgaagct agacaggctt atcttggaca agaagaagat  3600
cgcttggcct cgcgcgcaga tcagttggaa gaatttgtcc actacgtgaa aggcgagatc  3660
accaaggtag tcggcaaata accctcgagc attcaaggcg ccttgattat ttgacgtggt  3720
ttgatggcct ccacgcacgt tgtgatatgt agatgactcg taggaacaat ttcgggcccc  3780
tgcgtgttct tctgaggttc atcttttaca tttgcttctg ctggataatt ttcagaggca  3840
acaaggaaaa attagatggc aaaaagtcgt ctttcaagga aaaatcccca ccatctttcg  3900
agatcccctg taacttattg gcaactgaaa gaatgaaaag gaggaaaata caaaatatac  3960
tagaactgaa aaaaaaaaag tataaataga gacgatatat gccaatactt cacaatgttc  4020
gaatctattc ttcatttgca gctattgtaa aataataaaa catcaagaac aaacaagctc  4080
aacttgtctt ttctaagaac aaagaataaa cacaaaaaca aaaagttttt ttaattttaa  4140
tcaaaaaaca ggcccctttt cctttgtcga tatcatgtaa ttagttatgt cacgcttaca  4200
ttcacgccct ccccccacat ccgctctaac cgaaaaggaa ggagttagac aacctgaagt  4260
ctaggtccct atttattttt ttatagttat gttagtatta agaacgttat ttatatttca  4320
aatttttctt ttttttctgt acaaacgcgt gtacgcatgt aacattatac tgaaaacctt  4380
gcttgagaag gttttgggac gctcgaaggc tttaatttgt aatcattatc actttacggg  4440
tcctttccgg tgatccgaca ggttacgggg cggcgacctc gcgggttttc gctatttatg  4500
aaaatttttcc ggtttaaggc gtttccgttc ttcttcgtca taacttaatg tttttattta  4560
aaatacctcg cgagtggcaa cactgaaaat acccatggag cggcgtaacc gtcgcacagg  4620
atctaggtga agatcctttt tgataatctc atgaccaaaa tcccttaacg tgagttttcg  4680
ttccactgag cgtcagaccc cgtagaaaag atcaaaggat cttcttgaga tccttttttt  4740
ctgcgcgtaa tctgctgctt gcaaacaaaa aaaccaccgc taccagcggt ggtttgtttg  4800
ccggatcaag agctaccaac tctttttccg aaggtaactg gcttcagcag agcgcagata  4860
ccaaatactg tccttctagt gtagccgtag ttaggccacc acttcaagaa ctctgtagca  4920
ccgcctacat acctcgctct gctaatcctg ttaccagtgg ctgctgccag tggcgataag  4980
tcgtgtctta ccgggttgga ctcaagacga tagttaccgg ataaggcgca gcggtcgggc  5040
tgaacggggg gttcgtgcac acagcccagc ttggagcga                        5079
```

```
SEQ ID NO: 150          moltype = AA  length = 21
FEATURE                 Location/Qualifiers
source                  1..21
                        mol_type = protein
                        organism = Papaver rhoeas
SEQUENCE: 150
TQGLMSYKVV PLDILLTRRM L                                            21

SEQ ID NO: 151          moltype = AA  length = 60
FEATURE                 Location/Qualifiers
REGION                  1..60
                        note = Description of Artificial Sequence: Synthetic
                         polypeptide
source                  1..60
                        mol_type = protein
                        organism = synthetic construct
SEQUENCE: 151
TPGLMSYKVV PLDILLTHRR IKSCVQLASS ERDMESSGVP VITLSSGKVM PVLGMGTFEK  60

SEQ ID NO: 152          moltype = AA  length = 27
FEATURE                 Location/Qualifiers
source                  1..27
                        mol_type = protein
                        organism = Papaver rhoeas
SEQUENCE: 152
MDSSGVPVIP LSSGKGMPAL ALGTFET                                      27

SEQ ID NO: 153          moltype = AA  length = 900
FEATURE                 Location/Qualifiers
REGION                  1..900
                        note = Description of Artificial Sequence: Synthetic
                         polypeptide
source                  1..900
                        mol_type = protein
```

-continued

```
                    organism = synthetic construct
SEQUENCE: 153
MELQYISYFQ PTSSVVALLL ALVSILSSVV VLRKTFLNNY SSSPASSTKT AVLSHQRQQS  60
CALPISGLLH IFMNKNGLIH VTLGNMADKY GPIFSFPTGS HRTLVVSSWE MVKECFTGNN  120
DTAFSNRPIP LAFKTIFYAC GGIDSYGLSS VPYGKYWREL RKVCVHNLLS NQQLLKFRHL  180
IISQVDTSFN KLYELCKNSE DNQGNYPTTT TAAGMVRIDD WLAELSFNVI GRIVCGFQSG  240
PKTGAPSRVE QFKEAINEAS YFMSTSPVSD NVPMLGWIDQ LTGLTRNMKH CGKKLDLVVE  300
SIINDHRQKR RFSRTKGGDE KDDEQDDFID ICLSIMEQPQ LPGNNNPSQI PIKSIVLDMI  360
GGGTDTTKLT TIWTLSLLLN NPHVLDKAKQ EVDAHFRTKR RSTNDAAAAV VDFDDIRNLV  420
YIQAIIKESM RLYPASPVVE RLSGEDCVVG GFHVPAGTRL WANVWKMQRD PKVWDDPLVF  480
RPDRFLSDEQ KMVDVRGQNY ELLPFGAGRR VCPGVSFSLD LMQLVLTRLI LEFEMKSPSG  540
KVDMTATPGL MSYKVIPLDI LLTHRRIKPC VQSAASERDM ESSGVPVITL GSGKVMPVLG  600
MGTFEKVGKG SERERLAILK AIEVGYRYFD TAAAYETEEV LGEAIAEALQ LGLVKSRDEL  660
FISSMLWCTD AHADRVLLAL QNSLRNLKLE YVDLYMLPFP ASLKPGKITM DIPEEDICRM  720
DYRSVWAAME ECQNLGFTKS IGVSNFSCKK LQELMATANI PPAVNQVEMS PAFQQKKLRE  780
YCNANNILVS AISVLGSNGT PWGSNAVLGS EVLKKIAMAK GKSVAQVSMR WVYEQGASLV  840
VKSFSEERLR ENLNIFDWEL TKEDHEKIGE IPQCRILSAY FLVSPNGPFK SQEELWDDEA  900
```

METHODS OF PRODUCING MORPHINAN ALKALOIDS AND DERIVATIVES

CROSS-REFERENCE TO RELATED APPLICATIONS

This application is continuation application of U.S. application Ser. No. 16/984,900, filed Aug. 4, 2020, which is a continuation of International Application No. PCT/US19/17357, filed Feb. 8, 2019, which claims the benefit of U.S. Provisional Application No. 62/628,264, which was filed Feb. 8, 2018, which are herein incorporated by reference in their entireties, including any drawings.

SEQUENCE LISTING

This application incorporates by reference a Sequence Listing named "2023-11-20 Revised_Sequence_Listing_ST26 062074-511C02US.xml" which is 291,567 bytes in size, and replaces the original Sequence Listing file that was initially submitted with the application.

SUMMARY OF THE INVENTION

The present disclosure provides methods for the production of diverse benzylisoquinoline alkaloids (BIAs) in engineered host cells. The present disclosure further provides compositions of diverse alkaloids produced in engineered host cells. Additionally, the present disclosure provides methods for the production of a thebaine synthase in engineered host cells. In particular cases, the disclosure provides methods for producing diverse alkaloid products through the conversion of a promorphinan alkaloid into a morphinan alkaloid in an engineered host cell. In further particular cases, the present disclosure provides methods for producing diverse alkaloid products through the conversion of salutaridinol-7-O-acetate to thebaine.

An aspect of the invention provides an engineered non-plant cell having increased tyrosine hydroxylase activity relative to a non-engineered cell. Another aspect of the invention provides an engineered non-plant cell having increased tyrosine hydroxylase activity relative to a cell that expresses wild-type TyrH. An additional aspect of the invention provides an engineered non-plant cell having increased tyrosine hydroxylase activity relative to a cell that expresses wild-type TyrH without mutations that increase tyrosine hydroxylase activity as provided herein. In particular, the engineered non-plant cell has at least one modification selected from a group consisting of: a substrate inhibition alleviating mutation; a product inhibition alleviating mutation; and a cofactor recovery promoting mechanism.

An aspect of the invention provides an engineered plant cell having increased tyrosine hydroxylase activity relative to a non-engineered cell. Another aspect of the invention provides an engineered plant cell having increased tyrosine hydroxylase (TyrH) activity relative to a cell that expresses wild-type TyrH. An additional aspect of the invention provides an engineered plant cell having increased tyrosine hydroxylase activity relative to a cell that expresses wild-type TyrH without mutations that increase tyrosine hydroxylase activity as provided herein. In particular, the engineered plant cell has at least one modification selected from a group consisting of: a substrate inhibition alleviating mutation; a product inhibition alleviating mutation; and a cofactor recovery promoting mechanism.

In some embodiments, the disclosure provides methods for increasing production of diverse alkaloid products through the epimerization of a (S)-1-benzylisoquinoline alkaloid to a (R)-1-benyzlisoquinoline alkaloid via engineered epimerases in an engineered host cell. In further embodiments, the present disclosure provides methods for increasing production of diverse alkaloid products through the epimerization of (S)-reticuline to (R)-reticuline via an engineered epimerase comprising two separate enzymes encoding an oxidase and a reductase compared to the production of diverse alkaloid products through the epimerization of (S)-reticuline to (R)-reticuline via a wild-type epimerase.

While engineered split epimerases may be composed of a separate oxidase enzyme and reductase enzyme that originate from a parent or wild-type epimerase, engineered epimerases may also comprise a separate oxidase enzyme and reductase enzyme that originate from separate parent or wild-type epimerases. Examples of parent epimerases having an oxidase and reductase component comprise amino acid sequences selected from the group consisting of: SEQ ID NOs: 1, 2, 3, 4, 5, 6, 7, 8, 9, 10, 11, 12, 13, 14, 15, and 16, as listed in Table 1.

In some embodiments, the disclosure provides methods for increasing production of diverse alkaloid products through the conversion of a promorphinan alkaloid to a morphinan alkaloid via thebaine synthases in an engineered host cell. In further embodiments, the present disclosure provides methods for increasing production of diverse alkaloid products through the conversion of salutaridinol-7-O-acetate to thebaine via a thebaine synthase. Examples of parent thebaine synthases comprise amino acid sequences selected from the group consisting of: SEQ ID NOs: 30, 31, 32, 33, 34, 35, 36, and 37 as listed in Table 2.

In some embodiments, the disclosure provides methods for increasing production of diverse alkaloid products through the conversion of a promorphinan alkaloid to a morphinan alkaloid via engineered thebaine synthases in an engineered host cell. In further embodiments, the present disclosure provides methods for increasing production of diverse alkaloid products through the conversion of salutaridinol-7-O-acetate to thebaine via an engineered thebaine synthase.

In some embodiments, the engineered thebaine synthase is a fusion enzyme. In further embodiments, the thebaine synthase is fused to an acetyl transferase enzyme. In further embodiments, the thebaine synthase is encoded within an acetyl transferase enzyme. In other embodiments, the thebaine synthase is fused to a reductase enzyme.

In some examples, an engineered non-plant cell comprises a plurality of coding sequences each encoding an enzyme that is selected from the group of enzymes listed in Table 3. In some examples, the heterologous coding sequences may be operably connected. Heterologous coding sequences that are operably connected may be within the same pathway of producing a particular benzylisoquinoline alkaloid product via a thebaine synthase activity or an engineered thebaine synthase activity.

In some embodiments this disclosure provides a method of converting a tetracyclic promorphinan precursor to a thebaine, comprising contacting the tetracyclic promorphinan precursor with at least one enzyme, wherein contacting the tetracyclic promorphinan precursor with the at least one enzyme converts the tetracyclic promorphinan precursor to a thebaine. In some cases, the at least one enzyme is produced by culturing an engineered non-plant cell having a coding sequence for encoding the at least one enzyme. In some cases, the method further comprises adding a tetracyclic promorphinan precursor to the cell culture. In some cases, the method further comprises recovering the thebaine, or a derivative thereof, from the cell culture.

In some cases, the at least one enzyme comprises a thebaine synthase. In some cases, the thebaine synthase comprises an amino acid sequence selected from the group consisting of: SEQ ID NOs: 30, 31, 32, 33, 34, 35, 36, and 37. In some cases, the thebaine synthase enzyme is a Bet v 1 fold protein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the invention will be obtained by reference to the following detailed description that sets forth illustrative embodiments, in which the principles of the invention are utilized, and the accompanying drawings of which:

FIG. 4 illustrates an amino acid sequence of a parent DRS-DRR enzyme, in accordance with embodiments of the invention.

FIG. 5 illustrates amino acid sequences of a DRS enzyme and a DRR enzyme, respectively, that are derived from a parent fusion enzyme illustrated in FIG. 4, in accordance with embodiments of the invention.

FIG. 6 illustrates an enzyme having opioid 3-O-demethylase activity, in accordance with embodiments of the invention.

FIGS. 21-1-21-4 illustrate a phylogenetic tree generated through a bioinformatic search for morphinan alkaloid generating enzymes, in accordance with embodiments of the invention.

DETAILED DESCRIPTION OF THE INVENTION

Figure 1:
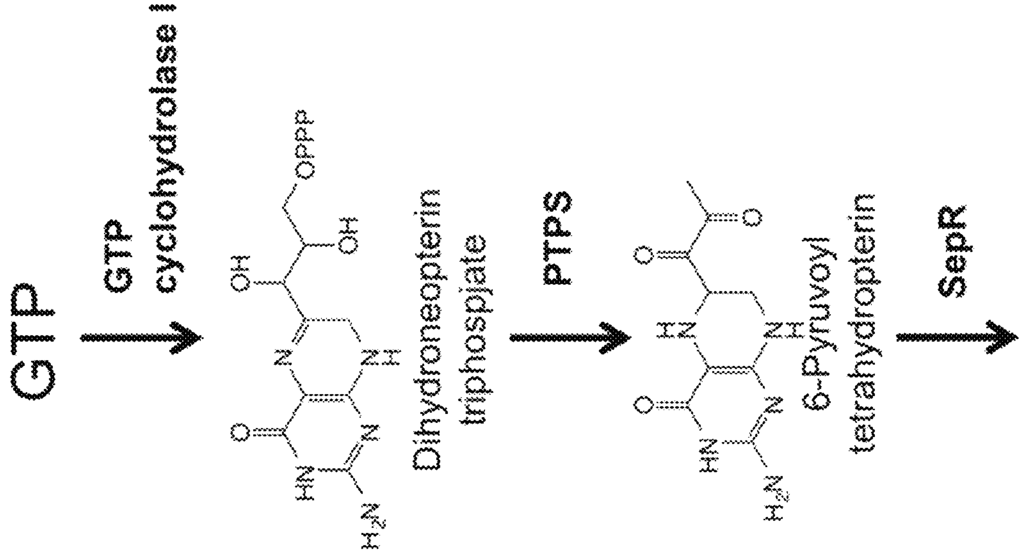
FIG. 1 illustrates examples of synthesis, recycling, and salvage pathways of tetrahydrobiopterin, in accordance with embodiments of the invention.
Figure 1:
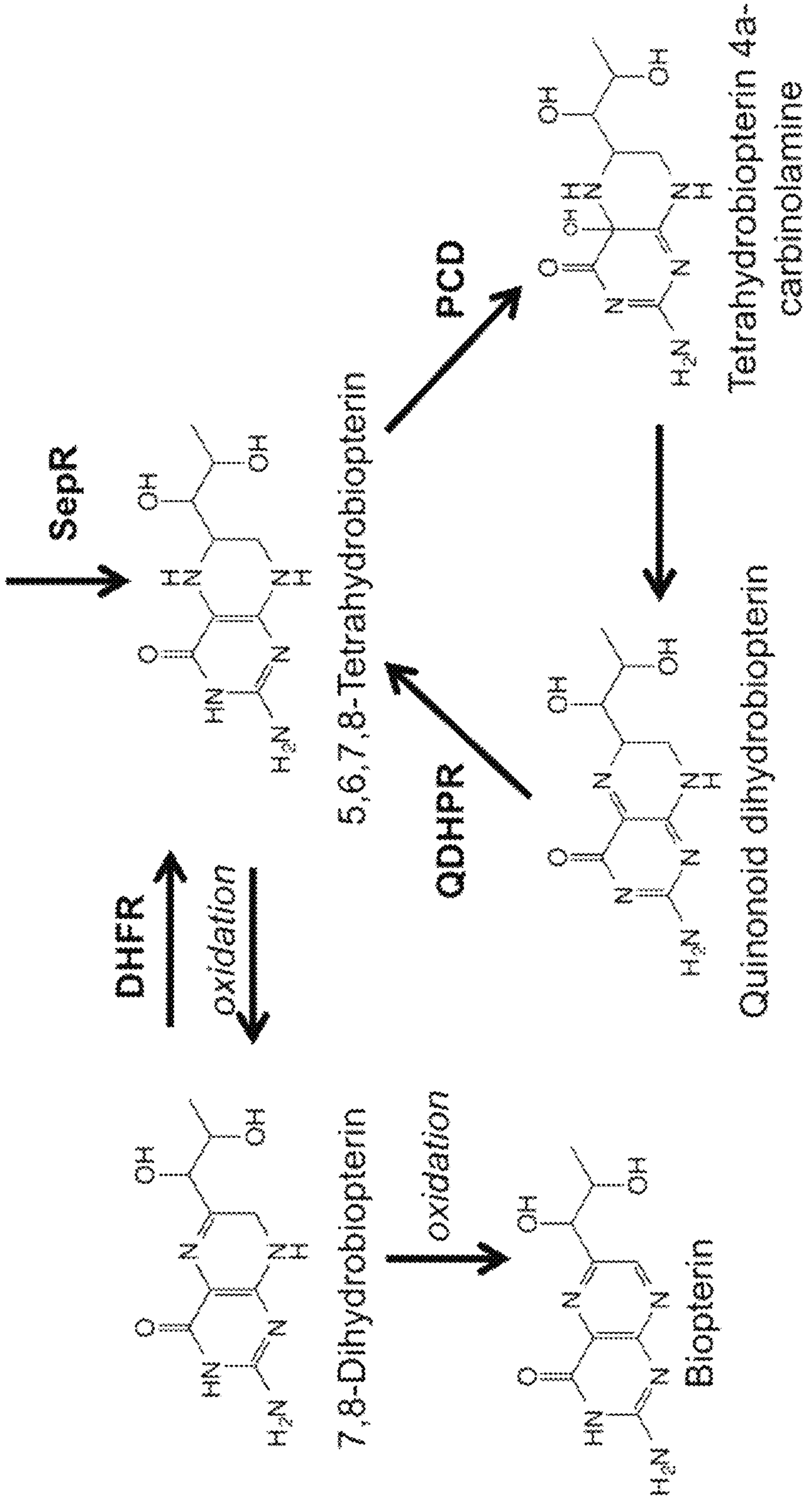

The present disclosure provides methods for the production of diverse benzylisoquinoline alkaloids (BIAs) in engineered host cells. The present disclosure further provides compositions of diverse alkaloids produced in engineered host cells. Additionally, the present disclosure provides methods for the production of a thebaine synthase in engineered host cells. Additionally, the present disclosure provides methods for the production of an engineered thebaine synthase in engineered host cells. In particular cases, the disclosure provides methods for producing promorphinan, morphinan, nal-opioid and nor-opioid alkaloid products through the increased conversion of a promorphinan alkaloid to a morphinan alkaloid in an engineered host cell. In further particular cases, the disclosure provides methods for producing morphinan, nal-opioid and nor-opioid alkaloid products through the increased conversion of a promorphinan alkaloid to a morphinan alkaloid in an engineered host cell. In further particular cases, the present disclosure provides methods for producing diverse alkaloid products through the increased conversion of a promorphinan alkaloid to a morphinan alkaloid.

Benzvlisoauinoline Alkaloids (BIAs) of Interest

Host cells which produce BIAs of interest are provided. In some examples, engineered strains of host cells such as the engineered strains of embodiments discussed herein may provide a platform for producing benzylisoquinoline alkaloids of interest and modifications thereof across several structural classes including, but not limited to, precursor BIAs, benzylisoquinolines, promorphinans, morphinans, nal-opioids, nor-opioids, and others. Each of these classes may include biosynthetic precursors, intermediates, and metabolites thereof, of any convenient member of an engineered host cell biosynthetic pathway that may lead to a member of the class. Non-limiting examples of compounds are given below for each of these structural classes. In some cases, the structure of a given example may or may not be characterized itself as a benzylisoquinoline alkaloid. In some cases, the present chemical entities may include all possible isomers, including single enantiomers, racemic mixtures, optically pure forms, mixtures of diastereomers, and intermediate mixtures.

BIA precursors may include, but are not limited to, norcoclaurine (NC) and norlaudanosoline (NL), as well as NC and NL precursors, such as tyrosine, tyramine, 4-hydroxyphenylacetaldehyde (4-HPA), 4-hydroxyphenylpyruvic acid (4-HPPA), L-3,4-dihydroxyphenylalanine (L-DOPA), 3,4-dihydroxyphenylacetaldehyde (3,4-DHPA), and dopamine. In some embodiments, the one or more BIA precursors are 3,4-dihydroxyphenylacetaldehyde (3,4-DHPA) and dopamine. In certain instances, the one or more BIA precursors are 4-hydroxyphenylacetaldehyde (4-HPA) and dopamine. In particular, NL and NC may be synthesized, respectively, from precursor molecules via a Pictet-Spengler condensation reaction, where the reaction may occur spontaneously or may by catalyzed by any convenient enzymes.

Benzylisoquinolines may include, but are not limited to, norcoclaurine, norlaudanosoline, coclaurine, 3'-hydroxycoclaurine, 4'-O-methylnorlaudanosoline, 4'-O-methyllaudanosoline, N-methylnorcoclaurine, laudanosoline, N-methylcoclaurine, 3'-hydroxy-N-methylcoclaurine, reticuline, norreticuline, papaverine, laudanine, laudanosine, tetrahydropapaverine, 1,2-dihydropapaverine, and orientaline.

Promorphinans may include, but are not limited to, salutaridine, salutaridinol, and salutaridinol-7-O-acetate.

Morphinans may include, but are not limited to, thebaine, codeinone, codeine, morphine, morphinone, oripavine, neopinone, neopine, neomorphine, hydrocodone, dihydrocodeine, 14-hydroxycodeinone, oxycodone, 14-hydroxycodeine, morphinone, hydromorphone, dihydromorphine, dihydroetorphine, ethylmorphine, etorphine, metopon, buprenorphine, pholcodine, heterocodeine, and oxymorphone. In particular, thebaine may be synthesized from salutaridinol-7-O-acetate, where the reaction may occur spontaneously or may be catalyzed by any convenient enzymes.

Nal-opioids may include, but are not limited to, naltrexone, naloxone, nalmefene, nalorphine, nalorphine, nalodeine, naldemedine, naloxegol, 6β-naltrexol, naltrindole, methylnaltrexone, methylsamidorphan, alvimopan, axelopran, bevenpran, dinicotinate, levallorphan, samidorphan, buprenorphine, dezocine, eptazocine, butorphanol, levorphanol, nalbuphine, pentazocine, phenazocine, norbinaltorphimine, and diprenorphine.

Nor-opioids may include, but are not limited to, norcodeine, noroxycodone, northebaine, norhydrocodone, nordihydro-codeine, nor-14-hydroxy-codeine, norcodeinone, nor-14-hydroxy-codeinone, normorphine, noroxymorphone, nororipavine, norhydro-morphone, nordihydro-morphine, nor-14-hydroxy-morphine, normorphinone, and nor-14-hydroxy-morphinone.

In certain embodiments, the engineered strains of the invention may provide a platform for producing compounds related to tetrahydrobiopterin synthesis including, but not limited to, dihydroneopterin triphosphate, 6-pyruvoyl tetrahydropterin, 5,6,7,8-tetrahydrobiopterin, 7,8-dihydrobiopterin, tetrahydrobiopterin 4a-carbinolamine, quinonoid dihydrobiopterin, and biopterin.

Host Cells

Any convenient cells may be utilized in the subject host cells and methods. In some cases, the host cells are non-plant cells. In some instances, the host cells may be characterized as microbial cells. In certain cases, the host cells are insect cells, mammalian cells, bacterial cells, or yeast cells. Any convenient type of host cell may be utilized in producing the subject BIA-producing cells, see, e.g., US2008/0176754, and US2014/0273109 the disclosures of which are incorporated by reference in their entirety. Host cells of interest include, but are not limited to, bacterial cells, which may be either Gram positive bacterial cells or Gram negative bacterial cells, insect cells such as *Drosophila melanogaster* S2 and *Spodoptera frugiperda* Sf9 cells, and yeast cells such as *Saccharomyces cerevisiae, Schizosaccharomyces pombe*, and *Pichia pastoris* cells. Non-limiting examples of bacterial cells include *Bacillus subtilis, Escherichia coli, Streptomyces, Anabaena, Arthrobacter, Acetobacter, Acetobacterium, Bacillus, Bifidobacterium, Brachybacterium, Brevibacterium, Carnobacterium, Clostridium, Corynebacterium, Enterobacter, Escherichia, Gluconacetobacter, Gluconobacter, Hafnia, Halomonas, Klebsiella, Kocuria, Lactobacillus, Leucononstoc, Macrococcus, Methylomonas, Methylobacter, Methylocella, Methylococcus, Microbacterium, Micrococcus, Microcystis, Moorella, Oenococcus, Pediococcus, Prochlorococcus, Propionibacterium, Proteus, Pseudoalteromonas, Pseudomonas, Psychrobacter, Rhodobacter, Rhodococcus, Rhodopseudomonas, Serratia, Staphylococcus, Streptococcus, Streptomyces, Synechococcus, Synechocystis, Tetragenococcus, Weissella, Zymomonas*, and *Salmonella typhimuium* cells. In some examples, the host cells are yeast cells or *E. coli* cells. In some cases, the host cells are yeast cells or *E. coli* cells. In some cases, the host cell is a yeast cell. In some instances, the host cell is from a strain of yeast engineered to produce a BIA of interest, such as a morphinan alkaloid. In some instances, the host cell is from a strain of yeast engineered to produce an enzyme of interest. In some instances, the host cell is from a strain of yeast engineered to produce a thebaine synthase.

The thebaine synthase may be able to more efficiently convert a salutaridinol-7-O-acetate to a thebaine relative to a spontaneous reaction. In some instances, the host cell is from a strain of yeast engineered to produce an engineered thebaine synthase. In some embodiments, an engineered thebaine synthase may be an engineered fusion enzyme. Additionally, the engineered thebaine synthase may be able to more efficiently convert a salutaridinol-7-O-acetate to a thebaine relative to a thebaine synthase. In some embodiments, the thebaine synthase may be a wild-type thebaine synthase. In some embodiments, a thebaine synthase may be substantially similar to a wild-type thebaine synthase. In some cases, a thebaine synthase that is substantially similar to a wild-type thebaine synthase may have an amino acid sequence that is at least 75% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more similar to an amino acid sequence of a wild-type thebaine synthase. The engineered thebaine synthase may be engineered as a fusion enzyme to another enzyme to more efficiently convert a salutaridinol-7-O-acetate to a thebaine relative to the thebaine synthase.

Any of the host cells described in US2008/0176754 and US2014/0273109 by Smolke et al. may be adapted for use in the subject cells and methods. In certain embodiments, the yeast cells may be of the species *Saccharomyces cerevisiae* (*S. cerevisiae*). In certain embodiments, the yeast cells may be of the species *Schizosaccharomyces pombe*. In certain embodiments, the yeast cells may be of the species *Pichia pastoris*. Yeast is of interest as a host cell because cytochrome P450 proteins are able to fold properly into the endoplasmic reticulum membrane so that their activity is maintained. In examples, cytochrome P450 proteins are involved in some biosynthetic pathways of interest. In additional examples, cytochrome P450 proteins are involved in the production of BIAs of interest. In further examples, cytochrome P450 proteins are involved in the production of an enzyme of interest.

Yeast strains of interest that find use in the invention include, but are not limited to, CEN.PK (Genotype: MATα/α urα3-52/urα3-52 trpl-289/trpl-289 leu2-3_112/leu2-3_112 his3 Δ1/his3 Δ1 MAL2-8C/MAL2-8C SUC2/SUC2), S288C, W303, D273-10B, X2180, A364A, Σ1278B, AB972, SK1, and FL100. In certain cases, the yeast strain is any of S288C (MATα; SUC2 mal mel gal2 CUP1 flo1 flo8-1 hap1), BY4741 (MATα; his3Δ1; leu2Δ0; met15Δ0; ura3Δ0), BY4742 (MATα; his3Δ1; leu2Δ0; lys2Δ0; ura3A0), BY4743 (MATα/MATα; his3Δ1/his3Δ1; leu2Δ0/Ieu2Δ0; met15Δ0/MET15; LYS2/lys2Δ0; ura3Δ0/ura3Δ0), and WAT11 or W(R), derivatives of the W303-B strain (MATα; ade2-1; his3-11, −15; leu2-3, −112; ura3-1; canR; cyr+) which express the *Arabidopsis thaliana* NADPH-P450 reductase ATR1 and the yeast NADPH-P450 reductase CPR1, respectively. In another embodiment, the yeast cell is W303alpha (MATα; his3-11,15 trpl-1 leu2-3 ura3-1 ade2-1). The identity and genotype of additional yeast strains of interest may be found at EUROSCARF (web.uni-frankfurt.de/fb15/mikro/euroscarf/col_index.html).

In some instances the host cell is a fungal cell. In certain embodiments, the fungal cells may be of the *Aspergillus* species and strains include *Aspergillus Niger* (ATCC 1015, ATCC 9029, CBS 513.88), *Aspergillus oryzae* (ATCC 56747, RIB40), *Aspergillus terreus* (NIH 2624, ATCC 20542) and *Aspergillus nidulans* (FGSC A4).

In certain embodiments, heterologous coding sequences may be codon optimized for expression in *Aspergillus* sp. and expressed from an appropriate promoter. In certain embodiments, the promoter may be selected from phosphoglycerate kinase promoter (PGK), MbfA promoter, cytochrome c oxidase subunit promoter (CoxA), SrpB promoter, TvdA promoter, malate dehydrogenase promoter (MdhA), beta-mannosidase promoter (ManB). In certain embodiments, a terminator may be selected from glucoamylase terminator (GlaA) or TrpC terminator. In certain embodiments, the expression cassette consisting of a promoter, heterologous coding sequence, and terminator may be expressed from a plasmid or integrated into the genome of the host. In certain embodiments, selection of cells maintaining the plasmid or integration cassette may be performed with antibiotic selection such as hygromycin or nitrogen source utilization, such as using acetamide as a sole nitrogen source. In certain embodiments, DNA constructs may be introduced into the host cells using established transformation methods such as protoplast transformation, lithium acetate, or electroporation. In certain embodiments, cells may be cultured in liquid ME or solid MEA (3% malt extract, 0.5% peptone, and ±1.5% agar) or in Vogel's minimal medium with or without selection.

In some instances the host cell is a bacterial cell. The bacterial cell may be selected from any bacterial genus. Examples of genuses from which the bacterial cell may come include *Anabaena, Arthrobacter, Acetobacter, Acetobacterium, Bacillus, Bifidobacterium, Brachybacterium, Brevibacterium, Carnobacterium, Clostridium, Corynebacterium, Enterobacter, Escherichia, Gluconacetobacter, Gluconobacter, Hafnia, Halomonas, Klebsiella, Kocuria, Lactobacillus, Leucononstoc, Macrococcus, Methylomonas, Methylobacter, Methylocella, Methylococcus, Microbacterium, Micrococcus, Microcystis, Moorella, Oenococcus, Pediococcus, Prochlorococcus, Propionibacterium, Proteus, Pseudoalteromonas, Pseudomonas, Psychrobacter, Rhodobacter, Rhodococcus, Rhodopseudomonas, Serratia, Staphylococcus, Streptococcus, Streptomyces, Synechococcus, Synechocystis, Tetragenococcus, Weissella*, and *Zymomonas*. Examples of bacterial species which may be used with the methods of this disclosure include *Arthrobacter nicotianae, Acetobacter aceti, Arthrobacter arilaitensis, Bacillus cereus, Bacillus coagulans, Bacillus lichenmformis, Bacillus pumilus, Bacillus sphaericus, Bacillus stearothermophilus, Bacillus subtilis, Bifidobacterium adolescentis, Brachybacterium tyrofermentans, Brevibacterium linens, Carnobacterium divergens, Corynebacteriumflavescens, Enterococcus faecium, Gluconacetobacter europaeus, Gluconacetobacter johannae, Gluconobacter oxydans, Hafnia alvei, Halomonas elongata, Kocuria rhizophila, Lactobacillus acidifarinae, Lactobacillus jensenii, Lactococcus lactis, Lactobacillus yamanashiensis, Leuconostoc citreum, Macrococcus caseolyticus, Microbacterium foliorum, Micrococcus lylae, Oenococcus oeni, Pediococcus acidilactici, Propionibacterium acidipropionici, Proteus vulgaris, Pseudomonas fluorescens, Psychrobacter celer, Staphylococcus condiments, Streptococcus thermophilus, Streptomyces griseus, Tetragenococcus halophilus, Weissella cibaria, Weissella koreensis, Zymomonas mobilis, Corynebacterium glutamicum, Bifidobacterium bifidum/breve/longum, Streptomyces lividans, Streptomyces coelicolor, Lactobacillus plantarum, Lactobacillus sakei, Lactobacillus casei, Pseudoalteromonas citrea, Pseudomonas putida, Clostridium ljungdahlii/aceticum/acetobutylicum/bejerinckii/butyricum*, and *Moorella themocellum/thermoacetica*.

In certain embodiments, the bacterial cells may be of a strain of *Escherichia coli*. In certain embodiments, the strain of *E. coli* may be selected from BL21 DH5α, XL1-Blue, HB101, BL21, and K12. In certain embodiments, heterologous coding sequences may be codon optimized for expression in *E. coli* and expressed from an appropriate promoter. In certain embodiments, the promoter may be selected from T7 promoter, tac promoter, trc promoter, tetracycline-inducible promoter (tet), lac operon promoter (lac), lacO1 promoter. In certain embodiments, the expression cassette consisting of a promoter, heterologous coding sequence, and terminator may be expressed from a plasmid or integrated into the genome. In certain embodiments, the plasmid is selected from pUC19 or pBAD. In certain embodiments, selection of cells maintaining the plasmid or integration cassette may be performed with antibiotic selection such as kanamycin, chloramphenicol, streptomycin, spectinomycin, gentamycin, erythromycin or ampicillin. In certain embodiments, DNA constructs may be introduced into the host cells using established transformation methods such as conjugation, heat shock chemical transformation, or electroporation. In certain embodiments, cells may be cultured in liquid Luria-Bertani (LB) media at about 37° C. with or without antibiotics.

In certain embodiments, the bacterial cells may be a strain of *Bacillus subtilis*. In certain embodiments, the strain of *B. subtilis* may be selected from 1779, GP25, RO—NN-1, 168, BSn5, BEST195, 1A382, and 62178. In certain embodiments, heterologous coding sequences may be codon optimized for expression in *Bacillus* sp. and expressed from an appropriate promoter. In certain embodiments, the promoter may be selected from grac promoter, p43 promoter, or trnQ promoter. In certain embodiments, the expression cassette consisting of the promoter, heterologous coding sequence, and terminator may be expressed from a plasmid or integrated into the genome. In certain embodiments, the plasmid is selected from pHP13, pE194, pC194, pHT01, or pHT43. In certain embodiments, integrating vectors such as pDG364 or pDG1730 may be used to integrate the expression cassette into the genome. In certain embodiments, selection of cells maintaining the plasmid or integration cassette may be performed with antibiotic selection such as erythromycin, kanamycin, tetracycline, and spectinomycin. In certain embodiments, DNA constructs may be introduced into the host cells using established transformation methods such as natural competence, heat shock, or chemical transformation. In certain embodiments, cells may be cultured in liquid Luria-Bertani (LB) media at 37° C. or M9 medium plus glucose and tryptophan.

Genetic Modifications to Host Cells

The host cells may be engineered to include one or more modifications (such as two or more, three or more, four or more, five or more, or even more modifications) that provide for the production of BIAs of interest. Additionally or alternatively, the host cells may be engineered to include one or more modifications (such as two or more, three or more, four or more, five or more, or even more modifications) that provide for the production of enzymes of interest. In some cases, a modification is a genetic modification, such as a mutation, addition, or deletion of a gene or fragment thereof, or transcription regulation of a gene or fragment thereof. As used herein, the term "mutation" refers to a deletion, insertion, or substitution of an amino acid(s) residue or nucleotide(s) residue relative to a reference sequence or motif. The mutation may be incorporated as a directed mutation to the native gene at the original locus. In some cases, the mutation may be incorporated as an additional copy of the gene introduced as a genetic integration at a separate locus, or as an additional copy on an episomal vector such as a 2μ or centromeric plasmid. In certain instances, the substrate inhibited copy of the enzyme is under the native cell transcriptional regulation. In some instances, the substrate inhibited copy of the enzyme is introduced with engineered constitutive or dynamic regulation of protein expression by placing it under the control of a synthetic promoter. In some examples, the object of one or more modifications may be a native gene. In some examples, the object of one or more modifications may be a non-native gene. In some examples, a non-native gene may be inserted into a host cell. In further examples, a non-native gene may be altered by one or more modifications prior to being inserted into a host cell.

An engineered host cell may overproduce one or more BIAs of interest. By overproduce is meant that the cell has an improved or increased production of a BIA molecule of interest relative to a control cell (e.g., an unmodified cell). By improved or increased production is meant both the production of some amount of the BIA of interest where the control has no BIA of interest production, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some BIA of interest production.

An engineered host cell may overproduce one or more (S)-1-benzylisoquinoline alkaloids. In some cases, the engineered host cell may produce some amount of the (S)-1-benzylisoquinoline alkaloid of interest where the control has no (S)-1-benzylisoquinoline alkaloid production, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some (S)-1-benzylisoquinoline alkaloid of interest production.

An engineered host cell may further overproduce one or more (R)-1-benzylisoquinoline alkaloids. In some cases, the engineered host cell may produce some amount of the (R)-1-benzylisoquinoline alkaloid of interest where the control has no (R)-1-benzylisoquinoline alkaloid production, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some (R)-1-benzylisoquinoline alkaloid of interest production.

An engineered host cell may further overproduce one or more morphinan alkaloids. In some cases, the engineered host cell may produce some amount of the morphinan alkaloid of interest where the control has no morphinan alkaloid production, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some morphinan alkaloid of interest production. An engineered host cell may further overproduce one or more of promorphinan, nor-opioid, or nal-opioid alkaloids.

In some cases, the engineered host cell is capable of producing an increased amount of (R)-reticuline relative to a control host cell that lacks the one or more modifications (e.g., as described herein). In some cases, the engineered host cell having an engineered split epimerase is capable of producing an increased amount of (R)-reticuline relative to a host cell having a fused epimerase. In some cases, the engineered host cell having modifications to an oxidase portion of an engineered epimerase is capable of producing an increased amount of (R)-reticuline relative to a control host cell that lacks the one or more modifications to the oxidase portion of the engineered epimerase. In certain instances, the increased amount of (R)-reticuline is about 10% or more relative to the control host cell, such as about 20% or more, about 30% or more, about 40% or more, about 50% or more, about 60% or more, about 80% or more, about 100% or more, about 2-fold or more, about 5-fold or more, or even about 10-fold or more relative to the control host cell. In some cases, (R)-reticuline is the product of an epimerization reaction within an engineered host cell. In some cases, (R)-reticuline is the product of an epimerization reaction catalyzed by at least one engineered epimerase within an engineered host cell. In these cases, (S)-reticuline may be the substrate of the epimerization reaction.

In some cases, the engineered host cell is capable of producing an increased amount of thebaine relative to a control host cell that lacks the one or more modifications (e.g., as described herein). In some cases, the engineered host cell having a thebaine synthase is capable of producing an increased amount of thebaine relative to a host cell that lacks a thebaine synthase.

In some cases, the engineered host cell having an engineered thebaine synthease is capable of producing an increased amount of thebaine relative to a host cell having a non-engineered thebaine synthase (e.g., as described herein). In certain instances, the increased amount of thebaine is about 10% or more relative to the control host cell, such as about 20% or more, about 30% or more, about 40% or more, about 50% or more, about 60% or more, about 80% or more, about 100% or more, about 2-fold or more, about 5-fold or more, or even about 10-fold or more relative to the control host cell. In some cases, thebaine is the product of a thebaine synthase reaction within an engineered host cell. In some cases, thebaine is the product of a thebaine synthase reaction catalyzed by at least one engineered thebaine synthase within an engineered host cell. In these cases, salutaridinol-7-O-acetate may be the substrate of the thebaine synthase reaction.

Additionally, an engineered host cell may overproduce one or more enzymes of interest. By overproduce is meant that the cell has an improved or increased production of an enzyme of interest relative to a control cell (e.g., an unmodified cell). By improved or increased production is meant both the production of some amount of the enzyme of interest where the control has no production, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some enzyme of interest production.

An engineered host cell may overproduce one or more DRS-DRR enzymes. In some cases, the engineered host cell may produce some amount of the DRS-DRR enzyme where the control has no DRS-DRR enzyme production, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some DRS-DRR enzyme production.

An engineered host cell may overproduce one or more engineered DRS-DRR enzymes. In some cases, the engineered host cell may produce some amount of the engineered DRS-DRR epimerase where the control has no DRS-DRR enzyme production, or where the control has a same level of production of wild-type epimerases in comparison to the engineered host cell, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some DRS-DRR enzyme production. In some cases, an engineered DRS-DRR epimerase may be an engineered split epimerase. In some cases, an engineered DRS-DRR epimerase may be an engineered fused epimerase.

An engineered host cell may further overproduce one or more enzymes that are derived from the DRS-DRR enzyme. In some cases, the engineered host cell may produce some amount of the enzymes that are derived from the DRS-DRR enzyme, where the control has no production of enzymes that are derived from the DRS-DRR enzyme, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some production of enzymes that are derived from the DRS-DRR enzyme.

An engineered host cell may overproduce one or more thebaine synthase enzymes. In some cases, the engineered host cell may produce some amount of the thebaine synthase enzyme where the control has no thebaine synthase enzyme production, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some thebaine synthase enzyme production.

An engineered host cell may overproduce one or more engineered thebaine synthase enzymes. In some cases, the engineered host cell may produce some amount of the engineered thebaine synthase where the control has no thebaine synthase enzyme production, or where the control has a same level of production of wild-type thebaine synthase in comparison to the engineered host cell, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some thebaine synthase enzyme production. In some cases, an engineered thebaine synthase may be an engineered fusion enzyme.

An engineered host cell may further overproduce one or more enzymes that are derived from the thebaine synthase enzyme. In some cases, the engineered host cell may produce some amount of the enzymes that are derived from the thebaine synthase enzyme, where the control has no production of enzymes that are derived from the thebaine synthase enzyme, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some production of enzymes that are derived from the thebaine synthase enzyme.

In some cases, the one or more (such as two or more, three or more, or four or more) modifications may be selected from: a substrate inhibition alleviating mutation in a biosynthetic enzyme gene; a product inhibition alleviating mutation in a biosynthetic enzyme gene; a cofactor recovery promoting mechanism; a feedback inhibition alleviating mutation in a biosynthetic enzyme gene; a transcriptional modulation modification of a biosynthetic enzyme gene; an inactivating mutation in an enzyme gene; an epimerization modification; and a heterologous coding sequence that encodes an enzyme. A cell that includes one or more modifications may be referred to as an engineered cell.

In some cases, the one or more (such as two or more, three or more, or four or more) modifications may be selected from: a localization mutation; a cytochrome P450 reductase interaction mutation; an accessibility mutation; an activity enhancing mutation; an engineered fused thebaine synthase modification, and an engineered split epimerase modification. A cell that includes one or more modifications may be referred to as an engineered cell.

Substrate Inhibition Alleviating Mutations

In some instances, the engineered host cells are cells that include one or more substrate inhibition alleviating mutations (such as two or more, three or more, four or more, five or more, or even more) in one or more biosynthetic enzyme genes of the cell. In some examples, the one or more biosynthetic enzyme genes are native to the cell (e.g., is present in an unmodified cell). In some examples, the one or more biosynthetic enzyme genes are non-native to the cell. As used herein, the term "substrate inhibition alleviating mutation" refers to a mutation that alleviates a substrate inhibition control mechanism of the cell.

A mutation that alleviates substrate inhibition reduces the inhibition of a regulated enzyme in the cell of interest relative to a control cell and provides for an increased level of the regulated compound or a downstream biosynthetic product thereof. In some cases, by alleviating inhibition of the regulated enzyme is meant that the $IC_{50}$ of inhibition is increased by 2-fold or more, such as by 3-fold or more, 5-fold or more, 10-fold or more, 30-fold or more, 100-fold or more, 300-fold or more, 1000-fold or more, or even more. By increased level is meant a level that is 110% or more of that of the regulated compound in a control cell or a downstream product thereof, such as 120% or more, 130% or more, 140% or more, 150% or more, 160% or more, 170% or more, 180% or more, 190% or more, or 200% or more, such as at least 3-fold or more, at least 5-fold or more, at least 10-fold or more or even more of the regulated compound in the engineered host cell or a downstream product thereof.

A variety of substrate inhibition control mechanisms and biosynthetic enzymes in the engineered host cell that are directed to regulation of levels of BIAs of interest, or precursors thereof, may be targeted for substrate inhibition alleviation. The engineered host cell may include one or more substrate inhibition alleviating mutations in one or more biosynthetic enzyme genes. The one or more mutations may be located in any convenient biosynthetic enzyme genes where the biosynthetic enzyme is subject to regulatory control. In some embodiments, the one or more biosynthetic enzyme genes encode one or more tyrosine hydroxylase enzymes. In certain instances, the one or more substrate inhibition alleviating mutations are present in a biosynthetic enzyme gene that is TyrH. In some embodiments, the engineered host cell may include one or more substrate inhibition alleviating mutations in one or more biosynthetic enzyme genes such as one of those genes described in Table 3.

In certain embodiments, the one or more substrate inhibition alleviating mutations are present in the TyrH gene. The TyrH gene encodes tyrosine hydroxylase, which is an enzyme that converts tyrosine to L-DOPA. However, TyrH is inhibited by its substrate, tyrosine. Mammalian tyrosine hydroxylase activity, such as that seen in humans or rats, can be improved through mutations to the TyrH gene that relieve substrate inhibition. In particular, substrate inhibition from tyrosine can be relieved by a point mutation W166Y in the TyrH gene. The point mutation W166Y in the TyrH gene may also improve the binding of the cosubstrate of tyrosine hydroxylase, $BH_4$, to catalyze the reaction of tyrosine to L-DOPA. The mutants of TyrH, when expressed in yeast strains to produce BIAs from sugar (such as those described in U.S. Provisional Patent Application Ser. No. 61/899,496) can significantly improve the production of BIAs.

Any convenient numbers and types of mutations may be utilized to alleviate a substrate inhibition control mechanism. In certain embodiments, the engineered host cells of the present invention may include 1 or more, 2 or more, 3 or more, 4 or more, 5 or more, 6 or more, 7 or more, 8 or more, 9 or more, 10 or more, 11 or more, 12 or more, 13 or more, 14 or more, or even 15 or more substrate inhibition alleviating mutations, such as 1, 2, 3, 4, 5, 6, 7, 8, 9, 10, 11, 12, 13, 14 or 15 substrate inhibition alleviating mutations in one or more biosynthetic enzyme genes within the engineered host cell.

Cofactor Recovery Promoting Mechanisms

In some instances, the engineered host cells are cells that include one or more cofactor recovery promoting mechanisms (such as two or more, three or more, four or more, five or more, or even more) in one or more biosynthetic enzyme genes of the cell. In some examples, the one or more biosynthetic enzyme genes are native to the cell (e.g., is present in an unmodified cell). In some examples, the one or more biosynthetic enzyme genes are non-native to the cell. As used herein, the term "cofactor recovery promoting mechanism" refers to a mechanism that promotes a cofactor recovery control mechanism of the cell.

A variety of cofactor recovery control mechanisms and biosynthetic enzymes in the engineered host cell that are directed to regulation of levels of BIAs of interest, or precursors thereof, may be targeted for cofactor recovery promotion. The engineered host cell may include one or more cofactor recovery promoting mechanism in one or more biosynthetic enzyme genes. In examples, the engineered host cell may include a heterologous coding sequence that encodes dihydrofolate reductase (DHFR). When DHFR is expressed, it may convert 7,8-dihydrobiopterin ($BH_2$) to the tetrahydrobiopterin ($BH_4$), thereby recovering $BH_4$ as a TyrH cosubstrate. In some examples, the engineered host cell may include one or more cofactor recovery promoting mechanisms in one or more biosynthetic enzyme genes such as one of those genes described in Table 2.

Any convenient numbers and types of mechanisms may be utilized to promote a cofactor recovery control mechanism. In certain embodiments, the engineered host cells of the present invention may include 1 or more, 2 or more, 3 or more, 4 or more, 5 or more, 6 or more, 7 or more, 8 or more, 9 or more, 10 or more, 11 or more, 12 or more, 13 or more, 14 or more, or even 15 or more cofactor recovery promoting mechanisms such as 1, 2, 3, 4, 5, 6, 7, 8, 9, 10, 11, 12, 13, 14 or 15 cofactor recovery promoting mechanisms in one or more biosynthetic enzyme genes within the engineered host cell.

Product Inhibition Alleviating Mutations

In some instances, the engineered host cells are cells that include one or more product inhibition alleviating mutations (such as two or more, three or more, four or more, five or more, or even more) in one or more biosynthetic enzyme genes of the cell. In some examples, the one or more biosynthetic enzyme genes are native to the cell (e.g., is present in an unmodified cell). In some examples, the one or more biosynthetic enzyme genes are non-native to the cell. As used herein, the term "product inhibition alleviating mutation" refers to a mutation that alleviates a short term and/or long term product inhibition control mechanism of an engineered host cell. Short term product inhibition is a control mechanism of the cell in which there is competitive binding at a cosubstrate binding site. Long term product inhibition is a control mechanism of the cell in which there is irreversible binding of a compound away from a desired pathway.

A mutation that alleviates product inhibition reduces the inhibition of a regulated enzyme in the cell of interest relative to a control cell and provides for an increased level of the regulated compound or a downstream biosynthetic product thereof. In some cases, by alleviating inhibition of the regulated enzyme is meant that the $IC_{50}$ of inhibition is increased by 2-fold or more, such as by 3-fold or more, 5-fold or more, 10-fold or more, 30-fold or more, 100-fold or more, 300-fold or more, 1000-fold or more, or even more. By increased level is meant a level that is 110% or more of that of the regulated compound in a control cell or a downstream product thereof, such as 120% or more, 130% or more, 140% or more, 150% or more, 160% or more, 170% or more, 180% or more, 190% or more, or 200% or more, such as at least 3-fold or more, at least 5-fold or more, at least 10-fold or more or even more of the regulated compound in the engineered host cell or a downstream product thereof.

A variety of product inhibition control mechanisms and biosynthetic enzymes in the engineered host cell that are directed to regulation of levels of BIAs of interest may be targeted for product inhibition alleviation. The engineered host cell may include one or more product inhibition alleviating mutations in one or more biosynthetic enzyme genes. The mutation may be located in any convenient biosynthetic enzyme genes where the biosynthetic enzyme is subject to regulatory control. In some embodiments, the one or more biosynthetic enzyme genes encode one or more tyrosine hydroxylase enzymes. In certain instances, the one or more product inhibition alleviating mutations are present in a biosynthetic enzyme gene that is TyrH. In some embodiments, the engineered host cell includes one or more product inhibition alleviating mutations in one or more biosynthetic enzyme genes such as one of those genes described in Table 3.

In certain embodiments, the one or more product inhibition alleviating mutations are present in the TyrH gene. The TyrH gene encodes tyrosine hydroxylase, which is an enzyme that converts tyrosine to L-DOPA. TyrH requires tetrahydrobiopterin ($BH_4$) as a cosubstrate to catalyze the hydroxylation reaction. Some microbial strains, such as *Saccharomyces cerevisiae*, do not naturally produce $BH_4$, but can be engineered to produce this substrate through a four-enzyme synthesis and recycling pathway, as illustrated in FIG. 1. FIG. 1 illustrates examples of synthesis, recycling, and salvage pathways of tetrahydrobiopterin, in accordance with embodiments of the invention. FIG. 1 provides the use of the enzymes PTPS, pyruvoyl tetrahydropterin synthase; SepR, sepiapterin reductase; PCD, pterin 4a-carbinolamine dehydratase; QDHPR, dihydropteridine reductase; and DHFR, dihydrofolate reductase. Of the enzymes that are illustrated in FIG. 1, yeast synthesizes an endogenous GTP cyclohydrolase I. GTP and dihydroneopterin triphosphate are naturally synthesized in yeast. Additionally, other metabolites in FIG. 1 are not naturally produced in yeast.

TyrH is inhibited by its product L-DOPA, as well as other catecholamines, particularly dopamine. Mammalian tyrosine hydroxylase activity, such as from humans or rats, can be improved through mutations that relieve product inhibition. For example, short term product inhibition, such as competitive binding at the cosubstrate binding site, can be relieved by a point mutation W166Y on the TyrH gene. In particular, the point mutation W166Y on the TyrH gene may improve binding of the cosubstrate. Additionally, short term product inhibition to relieve competitive binding at the cosubstrate binding site may be improved by a point mutation S40D on the TyrH gene. Short term product inhibition may also be improved by the joint mutations of R37E, R38E on the TyrH gene. In particular, R37E, R38E mutations may together specifically improve tyrosine hydroxylase activity in the presence of dopamine.

Additionally, long term product inhibition may be relieved by point mutations on the TyrH gene. Long term product inhibition relief may include the irreversible binding of catecholamine to iron in the active site such that there is less catecholamine present to act as a product inhibitor of tyrosine hydroxylase activity. Long term product inhibition can be relieved by the mutations E332D and Y371F, respectively, in the TyrH gene.

Combinations of the mutations can be made (such as two or three or more mutations at once) to relieve multiple types of substrate and product inhibition to further improve the activity of TyrH. The mutants of TyrH, when expressed in yeast strains to produce BIAs from sugar (such as those described in U.S. Provisional Patent Application Ser. No. 61/899,496) can significantly improve the production of BIAs.

Any convenient numbers and types of mutations may be utilized to alleviate a product inhibition control mechanism. In certain embodiments, the engineered host cells of the present invention may include 1 or more, 2 or more, 3 or more, 4 or more, 5 or more, 6 or more, 7 or more, 8 or more, 9 or more, 10 or more, 11 or more, 12 or more, 13 or more, 14 or more, or even 15 or more product inhibition alleviating mutations, such as 1, 2, 3, 4, 5, 6, 7, 8, 9, 10, 11, 12, 13, 14 or 15 product inhibition alleviating mutations in one or more biosynthetic enzyme genes within the engineered host cell.

Feedback Inhibition Alleviating Mutations

In some instances, the engineered host cells are cells that include one or more feedback inhibition alleviating mutations (such as two or more, three or more, four or more, five or more, or even more) in one or more biosynthetic enzyme genes of the cell. In some cases, the one or more biosynthetic enzyme genes are native to the cell (e.g., is present in an unmodified cell). Additionally or alternatively, in some examples the one or more biosynthetic enzyme genes are non-native to the cell. As used herein, the term "feedback inhibition alleviating mutation" refers to a mutation that alleviates a feedback inhibition control mechanism of an engineered host cell. Feedback inhibition is a control mechanism of the cell in which an enzyme in the synthetic pathway of a regulated compound is inhibited when that compound has accumulated to a certain level, thereby balancing the amount of the compound in the cell. A mutation that alleviates feedback inhibition reduces the inhibition of a regulated enzyme in the engineered host cell relative to a control cell. In this way, engineered host cell provides for an increased level of the regulated compound or a downstream biosynthetic product thereof. In some cases, by alleviating inhibition of the regulated enzyme is meant that the $IC_{50}$ of inhibition is increased by 2-fold or more, such as by 3-fold or more, 5-fold or more, 10-fold or more, 30-fold or more, 100-fold or more, 300-fold or more, 1000-fold or more, or even more. By increased level is meant a level that is 110% or more of that of the regulated compound in a control cell or a downstream product thereof, such as 120% or more, 130% or more, 140% or more, 150% or more, 160% or more, 170% or more, 180% or more, 190% or more, or 200% or more, such as at least 3-fold or more, at least 5-fold or more, at least 10-fold or more or even more of the regulated compound in the host cell or a downstream product thereof.

A variety of feedback inhibition control mechanisms and biosynthetic enzymes that are directed to regulation of levels of BIAs of interest may be targeted for alleviation in the host cell. The host cell may include one or more feedback inhibition alleviating mutations in one or more biosynthetic enzyme genes native to the cell. The one or more mutations may be located in any convenient biosynthetic enzyme genes where the biosynthetic enzyme is subject to regulatory control. In some embodiments, the one or more biosynthetic enzyme genes may encode one or more enzymes selected from a 3-deoxy-d-arabinose-heptulosonate-7-phosphate (DAHP) synthase and a chorismate mutase. In some embodiments, the one or more biosynthetic enzyme genes encode a 3-deoxy-d-arabinose-heptulosonate-7-phosphate (DAHP) synthase. In some instances, the one or more biosynthetic enzyme genes may encode a chorismate mutase. In certain instances, the one or more feedback inhibition alleviating mutations may be present in a biosynthetic enzyme gene selected from ARO4 and ARO7. In certain instances, the one or more feedback inhibition alleviating mutations may be present in a biosynthetic enzyme gene that is ARO4. In certain instances, the one or more feedback inhibition alleviating mutations are present in a biosynthetic enzyme gene that is ARO7. In some embodiments, the engineered host cell may include one or more feedback inhibition alleviating mutations in one or more biosynthetic enzyme genes such as one of those genes described in Table 3.

Any convenient numbers and types of mutations may be utilized to alleviate a feedback inhibition control mechanism. As used herein, the term "mutation" refers to a deletion, insertion, or substitution of an amino acid(s) residue or nucleotide(s) residue relative to a reference sequence or motif. The mutation may be incorporated as a directed mutation to the native gene at the original locus. In some cases, the mutation may be incorporated as an additional copy of the gene introduced as a genetic integration at a separate locus, or as an additional copy on an episomal vector such as a 2μ or centromeric plasmid. In certain instances, the feedback inhibited copy of the enzyme is under the native cell transcriptional regulation. In some instances, the feedback inhibited copy of the enzyme is introduced with engineered constitutive or dynamic regulation of protein expression by placing it under the control of a synthetic promoter.

In certain embodiments, the one or more feedback inhibition alleviating mutations may be present in the ARO4 gene. ARO4 mutations of interest may include, but are not limited to, substitution of the lysine residue at position 229 with a leucine, a substitution of the glutamine residue at position 166 with a lysine residue, or a mutation as described by Hartmann M, et al. ((2003) *Proc Natl Acad Sci USA* 100(3):862-867) or Fukuda et al. ((1992) *J Ferment Bioeng* 74(2):117-119). In some instances, mutations for conferring feedback inhibition may be selected from a mutagenized library of enzyme mutants. Examples of such selections may include rescue of growth of o-fluoro-D,L-phenylalanine or growth of aro3 mutant yeast strains in media with excess tyrosine as described by Fukuda et al. ((1990) Breeding of Brewing Yeast Producing a Large Amount of Beta-Phenylethyl Alcohol and Beta-Phenylethyl Acetate. *Agr Biol Chem Tokyo* 54(1):269-271).

In certain embodiments, the engineered host cells of the present invention may include 1 or more, 2 or more, 3 or more, 4 or more, 5 or more, 6 or more, 7 or more, 8 or more, 9 or more, 10 or more, 11 or more, 12 or more, 13 or more, 14 or more, or even 15 or more feedback inhibition alleviating mutations, such as 1, 2, 3, 4, 5, 6, 7, 8, 9, 10, 11, 12, 13, 14 or 15 feedback inhibition alleviating mutations in one or more biosynthetic enzyme genes within the engineered host cell.

Transcriptional Modulation Modifications

The host cells may include one or more transcriptional modulation modifications (such as two or more, three or more, four or more, five or more, or even more modifications) of one or more biosynthetic enzyme genes of the cell. In some examples, the one or more biosynthetic enzyme genes are native to the cell. In some examples, the one or more biosynthetic enzyme genes are non-native to the cell. Any convenient biosynthetic enzyme genes of the cell may be targeted for transcription modulation. By transcription modulation is meant that the expression of a gene of interest in a modified cell is modulated, e.g., increased or decreased, enhanced or repressed, relative to a control cell (e.g., an unmodified cell). In some cases, transcriptional modulation of the gene of interest includes increasing or enhancing expression. By increasing or enhancing expression is meant that the expression level of the gene of interest is increased by 2-fold or more, such as by 5-fold or more and sometimes by 25-, 50-, or 100-fold or more and in certain embodiments 300-fold or more or higher, as compared to a control, i.e., expression in the same cell not modified (e.g., by using any convenient gene expression assay). Alternatively, in cases where expression of the gene of interest in a cell is so low that it is undetectable, the expression level of the gene of interest is considered to be increased if expression is increased to a level that is easily detectable. In certain instances, transcriptional modulation of the gene of interest includes decreasing or repressing expression. By decreasing or repressing expression is meant that the expression level of the gene of interest is decreased by 2-fold or more, such as by 5-fold or more and sometimes by 25-, 50-, or 100-fold or more and in certain embodiments 300-fold or more or higher, as compared to a control. In some cases, expression is decreased to a level that is undetectable. Modifications of host cell processes of interest that may be adapted for use in the subject host cells are described in U.S. Publication No. 20140273109 (Ser. No. 14/211,611) by Smolke et al., the disclosure of which is herein incorporated by reference in its entirety.

Figure 2:
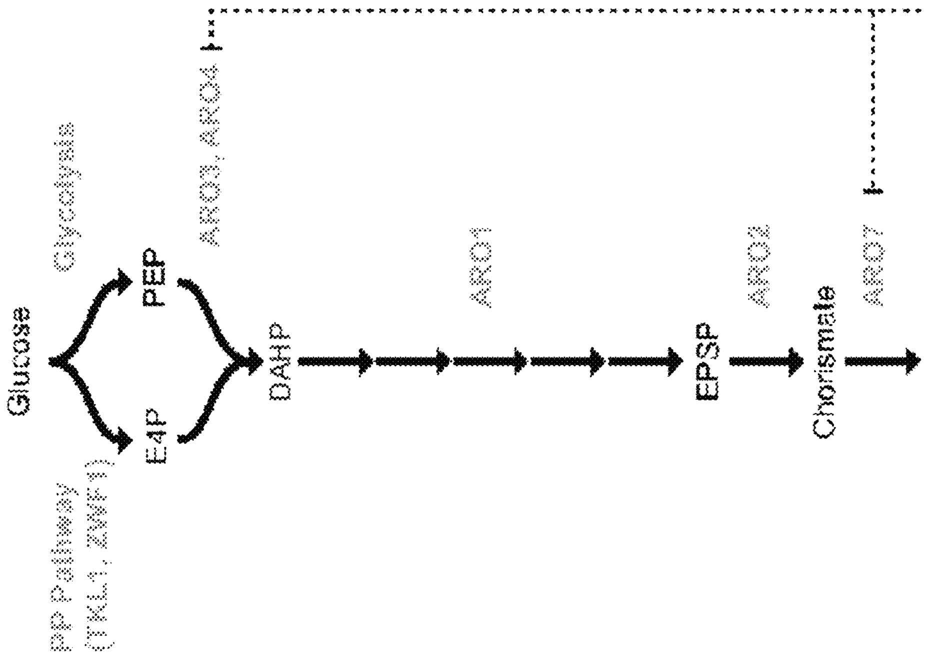
FIG. 2 illustrates a biosynthetic scheme for conversion of glucose to 4-HPA, dopamine, and 3,4-DHPA, in accordance with embodiments of the invention.
Figure 2:
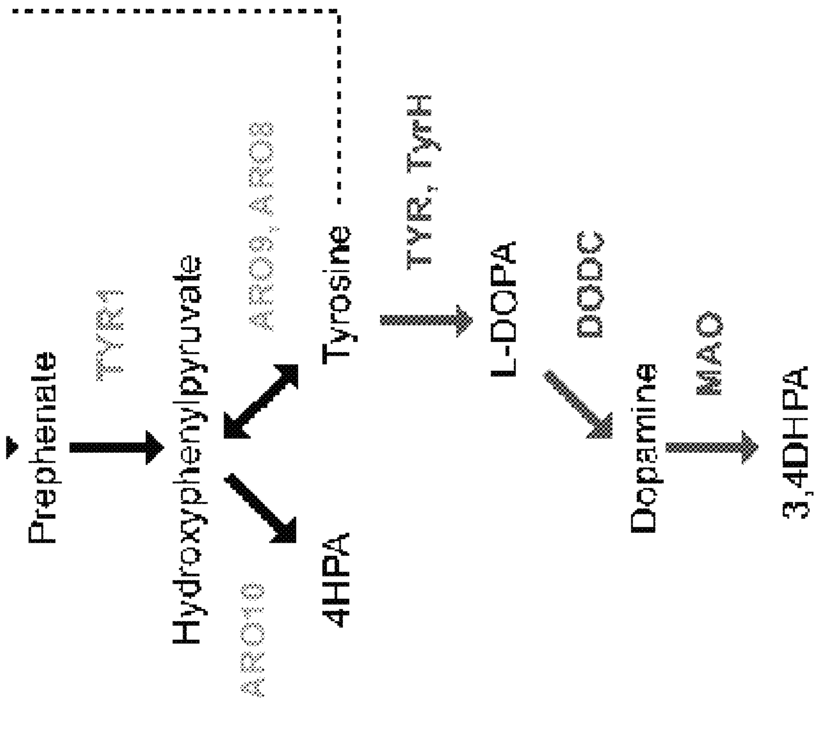

Any convenient biosynthetic enzyme genes may be transcriptionally modulated, and include but are not limited to, those biosynthetic enzymes described in FIG. 2. In particular, FIG. 2 illustrates a biosynthetic scheme for conversion of glucose to 4-HPA, dopamine, and 3,4-DHPA, in accordance with embodiments of the invention. Examples of enzymes described in FIG. 2 include ARO3, ARO4, ARO1, ARO7, TYR1, TYR, TyrH, DODC, MAO, ARO10, ARO9, ARO8, and TKL. In some instances, the one or more biosynthetic enzyme genes may be selected from ARO10, ARO9, ARO8, and TKL. In some cases, the one or more biosynthetic enzyme genes may be ARO10. In certain instances, the one or more biosynthetic enzyme genes may be ARO9. In some embodiments, the one or more biosynthetic enzyme genes may be TKL. In some embodiments, the host cell includes one or more transcriptional modulation modifications to one or more genes such as one of those genes described in Table 3.

In some embodiments, the transcriptional modulation modification may include a substitution of a strong promoter for a native promoter of the one or more biosynthetic enzyme genes or the expression of an additional copy(ies) of

19 the gene or genes under the control of a strong promoter. The promoters driving expression of the genes of interest may be constitutive promoters or inducible promoters, provided that the promoters may be active in the host cells. The genes of interest may be expressed from their native promoters. Additionally or alternatively, the genes of interest may be expressed from non-native promoters. Although not a requirement, such promoters may be medium to high strength in the host in which they are used. Promoters may be regulated or constitutive. In some embodiments, promoters that are not glucose repressed, or repressed only mildly by the presence of glucose in the culture medium, may be used. There are numerous suitable promoters, examples of which include promoters of glycolytic genes such as the promoter of the *B. subtilis* tsr gene (encoding fructose biphosphate aldolase) or GAPDH promoter from yeast *S. cerevisiae* (coding for glyceraldehyde-phosphate dehydrogenase) (Bitter G. A., *Meth. Enzymol.* 152:673 684 (1987)). Other strong promoters of interest include, but are not limited to, the ADHI promoter of baker's yeast (Ruohonen L., et al, *J. Biotechnol.* 39:193 203 (1995)), the phosphate-starvation induced promoters such as the PHO5 promoter of yeast (Hinnen, A., et al, in *Yeast Genetic Engineering*, Barr, P. J., et al. eds, *Butterworths* (1989), the alkaline phosphatase promoter from *B. lichenmformis* (Lee. J. W. K., et al., *J. Gen. Microbiol.* 137:1127 1133 (1991)), GPD1, and TEF1. Yeast promoters of interest include, but are not limited to, inducible promoters such as Ga11-10, Ga11, Ga1L, Ga1S, repressible promoter Met25, tetO, and constitutive promoters such as glyceraldehyde 3-phosphate dehydrogenase promoter (GPD), alcohol dehydrogenase promoter (ADH), translation-elongation factor-1-alpha promoter (TEF), cytochrome c-oxidase promoter (CYC1), MRP7 promoter, etc. In some instances, the strong promoter is GPD1. In certain instances, the strong promoter is TEF1. Autonomously replicating yeast expression vectors containing promoters inducible by hormones such as glucocorticoids, steroids, and thyroid hormones are also known and include, but are not limited to, the glucorticoid responsive element (GRE) and thyroid hormone responsive element (TRE), see e.g., those promoters described in U.S. Pat. No. 7,045,290. Vectors containing constitutive or inducible promoters such as alpha factor, alcohol oxidase, and PGH may be used. Additionally any promoter/enhancer combination (as per the Eukaryotic Promoter Data Base EPDB) could also be used to drive expression of genes of interest. It is understood that any convenient promoters specific to the host cell may be selected, e.g., *E. coli*. In some cases, promoter selection may be used to optimize transcription, and hence, enzyme levels to maximize production while minimizing energy resources.

Inactivating Mutations

The engineered host cells may include one or more inactivating mutations to an enzyme of the cell (such as two or more, three or more, four or more, five or more, or even more). The inclusion of one or more inactivating mutations may modify the flux of a synthetic pathway of an engineered host cell to increase the levels of a BIA of interest or a desirable enzyme or precursor leading to the same. In some examples, the one or more inactivating mutations are to an enzyme native to the cell. Additionally or alternatively, the one or more inactivating mutations are to an enzyme non-native to the cell. As used herein, by "inactivating mutation" is meant one or more mutations to a gene or regulatory DNA sequence of the cell, where the mutation(s) inactivates a

20 biological activity of the protein expressed by that gene of interest. In some cases, the gene is native to the cell. In some instances, the gene encodes an enzyme that is inactivated and is part of or connected to the synthetic pathway of a BIA of interest produced by the host cell. In some instances, an inactivating mutation is located in a regulatory DNA sequence that controls a gene of interest. In certain cases, the inactivating mutation is to a promoter of a gene. Any convenient mutations (e.g., as described herein) may be utilized to inactivate a gene or regulatory DNA sequence of interest. By "inactivated" or "inactivates" is meant that a biological activity of the protein expressed by the mutated gene is reduced by 10% or more, such as by 20% or more, 30% or more, 40% or more, 50% or more, 60/or more, 70% or more, 80% or more, 90% or more, 95% or more, 97% or more, or 99% or more, relative to a control protein expressed by a non-mutated control gene. In some cases, the protein is an enzyme and the inactivating mutation reduces the activity of the enzyme.

In some examples, the engineered host cell includes an inactivating mutation in an enzyme native to the cell. Any convenient enzymes may be targeted for inactivation. Enzymes of interest may include, but are not limited to those enzymes, described in Table 3 whose action in the synthetic pathway of the engineered host cell tends to reduce the levels of a BIA of interest. In some cases, the enzyme has glucose-6-phosphate dehydrogenase activity. In certain embodiments, the enzyme that includes an inactivating mutation is ZWF1. In some cases, the enzyme has alcohol dehydrogenase activity. In some embodiments, the enzyme that includes an inactivating mutation is selected from ADH2, ADH3, ADH4, ADH5, ADH6, ADH7, and SFA1. In certain embodiments, the enzyme that includes an inactivating mutation(s) is ADH2. In certain embodiments, the enzyme that includes an inactivating mutation(s) is ADH3. In certain embodiments, the enzyme that includes an inactivating mutation(s) is ADH4. In certain embodiments, the enzyme that includes an inactivating mutation(s) is ADH5. In certain embodiments, the enzyme that includes an inactivating mutation(s) is ADH6. In certain embodiments, the enzyme that includes an inactivating mutation(s) is ADH7. In some cases, the enzyme has aldehyde oxidoreductase activity. In certain embodiments, the enzyme that includes an inactivating mutation is selected from ALD2, ALD3, ALD4, ALD5, and ALD6. In certain embodiments, the enzyme that includes an inactivating mutation(s) is ALD2. In certain embodiments, the enzyme that includes an inactivating mutation(s) is ALD3. In certain embodiments, the enzyme that includes an inactivating mutation(s) is ALD4. In certain embodiments, the enzyme that includes an inactivating mutation(s) is ALD5. In certain embodiments, the enzyme that includes an inactivating mutation(s) is ALD6. In some embodiments, the host cell includes one or more inactivating mutations to one or more genes described in Table 3.

Epimerization Modifications

Figure 3:
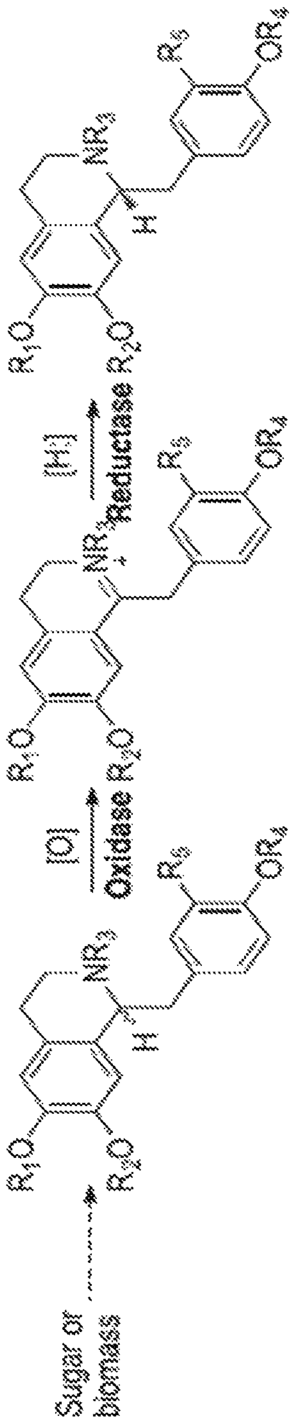
FIG. 3 illustrates a schematic example of (R)-1-benzylisoquinoline alkaloid formation, in accordance with embodiments of the invention.

Some methods, processes, and systems provided herein describe the conversion of (S)-1-benzylisoquinoline alkaloids to (R)-1-benzylisoquinoline alkaloids. Some of these methods, processes, and systems may comprise an engineered host cell. In some examples, the conversion of (S)-1-benzylisoquinoline alkaloids to (R)-1-benzylisoquinoline alkaloids is a key step in the conversion of a substrate to a diverse range of alkaloids. In some examples, the conversion of (S)-1-benzylisoquinoline alkaloids to (R)-1- benzylisoquinoline alkaloids comprises an epimerization reaction. In some examples, the conversion of (S)-1-benzylisoquinoline alkaloids to (R)-1-benzylisoquinoline alkaloids comprises an epimerization reaction via an engineered epimerase. In some cases, epimerization of a substrate alkaloid may be performed by oxidizing an (S)-substrate to the corresponding Schiff base or imine intermediate, then stereospecifically reducing this intermediate to an (R)-product as provided in FIG. 3 and as represented generally in Scheme 1. As provided in Scheme 1, $R_1$, $R_2$, $R_3$, and $R_4$ may be H or $CH_3$. $R_5$ may be H, OH, or $OCH_3$.

Scheme 1

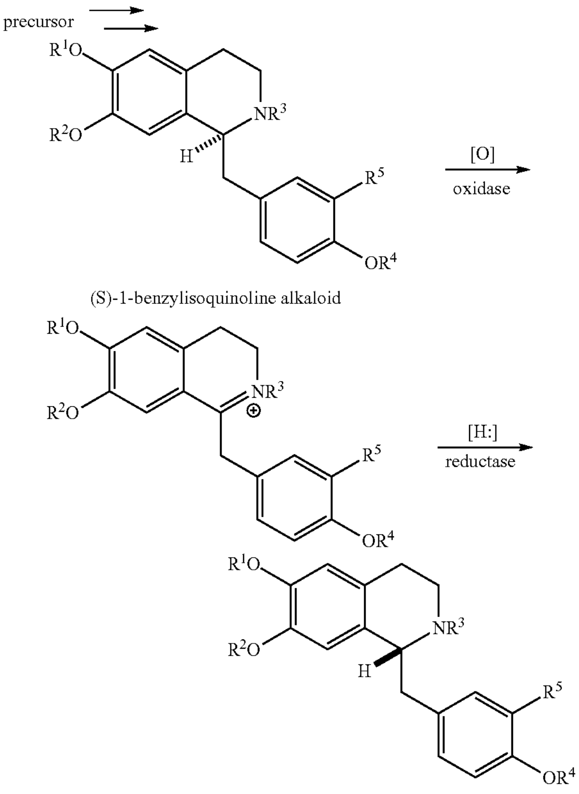

(S)-1-benzylisoquinoline alkaloid (R)-1-benzylisoquinoline alkaloid

In some examples, the conversion of the (S)-substrate to the (R)-product may involve at least one oxidation reaction and at least one reduction reaction. In some cases, an oxidation reaction is optionally followed by a reduction reaction. In some cases, at least one of the oxidation and reduction reactions is carried out in the presence of an enzyme. In some cases, at least one of the oxidation and reduction reactions is catalyzed by an enzyme. In some cases, the oxidation and reduction reactions are both carried out in the presence of at least one enzyme. In some cases, at least one enzyme is useful to catalyze the oxidation and reduction reactions. The oxidation and reduction reactions may be catalyzed by the same enzyme. In some cases, at least one of the oxidation and reduction reactions is catalyzed by an engineered epimerase. In some cases, the oxidation and reduction reactions are both carried out in the presence of an engineered fused epimerase. In some cases, the oxidation and reduction reactions are both carried out in the presence of an engineered split epimerase having a separately expressed oxidase component and reductase component, respectively. In some cases, an engineered epimerase is useful to catalyze the oxidation and reduction reactions. The oxidation and reduction reactions may be catalyzed by the same engineered epimerase.

In some methods, processes and systems described herein, an oxidation reaction may be performed in the presence of an enzyme. In some examples, the enzyme may be an oxidase. In some examples, the enzyme may be part of an engineered epimerase. In some examples, the engineered epimerase may have an oxidase component. In some cases, the oxidase component may be a component of an engineered fused epimerase. In some cases, the oxidase component may be independently expressed as part of an engineered split epimerase. The oxidase may use an (S)-1-benzylisoquinoline as a substrate. The oxidase may convert the (S)-substrate to a corresponding imine or Schiff base derivative. The oxidase may be referred to as 1,2-dehydroreticuline synthase (DRS). Non-limiting examples of enzymes suitable for oxidation of (S)-1-benzylisoquinoline alkaloids in this disclosure include a cytochrome P450 oxidase, a 2-oxoglutarate-dependent oxidase, and a flavoprotein oxidase. For example, (S)-tetrahydroprotoberberine oxidase (STOX, E.C 1.3.3.8) may oxidize (S)-norreticuline and other (S)-1-benzylisoquinoline alkaloids to 1,2-dehydronorreticuline and other corresponding 1,2-dehydro products. In some examples, a protein that comprises an oxidase domain of any one of the preceding examples may perform the oxidation. In some examples, the oxidase may catalyze the oxidation reaction within a host cell, such as an engineered host cell, as described herein.

In some examples, a reduction reaction may follow the oxidation reaction. In some examples, the reduction reaction may be performed by an enzyme. In some examples, the reduction reaction may be performed by an enzyme that is part of an engineered epimerase. In some examples, the reductase may use an imine or Schiff base derived from a 1-benzylisoquinoline as a substrate. The reductase may convert the imine or Schiff base derivative to an (R)-1-benzylisoquinoline. The reductase may be referred to as 1,2-dehydroreticuline reductase (DRR). Non-limiting examples of enzymes suitable for reduction of an imine or Schiff base derived from an (S)-1-benzylisoquinoline alkaloid include an aldo-keto reductase (e.g., a codeinone reductase-like enzyme (EC 1.1.1.247)) and a short chain dehydrogenase (e.g., a salutaridine reductase-like enzyme (EC 1.1.1.248)). In some examples, a protein that comprises a reductase domain of any one of the preceding examples may perform the reduction. In a further embodiment, the reduction is stereospecific. In some examples, the reductase may catalyze the reduction reaction within a host cell, such as an engineered host cell, as described herein.

An example of an enzyme that can perform an epimerization reaction that converts (S)-1-benzylisoquinoline alkaloids to (R)-1-benzylisoquinoline alkaloids includes an epimerase having an oxidase domain and a reductase domain. In particular, the epimerase may have a cytochrome P450 oxidase 82Y2-like domain. Additionally, the epimerase may have a codeinone reductase-like domain. Further, an epimerase having a cytochrome P450 oxidase 82Y2-like domain and also having a codeinone reductase-like domain may be referred to as a DRS-DRR enzyme. In particular, a DRS-DRR enzyme may be a fusion enzyme that is a fusion epimerase. Further, when a DRS-DRR enzyme is modified by at least one activity-increasing modification, the fusion enzyme may be an engineered fusion epimerase.

Figure 21:
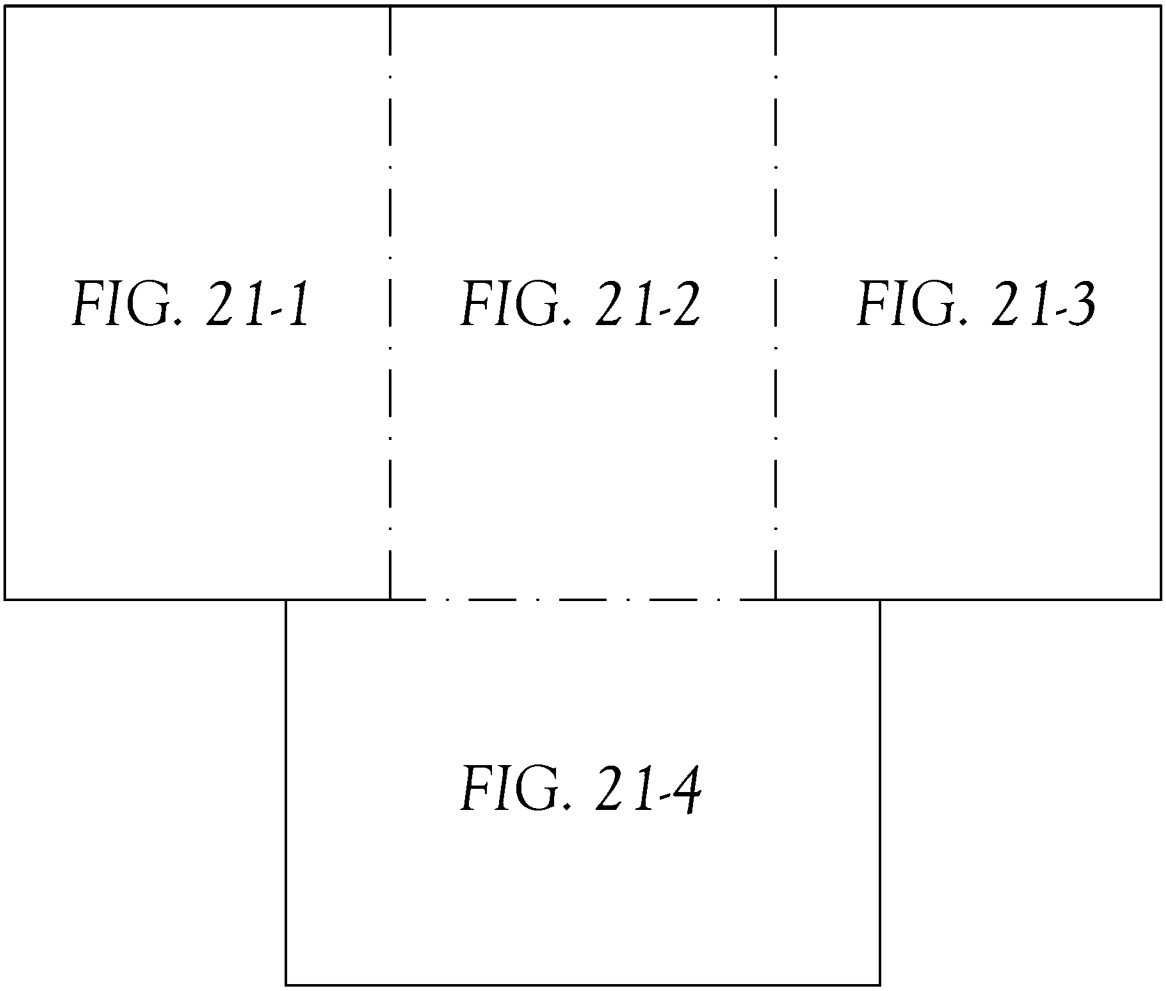
Figures 1, 21:
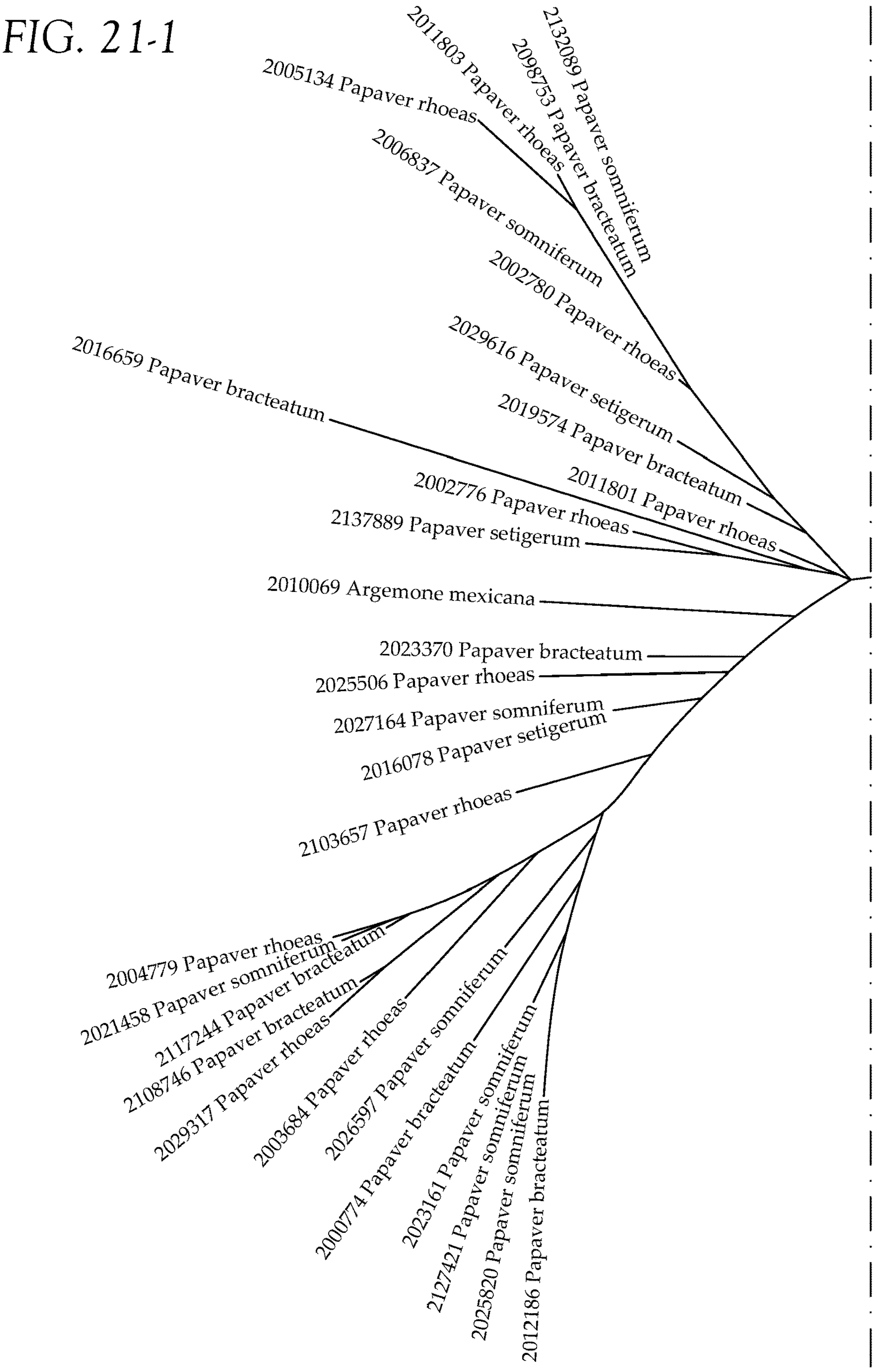
Figures 2, 21:
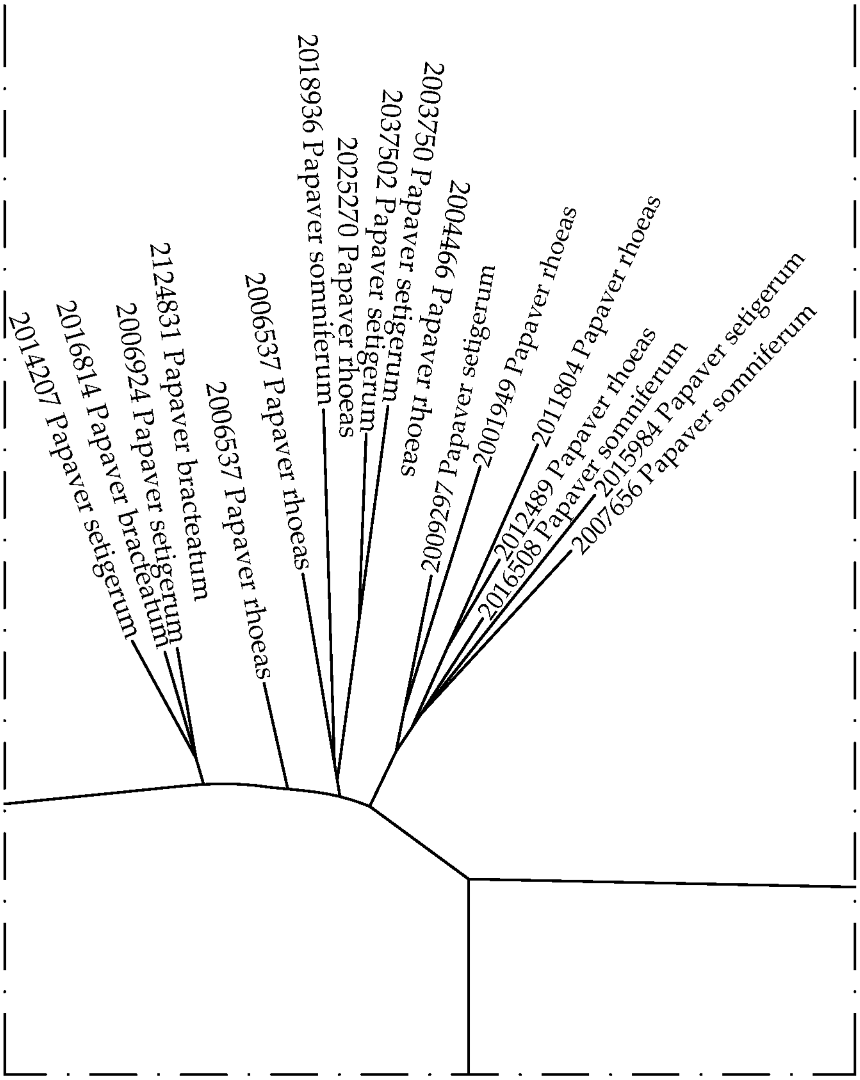
Figures 3, 21:
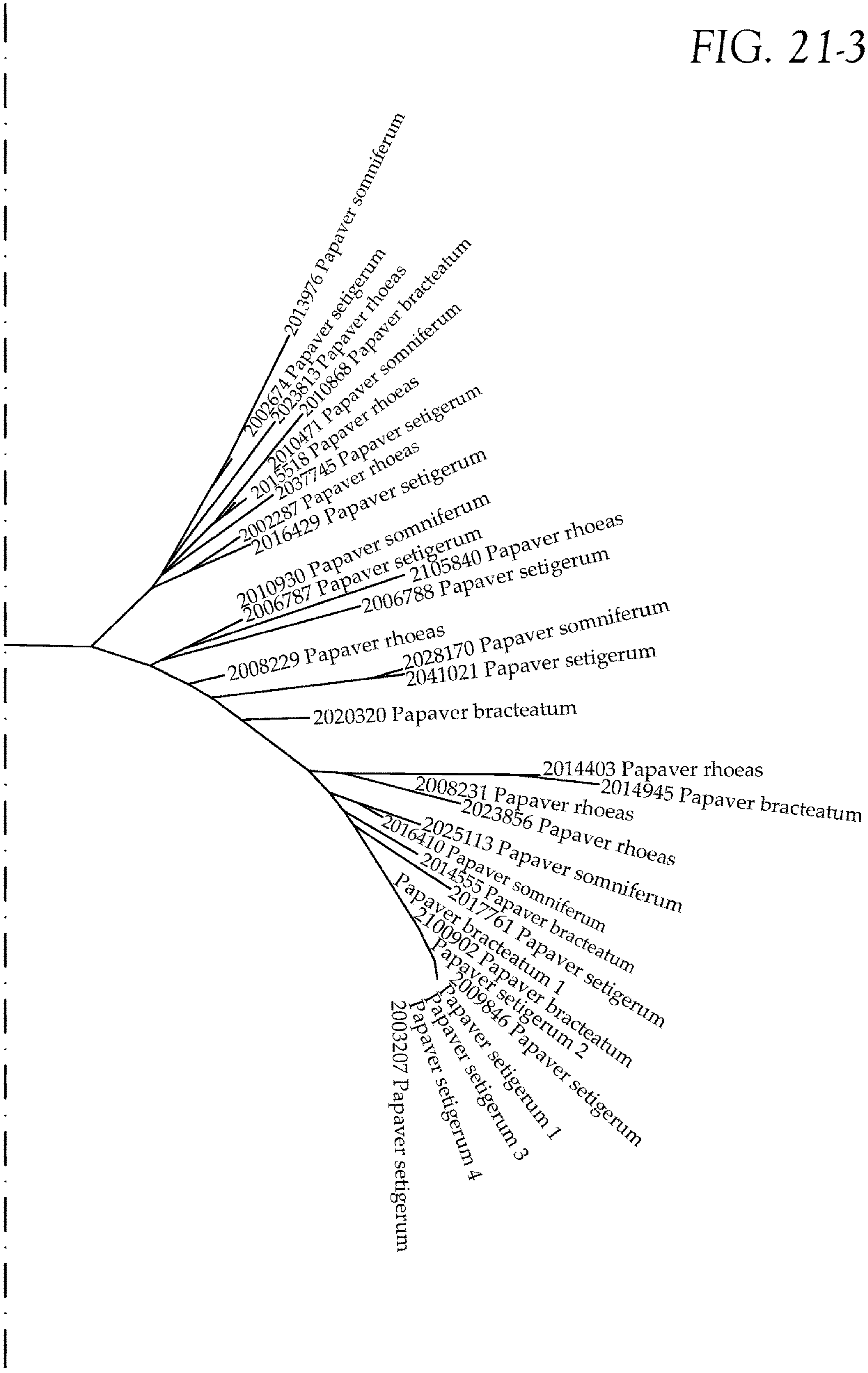
Figures 4, 21:
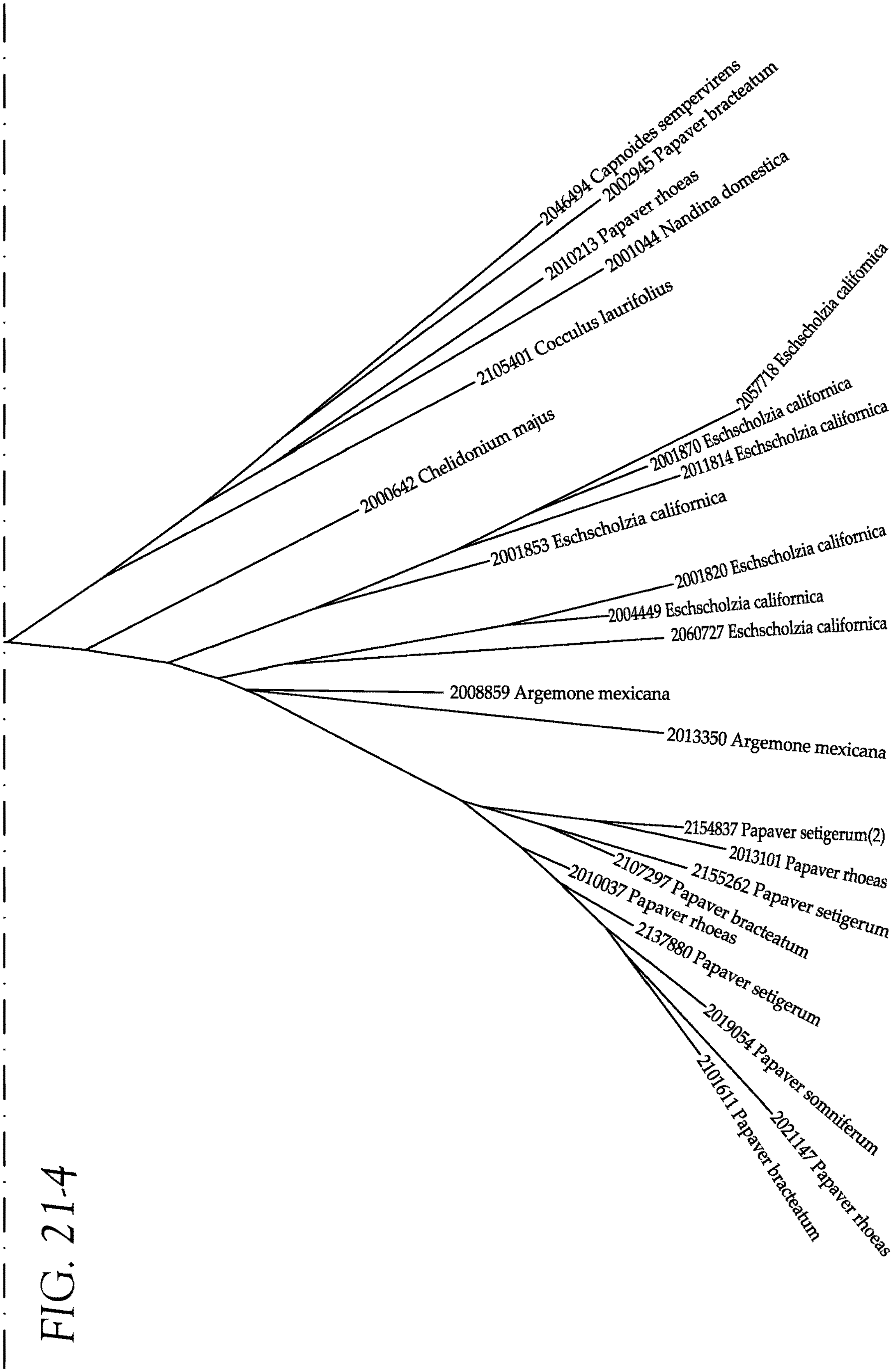

An example of an amino acid sequence of a DRS-DRR enzyme that may be used to perform the conversion of (S)-1-benzylisoquinoline alkaloids to (R)-1-benzylisoquinoline alkaloids is provided in FIG. 4. In particular, FIG. 4 illustrates an amino acid sequence of a DRS-DRR enzyme, in accordance with embodiments of the invention. As seen in FIG. 4, underlined text denotes the cytochrome P450 CYP82Y2-like domain (59% identity to AFB74617.1). The dotted underlined text denotes the aldo-keto reductase NADPH-dependent codeinone reductase-like domain (75% identity to ACM44066.1). Additional amino acid sequences of a DRS-DRR enzyme are set forth in Table 1. An amino acid sequence for an epimerase that is utilized in converting an (S)-1-benzylisoquinoline alkaloid to an (R)-1-benzylisoquinoline alkaloid may be 75% or more identical to a given amino acid sequence as listed in Table 1. For example, an amino acid sequence for such an epimerase may comprise an amino acid sequence that is at least 75% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more identical to an amino acid sequence as provided herein. Additionally, in certain embodiments, an "identical" amino acid sequence contains at least 80%-99% identity at the amino acid level to the specific amino acid sequence. In some cases an "identical" amino acid sequence contains at least about 85%, 86%, 87%, 88%, 89%, 90%, 91%, 92%, 93%, 94% and more in certain cases, at least 95%, 96%, 97%, 98% and 99% identity, at the amino acid level. In some cases, the amino acid sequence may be identical but the DNA sequence is altered such as to optimize codon usage for the host organism, for example.

An engineered host cell may be provided that produces an epimerase that converts (S)-1-benzylisoquinoline alkaloid to (R)-1-benzylisoquinoline alkaloid, wherein the epimerase comprises an amino acid sequence selected from the group consisting of: SEQ ID NOs: 1, 2, 3, 4, 5, 6, 7, 8, 9, 10, 11, 12, 13, 14, and 15. The epimerase that is produced within the engineered host cell may be recovered and purified so as to form a biocatalyst. In some cases, the epimerase may be split into one or more enzymes. Additionally, one or more enzymes that are produced by splitting the epimerase may be recovered from the engineered host cell. These one or more enzymes that result from splitting the epimerase may also be used to catalyze the conversion of (S)-1-benzylisoquinoline alkaloids to (R)-1-benzylisoquinoline alkaloids. In particular, the one or more enzymes that are recovered from the engineered host cell that produces the epimerase may be used in a process for converting an (S)-1-benzylisoquinoline alkaloid to an (R)-1-benzylisoquinoline alkaloid. The process may include contacting the (S)-1-benzylisoquinoline alkaloid with an epimerase in an amount sufficient to convert said (S)-1-benzylisoquinoline alkaloid to (R)-1-benzylisoquinoline alkaloid. In examples, the (S)-1-benzylisoquinoline alkaloid may be contacted with a sufficient amount of the one or more enzymes such that at least 5% of said (S)-1-benzylisoquinoline alkaloid is converted to (R)-1-benzylisoquinoline alkaloid. In further examples, the (S)-1-benzylisoquinoline alkaloid may be contacted with a sufficient amount of the one or more enzymes such that at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 82%, at least 84%, at least 86%, at least 88%, at least 90%, at least 91%, at least 92%, at least 93%, at least 94%, at least 95%, at least 96%, at least 97%, at least 98%, at least 99%, at least 99.5%, at least 99.7%, or 100% of said (S)-1-benzylisoquinoline alkaloid is converted to (R)-1-benzylisoquinoline alkaloid.

An example of an amino acid sequence of a DRS-DRR enzyme that may be used to perform the conversion of (S)-1-benzylisoquinoline alkaloids to (R)-1-benzylisoquinoline alkaloids is provided in FIG. 4. In particular, FIG. 4 illustrates an amino acid sequence of a DRS-DRR enzyme that has been codon-optimized, in accordance with embodiments of the invention. Further, FIG. 5 illustrates a split of an oxidase portion and reductase portion, each of the DRS-DRR enzyme of FIG. 4. Additional amino acid sequences of a DRS-DRR enzyme are set forth in Table 1. An amino acid sequence for an epimerase that is utilized in converting an (S)-1-benzylisoquinoline alkaloid to an (R)-1-benzylisoquinoline alkaloid may be 75% or more identical to a given amino acid sequence as listed in Table 1. For example, an amino acid sequence for such an epimerase may comprise an amino acid sequence that is at least 75% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more identical to an amino acid sequence as provided herein. Additionally, in certain embodiments, an "identical" amino acid sequence contains at least 80%-99% identity at the amino acid level to the specific amino acid sequence. In some cases an "identical" amino acid sequence contains at least about 85%, 86%, 87%, 88%, 89%, 90%, 91%, 92%, 93%, 94% and more in certain cases, at least 95%, 96%, 97%, 98% and 99% identity, at the amino acid level. In some cases, the amino acid sequence may be identical but the DNA sequence is altered such as to optimize codon usage for the host organism, for example.

Amino acid residues of homologous epimerases may be referenced according to the numbering scheme of SEQ ID NO. 16, and this numbering system is used throughout the disclosure to refer to specific amino acid residues of epimerases which are homologous to SEQ ID NO. 16. Epimerases homologous to SEQ ID NO. 16 may have at least about 70%, 75%, 80%, 85%, 90%, 95%, 97%, 98%, or 99% sequence identity to SEQ ID NO. 16. In some cases, an amino acid referred to as position 50 in a homologous epimerase may not be the $50^{th}$ amino acid in the homologous epimerase, but would be the amino acid which corresponds to the amino acid at position 50 in SEQ ID NO. 16 in a protein alignment of the homologous epimerase with SEQ ID NO. 16. In some cases, homologous enzymes may be aligned with SEQ ID NO. 16 either according to primary sequence, secondary structure, or tertiary structure.

An engineered host cell may be provided that produces an engineered epimerase that converts (S)-1-benzylisoquinoline alkaloid to (R)-1-benzylisoquinoline alkaloid, wherein the epimerase comprises an amino acid sequence selected from the group consisting of: SEQ ID NOs: 1, 2, 3, 4, 5, 6, 7, 8, 9, 10, 11, 12, 13, 14, 15, 16, 17, and 18, and having one or more activity-enhancing modifications. The epimerase that is produced within the engineered host cell may be recovered and purified so as to form a biocatalyst. In some cases, the epimerase may be split into one or more enzymes. Additionally, one or more enzymes that are produced by splitting the epimerase may be recovered from the engineered host cell. These one or more enzymes that result from splitting the epimerase may also be used to catalyze the conversion of (S)-1-benzylisoquinoline alkaloids to (R)-1-benzylisoquinoline alkaloids. Additionally, the use of an engineered split epimerase may be used to increase the production of benzylisoquinoline alkaloid products within a cell when compared to the production of benzylisoquinoline alkaloid products within a cell utilizing a fused epimerase.

In additional cases, the one or more enzymes that are recovered from the engineered host cell that produces the epimerase may be used in a process for converting an (S)-1-benzylisoquinoline alkaloid to an (R)-1-benzylisoquinoline alkaloid. The process may include contacting the (S)-1-benzylisoquinoline alkaloid with an epimerase in an amount sufficient to convert said (S)-1-benzylisoquinoline alkaloid to (R)-1-benzylisoquinoline alkaloid. In examples, the (S)-1-benzylisoquinoline alkaloid may be contacted with a sufficient amount of the one or more enzymes such that at least 5% of said (S)-1-benzylisoquinoline alkaloid is converted to (R)-1-benzylisoquinoline alkaloid. In further examples, the (S)-1-benzylisoquinoline alkaloid may be contacted with a sufficient amount of the one or more enzymes such that at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 82%, at least 84%, at least 86%, at least 88%, at least 90%, at least 91%, at least 92%, at least 93%, at least 94%, at least 95%, at least 96%, at least 97%, at least 98%, at least 99%, at least 99.5%, at least 99.7%, or 100% of said (S)-1-benzylisoquinoline alkaloid is converted to (R)-1-benzylisoquinoline alkaloid.

The one or more enzymes that may be used to convert an (S)-1-benzylisoquinoline alkaloid to an (R)-1-benzylisoquinoline alkaloid may contact the (S)-1-benzylisoquinoline alkaloid in vitro. Additionally, or alternatively, the one or more enzymes that may be used to convert an (S)-1-benzylisoquinoline alkaloid to an (R)-1-benzylisoquinoline alkaloid may contact the (S)-1-benzylisoquinoline alkaloid in vivo. Additionally, the one or more enzymes that may be used to convert an (S)-1-benzylisoquinoline alkaloid to an (R)-1-benzylisoquinoline alkaloid may be provided to a cell having the (S)-1-benzylisoquinoline alkaloid within, or may be produced within an engineered host cell.

In some examples, the methods provide for engineered host cells that produce an alkaloid product, wherein the epimerization of an (S)-substrate to an (R)-product may comprise a key step in the production of an alkaloid product. In some examples, the alkaloid produced is an (R)-1-benzylisoquinoline alkaloid. In still other embodiments, the alkaloid produced is derived from an (R)-1-benzylisoquinoline alkaloid, including, for example, 4-ring promorphinan and 5-ring morphinan alkaloids. In another embodiment, an (S)-1-benzylisoquinoline alkaloid is an intermediate toward the product of the engineered host cell. In still other embodiments, the alkaloid product is selected from the group consisting of 1-benzylisoquinoline, morphinan, promorphinan, nor-opioid, or nal-opioid alkaloids.

In some examples, the (S)-substrate is an (S)-1-benzylisoquinoline alkaloid selected from the group consisting of (S)-norreticuline, (S)-reticuline, (S)-tetrahydropapaverine, (S)-norcoclaurine, (S)-coclaurine, (S)—N-methylcoclaurine, (S)-3'-hydroxy-N-methylcoclaurine, (S)-norisoorientaline, (S)-orientaline, (S)-isoorientaline, (S)-norprotosinomenine, (S)-protosinomenine, (S)-norlaudanosoline, (S)-laudanosoline, (S)-4'-O-methyllaudanosoline, (S)-6-O-methylnorlaudanosoline, (S)-4'-O-methylnorlaudanosoline.

In some examples, the (S)-substrate is a compound of Formula I:

Formula I

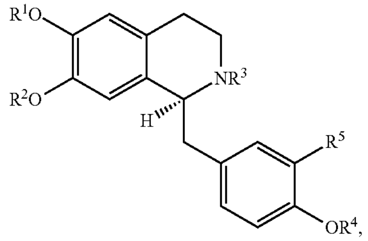

or a salt thereof, wherein:

$R^1$, $R^2$, $R^3$, and $R^4$ are independently selected from hydrogen and methyl; and $R^5$ is selected from hydrogen, hydroxy, and methoxy.

In some other examples, at least one of $R^1$, $R^2$, $R^3$, $R^4$, and $R^5$ is hydrogen.

In still other examples, the (S)-substrate is a compound of Formula II:

Formula II

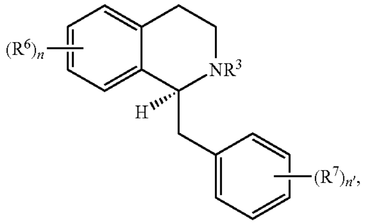

or a salt thereof, wherein:

$R^3$ is selected from hydrogen and $C_1$-$C_4$ alkyl;

$R^6$ and $R^7$ are independently selected at each occurrence from hydroxy, fluoro, chloro, bromo, carboxaldehyde, $C_1$-$C_4$ acyl, $C_1$-$C_4$ alkyl, and $C_1$-$C_4$ alkoxy;

n is 0, 1, 2, 3, or 4; and n' is 0, 1, 2, 3, 4 or 5.

When a bond is drawn across a ring, it means substitution may occur at a non-specific ring atom or position. For example, in Formula II shown above, the hydrogen of any —CH— in the 6-membered ring may be replaced with $R^7$ to form —$CR^7$—.

In some examples, $R^6$ and $R^7$ are independently methyl or methoxy. In some other examples, n and n' are independently 1 or 2. In still other embodiments, $R^3$ is hydrogen or methyl.

In some examples, the methods provide for engineered host cells that produce alkaloid products from (S)-reticuline. The epimerization of (S)-reticuline to (R)-reticuline may comprise a key step in the production of diverse alkaloid products from a precursor. In some examples, the precursor is L-tyrosine or a sugar (e.g., glucose). The diverse alkaloid products can include, without limitation, 1-benzylisoquinoline, morphinan, promorphinan, nor-opioid, or nal-opioid.alkaloids.

Any suitable carbon source may be used as a precursor toward an epimerized 1-benzylisoquinoline alkaloid. Suitable precursors can include, without limitation, monosaccharides (e.g., glucose, fructose, galactose, xylose), oligosaccharides (e.g., lactose, sucrose, raffinose), polysaccharides (e.g., starch, cellulose), or a combination thereof. In some examples, unpurified mixtures from renewable feedstocks can be used (e.g., cornsteep liquor, sugar beet molasses, barley malt, biomass hydrolysate). In still other embodiments, the carbon precursor can be a one-carbon compound (e.g., methanol, carbon dioxide) or a two-carbon compound (e.g., ethanol). In yet other embodiments, other carbon-containing compounds can be utilized, for example, methylamine, glucosamine, and amino acids (e.g., L-tyrosine). In some examples, a 1-benzylisoquinoline alkaloid may be added directly to an engineered host cell of the invention, including, for example, norlaudanosoline, laudanosoline, norreticuline, and reticuline. In still further embodiments, a 1-benzylisoquinoline alkaloid may be added to the engineered host cell as a single enantiomer (e.g., an (S)-1-benzylisoquinoline alkaloid), or a mixture of enantiomers, including, for example, a racemic mixture.

In some examples, the methods provide for the epimerization of a stereocenter of a 1-benzylisoquinoline alkaloid, or a derivative thereof. In a further embodiment, the method comprises contacting the 1-benzylisoquinoline alkaloid with at least one enzyme. The at least one enzyme may invert the stereochemistry of a stereocenter of a 1-benzylisoquinoline alkaloid, or derivative thereof, to the opposite stereochemistry. In some examples, the at least one enzyme converts an (S)-1-benzylisoquinoline alkaloid to an (R)-1-benzylisoquinoline alkaloid. In some examples of this conversion of an (S)-1-benzylisoquinoline alkaloid to an (R)-1-benzylisoquinoline alkaloid utilizing the at least one enzyme, the (S)-1-benzylisoquinoline alkaloid is selected from the group consisting of (S)-norreticuline, (S)-reticuline, (S)-tetrahydropapaverine, (S)-norcoclaurine, (S)-coclaurine, (S)—N-methylcoclaurine, (S)-3'-hydroxy-N-methylcoclaurine, (S)-norisoorientaline, (S)-orientaline, (S)-isoorientaline, (S)-norprotosinomenine, (S)-protosinomenine, (S)-norlaudanosoline, (S)-laudanosoline, (S)-4'-O-methyllaudanosoline, (S)-6-O-methylnorlaudanosoline, and (S)-4'-O-methylnorlaudanosoline.

In still other embodiments, the 1-benzylisoquinoline alkaloid that is epimerized may comprise two or more stereocenters, wherein only one of the two or more stereocenters is inverted to produce a diastereomer of the substrate (e.g., (S, R)-1-benzylisoquinoline alkaloid converted to (R, R)-1-benzylisoquinoline alkaloid). In examples where only one stereocenter of a 1-benzylisoquinoline alkaloid is inverted when contacted with the at least one enzyme, the product is referred to as an epimer of the 1-benzylisoquinoline alkaloid.

In some examples, the 1-benzylisoquinoline alkaloid is presented to the enzyme as a single stereoisomer. In some other examples, the 1-benzylisoquinoline alkaloid is presented to the enzyme as a mixture of stereoisomers. In still further embodiments, the mixture of stereoisomers may be a racemic mixture. In some other examples, the mixture of stereoisomers may be enriched in one stereoisomer as compared to another stereoisomer.

In some examples, an 1-benzylisoquinoline alkaloid, or a derivative thereof, is recovered. In some examples, the 1-benzylisoquinoline alkaloid is recovered from a cell culture. In still further embodiments, the recovered 1-benzylisoquinoline alkaloid is enantiomerically enriched in one stereoisomer as compared to the original mixture of 1-benzylisoquinoline alkaloids presented to the enzyme. In still further embodiments, the recovered 1-benzylisoquinoline alkaloid has an enantiomeric excess of at least 50%, at least 55%, at least 60%, at least 65%, at least 70%, at least 75%, at least 80%, at least 82%, at least 84%, at least 86%, at least 88%, at least 90%, at least 91%, at least 92%, at least 93%, at least 94%, at least 95%, at least 96%, at least 97%, at least 98%, at least 99%, at least 99.5%, at least 99.7%, or 100%.

In some examples, a promorphinan, or a derivative thereof, is recovered. In some examples, the promorphinan is recovered from a cell culture.

In some examples, a morphinan, or a derivative thereof, is recovered. In some examples, the morphinan is recovered from a cell culture.

In some examples, a nal-opioid, or a derivative thereof, is recovered. In some examples, the nal-opioid is recovered from a cell culture.

In some examples, a nor-opioid, or a derivative thereof, is recovered. In some examples, the nor-opioid is recovered from a cell culture.

"Isomers" are different compounds that have the same molecular formula. "Stereoisomers" are isomers that differ only in the way the atoms are arranged in space. "Enantiomers" are a pair of stereoisomers that are non superimposable mirror images of each other. A 1:1 mixture of a pair of enantiomers is a "racemic" mixture. "Diastereoisomers" or "diastereomers" are stereoisomers that have at least two asymmetric atoms but are not mirror images of each other. The term "epimer" as used herein refers to a compound having the identical chemical formula but a different optical configuration at a particular position. For example, the (R,S) and (S,S) stereoisomers of a compound are epimers of one another. In some examples, a 1-benzylisoquinoline alkaloid is converted to its epimer (e.g., epi-1-benzylisoquinoline alkaloid). The absolute stereochemistry is specified according to the Cahn-Ingold-Prelog R—S system. When a compound is a pure enantiomer, the stereochemistry at each chiral carbon can be specified by either R or S. Resolved compounds whose absolute configuration is unknown can be designated (+) or (−) depending on the direction (dextro- or levorotatory) in which they rotate plane polarized light at the wavelength of the sodium D line. Certain compounds described herein contain one or more asymmetric centers and can thus give rise to enantiomers, diastereomers, and other stereoisomeric forms that can be defined, in terms of absolute stereochemistry, as (R)- or (S)-.

TABLE 1 example amino acid sequences of DRS-DRR enzymes, split DRS and DRR enzymes, and other nucleotide sequences.

| Sequence | Description | SEQ. ID NO. |
|---|---|---|
| MELQYISYFQPTSSVVALLLALVSILSSVVVLRKTFLNNYSSSPASSTK TAVLSHQRQQSCALPISGLLHIFMNKNGLIHVTLGNMADKYGPIFSFPT GSHRTLVVSSWEMVKECFTGNNDTAFSNRPIPLAFKTIFYACGGIDSY GLSSVPYGKYWRELRKVCVHNLLSNQQLLKFRHLIISQVDTSFNKLYE LCKNSEDNHGNYTTTTTTAAGMVRIDDWLAELSFNVIGRIVCGFQSG PKTGAPSRVEQFKEAINEASYFMSTSPVSDNVPMLGWIDQLTGLTRN | *P. somniferum* plant source; full-length amino acid sequence >RQNK- | SEQ. ID NO. 1 |

TABLE 1-continued example amino acid sequences of DRS-DRR enzymes, split DRS and DRR enzymes, and other nucleotide sequences.

| Sequence | Description | SEQ. ID NO. |
| --- | --- | --- |
| MKHCGKKLDLVVESIINDHRQKRRFSRTKGGDEKDDEQDDFIDICLSI<br>MEQPQLPGNNNPSQIPIKSIVLDMIGGGTDTTKLTTIWTLSLLLNNPHV<br>LDKAKQEVDAHFRTKRRSTNDAAAAVVDFDDIRNLVYIQAIIKESMR<br>LYPASPVVERLSGEDCVVGGFHVPAGTRLWANVWKMQRDPKVWDD<br>PLVFRPDRFLSDEQKMVDVRGQNYELLPFGAGRRVCPGVSFSLDLMQ<br>LVLTRLILEFEMKSPSGKVDMTATPGLMSYKVIPLDILLTHRRIKPCVQ<br>SAASERDMESSGVPVITLGSGKVMPVLGMGTFEKVGKGSERERLAIL<br>KAIEVGYRYFDTAAAYETEEVLGEAIAEALQLGLVKSRDELFISSMLW<br>CTDAHADRVLLALQNSLRNLKLEYVDLYMLPFPASLKPGKITMDIPEE<br>DICRMDYRSVWAAMEECQNLGFTKSIGVSNFSCKKLQELMATANIPP<br>AVNQVEMSPAFQQKKLREYCNANNILVSAISVLGSNGTPWGSNAVLG<br>SEVLKKIAMAKGKSVAQVSMRWVYEQGASLVVKSFSEERLRENLNIF<br>DWELTKEDHEKIGEIPQCRILSAYFLVSPNGPFKSQEELWDDEA* | 2062398 (also FPYZ-2037562, BMRX-2007040, and MLPX-2016197) | |
| MELQYISYFQPTSSVVALLLALVSILSSVVVLRKTFLNNYSSSPASSTK<br>TAVLSHQRQQSCALPISGLLHIFMNKNGLIHVTLGNMADKYGPIFSFPT<br>GSHRTLVVSSWEMVKECFTGNNDTAFSNRPIPLAFKTIFYACGGIDSY<br>GLSSVPYGKYWRELRKVCVHNLLSNQQLLKFRHLIISQVDTSFNKLYE<br>LCKNSEDNHGNYTTXLLLPQLAWRQPWKLYYXTTTAAGMVRIDD<br>WLAELSFNVIGRIVCGFQSGPKTGAPSRVEQFKEAINEASYFMSTSPVS<br>DNVPMLGWIDQLTGLTRNMKHCGKKLDLVVESIINDHRQKRRFSRTK<br>GGDEKDDEQDDFIDICLSIMEQPQLPGNNNPSQIPIKSIVLDMIGGGTD<br>TTKLTTIWTLSLLLNNPHVLDKAKQEVDAHFRTKRRSTNDAAAAVVD<br>FDDIRNLVYIQAIIKESMRLYPASPVVERLSGEDCVVGGFHVPAGTRL<br>WANVWKMQRDPKVWDDPLVFRPDRFLSDEQKMVDVRGQNYELLPF<br>GAGRRVCPGVSFSLDLMQLVLTRLILEFEMKSPSGKVDMTATPGLMS<br>YKVIPLDILLTHRRIKPCVQSAASERDMESSGVPVITLGSGKVMPVLG<br>MGTFEKVGKGSERERLAILKAIEVGYRYFDTAAAYETEEVLGEAIAEA<br>LQLGLVKSRDELFISSMLWCTDAHADRVLLALQNSLRNLKLEYVDLY<br>MLPFPASLKPGKITMDIPEEDICRMDYRSVWAAMEECQNLGFTKSIGV<br>SNFSCKKLQELMATANIPPAVNQVEMSPAFQQKKLREYCNANNILVS<br>AISVLGSNGTPWGSNAVLGSEVLKKIAMAKGKSVAQVSMRWVYEQG<br>ASLVVKSFSEERLRENLNIFDWELTKEDHEKIGEIPQCRILSAYFLVSPN<br>GPFKSQEELWDDEA* | *P. somniferum* plant source; full-length amino acid sequence >KKCW-2026866 (also FPYZ-2037562, MLPX-2016197) | SEQ. ID NO. 2 |
| MELQYISYFQPTSSVVALLLALVSILSSVVVLRKTFLNNYSSSPASSTK<br>TAVLSHQRQQSCALPISGLLHIFMNKNGLIHVTLGNMADKYGPIFSFPT<br>GSHRTLVVSSWEMVKECFTGNNDTAFSNRPIPLAFKTIFYACGGIDSY<br>GLSSVPYGKYWRELRKVCVHNLLSNQQLLKFRHLIISQVDTSFNKLYE<br>LCKNSEDNHGNYTTTTTTAAGMVRIDDWLAELSFNVIGRIVCGFQSG<br>PKTGAPSRVEQFKEAINEASYFMSTSPVSDNVPMLGWIDQLTGLTRN<br>MKHCGKKLDLVVESIINDHRQKRRFSRTKGGDEKDDEQDDFIDICLSI<br>MEQPQLPGNNNPSQIPIKSIVLDMIGGGTDTTKLTTIWTLSLLLNNPHV<br>LDKAKQEVDAHFRTKRRSTNDAAAAVVDFDDIRNLVYIQAIIKESMR<br>LYPASPVVERLSGEDCVVGGFHVPAGTRLWANVWKMQRDPKVWDD<br>PLVFRPDRFLSDEQKMVDVRGQNYELLPFGAGRRVCPGVSFSLDLMQ<br>LVLTRLILEFEMKSPSGKVDMTATPGLMSYKVIPLDILLTHRRIKPCVQ<br>SAASERDMESSGVPVITLGSGKVMPVLGMGTFEKVGKGSERERLAIL<br>KAIEVGYRYFDTAAAYETEEVLGEAIAEALQLGLVKSRDELFISSMLW<br>CTDAHADRVLLALQNSLRNLKLEYVDLYMLPFPASLKPGKITMDIPEE<br>DICRMDYRXVSKPWLH* | *P. somniferum* plant source; partial-length amino acid sequence >SUFP-2025636 | SEQ. ID NO. 3 |
| MRWHRXIDSYGLSSVPYGKYWRELRKVCVHNLLSNQQLLKFRHLIIS<br>QVDTSFNKLYELCKNSEDNQGNYPTTTTAAGMVRIDDWLAELSFNVI<br>GRIVCGFQSGPKTGAPSRVEQFKEAINEASYFMSTSPVSDNVPMLGWI<br>DQLTGLTRNMKHCGKKLDLVVESIINDHRQKRRFSRTKGGDEKDDEQ<br>DDFIDICLSIMEQPQLPGNNNPSQIPIKSIVLDMIGGGTDTTKLTTIWTLS<br>LLLNNPHVLDKAKQEVDAHFRTKRRSTNDAAAAVVDFDDIRNLVYIQ<br>AIIKESMRLYPASPVVERLSGEDCVVGGFHVPAGTRLWANVWKMQR<br>DPKVWDDPLVFRPDRFLSDEQKMVDVRGQNYELLPFGAGRRVCPGV<br>SFSLDLMQLVLTRLILEFEMKSPSGKVDMTATPGLMSYKVIPLDILLTH<br>RRIKPCVQSAASERDMESSGVPVITLGSGKVMPVLGMGTFEKVGKGS<br>ERERLAILKAIEVGYRYFDTAAAYETEEVLGEAIAEALQLGLVKSRDE<br>LFISSMLWCTDAHADRVLLALQNSLRNLKLEYVDLYMLPFPASLKPG<br>KITMDIPEEDICRMDYRSVWAAMEECQNLGFTKSIGVSNFSCKKLQEL<br>MATANIPPAVNQVEMSPAFQQKKLREYCNANNILVSAISVLGSNGTP<br>WGSNAVLGSEVLKKIAMAKGKSVAQVSMRWVYEQGASLVVKSFSE<br>ERLRENLNIFDWELTKEDHEKIGEIPQCRILSAYFLVSPNGPFKSQEEL<br>WDDEA* | *P. somniferum* plant source; partial-length amino acid sequence >MIKW-2013651 | SEQ. ID NO. 4 |
| MELQYISYFQPTSSVVALLLALVSILSSVVVLRKTFLNNYSSSPASSTK<br>TAVLSHQRQQSCALPISGLLHIFMNKNGLIHVTLGNMADKYGPIFSFPT<br>GSHRTLVVSSWEMVKECFTGNNDTAFSNRPIPLAFKTIFYACGGIDSY<br>GLSSVPYGKYWRELRKVCVHNLLSNQQLLKFRHLIISQVDTSFNKLYE | *P. setigerum* plant source; full-length amino acid | SEQ. ID NO. 5 |

TABLE 1-continued example amino acid sequences of DRS-DRR enzymes, split DRS and DRR enzymes, and other nucleotide sequences.

| Sequence | Description | SEQ. ID NO. |
|---|---|---|
| LCKNSEDNQGNYTTTTTAAGMVRIDDWLAELSFNVIGRIVCGFQSGP<br>KTGAPSRVEQFKEAINEASYFMSTSPVSDNVPMLGWIDQLTGLTRNM<br>KHCGKKLDLVVESIINDHRQKRRFSRTKGGDEKDDEQDDFIDICLSIM<br>EQPQLPGNNNPSQIPIKSIVLDMIGGGTDTTKLTTIWTLSLLLNNPHVL<br>DKAKQEVDAHFRTKRRSTNDAAAAVVDFDDIRNLVYIQAIIKESMRL<br>YPASPVVERLSGEDCVVGGFHVPAGTRLWANVWKMQRDPKVWDDP<br>LVFRPDRFLSDEQKMVDVRGQNYELLPFGAGRRVCPGVSFSLDLMQL<br>VLTRLILEFEMKSPSGKVDMTATPGLMSYKVIPLDILLTHRRIKPCVQS<br>AASERDMESSGVPVITLGSGKVMPVLGMGTFEKVGKGSERERLAILK<br>AIEVGYRYFDTAAAYETEEVLGEAIAEALQLGLVKSRDELFISSMLWC<br>TDAHADRVLLALQNSLRNLKLEYVDLYMLPFPASLKPGKITMDIPEED<br>ICRMDYRSVWAAMEECQNLGFTKSIGVSNFSCKKLQELMATANIPPA<br>VNQVEMSPAFQQKKLREYCNANNILVSAISVLGSNGTPWGSNAVLGS<br>EVLKKIAMAKGKSVAQVSMRWVYEQGASLVVKSFSEERLRENLNIFD<br>WELTKEDHEKIGEIPQCRILSAYFLVSPNGPFKSQEELWDDEA* | sequence >EPRK-2027940 (also FPYZ-2037562, STDO-2019715, FNXH-2029312, MLPX-2016196, MLPX-2016197) | |
| MELQYISYFQPTSSVVALLLALVSILSSVVVLRKTFLNNYSSSPASSTK<br>TAVLSHQRQQSCALPISGLLHIFMNKNGLIHVTLGNMADKYGPIFSFPT<br>GSHRTLVVSSWEMVKECFTGNNDTAFSNRPIPLAFKTIFYACGGIDSY<br>GLSSVPYGKYWRELRKVCVHNLLSNQQLLKFRHLIISQVDTSFNKLYE<br>LCKNSEDNQGNYTTTTTAAGMVRIDDWLAELSFNVIGRIVCGFQSGP<br>KTGAPSRVEQFKEAINEASYFMSTSPVSDNVPMLGWIDQLTGLTRNM<br>KHCGKKLDLVVESIINDHRQKRRFSRTKGGDEKDDEQDDFIDICLSIM<br>EQPQLPGNNNPSQIPIKSIVLDMIGGGTDTTKLTTIWTLSLLLNNPHVL<br>DKAKQEVDAHFRTKRRSTNDAAAAVVDFDDIRNLVYIQALYPASPVV<br>ERLSGEDCVVGGFHVPAGTRLWANVWKMQRDPKVWDDPLVFRPDR<br>FLSDEQKMVDVRGQNYELLPFGAGRRVCPGVSFSLDLMQLVLTRLIL<br>EFEMKSPSGKVDMTATPGLMSYKVIPLDILLTHRRIKPCVQSAASERD<br>MESSGVPVITLGSGKVMPVLGMGTFEKVGKGSERERLAILKAIEVGY<br>RYFDTAAAYETEEVLGEAIAEALQLGLVKSRDELFISSMLWCTDAHA<br>DRVLLALQNSLRNLKLEYVDLYMLPFPASLKPGKITMDIPEEDICRMD<br>YRSVWAAMEE | *P. setigerum* plant source; partial-length amino acid sequence >QCOU-2000833 | SEQ. ID NO. 6 |
| MELQYFSYFQPTSSVVALLLALVSILFSVVVLRKTFSNNYSSPASSTET<br>AVLCHQRQQSCALPISGLLHVFMNKNGLIHVTLGNMADKYGPIFSFPT<br>GSHRTLVVSSWEMVKECFTGNNDTAFSNRPIPLAFQTIFYACGGIDSY<br>GLSSVPYGKYWRELRKVCVHNLLSNQQLLKFRHLIISQVDTSFNKLYE<br>LCKNSEDNQGMVRMDDWLAQLSFNVIGRIVCGFQSDPKTGAPSRVE<br>QFKEVINEASYFMSTSPVSDNVPMLGWIDQLTGLTRNMKHCGKKLDL<br>VVESIIKDHRQKRRFSRTKGGDEKDDEQDDFIDICLSIMEQPQLPGNNS<br>PPQIPIKSIVLDMIGGGTDTTKLTTIWTLSLLLNNPHVLDKAKQEVDAH<br>FRKKRRSTDDAAAAVVDFDDIRNLVYIQAIIKESMRLYPASPVVERLS<br>GEDCVVGGFHVPAGTRLWANVWKMQRDPKVWDDPLVFRPERFLSD<br>EQKMVDVRGQNYELLPFGAGRRICPGVSFSLDLMQLVLTRLILEFEM<br>KSPSGKVDMTATPGLMSYKVVPLDILLTHRRIKSCVQLASSERDMESS<br>GVPVITLSSGKVMPVLGMGTFEKVGKGSERERLAILKAIEVGYRYFDT<br>AAAYETEEVLGEAIAEALQLGLIESRDELFISSMLWCTDAHPDRVLLA<br>LQNSLRNLKLEYLDLYMLPFPASLKPGKITMDIPEEDICRMDYRSVWS<br>AMEECQNLGFTKSIGVSNFSSKKLQELMATANIPPAVNQVEMSPAFQ<br>QKKLREYCNANNILVSAVSILGSNGTPWGSNAVLGSEVLKQIAMAKG<br>KSVAQVSMRWVYEQGASLVVKSFSEERLRENLNIFDWELTKEDNEKI<br>GEIPQCRILTAYFLVSPNGPFKSQEELWDDKA* | *P. bracteatum* plant source; full-length amino acid sequence >SSDU-2015634 (also SSDU-2015636, ZSNV-2027701, RRID-2004435) | SEQ. ID NO. 7 |
| MELQYFSYFQPTSSVVALLLALVSILFSVVVLRKTFSNNYSSPASSTET<br>AVLCHQRQQSCALPISGLLHVFMNKNGLIHVTLGNMADKYGPIFSFPT<br>GSHRTLVVSSWEMVKECFTGNNDTAFSNRPIPLAFQTIFYACGGIDSY<br>GLSSVPYGKYWRELRKVCVHNLLSNQQLLKFRHLIISQVDTSFNKLYE<br>LCKNSEDNQGMVRMDDWLAQLSFNVIGRIVCGFQSDPKTGAPSRVE<br>QFKEVINEASYFMSTSPVSDNVPMLGWIDQLTGLTRNMKHCGKKLDL<br>VVESIIKDHRQKRRFSRTKGGDEKDDEQDDFIDICLSIMEQPQLPGNNS<br>PPQIPIKSIVLDMIGGGTDTTKLTTIWTLSLLLNNPHVLDKAKQEVDAH<br>FRKKRRSTDDAAAAVVDFDDIRNLVYIQAIIKESMRLYPASPVVERLS<br>GEDCVVGGFHVPAGTRLWANVWKMQRDPKVWDDPLVFRPERFLSD<br>EQKMVDVRGQNYELLPFGAGRRICPGVSFSLDLMQLVLTRLILEFEM<br>KSPSGKVDMTATPGLMSYKVVPLDILLTHRRIKSCVQLASSERDMESS<br>GVPVITLSSGKVMPVLGMGTFEKVGKGSERERLAILKAIEVGYRYFDT<br>AAAYETEEVLGEAIAEALQLGLIESRDELFISSMLWCTDAHPDRVLLA<br>LQNSLRNLKLEYLDLYMLPFPASLKPGKITMDIPEEDICRMDYRSVWS<br>AMEECQNLGFTKSIGVSNFSCKKLQELMATANIPPAVNQVEMSPAFQ<br>QKKLREYCNANNILVSAVSILGSNGTPWGSNAVLGSEVLKQIAMAKG<br>KSVAQVSMRWVYEQGASLVVKSFSEERLRENLNIFDWELTKEDNEKI<br>GEIPQCRILTAYFLVSPNGPFKSQEELWDDKA* | *P. bracteatum* plant source; full-length amino acid sequence >TMWO-2027322 (also RRID-2004435) | SEQ. ID NO. 8 |

TABLE 1-continued example amino acid sequences of DRS-DRR enzymes, split DRS and DRR enzymes, and other nucleotide sequences.

| Sequence | Description | SEQ. ID NO. |
|---|---|---|
| SSPASSTETAVLCHQRQQSCALPISGLLHIFMNKNGLIHVTLGNMADK<br>YGPIFSFPTGSHRILVVSSWEMVKECFTGNNDTAFSNRPIPLAFKTIFYA<br>CRGIDSYGLSSVPYGKYWRELRKVCVHNLLSNQQLLKFRHLIISQVDT<br>SFNKLYELCKNSEDNQGMVRMDDWLAQLSFSVIGRIVCGFQSDPKTG<br>APSRVEQFKEAINEASYFMSTSPVSDNVPMLGWIDQLTGLTRNMTHC<br>GKKLDLVVESIINDHRQKRRFSRTKGGDEKDDEQDDFIDICLSIMEQP<br>QLPGNNNPPKIPIKSIVLDMIGAGTDTTKLTIIWTLSLLLNNPNVLAKA<br>KQEVDAHFETKKRSTNEASVVVDFDDIGNLVYIQAIIKESMRLYPVSP<br>VVERLSSEDCVVGGFHVPAGTRLWANVWKMQRDPKVWDDPLVFRP<br>ERFLSDEQKMVDVRGQNYELLPFGAGRRICPGVSFSLDLMQLVLTRLI<br>LEFEMKSPSGKVDMTATPGLMSYKVVPLDILLTHRRIKSCVQLASSER<br>DMESSGVPVITLRSGKVMPVLGMGTFEKAGKGSERERLAILKAIEVG<br>YRYFDTAAAYETEEVLGEAIAEALQLGLIKSRDELFISSMLWCTDAHP<br>DRVLLALQNSLRNLKLEYVDLYMLPFPASLKPGKITMDIPEEDICPMD<br>YRSVWSAMEECQNLGLTKSIGVSNFSCKKLEELMATANIPPAVNQVE<br>MSPAFQQKKLREYCNANNILVSAVSILGSNGTPWGSNAVLGSEVLKKI<br>AMAKGKSVAQVSMRWVYEQGASLVVKSFSEERLRENLNIFDWQLTK<br>EDNEKIGEIPQCRILSAYFLVSPKGPFKSQEELWDDKA* | *P. bracteatum* plant source; partial-length amino acid sequence >pbr.PBRST1 PF_89405 | SEQ. ID NO. 9 |
| SSPASSTETAVLCHQRQQSCALPISGLLHIFMNKNGLIHVTLGNMADK<br>YGPIFSFPTGSHRILVVSSWEMVKECFTGNNDTFFSNRPIPLAFKIIFYA<br>GGVDSYGLALVPYGKYWRELRKICVHNLLSNQQLLKFRHLIISQVDTS<br>FNKLYELCKNSEDNQGMVRMDDWLAQLSFSVIGRIVCGFQSDPKTGA<br>PSRVEQFKEAINEASYFMSTSPVSDNVPMLGWIDQLTGLTRNMTHCG<br>KKLDLVVESIINDHRQKRRFSRTKGGDEKDDEQDDFIDICLSIMEQPQL<br>PGNNNPPKIPIKSIVLDMIGGGTDTTKLTTIWTLSLLLNNPHVLDKAKQ<br>EVDAHFLTKRRSTNDAAVVDFDDIRNLVYIQAIIKESMRLYPASPVVE<br>RLSGEDCVVGGFHVPAGTRLWVNVWKMQRDPNVWADPMVFRPERF<br>LSHGQKKMVDVRGKNYELLPFGAGRRICPGISFSLDLMQLVLTRLILE<br>FEMKSPSGKVDMTATPGLMSYKVVPLDILLTHRRIKSCVQLASSERD<br>MESSGVPVITLRSGKVMPVLGMGTFEKAGKGSERERLAILKAIEVGYR<br>YFDTAAAYETEEVLGEAIAEALQLGLIKSRDELFISSMLWCTDAHPDR<br>VLLALQNSLRNLKLEYVDLYMLPFPASLKPGKITMDIPEEDICPMDYR<br>SVWSAMEECQNLGLTKSIGVSNFSCKKLEELMATANIPPAVNQVEMS<br>PAFQQKKLREYCNANNILVSAVSILGSNGTPWGSNAVLGSEVLKKIA<br>MAKGKSVAQVSMRWVYEQGASLVVKSFSEERLRENLNIFDWQLTKE<br>DNEKIGEIPQCRILSAYFLVSPKGPFKSQEELWDDKA* | *P. bracteatum* plant source; partial-length amino acid sequence >pbr.PBRST1 PF_4328 | SEQ. ID NO. 10 |
| SSPASSTETAVLCHQRQQSCALPISGLLHIFMNKNGLIHVTLGNMADK<br>YGPIFSFPTGSHRILVVSSWEMVKECFTGNNDTFFSNRPIPLAFKIIFYA<br>GGVDSYGLALVPYGKYWRELRKICVHNLLSNQQLLNFRHLIISQVDTS<br>FNKLYDLSNKKKNTTTDSGTVRMDDWLAQLSFNVIGRIVCGFQTHTE<br>TSATSSVERFTEAIDEASRFMSIATVSDTFPWLGWIDQLTGLTRKMKH<br>YGKKLDLVVESIIEDHRQNRRISGTKQGDDFIDICLSIMEQPQIIPGNND<br>PPRQIPIKSIVLDMIGGGTDTTKLTTTWTLSLLLNNPHVLEKAREEVDA<br>HFGTKRRPTNDDAVMVEFDDIRNLVYIQAIIKESMRLYPASPVVERLS<br>GEDCVVGGFHVPAGTRLWVNVWKMQRDPNVWADPMVFRPERFLSD<br>EQKMVDVRGQNYELLPFGAGRRICPGVSFSLDLMQLVLTRLILEFEM<br>KSPSGKVDMTATPGLMSYKVVPLDILLTHRRIKSCVQLASSERDMESS<br>GVPVITLRSGKVMPVLGMGTFEKAGKGSERERLAILKAIEVGYRYFDT<br>AAAYETEEVLGEAIAEALQLGLIKSRDELFISSMLWCTDAHPDRVLLA<br>LQNSLRNLKLEYVDLYMLPFPASLKPGKITMDIPEEDICPMDYRSVWS<br>AMEECQNLGLTKSIGVSNFSCKKLEELMATANIPPAVNQVEMSPAFQ<br>QKKLREYCNANNILVSAVSILGSNGTPWGSNAVLGSEVLKKIAMAKG<br>KSVAQVSMRWVYEQGASLVVKSFSEERLRENLNIFDWQLTKEDNEKI<br>GEIPQCRILSAYFLVSPKGPFKSQEELWDDKA* | *P. bracteatum* plant source; partial-length amino acid sequence >pbr.PBRST1 PF_12180 | SEQ. ID NO. 11 |
| VALRKKILKNYYSSSSSTATAVSHQWPKASRALPLIDLLHVFFNKTDL<br>MHVTLGNMADKFGPIFSFPTGSHRTLVVSSWEKAKECFTGNNDIVFS<br>GRPLPLAFKLIFYAGGIDSYGISQVPYGKKWRELRNICVHNILSNQQLL<br>KFRHLMISQVDNSFNKLYEVCNSNKDEGDSATSTTAAGIVRMDDWL<br>GKLAFDVIARIVCGFQSQTETSTTSSMERFTEAMDEASRFMSVTAVSD<br>TVPWLGWIDQLTGLKRNMKHCGKKLNLVVKSIIEDHRQKRRLSSTKK<br>GDENIIDEDEQDDFIDICLSIMEQPQLPGNNNPPKIPIKSIVLDMIGGGTD<br>TTKLTTIWTLSLLLNNPHVLDKAKQEVDAHFLTKRRSTNDAAVVDFD<br>DIRNLVYIQAIIKESMRLYPASPVVERLSGEDCVVGGFHVPAGTRLWV<br>NVWKMQRDPNVWADPMVFRPERFLSDEQKMVDVRGQNYELLPFGA<br>GRRICPGVSFSLDLMQLVLTRLILEFEMKSPSGKVDMTATPGLMSYKV<br>VPLDILLTHRRIKSCVQLASSERDMESSGVPVITLRSGKVMPVLGMGT<br>FEKAGKGSERERLAILKAIEVGYRYFDTAAAYETEEVLGEAIAEALQL<br>GLIKSRDELFISSMLWCTDAHPDRVLLALQNSLRNLKLEYVDLYMLPF<br>PASLKPGKITMDIPEEDICPMDYRSVWSAMEECQNLGLTKSIGVSNFS<br>CKKLEELMATANIPPAVNQVEMSPAFQQKKLREYCNANNILVSAVSIL | *P. bracteatum* plant source; partial-length amino acid sequence >pbr.PBRST1 PF_4329 | SEQ. ID NO. 12 |

TABLE 1-continued example amino acid sequences of DRS-DRR enzymes, split DRS and DRR enzymes, and other nucleotide sequences.

| Sequence | Description | SEQ. ID NO. |
|---|---|---|
| GSNGTPWGSNAVLGSEVLKKIAMAKGKSVAQVSMRWVYEQGASLV<br>VKSFSEERLRENLNIFDWQLTKEDNEKIGEIPQCRILSAYFLVSPKGPFK<br>SQEELWDDKA* | | |
| MELQYFSYFQPTSSVVALLLALVSILFSVVVLRKTFSNNYSSPASSTET<br>AVLCHQRQQSCALPISGLLHVFMNKNGLIHVTLGNMADKYGPIFSFPT<br>GSHRTLVVSSWEMVKECFTGNNDTAFSNRPIPLAFQTIFYACGGIDSY<br>GLSSVPYGKYWRELRKVCVHNLLSNQQLLKFRHLIISQVDTSFNKLYE<br>LCKNSEDNQGMVRMDDWLAQLSFNVIGRIVCGFQSDPKTGAPSRVE<br>QFKEVINEASYFMSTSPVSDNVPMLGWIDQLTGLTRNMKHCGKKLDL<br>VVESIIKDHRQKRRFSRTKGGDEKDDEQDDFIDICLSIMEQPQLPGNNS<br>PPQIPIKSIVLDMIGGGTDTTKLTTIWTLSLLLNNPHVLDKAKQEVDAH<br>FRKKRRSTDDAAAAVVDFDDIRNLVYIQAIIKESMRLYPASPVVERLS<br>GEDCVVGGFHVPAGTRLWANVWKMQRDPKVWDDPLVFRPERFLSD<br>EQKMVDVRGQNYELLPFGAGRRICPGVSFSLDLMQLVLTRLILEFEM<br>KSPSGKVDMTATPGLMSYKVVPLDILLTHRRIKSCVQLASSERDMESS<br>GVPVITLSSGKVMPVLGMGTFEKVGKGSERERLAILKAIEVGYRYFDT<br>AAAYETEEVLGEAIAEALQLGLIESRDELFISSMLWCTDAHPDRVLLA<br>LQNSLRNLKLEYLDLYMLPFPASLKPGKITMDIPEEDICRMDYRSVWS<br>AMEECQNLGFTKSIGVSNFSSKKLQELMATANIPPAVNQVEMSPAFQ<br>QKKLREYCNANNILVSAVSILGSNGTPWGSNAVLGSEVLKQIAMAKG<br>KSVAQVSMRWVXKFSAYAIVWSLFFGHRICITLYSFLIRNVAYICITY* | *P. bracteatum* plant source; partial-length amino acid sequence >SSDU-2015635 | SEQ. ID NO. 13 |
| MELQYFSYFQPTSSVVALLLALVSILFSVVVLRKTFSNNYSSPASSTET<br>AVLCHQRQQSCALPISGLLHVFMNKNGLIHVTLGNMADKYGPIFSFPT<br>GSHRTLVVSSWEMVKECFTGNNDTAFSNRPIPLAFQTIFYACGGIDSY<br>GLSSVPYGKYWRELRKVCVHNLLSNQQLLKFRHLIISQVDTSFNKLYE<br>LCKNSEDNQGMVRMDDWLAQLSFNVIGRIVCGFQSDPKTGAPSRVE<br>QFKEVINEASYFMSTSPVSDNVPMLGWIDQLTGLTRNMKHCGKKLDL<br>VVESIIKDHRQKRRFSRTKGGDEKDDEQDDFIDICLSIMEQPQLPGNNS<br>PPQIPIKSIVLDMIGGGTDTTKLTTIWTLSLLLNNPHVLDKAKQEVDAH<br>FRKKRRSTDDAAAAVVDFDDIRNLVYIQAIIKESMRLYPASPVVERLS<br>GEDCVVGGFHVPAGTRLWANVWKMQRDPKVWDDPLVFRPERFLSD<br>EQKMVDVRGQNYELLPFGAGRRICPGVSFSLDLMQLVLTRLILEFEM<br>KSPSGKVDMTATPGLMSYKVVPLDILLTHRRIKSCVQLASSERDMESS<br>GVPVITLSSGKVMPVLGMGTFEKVGKGSERERLAILKAIEVGYRYFDT<br>AAAYETEEVLGEAIAEALQLGLIESRDELFISSMLWCTDAHPDRVLLA<br>LQNSLRQVFLMQIRLIYICTYQQVHLNIYFQINEFVLCDMYRNLKLEY | *P. bracteatum* plant source; partial-length amino acid sequence >SSDU-2015637 | SEQ. ID NO. 14 |
| LNNYSSSPASSTKTAVLSHQRQQSCALPISGLLHIFMNKNGLIHVTLGN<br>MADKYGPIFSFPTGSHRTLVVSSWEMVKECFTGNNDTAFSNRPIPLAF<br>KTIFYACGGIDSYGLSSVPYGKYWRELRKVCVHNLLSNQQLLKFRHLI<br>ISQVDTSFNKLYELCKNSEDNQGNYPTTTTAAGMVRIDDWLAELSFN<br>VIGRIVCGFQSGPKTGAPSRVEQFKEAINEASYFMSTSPVSDNVPMLG<br>WIDQLTGLTRNMKHCGKKLDLVVESIINDHRQKRRFSRTKGGDEKDD<br>EQDDFIDICLSIMEQPQLPGNNNPSQIPIKSIVLDMIGGGTDTTKLTTIW<br>TLSLLLNNPHVLDKAKQEVDAHFRTKRRSTNDAAAAVVDFDDIRNLV<br>YIQAIIKESMRLYPASPVVERLSGEDCVVGGFHVPAGTRLWANVWKM<br>QRDPKVWDDPLVFRPDRFLSDEQKMVDVRGQNYELLPFGAGRRVCP<br>GVSFSLDLMQLVLTRLILEFEMKSPSGKVDMTATPGLMSYKVIPLDIL<br>LTHRRIKPCVQSAASERDMESSGVPVITLGSGKVMPVLGMGTFEKVG<br>KGSERERLAFLKAIEVGYRYFDTAAAYETEEFLGEAIAEALQLGLIKSR<br>DELFITSKLWPCDAHPDLVVPALQNSLRNLKLEYVDLYMLPFPASLKP<br>GKITMDIPEEDICRMDYRSVWAAMEECQNLGFTKSIGVSNFSCKKLQE<br>LMATANIPPAVNQVEMSPAFQQKKLREYCNANNILVSAISVLGSNGTP<br>WGSNAVLGSEVLKKIAMAKGKSVAQVSMRWVYEQGASLVVKSFSE<br>ERLRENLNIFDWELTKEDHEKIGEIPQCRILSAYFLVSPNGPFKSQEEL<br>WDDEA* | *C. majus* plant source; partial-length amino acid sequence >chm.CMAS T2PF_14984 | SEQ. ID NO. 15 |
| MELQYFSYFQPTSSVVALLLALVSILFSVVVLRKTFSNNYSSPASSTET<br>AVLCHQRQQSCALPISGLLHVFMNKNGLIHVTLGNMADKYGPIFSFPT<br>GSHRTLVVSSWEMVKECFTGNNDTAFSNRPIPLAFQTIFYACGGIDSY<br>GLSSVPYGKYWRELRKVCVHNLLSNQQLLKFRHLIISQVDTSFNKLYE<br>LCKNSEDNQGMVRMDDWLAQLSFNVIGRIVCGFQSDPKTGAPSRVE<br>QFKEVINEASYFMSTSPVSDNVPMLGWIDQLTGLTRNMKHCGKKLDL<br>VVESIIKDHRQKRRFSRTKGGDEKDDEQDDFIDICLSIMEQPQLPGNNS<br>PPQIPIKSIVLDMIGGGTDTTKLTTIWTLSLLLNNPHVLDKAKQEVDAH<br>FRKKRRSTDDAAAAVVDFDDIRNLVYIQAIIKESMRLYPASPVVERLS<br>GEDCVVGGFHVPAGTRLWANVWKMQRDPKVWDDPLVFRPERFLSD<br>EQKMVDVRGQNYELLPFGAGRRICPGVSFSLDLMQLVLTRLILEFEM<br>KSPSGKVDMTATPGLMSYKVVPLDILLTHRRIKSCVQLASSERDMESS<br>GVPVITLSSGKVMPVLGMGTFEKVGKGSERERLAILKAIEVGYRYFDT<br>AAAYETEEVLGEAIAEALQLGLIESRDELFISSMLWCTDAHPDRVLLA<br>LQNSLRNLKLEYLDLYMLPFPASLKPGKITMDIPEEDICRMDYRSVWS | *P. bracteatum* DRS-DRR | SEQ. ID NO. 16 |

TABLE 1-continued example amino acid sequences of DRS-DRR enzymes, split DRS and DRR enzymes, and other nucleotide sequences.

| Sequence | Description | SEQ. ID NO. |
|---|---|---|
| AMEECQNLGFTKSIGVSNFSCKKLQELMATANIPPAVNQVEMSPAFQ QKKLREYCNANNILVSAVSILGSNGTPWGSNAVLGSEVLKQIAMAKG KSVAQVSMRWVYEQGASLVVKSFSEERLRENLNIFDWELTKEDNEKI GEIPQCRILTAYFLVSPNGPFKSQEELWDDKA* | | |
| MELQYFSYFQPTSSVVALLLALVSILFSVVVLRKTFSNNYSSPASSTET AVLCHQRQQSCALPISGLLHVFMNKNGLIHVTLGNMADKYGPIFSFPT GSHRTLVVSSWEMVKECFTGNNDTAFSNRPIPLAFQTIFYACGGIDSY GLSSVPYGKYWRELRKVCVHNLLSNQQLLKFRHLIISQVDTSFNKLYE LCKNSEDNQGMVRMDDWLAQLSFNVIGRIVCGFQSDPKTGAPSRVE QFKEVINEASYFMSTSPVSDNVPMLGWIDQLTGLTRNMKHCGKKLDL VVESIIKDHRQKRRFSRTKGGDEKDDEQDDFIDICLSIMEQPQLPGNNS PPQIPIKSIVLDMIGGGTDTTKLTTIWTLSLLLNNPHVLDKAKQEVDAH FRKKRRSTDDAAAAVVDFDDIRNLVYIQAIIKESMRLYPASPVVERLS GEDCVVGGFHVPAGTRLWANVWKMQRDPKVWDDPLVFRPERFLSD EQKMVDVRGQNYELLPFGAGRRICPGVSFSLDLMQLVLTRLILEFEM KSPSGKVDMTATPGLMSYKVVPLDILLTHRRIKSCVQLASSERD | *P. bracteatum* DRS | SEQ. ID NO. 17 |
| MESSGVPVITLSSGKVMPVLGMGTFEKVGKGSERERLAILKAIEVGYR YFDTAAAYETEEVLGEAIAEALQLGLIESRDELFISSMLWCTDAHPDR VLLALQNSLRNLKLEYLDLYMLPFPASLKPGKITMDIPEEDICRMDYR SVWSAMEECQNLGFTKSIGVSNFSCKKLQELMATANIPPAVNQVEMS PAFQQKKLREYCNANNILVSAVSILGSNGTPWGSNAVLGSEVLKQIA MAKGKSVAQVSMRWVYEQGASLVVKSFSEERLRENLNIFDWELTKE DNEKIGEIPQCRILTAYFLVSPNGPFKSQEELWDDKA* | *P. bracteatum* DRR | SEQ. ID NO. 18 |
| TTCAGTTCGAGTTTATCATTATCAATACTGCCATTTCAAAGAATAC GTAAATAATTAATAGTAGTGATTTTCCTAACTTTATTTAGTCAAAA AATTAGCCTTTTAATTCTGCTGTAACCCGTACATGCCCAAAATAGG GGGCGGGTTACACAGAATATATAACATCGTAGGTGTCTGGGTGAA CAGTTTATTCCTGGCATCCACTAAATATAATGGAGCCCGCTTTTTA AGCTGGCATCCAGAAAAAAAAAGAATCCCAGCACCAAAATATTGT TTTCTTCACCAACCATCAGTTCATAGGTCCATTCTCTTAGCGCAACT ACAGAGAACAGGGGCACAAACAGGCAAAAAACGGGCACAACCTC AATGGAGTGATGCAACCTGCCTGGAGTAAATGATGACACAAGGCA ATTGACCCACGCATGTATCTATCTCATTTTCTTACACCTTCTATTAC CTTCTGCTCTCTCTGATTTGGAAAAAGCTGAAAAAAAAGGTTGAAA CCAGTTCCCTGAAATTATTCCCCTACTTGACTAATAAGTATATAAA GACGGTAGGTATTGATTGTAATTCTGTAAATCTATTTCTTAAACTTC TTAAATTCTACTTTTATAGTTAGTCTTTTTTTTAGTTTTAAAACACC AAGAACTTAGTTTCGAATAAACACACATAAACAAACAAA | TDH3 Promoter | SEQ. ID NO. 19 |
| GAGCGTTGGTTGGTGGATCAAGCCCACGCGTAGGCAATCCTCGAG CAGATCCGCCAGGCGTGTATATATAGCGTGGATGGCCAGGCAACT TTAGTGCTGACACATACAGGCATATATATATGTGTGCGACGACACA TGATCATATGGCATGCATGTGCTCTGTATGTATATAAAACTCTTGT TTTCTTCTTTTCTCTAAATATTCTTTCCTTATACATTAGGACCTTTGC AGCATAAATTACTATACTTCTATAGACACACAAACACAAATACAC ACACTAAATTAATA | CYC1 Promoter | SEQ. ID NO. 20 |
| CATAGCTTCAAAATGTTTCTACTCCTTTTTTACTCTTCCAGATTTTC TCGGACTCCGCGCATCGCCGTACCACTTCAAAACACCCAAGCACA GCATACTAAATTTCCCCTCTTTCTTCCTCTAGGGTGTCGTTAATTAC CCGTACTAAAGGTTTGGAAAAGAAAAAAGAGACCGCCTCGTTTCT TTTTCTTCGTCGAAAAAGGCAATAAAAATTTTTATCACGTTTCTTTT TCTTGAAAATTTTTTTTTTTGATTTTTTTCTCTTTCGATGACCTCCCA TTGATATTTAAGTTAATAAACGGTCTTCAATTTCTCAAGTTTCAGTT TCATTTTTCTTGTTCTATTACAACTTTTTTTACTTCTTGCTCATTAGA AAGAAAGCATAGCAATCTAATCTAAGTTTTAATTACAAA | TEF1 Promoter | SEQ. ID NO. 21 |
| ACAGGCCCCTTTTCCTTTGTCGATATCATGTAATTAGTTATGTCACG CTTACATTCACGCCCTCCTCCCACATCCGCTCTAACCGAAAAGGAA GGAGTTAGACAACCTGAAGTCTAGGTCCCTATTTATTTTTTTTAAT AGTTATGTTAGTATTAAGAACGTTATTTATATTTCAAATTTTTCTTT TTTTTCTGTACAAACGCGTGTACGCATGTAACATTATACTGAAAAC CTTGCTTGAGAAGGTTTTGGGACGCTCGAAGGCTTTAATTTG | CYC1 Terminator | SEQ. ID NO. 22 |
| GCGAATTTCTTATGATTTATGATTTTTATTATTAAATAAGTTATAAA AAAAATAAGTGTATACAAATTTTAAAGTGACTCTTAGGTTTTAAAA CGAAAATTCTTATTCTTGAGTAACTCTTTCCTGTAGGTCAGGTTGCT TTCTCAGGTA | ADH1 Terminator | SEQ. ID NO. 23 |

TABLE 1-continued example amino acid sequences of DRS-DRR enzymes, split DRS and DRR enzymes, and other nucleotide sequences.

| Sequence | Description | SEQ. ID NO. |
|---|---|---|
| CCTCGCCGCAGTTAATTAAAGTCAGTGAGCGAGGAAGCGCGTAAC<br>TATAACGGTCCTAAGGTAGCGAATCCTGATGCGGTATTTTCTCCTT<br>ACGCATCTGTGCGGTATTTCACACCGCATAGATCGGCAAGTGCACA<br>AACAATACTTAAATAAATACTACTCAGTAATAACCTATTTCTTAGC<br>ATTTTTGACGAAATTTGCTATTTTGTTAGAGTCTTTTACACCATTTG<br>TCTCCACACCTCCGCTTACATCAACACCAATAACGCCATTTAATCT<br>AAGCGCATCACCAACATTTTCTGGCGTCAGTCCACCAGCTAACATA<br>AAATGTAAGCTTTCGGGGCTCTCTTGCCTTCCAACCCAGTCAGAAA<br>TCGAGTTCCAATCCAAAAGTTCACCTGTCCCACCTGCTTCTGAATC<br>AAACAAGGGAATAAACGAATGAGGTTTCTGTGAAGCTGCACTGAG<br>TAGTATGTTGCAGTCTTTTGGAAATACGAGTCTTTTAATAACTGGC<br>AAACCGAGGAACTCTTGGTATTCTTGCCACGACTCATCTCCATGCA<br>GTTGGACGATATCAATGCCGTAATCATTGACCAGAGCCAAAACAT<br>CCTCCTTAAGTTGATTACGAAACACGCCAACCAAGTATTTCGGAGT<br>GCCTGAACTATTTTTATATGCTTTTACAAGACTTGAAATTTTCCTTG<br>CAATAACCGGGTCAATTGTTCTCTTTCTATTGGGCACACATATAAT<br>ACCCAGCAAGTCAGCATCGGAATCTAGAGCACATTCTGCGGCCTCT<br>GTGCTCTGCAAGCCGCAAACTTTCACCAATGGACCAGAACTACCTG<br>TGAAATTAATAACAGACATACTCCAAGCTGCCTTTGTGTGCTTAAT<br>CACGTATACTCACGTGCTCAATAGTCACCAATGCCCTCCCTCTTGG<br>CCCTCTCCTTTTCTTTTTTCGACCGAATTAATTCTTAATCGGCAAAA<br>AAAGAAAAGCTCCGGATCAAGATTGTACGTAAGGTGACAAGCTAT<br>TTTTCAATAAAGAATATCTTCCACTACTGCCATCTGGCGTCATAAC<br>TGCAAAGTACACATATATTACGATGCTGTTCTATTAAATGCTTCCT<br>ATATTATATATATAGTAATGTCGTGATCTATGGTGCACTCTCAGTA<br>CAATCTGCTCTGATGCCGCATAGTTAAGCCAGCCCCGACACCCGCC<br>AACACCCGCTGACGCGCCCTGACGGGCTTGTCTGCTCCCGGCATCC<br>GCTTACAGACAAGCTGTGACCGTCTCCGGGAGCTGCATGTGTCAG<br>AGGTTTTCACCGTCATCACCGAAACGCGCGAGACGAAAGGGCCTC<br>GTGATACGCCTATTTTTATAGGTTAATGTCATGATAATAATGGTTT<br>CTTAGACGGATCGCTTGCCTGTAACTTACACGCGCCTCGTATCTTTT<br>AATGATGGAATAATTTGGGAATTTACTCTGTGTTTATTTATTTTTAT<br>GTTTTGTATTTGGATTTTAGAAAGTAAATAAAGAAGGTAGAAGAG<br>TTACGGAATGAAGAAAAAAAAATAAACAAAGGTTTAAAAAATTTC<br>AACAAAAAGCGTACTTTACATATATATTTATTAGACAAGAAAAGC<br>AGATTAAATAGATATACATTCGATTAACGATAAGTAAAATGTAAA<br>ATCACAGGATTTTCGTGTGTGGTCTTCTACACAGACAAGGTGAAAC<br>AATTCGGCATTAATACCTGAGAGCAGGAAGAGCAAGATAAAAGGT<br>AGTATTTGTTGGCGATCCCCCTAGAGTCTTTTACATCTTCGGAAAA<br>CAAAAACTATTTTTTCTTTAATTTCTTTTTTTACTTTCTATTTTTAAT<br>TTATATATTTATATTAAAAAATTTAAATTATAATTATTTTTATAGCA<br>CGTGATGAAAAGGACCCAGGTGGCACTTTTCGGGGAAATGTGCGC<br>GGAACCCCTATTTGTTTATTTTTCTAAATACATTCAAATATGTATCC<br>GCTCATGAGACAATAACCCTGATAAATGCTTCAATAATATTGAAA<br>AAGGAAGAGTATGAGTATTCAACATTTCCGTGTCGCCCTTATTCCC<br>TTTTTTGCGGCATTTTGCCTTCCTGTTTTTGCTCACCCAGAAACGCT<br>GGTGAAAGTAAAAGATGCTGAAGATCAGTTGGGACGCGTAGTCTA<br>GACCAGCCAGGACAGAAATGCCTCGACTTCGCTGCTACCCAAGGT<br>TGCCGGGTGACGCACACCGTGGAAACGGATGAAGGCACGAACCCA<br>GTGGACATAAGCCTGTTCGGTTCGTAAGCTGTAATGCAAGTAGCGT<br>ATGCGCTCACGCAACTGGTCCAGAACCTTGACCGAACGCAGCGGT<br>GGTAACGGCGCAGTGGCGGTTTTCATGGCTTGTTATGACTGTTTTT<br>TTGGGGTACAGTCTATGCCTCGGGCATCCAAGCAGCAAGCGCGTT<br>ACGCCGTGGGTCGATGTTTGATGTTATGGAGCAGCAACGATGTTAC<br>GCAGCAGGGCAGTCGCCCTAAAACAAAGTTAAACATTATGAGGGA<br>AGCGGTGATCGCCGAAGTATCGACTCAACTATCAGAGGTAGTTGG<br>CGCCATCGAGCGCCATCTCGAACCGACGTTGCTGGCCGTACATTTG<br>TACGGCTCCGCAGTGGATGGCGGCCTGAAGCCACACAGTGATATT<br>GATTTGCTGGTTACGGTGACCGTAAGGCTTGATGAAACAACGCGG<br>CGAGCTTTGATCAACGACCTTTTGGAAACTTCGGCTTCCCCTGGAG<br>AGAGCGAGATTCTCCGCGCTGTAGAAGTCACCATTGTTGTGCACGA<br>CGACATCATTCCGTGGCGTTATCCAGCTAAGCGCGAACTGCAATTT<br>GGAGAATGGCAGCGCAATGACATTCTTGCAGGTATCTTCGAGCCA<br>GCCACGATCGACATTGATCTGGCTATCTTGCTGACAAAAGCAAGA<br>GAACATAGCGTTGCCTTGGTAGGTCCAGCGGCGGAGGAACTCTTT<br>GATCCGGTTCCTGAACAGGATCTATTTGAGGCGCTAAATGAAACCT<br>TAACGCTATGGAACTCGCCGCCCGACTGGGCTGGCGATGAGCGAA<br>ATGTAGTGCTTACGTTGTCCCGCATTTGGTACAGCGCAGTAACCGG<br>CAAAATCGCGCCGAAGGATGTCGCTGCCGGCTGGGCAATGGAGCG<br>CCTGCCGGCCCAGTATCAGCCCGTCATACTTGAAGCTAGACAGGCT<br>TATCTTGGACAAGAAGAAGATCGCTTGGCCTCGCGCGCAGATCAG<br>TTGGAAGAATTTGTCCACTACGTGAAAGGCGAGATCACCAAGGTA<br>GTCGGCAAATAACCCTCGAGCATTCAAGGCGCCTTGATTATTTGAC | pDW10 | SEQ. ID NO. 24 |

TABLE 1-continued example amino acid sequences of DRS-DRR enzymes, split DRS and DRR enzymes, and other nucleotide sequences.

| Sequence | Description | SEQ. ID NO. |
|---|---|---|
| GTGGTTTGATGGCCTCCACGCACGTTGTGATATGTAGATGATTCAG | | |
| TTCGAGTTTATCATTATCAATACTGCCATTTCAAAGAATACGTAAA | | |
| TAATTAATAGTAGTGATTTTCCTAACTTTATTTAGTCAAAAAATTA | | |
| GCCTTTTAATTCTGCTGTAACCCGTACATGCCCAAAATAGGGGGCG | | |
| GGTTACACAGAATATATAACATCGTAGGTGTCTGGGTGAACAGTTT | | |
| ATTCCTGGCATCCACTAAATATAATGGAGCCCGCTTTTTAAGCTGG | | |
| CATCCAGAAAAAAAAAGAATCCCAGCACCAAAATATTGTTTTCTTC | | |
| ACCAACCATCAGTTCATAGGTCCATTCTCTTAGCGCAACTACAGAG | | |
| AACAGGGGCACAAACAGGCAAAAAACGGGCACAACCTCAATGGA | | |
| GTGATGCAACCTGCCTGGAGTAAATGATGACACAAGGCAATTGAC | | |
| CCACGCATGTATCTATCTCATTTTCTTACACCTTCTATTACCTTCTG | | |
| CTCTCTCTGATTTGGAAAAAGCTGAAAAAAAAGGTTGAAACCAGT | | |
| TCCCTGAAATTATTCCCCTACTTGACTAATAAGTATATAAAGACGG | | |
| TAGGTATTGATTGTAATTCTGTAAATCTATTTCTTAAACTTCTTAAA | | |
| TTCTACTTTTATAGTTAGTCTTTTTTTTAGTTTTAAAACACCAAGAA | | |
| CTTAGTTTCGAATAAACACACATAAACAAACAAAATGGAACTTCA | | |
| GTACTTCTCCTATTTTCAACCCACTTCATCTGTCGTAGCCCTACTAC | | |
| TAGCACTAGTGAGTATTTTATTTAGCGTAGTTGTTTTGAGGAAGAC | | |
| TTTCAGTAACAATTACTCCAGCCCCGCGTCAAGTACGGAAACCGCT | | |
| GTGCTGTGTCATCAGAGGCAACAGAGTTGCGCCCTACCTATCAGCG | | |
| GCCTTCTTCACGTGTTCATGAATAAGAACGGCCTGATTCATGTCAC | | |
| CTTGGGAAATATGGCTGACAAATATGGCCCTATCTTCAGTTTTCCG | | |
| ACAGGCAGCCACCGTACTTTAGTAGTCAGTTCCTGGGAAATGGTG | | |
| AAAGAGTGTTTCACCGGTAATAACGACACGGCATTCTCCAACAGA | | |
| CCAATCCCTTTGGCTTTTCAAACCATATTCTACGCCTGTGGCGGCA | | |
| TTGATTCTTACGGTTTAAGTAGTGTCCCGTATGGTAAATACTGGAG | | |
| GGAGTTGAGAAAGGTGTGTGTTCACAACCTGCTGAGTAATCAGCA | | |
| ATTGCTGAAGTTCAGACATCTTATAATCTCCCAAGTGGATACGTCT | | |
| TTTAACAAGTTGTATGAGCTGTGTAAGAACTCTGAAGATAATCAAG | | |
| GTATGGTAAGGATGGATGATTGGCTAGCTCAACTTTCCTTTAACGT | | |
| CATCGGTAGGATCGTTTGCGGATTCCAGTCTGACCCAAAGACGGGT | | |
| GCACCTTCAAGGGTAGAACAGTTTAAGGAAGTCATAAATGAGGCG | | |
| TCATATTTTATGTCAACAAGTCCAGTCTCCGATAACGTACCAATGT | | |
| TGGGATGGATCGACCAATTGACCGGTCTGACGAGGAACATGAAGC | | |
| ATTGTGGGAAGAAGCTTGACTTAGTAGTGGAGTCAATTATCAAGG | | |
| ACCATAGGCAAAAGAGACGTTTTTCACGTACAAAAGGTGGCGATG | | |
| AGAAGGATGACGAACAGGACGACTTTATTGATATTTGCTTGAGCA | | |
| TCATGGAGCAGCCACAGTTGCCCGGGAACAATTCTCCCCCTCAAAT | | |
| TCCGATCAAATCTATCGTGCTAGACATGATTGGGGGTGGTACCGAC | | |
| ACTACGAAACTTACAACCATATGGACCCTATCACTTTTGTTGAACA | | |
| ATCCTCACGTGTTAGATAAAGCTAAACAAGAGGTCGACGCTCACTT | | |
| TCGTAAAAAGAGAAGATCAACAGATGACGCAGCAGCGGCAGTCGT | | |
| TGATTTTGACGACATAAGAAATTTAGTATACATCCAAGCCATCATT | | |
| AAAGAAAGTATGAGGCTTTATCCAGCCAGCCCGGTGGTTGAGCGT | | |
| CTTTCCGGCGAGGATTGCGTTGTTGGAGGTTTTCACGTGCCTGCTG | | |
| GTACGAGACTATGGGCTAACGTTTGGAAGATGCAAAGAGATCCCA | | |
| AAGTTTGGGACGATCCTCTAGTATTCAGACCTGAAAGGTTTTTGAG | | |
| CGACGAGCAAAAGATGGTAGACGTTCGTGGCCAAAACTATGAACT | | |
| TCTGCCATTCGGCGCAGGAAGAAGAATCTGTCCAGGCGTTTCCTTT | | |
| AGTCTTGACCTTATGCAACTTGTCCTAACCAGGTTAATCCTAGAGT | | |
| TCGAAATGAAGTCCCCGTCCGGCAAGGTAGATATGACCGCAACTC | | |
| CAGGACTAATGTCTTACAAGGTGGTTCCATTGGACATATTGCTGAC | | |
| TCACCGTCGTATCAAGTCATGCGTTCAATTGGCGTCTTCTGAACGT | | |
| GATATGGAAAGTTCTGGGGTGCCTGTGATCACATTGTCCTCAGGTA | | |
| AAGTAATGCCCGTACTGGGCATGGGAACCTTCGAAAAGGTGGGTA | | |
| AGGGGTCTGAACGTGAGCGTTTAGCCATTCTTAAAGCGATCGAAG | | |
| TTGGTTACCGTTACTTTGATACCGCAGCGGCATATGAAACGGAAGA | | |
| AGTTCTAGGGGAAGCCATTGCTGAAGCTTTACAATTGGGTCTGATA | | |
| GAGAGCCGTGACGAGCTGTTCATCAGCTCAATGCTTTGGTGCACCG | | |
| ACGCACATCCAGACCGTGTGCTACTTGCTCTGCAAAACAGTCTGAG | | |
| AAATCTAAAACTTGAATATCTAGACCTATATATGTTGCCGTTTCCT | | |
| GCCAGCCTTAAGCCGGGCAAAATTACGATGGATATTCCTGAGGAG | | |
| GATATTTGCCGTATGGATTATCGTTCAGTCTGGAGCGCCATGGAAG | | |
| AGTGTCAAAACTTAGGATTTACTAAAAGTATTGGTGTAAGCAACTT | | |
| TTCTTGCAAGAAATTACAAGAATTAATGGCCACTGCAAATATCCCG | | |
| CCCGCGGTAAATCAAGTAGAGATGTCACCAGCTTTCCAACAGAAA | | |
| AAACTGAGGGAATATTGTAACGCAAACAACATATTGGTATCCGCA | | |
| GTAAGCATTCTGGGATCAAACGGGACGCCCTGGGGTAGTAATGCT | | |
| GTTCTTGGAAGCGAAGTTTTGAAACAGATCGCGATGGCGAAAGGC | | |
| AAAAGCGTTGCGCAAGTCAGTATGAGGTGGGTCTATGAGCAGGGC | | |
| GCGTCTTTAGTAGTCAAGAGTTTCTCTGAAGAACGTTTAAGAGAAA | | |
| ACCTGAATATTTTTGACTGGGAGCTTACGAAAGAAGACAATGAGA | | |
| AGATAGGCGAAATCCCGCAATGTAGAATCCTTACTGCGTACTTCCT | | |
| TGTCTCCCCGAACGGCCCGTTTAAATCTCAGGAAGAGCTTTGGGAT | | |

TABLE 1-continued example amino acid sequences of DRS-DRR enzymes, split DRS and DRR enzymes, and other nucleotide sequences.

| Sequence | Description | SEQ. ID NO. |
| --- | --- | --- |
| GACAAGGCAtaaACAGGCCCCTTTTCCTTTGTCGATATCATGTAATT<br>AGTTATGTCACGCTTACATTCACGCCCTCCTCCCACATCCGCTCTA<br>ACCGAAAAGGAAGGAGTTAGACAACCTGAAGTCTAGGTCCCTATT<br>TATTTTTTTTAATAGTTATGTTAGTATTAAGAACGTTATTTATATTT<br>CAAATTTTTCTTTTTTTTCTGTACAAACGCGTGTACGCATGTAACAT<br>TATACTGAAAACCTTGCTTGAGAAGGTTTTGGGACGCTCGAAGGCT<br>TTAATTTGTAATCATTATCACTTTACGGGTCCTTTCCGGTGATCCGA<br>CAGGTTACGGGGCGGCGACCTCGCGGGTTTTCGCTATTTATGAAAA<br>TTTTCCGGTTTAAGGCGTTTCCGTTCTTCTTCGTCATAACTTAATGT<br>TTTTATTTAAAATACCTCGCGAGTGGCAACACTGAAAATACCCATG<br>GAGCGGCGTAACCGTCGCACAGgatctaggtgaagatcctttttgata<br>atctcatgaccaaaatcccttaacgtgagttttcgttccactgagcgt<br>cagaccccgtagaaaagatcaaaggatcttcttgagatcctttttttc<br>tgcgcgtaatctgctgcttgcaaacaaaaaaaccaccgctaccagcgg<br>tggtttgtttgccggatcaagagctaccaactctttttccgaaggtaa<br>ctggcttcagcagagcgcagataccaaatactgtccttctagtgtagc<br>cgtagttaggccaccacttcaagaactctgtagcaccgcctacatacc<br>tcgctctgctaatcctgttaccagtggctgctgccagtggcgataagt<br>cgtgtcttaccgggttggactcaagacgatagttaccggataaggcgc<br>agcggtcgggctgaacggggggttcgtgcacacagcccagcttggagc<br>gaacgacctacaccgaactgagatacctacagcgtgagctatgagaaa<br>gcgccacgcttcccgaagggagaaaggcggacaggtatccggtaagcg<br>gcagggtcggaacaggagagcgcacgagggagcttccagggggaaacg<br>cctggtatctttatagtcctgtcgggtttcgccacctctgacttgagc<br>gtcgatttttgtgatgctcgtcaggggggcggagcctatggaaaaacg<br>ccagcaacgcggcagtggaacgTGCATTATGAATTAGTTACGCTAGGG<br>ATAACAGGGTAATATAGAACCCGAACGACCGAGCGCAGCGGCGGCCGC<br>GCTGATACCGCCGC | | |
| CCTCGCCGCAGTTAATTAAAGTCAGTGAGCGAGGAAGCGCGTAAC<br>TATAACGGTCCTAAGGTAGCGAATCCTGATGCGGTATTTTCTCCTT<br>ACGCATCTGTGCGGTATTTCACACCGCATAGATCGGCAAGTGCACA<br>AACAATACTTAAATAAATACTACTCAGTAATAACCTATTTCTTAGC<br>ATTTTTGACGAAATTTGCTATTTTGTTAGAGTCTTTTACACCATTTG<br>TCTCCACACCTCCGCTTACATCAACACCAATAACGCCATTTAATCT<br>AAGCGCATCACCAACATTTTCTGGCGTCAGTCCACCAGCTAACATA<br>AAATGTAAGCTTTCGGGGCTCTCTTGCCTTCCAACCCAGTCAGAAA<br>TCGAGTTCCAATCCAAAAGTTCACCTGTCCCACCTGCTTCTGAATC<br>AAACAAGGGAATAAACGAATGAGGTTTCTGTGAAGCTGCACTGAG<br>TAGTATGTTGCAGTCTTTTGGAAATACGAGTCTTTTAATAACTGGC<br>AAACCGAGGAACTCTTGGTATTCTTGCCACGACTCATCTCCATGCA<br>GTTGGACGATATCAATGCCGTAATCATTGACCAGAGCCAAAACAT<br>CCTCCTTAAGTTGATTACGAAACACGCCAACCAAGTATTTCGGAGT<br>GCCTGAACTATTTTTATATGCTTTTACAAGACTTGAAATTTTCCTTG<br>CAATAACCGGGTCAATTGTTCTCTTTCTATTGGGCACACATATAAT<br>ACCCAGCAAGTCAGCATCGGAATCTAGAGCACATTCTGCGGCCTCT<br>GTGCTCTGCAAGCCGCAAACTTTCACCAATGGACCAGAACTACCTG<br>TGAAATTAATAACAGACATACTCCAAGCTGCCTTTGTGTGCTTAAT<br>CACGTATACTCACGTGCTCAATAGTCACCAATGCCCTCCCTCTTGG<br>CCCTCTCCTTTTCTTTTTTCGACCGAATTAATTCTTAATCGGCAAAA<br>AAAGAAAAGCTCCGGATCAAGATTGTACGTAAGGTGACAAGCTAT<br>TTTTCAATAAAGAATATCTTCCACTACTGCCATCTGGCGTCATAAC<br>TGCAAAGTACACATATATTACGATGCTGTTCTATTAAATGCTTCCT<br>ATATTATATATATAGTAATGTCGTGATCTATGGTGCACTCTCAGTA<br>CAATCTGCTCTGATGCCGCATAGTTAAGCCAGCCCCGACACCCGCC<br>AACACCCGCTGACGCGCCCTGACGGGCTTGTCTGCTCCCGGCATCC<br>GCTTACAGACAAGCTGTGACCGTCTCCGGGAGCTGCATGTGTCAG<br>AGGTTTTCACCGTCATCACCGAAACGCGCGAGACGAAAGGGCCTC<br>GTGATACGCCTATTTTTATAGGTTAATGTCATGATAATAATGGTTT<br>CTTAGACGGATCGCTTGCCTGTAACTTACACGCGCCTCGTATCTTTT<br>AATGATGGAATAATTTGGGAATTTACTCTGTGTTTATTTATTTTTAT<br>GTTTTGTATTTGGATTTTAGAAAGTAAATAAAGAAGGTAGAAGAG<br>TTACGGAATGAAGAAAAAAAAATAAACAAAGGTTTAAAAAATTTC<br>AACAAAAAGCGTACTTTACATATATATTTATTAGACAAGAAAAGC<br>AGATTAAATAGATATACATTCGATTAACGATAAGTAAAATGTAAA<br>ATCACAGGATTTTCGTGTGTGGTCTTCTACACAGACAAGGTGAAAC<br>AATTCGGCATTAATACCTGAGAGCAGGAAGAGCAAGATAAAAGGT<br>AGTATTTGTTGGCGATCCCCCTAGAGTCTTTTACATCTTCGGAAAA<br>CAAAAACTATTTTTTCTTTAATTTCTTTTTTTACTTTCTATTTTTAAT<br>TTATATATTTATATTAAAAAATTTAAATTATAATTATTTTTATAGCA<br>CGTGATGAAAAGGACCCAGGTGGCACTTTTCGGGGAAATGTGCGC<br>GGAACCCCTATTTGTTTATTTTTCTAAATACATTCAAATATGTATCC<br>GCTCATGAGACAATAACCCTGATAAATGCTTCAATAATATTGAAA<br>AAGGAAGAGTATGAGTATTCAACATTTCCGTGTCGCCCTTATTCCC | pDW18 | SEQ. ID NO. 25 |

TABLE 1-continued example amino acid sequences of DRS-DRR enzymes, split DRS and DRR enzymes, and other nucleotide sequences.

| Sequence | Description | SEQ. ID NO. |
|---|---|---|
| TTTTTTGCGGCATTTTGCCTTCCTGTTTTTGCTCACCCAGAAACGCT | | |
| GGTGAAAGTAAAAGATGCTGAAGATCAGTTGGGACGCGTAGTCTA | | |
| GACCAGCCAGGACAGAAATGCCTCGACTTCGCTGCTACCCAAGGT | | |
| TGCCGGGTGACGCACACCGTGGAAACGGATGAAGGCACGAACCCA | | |
| GTGGACATAAGCCTGTTCGGTTCGTAAGCTGTAATGCAAGTAGCGT | | |
| ATGCGCTCACGCAACTGGTCCAGAACCTTGACCGAACGCAGCGGT | | |
| GGTAACGGCGCAGTGGCGGTTTTCATGGCTTGTTATGACTGTTTTT | | |
| TTGGGGTACAGTCTATGCCTCGGGCATCCAAGCAGCAAGCGCGTT | | |
| ACGCCGTGGGTCGATGTTTGATGTTATGGAGCAGCAACGATGTTAC | | |
| GCAGCAGGGCAGTCGCCCTAAAACAAAGTTAAACATTATGAGGGA | | |
| AGCGGTGATCGCCGAAGTATCGACTCAACTATCAGAGGTAGTTGG | | |
| CGCCATCGAGCGCCATCTCGAACCGACGTTGCTGGCCGTACATTTG | | |
| TACGGCTCCGCAGTGGATGGCGGCCTGAAGCCACACAGTGATATT | | |
| GATTTGCTGGTTACGGTGACCGTAAGGCTTGATGAAACAACGCGG | | |
| CGAGCTTTGATCAACGACCTTTTGGAAACTTCGGCTTCCCCTGGAG | | |
| AGAGCGAGATTCTCCGCGCTGTAGAAGTCACCATTGTTGTGCACGA | | |
| CGACATCATTCCGTGGCGTTATCCAGCTAAGCGCGAACTGCAATTT | | |
| GGAGAATGGCAGCGCAATGACATTCTTGCAGGTATCTTCGAGCCA | | |
| GCCACGATCGACATTGATCTGGCTATCTTGCTGACAAAAGCAAGA | | |
| GAACATAGCGTTGCCTTGGTAGGTCCAGCGGCGGAGGAACTCTTT | | |
| GATCCGGTTCCTGAACAGGATCTATTTGAGGCGCTAAATGAAACCT | | |
| TAACGCTATGGAACTCGCCGCCCGACTGGGCTGGCGATGAGCGAA | | |
| ATGTAGTGCTTACGTTGTCCCGCATTTGGTACAGCGCAGTAACCGG | | |
| CAAAATCGCGCCGAAGGATGTCGCTGCCGGCTGGGCAATGGAGCG | | |
| CCTGCCGGCCCAGTATCAGCCCGTCATACTTGAAGCTAGACAGGCT | | |
| TATCTTGGACAAGAAGAAGATCGCTTGGCCTCGCGCGCAGATCAG | | |
| TTGGAAGAATTTGTCCACTACGTGAAAGGCGAGATCACCAAGGTA | | |
| GTCGGCAAATAACCCTCGAGCATTCAAGGCGCCTTGATTATTTGAC | | |
| GTGGTTTGATGGCCTCCACGCACGTTGTGATATGTAGATGAGAGCG | | |
| TTGGTTGGTGGATCAAGCCCACGCGTAGGCAATCCTCGAGCAGAT | | |
| CCGCCAGGCGTGTATATATAGCGTGGATGGCCAGGCAACTTTAGT | | |
| GCTGACACATACAGGCATATATATATGTGTGCGACGACACATGAT | | |
| CATATGGCATGCATGTGCTCTGTATGTATATAAAACTCTTGTTTTCT | | |
| TCTTTTCTCTAAATATTCTTTCCTTATACATTAGGACCTTTGCAGCA | | |
| TAAATTACTATACTTCTATAGACACACAAACACAAATACACACACT | | |
| AAATTAATAATGGAACTTCAGTACTTCTCCTATTTTCAACCCACTTC | | |
| ATCTGTCGTAGCCCTACTACTAGCACTAGTGAGTATTTTATTTAGC | | |
| GTAGTTGTTTTGAGGAAGACTTTCAGTAACAATTACTCCAGCCCCG | | |
| CGTCAAGTACGGAAACCGCTGTGCTGTGTCATCAGAGGCAACAGA | | |
| GTTGCGCCCTACCTATCAGCGGCCTTCTTCACGTGTTCATGAATAA | | |
| GAACGGCCTGATTCATGTCACCTTGGGAAATATGGCTGACAAATAT | | |
| GGCCCTATCTTCAGTTTTCCGACAGGCAGCCACCGTACTTTAGTAG | | |
| TCAGTTCCTGGGAAATGGTGAAAGAGTGTTTCACCGGTAATAACG | | |
| ACACGGCATTCTCCAACAGACCAATCCCTTTGGCTTTTCAAACCAT | | |
| ATTCTACGCCTGTGGCGGCATTGATTCTTACGGTTTAAGTAGTGTC | | |
| CCGTATGGTAAATACTGGAGGGAGTTGAGAAAGGTGTGTGTTCAC | | |
| AACCTGCTGAGTAATCAGCAATTGCTGAAGTTCAGACATCTTATAA | | |
| TCTCCCAAGTGGATACGTCTTTTAACAAGTTGTATGAGCTGTGTAA | | |
| GAACTCTGAAGATAATCAAGGTATGGTAAGGATGGATGATTGGCT | | |
| AGCTCAACTTTCCTTTAACGTCATCGGTAGGATCGTTTGCGGATTC | | |
| CAGTCTGACCCAAAGACGGGTGCACCTTCAAGGGTAGAACAGTTT | | |
| AAGGAAGTCATAAATGAGGCGTCATATTTTATGTCAACAAGTCCA | | |
| GTCTCCGATAACGTACCAATGTTGGGATGGATCGACCAATTGACCG | | |
| GTCTGACGAGGAACATGAAGCATTGTGGGAAGAAGCTTGACTTAG | | |
| TAGTGGAGTCAATTATCAAGGACCATAGGCAAAAGAGACGTTTTT | | |
| CACGTACAAAAGGTGGCGATGAGAAGGATGACGAACAGGACGAC | | |
| TTTATTGATATTTGCTTGAGCATCATGGAGCAGCCACAGTTGCCCG | | |
| GGAACAATTCTCCCCCTCAAATTCCGATCAAATCTATCGTGCTAGA | | |
| CATGATTGGGGGTGGTACCGACACTACGAAACTTACAACCATATG | | |
| GACCCTATCACTTTTGTTGAACAATCCTCACGTGTTAGATAAAGCT | | |
| AAACAAGAGGTCGACGCTCACTTTCGTAAAAAGAGAAGATCAACA | | |
| GATGACGCAGCAGCGGCAGTCGTTGATTTTGACGACATAAGAAAT | | |
| TTAGTATACATCCAAGCCATCATTAAAGAAAGTATGAGGCTTTATC | | |
| CAGCCAGCCCGGTGGTTGAGCGTCTTTCCGGCGAGGATTGCGTTGT | | |
| TGGAGGTTTTCACGTGCCTGCTGGTACGAGACTATGGGCTAACGTT | | |
| TGGAAGATGCAAAGAGATCCCAAAGTTTGGGACGATCCTCTAGTA | | |
| TTCAGACCTGAAAGGTTTTTGAGCGACGAGCAAAAGATGGTAGAC | | |
| GTTCGTGGCCAAAACTATGAACTTCTGCCATTCGGCGCAGGAAGA | | |
| AGAATCTGTCCAGGCGTTTCCTTTAGTCTTGACCTTATGCAACTTGT | | |
| CCTAACCAGGTTAATCCTAGAGTTCGAAATGAAGTCCCCGTCCGGC | | |
| AAGGTAGATATGACCGCAACTCCAGGACTAATGTCTTACAAGGTG | | |
| GTTCCATTGGACATATTGCTGACTCACCGTCGTATCAAGTCATGCG | | |
| TTCAATTGGCGTCTTCTGAACGTGATATGGAAAGTTCTGGGGTGCC | | |
| TGTGATCACATTGTCCTCAGGTAAAGTAATGCCCGTACTGGGCATG | | |

TABLE 1-continued example amino acid sequences of DRS-DRR enzymes, split DRS and DRR enzymes, and other nucleotide sequences.

| Sequence | Description | SEQ. ID NO. |
|---|---|---|
| GGAACCTTCGAAAAGGTGGGTAAGGGGTCTGAACGTGAGCGTTTA<br>GCCATTCTTAAAGCGATCGAAGTTGGTTACCGTTACTTTGATACCG<br>CAGCGGCATATGAAACGGAAGAAGTTCTAGGGGAAGCCATTGCTG<br>AAGCTTTACAATTGGGTCTGATAGAGAGCCGTGACGAGCTGTTCAT<br>CAGCTCAATGCTTTGGTGCACCGACGCACATCCAGACCGTGTGCTA<br>CTTGCTCTGCAAAACAGTCTGAGAAATCTAAAACTTGAATATCTAG<br>ACCTATATATGTTGCCGTTTCCTGCCAGCCTTAAGCCGGGCAAAAT<br>TACGATGGATATTCCTGAGGAGGATATTTGCCGTATGGATTATCGT<br>TCAGTCTGGAGCGCCATGGAAGAGTGTCAAAACTTAGGATTTACT<br>AAAAGTATTGGTGTAAGCAACTTTTCTTGCAAGAAATTACAAGAAT<br>TAATGGCCACTGCAAATATCCCGCCCGCGGTAAATCAAGTAGAGA<br>TGTCACCAGCTTTCCAACAGAAAAAACTGAGGGAATATTGTAACG<br>CAAACAACATATTGGTATCCGCAGTAAGCATTCTGGGATCAAACG<br>GGACGCCCTGGGGTAGTAATGCTGTTCTTGGAAGCGAAGTTTTGAA<br>ACAGATCGCGATGGCGAAAGGCAAAAGCGTTGCGCAAGTCAGTAT<br>GAGGTGGGTCTATGAGCAGGGCGCGTCTTTAGTAGTCAAGAGTTTC<br>TCTGAAGAACGTTTAAGAGAAAACCTGAATATTTTTGACTGGGAG<br>CTTACGAAAGAAGACAATGAGAAGATAGGCGAAATCCCGCAATGT<br>AGAATCCTTACTGCGTACTTCCTTGTCTCCCCGAACGGCCCGTTTA<br>AATCTCAGGAAGAGCTTTGGGATGACAAGGCAtaaACAGGCCCCTTT<br>TCCTTTGTCGATATCATGTAATTAGTTATGTCACGCTTACATTCACG<br>CCCTCCTCCCACATCCGCTCTAACCGAAAAGGAAGGAGTTAGACA<br>ACCTGAAGTCTAGGTCCCTATTTATTTTTTTTAATAGTTATGTTAGT<br>ATTAAGAACGTTATTTATATTTCAAATTTTTCTTTTTTTTCTGTACA<br>AACGCGTGTACGCATGTAACATTATACTGAAAACCTTGCTTGAGAA<br>GGTTTTGGGACGCTCGAAGGCTTTAATTTGTAATCATTATCACTTT<br>ACGGGTCCTTTCCGGTGATCCGACAGGTTACGGGGCGGCGACCTC<br>GCGGGTTTTCGCTATTTATGAAAATTTTCCGGTTTAAGGCGTTTCCG<br>TTCTTCTTCGTCATAACTTAATGTTTTTATTTAAAATACCTCGCGAG<br>TGGCAACACTGAAAATACCCATGGAGCGGCGTAACCGTCGCACAG<br>gatctaggtgaagatcctttttgataatctcatgaccaaaatccctta<br>acgtgagttttcgttccactgagcgtcagaccccgtagaaaagatcaa<br>aggatcttcttgagatcctttttttctgcgcgtaatctgctgcttgca<br>aacaaaaaaaccaccgctaccagcggtggtttgtttgccggatcaaga<br>gctaccaactctttttccgaaggtaactggcttcagcagagcgcagat<br>accaaatactgtccttctagtgtagccgtagttaggccaccacttcaa<br>gaactctgtagcaccgcctacatacctcgctctgctaatcctgttacc<br>agtggctgctgccagtggcgataagtcgtgtcttaccgggttggactc<br>aagacgatagttaccggataaggcgcagcggtcgggctgaacgggggg<br>ttcgtgcacacagcccagcttggagcgaacgacctacaccgaactgag<br>atacctacagcgtgagctatgagaaagcgccacgcttcccgaagggag<br>aaaggcggacaggtatccggtaagcggcagggtcggaacaggagagcg<br>cacgagggagcttccagggggaaacgcctggtatctttatagtcctgt<br>cgggtttcgccacctctgacttgagcgtcgatttttgtgatgctcgtc<br>aggggggcggagcctatggaaaaacgccagcaacgcggcagtggaacg<br>TGCATTATGAATTAGTTACGCTAGGGATAACAGGGTAATATAGAACCC<br>GAACGACCGAGCGCAGCGGCGGCCGCGCTGATACCGCCGC | | |
| CCTCGCCGCAGTTAATTAAAGTCAGTGAGCGAGGAAGCGCGTAAC<br>TATAACGGTCCTAAGGTAGCGAATCCTGATGCGGTATTTTCTCCTT<br>ACGCATCTGTGCGGTATTTCACACCGCATAGATCGGCAAGTGCACA<br>AACAATACTTAAATAAATACTACTCAGTAATAACCTATTTCTTAGC<br>ATTTTTGACGAAATTTGCTATTTTGTTAGAGTCTTTTACACCATTTG<br>TCTCCACACCTCCGCTTACATCAACACCAATAACGCCATTTAATCT<br>AAGCGCATCACCAACATTTTCTGGCGTCAGTCCACCAGCTAACATA<br>AAATGTAAGCTTTCGGGGCTCTCTTGCCTTCCAACCCAGTCAGAAA<br>TCGAGTTCCAATCCAAAAGTTCACCTGTCCCACCTGCTTCTGAATC<br>AAACAAGGGAATAAACGAATGAGGTTTCTGTGAAGCTGCACTGAG<br>TAGTATGTTGCAGTCTTTTGGAAATACGAGTCTTTTAATAACTGGC<br>AAACCGAGGAACTCTTGGTATTCTTGCCACGACTCATCTCCATGCA<br>GTTGGACGATATCAATGCCGTAATCATTGACCAGAGCCAAAACAT<br>CCTCCTTAAGTTGATTACGAAACACGCCAACCAAGTATTTCGGAGT<br>GCCTGAACTATTTTTATATGCTTTTACAAGACTTGAAATTTTCCTTG<br>CAATAACCGGGTCAATTGTTCTCTTTCTATTGGGCACACATATAAT<br>ACCCAGCAAGTCAGCATCGGAATCTAGAGCACATTCTGCGGCCTCT<br>GTGCTCTGCAAGCCGCAAACTTTCACCAATGGACCAGAACTACCTG<br>TGAAATTAATAACAGACATACTCCAAGCTGCCTTTGTGTGCTTAAT<br>CACGTATACTCACGTGCTCAATAGTCACCAATGCCCTCCCTCTTGG<br>CCCTCTCCTTTTCTTTTTTCGACCGAATTAATTCTTAATCGGCAAAA<br>AAAGAAAAGCTCCGGATCAAGATTGTACGTAAGGTGACAAGCTAT<br>TTTTCAATAAAGAATATCTTCCACTACTGCCATCTGGCGTCATAAC<br>TGCAAAGTACACATATATTACGATGCTGTTCTATTAAATGCTTCCT<br>ATATTATATATATAGTAATGTCGTGATCTATGGTGCACTCTCAGTA<br>CAATCTGCTCTGATGCCGCATAGTTAAGCCAGCCCCGACACCCGCC | pDW21 | SEQ. ID NO. 26 |

TABLE 1-continued example amino acid sequences of DRS-DRR enzymes, split DRS and DRR enzymes, and other nucleotide sequences.

| Sequence | Description | SEQ. ID NO. |
|---|---|---|
| AACACCCGCTGACGCGCCCTGACGGGCTTGTCTGCTCCCGGCATCC | | |
| GCTTACAGACAAGCTGTGACCGTCTCCGGGAGCTGCATGTGTCAG | | |
| AGGTTTTCACCGTCATCACCGAAACGCGCGAGACGAAAGGGCCTC | | |
| GTGATACGCCTATTTTTATAGGTTAATGTCATGATAATAATGGTTT | | |
| CTTAGACGGATCGCTTGCCTGTAACTTACACGCGCCTCGTATCTTTT | | |
| AATGATGGAATAATTTGGGAATTTACTCTGTGTTTATTTATTTTTAT | | |
| GTTTTGTATTTGGATTTTAGAAAGTAAATAAAGAAGGTAGAAGAG | | |
| TTACGGAATGAAGAAAAAAAAATAAACAAAGGTTTAAAAAATTTC | | |
| AACAAAAAGCGTACTTTACATATATATTTATTAGACAAGAAAAGC | | |
| AGATTAAATAGATATACATTCGATTAACGATAAGTAAAATGTAAA | | |
| ATCACAGGATTTTCGTGTGTGGTCTTCTACACAGACAAGGTGAAAC | | |
| AATTCGGCATTAATACCTGAGAGCAGGAAGAGCAAGATAAAAGGT | | |
| AGTATTTGTTGGCGATCCCCCTAGAGTCTTTTACATCTTCGGAAAA | | |
| CAAAAACTATTTTTTCTTTAATTTCTTTTTTTACTTTCTATTTTTAAT | | |
| TTATATATTTATATTAAAAAATTTAAATTATAATTATTTTTATAGCA | | |
| CGTGATGAAAAGGACCCAGGTGGCACTTTTCGGGGAAATGTGCGC | | |
| GGAACCCCTATTTGTTTATTTTTCTAAATACATTCAAATATGTATCC | | |
| GCTCATGAGACAATAACCCTGATAAATGCTTCAATAATATTGAAA | | |
| AAGGAAGAGTATGAGTATTCAACATTTCCGTGTCGCCCTTATTCCC | | |
| TTTTTTGCGGCATTTTGCCTTCCTGTTTTTGCTCACCCAGAAACGCT | | |
| GGTGAAAGTAAAAGATGCTGAAGATCAGTTGGGACGCGTAGTCTA | | |
| GACCAGCCAGGACAGAAATGCCTCGACTTCGCTGCTACCCAAGGT | | |
| TGCCGGGTGACGCACACCGTGGAAACGGATGAAGGCACGAACCCA | | |
| GTGGACATAAGCCTGTTCGGTTCGTAAGCTGTAATGCAAGTAGCGT | | |
| ATGCGCTCACGCAACTGGTCCAGAACCTTGACCGAACGCAGCGGT | | |
| GGTAACGGCGCAGTGGCGGTTTTCATGGCTTGTTATGACTGTTTTT | | |
| TTGGGGTACAGTCTATGCCTCGGGCATCCAAGCAGCAAGCGCGTT | | |
| ACGCCGTGGGTCGATGTTTGATGTTATGGAGCAGCAACGATGTTAC | | |
| GCAGCAGGGCAGTCGCCCTAAAACAAAGTTAAACATTATGAGGGA | | |
| AGCGGTGATCGCCGAAGTATCGACTCAACTATCAGAGGTAGTTGG | | |
| CGCCATCGAGCGCCATCTCGAACCGACGTTGCTGGCCGTACATTTG | | |
| TACGGCTCCGCAGTGGATGGCGGCCTGAAGCCACACAGTGATATT | | |
| GATTTGCTGGTTACGGTGACCGTAAGGCTTGATGAAACAACGCGG | | |
| CGAGCTTTGATCAACGACCTTTTGGAAACTTCGGCTTCCCCTGGAG | | |
| AGAGCGAGATTCTCCGCGCTGTAGAAGTCACCATTGTTGTGCACGA | | |
| CGACATCATTCCGTGGCGTTATCCAGCTAAGCGCGAACTGCAATTT | | |
| GGAGAATGGCAGCGCAATGACATTCTTGCAGGTATCTTCGAGCCA | | |
| GCCACGATCGACATTGATCTGGCTATCTTGCTGACAAAAGCAAGA | | |
| GAACATAGCGTTGCCTTGGTAGGTCCAGCGGCGGAGGAACTCTTT | | |
| GATCCGGTTCCTGAACAGGATCTATTTGAGGCGCTAAATGAAACCT | | |
| TAACGCTATGGAACTCGCCGCCCGACTGGGCTGGCGATGAGCGAA | | |
| ATGTAGTGCTTACGTTGTCCCGCATTTGGTACAGCGCAGTAACCGG | | |
| CAAAATCGCGCCGAAGGATGTCGCTGCCGGCTGGGCAATGGAGCG | | |
| CCTGCCGGCCCAGTATCAGCCCGTCATACTTGAAGCTAGACAGGCT | | |
| TATCTTGGACAAGAAGAAGATCGCTTGGCCTCGCGCGCAGATCAG | | |
| TTGGAAGAATTTGTCCACTACGTGAAAGGCGAGATCACCAAGGTA | | |
| GTCGGCAAATAACCCTCGAGCATTCAAGGCGCCTTGATTATTTGAC | | |
| GTGGTTTGATGGCCTCCACGCACGTTGTGATATGTAGATGAGAGCG | | |
| TTGGTTGGTGGATCAAGCCCACGCGTAGGCAATCCTCGAGCAGAT | | |
| CCGCCAGGCGTGTATATATAGCGTGGATGGCCAGGCAACTTTAGT | | |
| GCTGACACATACAGGCATATATATATGTGTGCGACGACACATGAT | | |
| CATATGGCATGCATGTGCTCTGTATGTATATAAAACTCTTGTTTTCT | | |
| TCTTTTCTCTAAATATTCTTTCCTTATACATTAGGACCTTTGCAGCA | | |
| TAAATTACTATACTTCTATAGACACACAAACACAAATACACACACT | | |
| AAATTAATAATGGAACTTCAGTACTTCTCCTATTTTCAACCCACTTC | | |
| ATCTGTCGTAGCCCTACTACTAGCACTAGTGAGTATTTTATTTAGC | | |
| GTAGTTGTTTTGAGGAAGACTTTCAGTAACAATTACTCCAGCCCCG | | |
| CGTCAAGTACGGAAACCGCTGTGCTGTGTCATCAGAGGCAACAGA | | |
| GTTGCGCCCTACCTATCAGCGGCCTTCTTCACGTGTTCATGAATAA | | |
| GAACGGCCTGATTCATGTCACCTTGGGAAATATGGCTGACAAATAT | | |
| GGCCCTATCTTCAGTTTTCCGACAGGCAGCCACCGTACTTTAGTAG | | |
| TCAGTTCCTGGGAAATGGTGAAAGAGTGTTTCACCGGTAATAACG | | |
| ACACGGCATTCTCCAACAGACCAATCCCTTTGGCTTTTCAAACCAT | | |
| ATTCTACGCCTGTGGCGGCATTGATTCTTACGGTTTAAGTAGTGTC | | |
| CCGTATGGTAAATACTGGAGGGAGTTGAGAAAGGTGTGTGTTCAC | | |
| AACCTGCTGAGTAATCAGCAATTGCTGAAGTTCAGACATCTTATAA | | |
| TCTCCCAAGTGGATACGTCTTTTAACAAGTTGTATGAGCTGTGTAA | | |
| GAACTCTGAAGATAATCAAGGTATGGTAAGGATGGATGATTGGCT | | |
| AGCTCAACTTTCCTTTAACGTCATCGGTAGGATCGTTTGCGGATTC | | |
| CAGTCTGACCCAAAGACGGGTGCACCTTCAAGGGTAGAACAGTTT | | |
| AAGGAAGTCATAAATGAGGCGTCATATTTTATGTCAACAAGTCCA | | |
| GTCTCCGATAACGTACCAATGTTGGGATGGATCGACCAATTGACCG | | |
| GTCTGACGAGGAACATGAAGCATTGTGGGAAGAAGCTTGACTTAG | | |
| TAGTGGAGTCAATTATCAAGGACCATAGGCAAAAGAGACGTTTTT | | |

TABLE 1-continued example amino acid sequences of DRS-DRR enzymes, split DRS and DRR enzymes, and other nucleotide sequences.

| Sequence | Description | SEQ. ID NO. |
|---|---|---|
| CACGTACAAAAGGTGGCGATGAGAAGGATGACGAACAGGACGAC<br>TTTATTGATATTTGCTTGAGCATCATGGAGCAGCCACAGTTGCCCG<br>GGAACAATTCTCCCCCTCAAATTCCGATCAAATCTATCGTGCTAGA<br>CATGATTGGGGGTGGTACCGACACTACGAAACTTACAACCATATG<br>GACCCTATCACTTTTGTTGAACAATCCTCACGTGTTAGATAAAGCT<br>AAACAAGAGGTCGACGCTCACTTTCGTAAAAAGAGAAGATCAACA<br>GATGACGCAGCAGCGGCAGTCGTTGATTTTGACGACATAAGAAAT<br>TTAGTATACATCCAAGCCATCATTAAAGAAAGTATGAGGCTTTATC<br>CAGCCAGCCCGGTGGTTGAGCGTCTTTCCGGCGAGGATTGCGTTGT<br>TGGAGGTTTTCACGTGCCTGCTGGTACGAGACTATGGGCTAACGTT<br>TGGAAGATGCAAAGAGATCCCAAAGTTTGGGACGATCCTCTAGTA<br>TTCAGACCTGAAAGGTTTTTGAGCGACGAGCAAAAGATGGTAGAC<br>GTTCGTGGCCAAAACTATGAACTTCTGCCATTCGGCGCAGGAAGA<br>AGAATCTGTCCAGGCGTTTCCTTTAGTCTTGACCTTATGCAACTTGT<br>CCTAACCAGGTTAATCCTAGAGTTCGAAATGAAGTCCCCGTCCGGC<br>AAGGTAGATATGACCGCAACTCCAGGACTAATGTCTTACAAGGTG<br>GTTCCATTGGACATATTGCTGACTCACCGTCGTATCAAGTCATGCG<br>TTCAATTGGCGTCTTCTGAACGTGATtaaGCGAATTTCTTATGATTTA<br>TGATTTTTATTATTAAATAAGTTATAAAAAAAATAAGTGTATACAA<br>ATTTTAAAGTGACTCTTAGGTTTTAAAACGAAAATTCTTATTCTTG<br>AGTAACTCTTTCCTGTAGGTCAGGTTGCTTTCTCAGGTACATAGCTT<br>CAAAATGTTTCTACTCCTTTTTTACTCTTCCAGATTTTCTCGGACTC<br>CGCGCATCGCCGTACCACTTCAAAACACCCAAGCACAGCATACTA<br>AATTTCCCCTCTTTCTTCCTCTAGGGTGTCGTTAATTACCCGTACTA<br>AAGGTTTGGAAAAGAAAAAAGAGACCGCCTCGTTTCTTTTTCTTCG<br>TCGAAAAAGGCAATAAAAATTTTTATCACGTTTCTTTTTCTTGAAA<br>ATTTTTTTTTTTGATTTTTTTCTCTTTCGATGACCTCCCATTGATATT<br>TAAGTTAATAAACGGTCTTCAATTTCTCAAGTTTCAGTTTCATTTTT<br>CTTGTTCTATTACAACTTTTTTTACTTCTTGCTCATTAGAAAGAAAG<br>CATAGCAATCTAATCTAAGTTTTAATTACAAAATGGAAAGTTCTGG<br>GGTGCCTGTGATCACATTGTCCTCAGGTAAAGTAATGCCCGTACTG<br>GGCATGGGAACCTTCGAAAAGGTGGGTAAGGGGTCTGAACGTGAG<br>CGTTTAGCCATTCTTAAAGCGATCGAAGTTGGTTACCGTTACTTTG<br>ATACCGCAGCGGCATATGAAACGGAAGAAGTTCTAGGGGAAGCCA<br>TTGCTGAAGCTTTACAATTGGGTCTGATAGAGAGCCGTGACGAGCT<br>GTTCATCAGCTCAATGCTTTGGTGCACCGACGCACATCCAGACCGT<br>GTGCTACTTGCTCTGCAAAACAGTCTGAGAAATCTAAAACTTGAAT<br>ATCTAGACCTATATATGTTGCCGTTTCCTGCCAGCCTTAAGCCGGG<br>CAAAATTACGATGGATATTCCTGAGGAGGATATTTGCCGTATGGAT<br>TATCGTTCAGTCTGGAGCGCCATGGAAGAGTGTCAAAACTTAGGA<br>TTTACTAAAAGTATTGGTGTAAGCAACTTTTCTTGCAAGAAATTAC<br>AAGAATTAATGGCCACTGCAAATATCCCGCCCGCGGTAAATCAAG<br>TAGAGATGTCACCAGCTTTCCAACAGAAAAAACTGAGGGAATATT<br>GTAACGCAAACAACATATTGGTATCCGCAGTAAGCATTCTGGGAT<br>CAAACGGGACGCCCTGGGGTAGTAATGCTGTTCTTGGAAGCGAAG<br>TTTTGAAACAGATCGCGATGGCGAAAGGCAAAAGCGTTGCGCAAG<br>TCAGTATGAGGTGGGTCTATGAGCAGGGCGCGTCTTTAGTAGTCAA<br>GAGTTTCTCTGAAGAACGTTTAAGAGAAAACCTGAATATTTTTGAC<br>TGGGAGCTTACGAAAGAAGACAATGAGAAGATAGGCGAAATCCC<br>GCAATGTAGAATCCTTACTGCGTACTTCCTTGTCTCCCCGAACGGC<br>CCGTTTAAATCTCAGGAAGAGCTTTGGGATGACAAGGCAtaaACAG<br>GCCCCTTTTCCTTTGTCGATATCATGTAATTAGTTATGTCACGCTTA<br>CATTCACGCCCTCCTCCCACATCCGCTCTAACCGAAAAGGAAGGA<br>GTTAGACAACCTGAAGTCTAGGTCCCTATTTATTTTTTTTAATAGTT<br>ATGTTAGTATTAAGAACGTTATTTATATTTCAAATTTTTCTTTTTTTT<br>CTGTACAAACGCGTGTACGCATGTAACATTATACTGAAAACCTTGC<br>TTGAGAAGGTTTTGGGACGCTCGAAGGCTTTAATTTGTAATCATTA<br>TCACTTTACGGGTCCTTTCCGGTGATCCGACAGGTTACGGGGCGGC<br>GACCTCGCGGGTTTTCGCTATTTATGAAAATTTTCCGGTTTAAGGC<br>GTTTCCGTTCTTCTTCGTCATAACTTAATGTTTTTATTTAAAATACC<br>TCGCGAGTGGCAACACTGAAAATACCCATGGAGCGGCGTAACCGT<br>CGCACAGgatctaggtgaagatcctttttgataatctcatgaccaaaa<br>tcccttaacgtgagttttcgttccactgagcgtcagaccccgtagaaa<br>agatcaaaggatcttcttgagatcctttttttctgcgcgtaatctgct<br>gcttgcaaacaaaaaaaccaccgctaccagcggtggtttgtttgccgg<br>atcaagagctaccaactctttttccgaaggtaactggcttcagcagag<br>cgcagataccaaatactgtccttctagtgtagccgtagttaggccacc<br>acttcaagaactctgtagcaccgcctacatacctcgctctgctaatcc<br>tgttaccagtggctgctgccagtggcgataagtcgtgtcttaccgggt<br>tggactcaagacgatagttaccggataaggcgcagcggtcgggctgaa<br>cggggggttcgtgcacacagcccagcttggagcgaacgacctacaccg<br>aactgagatacctacagcgtgagctatgagaaagcgccacgcttcccg<br>aagggagaaaggcggacaggtatccggtaagcggcagggtcggaacag<br>gagagcgcacgagggagcttccagggggaaacgcctggtatctttata | | |

TABLE 1-continued example amino acid sequences of DRS-DRR enzymes, split DRS and DRR enzymes, and other nucleotide sequences.

| Sequence | Description | SEQ. ID NO. |
|---|---|---|
| gtcctgtcgggtttcgccacctctgacttgagcgtcgatttttgtgat<br>gctcgtcaggggggcggagcctatggaaaaacgccagcaacgcggcag<br>tggaacgTGCATTATGAATTAGTTACGCTAGGGATAACAGGGTAATAT<br>AGAACCCGAACGACCGAGCGCAGCGGCGGCCGCGCTGATACCGCCGC | | |
| CCTCGCCGCAGTTAATTAAAGTCAGTGAGCGAGGAAGCGCGTAAC<br>TATAACGGTCCTAAGGTAGCGAATCCTGATGCGGTATTTTCTCCTT<br>ACGCATCTGTGCGGTATTTCACACCGCATAGATCGGCAAGTGCACA<br>AACAATACTTAAATAAATACTACTCAGTAATAACCTATTTCTTAGC<br>ATTTTTGACGAAATTTGCTATTTTGTTAGAGTCTTTTACACCATTTG<br>TCTCCACACCTCCGCTTACATCAACACCAATAACGCCATTTAATCT<br>AAGCGCATCACCAACATTTTCTGGCGTCAGTCCACCAGCTAACATA<br>AAATGTAAGCTTTCGGGGCTCTCTTGCCTTCCAACCCAGTCAGAAA<br>TCGAGTTCCAATCCAAAAGTTCACCTGTCCCACCTGCTTCTGAATC<br>AAACAAGGGAATAAACGAATGAGGTTTCTGTGAAGCTGCACTGAG<br>TAGTATGTTGCAGTCTTTTGGAAATACGAGTCTTTTAATAACTGGC<br>AAACCGAGGAACTCTTGGTATTCTTGCCACGACTCATCTCCATGCA<br>GTTGGACGATATCAATGCCGTAATCATTGACCAGAGCCAAAACAT<br>CCTCCTTAAGTTGATTACGAAACACGCCAACCAAGTATTTCGGAGT<br>GCCTGAACTATTTTTATATGCTTTTACAAGACTTGAAATTTTCCTTG<br>CAATAACCGGGTCAATTGTTCTCTTTCTATTGGGCACACATATAAT<br>ACCCAGCAAGTCAGCATCGGAATCTAGAGCACATTCTGCGGCCTCT<br>GTGCTCTGCAAGCCGCAAACTTTCACCAATGGACCAGAACTACCTG<br>TGAAATTAATAACAGACATACTCCAAGCTGCCTTTGTGTGCTTAAT<br>CACGTATACTCACGTGCTCAATAGTCACCAATGCCCTCCCTCTTGG<br>CCCTCTCCTTTTCTTTTTTCGACCGAATTAATTCTTAATCGGCAAAA<br>AAAGAAAAGCTCCGGATCAAGATTGTACGTAAGGTGACAAGCTAT<br>TTTTCAATAAAGAATATCTTCCACTACTGCCATCTGGCGTCATAAC<br>TGCAAAGTACACATATATTACGATGCTGTTCTATTAAATGCTTCCT<br>ATATTATATATATAGTAATGTCGTGATCTATGGTGCACTCTCAGTA<br>CAATCTGCTCTGATGCCGCATAGTTAAGCCAGCCCCGACACCCGCC<br>AACACCCGCTGACGCGCCCTGACGGGCTTGTCTGCTCCCGGCATCC<br>GCTTACAGACAAGCTGTGACCGTCTCCGGGAGCTGCATGTGTCAG<br>AGGTTTTCACCGTCATCACCGAAACGCGCGAGACGAAAGGGCCTC<br>GTGATACGCCTATTTTTATAGGTTAATGTCATGATAATAATGGTTT<br>CTTAGACGGATCGCTTGCCTGTAACTTACACGCGCCTCGTATCTTTT<br>AATGATGGAATAATTTGGGAATTTACTCTGTGTTTATTTATTTTTAT<br>GTTTTGTATTTGGATTTTAGAAAGTAAATAAAGAAGGTAGAAGAG<br>TTACGGAATGAAGAAAAAAAAATAAACAAAGGTTTAAAAAATTTC<br>AACAAAAAGCGTACTTTACATATATATTTATTAGACAAGAAAAGC<br>AGATTAAATAGATATACATTCGATTAACGATAAGTAAAATGTAAA<br>ATCACAGGATTTTCGTGTGTGGTCTTCTACACAGACAAGGTGAAAC<br>AATTCGGCATTAATACCTGAGAGCAGGAAGAGCAAGATAAAAGGT<br>AGTATTTGTTGGCGATCCCCCTAGAGTCTTTTACATCTTCGGAAAA<br>CAAAAACTATTTTTTCTTTAATTTCTTTTTTTACTTTCTATTTTTAAT<br>TTATATATTTATATTAAAAAATTTAAATTATAATTATTTTTATAGCA<br>CGTGATGAAAAGGACCCAGGTGGCACTTTTCGGGGAAATGTGCGC<br>GGAACCCCTATTTGTTTATTTTTCTAAATACATTCAAATATGTATCC<br>GCTCATGAGACAATAACCCTGATAAATGCTTCAATAATATTGAAA<br>AAGGAAGAGTATGAGTATTCAACATTTCCGTGTCGCCCTTATTCCC<br>TTTTTTGCGGCATTTTGCCTTCCTGTTTTTGCTCACCCAGAAACGCT<br>GGTGAAAGTAAAAGATGCTGAAGATCAGTTGGGACGCGTAGTCTA<br>GACCAGCCAGGACAGAAATGCCTCGACTTCGCTGCTACCCAAGGT<br>TGCCGGGTGACGCACACCGTGGAAACGGATGAAGGCACGAACCCA<br>GTGGACATAAGCCTGTTCGGTTCGTAAGCTGTAATGCAAGTAGCGT<br>ATGCGCTCACGCAACTGGTCCAGAACCTTGACCGAACGCAGCGGT<br>GGTAACGGCGCAGTGGCGGTTTTCATGGCTTGTTATGACTGTTTTT<br>TTGGGGTACAGTCTATGCCTCGGGCATCCAAGCAGCAAGCGCGTT<br>ACGCCGTGGGTCGATGTTTGATGTTATGGAGCAGCAACGATGTTAC<br>GCAGCAGGGCAGTCGCCCTAAAACAAAGTTAAACATTATGAGGGA<br>AGCGGTGATCGCCGAAGTATCGACTCAACTATCAGAGGTAGTTGG<br>CGCCATCGAGCGCCATCTCGAACCGACGTTGCTGGCCGTACATTTG<br>TACGGCTCCGCAGTGGATGGCGGCCTGAAGCCACACAGTGATATT<br>GATTTGCTGGTTACGGTGACCGTAAGGCTTGATGAAACAACGCGG<br>CGAGCTTTGATCAACGACCTTTTGGAAACTTCGGCTTCCCCTGGAG<br>AGAGCGAGATTCTCCGCGCTGTAGAAGTCACCATTGTTGTGCACGA<br>CGACATCATTCCGTGGCGTTATCCAGCTAAGCGCGAACTGCAATTT<br>GGAGAATGGCAGCGCAATGACATTCTTGCAGGTATCTTCGAGCCA<br>GCCACGATCGACATTGATCTGGCTATCTTGCTGACAAAAGCAAGA<br>GAACATAGCGTTGCCTTGGTAGGTCCAGCGGCGGAGGAACTCTTT<br>GATCCGGTTCCTGAACAGGATCTATTTGAGGCGCTAAATGAAACCT<br>TAACGCTATGGAACTCGCCGCCCGACTGGGCTGGCGATGAGCGAA<br>ATGTAGTGCTTACGTTGTCCCGCATTTGGTACAGCGCAGTAACCGG<br>CAAAATCGCGCCGAAGGATGTCGCTGCCGGCTGGGCAATGGAGCG | pJL29 | SEQ. ID NO. 27 |

TABLE 1-continued example amino acid sequences of DRS-DRR enzymes, split DRS and DRR enzymes, and other nucleotide sequences.

| Sequence | Description | SEQ. ID NO. |
|---|---|---|
| CCTGCCGGCCCAGTATCAGCCCGTCATACTTGAAGCTAGACAGGCT<br>TATCTTGGACAAGAAGAAGATCGCTTGGCCTCGCGCGCAGATCAG<br>TTGGAAGAATTTGTCCACTACGTGAAAGGCGAGATCACCAAGGTA<br>GTCGGCAAATAACCCTCGAGCATTCAAGGCGCCTTGATTATTTGAC<br>GTGGTTTGATGGCCTCCACGCACGTTGTGATATGTAGATGATTCAG<br>TTCGAGTTTATCATTATCAATACTGCCATTTCAAAGAATACGTAAA<br>TAATTAATAGTAGTGATTTTCCTAACTTTATTTAGTCAAAAAATTA<br>GCCTTTTAATTCTGCTGTAACCCGTACATGCCCAAAATAGGGGGCG<br>GGTTACACAGAATATATAACATCGTAGGTGTCTGGGTGAACAGTTT<br>ATTCCTGGCATCCACTAAATATAATGGAGCCCGCTTTTTAAGCTGG<br>CATCCAGAAAAAAAAAGAATCCCAGCACCAAAATATTGTTTTCTTC<br>ACCAACCATCAGTTCATAGGTCCATTCTCTTAGCGCAACTACAGAG<br>AACAGGGGCACAAACAGGCAAAAAACGGGCACAACCTCAATGGA<br>GTGATGCAACCTGCCTGGAGTAAATGATGACACAAGGCAATTGAC<br>CCACGCATGTATCTATCTCATTTTCTTACACCTTCTATTACCTTCTG<br>CTCTCTCTGATTTGGAAAAAGCTGAAAAAAAAGGTTGAAACCAGT<br>TCCCTGAAATTATTCCCCTACTTGACTAATAAGTATATAAAGACGG<br>TAGGTATTGATTGTAATTCTGTAAATCTATTTCTTAAACTTCTTAAA<br>TTCTACTTTTATAGTTAGTCTTTTTTTTAGTTTTAAAACACCAAGAA<br>CTTAGTTTCGAATAAACACACATAAACAAACAAAATGGAACTTCA<br>GTACTTCTCCTATTTTCAACCCACTTCATCTGTCGTAGCCCTACTAC<br>TAGCACTAGTGAGTATTTTATTTAGCGTAGTTGTTTTGAGGAAGAC<br>TTTCAGTAACAATTACTCCAGCCCCGCGTCAAGTACGGAAACCGCT<br>GTGCTGTGTCATCAGAGGCAACAGAGTTGCGCCCTACCTATCAGCG<br>GCCTTCTTCACGTGTTCATGAATAAGAACGGCCTGATTCATGTCAC<br>CTTGGGAAATATGGCTGACAAATATGGCCCTATCTTCAGTTTTCCG<br>ACAGGCAGCCACCGTACTTTAGTAGTCAGTTCCTGGGAAATGGTG<br>AAAGAGTGTTTCACCGGTAATAACGACACGGCATTCTCCAACAGA<br>CCAATCCCTTTGGCTTTTCAAACCATATTCTACGCCTGTGGCGGCA<br>TTGATTCTTACGGTTTAAGTAGTGTCCCGTATGGTAAATACTGGAG<br>GGAGTTGAGAAAGGTGTGTGTTCACAACCTGCTGAGTAATCAGCA<br>ATTGCTGAAGTTCAGACATCTTATAATCTCCCAAGTGGATACGTCT<br>TTTAACAAGTTGTATGAGCTGTGTAAGAACTCTGAAGATAATCAAG<br>GTATGGTAAGGATGGATGATTGGCTAGCTCAACTTTCCTTTAACGT<br>CATCGGTAGGATCGTTTGCGGATTCCAGTCTGACCCAAAGACGGGT<br>GCACCTTCAAGGGTAGAACAGTTTAAGGAAGTCATAAATGAGGCG<br>TCATATTTTATGTCAACAAGTCCAGTCTCCGATAACGTACCAATGT<br>TGGGATGGATCGACCAATTGACCGGTCTGACGAGGAACATGAAGC<br>ATTGTGGGAAGAAGCTTGACTTAGTAGTGGAGTCAATTATCAAGG<br>ACCATAGGCAAAAGAGACGTTTTTCACGTACAAAAGGTGGCGATG<br>AGAAGGATGACGAACAGGACGACTTTATTGATATTTGCTTGAGCA<br>TCATGGAGCAGCCACAGTTGCCCGGGAACAATTCTCCCCCTCAAAT<br>TCCGATCAAATCTATCGTGCTAGACATGATTGGGGGTGGTACCGAC<br>ACTACGAAACTTACAACCATATGGACCCTATCACTTTTGTTGAACA<br>ATCCTCACGTGTTAGATAAAGCTAAACAAGAGGTCGACGCTCACTT<br>TCGTAAAAAGAGAAGATCAACAGATGACGCAGCAGCGGCAGTCGT<br>TGATTTTGACGACATAAGAAATTTAGTATACATCCAAGCCATCATT<br>AAAGAAAGTATGAGGCTTTATCCAGCCAGCCCGGTGGTTGAGCGT<br>CTTTCCGGCGAGGATTGCGTTGTTGGAGGTTTTCACGTGCCTGCTG<br>GTACGAGACTATGGGCTAACGTTTGGAAGATGCAAAGAGATCCCA<br>AAGTTTGGGACGATCCTCTAGTATTCAGACCTGAAAGGTTTTTGAG<br>CGACGAGCAAAAGATGGTAGACGTTCGTGGCCAAAACTATGAACT<br>TCTGCCATTCGGCGCAGGAAGAAGAATCTGTCCAGGCGTTTCCTTT<br>AGTCTTGACCTTATGCAACTTGTCCTAACCAGGTTAATCCTAGAGT<br>TCGAAATGAAGTCCCCGTCCGGCAAGGTAGATATGACCGCAACTC<br>CAGGACTAATGTCTTACAAGGTGGTTCCATTGGACATATTGCTGAC<br>TCACCGTCGTATCAAGTCATGCGTTCAATTGGCGTCTTCTGAACGT<br>GATtaaGCGAATTTCTTATGATTTATGATTTTTATTATTAAATAAGTT<br>ATAAAAAAAATAAGTGTATACAAATTTTAAAGTGACTCTTAGGTTT<br>TAAAACGAAAATTCTTATTCTTGAGTAACTCTTTCCTGTAGGTCAG<br>GTTGCTTTCTCAGGTACATAGCTTCAAAATGTTTCTACTCCTTTTTT<br>ACTCTTCCAGATTTTCTCGGACTCCGCGCATCGCCGTACCACTTCA<br>AAACACCCAAGCACAGCATACTAAATTTCCCCTCTTTCTTCCTCTA<br>GGGTGTCGTTAATTACCCGTACTAAAGGTTTGGAAAAGAAAAAAG<br>AGACCGCCTCGTTTCTTTTTCTTCGTCGAAAAAGGCAATAAAAATT<br>TTTATCACGTTTCTTTTTCTTGAAAATTTTTTTTTTTGATTTTTTTCTC<br>TTTCGATGACCTCCCATTGATATTTAAGTTAATAAACGGTCTTCAA<br>TTTCTCAAGTTTCAGTTTCATTTTTCTTGTTCTATTACAACTTTTTTT<br>ACTTCTTGCTCATTAGAAAGAAAGCATAGCAATCTAATCTAAGTTT<br>TAATTACAAAATGGAAAGTTCTGGGGTGCCTGTGATCACATTGTCC<br>TCAGGTAAAGTAATGCCCGTACTGGGCATGGGAACCTTCGAAAAG<br>GTGGGTAAGGGGTCTGAACGTGAGCGTTTAGCCATTCTTAAAGCG<br>ATCGAAGTTGGTTACCGTTACTTTGATACCGCAGCGGCATATGAAA<br>CGGAAGAAGTTCTAGGGGAAGCCATTGCTGAAGCTTTACAATTGG | | |

TABLE 1-continued example amino acid sequences of DRS-DRR enzymes, split DRS and DRR enzymes, and other nucleotide sequences.

| Sequence | Description | SEQ. ID NO. |
|---|---|---|
| GTCTGATAGAGAGCCGTGACGAGCTGTTCATCAGCTCAATGCTTTG<br>GTGCACCGACGCACATCCAGACCGTGTGCTACTTGCTCTGCAAAAC<br>AGTCTGAGAAATCTAAAACTTGAATATCTAGACCTATATATGTTGC<br>CGTTTCCTGCCAGCCTTAAGCCGGGCAAAATTACGATGGATATTCC<br>TGAGGAGGATATTTGCCGTATGGATTATCGTTCAGTCTGGAGCGCC<br>ATGGAAGAGTGTCAAAACTTAGGATTTACTAAAAGTATTGGTGTA<br>AGCAACTTTTCTTGCAAGAAATTACAAGAATTAATGGCCACTGCAA<br>ATATCCCGCCCGCGGTAAATCAAGTAGAGATGTCACCAGCTTTCCA<br>ACAGAAAAAACTGAGGGAATATTGTAACGCAAACAACATATTGGT<br>ATCCGCAGTAAGCATTCTGGGATCAAACGGGACGCCCTGGGGTAG<br>TAATGCTGTTCTTGGAAGCGAAGTTTTGAAACAGATCGCGATGGCG<br>AAAGGCAAAAGCGTTGCGCAAGTCAGTATGAGGTGGGTCTATGAG<br>CAGGGCGCGTCTTTAGTAGTCAAGAGTTTCTCTGAAGAACGTTTAA<br>GAGAAAACCTGAATATTTTTGACTGGGAGCTTACGAAAGAAGACA<br>ATGAGAAGATAGGCGAAATCCCGCAATGTAGAATCCTTACTGCGT<br>ACTTCCTTGTCTCCCCGAACGGCCCGTTTAAATCTCAGGAAGAGCT<br>TTGGGATGACAAGGCAtaaACAGGCCCCTTTTCCTTTGTCGATATCA<br>TGTAATTAGTTATGTCACGCTTACATTCACGCCCTCCTCCCACATCC<br>GCTCTAACCGAAAAGGAAGGAGTTAGACAACCTGAAGTCTAGGTC<br>CCTATTTATTTTTTTTAATAGTTATGTTAGTATTAAGAACGTTATTT<br>ATATTTCAAATTTTTCTTTTTTTTCTGTACAAACGCGTGTACGCATG<br>TAACATTATACTGAAAACCTTGCTTGAGAAGGTTTTGGGACGCTCG<br>AAGGCTTTAATTTGTAATCATTATCACTTTACGGGTCCTTTCCGGTG<br>ATCCGACAGGTTACGGGGCGGCGACCTCGCGGGTTTTCGCTATTTA<br>TGAAAATTTTCCGGTTTAAGGCGTTTCCGTTCTTCTTCGTCATAACT<br>TAATGTTTTTATTTAAAATACCTCGCGAGTGGCAACACTGAAAATA<br>CCCATGGAGCGGCGTAACCGTCGCACAGgatctaggtgaagatccttt<br>ttgataatctcatgaccaaaatcccttaacgtgagttttcgttccact<br>gagcgtcagaccccgtagaaaagatcaaaggatcttcttgagatcctt<br>tttttctgcgcgtaatctgctgcttgcaaacaaaaaaaccaccgctac<br>cagcggtggtttgtttgccggatcaagagctaccaactctttttccga<br>aggtaactggcttcagcagagcgcagataccaaatactgtccttctag<br>tgtagccgtagttaggccaccacttcaagaactctgtagcaccgccta<br>catacctcgctctgctaatcctgttaccagtggctgctgccagtggcg<br>ataagtcgtgtcttaccgggttggactcaagacgatagttaccggata<br>aggcgcagcggtcgggctgaacggggggttcgtgcacacagcccagct<br>tggagcgaacgacctacaccgaactgagatacctacagcgtgagctat<br>gagaaagcgccacgcttcccgaagggagaaaggcggacaggtatccgg<br>taagcggcagggtcggaacaggagagcgcacgagggagcttccagggg<br>gaaacgcctggtatctttatagtcctgtcgggtttcgccacctctgac<br>ttgagcgtcgatttttgtgatgctcgtcaggggggcggagcctatgga<br>aaaacgccagcaacgcggcagtggaacgTGCATTATGAATTAGTTACG<br>CTAGGGATAACAGGGTAATATAGAACCCGAACGACCGAGCGCAGCGGC<br>GGCCGCGCTGATACCGCCGC | | |
| CCTCGCCGCAGTTAATTAAAGTCAGTGAGCGAGGAAGCGCGTAAC<br>TATAACGGTCCTAAGGTAGCGAATCCTGATGCGGTATTTTCTCCTT<br>ACGCATCTGTGCGGTATTTCACACCGCATAGATCGGCAAGTGCACA<br>AACAATACTTAAATAAATACTACTCAGTAATAACCTATTTCTTAGC<br>ATTTTTGACGAAATTTGCTATTTTGTTAGAGTCTTTTACACCATTTG<br>TCTCCACACCTCCGCTTACATCAACACCAATAACGCCATTTAATCT<br>AAGCGCATCACCAACATTTTCTGGCGTCAGTCCACCAGCTAACATA<br>AAATGTAAGCTTTCGGGGCTCTCTTGCCTTCCAACCCAGTCAGAAA<br>TCGAGTTCCAATCCAAAAGTTCACCTGTCCCACCTGCTTCTGAATC<br>AAACAAGGGAATAAACGAATGAGGTTTCTGTGAAGCTGCACTGAG<br>TAGTATGTTGCAGTCTTTTGGAAATACGAGTCTTTTAATAACTGGC<br>AAACCGAGGAACTCTTGGTATTCTTGCCACGACTCATCTCCATGCA<br>GTTGGACGATATCAATGCCGTAATCATTGACCAGAGCCAAAACAT<br>CCTCCTTAAGTTGATTACGAAACACGCCAACCAAGTATTTCGGAGT<br>GCCTGAACTATTTTTATATGCTTTTACAAGACTTGAAATTTTCCTTG<br>CAATAACCGGGTCAATTGTTCTCTTTCTATTGGGCACACATATAAT<br>ACCCAGCAAGTCAGCATCGGAATCTAGAGCACATTCTGCGGCCTCT<br>GTGCTCTGCAAGCCGCAAACTTTCACCAATGGACCAGAACTACCTG<br>TGAAATTAATAACAGACATACTCCAAGCTGCCTTTGTGTGCTTAAT<br>CACGTATACTCACGTGCTCAATAGTCACCAATGCCCTCCCTCTTGG<br>CCCTCTCCTTTTCTTTTTTCGACCGAATTAATTCTTAATCGGCAAAA<br>AAAGAAAAGCTCCGGATCAAGATTGTACGTAAGGTGACAAGCTAT<br>TTTTCAATAAAGAATATCTTCCACTACTGCCATCTGGCGTCATAAC<br>TGCAAAGTACACATATATTACGATGCTGTTCTATTAAATGCTTCCT<br>ATATTATATATATAGTAATGTCGTGATCTATGGTGCACTCTCAGTA<br>CAATCTGCTCTGATGCCGCATAGTTAAGCCAGCCCCGACACCCGCC<br>AACACCCGCTGACGCGCCCTGACGGGCTTGTCTGCTCCCGGCATCC<br>GCTTACAGACAAGCTGTGACCGTCTCCGGGAGCTGCATGTGTCAG<br>AGGTTTTCACCGTCATCACCGAAACGCGCGAGACGAAAGGGCCTC | pJL32 | SEQ. ID NO. 28 |

TABLE 1-continued example amino acid sequences of DRS-DRR enzymes, split DRS and DRR enzymes, and other nucleotide sequences.

| Sequence | Description | SEQ. ID NO. |
|---|---|---|
| GTGATACGCCTATTTTTATAGGTTAATGTCATGATAATAATGGTTT<br>CTTAGACGGATCGCTTGCCTGTAACTTACACGCGCCTCGTATCTTTT<br>AATGATGGAATAATTTGGGAATTTACTCTGTGTTTATTTATTTTTAT<br>GTTTTGTATTTGGATTTTAGAAAGTAAATAAAGAAGGTAGAAGAG<br>TTACGGAATGAAGAAAAAAAAAATAAACAAAGGTTTAAAAAATTTC<br>AACAAAAAGCGTACTTTACATATATATTTATTAGACAAGAAAAGC<br>AGATTAAATAGATATACATTCGATTAACGATAAGTAAAATGTAAA<br>ATCACAGGATTTTCGTGTGTGGTCTTCTACACAGACAAGGTGAAAC<br>AATTCGGCATTAATACCTGAGAGCAGGAAGAGCAAGATAAAAGGT<br>AGTATTTGTTGGCGATCCCCCTAGAGTCTTTTACATCTTCGGAAAA<br>CAAAAACTATTTTTTCTTTAATTTCTTTTTTTACTTTCTATTTTTAAT<br>TTATATATTTATATTAAAAAATTTAAATTATAATTATTTTTATAGCA<br>CGTGATGAAAAGGACCCAGGTGGCACTTTTCGGGGAAATGTGCGC<br>GGAACCCCTATTTGTTTATTTTTCTAAATACATTCAAATATGTATCC<br>GCTCATGAGACAATAACCCTGATAAATGCTTCAATAATATTGAAA<br>AAGGAAGAGTATGAGTATTCAACATTTCCGTGTCGCCCTTATTCCC<br>TTTTTTGCGGCATTTTGCCTTCCTGTTTTTGCTCACCCAGAAACGCT<br>GGTGAAAGTAAAAGATGCTGAAGATCAGTTGGGACGCGTAGTCTA<br>GACCAGCCAGGACAGAAATGCCTCGACTTCGCTGCTACCCAAGGT<br>TGCCGGGTGACGCACACCGTGGAAACGGATGAAGGCACGAACCCA<br>GTGGACATAAGCCTGTTCGGTTCGTAAGCTGTAATGCAAGTAGCGT<br>ATGCGCTCACGCAACTGGTCCAGAACCTTGACCGAACGCAGCGGT<br>GGTAACGGCGCAGTGGCGGTTTTCATGGCTTGTTATGACTGTTTTT<br>TTGGGGTACAGTCTATGCCTCGGGCATCCAAGCAGCAAGCGCGTT<br>ACGCCGTGGGTCGATGTTTGATGTTATGGAGCAGCAACGATGTTAC<br>GCAGCAGGGCAGTCGCCCTAAAACAAAGTTAAACATTATGAGGGA<br>AGCGGTGATCGCCGAAGTATCGACTCAACTATCAGAGGTAGTTGG<br>CGCCATCGAGCGCCATCTCGAACCGACGTTGCTGGCCGTACATTTG<br>TACGGCTCCGCAGTGGATGGCGGCCTGAAGCCACACAGTGATATT<br>GATTTGCTGGTTACGGTGACCGTAAGGCTTGATGAAACAACGCGG<br>CGAGCTTTGATCAACGACCTTTTGGAAACTTCGGCTTCCCCTGGAG<br>AGAGCGAGATTCTCCGCGCTGTAGAAGTCACCATTGTTGTGCACGA<br>CGACATCATTCCGTGGCGTTATCCAGCTAAGCGCGAACTGCAATTT<br>GGAGAATGGCAGCGCAATGACATTCTTGCAGGTATCTTCGAGCCA<br>GCCACGATCGACATTGATCTGGCTATCTTGCTGACAAAAGCAAGA<br>GAACATAGCGTTGCCTTGGTAGGTCCAGCGGCGGAGGAACTCTTT<br>GATCCGGTTCCTGAACAGGATCTATTTGAGGCGCTAAATGAAACCT<br>TAACGCTATGGAACTCGCCGCCCGACTGGGCTGGCGATGAGCGAA<br>ATGTAGTGCTTACGTTGTCCCGCATTTGGTACAGCGCAGTAACCGG<br>CAAAATCGCGCCGAAGGATGTCGCTGCCGGCTGGGCAATGGAGCG<br>CCTGCCGGCCCAGTATCAGCCCGTCATACTTGAAGCTAGACAGGCT<br>TATCTTGGACAAGAAGAAGATCGCTTGGCCTCGCGCGCAGATCAG<br>TTGGAAGAATTTGTCCACTACGTGAAAGGCGAGATCACCAAGGTA<br>GTCGGCAAATAACCCTCGAGCATTCAAGGCGCCTTGATTATTTGAC<br>GTGGTTTGATGGCCTCCACGCACGTTGTGATATGTAGATGAGAGCG<br>TTGGTTGGTGGATCAAGCCCACGCGTAGGCAATCCTCGAGCAGAT<br>CCGCCAGGCGTGTATATATAGCGTGGATGGCCAGGCAACTTTAGT<br>GCTGACACATACAGGCATATATATATGTGTGCGACGACACATGAT<br>CATATGGCATGCATGTGCTCTGTATGTATATAAAACTCTTGTTTTCT<br>TCTTTTCTCTAAATATTCTTTCCTTATACATTAGGACCTTTGCAGCA<br>TAAATTACTATACTTCTATAGACACACAAACACAAATACACACACT<br>AAATTAATAATGGAACTTCAGTACTTCTCCTATTTTCAACCCACTTC<br>ATCTGTCGTAGCCCTACTACTAGCACTAGTGAGTATTTTATTTAGC<br>GTAGTTGTTTTGAGGAAGACTTTCAGTAACAATTACTCCAGCCCCG<br>CGTCAAGTACGGAAACCGCTGTGCTGTGTCATCAGAGGCAACAGA<br>GTTGCGCCCTACCTATCAGCGGCCTTCTTCACGTGTTCATGAATAA<br>GAACGGCCTGATTCATGTCACCTTGGGAAATATGGCTGACAAATAT<br>GGCCCTATCTTCAGTTTTCCGACAGGCAGCCACCGTACTTTAGTAG<br>TCAGTTCCTGGGAAATGGTGAAAGAGTGTTTCACCGGTAATAACG<br>ACACGGCATTCTCCAACAGACCAATCCCTTTGGCTTTTCAAACCAT<br>ATTCTACGCCTGTGGCGGCATTGATTCTTACGGTTTAAGTAGTGTC<br>CCGTATGGTAAATACTGGAGGGAGTTGAGAAAGGTGTGTGTTCAC<br>AACCTGCTGAGTAATCAGCAATTGCTGAAGTTCAGACATCTTATAA<br>TCTCCCAAGTGGATACGTCTTTTAACAAGTTGTATGAGCTGTGTAA<br>GAACTCTGAAGATAATCAAGGTATGGTAAGGATGGATGATTGGCT<br>AGCTCAACTTTCCTTTAACGTCATCGGTAGGATCGTTTGCGGATTC<br>CAGTCTGACCCAAAGACGGGTGCACCTTCAAGGGTAGAACAGTTT<br>AAGGAAGTCATAAATGAGGCGTCATATTTTATGTCAACAAGTCCA<br>GTCTCCGATAACGTACCAATGTTGGGATGGATCGACCAATTGACCG<br>GTCTGACGAGGAACATGAAGCATTGTGGGAAGAAGCTTGACTTAG<br>TAGTGGAGTCAATTATCAAGGACCATAGGCAAAAGAGACGTTTTT<br>CACGTACAAAAGGTGGCGATGAGAAGGATGACGAACAGGACGAC<br>TTTATTGATATTTGCTTGAGCATCATGGAGCAGCCACAGTTGCCCG<br>GGAACAATTCTCCCCCTCAAATTCCGATCAAATCTATCGTGCTAGA | | |

TABLE 1-continued example amino acid sequences of DRS-DRR enzymes, split DRS and DRR enzymes, and other nucleotide sequences.

| Sequence | Description | SEQ. ID NO. |
|---|---|---|
| CATGATTGGGGGTGGTACCGACACTACGAAACTTACAACCATATG<br>GACCCTATCACTTTTGTTGAACAATCCTCACGTGTTAGATAAAGCT<br>AAACAAGAGGTCGACGCTCACTTTCGTAAAAAGAGAAGATCAACA<br>GATGACGCAGCAGCGGCAGTCGTTGATTTTGACGACATAAGAAAT<br>TTAGTATACATCCAAGCCATCATTAAAGAAAGTATGAGGCTTTATC<br>CAGCCAGCCCGGTGGTTGAGCGTCTTTCCGGCGAGGATTGCGTTGT<br>TGGAGGTTTTCACGTGCCTGCTGGTACGAGACTATGGGCTAACGTT<br>TGGAAGATGCAAAGAGATCCCAAAGTTTGGGACGATCCTCTAGTA<br>TTCAGACCTGAAAGGTTTTTGAGCGACGAGCAAAAGATGGTAGAC<br>GTTCGTGGCCAAAACTATGAACTTCTGCCATTCGGCGCAGGAAGA<br>AGAATCTGTCCAGGCGTTTCCTTTAGTCTTGACCTTATGCAACTTGT<br>CCTAACCAGGTTAATCCTAGAGTTCGAAATGAAGTCCCCGTCCGGC<br>AAGGTAGATATGACCGCAACTCCAGGACTAATGTCTTACAAGGTG<br>GTTCCATTGGACATATTGCTGACTCACCGTCGTATCAAGTCATGCG<br>TTCAATTGGCGTCTTCTGAACGTGATtaaGCGAATTTCTTATGATTTA<br>TGATTTTTATTATTAAATAAGTTATAAAAAAAATAAGTGTATACAA<br>ATTTTAAAGTGACTCTTAGGTTTTAAAACGAAAATTCTTATTCTTG<br>AGTAACTCTTTCCTGTAGGTCAGGTTGCTTTCTCAGGTATTCAGTTC<br>GAGTTTATCATTATCAATACTGCCATTTCAAAGAATACGTAAATAA<br>TTAATAGTAGTGATTTTCCTAACTTTATTTAGTCAAAAAATTAGCCT<br>TTTAATTCTGCTGTAACCCGTACATGCCCAAAATAGGGGGCGGGTT<br>ACACAGAATATATAACATCGTAGGTGTCTGGGTGAACAGTTTATTC<br>CTGGCATCCACTAAATATAATGGAGCCCGCTTTTTAAGCTGGCATC<br>CAGAAAAAAAAAGAATCCCAGCACCAAAATATTGTTTTCTTCACC<br>AACCATCAGTTCATAGGTCCATTCTCTTAGCGCAACTACAGAGAAC<br>AGGGGCACAAACAGGCAAAAAACGGGCACAACCTCAATGGAGTG<br>ATGCAACCTGCCTGGAGTAAATGATGACACAAGGCAATTGACCCA<br>CGCATGTATCTATCTCATTTTCTTACACCTTCTATTACCTTCTGCTCT<br>CTCTGATTTGGAAAAAGCTGAAAAAAAAGGTTGAAACCAGTTCCC<br>TGAAATTATTCCCCTACTTGACTAATAAGTATATAAAGACGGTAGG<br>TATTGATTGTAATTCTGTAAATCTATTTCTTAAACTTCTTAAATTCT<br>ACTTTTATAGTTAGTCTTTTTTTTAGTTTTAAAACACCAAGAACTTA<br>GTTTCGAATAAACACACATAAACAAACAAAATGGAAAGTTCTGGG<br>GTGCCTGTGATCACATTGTCCTCAGGTAAAGTAATGCCCGTACTGG<br>GCATGGGAACCTTCGAAAAGGTGGGTAAGGGGTCTGAACGTGAGC<br>GTTTAGCCATTCTTAAAGCGATCGAAGTTGGTTACCGTTACTTTGA<br>TACCGCAGCGGCATATGAAACGGAAGAAGTTCTAGGGGAAGCCAT<br>TGCTGAAGCTTTACAATTGGGTCTGATAGAGAGCCGTGACGAGCT<br>GTTCATCAGCTCAATGCTTTGGTGCACCGACGCACATCCAGACCGT<br>GTGCTACTTGCTCTGCAAAACAGTCTGAGAAATCTAAAACTTGAAT<br>ATCTAGACCTATATATGTTGCCGTTTCCTGCCAGCCTTAAGCCGGG<br>CAAAATTACGATGGATATTCCTGAGGAGGATATTTGCCGTATGGAT<br>TATCGTTCAGTCTGGAGCGCCATGGAAGAGTGTCAAAACTTAGGA<br>TTTACTAAAAGTATTGGTGTAAGCAACTTTTCTTGCAAGAAATTAC<br>AAGAATTAATGGCCACTGCAAATATCCCGCCCGCGGTAAATCAAG<br>TAGAGATGTCACCAGCTTTCCAACAGAAAAAACTGAGGGAATATT<br>GTAACGCAAACAACATATTGGTATCCGCAGTAAGCATTCTGGGAT<br>CAAACGGGACGCCCTGGGGTAGTAATGCTGTTCTTGGAAGCGAAG<br>TTTTGAAACAGATCGCGATGGCGAAAGGCAAAAGCGTTGCGCAAG<br>TCAGTATGAGGTGGGTCTATGAGCAGGGCGCGTCTTTAGTAGTCAA<br>GAGTTTCTCTGAAGAACGTTTAAGAGAAAACCTGAATATTTTTGAC<br>TGGGAGCTTACGAAAGAAGACAATGAGAAGATAGGCGAAATCCC<br>GCAATGTAGAATCCTTACTGCGTACTTCCTTGTCTCCCCGAACGGC<br>CCGTTTAAATCTCAGGAAGAGCTTTGGGATGACAAGGCAtaaACAG<br>GCCCCTTTTCCTTTGTCGATATCATGTAATTAGTTATGTCACGCTTA<br>CATTCACGCCCTCCTCCCACATCCGCTCTAACCGAAAAGGAAGGA<br>GTTAGACAACCTGAAGTCTAGGTCCCTATTTATTTTTTTTAATAGTT<br>ATGTTAGTATTAAGAACGTTATTTATATTTCAAATTTTTCTTTTTTTT<br>CTGTACAAACGCGTGTACGCATGTAACATTATACTGAAAACCTTGC<br>TTGAGAAGGTTTTGGGACGCTCGAAGGCTTTAATTTGTAATCATTA<br>TCACTTTACGGGTCCTTTCCGGTGATCCGACAGGTTACGGGGCGGC<br>GACCTCGCGGGTTTTCGCTATTTATGAAAATTTTCCGGTTTAAGGC<br>GTTTCCGTTCTTCTTCGTCATAACTTAATGTTTTTATTTAAAATACC<br>TCGCGAGTGGCAACACTGAAAATACCCATGGAGCGGCGTAACCGT<br>CGCACAGgatctaggtgaagatcctttttgataatctcatgaccaaaa<br>tcccttaacgtgagttttcgttccactgagcgtcagaccccgtagaaa<br>agatcaaaggatcttcttgagatcctttttttctgcgcgtaatctgct<br>gcttgcaaacaaaaaaaccaccgctaccagcggtggtttgtttgccgg<br>atcaagagctaccaactctttttccgaaggtaactggcttcagcagag<br>cgcagataccaaatactgtccttctagtgtagccgtagttaggccacc<br>acttcaagaactctgtagcaccgcctacatacctcgctctgctaatcc<br>tgttaccagtggctgctgccagtggcgataagtcgtgtcttaccgggt<br>tggactcaagacgatagttaccggataaggcgcagcggtcgggctgaa<br>cggggggttcgtgcacacagcccagcttggagcgaacgacctacaccg | | |

TABLE 1-continued example amino acid sequences of DRS-DRR enzymes, split DRS and DRR enzymes, and other nucleotide sequences.

| Sequence | Description | SEQ. ID NO. |
|---|---|---|
| aactgagatacctacagcgtgagctatgagaaagcgccacgcttcccg<br>aagggagaaaggcggacaggtatccggtaagcggcagggtcggaacag<br>gagagcgcacgagggagcttccagggggaaacgcctggtatctttata<br>gtcctgtcgggtttcgccacctctgacttgagcgtcgatttttgtgat<br>gctcgtcaggggggcggagcctatggaaaaacgccagcaacgcggcag<br>tggaacgTGCATTATGAATTAGTTACGCTAGGGATAACAGGGTAATAT<br>AGAACCCGAACGACCGAGCGCAGCGGCGGCCGCGCTGATACCGCCGC | | |
| CCTCGCCGCAGTTAATTAAAGTCAGTGAGCGAGGAAGCGCGTAAC<br>TATAACGGTCCTAAGGTAGCGAATCCTGATGCGGTATTTTCTCCTT<br>ACGCATCTGTGCGGTATTTCACACCGCATAGATCGGCAAGTGCACA<br>AACAATACTTAAATAAATACTACTCAGTAATAACCTATTTCTTAGC<br>ATTTTTGACGAAATTTGCTATTTTGTTAGAGTCTTTTACACCATTTG<br>TCTCCACACCTCCGCTTACATCAACACCAATAACGCCATTTAATCT<br>AAGCGCATCACCAACATTTTCTGGCGTCAGTCCACCAGCTAACATA<br>AAATGTAAGCTTTCGGGGCTCTCTTGCCTTCCAACCCAGTCAGAAA<br>TCGAGTTCCAATCCAAAAGTTCACCTGTCCCACCTGCTTCTGAATC<br>AAACAAGGGAATAAACGAATGAGGTTTCTGTGAAGCTGCACTGAG<br>TAGTATGTTGCAGTCTTTTGGAAATACGAGTCTTTTAATAACTGGC<br>AAACCGAGGAACTCTTGGTATTCTTGCCACGACTCATCTCCATGCA<br>GTTGGACGATATCAATGCCGTAATCATTGACCAGAGCCAAAACAT<br>CCTCCTTAAGTTGATTACGAAACACGCCAACCAAGTATTTCGGAGT<br>GCCTGAACTATTTTTATATGCTTTTACAAGACTTGAAATTTTCCTTG<br>CAATAACCGGGTCAATTGTTCTCTTTCTATTGGGCACACATATAAT<br>ACCCAGCAAGTCAGCATCGGAATCTAGAGCACATTCTGCGGCCTCT<br>GTGCTCTGCAAGCCGCAAACTTTCACCAATGGACCAGAACTACCTG<br>TGAAATTAATAACAGACATACTCCAAGCTGCCTTTGTGTGCTTAAT<br>CACGTATACTCACGTGCTCAATAGTCACCAATGCCCTCCCTCTTGG<br>CCCTCTCCTTTTCTTTTTTCGACCGAATTAATTCTTAATCGGCAAAA<br>AAAGAAAAGCTCCGGATCAAGATTGTACGTAAGGTGACAAGCTAT<br>TTTTCAATAAAGAATATCTTCCACTACTGCCATCTGGCGTCATAAC<br>TGCAAAGTACACATATATTACGATGCTGTTCTATTAAATGCTTCCT<br>ATATTATATATATAGTAATGTCGTGATCTATGGTGCACTCTCAGTA<br>CAATCTGCTCTGATGCCGCATAGTTAAGCCAGCCCCGACACCCGCC<br>AACACCCGCTGACGCGCCCTGACGGGCTTGTCTGCTCCCGGCATCC<br>GCTTACAGACAAGCTGTGACCGTCTCCGGGAGCTGCATGTGTCAG<br>AGGTTTTCACCGTCATCACCGAAACGCGCGAGACGAAAGGGCCTC<br>GTGATACGCCTATTTTTATAGGTTAATGTCATGATAATAATGGTTT<br>CTTAGACGGATCGCTTGCCTGTAACTTACACGCGCCTCGTATCTTTT<br>AATGATGGAATAATTTGGGAATTTACTCTGTGTTTATTTATTTTTAT<br>GTTTTGTATTTGGATTTTAGAAAGTAAATAAAGAAGGTAGAAGAG<br>TTACGGAATGAAGAAAAAAAAATAAACAAAGGTTTAAAAAATTTC<br>AACAAAAAGCGTACTTTACATATATATTTATTAGACAAGAAAAGC<br>AGATTAAATAGATATACATTCGATTAACGATAAGTAAAATGTAAA<br>ATCACAGGATTTTCGTGTGTGGTCTTCTACACAGACAAGGTGAAAC<br>AATTCGGCATTAATACCTGAGAGCAGGAAGAGCAAGATAAAAGGT<br>AGTATTTGTTGGCGATCCCCCTAGAGTCTTTTACATCTTCGGAAAA<br>CAAAAACTATTTTTTCTTTAATTTCTTTTTTTACTTTCTATTTTTAAT<br>TTATATATTTATATTAAAAAATTTAAATTATAATTATTTTTATAGCA<br>CGTGATGAAAAGGACCCAGGTGGCACTTTTCGGGGAAATGTGCGC<br>GGAACCCCTATTTGTTTATTTTTCTAAATACATTCAAATATGTATCC<br>GCTCATGAGACAATAACCCTGATAAATGCTTCAATAATATTGAAA<br>AAGGAAGAGTATGAGTATTCAACATTTCCGTGTCGCCCTTATTCCC<br>TTTTTTGCGGCATTTTGCCTTCCTGTTTTTGCTCACCCAGAAACGCT<br>GGTGAAAGTAAAAGATGCTGAAGATCAGTTGGGACGCGTAGTCTA<br>GACCAGCCAGGACAGAAATGCCTCGACTTCGCTGCTACCCAAGGT<br>TGCCGGGTGACGCACACCGTGGAAACGGATGAAGGCACGAACCCA<br>GTGGACATAAGCCTGTTCGGTTCGTAAGCTGTAATGCAAGTAGCGT<br>ATGCGCTCACGCAACTGGTCCAGAACCTTGACCGAACGCAGCGGT<br>GGTAACGGCGCAGTGGCGGTTTTCATGGCTTGTTATGACTGTTTTT<br>TTGGGGTACAGTCTATGCCTCGGGCATCCAAGCAGCAAGCGCGTT<br>ACGCCGTGGGTCGATGTTTGATGTTATGGAGCAGCAACGATGTTAC<br>GCAGCAGGGCAGTCGCCCTAAAACAAAGTTAAACATTATGAGGGA<br>AGCGGTGATCGCCGAAGTATCGACTCAACTATCAGAGGTAGTTGG<br>CGCCATCGAGCGCCATCTCGAACCGACGTTGCTGGCCGTACATTTG<br>TACGGCTCCGCAGTGGATGGCGGCCTGAAGCCACACAGTGATATT<br>GATTTGCTGGTTACGGTGACCGTAAGGCTTGATGAAACAACGCGG<br>CGAGCTTTGATCAACGACCTTTTGGAAACTTCGGCTTCCCCTGGAG<br>AGAGCGAGATTCTCCGCGCTGTAGAAGTCACCATTGTTGTGCACGA<br>CGACATCATTCCGTGGCGTTATCCAGCTAAGCGCGAACTGCAATTT<br>GGAGAATGGCAGCGCAATGACATTCTTGCAGGTATCTTCGAGCCA<br>GCCACGATCGACATTGATCTGGCTATCTTGCTGACAAAAGCAAGA<br>GAACATAGCGTTGCCTTGGTAGGTCCAGCGGCGGAGGAACTCTTT<br>GATCCGGTTCCTGAACAGGATCTATTTGAGGCGCTAAATGAAACCT | PjL35 | SEQ. ID NO. 29 |

TABLE 1-continued example amino acid sequences of DRS-DRR enzymes, split DRS and DRR enzymes, and other nucleotide sequences.

| Sequence | Description | SEQ. ID NO. |
|---|---|---|
| TAACGCTATGGAACTCGCCGCCCGACTGGGCTGGCGATGAGCGAA | | |
| ATGTAGTGCTTACGTTGTCCCGCATTTGGTACAGCGCAGTAACCGG | | |
| CAAAATCGCGCCGAAGGATGTCGCTGCCGGCTGGGCAATGGAGCG | | |
| CCTGCCGGCCCAGTATCAGCCCGTCATACTTGAAGCTAGACAGGCT | | |
| TATCTTGGACAAGAAGAAGATCGCTTGGCCTCGCGCGCAGATCAG | | |
| TTGGAAGAATTTGTCCACTACGTGAAAGGCGAGATCACCAAGGTA | | |
| GTCGGCAAATAACCCTCGAGCATTCAAGGCGCCTTGATTATTTGAC | | |
| GTGGTTTGATGGCCTCCACGCACGTTGTGATATGTAGATGATTCAG | | |
| TTCGAGTTTATCATTATCAATACTGCCATTTCAAAGAATACGTAAA | | |
| TAATTAATAGTAGTGATTTTCCTAACTTTATTTAGTCAAAAAATTA | | |
| GCCTTTTAATTCTGCTGTAACCCGTACATGCCCAAAATAGGGGGCG | | |
| GGTTACACAGAATATATAACATCGTAGGTGTCTGGGTGAACAGTTT | | |
| ATTCCTGGCATCCACTAAATATAATGGAGCCCGCTTTTTAAGCTGG | | |
| CATCCAGAAAAAAAAAGAATCCCAGCACCAAAATATTGTTTTCTTC | | |
| ACCAACCATCAGTTCATAGGTCCATTCTCTTAGCGCAACTACAGAG | | |
| AACAGGGGCACAAACAGGCAAAAAACGGGCACAACCTCAATGGA | | |
| GTGATGCAACCTGCCTGGAGTAAATGATGACACAAGGCAATTGAC | | |
| CCACGCATGTATCTATCTCATTTTCTTACACCTTCTATTACCTTCTG | | |
| CTCTCTCTGATTTGGAAAAAGCTGAAAAAAAAGGTTGAAACCAGT | | |
| TCCCTGAAATTATTCCCCTACTTGACTAATAAGTATATAAAGACGG | | |
| TAGGTATTGATTGTAATTCTGTAAATCTATTTCTTAAACTTCTTAAA | | |
| TTCTACTTTTATAGTTAGTCTTTTTTTTAGTTTTAAAACACCAAGAA | | |
| CTTAGTTTCGAATAAACACACATAAACAAACAAAATGGAACTTCA | | |
| GTACTTCTCCTATTTTCAACCCACTTCATCTGTCGTAGCCCTACTAC | | |
| TAGCACTAGTGAGTATTTTATTTAGCGTAGTTGTTTTGAGGAAGAC | | |
| TTTCAGTAACAATTACTCCAGCCCCGCGTCAAGTACGGAAACCGCT | | |
| GTGCTGTGTCATCAGAGGCAACAGAGTTGCGCCCTACCTATCAGCG | | |
| GCCTTCTTCACGTGTTCATGAATAAGAACGGCCTGATTCATGTCAC | | |
| CTTGGGAAATATGGCTGACAAATATGGCCCTATCTTCAGTTTTCCG | | |
| ACAGGCAGCCACCGTACTTTAGTAGTCAGTTCCTGGGAAATGGTG | | |
| AAAGAGTGTTTCACCGGTAATAACGACACGGCATTCTCCAACAGA | | |
| CCAATCCCTTTGGCTTTTCAAACCATATTCTACGCCTGTGGCGGCA | | |
| TTGATTCTTACGGTTTAAGTAGTGTCCCGTATGGTAAATACTGGAG | | |
| GGAGTTGAGAAAGGTGTGTGTTCACAACCTGCTGAGTAATCAGCA | | |
| ATTGCTGAAGTTCAGACATCTTATAATCTCCCAAGTGGATACGTCT | | |
| TTTAACAAGTTGTATGAGCTGTGTAAGAACTCTGAAGATAATCAAG | | |
| GTATGGTAAGGATGGATGATTGGCTAGCTCAACTTTCCTTTAACGT | | |
| CATCGGTAGGATCGTTTGCGGATTCCAGTCTGACCCAAAGACGGGT | | |
| GCACCTTCAAGGGTAGAACAGTTTAAGGAAGTCATAAATGAGGCG | | |
| TCATATTTTATGTCAACAAGTCCAGTCTCCGATAACGTACCAATGT | | |
| TGGGATGGATCGACCAATTGACCGGTCTGACGAGGAACATGAAGC | | |
| ATTGTGGGAAGAAGCTTGACTTAGTAGTGGAGTCAATTATCAAGG | | |
| ACCATAGGCAAAAGAGACGTTTTTCACGTACAAAAGGTGGCGATG | | |
| AGAAGGATGACGAACAGGACGACTTTATTGATATTTGCTTGAGCA | | |
| TCATGGAGCAGCCACAGTTGCCCGGGAACAATTCTCCCCCTCAAAT | | |
| TCCGATCAAATCTATCGTGCTAGACATGATTGGGGGTGGTACCGAC | | |
| ACTACGAAACTTACAACCATATGGACCCTATCACTTTTGTTGAACA | | |
| ATCCTCACGTGTTAGATAAAGCTAAACAAGAGGTCGACGCTCACTT | | |
| TCGTAAAAAGAGAAGATCAACAGATGACGCAGCAGCGGCAGTCGT | | |
| TGATTTTGACGACATAAGAAATTTAGTATACATCCAAGCCATCATT | | |
| AAAGAAAGTATGAGGCTTTATCCAGCCAGCCCGGTGGTTGAGCGT | | |
| CTTTCCGGCGAGGATTGCGTTGTTGGAGGTTTTCACGTGCCTGCTG | | |
| GTACGAGACTATGGGCTAACGTTTGGAAGATGCAAAGAGATCCCA | | |
| AAGTTTGGGACGATCCTCTAGTATTCAGACCTGAAAGGTTTTTGAG | | |
| CGACGAGCAAAAGATGGTAGACGTTCGTGGCCAAAACTATGAACT | | |
| TCTGCCATTCGGCGCAGGAAGAAGAATCTGTCCAGGCGTTTCCTTT | | |
| AGTCTTGACCTTATGCAACTTGTCCTAACCAGGTTAATCCTAGAGT | | |
| TCGAAATGAAGTCCCCGTCCGGCAAGGTAGATATGACCGCAACTC | | |
| CAGGACTAATGTCTTACAAGGTGGTTCCATTGGACATATTGCTGAC | | |
| TCACCGTCGTATCAAGTCATGCGTTCAATTGGCGTCTTCTGAACGT | | |
| GATtaaGCGAATTTCTTATGATTTATGATTTTTATTATTAAATAAGTT | | |
| ATAAAAAAAATAAGTGTATACAAATTTTAAAGTGACTCTTAGGTTT | | |
| TAAAACGAAAATTCTTATTCTTGAGTAACTCTTTCCTGTAGGTCAG | | |
| GTTGCTTTCTCAGGTAGAGCGTTGGTTGGTGGATCAAGCCCACGCG | | |
| TAGGCAATCCTCGAGCAGATCCGCCAGGCGTGTATATATAGCGTG | | |
| GATGGCCAGGCAACTTTAGTGCTGACACATACAGGCATATATATAT | | |
| GTGTGCGACAACACATGATCATATGGCATGCATGTGCTCTGTATGT | | |
| ATATAAAACTCTTGTTTTCTTCTTTTCTCTAAATATTCTTTCCTTATA | | |
| CATTAGGACCTTTGCAGCATAAATTACTATACTTCTATAGACACAC | | |
| AAACACAAATACACACACTAAATTAATAATGGAAAGTTCTGGGGT | | |

TABLE 1-continued example amino acid sequences of DRS-DRR enzymes, split DRS and DRR enzymes, and other nucleotide sequences.

| Sequence | Description | SEQ. ID NO. |
|---|---|---|
| GCCTGTGATCACATTGTCCTCAGGTAAAGTAATGCCCGTACTGGGC<br>ATGGGAACCTTCGAAAAGGTGGGTAAGGGGTCTGAACGTGAGCGT<br>TTAGCCATTCTTAAAGCGATCGAAGTTGGTTACCGTTACTTTGATA<br>CCGCAGCGGCATATGAAACGGAAGAAGTTCTAGGGGAAGCCATTG<br>CTGAAGCTTTACAATTGGGTCTGATAGAGAGCCGTGACGAGCTGTT<br>CATCAGCTCAATGCTTTGGTGCACCGACGCACATCCAGACCGTGTG<br>CTACTTGCTCTGCAAAACAGTCTGAGAAATCTAAAACTTGAATATC<br>TAGACCTATATATGTTGCCGTTTCCTGCCAGCCTTAAGCCGGGCAA<br>AATTACGATGGATATTCCTGAGGAGGATATTTGCCGTATGGATTAT<br>CGTTCAGTCTGGAGCGCCATGGAAGAGTGTCAAAACTTAGGATTT<br>ACTAAAAGTATTGGTGTAAGCAACTTTTCTTGCAAGAAATTACAAG<br>AATTAATGGCCACTGCAAATATCCCGCCCGCGGTAAATCAAGTAG<br>AGATGTCACCAGCTTTCCAACAGAAAAAACTGAGGGAATATTGTA<br>ACGCAAACAACATATTGGTATCCGCAGTAAGCATTCTGGGATCAA<br>ACGGGACGCCCTGGGGTAGTAATGCTGTTCTTGGAAGCGAAGTTTT<br>GAAACAGATCGCGATGGCGAAAGGCAAAAGCGTTGCGCAAGTCA<br>GTATGAGGTGGGTCTATGAGCAGGGCGCGTCTTTAGTAGTCAAGA<br>GTTTCTCTGAAGAACGTTTAAGAGAAAACCTGAATATTTTTGACTG<br>GGAGCTTACGAAAGAAGACAATGAGAAGATAGGCGAAATCCCGC<br>AATGTAGAATCCTTACTGCGTACTTCCTTGTCTCCCCGAACGGCCC<br>GTTTAAATCTCAGGAAGAGCTTTGGGATGACAAGGCAtaaACAGGC<br>CCCTTTTCCTTTGTCGATATCATGTAATTAGTTATGTCACGCTTACA<br>TTCACGCCCTCCTCCCACATCCGCTCTAACCGAAAAGGAAGGAGTT<br>AGACAACCTGAAGTCTAGGTCCCTATTTATTTTTTTTAATAGTTATG<br>TTAGTATTAAGAACGTTATTTATATTTCAAATTTTTCTTTTTTTTCTG<br>TACAAACGCGTGTACGCATGTAACATTATACTGAAAACCTTGCTTG<br>AGAAGGTTTTGGGACGCTCGAAGGCTTTAATTTGTAATCATTATCA<br>CTTTACGGGTCCTTTCCGGTGATCCGACAGGTTACGGGGCGGCGAC<br>CTCGCGGGTTTTCGCTATTTATGAAAATTTTCCGGTTTAAGGCGTTT<br>CCGTTCTTCTTCGTCATAACTTAATGTTTTTATTTAAAATACCTCGC<br>GAGTGGCAACACTGAAAATACCCATGGAGCGGCGTAACCGTCGCA<br>CAGgatctaggtgaagatcctttttgataatctcatgaccaaaatccc<br>ttaacgtgagttttcgttccactgagcgtcagaccccgtagaaaagat<br>caaaggatcttcttgagatcctttttttctgcgcgtaatctgctgctt<br>gcaaacaaaaaaaccaccgctaccagcggtggtttgtttgccggatca<br>agagctaccaactctttttccgaaggtaactggcttcagcagagcgca<br>gataccaaatactgtccttctagtgtagccgtagttaggccaccactt<br>caagaactctgtagcaccgcctacatacctcgctctgctaatcctgtt<br>accagtggctgctgccagtggcgataagtcgtgtcttaccgggttgga<br>ctcaagacgatagttaccggataaggcgcagcggtcgggctgaacggg<br>gggttcgtgcacacagcccagcttggagcgaacgacctacaccgaact<br>gagatacctacagcgtgagctatgagaaagcgccacgcttcccgaagg<br>gagaaaggcggacaggtatccggtaagcggcagggtcggaacaggaga<br>gcgcacgagggagcttccagggggaaacgcctggtatctttatagtcc<br>tgtcgggtttcgccacctctgacttgagcgtcgatttttgtgatgctc<br>gtcaggggggcggagcctatggaaaaacgccagcaacgcggcagtgga<br>acgTGCATTATGAATTAGTTACGCTAGGGATAACAGGGTAATATAGAA<br>CCCGAACGACCGAGCGCAGCGGCGGCCGCGCTGATACCGCCGC | | |

Morphinan Alkaloid Generating Modifications

Figure 20:
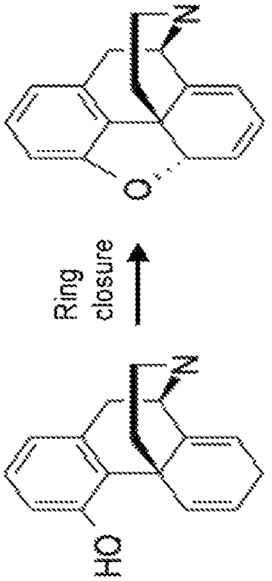
FIG. 20 illustrates the general ring closure reaction converting a tetracyclic scaffold to a pentacyclic scaffold, in accordance with embodiments of the invention.

Some methods, processes, and systems provided herein describe the conversion of promorphinan alkaloids to morphinan alkaloids. Some of the methods, processes, and systems describe the conversion of a tetracyclic scaffold to a pentacyclic scaffold (FIG. 20). Some of the methods, processes, and systems may comprise an engineered host cell. In some examples, the production of pentacyclic thebaine, or a morphinan alkaloid, from a tetracyclic precursor, or a promorphinan alkaloid is described. In some examples, the conversion of promorphinan alkaloids to thebaine are key steps in the conversion of a substrate to a diverse range of benzylisoquinoline alkaloids.

In some examples, the tetracyclic precursor may be salutaridine, salutaridinol, or salutaridinol-7-O-acetate. The tetracyclic precursor may be converted to pentacyclic thebaine by closure of an oxide bridge between C4 and C-5. In some examples, the tetracyclic precursor salutaridine may be prepared for ring closure by stepwise hydroxylation and O-acetylation at C-7. Ring closure may be activated by elimination of an acetate leaving group. In some examples, the allylic elimination and oxide ring closure that generates thebaine occurs spontaneously. In other examples, the ring closure reaction that generates pentacyclic thebaine is promoted by factors such as pH or solvent. In other examples, the thebaine-generating ring closure reaction is promoted by contact with a protein or enzyme. These conversion steps are provided in FIG. 14 and represented generally in Scheme 2. $R_1$, $R_2$, and $R_3$ may be H or $CH_3$. $R_4$ may be $CH_3$, $CH_3CH_2$, $CH_3CH_2CH_2$, or other appropriate alkyl group. In some cases, $R_1$, $R_2$, $R_3$, and $R_4$ may be $CH_3$ as provided in FIG. 14.

Scheme 2

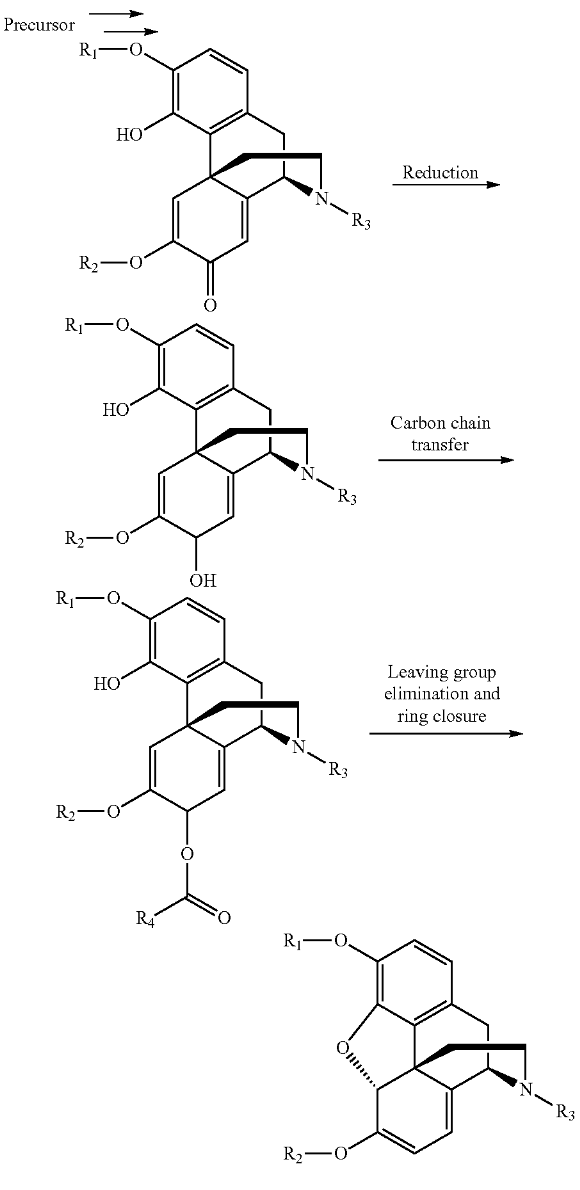

In some examples, the first enzyme that prepares the tetracyclic precursor is salutaridine reductase (SaR). In some cases, SalR hydroxylates the substrate salutaridine at the C-7 position (see Formula I). The product of this reaction may be one or more salutaridinol epimers. In some examples, the product is (7S)-salutaridinol. In some examples, the salutaridine reductase may catalyze the reduction reaction within a host cell, such as an engineered host, as described herein.

In some examples, the second enzymethat prepares the tetracyclic precursor is salutaridinol 7-o-acetyltransferase (SalAT). In some cases, SalAT transfers the acetyl from acetyl-CoA to the 7-OH of salutaridinol (see Formula IV). In other cases, SalAT may utilize a novel cofactor such as n-propionyl-CoA and transfer the propionyl to the 7-OH of salutaridinol. In some examples, the product of SalAT is (7S)-salutaridinol-7-o-acetate. In some examples, the salutaridinol 7-O-acetyltransferase may catalyze the acetyl transfer reaction within a host cell, such as an engineered host, as described herein.

In some examples, the tetracyclic precursor of thebaine is (7S)-salutaridinol-7-O-acetate. In some examples (7S)-salutaridinol-7-O-acetate is unstable and spontaneously eliminates the acetate at C-7 and closes the oxide bridge between C4 and C-5 to form thebaine (see Formula V). In some examples, the rate of elimination of the acetate leaving group is promoted by pH. In some examples, the allylic elimination and oxide bridge closure is catalyzed by an enzyme with thebaine synthase activity, or a thebaine synthase. In some examples, this enzyme is a Bet v 1-fold protein. In some examples, this enzyme is an engineered thebaine synthase, an engineered SalAT, a dirigent (DIR) protein, or a chalcone isomerase (CHI). In some examples, the enzyme encoding thebaine synthase activity may catalyze the ring closure reaction within a host cell, such as an engineered host, as described herein.

In some examples, the salutaridine reductase enzyme may be SalR or a SalR-like enzyme from plants in the *Ramunculales* order that biosynthesize thebaine, for example *Papaver somniferum*. In other examples, the enzyme with salutaridine reductase activity may be from mammals or any other vertebrate or invertebrate that biosynthesizes endogenous morphine.

In some examples, the salutaridinol 7-O-acetyltransferase enzyme may be SalAT or a SalAT-like enzyme from plants in the *Ramunculales* order that biosynthesize thebaine, for example *P. somniferum*. In other examples, the enzyme with salutaridinol 7-O-acetyltransferase activity may be from mammals or any other vertebrate or invertebrate that biosynthesizes endogenous morphine.

In some examples, the thebaine synthase enzyme may be a Bet v 1 fold protein from plants in the *Ramunculales* order that biosynthesize thebaine, for example *P. somniferum*. In some examples, the Bet v 1 protein includes the following domains in order from the N-terminus to C-terminus: a β-strand, one or two α-helices, six β-strands, and one or two α-helices. The protein is organized such that it has a Bet v 1 fold and an active site that accepts large, bulky, hydrophobic molecules, such as morphinan alkaloids. This protein may be any plant Bet v 1 protein, pathogenesis-related 10 protein (PR-10), a major latex protein (MLP), fruit or pollen allergen, plant hormone binding protein (e.g., binding to cytokinin or brassinosteroids), plant polyketide cyclase-like protein, or norcoclaurine synthase (NCS)-related protein that has a Bet v 1 fold. Other non-plant examples of the Bet v 1 fold protein are polyketide cyclases, activator of Hsp90 ATPase homolog 1 (AHA1) proteins, SMU440-like proteins (e.g., from *Streptococcus mutans*), PA1206-related proteins (e.g., from *Pseudomonas aeruginosa*), CalC calicheamicin resistance protein (e.g., from *Micromonospora echinospora*), and the CoxG protein from carbon monoxide metabolizing *Oligotropha carboxidovorans*. Further examples from Bet v 1-related families include START lipid transfer proteins, phosphatidylinositol transfer proteins, and ring hydroxylases.

In some examples, the thebaine synthase enzyme may be a dirigent protein from plants in the *Ramunculales* order that biosynthesize thebaine, for example *P. somniferum*. In other examples, the enzyme may be any dirigent protein from plants.

In some examples, the thebaine synthase enzyme may be a chalcone isomerase protein from plants in the *Ramunculales* order that biosynthesize thebaine, for example *P. somniferum*. In other examples, the enzyme may be any chalcone isomerase protein from plants.

In some examples, the thebaine synthase enzyme may be a SalAT-like enzyme from plants in the *Ramunculales* order that biosynthesize thebaine, for example *P. somniferum*. In other examples, the enzyme may be any SalAT-like protein from plants.

In some examples, the enzyme with thebaine synthase activity may be from mammals or any other vertebrate or invertebrate that biosynthesizes endogenous morphine.

In some examples, any combination of the above enzymes together with additional accessory proteins may function to convert any tetracyclic precursor into thebaine. In some examples, these enzymes catalyze the reactions within a host cell, such as an engineered host, as described herein.

Examples of amino acid sequences for thebaine synthase activity are set forth in Table 2. An amino acid sequence for a thebaine synthase that is utilized in a tetracyclic precursor to thebaine may be 45% or more identical to a given amino acid sequence as listed in Table 2. For example, an amino acid sequence for such a thebaine synthase may comprise an amino acid sequence that is at least 45% or more, 46% or more, 47% or more, 48% or more, 49% or more, 50% or more, 51% or more, 52% or more, 53% or more, 54% or more, 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more identical to an amino acid sequence as provided herein. Additionally, in certain embodiments, an "identical" amino acid sequence contains at least 80%-99% identity at the amino acid level to the specific amino acid sequence. In some cases an "identical" amino acid sequence contains at least about 85%, 86%, 87%, 88%, 89%, 90%, 91%, 92%, 93%, 94% and more in certain cases, at least 95%, 96%, 97%, 98% and 99% identity, at the amino acid level. In some cases, the amino acid sequence may be identical but the DNA sequence is altered such as to optimize codon usage for the host organism, for example.

An engineered host cell may be provided that produces a salutaridine reductase, salutaridinol 7-O-acetyltransferase, and thebaine synthase that converts a tetracyclic precursor into thebaine, wherein the thebaine synthase comprises an amino acid sequence selected from the group consisting of SEQ ID NOs: 30, 31, 32, 33, 34, 35, 36, and 37. In some cases, the thebaine synthase may form a fusion protein with other enzymes. The enzymes that are produced within the engineered host cell may be recovered and purified so as to form a biocatalyst. These one or more enzymes may also be used to catalyze the conversion of a tetracyclic promorphinan precursor to thebaine.

In other examples, the thebaine synthase comprises an amino acid sequence selected from the group consisting of SEQ ID NOs: 38, 39, 40, 41, 42, 43, 44, 45, 46, 47, 48, 49, 50, 51, 52, 53, 54, 55, 56, 57, 58, 59, 60, and 61.

In additional cases, the one or more enzymes that are recovered from the engineered host cell may be used in a process for converting a tetracyclic promorphinan precursor to a thebaine. The process may include contacting the tetracyclic promorphinan precursor with the recovered enzymes in an amount sufficient to convert said tetracyclic promorphinan precursor to thebaine. In examples, the tetracyclic promorphinan precursor may be contacted with a sufficient amount of the one or more enzymes such that at least 5% of said tetracyclic promorphinan precursor is converted to thebaine. In further examples, the tetracyclic promorphinan precursor may be contacted with a sufficient amount of the one or more enzymes such that at least 10%, at least 15%, at least 20%, at least 25%, at least 30%, at least 35%, at least 40%, at least 45%, at least 50%, at least 55%, at least 60%, at least 65%, at least 70%, at least 80%, at least 82%, at least 84%, at least 86%, at least 88%, at least 90%, at least 91%, at least 92%, at least 93%, at least 94%, at least 95%, at least 96%, at least 97%, at least 98%, at least 99%, at least 99.5%, at least 99.7%, or 100% of said tetracyclic promorphinan precursor is converted to thebaine.

In some examples, process conditions are implemented to support the formation of thebaine in engineered host cells. In some cases, engineered host cells are grown at pH 3.3, and once high cell density is reached the pH is adjusted to pH 8.0 to support continued production of thebaine at higher pH. In some cases, the engineered host cells produce additional enzymes to convert sugar and other simple precursors, such as tyrosine, to thebaine. In some cases, the SalAT enzyme has been engineered to exhibit higher activity at pH 8.0 and is expressed from a late stage promoter.

In some examples, one or more of the enzymes converting a tetracyclic promorphinan precursor to a thebaine are localized to cellular compartments. In some examples, SalR, SalAT, and Bet v 1 may be modified such that they encode targeting sequences that localize them to the endoplasmic reticulum membrane of the engineered host cell (see for example WO2014143744). In other examples, SalAT and Bet v 1 may be co-localized in to a single protein fusion. In some examples, the fusion is created between SalAT and Bet v 1 by one of several methods, including, direct fusion, co-localization to a yeast organelle, or by enzyme co-localization tools such as leucine zippers, protein scaffolds that utilize adaptor domains, or RNA scaffolds that utilize aptamers. Co-localizing the thebaine synthesis enzyme may facilitate substrate channeling between the active sites of the enzymes and limit the diffusion of unstable intermediates such as salutaridinol-7-O-acetate.

In some examples, an engineered salutaridinol 7-O-acetyltransferase (SalAT) enzyme is used in converting a tetracyclic promorphinan precursor to a thebaine. In some examples, a SalAT enzyme is engineered to combine two functions: (1) the transfer of an acyl group from acetyl-CoA to the 7-OH of salutaridinol, and (2) the subsequent elimination of the acetyl group and closure of an oxide bridge between carbons C4 and C5 to form thebaine.

In some examples, an enzyme with salutaridinol 7-O-acetyltransferase activity is fused to a peptide with a Bet v 1 fold. In some examples, salutaridinol 7-O-acetyltransferase enzyme and the Bet v 1 fold protein may be fused in any order from N-terminus to C-terminus, C-terminus to N-terminus, N-terminus to N-terminus, or C-terminus to C-terminus. In some examples, the two protein sequences may be fused directly or fused through a peptide linker region.

In some examples, an enzyme with salutaridinol 7-O-acetyltransferase activity is fused to a peptide with a Bet v 1 fold by circular permutation. In some cases, the N- and C-termini of SalAT are fused and the Bet v 1 sequence is then inserted randomly within this sequence. In some cases, the resulting fusion protein library is screened for thebaine production. In other cases, a circular permutation SalAT library is first screened for activity in the absence of Bet v 1. In other cases, the N- and C-termini of SalAT are fused and the enzyme is digested and blunt end cloned. In other cases, this library of circularly permuted SalAT is screened for salutaridinol 7-O-acetyltransferase activity. In other cases, active variants from the circularly permuted SalAT library are then used to design protein fusions with a peptide with a Bet v 1 fold.

The one or more enzymes that may be used to convert a tetracyclic promorphinan precursor to a thebaine may contact the tetracyclic promorphinan precursor in vitro. Additionally, or alternatively, the one or more enzymes that may be used to convert a tetracyclic promorphinan precursor to thebaine may contact the tetracyclic promorphinan precursor in vivo. Additionally, the one or more enzymes that may be used to convert a tetracyclic promorphinan precursor to thebaine may be provided to a cell having the tetracyclic promorphinan precursor within, or may be produced within an engineered host cell.

In some examples, the methods provide for engineered host cells that produce an alkaloid product, wherein the conversion of a tetracyclic promorphinan precursor to a thebaine may comprise a key step in the production of an alkaloid product. In some examples, the alkaloid product is a thebaine. In still other embodiments, the alkaloid product is derived from a thebaine, including for example, downstream morphinan alkaloids. In another embodiment, a tetracyclic promorphinan precursor is an intermediate toward the product in of the engineered host cell. In still other embodiments, the alkaloid product is selected from the group consisting of morphinan, nor-opioid, or nal-opioid alkaloids.

In some examples, the substrate of the reduction reaction is a compound of Formula III:

Formula III

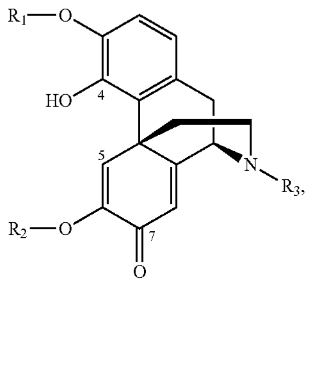

or a salt thereof, wherein:

$R_1$, $R_2$, and $R_3$ are independently selected from hydrogen and methyl.

In some other examples, $R_1$, $R_2$, and $R_3$ are methyl, and the reduction reaction is catalyzed by a salutaridine reductase.

In some examples, the substrate of the carbon chain transfer reaction is a compound of Formula IV:

Formula IV

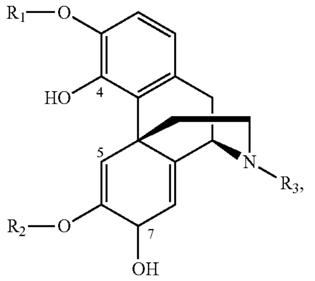

or a salt thereof, wherein:

$R_1$, $R_2$, and $R_3$ are independently selected from hydrogen and methyl.

In some other examples, $R_1$, $R_2$, and $R_3$ are methyl, and the carbon chain transfer reaction is catalyzed by a salutaridinol 7-O-acetyltransferase.

In some examples, the substrate of thebaine synthase is a compound of Formula V:

Formula V

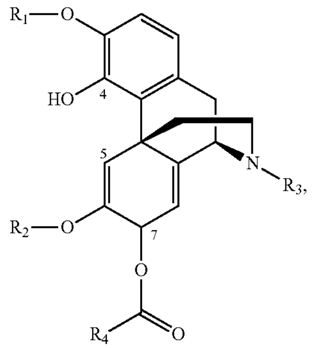

or a salt thereof, wherein:

$R_1$, $R_2$, and $R_3$ are independently selected from hydrogen and methyl; and $R_4$ is selected from methyl, ethyl, propyl, and other appropriate alkyl group.

In some other examples, $R_1$, $R_2$, $R_3$, and $R_4$ are methyl, and the ring closure reaction is catalyzed by a thebaine synthase. In some examples, the thebaine synthase is a Bet v 1 protein.

In some examples, the methods provide for engineered host cells that produce alkaloid products from salutaridine. The conversion of salutardine to thebaine may comprise a key step in the production of diverse alkaloid products from a precursor. In some examples, the precursor is L-tyrosine or a sugar (e.g., glucose). The diverse alkaloid products can include, without limitation, morphinan, nor-opioid, or nal-opioid alkaloids.

Any suitable carbon source may be used as a precursor toward a pentacyclic morphinan alkaloid. Suitable precursors can include, without limitation, monosaccharides (e.g., glucose, fructose, galactose, xylose), oligosaccharides (e.g., lactose, sucrose, raffinose), polysaccharides (e.g., starch, cellulose), or a combination thereof. In some examples, unpurified mixtures from renewable feedstocks can be used (e.g., cornsteep liquor, sugar beet molasses, barley malt, biomass hydrolysate). In still other embodiments, the carbon precursor can be a one-carbon compound (e.g., methanol, carbon dioxide) or a two-carbon compound (e.g., ethanol). In yet other embodiments, other carbon-containing compounds can be utilized, for example, methylamine, glucosamine, and amino acids (e.g., L-tyrosine). In some examples, a 1-benzylisoquinoline alkaloid may be added directly to an engineered host cell of the invention, including, for example, norlaudanosoline, laudanosoline, norreticuline, and reticuline.

In some examples, the benzylisoquinoline alkaloid product, or a derivative thereof, is recovered. In some examples, the benzylisoquinoline alkaloid product is recovered from a cell culture. In some examples, the benzylisoquinoline alkaloid product is a morphinan, nor-opioid, or nal-opioid alkaloid.

TABLE 2

Example amino acid sequences of morphinan alkaloid generating enzymes.

| Sequence Name | Description | Sequence | SEQ. ID NO. |
|---|---|---|---|
| Bet v1 | | | |
| | *P. bracteatum* | MAPRGVSGLVGKLSTELDVNCDAEKYYNMYKNGEDVQKA VPHLCMDVKVISGDATRSGCIKEWNVNIDGKTIRSVEETTH NDETKTLRHRVFEGDMMKDYKKFDTIMEVNPKPDGNGCV VTRSIEYEKVNENSPTPFDYLQFGHQAMEDMNKY | SEQ. ID. NO. 30 |
| | *P. setigerum* | MLVGKLSTELEVDCDAEKYYNMYKHGEDVKKALCVDVKVI SGDPTRSGCIKEWNVNIDGKTIRSVEETTHNDETKTLRHRV FEGDMMKDFKKFDTIMVVNPKPDGNGCVVTRSIEYEKTNE NSPTPFDYLQFGHQAIEDMNKYL | SEQ. ID. NO. 31 |
| | *P. setigerum* | MLVGKLSTELEVDCDAEKYYNMYKHGEDKRQCVDVKVISG DPTRSGCIKEWNVNIDGKTIRSVEETTHNDETKTLRHRVFE GDMMKDFKKFDTIMVVNPKPDGNGCVVTRSIEYEKTNENS PTPFDYLQFGHQAIEDMNKY | SEQ. ID. NO. 32 |
| | *P. setigerum* | MLVGKLSTELEVDCDAEKYYNMYKHGEDVKKAVPHLCVDV KIISGDPTSSGCIKEWNVNIDGKTIRSVEETTHDDETKTLRH RVFEGDVMKDFKKFDTIMVVNPKPDGNGCVVTRSIEYEKT NENSPTPFDYLQFGHQAIEDMNKYL | SEQ. ID. NO. 33 |
| | *P. setigerum* | MVKIISGDPTSSGCIKEWNVNIDGKTIRSVEETTHDDETKTL RHRVFEGDVMKDFKKFDTIMVVNPKPDGNGCVVTRSIEYE KTNENSPTPFDYLQFGHQAIEDMNKYL | SEQ. ID. NO. 34 |
| | *P. somniferum* | MDSINSSIYFCAYFRELIIKLLMAPPGVSGLVGKLSTELEVNC DAEKYYNMYKHGEDVQKAVPHLCVDVKVISGDPTRSGCIKE WNVNIDGKTIRSVEETTHNDETKTLRHRVFEGDVMKDFKK FDTIMVVNPKPDGNGCVVTRSIEYEKTNDNSPTPFDYLQFG HQAIEDMNKYLRDSE | SEQ. ID. NO. 35 |
| | *P. somniferum* | MNFFIKDHLYICLVGKLSTELEVDCDAEKYYNMYKHGEDVK KAVPHLCVDVKIISGDPTSSGCIKEWNVNIDGKTIRSVEETT HDDETKTLRHRVFEGDVMKDFKKFDTIMVVNPKPDGNGC VVTRSIEYEKTNENSPTPFDYLQFGHQAIEDMNKYLRDSES N | SEQ. ID. NO. 36 |
| | *P. somniferum* | MAPLGVSGLVGKLSTELEVDCDAEKYYNMYKHGEDVKKAV PHLCVDVKIISGDPTSSGCIKEWNVNIDGKTIRSVEETTHDD ETKTLRHRVFEGDVMKDFKKFDTIMVVNPKPDGNGCVVTR SIEYEKTNENSPTPFDYLQFGHQAIEDMNKYLRDSESN | SEQ. ID. NO. 37 |
| SalAT | | | |
| | *P. somniferum* | MMKVCVSSREKIKPSRPTPGHLKTHKLSFLDQVAARIYVPL LLYYAGNKENVDTDTRCNIIKKSLAETLTKFYILAGKIVNDEI ERFVNCNDDGVDFCVTKVSNCQLFQVIKRPDIFDQVTLFLP FDPCDNEITASGDFLLSVQVNVFEDCRGMVIGLCINHKVAD ASSITTFVNYWATIARGLVLNVDDRQIQDPCFQVQSIFPQKE KGIGFKISSSSIDGTLVTKKFGFEASKLAELKERCKFAGATED IRGGYKPNRVEALSTFLWKCFIDIDQAKTKAAAPARVYLAS NAVNIRSRIVPQLPTSSFGNMVAITDAIFTVNSNENNGINDP YYPKLVQKFRDAVKRVDGEYIEALQSTDLLLNNVTKLFKHI LNGQTLSISFTSWCRFPFYDTDLLD | SEQ. ID. NO. 38 |

TABLE 2-continued

Example amino acid sequences of morphinan alkaloid generating enzymes.

| Sequence Name | Description | Sequence | SEQ. ID NO. |
|---|---|---|---|
| | *P. somniferum* | MKVQVISKELIKPSTPTPPRLRNFKLSLLDQLLPPFYVPIIIFY PANDDHESNNNDQCIKANILKKSLSETLTRFYPIAGRIRDKI LVECNDEGVHYIEAKVNAVMSDFMSLDVIHQLHPSYITLDD LAEEAQLAVQVTMFDCGGIALSICSSHKIIDGCTSTTFLNSW AATARAPSNPEIVYPTFDAAAIFPAQPSGVQVSTLESDDRLQ GENVVTKRFLFSASKITALRARIAESRSSNILSKYPSRSEAVS ALVWKSFMETSRVKVTREHTFSAEASTKPIVRSIANFVVNL RTRLNPPLPNVSFGNIIMDATAESLIIDNGENTLGFVETLDG LISQLRLGVTKMDDEYVRKLREDDVEFLKSLDEASHPSNGE GDGNGERV | SEQ. ID. NO. 39 |
| | *P. setigerum* | MNDTMKIEVVSKESIKPSYPTPNNLKIHNLSNLDQLIPAFY MDHILYYPSLDSNDSSLGDDEEDKKMIFSASSRHRCDVVKK SLAETLTRYYPLAGRIKDEKSVECNDEGVDYIEARVVGITVS QVIQLASSDIEVMEPFLPYEPYGGTGSAFRRAGIHSNSKPLL KIQVNVFDCGGMVICLSGSHKVIDATSILNFVNDWAATARG GFDTHDDELKVAVVDKPCYIFSSMFPPTSFGNQEEKDTADQ AQLVPDRIEIVTKRFVFKDSSIAKLKKKCIHVNTNNGSDHQV DKQEHNMQQMPSRIEALTSLIWMCFMDVDRRFRVKQIDD AVSPVNTVNEVSLPKQVQYVAGFAINLRTRTIQPLPTNSFG NMTDTAIAEVTLNLTGSDHFNNEKGIRDQSQNYPELVSKIK DSIKLVDNKHIEAMKRNLAISCNNIKMHQMMKESTFDQNT RELLMFSSWCRFPIYEADFGWGKPSWASITKLLYKNCVMF LDTSSGDGIEAWVSLKEEDMVEFERHEELVALAS | SEQ. ID. NO. 40 |
| | *P. somniferum* | MKVQVISKEIIKPSSPTPPHLRNFKLSLLDQILPPFYVPIVMF YPAGDDYVTNNNIHDQSSKSEFLKKSLSETLTRFYPIAGRIK DNILIDCNNEGVDYIEAKVNGIMSDFMSVDVVHQLHPSHIM LDDVAKEAQLAVQVNLFDCGGIAISISMSHKIVDACTAITFIN GWAATARAAPKQEIVCPTFDSAAIFPALPPGVQVSSLESDDS VQGVNVVTKMFAFTAPKIASLRARIAELRSSSDGLSKYPTRT EALSALVWKSFIRTSRVKAARKYSLSPASTKPVIKSVANYAV NLRTRLNPPLPQVSFGNILMDATAESTTTIDDDDSHEFADT LAGLIGQLRLGVSRINGDYIRKLQEGDLAFLKSLDEASHDSN GEKVQICWISSLCRFPFYEADFGWGKPSWVALNTNAEYKN SLFLMDTKCGTGIEAWVSLEEDDMAIFEEDQDLLQCVKSIN | SEQ. ID. NO. 41 |
| | *P. setigerum* | MENMKVEVVLKQTIKPSTQTPLHSKTFNLSFLDQHLGPPIYI PFTLYYESGDVNNKNNHCDGYKNNLEEACEHRVSVIKQSLS ETLARYYPLAGRMKEDNLAVECNDEGVEYFETRVSDVRLS QVIKRSPNHNSVLRKFLPPCISSCDNSMSIPFDYGFKSKTLLA IQVNIFECGGIVIGMCMAHRLADASTMFTFITDWAATARGA IEDIKGPSFDFSYTLFPQKDVINNFKPFDPMLTREEDLVTKY FVFPASKIVELKRRNVNNIVCQDTSQQNTSPCTRVEAVTSF MWKRYMDSVRAKNQTQATSVEKYGALYTVNLRSRITPPLP ANSFGNIYTFTIALSTPSDENDIDDGLRKDVSSPNDLNLVGK VRDAIKKIDDKYTRKLQSSEDELVNDVKPLTSGEAIFLGFSS WCRFPIYEADFGWGKPTWVSIGTMALRNTVFLMDTKSGD GIEAFVNMAKEDMDNFEVKLLADQ | SEQ. ID. NO. 42 |
| | *P. setigerum* | MENMKVEVVLEQTIKPSTQTPLHSKTFNLSFLDQHLGPPIYI PFTLYYESGDVNNKNNHCDGYKNNLEEVCEHRVSVIKQSLS ETLARYYPLAGRMKEDNLAVECNDEGVEYFETRVSDVRLS QVIKRSPNHNSVLRKFLPPCISSCDNSMSIPFDYGFKSKTLLA IQVNIFECGGIVIGMCMAHRLADASTMFTFITDWAATARGA IEDIKGPSFDFSYTLFPQKDVINNFKPFDPMLTREEDLVTKY FVFPASKIVELKRRNVNNIVCQDTSQQNTSPCTRVEAVTSF MWKRYMDSVRAKNQTQATSVEKYGALYTVNLRSRITPPLP ANSFGNIYTFTIALSTPSDENDIDDGLRKDVSSPNDLNLVGK VRDAIKKIDDKYTRKLQSSEDELVNDVKPLTSGEAIFLGFSS WCRFPIYEADFGWGKPTWVSIGTMALRNTVFLMDTKSGD GIEAFVNMAKEDMDNFEVKLLADQLLHVHPTV | SEQ. ID. NO. 43 |

TABLE 2-continued

Example amino acid sequences of morphinan alkaloid generating enzymes.

| Sequence Name | Description | Sequence | SEQ. ID NO. |
|---|---|---|---|
| | *P. setigerum* | MSSTVEVISKQTIKPSTPTPIQRKNHSLSLIDQHFAPIYIPIVL FYPAAAVNDTGNVQHGDNTCVLKRSLSETLVHFYPLAGRM KDNIVVDCNDQGVEFTEVKVSGTMCDFLMKPDEQLSGLLP SEAVCMNFVREAQVMIQVNTFDCGSKAISLCVSHKIADASTI TTFSRCWAETTIAVSKSTSAVTPIVSSKFHPTFDAASLFPPIK QLISPSGVTPALPELIPSEESKFGKIISKRFLFSATTINSVREKL SALMADKLKYRRLTRVEVVSALIWNSFDKLATTGSVAVMV KHAVNLRKRIDPPLPDVSFGNILEFTKAVVGEAAANTTTQG TVGSSSKLLEELSEFAGQLREPVSKMNKGDHDFDMENTDY EERDLWMSSWCNYGLYDIDFGCGKPVWVTTVATMYPYSD GFFMNDTRCGQGIEVWGNLVEEDMANFQLNLSELLDRI | SEQ. ID. NO. 44 |
| | *P. somniferum* | MMKVCVSSREKIKPSRPTPGHLKTHKLSFLDQVAARIYVPL LLYYAGNKENVDTDTRCNIIKKSLAETLTKFYILAGKIVNDEI ERFVNCNDDGVDFCVTKVSNCQLFQVIKRPDIFDQVTLFLP FDPCDNEITASGDFLLSVQVNVFEDCRGMVIGLCINHKVAD ASSITTFVNYWATIARGLVLNVDDRQIQDPCFQVQSIFPQKE KGIGFKISSSSIDGTLVTKKFGFEASKLAELKERCKFTTEPED GYKPTRVEALSAFLWKCFIDIDQAKLKGVARTKVYLATNAV NMRSRMVPQLPTSSFGNIISITDAVFSINNDDSTGINDPYYP KLVRKFRDAIKKIDRDYIEALRSTDLLLNNMMKLIEHVLSG HTLSIYFSSWCRFPLYETDFGWGKPIWVSTCTIPQKNVIVL MDSNSSADGIEAYVTLAKEDMGELEHHEELLALIS | SEQ. ID. NO. 45 |
| Dirigent proteins | | | |
| | *P. somniferum* | MGAMKFFSFLAVAMVLSLAHIQAQQGNWGDETVPYTMGP EKITKLRFYFHDIVTGNNPTAVQIAQATGTNSSSTLFGALFM IDDPLTEGPDPDSRLVGRAQGFYGSAGQNEAALILGMSLVF TGNEKFNGSTISVLSRNPVTHTEREFAIVGGTGYFQFARGFI SAKTYSLVGPNAVVEYNCTIVHPSSVSESGKSNSSPGKSDSN SGSQISLGSNLVFVSVIAYVTIILSL | SEQ. ID. NO. 46 |
| | *P. setigerum* | MVLSMSHSQAQEGNWGDESVPYTMGPEKMTKLRFYFHDII TGNSPTAVQIAQATGTNTSATMFGALMMIDDPLTEGPDPN SRLVGRAQGFYGSAGQNELALILGMSLVFTGNEKFNGSTISV LSRNPVMHTEREFAIVGGTGYFQFARGFISAKTYSLVGPNA VVEYNCTIVHPSSVSESGKSDSSSGKSDSSSGSQISLGTNLVF LSVIAFVTIIVSPQHFSW | SEQ. ID. NO. 47 |
| Chalcone isomerase | | | |
| | *P. somniferum* | MTKTVLVDDIPFPQNITTVTTEKQLPLLGQGITDMEIH FLQIKFTAIGTAIGVYLEPEIASHLQQWKGKTGAELSQ DDEFFAAVVSASVEKYVRVVVIKEIKGSQYMLQLES WVRDELAAADKYEDEEEESLDKVIEFFQSKYLKQLSF IPSHFSATTPAVAEIGLEIEGQKDLKIKVENGNVIEMIQ KWYLGGTRGVSPSTTQSLATSL | SEQ. ID. NO. 48 |
| | *P. somniferum* | MPFLKAIEIEGCKFRPFVTPPGSTQILFLAGSGVKEEFG DSKSMKYSSCAIYLQPTCILYLAKAWAQKSVVDITQS LNFFMDIATGPFEKYCRITMLETAKGEDYAAMITKNC EEMLTNSKRYSETAKAALTKESEAFNGRTLASGSSIH VTVSTSNSVTLAFTEDGSTPKQGDVTLDCKEVGEAFL MSTISLHTTIRESMGSRISGLYK | SEQ. ID. NO. 49 |
| | *P. setigerum* | MAPMAQLSEIQVEQFVFPPTMTPPSSTESLFLGGAGVR GLQIQDRFIKFTAIGVYLAEEAIPSLSPKWKSKSPEELT DDVEFFMDIVTGPFEKFVKITMILPLTGDQYAEKVTEN CIQYLKSKDMYTDAEAKAVERFIEIFKNEMFPPASSIL FTISPAGSLTVGF* | SEQ. ID. NO. 50 |
| | *P. rhoeas* | MVYLEPEIATHLKQWKGKTGAELSQDDDFFSAVVSA PVEKYVRVVVIKEIKGSQYMLQLESWVRDELAAADK YEDEEEESLDKVIEFFQSKYLKQHSVIITFHFSATTPAV AEIGLEIEGQKDLKIKVENGNVVEMIQKWYLGGTRGV SPSTTQSLATSL | SEQ. ID. NO. 51 |

TABLE 2-continued

Example amino acid sequences of morphinan alkaloid generating enzymes.

| Sequence Name | Description | Sequence | SEQ. ID NO. |
|---|---|---|---|
| | *P. bracteatum* | MTKMVLVDDIPFPQNITTATTAKQLPLLGQGITDMEIH<br>FLQIKFTAIGVYLEPEIASHLKQWKGKTGAELSQDDEF<br>FSAIVSAPVEKYVRVVVIKEIKGSQYMLQLESWVRDE<br>LAAADKYEDEEEESLEKVIEFFQSKYLKQHSVIPFHFS<br>ATTPAVAEIGLEIEGHKDLKMKVENGNVVEMIQKWY<br>LAGTRGVSPSTTQSLATSL | SEQ. ID. NO. 52 |
| | *P. bracteatum* | MAPMAQLSEIQVEQFVFPPTMTPPSSTESLFLGGAGVR<br>GLQIQDRFIKFTAIGVYLAEEAIPSLSPKWKSKTPEELT<br>NDVEFFMDIVTGPFEKFVKITMILPLTGDQYAEKVTEN<br>CVEYLKSKDLYTDAEAKAVERFIEIFKNEMFPPASSIL<br>FTISPTGSLTVGFSKDTSIPEARNAVIENKALSESILESII<br>GKNGVSPAAKQSLAERISELLK | SEQ. ID. NO. 53 |
| Other | | | |
| | *P. ginseng* | MGLTGKLICQTGIKSDGDVFHELFGTRPHHVPNITPANIQGC<br>DLHEGEFGKVGSVVIWNYSIDGNAMIAKEEIVAIDEEDKSVT<br>FKVVEGHLFEEFKSIVFSVHVDTKGEDNLVTWSIDYEKLNE<br>SVKDPTSYLDFLLSVTRDIEAHHLPK | SEQ. ID. NO. 54 |
| | *A. hypogaea* | MGVFTFEDEITSTVPPAKLYNAMKDADSITPKIIDDVKSVEI<br>VEGNGGPGTIKKLTIVEDGETKFILHKVESIDEANYAYNYSV<br>VGGVALPPTAEKITFETKLVEGPNGGSIGKLTLKYHTKGDA<br>KPDEEELKKGKAKGEGLFRAIEGYVLANPTQY | SEQ. ID. NO. 55 |
| | *H. perforatum* | MGIDPFTMAAYTIVKEEESPIAPHRLFKALVLERHQVLVKA<br>QPHVFKSGEIIEGDGGVGTVTKITFVDGHPLTYMLHKFDEID<br>AANFYCKYTLFEGDVLRDNIEKVVYEVKLEAVGGGSKGKIT<br>VTYHPKPGCTVNEEEVKIGEKKAYEFYKQVEEYLAANPEVF<br>A | SEQ. ID. NO. 56 |
| | *L. luteus* | MGVFTFQDEYTSTIAPAKLYKALVTDADIIIPKAVETIQSVEI<br>VEGNGGPGTIKKLTFIEGGESKYVLHKIEAIDEANLGYNYSIV<br>GGVGLPDTIEKISFETKLVEGANGGSIGKVTIKIETKGDAQPN<br>EEEGKAAKARGDAFFKAIESYLSAHPDYN | SEQ. ID. NO. 57 |
| | Strawberry (*Fragaria* x *ananassa*) | MAGVFTYETEFTSVIPPPRLFKAFILDADNLIPKIAPQAVKC<br>AEIIEGDGGVGTIKKITFGEGSQFGSVTHKIDGIDKENFVYSY<br>SLIEGDALSDKIEKISYETKLVSSSDGGSIIKSTSNYHTKGDVE<br>IKEEHVKAGKEKFSHLFKLVEGYLLANPNEYC | SEQ. ID. NO. 58 |
| | *A. deliciosa* | MDLSGKMVKQVEILSDGIVFYEIFRYRLYLISEMSPVNIQGV<br>DLLEGNWGTVGSVIFFKYTIDGKEKTAKDIVEAIDEETKSVT<br>FKIVEGDLMELYKTFIIIVQVDTKGEHNSVTWTFHYEKLKE<br>DVEEPNTLMNFCIEITKDIETYHLK | SEQ. ID. NO. 59 |
| | *T. flavum* | MGIINQVSTVTKVIHHELEVAASADDIWTVYSWPGLAKHLP<br>DLLPGAFEKLEIIGDGGVGTILDMTFVPGEFPHEYKEKFILV<br>DNEHRLKKVQMIEGGYLDLGVTYYMDTIHVVPTGKDSCVIK<br>SSTEYHVKPEFVKIVEPLITTGPLAAMADAISKLVLEHKS | SEQ. ID. NO. 60 |
| | *V. radiata* | MVKEFNTQTELSVRLEALWAVLSKDFITVVPKVLPHIVKDV<br>QLIEGDGGVGTILIFNFLPEVSPSYQREEITEFDESSHEIGLQV<br>IEGGYLSQGLSYYKTTFKLSEIEEDKTLVNVKISYDHDSDIEE<br>KVTPTKTSQSTLMYLRRLERYLSNGSA | SEQ. ID. NO. 61 |

BIA Generating Modifications

Once BIAs are formed, the BIAs may be further derivatized or modified. The BIAs may be derivatized or modified utilizing one or more enzymes that are produced by the engineered host cell. In particular, the BIAs may be derivatized or modified by contacting the BIAs with one or more enzymes that are produced by the engineered host cell. Additionally or alternatively, the BIAs may be derivatized or modified by contacting the BIAs with one or more enzymes that are provided to the BIAs from a source that is external to the engineered host cell. The one or more enzymes that may be used to derivatize or modify the BIAs may be used to perform tailoring reactions. Examples of tailoring reactions include oxidation, reduction, O-methylation, N-methylation, O-demethylation, acetylation, methylenedioxy-bridge formation, and O,O-demethylenation. A BIA may be derivatized or modified using one or more tailoring reactions.

Examples of tailoring reactions are provided in Table 9. In some examples, tailoring enzymes may be used to catalyze carbon-carbon coupling reactions performed on a BIA, or a derivative thereof. Examples of tailoring enzymes that may be used to catalyze carbon-carbon coupling reactions include a Berberine bridge enzyme (BBE) from *Papaver somniferum, Eschscholzia californica, Coptis japonica, Berberis stolonifer, Thalictrum flavum*, or another species; Salutaridine synthase (SalSyn) from *Papaver somniferum* or another species; and Corytuberine synthase (CorSyn) from *Coptis japonica* or another species. Non-limiting examples of reactions that can be catalyzed by tailoring enzymes are shown in Scheme 3, wherein $R^a$, $R^b$, $R^c$, and $R^d$ are independently selected from hydrogen, hydroxy, fluoro, chloro, bromo, carboxaldehyde, $C_1$-$C_4$ acyl, $C_1$-$C_4$alkyl, and $C_1$-$C_4$alkoxy. In some examples, RV, $R^b$, and the carbon atoms to which they are attached optionally form a carbocycle or heterocycle. In some examples, $R^c$, $R^d$, and the carbon atoms to which they are attached optionally form a carbocycle or heterocycle.

In other examples, tailoring enzymes may be used to catalyze O-methylation reactions performed on a BIA, or a derivative thereof. Examples of tailoring enzymes that may be used to catalyze O-methylation reactions include a Norcoclaurine 6-O-methyltransferase (6OMT) from *Papaver somniferum, Thalictrum flavum, Coptis japonica, Papaver bracteatum*, or another species; 3'hydroxy-N-methylcoclaurine 4'-O-methyltransferase (4'OMT) from *Papaver somniferum, Thalictrum flavum, Coptis japonica, Coptis chinensis*, or another species; Reticuline 7-O-methyltransferase (7OMT) from *Papaver somniferum, Eschscholzia californica*, or another species; and Scoulerine 9-O-methyltransferase (9OMT) from *Papaver somniferum, Thalictrum flavum, Coptis japonica, Coptis chinensis*, or another species.

Scheme 3

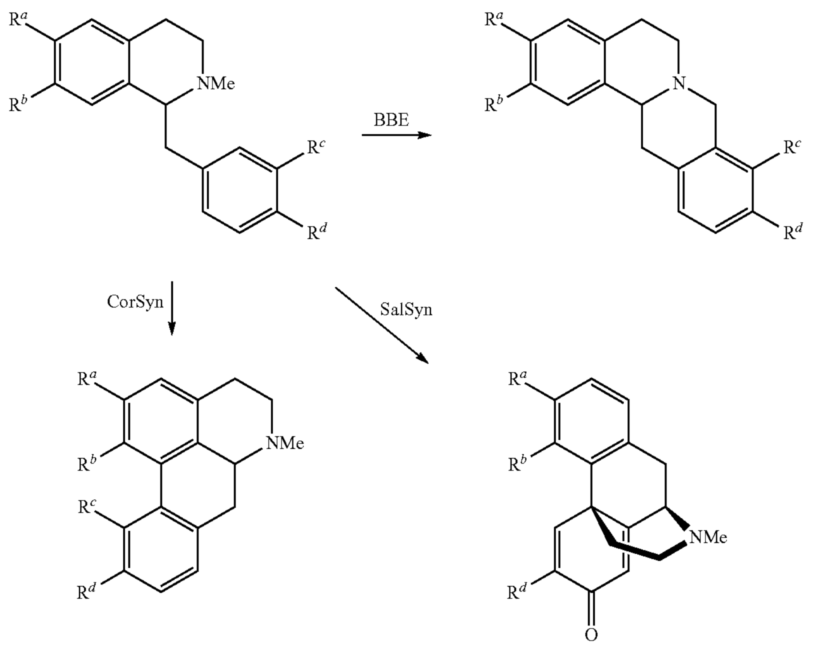

In some examples, tailoring enzymes may be used to catalyze oxidation reactions performed on a BIA, or a derivative thereof. Examples of tailoring enzymes that may be used to catalyze oxidation reactions include a Tetrahydroprotoberberine oxidase (STOX) from *Coptis japonica, Argemone mexicana, Berberis wilsonae*, or another species; Dihydrobenzophenanthridine oxidase (DBOX) from *Papaver somniferum* or another species; Methylstylopine hydroxylase (MSH) from *Papaver somniferum* or another species; and Protopine 6-hydroxylase (P6H) from *Papaver somniferum, Eschscholzia californica*, or another species.

Tailoring enzymes may also be used to catalyze methylenedioxy bridge formation reactions performed on a BIA, or a derivative thereof. Examples of tailoring enzymes that may be used to catalyze methylenedioxy bridge formation reactions include a Stylopine synthase (StySyn) from *Papaver somniferum, Eschscholzia californica, Argemone mexicana*, or another species; Cheilanthifoline synthase (CheSyn) from *Papaver somniferum, Eschscholzia californica, Argemone mexicana*, or another species; and Canadine synthase (CAS) from *Thalictrum flavum, Coptis chinensis*, or another species.

Additionally, tailoring enzymes may be used to catalyze N-methylation reactions performed on a BIA, or a derivative thereof. Examples of tailoring enzymes that may be used to catalyze N-methylation reactions include Coclaurine N-methyltransferase (CNMT) from *Papaver somniferum, Thalictrum flavum, Coptis japonica*, or another species; Tetrahydroprotoberberine N-methyltransferase (TNMT) from *Papaver somniferum, Eschscholzia californica, Papaver bracteatum*, or another species.

Further, tailoring enzymes may be used to catalyze O-demethylation reactions performed on a BIA, or a derivative thereof. Examples of tailoring enzymes that may be used to catalyze O-demethylation reactions include Thebaine demethylase (T6ODM) from *Papaver somniferum* or another species; and Codeine demethylase (CODM) from *Papaver somniferum*, or another species.

Tailoring enzymes may also be used to catalyze reduction reactions performed on a BIA, or a derivative thereof. Examples of tailoring enzymes that may be used to catalyze reduction reactions include Salutaridine reductase (SalR) from *Papaver somniferum, Papaver bracteatum*, or another species; Codeinone reductase (COR) from *Papaver som-*

*niferum* or another species; and Sanguinarine reductase (SanR) from *Eschscholzia californica* or another species. In other examples, tailoring enzymes may be used to catalyze acetylation reactions performed on a BIA, or a derivative thereof. An example of a tailoring enzyme that may be used to catalyze acetylation reactions includes Salutaridine acetyltransferase (SalAT) from *Papaver somniferum* or another species.

O-Demethylation Modifications

Some methods, processes, and systems provided herein describe the conversion of a first benzylisoquinoline alkaloid to a second benzylisoquinoline alkaloid by the removal of an O-linked methyl group. Some of these methods, processes, and systems may comprise an engineered host cell. In some examples, the conversion of a first benzylisoquinoline alkaloid to a second benzylisoquinoline alkaloid is a key step in the conversion of a substrate to a nor-opioids or nal-opioids. In some examples, the conversion of a first alkaloid to a second alkaloid comprises a demethylase reaction.

FIG. 6 illustrates an enzyme having opioid 3-O-demethylase activity, in accordance with embodiments of the invention. Specifically, the enzyme may act on any morphinan alkaloid structure to remove the methyl group from the oxygen bound to carbon 3.

Examples of amino acid sequences of ODM enzymes are set forth in Table 4. An amino acid sequence for an ODM that is utilized in converting a first alkaloid to a second alkaloid may be 75% or more identical to a given amino acid sequence as listed in Table 4. For example, an amino acid sequence for such an epimerase may comprise an amino acid sequence that is at least 75% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more identical to an amino acid sequence as provided herein. Additionally, in certain embodiments, an "identical" amino acid sequence contains at least 80%-99% identity at the amino acid level to the specific amino acid sequence. In some cases an "identical" amino acid sequence contains at least about 85%, 86%, 87%, 88%, 89%, 90%, 91%, 92%, 93%, 94% and more in certain cases, at least 95%, 96%, 97%, 98% and 99% identity, at the amino acid level. In some cases, the amino acid sequence may be identical but the DNA sequence is altered such as to optimize codon usage for the host organism, for example.

An engineered host cell may be provided that produces an ODM that converts a first alkaloid to a second alkaloid, wherein the ODM comprises a given amino acid sequence as listed in Table 4. An engineered host cell may be provided that produces one or more ODM enzymes. The ODM that is produced within the engineered host cell may be recovered and purified so as to form a biocatalyst. The process may include contacting the first alkaloid with an ODM in an amount sufficient to convert said first alkaloid to a second alkaloid. In examples, the first alkaloid may be contacted with a sufficient amount of the one or more enzymes such that at least 5% of said first alkaloid is converted to a second alkaloid. In further examples, the first alkaloid may be contacted with a sufficient amount of the one or more enzymes such that at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 82%, at least 84%, at least 86%, at least 88%, at least 90%, at least 91%, at least 92%, at least 93%, at least 94%, at least 95%, at least 96%, at least 97%, at least 98%, at least 99%, at least 99.5%, at least 99.7%, or 100% of said first alkaloid is converted to a second alkaloid.

The one or more enzymes that may be used to convert a first alkaloid to a second alkaloid may contact the first alkaloid in vitro. Additionally, or alternatively, the one or more enzymes that may be used to convert a first alkaloid to a second alkaloid may contact the first alkaloid in vivo. In some examples, the one or more enzymes that may be used to convert a first alkaloid to a second alkaloid may be provided to a cell having the first alkaloid within. In some examples, the one or more enzymes that may be used to convert a first alkaloid to a second alkaloid may be produced within an engineered host cell.

In some examples, the methods provide for engineered host cells that produce an alkaloid product, wherein the O-demethylation of a substrate to a product may comprise a key step in the production of an alkaloid product. In some examples, the alkaloid produced is a nor-opioid or a nal-opioid. In still other embodiments, the alkaloid produced is derived from a nor-opioid or a nal-opioid. In another embodiment, a first alkaloid is an intermediate toward the product of the engineered host cell. In still other embodiments, the alkaloid product is selected from the group consisting of morphine, oxymorphine, oripavine, hydromorphone, dihydromorphine, 14-hydroxymorphine, morphinone, and 14-hydroxymorphinone.

In some examples, the substrate alkaloid is an opioid selected from the group consisting of codeine, oxycodone, thebaine, hydrocodone, dihydrocodeine, 14-hydroxycodeine, codeinone, and 14-hydroxycodeinone.

N-Demethylation Modifications

Some methods, processes, and systems provided herein describe the conversion of a first alkaloid to a second alkaloid by the removal of an N-linked methyl group. Some of these methods, processes, and systems may comprise an engineered host cell. In some examples, the conversion of a first alkaloid to a second alkaloid is a key step in the conversion of a substrate to a nor-opioids or nal-opioids. In some examples, the conversion of a first alkaloid to a second alkaloid comprises a demethylase reaction.

Figure 7:
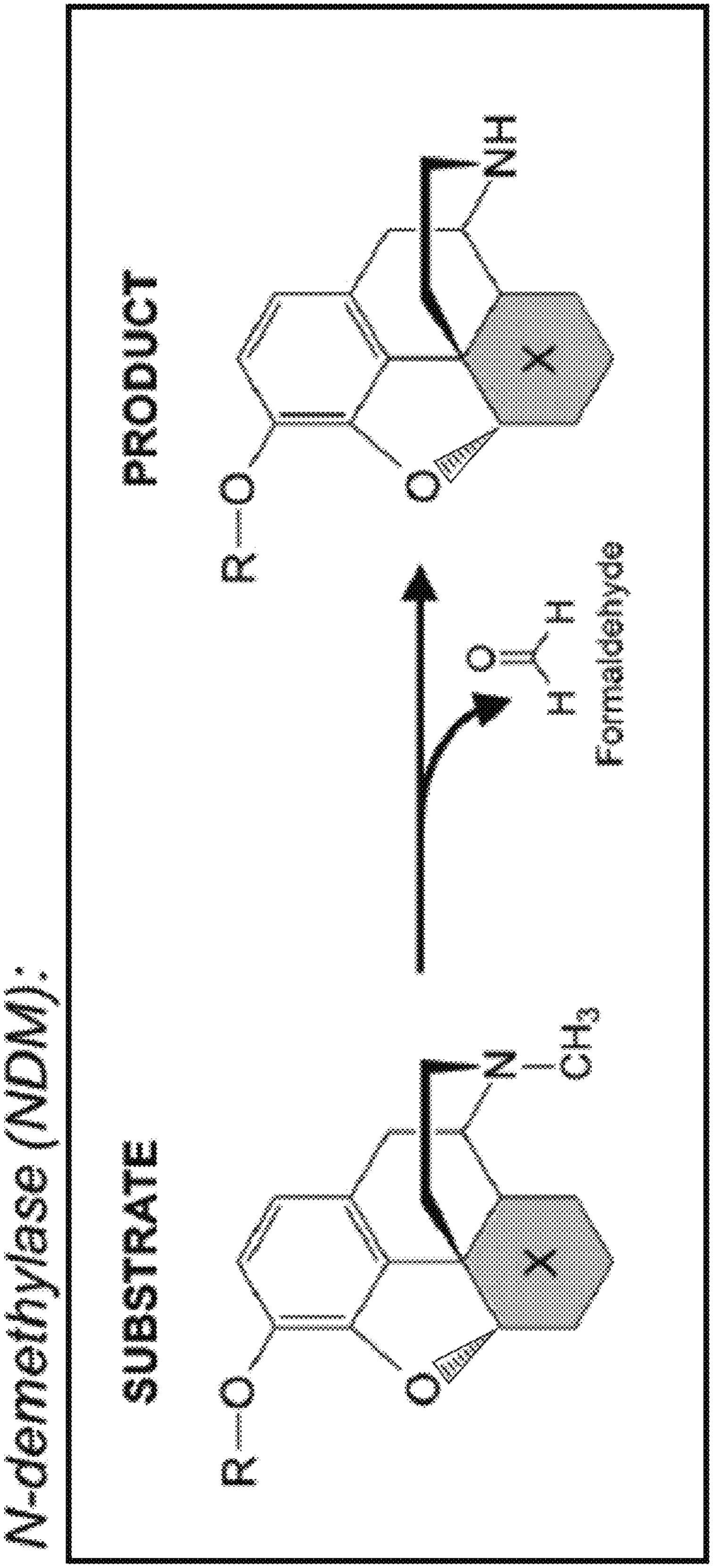
FIG. 7 illustrates an enzyme having opioid N-demethylase activity, in accordance with embodiments of the invention.

FIG. 7 illustrates an enzyme having opioid N-demethylase activity, in accordance with embodiments of the invention. Specifically, the enzyme may act on any morphinan alkaloid structure to remove the methyl group from the nitrogen.

Examples of an amino acid sequence of an N-demethylase enzyme that may be used to perform the conversion a first alkaloid to a second alkaloid are provided in Table 5. An amino acid sequence for an NDM that is utilized in converting a first alkaloid to a second alkaloid may be 75% or more identical to a given amino acid sequence as listed in Table 5. For example, an amino acid sequence for such an epimerase may comprise an amino acid sequence that is at least 75% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more identical to an amino acid sequence as provided herein. Additionally, in certain embodiments, an "identical" amino acid sequence contains at least 80%-99% identity at the amino acid level to the specific amino acid sequence. In some cases an "identical" amino acid sequence contains at least about 85%, 86%, 87%, 88%, 89%, 90%, 91%, 92%, 93%, 94% and more in certain cases, at least 95%, 96%, 97%, 98% and 99% identity, at the amino acid level. In some cases, the amino acid sequence may be identical but the DNA sequence is altered such as to optimize codon usage for the host organism, for example.

An engineered host cell may be provided that produces an NDM that converts a first alkaloid to a second alkaloid, wherein the NDM comprises an amino acid sequence as listed in Table 5. An engineered host cell may be provided that produces one or more NDM enzymes. The NDM that is produced within the engineered host cell may be recovered and purified so as to form a biocatalyst. The process may include contacting the first alkaloid with an NDM in an amount sufficient to convert said first alkaloid to a second alkaloid. In examples, the first alkaloid may be contacted with a sufficient amount of the one or more enzymes such that at least 5% of said first alkaloid is converted to a second alkaloid. In further examples, the first alkaloid may be contacted with a sufficient amount of the one or more enzymes such that at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 82%, at least 84%, at least 86%, at least 88%, at least 90%, at least 91%, at least 92%, at least 93%, at least 94%, at least 95%, at least 96%, at least 97%, at least 98%, at least 99%, at least 99.5%, at least 99.7%, or 100% of said first alkaloid is converted to a second alkaloid.

The one or more enzymes that may be used to convert a first alkaloid to a second alkaloid may contact the first alkaloid in vitro. Additionally, or alternatively, the one or more enzymes that may be used to convert a first alkaloid to a second alkaloid may contact the first alkaloid in vivo. In some examples, the one or more enzymes that may be used to convert a first alkaloid to a second alkaloid may be provided to a cell having the first alkaloid within. In some examples, the one or more enzymes that may be used to convert a first alkaloid to a second alkaloid may be produced within an engineered host cell.

In some examples, the methods provide for engineered host cells that produce an alkaloid product, wherein the N-demethylation of a substrate to a product may comprise a key step in the production of an alkaloid product. In some examples, the alkaloid produced is a nor-opioid or a nal-opioid. In still other embodiments, the alkaloid produced is derived from a nor-opioid or a nal-opioid. In another embodiment, a first alkaloid is an intermediate toward the product of the engineered host cell. In still other embodiments, the alkaloid product is selected from the group consisting of norcodeine, noroxycodone, northebaine, norhydrocodone, nordihydro-codeine, nor-14-hydroxy-codeine, norcodeinone, nor-14-hydroxy-codeinone, normorphine, noroxymorphone, nororipavine, norhydro-morphone, nordihydro-morphine, nor-14-hydroxy-morphine, normorphinone, and nor-14-hydroxy-morphinone.

In some examples, the substrate alkaloid is an opioid selected from the group consisting of codeine, oxycodone, thebaine, hydrocodone, dihydrocodeine, 14-hydroxycodeine, codeinone, and 14-hydroxycodeinone, morphine, oxymorphone, oripavine, hydromorphone, dihydromorphine, 14-hydroxy-morphine, morphinone, or 14-hydroxy-morphinone.

N-Linked Modifications

Some methods, processes, and systems provided herein describe the conversion of a first alkaloid to a second alkaloid by the addition of an N-linked sidechain group. Some methods, processes, and systems provided herein describe the conversion of a first alkaloid to a second alkaloid by the transfer of a sidechain group from a cosubstrate to the first alkaloid. Some of these methods, processes, and systems may comprise an engineered host cell. In some examples, the conversion of a first alkaloid to a second alkaloid is a key step in the conversion of a substrate to a nal-opioid. In some examples, the conversion of a first alkaloid to a second alkaloid comprises a methyltransferase reaction.

Figure 8:
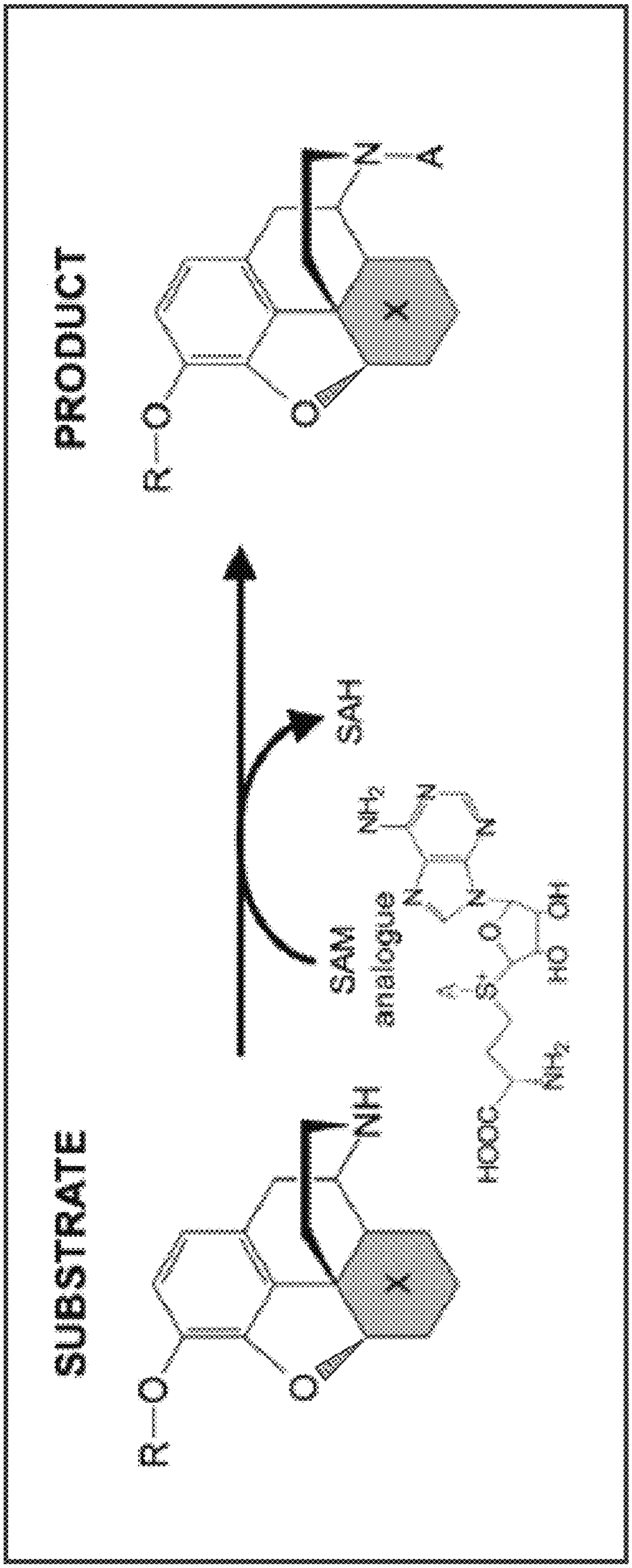
FIG. 8 illustrates an enzyme having N-methyltransferase activity, in accordance with embodiments of the invention.
Figure 8:
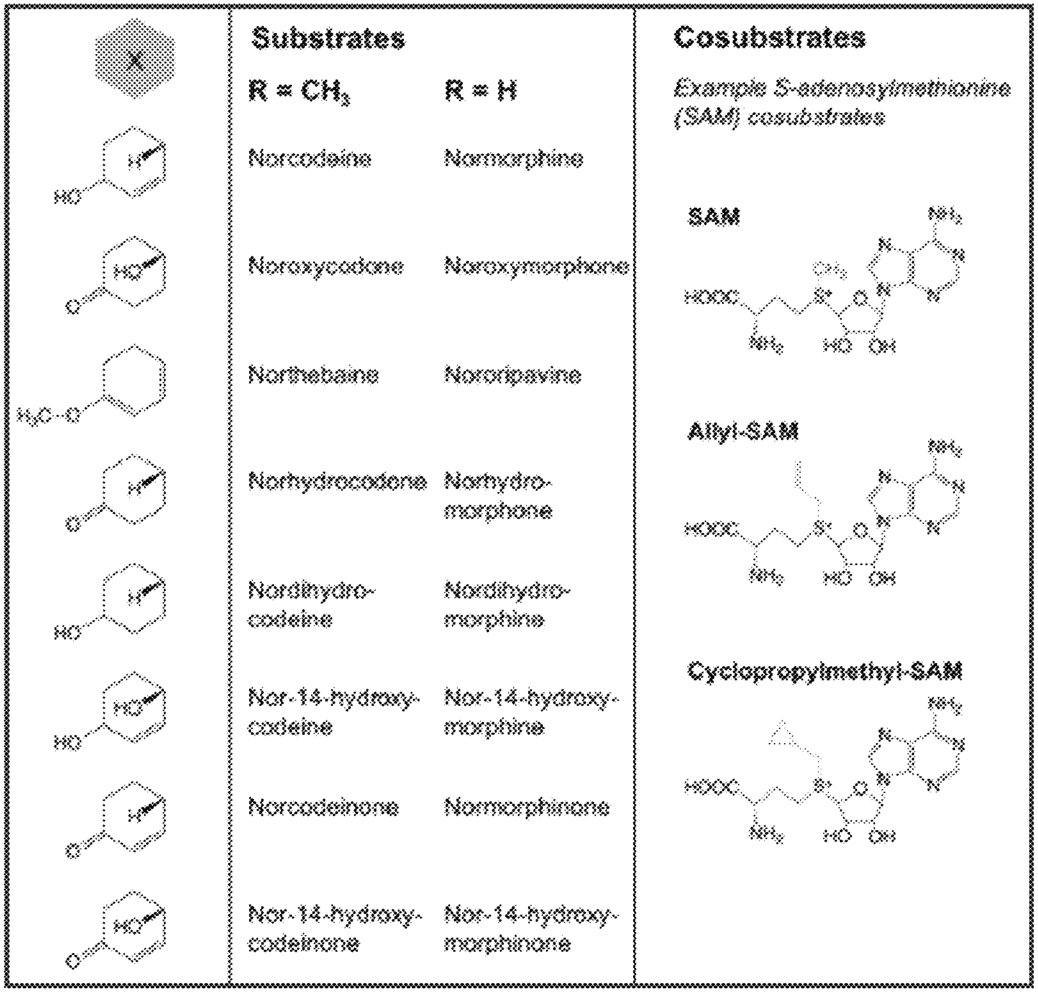

FIG. 8 illustrates an enzyme having N-methyltransferase activity, in accordance with embodiments of the invention. Specifically, the enzyme may act on any morphinan alkaloid structure to add a methyl group or other carbon moiety to the nitrogen. S-Adenosyl methionine (SAM) may act as the donor of the functional group (methyl, allyl, cyclopropylmethyl, or other).

Examples of amino acid sequences of NMT enzymes are set forth in Table 6. An amino acid sequence for an NMT that is utilized in converting a first alkaloid to a second alkaloid may be 75% or more identical to a given amino acid sequence as listed in Table 6. For example, an amino acid sequence for such an epimerase may comprise an amino acid sequence that is at least 75% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more identical to an amino acid sequence as provided herein. Additionally, in certain embodiments, an "identical" amino acid sequence contains at least 80%-99% identity at the amino acid level to the specific amino acid sequence. In some cases an "identical" amino acid sequence contains at least about 85%, 86%, 87%, 88%, 89%, 90%, 91%, 92%, 93%, 94% and more in certain cases, at least 95%, 96%, 97%, 98% and 99% identity, at the amino acid level. In some cases, the amino acid sequence may be identical but the DNA sequence is altered such as to optimize codon usage for the host organism, for example.

An engineered host cell may be provided that produces an NMT that converts a first alkaloid to a second alkaloid, wherein the NMT comprises an amino acid sequence as provided in Table 6. An engineered host cell may be provided that produces one or more NMT enzymes. The NMT that is produced within the engineered host cell may be recovered and purified so as to form a biocatalyst. The process may include contacting the first alkaloid with an NMT in an amount sufficient to convert said first alkaloid to a second alkaloid. In examples, the first alkaloid may be contacted with a sufficient amount of the one or more enzymes such that at least 5% of said first alkaloid is converted to a second alkaloid. In further examples, the first alkaloid may be contacted with a sufficient amount of the one or more enzymes such that at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 82%, at least 84%, at least 86%, at least 88%, at least 90%, at least 91%, at least 92%, at least 93%, at least 94%, at least 95%, at least 96%, at least 97%, at least 98%, at least 99%, at least 99.5%, at least 99.7%, or 100% of said first alkaloid is converted to a second alkaloid.

The one or more enzymes that may be used to convert a first alkaloid to a second alkaloid may contact the first alkaloid in vitro. Additionally, or alternatively, the one or more enzymes that may be used to convert a first alkaloid to a second alkaloid may contact the first alkaloid in vivo. In some examples, the one or more enzymes that may be used to convert a first alkaloid to a second alkaloid may be provided to a cell having the first alkaloid within. In some examples, the one or more enzymes that may be used to convert a first alkaloid to a second alkaloid may be produced within an engineered host cell.

In some examples, the methods provide for engineered host cells that produce an alkaloid product, wherein the N-methyltransferase of a substrate to a product may comprise a key step in the production of an alkaloid product. In some examples, the alkaloid produced is a nal-opioid. In still other embodiments, the alkaloid produced is derived from a nor-opioid or a nal-opioid. In another embodiment, a first alkaloid is an intermediate toward the product of the engineered host cell. In still other embodiments, the alkaloid product is selected from the group including naloxone, naltrexone, and nalmefene.

In some examples, the substrate alkaloid is an opioid selected from the group consisting of norcodeine, noroxycodone, northebaine, norhydrocodone, nordihydro-codeine, nor-14-hydroxy-codeine, norcodeinone, nor-14-hydroxycodeinone, normorphine, noroxymorphone, nororipavine, norhydro-morphone, nordihydro-morphine, nor-14-hydroxy-morphine, normorphinone, and nor-14-hydroxy-morphinone. In some examples, the cosubstrate is S-adenosylmethionine, Allyl-S-adenosylmethionine, or cyclopropylmethyl-S-adenosylmethionine.

Heterologous Coding Sequences

In some instances, the engineered host cells harbor one or more heterologous coding sequences (such as two or more, three or more, four or more, five or more) which encode activity(ies) that enable the engineered host cells to produce desired enzymes of interest and/or BIAs of interest, e.g., as described herein. As used herein, the term "heterologous coding sequence" is used to indicate any polynucleotide that codes for, or ultimately codes for, a peptide or protein or its equivalent amino acid sequence, e.g., an enzyme, that is not normally present in the host organism and may be expressed in the host cell under proper conditions. As such, "heterologous coding sequences" includes multiple copies of coding sequences that are normally present in the host cell, such that the cell is expressing additional copies of a coding sequence that are not normally present in the cells. The heterologous coding sequences may be RNA or any type thereof, e.g., mRNA, DNA or any type thereof, e.g., cDNA, or a hybrid of RNA/DNA. Coding sequences of interest include, but are not limited to, full-length transcription units that include such features as the coding sequence, introns, promoter regions, 3'-UTRs, and enhancer regions.

In examples, the engineered host cells may comprise a plurality of heterologous coding sequences each encoding an enzyme, such as an enzyme listed in Table 3. In some examples, the plurality of enzymes encoded by the plurality of heterologous coding sequences may be distinct from each other. In some examples, some of the plurality of enzymes encoded by the plurality of heterologous coding sequences may be distinct from each other and some of the plurality of enzymes encoded by the plurality of heterologous coding sequences may be duplicate copies.

In some examples, the heterologous coding sequences may be operably connected. Heterologous coding sequences that are operably connected may be within the same pathway of producing a particular benzylisoquinoline alkaloid product and/or thebaine synthase product. In some examples, the operably connected heterologous coding sequences may be directly sequential along the pathway of producing a particular benzylisoquinoline alkaloid product and/or thebaine synthase product. In some examples, the operably connected heterologous coding sequences may have one or more native enzymes between one or more of the enzymes encoded by the plurality of heterologous coding sequences. In some examples, the heterologous coding sequences may have one or more heterologous enzymes between one or more of the enzymes encoded by the plurality of heterologous coding sequences. In some examples, the heterologous coding sequences may have one or more non-native enzymes between one or more of the enzymes encoded by the plurality of heterologous coding sequences.

The engineered host cells may also be modified to possess one or more genetic alterations to accommodate the heterologous coding sequences. Alterations of the native host genome include, but are not limited to, modifying the genome to reduce or ablate expression of a specific protein that may interfere with the desired pathway. The presence of such native proteins may rapidly convert one of the intermediates or final products of the pathway into a metabolite or other compound that is not usable in the desired pathway. Thus, if the activity of the native enzyme were reduced or altogether absent, the produced intermediates would be more readily available for incorporation into the desired product.

Heterologous coding sequences include but are not limited to sequences that encode enzymes, either wild-type or equivalent sequences, that are normally responsible for the production of BIAs of interest in plants. In some cases, the enzymes for which the heterologous sequences code may be any of the enzymes in the 1-BIA pathway, and may be from any convenient source. The choice and number of enzymes encoded by the heterologous coding sequences for the particular synthetic pathway may be selected based upon the desired product. In certain embodiments, the host cells of the invention may include 1 or more, 2 or more, 3 or more, 4 or more, 5 or more, 6 or more, 7 or more, 8 or more, 9 or more, 10 or more, 11 or more, 12 or more, 13 or more, 14 or more, or even 15 or more heterologous coding sequences, such as 1, 2, 3, 4, 5, 6, 7, 8, 9, 10, 11, 12, 13, 14, or 15 heterologous coding sequences.

As used herein, the term "heterologous coding sequences" also includes the coding portion of the peptide or enzyme, i.e., the cDNA or mRNA sequence, of the peptide or enzyme, as well as the coding portion of the full-length transcriptional unit, i.e., the gene including introns and exons, as well as "codon optimized" sequences, truncated sequences or other forms of altered sequences that code for the enzyme or code for its equivalent amino acid sequence, provided that the equivalent amino acid sequence produces a functional protein. Such equivalent amino acid sequences may have a deletion of one or more amino acids, with the deletion being N-terminal, C-terminal, or internal. Truncated forms are envisioned as long as they have the catalytic capability indicated herein. Fusions of two or more enzymes are also envisioned to facilitate the transfer of metabolites in the pathway, provided that catalytic activities are maintained.

Operable fragments, mutants, or truncated forms may be identified by modeling and/or screening. In some cases, this is achieved by deletion of, for example, N-terminal, C-terminal, or internal regions of the protein in a step-wise fashion, followed by analysis of the resulting derivative with regard to its activity for the desired reaction compared to the original sequence. If the derivative in question operates in this capacity, it is considered to constitute an equivalent derivative of the enzyme proper.

In examples, some heterologous proteins may show occurrences where they are incorrectly processed when expressed in a recombinant host. For example, plant proteins such as cytochrome P450 enzymes expressed in microbial production hosts may have occurrences of incorrect processing. In particular, salutaridine synthase may undergo N-linked glycosylation when heterologously expressed in yeast. This N-linked glycosylation may not be observed in plants, which may be indicative of incorrect N-terminal sorting of the nascent SalSyn transcript so as to reduce the activity of the enzyme in the heterologous microbial host. In such examples, protein engineering directed at correcting N-terminal sorting of the nascent transcript so as to remove the N-linked glycosylation pattern may result in improved activity of the salutaridine synthase enzyme in the recombinant production host, see for example WO2016183023A1.

Some aspects of the invention also relate to heterologous coding sequences that code for amino acid sequences that are equivalent to the native amino acid sequences for the various enzymes. An amino acid sequence that is "equivalent" is defined as an amino acid sequence that is not identical to the specific amino acid sequence, but rather contains at least some amino acid changes (deletions, substitutions, inversions, insertions, etc.) that do not essentially affect the biological activity of the protein as compared to a similar activity of the specific amino acid sequence, when used for a desired purpose. The biological activity refers to, in the example of a thebaine synthase, its catalytic activity. Equivalent sequences are also meant to include those which have been engineered and/or evolved to have properties different from the original amino acid sequence. Mutable properties of interest include catalytic activity, substrate specificity, selectivity, stability, solubility, localization, etc.

In some instances, the expression of each type of enzyme is increased through additional gene copies (i.e., multiple copies), which increases intermediate accumulation and/or BIA of interest production. Some embodiments of the invention include increased BIA of interest production in a host cell through simultaneous expression of multiple species variants of a single or multiple enzymes. In some cases, additional gene copies of a single or multiple enzymes are included in the host cell. Any convenient methods may be utilized including multiple copies of a heterologous coding sequence for an enzyme in the host cell.

In some examples, the engineered host cell includes multiple copies of a heterologous coding sequence for an enzyme, such as 2 or more, 3 or more, 4 or more, 5 or more, or even 10 or more copies. In certain embodiments, the engineered host cell includes multiple copies of heterologous coding sequences for one or more enzymes, such as multiple copies of two or more, three or more, four or more, etc. In some cases, the multiple copies of the heterologous coding sequence for an enzyme are derived from two or more different source organisms as compared to the host cell. For example, the engineered host cell may include multiple copies of one heterologous coding sequence, where each of the copies is derived from a different source organism. As such, each copy may include some variations in explicit sequences based on inter-species differences of the enzyme of interest that is encoded by the heterologous coding sequence.

In certain embodiments, the engineered host cell includes multiple copies of heterologous coding sequences for one or more enzymes, such as multiple copies of two or more, three or more, four or more, etc. In some cases, the multiple copies of the heterologous coding sequence for an enzyme are derived from two or more different source organisms as compared to the host cell. For example, the engineered host cell may include multiple copies of one heterologous coding sequence, where each of the copies is derived from a different source organism. As such, each copy may include some variations in explicit sequences based on inter-species differences of the enzyme of interest that is encoded by the heterologous coding sequence.

The engineered host cell medium may be sampled and monitored for the production of BIAs of interest. The BIAs of interest may be observed and measured using any convenient methods. Methods of interest include, but are not limited to, LC-MS methods (e.g., as described herein) where a sample of interest is analyzed by comparison with a known amount of a standard compound. Additionally, there are other ways that BIAs of interest may be observed and/or measured. Examples of alternative ways of observing and/or measuring BIAs include GC-MS, UV-vis spectroscopy, NMR, LC-NMR, LC-UV, TLC, capillary electrophoresis, among others. Identity may be confirmed, e.g., by m/z and MS/MS fragmentation patterns, and quantitation or measurement of the compound may be achieved via LC trace peaks of know retention time and/or EIC MS peak analysis by reference to corresponding LC-MS analysis of a known amount of a standard of the compound.

Additionally, a culture of the engineered host cell may be sampled and monitored for the production of enzymes of interest, such as a thebaine synthase enzyme. The enzymes of interest may be observed and measured using any convenient methods. Methods of interest include enzyme activity assays, polyacrylamide gel electrophoresis, carbon monoxide spectroscopy, and western blot analysis.

Methods

Methods for Culturing Host Cells for BIA Production

As summarized above, some aspects of the invention include methods of preparing benzylisoquinoline alkaloids (BIAs) of interest. Additionally, some aspects of the invention include methods of preparing enzymes of interest. As such, some aspects of the invention include culturing an engineered host cell under conditions in which the one or more host cell modifications (e.g., as described herein) are functionally expressed such that the cell converts starting compounds of interest into product enzymes and/or BIAs of interest. Also provided are methods that include culturing an engineered host cell under conditions suitable for protein production such that one or more heterologous coding sequences are functionally expressed and convert starting compounds of interest into product enzymes or BIAs of interest. In examples, the method is a method of preparing a benzylisoquinoline alkaloid (BIA) that includes culturing an engineered host cell (e.g., as described herein); adding a starting compound to the cell culture; and recovering the BIA from the cell culture. In some examples, the method is a method of preparing an enzyme that includes culturing an engineered host cell (e.g., as described herein); adding a starting compound to the cell culture; and recovering the enzyme from the cell culture.

Fermentation media may contain suitable carbon substrates. The source of carbon suitable to perform the methods of this disclosure may encompass a wide variety of carbon containing substrates. Suitable substrates may include, without limitation, monosaccharides (e.g., glucose, fructose, galactose, xylose), oligosaccharides (e.g., lactose, sucrose, raffinose), polysaccharides (e.g., starch, cellulose), or a combination thereof. In some cases, unpurified mixtures from renewable feedstocks may be used (e.g., cornsteep liquor, sugar beet molasses, barley malt). In some cases, the carbon substrate may be a one-carbon substrate (e.g., methanol, carbon dioxide) or a two-carbon substrate (e.g., ethanol). In other cases, other carbon containing compounds may be utilized, for example, methylamine, glucosamine, and amino acids.

Any convenient methods of culturing engineered host cells may be employed for producing the enzymes and/or BIAs of interest. The particular protocol that is employed may vary, e.g., depending on the engineered host cell, the heterologous coding sequences, the enzymes of interest, the BIAs of interest, etc. The cells may be present in any convenient environment, such as an environment in which the cells are capable of expressing one or more functional heterologous enzymes. In some embodiments, the cells are cultured under conditions that are conducive to enzyme expression and with appropriate substrates available to allow production of enzymes and/or BIAs of interest in vivo. In some embodiments, the functional enzymes are extracted from the engineered host for production of enzymes and/or BIAs of interest under in vitro conditions. In some instances, the engineered host cells are placed back into a multicellular host organism. The engineered host cells are in any phase of growth, including, but not limited to, stationary phase and log-growth phase, etc. In addition, the cultures themselves may be continuous cultures or they may be batch cultures.

Cells may be grown in an appropriate fermentation medium at a temperature between 14-40° C. Cells may be grown with shaking at any convenient speed (e.g., 200 rpm). Cells may be grown at a suitable pH. Suitable pH ranges for the fermentation may be between pH 5-9. Fermentations may be performed under aerobic, anaerobic, or microaerobic conditions. Any suitable growth medium may be used. Suitable growth media may include, without limitation, common commercially prepared media such as synthetic defined (SD) minimal media or yeast extract peptone dextrose (YEPD) rich media. Any other rich, defined, or synthetic growth media appropriate to the microorganism may be used.

Cells may be cultured in a vessel of essentially any size and shape. Examples of vessels suitable to perform the methods of this disclosure may include, without limitation, multi-well shake plates, test tubes, flasks (baffled and non-baffled), and bioreactors. The volume of the culture may range from 10 microliters to greater than 10,000 liters.

The addition of agents to the growth media that are known to modulate metabolism in a manner desirable for the production of alkaloids may be included. In a non-limiting example, cyclic adenosine 2'3'-monophosphate may be added to the growth media to modulate catabolite repression.

Any convenient cell culture conditions for a particular cell type may be utilized. In certain embodiments, the host cells that include one or more modifications are cultured under standard or readily optimized conditions, with standard cell culture media and supplements. As one example, standard growth media when selective pressure for plasmid maintenance is not required may contain 20 g/L yeast extract, 10 g/L peptone, and 20 g/L dextrose (YPD). Host cells containing plasmids are grown in synthetic complete (SC) media containing 1.7 g/L yeast nitrogen base, 5 g/L ammonium sulfate, and 20 g/L dextrose supplemented with the appropriate amino acids required for growth and selection. Alternative carbon sources which may be useful for inducible enzyme expression include, but are not limited to, sucrose, raffinose, and galactose. Cells are grown at any convenient temperature (e.g., 30° C.) with shaking at any convenient rate (e.g., 200 rpm) in a vessel, e.g., in test tubes or flasks in volumes ranging from 1-1000 mL, or larger, in the laboratory.

Culture volumes may be scaled up for growth in larger fermentation vessels, for example, as part of an industrial process. The industrial fermentation process may be carried out under closed-batch, fed-batch, or continuous chemostat conditions, or any suitable mode of fermentation. In some cases, the cells may be immobilized on a substrate as whole cell catalysts and subjected to fermentation conditions for alkaloid production.

A batch fermentation is a closed system, in which the composition of the medium is set at the beginning of the fermentation and not altered during the fermentation process. The desired organism(s) are inoculated into the medium at the beginning of the fermentation. In some instances, the batch fermentation is run with alterations made to the system to control factors such as pH and oxygen concentration (but not carbon). In this type of fermentation system, the biomass and metabolite compositions of the system change continuously over the course of the fermentation. Cells typically proceed through a lag phase, then to a log phase (high growth rate), then to a stationary phase (growth rate reduced or halted), and eventually to a death phase (if left untreated).

A continuous fermentation is an open system, in which a defined fermentation medium is added continuously to the bioreactor and an equal amount of fermentation media is continuously removed from the vessel for processing. Continuous fermentation systems are generally operated to maintain steady state growth conditions, such that cell loss due to medium being removed must be balanced by the growth rate in the fermentation. Continuous fermentations are generally operated at conditions where cells are at a constant high cell density. Continuous fermentations allow for the modulation of one or more factors that affect target product concentration and/or cell growth.

The liquid medium may include, but is not limited to, a rich or synthetic defined medium having an additive component described above. Media components may be dissolved in water and sterilized by heat, pressure, filtration, radiation, chemicals, or any combination thereof. Several media components may be prepared separately and sterilized, and then combined in the fermentation vessel. The culture medium may be buffered to aid in maintaining a constant pH throughout the fermentation.

Process parameters including temperature, dissolved oxygen, pH, stirring, aeration rate, and cell density may be monitored or controlled over the course of the fermentation. For example, temperature of a fermentation process may be monitored by a temperature probe immersed in the culture medium. The culture temperature may be controlled at the set point by regulating the jacket temperature. Water may be cooled in an external chiller and then flowed into the bioreactor control tower and circulated to the jacket at the temperature required to maintain the set point temperature in the vessel.

Additionally, a gas flow parameter may be monitored in a fermentation process. For example, gases may be flowed into the medium through a sparger. Gases suitable for the methods of this disclosure may include compressed air, oxygen, and nitrogen. Gas flow may be at a fixed rate or regulated to maintain a dissolved oxygen set point.

The pH of a culture medium may also be monitored. In examples, the pH may be monitored by a pH probe that is immersed in the culture medium inside the vessel. If pH control is in effect, the pH may be adjusted by acid and base pumps which add each solution to the medium at the required rate. The acid solutions used to control pH may be sulfuric acid or hydrochloric acid. The base solutions used to control pH may be sodium hydroxide, potassium hydroxide, or ammonium hydroxide.

Further, dissolved oxygen may be monitored in a culture medium by a dissolved oxygen probe immersed in the culture medium. If dissolved oxygen regulation is in effect, the oxygen level may be adjusted by increasing or decreasing the stirring speed. The dissolved oxygen level may also be adjusted by increasing or decreasing the gas flow rate. The gas may be compressed air, oxygen, or nitrogen.

Stir speed may also be monitored in a fermentation process. In examples, the stirrer motor may drive an agitator. The stirrer speed may be set at a consistent rpm throughout the fermentation or may be regulated dynamically to maintain a set dissolved oxygen level.

Additionally, turbidity may be monitored in a fermentation process. In examples, cell density may be measured using a turbidity probe. Alternatively, cell density may be measured by taking samples from the bioreactor and analyzing them in a spectrophotometer. Further, samples may be removed from the bioreactor at time intervals through a sterile sampling apparatus. The samples may be analyzed for alkaloids produced by the host cells. The samples may also be analyzed for other metabolites and sugars, the depletion of culture medium components, or the density of cells.

In another example, a feed stock parameter may be monitored during a fermentation process. In particular, feed stocks including sugars and other carbon sources, nutrients, and cofactors that may be added into the fermentation using an external pump. Other components may also be added during the fermentation including, without limitation, antifoam, salts, chelating agents, surfactants, and organic liquids.

Any convenient codon optimization techniques for optimizing the expression of heterologous polynucleotides in host cells may be adapted for use in the subject host cells and methods, see e.g., Gustafsson, C. et al. (2004) *Trends Biotechnol,* 22, 346-353, which is incorporated by reference in its entirety.

The subject method may also include adding a starting compound to the cell culture. Any convenient methods of addition may be adapted for use in the subject methods. The cell culture may be supplemented with a sufficient amount of the starting materials of interest (e.g., as described herein), e.g., a mM to μM amount such as between about 1-5 mM of a starting compound. It is understood that the amount of starting material added, the timing and rate of addition, the form of material added, etc., may vary according to a variety of factors. The starting material may be added neat or pre-dissolved in a suitable solvent (e.g., cell culture media, water, or an organic solvent). The starting material may be added in concentrated form (e.g., 10× over desired concentration) to minimize dilution of the cell culture medium upon addition. The starting material may be added in one or more batches, or by continuous addition over an extended period of time (e.g., hours or days).

Methods for Isolating Products from the Fermentation Medium

The subject methods may also include recovering the enzymes and/or BIAs of interest from the cell culture. Any convenient methods of separation and isolation (e.g., chromatography methods or precipitation methods) may be adapted for use in the subject methods to recover the enzymes and/or BIAs of interest from the cell culture. Filtration methods may be used to separate soluble from insoluble fractions of the cell culture. In some cases, liquid chromatography methods (e.g., reverse phase HPLC, size exclusion, normal phase chromatography) may be used to separate the BIA of interest from other soluble components of the cell culture. In some cases, extraction methods (e.g., liquid extraction, pH based purification, solid phase extraction, affinity chromatography, ion exchange, etc.) may be used to separate the enzymes and/or BIAs of interest from other components of the cell culture.

The produced alkaloids may be isolated from the fermentation medium using methods known in the art. A number of recovery steps may be performed immediately after (or in some instances, during) the fermentation for initial recovery of the desired product. Through these steps, the alkaloids (e.g., BIAs) may be separated from the cells, cellular debris and waste, and other nutrients, sugars, and organic molecules may remain in the spent culture medium. This process may be used to yield a BIA-enriched product.

In an example, a product stream having a benzylisoquinoline alkaloid (BIA) product is formed by providing engineered yeast cells and a feedstock including nutrients and water to a batch reactor. In particular, the engineered yeast cells may be subjected to fermentation by incubating the engineered yeast cells for a time period of at least about 5 minutes to produce a solution comprising the BIA product and cellular material. Once the engineered yeast cells have been subjected to fermentation, at least one separation unit may be used to separate the BIA product from the cellular material to provide the product stream comprising the BIA product. In particular, the product stream may include the BIA product as well as additional components, such as a clarified yeast culture medium. Additionally, a BIA product may comprise one or more BIAs of interest, such as one or more BIA compounds.

Different methods may be used to remove cells from a bioreactor medium that include an enzyme and/or BIA of interest. In examples, cells may be removed by sedimentation over time. This process of sedimentation may be accelerated by chilling or by the addition of fining agents such as silica. The spent culture medium may then be siphoned from the top of the reactor or the cells may be decanted from the base of the reactor. Alternatively, cells may be removed by filtration through a filter, a membrane, or other porous material. Cells may also be removed by centrifugation, for example, by continuous flow centrifugation or by using a continuous extractor.

If some valuable enzymes and/or BIAs of interest are present inside the cells, the cells may be permeabilized or lysed and the cell debris may be removed by any of the methods described above. Agents used to permeabilize the cells may include, without limitation, organic solvents (e.g., DMSO) or salts (e.g., lithium acetate). Methods to lyse the cells may include the addition of surfactants such as sodium dodecyl sulfate, or mechanical disruption by bead milling or sonication.

Enzymes and/or BIAs of interest may be extracted from the clarified spent culture medium through liquid-liquid extraction by the addition of an organic liquid that is immiscible with the aqueous culture medium. In examples, the use of liquid-liquid extraction may be used in addition to other processing steps. Examples of suitable organic liquids include, but are not limited to, isopropyl myristate, ethyl acetate, chloroform, butyl acetate, methylisobutyl ketone, methyl oleate, toluene, oleyl alcohol, ethyl butyrate. The organic liquid may be added to as little as 10% or as much as 100% of the volume of aqueous medium.

In some cases, the organic liquid may be added at the start of the fermentation or at any time during the fermentation. This process of extractive fermentation may increase the yield of enzymes and/or BIAs of interest from the host cells by continuously removing enzymes and/or BIAs to the organic phase.

Agitation may cause the organic phase to form an emulsion with the aqueous culture medium. Methods to encourage the separation of the two phases into distinct layers may include, without limitation, the addition of a demulsifier or a nucleating agent, or an adjustment of the pH. The emulsion may also be centrifuged to separate the two phases, for example, by continuous conical plate centrifugation.

Alternatively, the organic phase may be isolated from the aqueous culture medium so that it may be physically removed after extraction. For example, the solvent may be encapsulated in a membrane.

In examples, enzymes and/or BIAs of interest may be extracted from a fermentation medium using adsorption methods. In examples, BIAs of interest may be extracted from clarified spent culture medium by the addition of a resin such as Amberlite® XAD4 or another agent that removes BIAs by adsorption. The BIAs of interest may then be released from the resin using an organic solvent. Examples of suitable organic solvents include, but are not limited to, methanol, ethanol, ethyl acetate, or acetone.

BIAs of interest may also be extracted from a fermentation medium using filtration. At high pH, the BIAs of interest may form a crystalline-like precipitate in the bioreactor. This precipitate may be removed directly by filtration through a filter, membrane, or other porous material. The precipitate may also be collected by centrifugation and/or decantation.

The extraction methods described above may be carried out either in situ (in the bioreactor) or ex situ (e.g., in an external loop through which media flows out of the bioreactor and contacts the extraction agent, then is recirculated back into the vessel). Alternatively, the extraction methods may be performed after the fermentation is terminated using the clarified medium removed from the bioreactor vessel.

Methods for Purifying Products from Alkaloid-Enriched Solutions

Subsequent purification steps may involve treating the post-fermentation solution enriched with BIA product(s) of interest using methods known in the art to recover individual product species of interest to high purity.

In one example, BIAs of interest extracted in an organic phase may be transferred to an aqueous solution. In some cases, the organic solvent may be evaporated by heat and/or vacuum, and the resulting powder may be dissolved in an aqueous solution of suitable pH. In a further example, the BIAs of interest may be extracted from the organic phase by addition of an aqueous solution at a suitable pH that promotes extraction of the BIAs of interest into the aqueous phase.

The aqueous phase may then be removed by decantation, centrifugation, or another method. The BIA-containing solution may be further treated to remove metals, for example, by treating with a suitable chelating agent. The BIA of interest-containing solution may be further treated to remove other impurities, such as proteins and DNA, by precipitation. In one example, the BIA of interest-containing solution is treated with an appropriate precipitation agent such as ethanol, methanol, acetone, or isopropanol. In an alternative example, DNA and protein may be removed by dialysis or by other methods of size exclusion that separate the smaller alkaloids from contaminating biological macromolecules.

In further examples, the solution containing BIAs of interest may be extracted to high purity by continuous cross-flow filtration using methods known in the art.

If the solution contains a mixture of BIAs of interest, it may be subjected to acid-base treatment to yield individual BIA of interest species using methods known in the art. In this process, the pH of the aqueous solution is adjusted to precipitate individual BIAs.

For high purity, small-scale preparations, the BIAs may be purified in a single step by liquid chromatography.

Liquid Chromatography Mass Spectrometry (LCMS) Method

The BIA compounds of interest, including morphinan, nal-opioids, and nor-opioids, may be separated using liquid chromatography, and detected and quantified using mass spectrometry. Compound identity may be confirmed by characteristic elution time, mass-to-charge ratio (m/z) and fragmentation patterns (MS/MS). Quantitation may be performed by comparison of compound peak area to a standard curve of a known reference standard compound. Additionally, BIAs of interest may be detected by alternative methods such as GC-MS, UV-vis spectroscopy, NMR, LC-NMR, LC-UV, TLC, and capillary electrophoresis.

Purpald Assay Method

For high throughput screening of demethylation reactions a purpald assay may be used. For example, demethylation catalyzed by 2-oxoglutarate dependent dioxygenases produces formaldehyde a as product as shown in the generalized chemical equation: [substrate]+2-$\rightleftarrows$ oxoglutarate+$O_2$ $\rightleftarrows$ [product]+formaldehyde+succinate+$CO_2$. Purpald reagent in alkaline conditions undergoes a color change in the presence of formaldehyde that can be quantified to concentrations as low as 1 nM with a spectrophotometer at 510 nm.

Yeast-Derived Alkaloid APIs Versus Plant-Derived APIs

The clarified yeast culture medium (CYCM) may contain a plurality of impurities. The clarified yeast culture medium may be dehydrated by vacuum and/or heat to yield an alkaloid-rich powder. This product is analogous to the concentrate of poppy straw (CPS) or opium, which is exported from poppy-growing countries and purchased by API manufacturers. For the purposes of this invention, CPS is a representative example of any type of purified plant extract from which the desired alkaloids product(s) may ultimately be further purified. Table 10 and Table 11 highlight the impurities in these two products that may be specific to either CYCM or CPS or may be present in both. While some BIAs may have a pigment as an impurity, other BIAs may be categorized as pigments themselves. Accordingly, these BIAs may be assessed for impurities based on non-pigment impurities. By analyzing a product of unknown origin for a subset of these impurities, a person of skill in the art could determine whether the product originated from a yeast or plant production host.

API-grade pharmaceutical ingredients are highly purified molecules. As such, impurities that could indicate the plant- or yeast-origin of an API (such as those listed in Table 10 and Table 11) may not be present at the API stage of the product. Indeed, many of the API products derived from yeast strains of the present invention may be largely indistinguishable from the traditional plant-derived APIs. In some cases, however, conventional alkaloid compounds may be subjected to chemical modification using chemical synthesis approaches, which may show up as chemical impurities in plant-based products that require such chemical modifications. For example, chemical derivatization may often result in a set of impurities related to the chemical synthesis processes. In certain situations, these modifications may be performed biologically in the yeast production platform, thereby avoiding some of the impurities associated with chemical derivation from being present in the yeast-derived product. In particular, these impurities from the chemical derivation product may be present in an API product that is produced using chemical synthesis processes but may be absent from an API product that is produced using a yeast-derived product. Alternatively, if a yeast-derived product is mixed with a chemically-derived product, the resulting impurities may be present but in a lesser amount than would be expected in an API that only or primarily contains chemically-derived products. In this example, by analyzing the API product for a subset of these impurities, a person of skill in the art could determine whether the product originated from a yeast production host or the traditional chemical derivatization route.

Non-limiting examples of impurities that may be present in chemically-derivatized morphinan APIs but not in biosynthesized APIs include a codeine-O(6)-methyl ether impurity in API codeine; 8,14-dihydroxy-7,8-dihydrocodeinone in API oxycodone; and tetrahydrothebaine in API hydrocodone. The codeine-O(6)-methyl ether may be formed by chemical over-methylation of morphine. The 8,14-dihydroxy-7,8-dihydrocodeinone in API oxycodone may be formed by chemical over-oxidation of thebaine. Additionally, the tetrahydrothebaine in API hydrocodone may be formed by chemical over-reduction of thebaine.

However, in the case where the yeast-derived compound and the plant-derived compound are both subjected to chemical modification through chemical synthesis approaches, the same impurities associated with the chemical synthesis process may be expected in the products. In such a situation, the starting material (e.g., CYCM or CPS) may be analyzed as described above.

Host Cell Derived Nal-Opioids Vs Chemically Derived Nal-Opioids

Nal-opioids produced by chemical synthesis may contain a plurality of impurities. These impurities may arise from many different causes, for example, unreacted starting materials, incomplete reactions, the formation of byproducts, persistence of intermediates, dimerization, or degradation. An example of an unreacted starting material could be oxymorphone remaining in a preparation of naltrexone. An example of an impurity arising from an incomplete reaction could be 3-O-Methylbuprenorphine resulting from the incomplete 3-O-demethylation of thebaine. Chemical modification can result in the addition or removal of functional groups at off-target sites. For example, the oxidation of C10 to create 10-hydroxynaltrexone and 10-ketonaltrexone during naltrexone synthesis, or the removal of the 6-O-methyl group to give 6-O-desmethylbuprenorphine during buprenorphine synthesis. Impurites may arise from the persistence of reaction intermediates, for example the persistence of N-oxides like oxymorphone N-oxide formed during the N-demethylation process. Another source of impurities is dimerization, the conjugation of two opioid molecules, for example two buprenorphine molecules (2,2'-bisbuprenorphine), two naltrexone molecules (2,2'-bisnaltrexone), or two naloxone molecules (2,2'-bisnaloxone). Impurities may arise from degradation of starting materials, reaction intermediates, or reaction products. The extreme physical conditions used in chemical syntheses may make the presence of degradation more likely. An example of an impurity that may arise from degradation is dehydrobuprenorphine produced by oxidizing conditions during buprenorphine synthesis.

Nal-opioids produced by enzyme catalysis in a host cell may contain different impurities than nal-opioids produced by chemical synthesis. Nal-opioids produced by enzyme catalysis in a host cell may contain fewer impurities than nal-opioids produced by chemical synthesis. Nal-opioids produced by enzyme catalysis in a host cell may lack certain impurities that are found in nal-opioids produced by chemical synthesis. In examples, key features of enzyme synthesis may include, (1) enzymes target a specific substrate and residue with high fidelity; (2) enzymes perform reactions in the mild physiological conditions within the cell which do not compromise the stability of the molecules; and (3) enzymes are engineered to be efficient catalysts that drive reactions to completion.

Table 12 highlights some of the impurities that may be specific to chemically produced nal-opioids. Accordingly, nal-opioids may be assessed for impurities to determine the presence or absence of any impurity from Table 12. By analyzing a product of unknown origin for a subset of these impurities, a person of skill in the art could determine whether the product originated from a chemical or enzymatic synthesis.

Methods of Engineering Host Cells

Also included are methods of engineering host cells for the purpose of producing enzymes and/or BIAs of interest. Inserting DNA into host cells may be achieved using any convenient methods. The methods are used to insert the heterologous coding sequences into the engineered host cells such that the host cells functionally express the enzymes and convert starting compounds of interest into product enzymes and/or BIAs of interest.

Any convenient promoters may be utilized in the subject engineered host cells and methods. The promoters driving expression of the heterologous coding sequences may be constitutive promoters or inducible promoters, provided that the promoters are active in the engineered host cells. The heterologous coding sequences may be expressed from their native promoters, or non-native promoters may be used. Such promoters may be low to high strength in the host in which they are used. Promoters may be regulated or constitutive. In certain embodiments, promoters that are not glucose repressed, or repressed only mildly by the presence of glucose in the culture medium, are used. Promoters of interest include but are not limited to, promoters of glycolytic genes such as the promoter of the *B. subtilis* tsr gene (encoding the promoter region of the fructose bisphosphate aldolase gene) or the promoter from yeast *S. cerevisiae* gene coding for glyceraldehyde 3-phosphate dehydrogenase (GPD, GAPDH, or TDH3), the ADH1 promoter of baker's yeast, the phosphate-starvation induced promoters such as the PHO5 promoter of yeast, the alkaline phosphatase promoter from *B. lichenmformis*, yeast inducible promoters such as Ga11-10, Ga11, Ga1L, Ga1S, repressible promoter Met25, tetO, and constitutive promoters such as glyceraldehyde 3-phosphate dehydrogenase promoter (GPD), alcohol dehydrogenase promoter (ADH), translation-elongation factor-1-α promoter (TEF), cytochrome c-oxidase promoter (CYC1), MRP7 promoter, etc. Autonomously replicating yeast expression vectors containing promoters inducible by hormones such as glucocorticoids, steroids, and thyroid hormones may also be used and include, but are not limited to, the glucorticoid responsive element (GRE) and thyroid hormone responsive element (TRE). These and other examples are described U.S. Pat. No. 7,045,290, which is incorporated by reference, including the references cited therein. Additional vectors containing constitutive or inducible promoters such as a factor, alcohol oxidase, and PGH may be used. Additionally any promoter/enhancer combination (as per the Eukaryotic Promoter Data Base EPDB) could also be used to drive expression of genes. Any convenient appropriate promoters may be selected for the host cell, e.g., *E. coli*. One may also use promoter selection to optimize transcript, and hence, enzyme levels to maximize production while minimizing energy resources.

Figure 11:
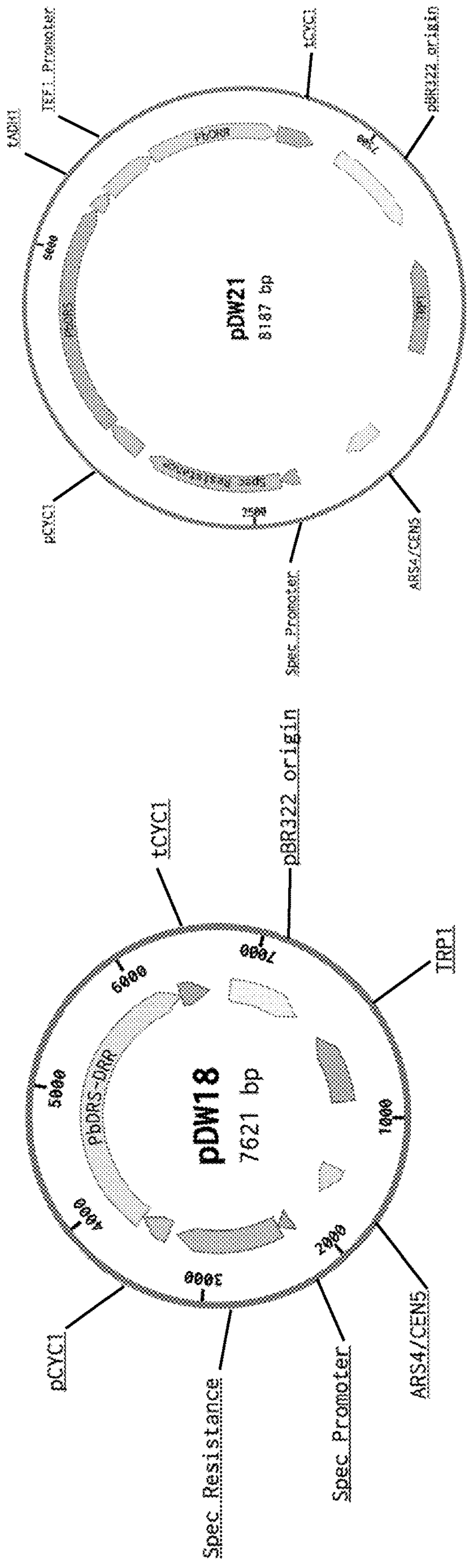
FIG. 11 illustrates plasmid/YAC vectors for enzyme expression and engineering, in accordance with embodiments of the invention.
Figure 11:
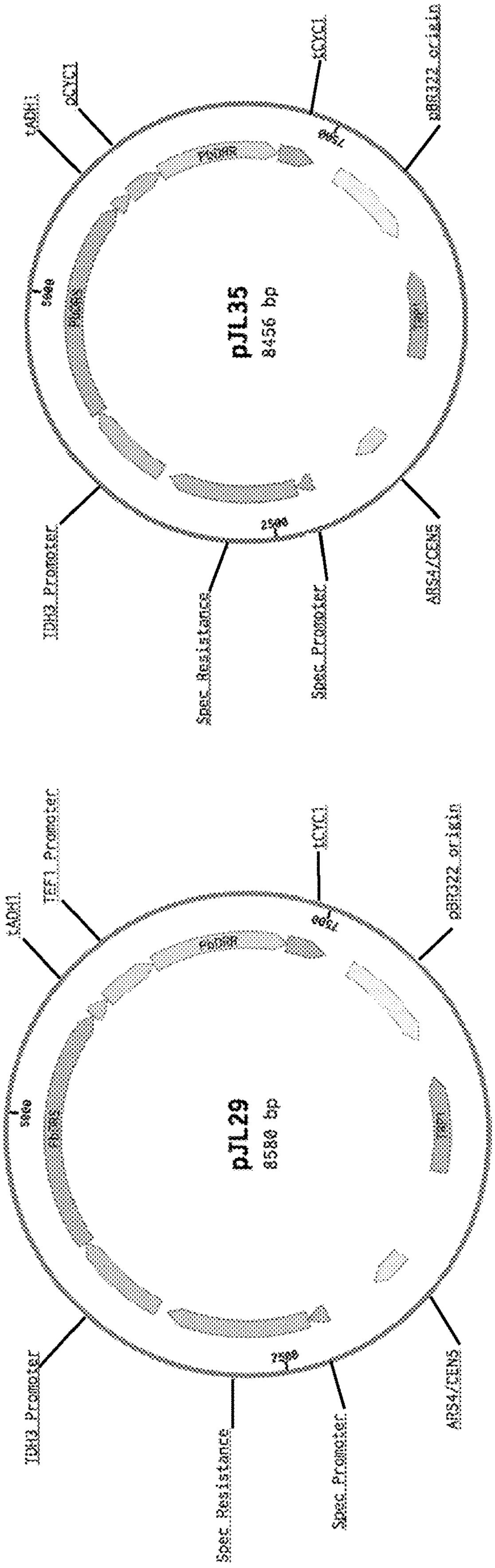

Any convenient vectors may be utilized in the subject engineered host cells and methods. Vectors of interest include vectors for use in yeast and other cells. The types of yeast vectors may be broken up into 4 general categories: integrative vectors (YIp), autonomously replicating high copy-number vectors (YEp or 2μ plasmids), autonomously replicating low copy-number vectors (YCp or centromeric plasmids) and vectors for cloning large fragments (YACs). Vector DNA is introduced into prokaryotic or eukaryotic cells via any convenient transformation or transfection techniques. DNA of another source (e.g. PCR-generated double stranded DNA product, or synthesized double stranded or single stranded oligonucleotides) may be used to engineer the yeast by integration into the genome. Any single transformation event may include one or several nucleic acids (vectors, double stranded or single stranded DNA fragments) to genetically modify the host cell. FIG. 11 illustrates examples of convenient vectors.

Utility

The engineered host cells and methods of the invention, e.g., as described above, find use in a variety of applications. Applications of interest include, but are not limited to: research applications and therapeutic applications. Methods of the invention find use in a variety of different applications including any convenient application where the production of enzymes and/or BIAs is of interest.

The subject engineered host cells and methods find use in a variety of therapeutic applications. Therapeutic applications of interest include those applications in which the preparation of pharmaceutical products that include BIAs is of interest. The engineered host cells described herein produce BIAs of interest and enzymes of interest. Reticuline is a major branch point intermediate of interest in the synthesis of BIAs including engineering efforts to produce end products such as opioid products. The subject host cells may be utilized to produce BIAs of interest from simple and inexpensive starting materials that may find use in the production of BIAs of interest, including reticuline, and BIA end products. As such, the subject host cells find use in the supply of therapeutically active BIAs of interest.

In some instances, the engineered host cells and methods find use in the production of commercial scale amounts of BIAs thereof where chemical synthesis of these compounds is low yielding and not a viable means for large-scale production. In certain cases, the host cells and methods are utilized in a fermentation facility that would include bioreactors (fermenters) of e.g., 5,000-200,000 liter capacity allowing for rapid production of BIAs of interest thereof for therapeutic products. Such applications may include the industrial-scale production of BIAs of interest from fermentable carbon sources such as cellulose, starch, and free sugars.

The subject engineered host cells and methods find use in a variety of research applications. The subject host cells and methods may be used to analyze the effects of a variety of enzymes on the biosynthetic pathways of a variety of enzymes and/or BIAs of interest. In addition, the engineered host cells may be engineered to produce enzymes and/or BIAs of interest that find use in testing for bioactivity of interest in as yet unproven therapeutic functions. In some cases, the engineering of host cells to include a variety of heterologous coding sequences that encode for a variety of enzymes elucidates the high yielding biosynthetic pathways towards enzymes and/or BIAs of interest. In certain cases, research applications include the production of enzymes and/or BIAs of interest for therapeutic molecules of interest that may then be further chemically modified or derivatized to desired products or for screening for increased therapeutic activities of interest. In some instances, host cell strains are used to screen for enzyme activities that are of interest in such pathways, which may lead to enzyme discovery via conversion of BIA metabolites produced in these strains.

The subject engineered host cells and methods may be used as a production platform for plant specialized metabolites. The subject host cells and methods may be used as a platform for drug library development as well as plant enzyme discovery. For example, the subject engineered host cells and methods may find use in the development of natural product based drug libraries by taking yeast strains producing interesting scaffold molecules, such as protopine, and further functionalizing the compound structure through combinatorial biosynthesis or by chemical means. By producing drug libraries in this way, any potential drug hits are already associated with a production host that is amenable to large-scale culture and production. As another example, these subject engineered host cells and methods may find use in plant enzyme discovery. The subject host cells provide a clean background of defined metabolites to express plant EST libraries to identify new enzyme activities. The subject host cells and methods provide expression methods and culture conditions for the functional expression and increased activity of plant enzymes in yeast.

Kits and Systems

Aspects of the invention further include kits and systems, where the kits and systems may include one or more components employed in methods of the invention, e.g., engineered host cells, starting compounds, heterologous coding sequences, vectors, culture medium, etc., as described herein. In some embodiments, the subject kit includes an engineered host cell (e.g., as described herein), and one or more components selected from the following: starting compounds, a heterologous coding sequence and/or a vector including the same, vectors, growth feedstock, components suitable for use in expression systems (e.g., cells, cloning vectors, multiple cloning sites (MCS), bidirectional promoters, an internal ribosome entry site (IRES), etc.), and a culture medium.

Any of the components described herein may be provided in the kits, e.g., host cells including one or more modifications, starting compounds, culture medium, etc. A variety of components suitable for use in making and using heterologous coding sequences, cloning vectors and expression systems may find use in the subject kits. Kits may also include tubes, buffers, etc., and instructions for use. The various reagent components of the kits may be present in separate containers, or some or all of them may be pre-combined into a reagent mixture in a single container, as desired.

Also provided are systems for producing enzymes and/or BIAs of interest, where the systems may include engineered host cells including one or more modifications (e.g., as described herein), starting compounds, culture medium, a fermenter and fermentation equipment, e.g., an apparatus suitable for maintaining growth conditions for the host cells, sampling and monitoring equipment and components, and the like. A variety of components suitable for use in large scale fermentation of yeast cells may find use in the subject systems.

In some cases, the system includes components for the large scale fermentation of engineered host cells, and the monitoring and purification of enzymes and/or BIA compounds produced by the fermented host cells. In certain embodiments, one or more starting compounds (e.g., as described herein) are added to the system, under conditions by which the engineered host cells in the fermenter produce one or more desired BIA products of interest. In some instances, the host cells produce a BIA of interest (e.g., as described herein). In certain cases, the BIA products of interest are opioid products, such as thebaine, codeine, neopine, morphine, neomorphine, hydrocodone, oxycodone, hydromorphone, dihydrocodeine, 14-hydroxycodeine, dihydromorphine, or oxymorphone.

In some cases, the system includes processes for monitoring and or analyzing one or more enzymes and/or BIAs of interest compounds produced by the subject host cells. For example, a LC-MS analysis system as described herein, a chromatography system, or any convenient system where the sample may be analyzed and compared to a standard, e.g., as described herein. The fermentation medium may be monitored at any convenient times before and during fermentation by sampling and analysis. When the conversion of starting compounds to enzymes and/or BIA products of interest is complete, the fermentation may be halted and purification of the BIA products may be done. As such, in some cases, the subject system includes a purification component suitable for purifying the enzymes and/or BIA products of interest from the host cell medium into which it is produced. The purification component may include any convenient means that may be used to purify the enzymes and/or BIA products of interest produced by fermentation, including but not limited to, silica chromatography, reverse-phase chromatography, ion exchange chromatography, HIC chromatography, size exclusion chromatography, liquid extraction, and pH extraction methods. In some cases, the subject system provides for the production and isolation of enzyme and/or BIA fermentation products of interest following the input of one or more starting compounds to the system.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.), but some experimental errors and deviations should be accounted for. Unless indicated otherwise, parts are parts by weight, molecular weight is weight average molecular weight, temperature is in degrees Centigrade, and pressure is at or near atmospheric.

Discussion of Enzyme List

The host cells may be engineered to include one or more modifications (such as two or more, three or more, four or more, five or more, or even more modifications) that provide for the production of BIAs of interest and/or enzymes of interest. Table 3 provides a list of exemplary genes that may be acted upon by one or more modifications so as to provide for the production of BIAs of interest and/or enzymes of interest in an engineered host cell.

Modifications of genes as provided in Table 3 may be used to produce BIAs of interest from engineered host cells that are supplied with a medium containing the minimal nutrients required for growth. This minimal medium may contain a carbon source, a nitrogen source, amino acids, vitamins, and salts. For example, modifications of genes as provided in Table 3 may be used to produce BIAs of interest from engineered host cells that are fed sugar. Additionally, modifications of one or more genes as provided in Table 3 may be used to augment the biosynthetic processes of host cells that may be engineered for drug production.

Additionally, the use of these modifications to provide for the production of BIAs of interest and/or enzymes of interest in engineered host cells is not readily apparent from the mere identification of enzymes that may be produced by the genes. In particular, synthetic pathways that have been reconstructed in host cells, such as yeast cells, as described herein comprise a variety of enzymes that do not act together in nature within a single organism. Additionally, some of the enzymes discussed herein do not act for BIA biosynthesis in their natural context. Further, some of the enzymes described herein are not evolved to function in particular host cells, such as yeast cells, and are not evolved to function together. In these cases, it would not be obvious that the enzymes would exhibit sufficient activity in the context of the synthetic BIA pathway in a host cell, such as yeast, to have sufficient flux through the pathway to produce downstream BIA end products.

For example, plant enzymes are often difficult to functionally express in heterologous microbial hosts, such as yeast. In many cases the enzymes may be misfolded, not correctly localized within the host cell, and/or incorrectly processed. The differences in protein translation and processing between yeast and plants can lead to these enzymes exhibiting substantially reduced to no detectable activities in the yeast host. These challenges arise commonly for endomembrane localized enzymes, such as cytochrome P450s, which are strongly represented in the BIA pathways. Even reduced enzyme activities may pose a substantial challenge to engineering yeast to produce complex BIAs, which requires sufficient activity at each step to ensure high-level accumulation of the desired BIA products.

Additionally, there are endogenous enzymes/pathways in some host cells, such as yeast, that may act on many of the early precursors in the BIA pathway (i.e., intermediates from tyrosine to norcoclaurine), and thus it may not be readily apparent that there would be sufficient flux through the heterologous pathway to achieve substantial BIA production given these competing endogenous pathways. For example, the Erlich pathway (Hazelwood, et al. 2008. *Appl. Environ. Microbiol.* 74: 2259-66; Larroy, et al. 2003. *Chem. Biol. Interact.* 143-144: 229-38; Larroy, et al. 2002. *Eur. J. Biochem.* 269: 5738-45) in yeast is the main endogenous pathway that would act to convert many of the intermediates in the early BIA pathway to undesired products and divert flux from the synthetic pathway.

Further, many of the enzymes as discussed herein, and as provided in Table 3, may function under very specific regulation strategies, including spatial regulation, in the native plant hosts, which may be lost upon transfer to the heterologous yeast host. In addition, plants present very different biochemical environments than yeast cells under which the enzymes are evolved to function, including pH, redox state, and substrate, cosubstrate, coenzyme, and cofactor availabilities. Given the differences in biochemical environments and regulatory strategies between the native hosts and the heterologous yeast hosts, it is not obvious that the enzymes would exhibit substantial activities when in the context of the yeast environment and further not obvious that they would work together to direct simple precursors such as sugar to complex BIA compounds. Maintaining the activities of the enzymes in the yeast host is particularly important as many of the pathways have many reaction steps (>10), such that if these steps are not efficient then one would not expect accumulation of desired downstream products.

In addition, in the native plant hosts, the associated metabolites in these pathways may be localized across different cell and tissue types. In several examples, there are cell types that may be specialized for biosynthesis and cell types that may be synthesized for metabolite accumulation. This type of cell specialization may be lost when expressing the pathways within a heterologous yeast host, and may play an important role in controlling the toxicity of these metabolites on the cells. Thus, it is not obvious that yeast could be successfully engineered to biosynthesize and accumulate these metabolites without being harmed by the toxicity of these compounds.

As one example, in the native plant hosts, the enzyme BBE is reported to have dynamic subcellular localization. In particular, the enzyme BBE initially starts in the ER and then is sorted to the vacuole (Bird and Facchini. 2001. *Planta.* 213: 888-97). It has been suggested that the ER-association of BBE in plants (Alcantara, et al. 2005. *Plant Physiol.* 138: 173-83) provides the optimal basic pH (pH-8.8) for BBE activity (Ziegler and Facchini. 2008. *Annu. Rev. Plant Biol.* 59: 735-69). As another example, there is evidence that sanguinarine biosynthesis occurs in specialized vesicles within plant cells (Amann, et al. 1986. *Planta.* 167: 310-20), but only some of the intermediates accumulate in the vesicles. This may occur so as to sequester them from other enzyme activities and/or toxic effects.

As another example, the biosynthetic enzymes in the morphinan pathway branch are all localized to the phloem, which is part of the vascular tissue in plants. In the phloem, the pathway enzymes may be further divided between two cell types: the sieve elements common to all plants, and the laticifer which is a specialized cell type present only in certain plants which make specialized secondary metabolites. The upstream enzymes (i.e., from NCS through to SalAT) are predominantly in the sieve elements, and the downstream enzymes (i.e., T6ODM, COR, CODM) are mostly in the laticifer (Onoyovwe, et al. 2013. *Plant Cell.* 25: 4110-22). Additionally, it was discovered that the final steps in the noscapine biosynthetic pathway take place in the laticifer (Chen and Facchini. 2014. *Plant J.* 77: 173-84). This compartmentalization is thought to be highly important for regulating biosynthesis by isolating or trafficking intermediates, providing optimal pH, enhancing supply of cofactors, although the nature of the poppy laticifer microenvironment is still under investigation (Ziegler and Facchini. 2008. *Annu. Rev. Plant Biol.* 59: 735-69). Further, it is predicted that several of the enzymes may function as multi-enzyme complexes or metabolic channels common to plant secondary metabolism (Kempe, et al. 2009. *Phytochemistry.* 70: 579-89; Allen, et al. 2004. *Nat. Biotechnol.* 22: 1559-66). When biosynthetic enzymes are combined from different hosts and/or expressed recombinantly in a heterologous yeast cell it is not clear that these complexes or channels will form as they would in the native host. In an additional example, in *Coptis japonica*, berberine is biosynthesized in root tissues and then accumulated within the rhizome via the action of specialized ATP-binding cassette transport proteins (Shitan, et al. 2013. *Phytochemistry.* 91: 109-16). In opium poppy, morphinan alkaloids are accumulated within the latex (cytoplasm of laticifer cells) (Martin, et al. 1967. *Biochemistry.* 6: 2355-63).

Further, even without these considerations, it is also the case that the plant enzymes for several of the steps in the pathways described herein have not yet been characterized. For example, the conversion of tyrosine to the early benzylisoquinoline alkaloid scaffold norcoclaurine has not yet been characterized. Additionally, the conversion of (S)-reticuline to (R)-reticuline has only recently been characterized as described herein. Thus, for several of the steps in the pathways described herein, alternative biosynthetic scheme were produced by bringing together enzyme activities that do not normally occur together in nature for the biosynthesis of BIAs or identifying new enzyme activities from genome sequence information to use in the reconstructed pathways.

For example, the two-step conversion of tyrosine to dopamine may be achieved by combining at least 5 mammalian enzymes and 1 bacterial enzyme, which do not naturally occur together and were not evolved to function in the context of this pathway or with plant enzymes. In these instances, it may not be obvious to utilize these enzymes for the biosynthesis of compounds they were not evolved for in nature and that they would function effectively in the context of a heterologous microbial host and this pathway. In these instances, it may not be obvious to utilize these enzymes for the biosynthesis of compounds they were not evolved for in nature and that they would function effectively in the context of a heterologous microbial host and this pathway.

As another example, until recent years the enzyme responsible for the conversion of (S)-reticuline to (R)-reticuline was unknown. Even when a fused epimerase enzyme was discovered, evolutionary analysis suggested that morphine-producing poppies evolved a fusion enzyme between the oxidase and reductase for an epimerase reaction, which was in contrast to non-morphine producing poppies where the epimerase enzymes were non-fused. Based on this analysis, some scholars believed the fusion of the oxidase and reductase portions was necessary to efficiently catalyze the conversion of (S)-Reticuline to (R)-Reticuline. Novel methods of using engineered split epimerases as discussed herein may perform this epimerization reaction in yeast and in the context of the synthetic BIA pathway, and may perform this epimerization with greater efficiency than performing an epimerization with a wild-type epimerase.

Examples of the genes that are the object of modifications so as to produce BIAs of interest and/or enzymes of interest are discussed below. Additionally, the genes are discussed in the context of a series of Figures that illustrate pathways that are used in generating BIAs of interest and/or enzymes of interest.

[TKL1] In some examples, the engineered host cell may modify the expression of the enzyme transketolase. Transketolase is encoded by the TKL1 gene. In examples, transketolase catalyzes the reaction of fructose-6-phosphate+glyceraldehyde-3-phosphate↔xylulose-5-phosphate+erythrose-4-phosphate, as referenced in FIG. 2. An engineered host cell may be modified to include constitutive overexpression of the TKL1 gene in the engineered host cell. Additionally or alternatively, the engineered host cell may be modified to synthetically regulate the expression of the TKL1 gene in the engineered host cell. In examples, the engineered host cell may be modified to incorporate a copy, copies, or additional copies, of the TKL1 gene. Additionally or alternatively, the engineered host cell may be modified to incorporate the introduction of a strong promoter element for the overexpression of the TKL1 gene within the engineered host cell. The TKL1 gene may be derived from *Saccharomyces cerevisiae* or another species. In some examples, the TKL1 gene may be 100% similar to the naturally occurring gene.

[ZWF1] In some examples, the engineered host cell may modify the expression of the enzyme glucose-6-phosphate dehydrogenase. Glucose-6-phosphate dehydrogenase is encoded by the ZWF1 gene. In examples, glucose-6-phosphate dehydrogenase catalyzes the reaction of glucose-6-phosphate→6-phosphogluconolactone, as referenced in FIG. 2. An engineered host cell may be modified to delete the coding region of the ZWF1 gene in the engineered host cell. Alternatively, the engineered host cell may be modified to disable the functionality of the ZWF1 gene, such as by introducing an inactivating mutation.

[ARO4] In some examples, the engineered host cell may modify the expression of the enzyme 3-deoxy-D-arabino-heptulosonate-7-phosphate (DAHP) synthase. DAHP synthase is encoded by the ARO4 gene. In examples, DAHP synthase catalyzes the reaction of erythrose-4-phosphate+phosphoenolpyruvic acid→DAHP, as referenced in FIG. 2. An engineered host cell may modify the ARO4 gene to incorporate one or more feedback inhibition alleviating mutations. In particular, a feedback inhibition alleviating mutation (e.g., $ARO4^{FBR}$) may be incorporated as a directed mutation to a native ARO4 gene at the original locus; as an additional copy introduced as a genetic integration at a separate locus; or as an additional copy on an episomal vector such as a 2 μm or centromeric plasmid. The identifier "FBR" in the mutation $ARO4^{FBR}$ refers to feedback resistant mutants and mutations. The feedback inhibited copy of the DAHP synthase enzyme may be under a native yeast transcriptional regulation, such as when the engineered host cell is a yeast cell. Alternatively, the feedback inhibited copy of the DAHP synthase enzyme may be introduced to the engineered host cell with engineered constitutive or dynamic regulation of protein expression by placing it under the control of a synthetic promoter. In some cases, the ARO4 gene may be derived from *Saccharomyces cerevisiae*. In some cases, the ARO4 gene may be 100% similar to the naturally occurring gene. Examples of modifications to the ARO4 gene include a feedback inhibition resistant mutation, K229L, or Q166K.

[ARO7] In some examples, the engineered host cell may modify the expression of the enzyme chorismate mutase. Chorismate mutase is encoded by the ARO7 gene. In examples, chorismate mutase catalyzes the reaction of chorismate→prephenate, as referenced in FIG. 2. An engineered host cell may modify the ARO7 gene to incorporate one or more feedback inhibition alleviating mutations. In particular, a feedback inhibition alleviating mutation (e.g., $ARO7^{FBR}$) may be incorporated as a directed mutation to a native ARO7 gene at the original locus; as an additional copy introduced as a genetic integration at a separate locus; or as an additional copy on an episomal vector such as a 2-μm or centromeric plasmid. The identifier "FBR" in the mutation $ARO7^{FBR}$ refers to feedback resistant mutants and mutations. The feedback inhibited copy of the chorismate mutase enzyme may be under a native yeast transcriptional regulation, such as when the engineered host cell is a yeast cell. Alternatively, the feedback inhibited copy of the chorismate mutase enzyme may be introduced to the engineered host cell with engineered constitutive or dynamic regulation of protein expression by placing it under the control of a synthetic promoter. In some cases, the ARO7 gene may be derived from *Saccharomyces cerevisiae*. In some cases, the ARO7 gene may be 100% similar to the naturally occurring gene. Examples of modifications to the ARO7 gene include a feedback inhibition resistant mutation or T2261.

[ARO10] In some examples, the engineered host cell may modify the expression of the enzyme phenylpyruvate decarboxylase. Phenylpyruvate decarboxylase is encoded by the ARO10 gene. In examples, phenylpyruvate decarboxylase catalyzes the reaction of hydroxyphenylpyruvate→4-hydroxyphenylacetate (4HPA), as referenced in FIG. 2. An engineered host cell may be modified to include constitutive overexpression of the ARO10 gene in the engineered host cell. Additionally or alternatively, the engineered host cell may be modified to synthetically regulate the expression of the ARO10 gene in the engineered host cell. In examples, the engineered host cell may be modified to incorporate a copy, copies, or additional copies, of the ARO10 gene. Additionally or alternatively, the engineered host cell may be modified to incorporate the introduction of a strong promoter element for the overexpression of the ARO10 gene within the engineered host cell. The ARO10 gene may be derived from *Saccharomyces cerevisiae* or another species. In some examples, the ARO10 gene may be 100% similar to the naturally occurring gene.

[ADH2-7, SFA1] In some examples, the engineered host cell may modify the expression of alcohol dehydrogenase enzymes. Alcohol dehydrogenase enzymes may be encoded by one or more of the ADH2, ADH3, ADH4, ADH5, ADH6, ADH7, and SFA1 genes. In examples, alcohol dehydrogenase catalyzes the reaction of 4HPA→tyrosol. An engineered host cell may be modified to delete the coding region of one or more of the ADH2, ADH3, ADH4, ADH5, ADH6, ADH7, and SFA1 genes in the engineered host cell. Alternatively, the engineered host cell may be modified to disable the functionality of one or more of the ADH2, ADH3, ADH4, ADH5, ADH6, ADH7, and SFA1 genes, such as by introducing an inactivating mutation.

[ALD2-6] In some examples, the engineered host cell may modify the expression of aldehyde oxidase enzymes. Aldehyde oxidase enzymes may be encoded by one or more of the ALD2, ALD3, ALD4, ALD5, and ALD6 genes. In examples, aldehyde oxidase catalyzes the reaction of 4HPA→4 hydroxyphenylacetic acid. An engineered host cell may be modified to delete the coding region of one or more of the ALD2, ALD3, ALD4, ALD5, and ALD6 genes in the engineered host cell. Alternatively, the engineered host cell may be modified to disable the functionality of one or more of the ALD2, ALD3, ALD4, ALD5, and ALD6 genes, such as by introducing an inactivating mutation.

[ARO9] In some examples, the engineered host cell may modify the expression of the enzyme aromatic aminotransferase. Aromatic aminotransferase is encoded by the ARO9 gene. In examples, aromatic aminotransferase catalyzes the reaction of hydroxyphenylpyruvate+L-alanine↔tyrosine+pyruvate, as referenced in FIG. 2. An engineered host cell may be modified to include constitutive overexpression of the ARO9 gene in the engineered host cell. Additionally or alternatively, the engineered host cell may be modified to synthetically regulate the expression of the ARO9 gene in the engineered host cell. In examples, the engineered host cell may be modified to incorporate a copy, copies, or additional copies, of the ARO9 gene. Additionally or alternatively, the engineered host cell may be modified to incorporate the introduction of a strong promoter element for the overexpression of the ARO9 gene within the engineered host cell. The ARO9 gene may be derived from *Saccharomyces cerevisiae* or another species. In some examples, the ARO9 gene may be 100% similar to the naturally occurring gene.

[ARO8] In some examples, the engineered host cell may modify the expression of the enzyme aromatic aminotransferase. Aromatic aminotransferase is encoded by the ARO8 gene. In examples, aromatic aminotransferase catalyzes the reaction of hydroxyphenylpyruvate+glutamate↔tyrosine+alpha-ketogluterate, as referenced in FIG. 2. An engineered host cell may be modified to include constitutive overexpression of the ARO8 gene in the engineered host cell. Additionally or alternatively, the engineered host cell may be modified to synthetically regulate the expression of the ARO8 gene in the engineered host cell. In examples, the engineered host cell may be modified to incorporate a copy, copies, or additional copies, of the ARO8 gene. Additionally or alternatively, the engineered host cell may be modified to incorporate the introduction of a strong promoter element for the overexpression of the ARO8 gene within the engineered host cell. The ARO8 gene may be derived from *Saccharomyces cerevisiae* or another species. In some examples, the ARO8 gene may be 100% similar to the naturally occurring gene.

[TYR1] In some examples, the engineered host cell may modify the expression of the enzyme prephenate dehydrogenase. Prephenate dehydrogenase is encoded by the TYR1 gene. In examples, prephenate dehydrogenase catalyzes the reaction of prephenate+$NADP^+$→4-hydroxyphenylpyruvate+$CO_2$+NADPH, as referenced in FIG. 2. An engineered host cell may be modified to include constitutive overexpression of the TYR1 gene in the engineered host cell. Additionally or alternatively, the engineered host cell may be modified to synthetically regulate the expression of the TYR1 gene in the engineered host cell. In examples, the engineered host cell may be modified to incorporate a copy, copies, or additional copies, of the TYR1 gene. Additionally or alternatively, the engineered host cell may be modified to incorporate the introduction of a strong promoter element for the overexpression of the TYR1 gene within the engineered host cell. The TYR1 gene may be derived from *Saccharomyces cerevisiae* or another species. In some examples, the TYR1 gene may be 100% similar to the naturally occurring gene.

[TYR] In some examples, the engineered host cell may modify the expression of the enzyme tyrosinase. Tyrosinase is encoded by the TYR gene. In examples, tyrosinase catalyzes the reaction of tyrosine→L-DOPA, as referenced in FIGS. 2, 12, and 13. In other examples, tyrosinase catalyzes the reaction of L-DOPA→dopaquinone. An engineered host cell may be modified to include constitutive expression of the TYR gene in the engineered host cell. Additionally or alternatively, the engineered host cell may be modified to synthetically regulate the expression of the TYR gene in the engineered host cell. In examples, the engineered host cell may be modified to incorporate a copy, copies, or additional copies, of the TYR gene. Additionally or alternatively, the engineered host cell may be modified to incorporate the introduction of a strong promoter element for the overexpression of the TYR gene within the engineered host cell. The TYR gene may be derived from *Ralstonia solanacearum, Agaricus bisporus*, or another species. In some examples, the TYR gene may be 100% similar to the naturally occurring gene.

[TyrH] In some examples, the engineered host cell may modify the expression of the enzyme tyrosine hydroxylase. Tyrosine hydroxylase is encoded by the TyrH gene. In examples, tyrosine hydroxylase catalyzes the reaction of tyrosine→L-DOPA, as referenced in FIGS. 2, 12, and 13. An engineered host cell may be modified to include constitutive expression of the TyrH gene in the engineered host cell. Additionally or alternatively, the engineered host cell may be modified to synthetically regulate the expression of the TyrH gene in the engineered host cell. In examples, the engineered host cell may be modified to incorporate a copy, copies, or additional copies, of the TyrH gene. Additionally or alternatively, the engineered host cell may be modified to incorporate the introduction of a strong promoter element for the overexpression of the TyrH gene within the engineered host cell. The TyrH gene may be derived from *Homo sapiens, Rattus norvegicus, Mus musculus*, or another species. In some examples, the TyrH gene may be 100% similar to the naturally occurring gene.

[DODC] In some examples, the engineered host cell may modify the expression of the enzyme L-DOPA decarboxylase. L-DOPA decarboxylase is encoded by the DODC gene. In examples, L-DOPA decarboxylase catalyzes the reaction of L-DOPA→dopamine, as referenced in FIGS. 2, 12, and 13. An engineered host cell may be modified to include constitutive expression of the DODC gene in the engineered host cell. Additionally or alternatively, the engineered host cell may be modified to synthetically regulate the expression of the DODC gene in the engineered host cell. In examples, the engineered host cell may be modified to incorporate a copy, copies, or additional copies, of the DODC gene. Additionally or alternatively, the engineered host cell may be modified to incorporate the introduction of a strong promoter element for the overexpression of the DODC gene within the engineered host cell. The DODC gene may be derived from *Pseudomonas putida, Rattus norvegicus*, or another species. In some examples, the DODC gene may be 100% similar to the naturally occurring gene.

[TYDC] In some examples, the engineered host cell may modify the expression of the enzyme tyrosine/DOPA decarboxylase. Tyrosine/DOPA decarboxylase is encoded by the TYDC gene. In examples, tyrosine/DOPA decarboxylase catalyzes the reaction of L-DOPA→dopamine, as referenced in FIGS. 2, 12, and 13. An engineered host cell may be modified to include constitutive expression of the TYDC gene in the engineered host cell. Additionally or alternatively, the engineered host cell may be modified to synthetically regulate the expression of the TYDC gene in the engineered host cell. In examples, the engineered host cell may be modified to incorporate a copy, copies, or additional copies, of the TYDC gene. Additionally or alternatively, the engineered host cell may be modified to incorporate the introduction of a strong promoter element for the overexpression of the TYDC gene within the engineered host cell. The TYDC gene may be derived from *Papaver somniferum* or another species. In some examples, the TYDC gene may be 100% similar to the naturally occurring gene.

[MAO] In some examples, the engineered host cell may modify the expression of the enzyme monoamine oxidase. Monoamine oxidase is encoded by the MAO gene. In examples, monoamine oxidase catalyzes the reaction of dopamine→3,4-DHPA, as referenced in FIGS. 2 and 13. An engineered host cell may be modified to include constitutive expression of the MAO gene in the engineered host cell. Additionally or alternatively, the engineered host cell may be modified to synthetically regulate the expression of the MAO gene in the engineered host cell. In examples, the engineered host cell may be modified to incorporate a copy, copies, or additional copies, of the MAO gene. Additionally or alternatively, the engineered host cell may be modified to incorporate the introduction of a strong promoter element for the overexpression of the MAO gene within the engineered host cell. In some cases, the MAO gene may be codon optimized for expression in *Saccharomyces cerevisiae*. The MAO gene may be derived from *Escherichia coli, Homo sapiens, Micrococcus luteus*, or another species. In some examples, the MAO gene may be 77% similar to the naturally occurring gene.

Figure 12:
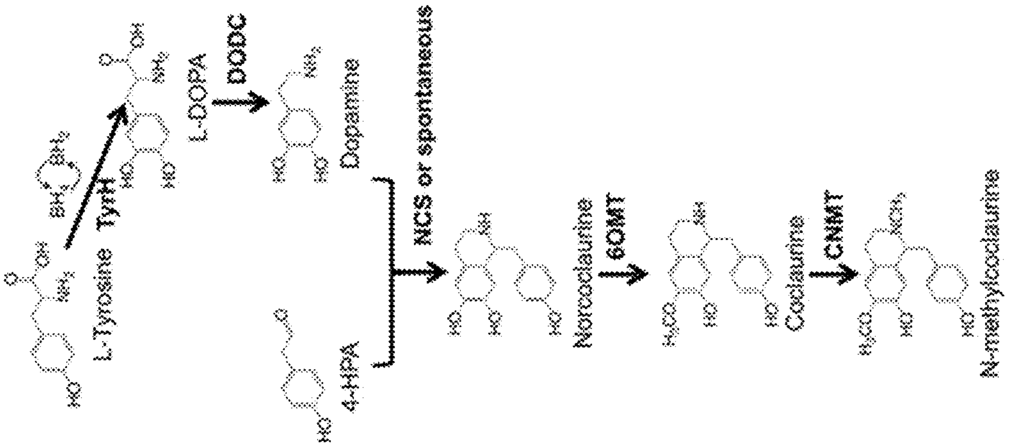
FIG. 12 illustrates a biosynthetic scheme for conversion of L-tyrosine to reticuline via norcoclaurine, in accordance with embodiments of the invention.
Figure 12:
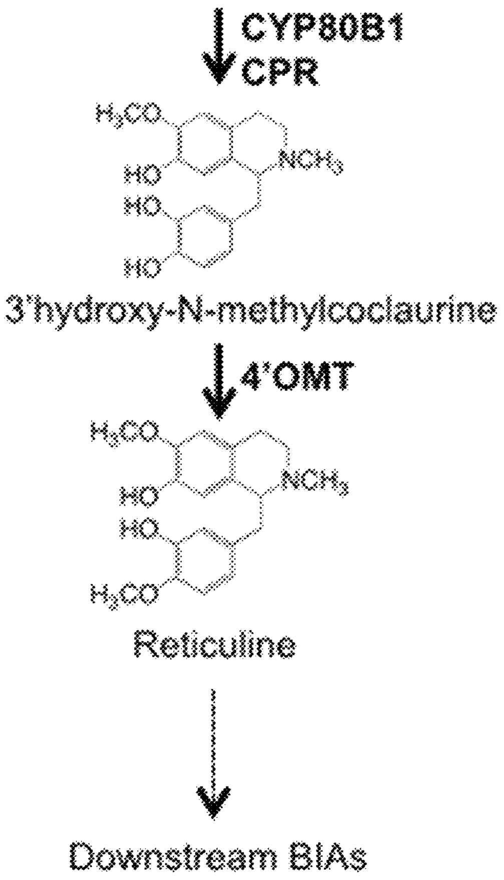

[NCS] In some examples, the engineered host cell may modify the expression of the enzyme norcoclaurine synthase. Norcoclaurine synthase is encoded by the NCS gene. In examples, norcoclaurine synthase catalyzes the reaction of 4HPA+dopamine→(S)-norcoclaurine, as referenced in FIGS. 12 and 13. In particular, FIG. 12 illustrates a biosynthetic scheme for conversion of L-tyrosine to reticuline via norcoclaurine, in accordance with embodiments of the invention. FIG. 12 provides the use of the enzymes TyrH, tyrosine hydroxylase; DODC, DOPA decarboxylase; NCS, norcoclaurine synthase, as discussed herein; 6OMT, 6-O-methyltransferase; CNMT, coclaurine N-methyltransferase; CYP80B1, cytochrome P450 80B1; CPR, cytochrome P450 NADPH reductase; 4'OMT, 3'hydroxy-N-methylcoclaurine 4'-O-methyltransferase. L-DOPA, L-3,4-dihydroxyphenylalanine; and 4-HPA, 4-hydroxyphenylacetylaldehyde. Of the enzymes that are illustrated in FIG. 12, 4-HPA and L-tyrosine are naturally synthesized in yeast. All other metabolites shown are not naturally produced in yeast. Additionally, although TyrH is depicted as catalyzing the conversion of L-tyrosine to L-DOPA, other enzymes may also be used to perform this step as described in the specification. For example, tyrosinases may also be used to perform the conversion of L-tyrosine to L-DOPA. In addition, other enzymes such as cytochrome P450 oxidases may also be used to perform the conversion of L-tyrosine to L-DOPA. Such enzymes may exhibit oxidase activity on related BIA precursor compounds including L-DOPA and L-tyrosine.

Figure 13:
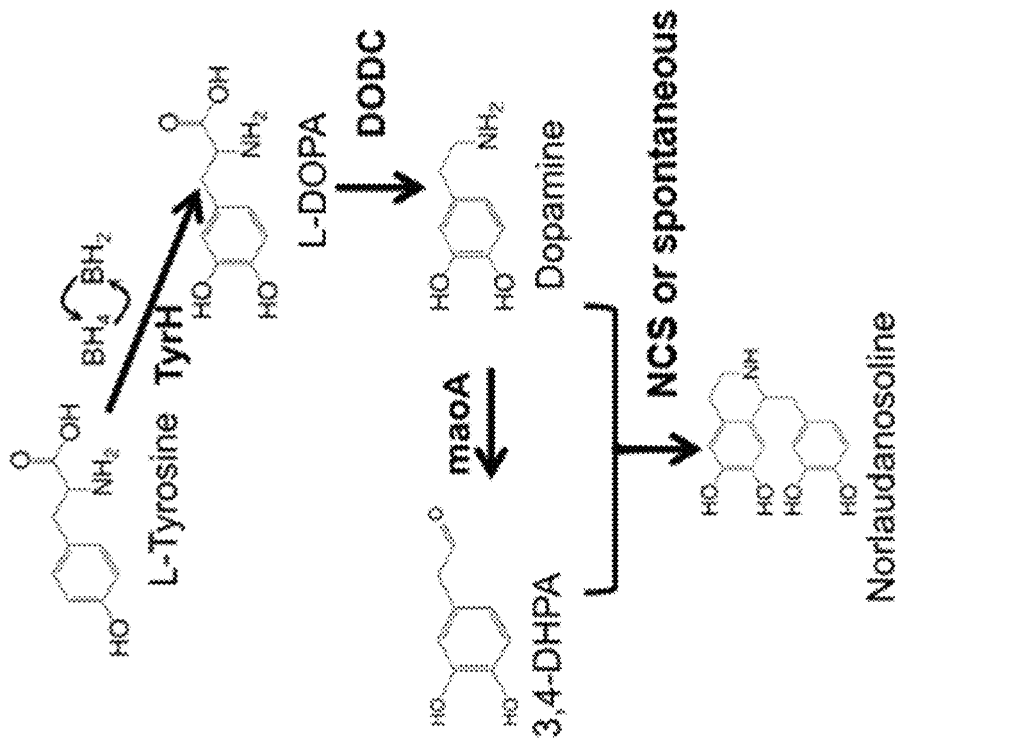
FIG. 13 illustrates a biosynthetic scheme for conversion of L-tyrosine to reticuline via norlaudanosoline, in accordance with embodiments of the invention.
Figure 13:
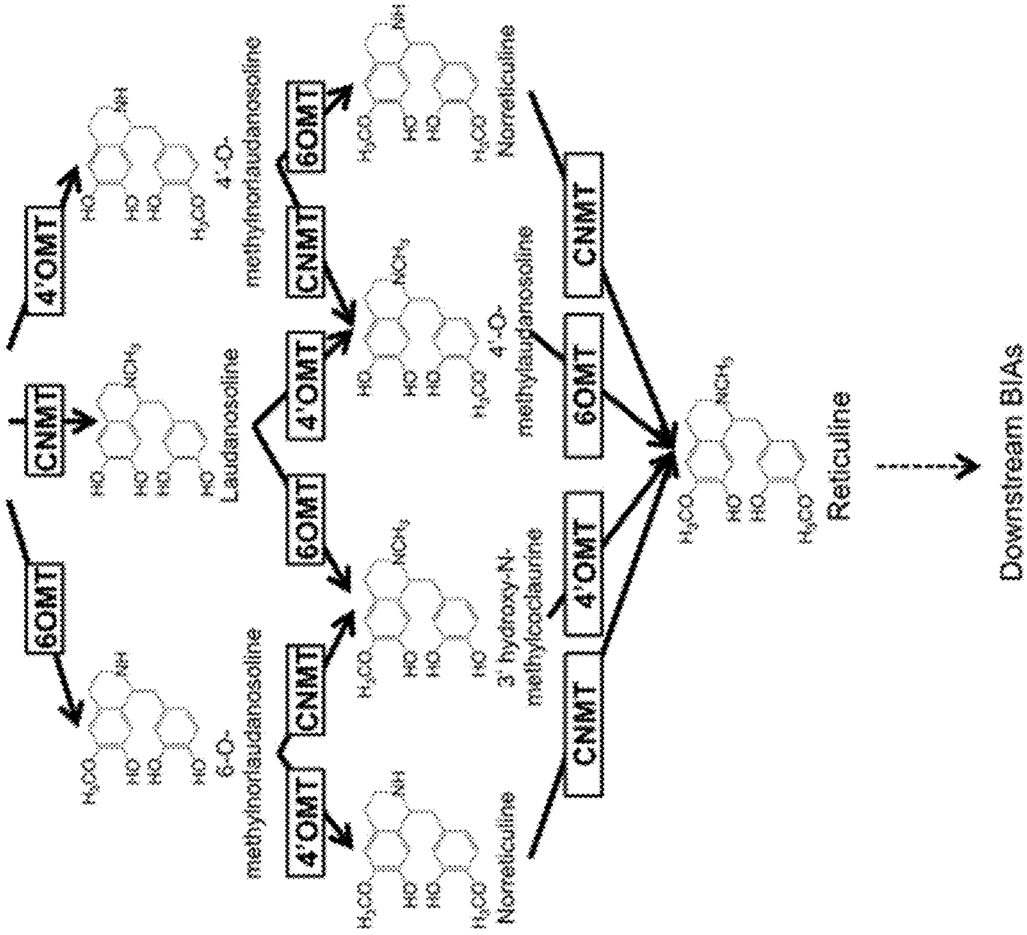

Additionally, norcoclaurine synthase catalyzes the reaction of 3,4-DHPA+dopamine→(S)-norlaudanosoline, as referenced in FIG. 13. In particular, FIG. 13 illustrates a biosynthetic scheme for conversion of L-tyrosine to reticuline via norlaudanosoline, in accordance with embodiments of the invention. FIG. 13 provides the use of the enzymes TyrH, tyrosine hydroxylase; DODC, DOPA decarboxylase; maoA, monoamine oxidase; NCS, norcoclaurine synthase; 6OMT, 6-O-methyltransferase; CNMT, coclaurine N-methyltransferase; 4'OMT, 3'hydroxy-N-methylcoclaurine 4'-O-methyltransferase. L-DOPA, L-3,4-dihydroxyphenylalanine; and 3,4-DHPA, 3,4-dihydroxyphenylacetaldehyde. Of the enzymes that are illustrated in FIG. 13, L-tyrosine is naturally synthesized in yeast. Other metabolites that are shown in FIG. 13 are not naturally produced in yeast.

An engineered host cell may be modified to include constitutive expression of the NCS gene in the engineered host cell. Additionally or alternatively, the engineered host cell may be modified to synthetically regulate the expression of the NCS gene in the engineered host cell. In examples, the engineered host cell may be modified to incorporate a copy, copies, or additional copies, of the NCS gene. Additionally or alternatively, the engineered host cell may be modified to incorporate the introduction of a strong promoter element for the overexpression of the NCS gene within the engineered host cell. Additionally, the norcoclaurine synthase may have an N-terminal truncation. In some cases, the NCS gene may be codon optimized for expression in *Saccharomyces cerevisiae*. The NCS gene may be derived from *Coptis japonica, Papaver somniferum, Papver bracteatum, Thalicitum flavum, Corydalis saxicola*, or another species. In some examples, the NCS gene may be 80% similar to the naturally occurring gene.

[6OMT] In some examples, the engineered host cell may modify the expression of the enzyme norcoclaurine 6-O-methyltransferase. Norcoclaurine 6-O-methyltransferase is encoded by the 6OMT gene. In some examples, norcoclaurine 6-O-methyltransferase catalyzes the reaction of norcoclaurine→coclaurine, as referenced in FIG. 12. In other examples, norcoclaurine 6-O-methyltransferase catalyzes the reaction of norlaudanosoline→3'hydroxycoclaurine, as well as other reactions detailed herein, such as those provided in FIG. 13. Additionally, the engineered host cell may be modified to include constitutive expression of the 6OMT gene in the engineered host cell. Additionally or alternatively, the engineered host cell may be modified to synthetically regulate the expression of the 6OMT gene in the engineered host cell. In examples, the engineered host cell may be modified to incorporate a copy, copies, or additional copies, of the 6OMT gene. Additionally or alternatively, the engineered host cell may be modified to incorporate the introduction of a strong promoter element for the overexpression of the 6OMT gene within the engineered host cell. The 6OMT gene may be derived from *P. somniferum, T flavum, Coptis japonica*, or another species. In some examples, the 6OMT gene may be 100% similar to the naturally occurring gene.

[CNMT] In some examples, the engineered host cell may modify the expression of the enzyme coclaurine-N-methyltransferase. Coclaurine-N-methyltransferase is encoded by the CNMT gene. In some examples, coclaurine-N-methyltransferase catalyzes the reaction of coclaurine→N-methylcoclaurine, as referenced in FIG. 12. In other examples, the coclaurine-N-methyltransferase enzyme may catalyze the reaction of 3'hydroxycoclaurine→3'hydroxy-N-methylcoclaurine. In other examples, coclaurine-N-methyltransferase may catalyze other reactions detailed herein, such as those provided in FIG. 13. Additionally, the engineered host cell may be modified to include constitutive expression of the CNMT gene in the engineered host cell. Additionally or alternatively, the engineered host cell may be modified to synthetically regulate the expression of the CNMT gene in the engineered host cell. In examples, the engineered host cell may be modified to incorporate a copy, copies, or additional copies, of the CNMT gene. Additionally or alternatively, the engineered host cell may be modified to incorporate the introduction of a strong promoter element for the overexpression of the CNMT gene within the engineered host cell. The CNMT gene may be derived from *P. som-*

*niferum, T flavum, Coptis japonica*, or another species. In some examples, the CNMT gene may be 100% similar to the naturally occurring gene.

[4'OMT] In some examples, the engineered host cell may modify the expression of the enzyme 4'-O-methyltransferase. 4'-O-methyltransferase is encoded by the 4'OMT gene. In some examples, 4'-O-methyltransferase catalyzes the reaction of 3'-hydroxy-N-methylcoclaurine→reticuline, as referenced in FIG. 12. In other examples, 4'-O-methyltransferase catalyzes other reactions detailed herein, such as those provided in FIG. 13. Additionally, the engineered host cell may be modified to include constitutive expression of the 4'OMT gene in the engineered host cell. Additionally or alternatively, the engineered host cell may be modified to synthetically regulate the expression of the 4'OMT gene in the engineered host cell. In examples, the engineered host cell may be modified to incorporate a copy, copies, or additional copies, of the 4'OMT gene. Additionally or alternatively, the engineered host cell may be modified to incorporate the introduction of a strong promoter element for the overexpression of the 4'OMT gene within the engineered host cell. The 4'OMT gene may be derived from *P. somniferum, T flavum, Coptis japonica*, or another species. In some examples, the 4'OMT gene may be 100% similar to the naturally occurring gene.

[CYPSOB1] In some examples, the engineered host cell may modify the expression of the enzyme cytochrome P450 80B1. Cytochrome P450 80B1 is encoded by the CYP80B1 gene. In examples, cytochrome P450 80B1 catalyzes the reaction of N-methylcoclaurine→3'-hydroxy-N-methylcoclaurine, as referenced in FIG. 12. An engineered host cell may be modified to include constitutive expression of the cytochrome P450 80B1 gene in the engineered host cell. Additionally or alternatively, the engineered host cell may be modified to synthetically regulate the expression of the cytochrome P450 80B1 gene in the engineered host cell. In examples, the engineered host cell may be modified to incorporate a copy, copies, or additional copies, of the cytochrome P450 80B1 gene. Additionally or alternatively, the engineered host cell may be modified to incorporate the introduction of a strong promoter element for the overexpression of the cytochrome P450 80B1 gene within the engineered host cell. In some cases, the CYP80B1 gene may be codon optimized for expression in *Saccharomyces cerevisiae*. The cytochrome P450 80B1 gene may be derived from *P. somniferum, E. californica, T flavum*, or another species. In some examples, the P450 80B1 gene may be 77% similar to the naturally occurring gene.

[FOL2] In some examples, the engineered host cell may modify the expression of the enzyme GTP cyclohydrolase. GTP cyclohydrolase is encoded by the FOL2 gene. In some examples, GTP cyclohydrolase catalyzes the reaction of GTP→dihydroneopterin triphosphate, as referenced in FIG. 1. The engineered host cell may be modified to include constitutive overexpression of the FOL2 gene in the engineered host cell. The engineered host cell may also be modified to include native regulation. Additionally or alternatively, the engineered host cell may be modified to synthetically regulate the expression of the FOL2 gene in the engineered host cell. In examples, the engineered host cell may be modified to incorporate a copy, copies, or additional copies, of the FOL2 gene. Additionally or alternatively, the engineered host cell may be modified to incorporate the introduction of a strong promoter element for the overexpression of the FOL2 gene within the engineered host cell. The FOL2 gene may be derived from *Saccharomyces cerevisiae, Homo sapiens, Mus musculus*, or another species. In some examples, the FOL2 gene may be 100% similar to the naturally occurring gene.

[PTPS] In some examples, the engineered host cell may modify the expression of the enzyme 6-pyruvoyl tetrahydrobiopterin (PTP) synthase. Pyruvoyl tetrahydrobiopterin synthase is encoded by the PTPS gene. In some examples, 6-pyruvoyl tetrahydrobiopterin synthase catalyzes the reaction of dihydroneopterin triphosphate→PTP, as referenced in FIG. 1. The engineered host cell may be modified to include constitutive expression of the PTPS gene in the engineered host cell. Additionally or alternatively, the engineered host cell may be modified to synthetically regulate the expression of the PTPS gene in the engineered host cell. In examples, the engineered host cell may be modified to incorporate a copy, copies, or additional copies, of the PTPS gene. Additionally or alternatively, the engineered host cell may be modified to incorporate the introduction of a strong promoter element for the overexpression of the PTPS gene within the engineered host cell. In some cases, the PTPS gene may be codon optimized for expression in *Saccharomyces cerevisiae*. The PTPS gene may be derived from *Rattus norvegicus, Homo sapiens, Mus musculus*, or another species. In some examples, the PTPS gene may be 80% similar to the naturally occurring gene.

[SepR] In some examples, the engineered host cell may modify the expression of the enzyme sepiapterin reductase. Sepiapterin reductase is encoded by the SepR gene. In some examples, sepiapterin reductase catalyzes the reaction of PTP→$BH_4$, as referenced in FIG. 1. The engineered host cell may be modified to include constitutive expression of the SepR gene in the engineered host cell. Additionally or alternatively, the engineered host cell may be modified to synthetically regulate the expression of the SepR gene in the engineered host cell. In examples, the engineered host cell may be modified to incorporate a copy, copies, or additional copies, of the SepR gene. Additionally or alternatively, the engineered host cell may be modified to incorporate the introduction of a strong promoter element for the overexpression of the SepR gene within the engineered host cell. In some cases, the SepR gene may be codon optimized for expression in *Saccharomyces cerevisiae*. The SepR gene may be derived from *Rattus norvegicus, Homo sapiens, Mus musculus*, or another species. In some examples, the SepR gene may be 72% similar to the naturally occurring gene.

[PCD] In some examples, the engineered host cell may modify the expression of the enzyme 4a-hydroxytetrahydrobiopterin (pterin-4a-carbinolamine) dehydratase. 4a-hydroxytetrahydrobiopterin dehydratase is encoded by the PCD gene. In some examples, 4a-hydroxytetrahydrobiopterin dehydratase catalyzes the reaction of 4a-hydroxytetrahydrobiopterin→$H_2O$+quinonoid dihydropteridine, as referenced in FIG. 1. The engineered host cell may be modified to include constitutive expression of the PCD gene in the engineered host cell. Additionally or alternatively, the engineered host cell may be modified to synthetically regulate the expression of the PCD gene in the engineered host cell. In examples, the engineered host cell may be modified to incorporate a copy, copies, or additional copies, of the PCD gene. Additionally or alternatively, the engineered host cell may be modified to incorporate the introduction of a strong promoter element for the overexpression of the PCD gene within the engineered host cell. In some cases, the PCD gene may be codon optimized for expression in *Saccharomyces cerevisiae*. The PCD gene may be derived from *Rattus norvegicus, Homo sapiens, Mus*

*musculus*, or another species. In some examples, the PCD gene may be 79% similar to the naturally occurring gene.

[QDHPR] In some examples, the engineered host cell may modify the expression of the enzyme quinonoid dihydropteridine reductase. Quinonoid dihydropteridine reductase is encoded by the QDHPR gene. In some examples, quinonoid dihydropteridine reductase catalyzes the reaction of quinonoid dihydropteridine→$BH_4$, as referenced in FIG. 1. The engineered host cell may be modified to include constitutive expression of the QDHPR gene in the engineered host cell. Additionally or alternatively, the engineered host cell may be modified to synthetically regulate the expression of the QDHPR gene in the engineered host cell. In examples, the engineered host cell may be modified to incorporate a copy, copies, or additional copies, of the QDHPR gene. Additionally or alternatively, the engineered host cell may be modified to incorporate the introduction of a strong promoter element for the overexpression of the QDHPR gene within the engineered host cell. In some cases, the QDHPR gene may be codon optimized for expression in *Saccharomyces cerevisiae*. The QDHPR gene may be derived from *Rattus norvegicus, Homo sapiens, Mus musculus*, or another species. In some examples, the QDHPR gene may be 75% similar to the naturally occurring gene.

[DHFR] In some examples, the engineered host cell may modify the expression of the enzyme dihydrofolate reductase. Dihydrofolate reductase is encoded by the DHFR gene. In some examples, dihydrofolate reductase catalyzes the reaction of 7,8-dihydrobiopterin ($BH_2$)→5,6,7,8-tetrahydrobiopterin ($BH_4$), as referenced in FIG. 1. This reaction may be useful in recovering $BH_4$ as a co-substrate for the converstion of tyrosine to L-DOPA, as illustrated in FIG. 12. The engineered host cell may be modified to include constitutive expression of the DHFR gene in the engineered host cell. Additionally or alternatively, the engineered host cell may be modified to synthetically regulate the expression of the DHFR gene in the engineered host cell. In examples, the engineered host cell may be modified to incorporate a copy, copies, or additional copies, of the DHFR gene. Additionally or alternatively, the engineered host cell may be modified to incorporate the introduction of a strong promoter element for the overexpression of the DHFR gene within the engineered host cell. In some cases, the DHFR gene may be codon optimized for expression in *Saccharomyces cerevisiae*. The DHFR gene may be derived from *Rattus norvegicus, Homo sapiens*, or another species. In some examples, the DHFR gene may be 77% similar to the naturally occurring gene.

Figure 14:
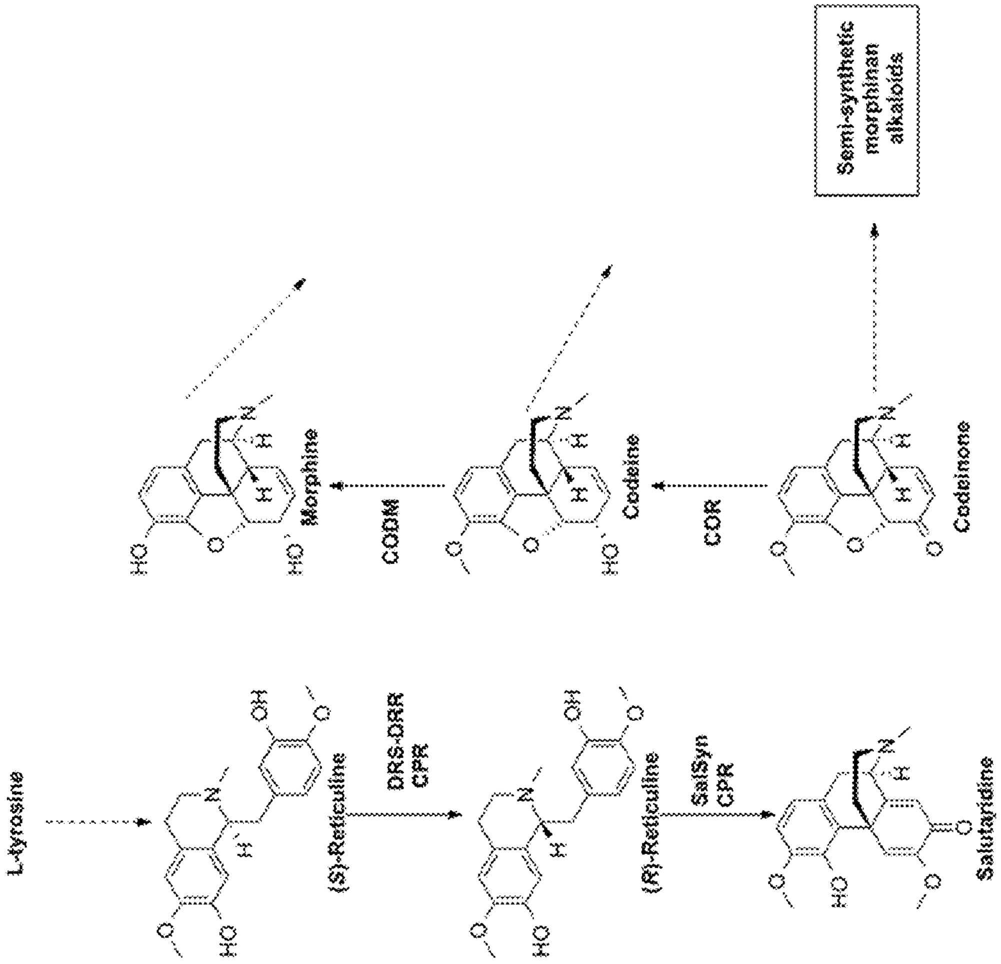
FIG. 14 illustrates a biosynthetic scheme for conversion of L-tyrosine to morphinan alkaloids, in accordance with embodiments of the invention.
Figure 14:
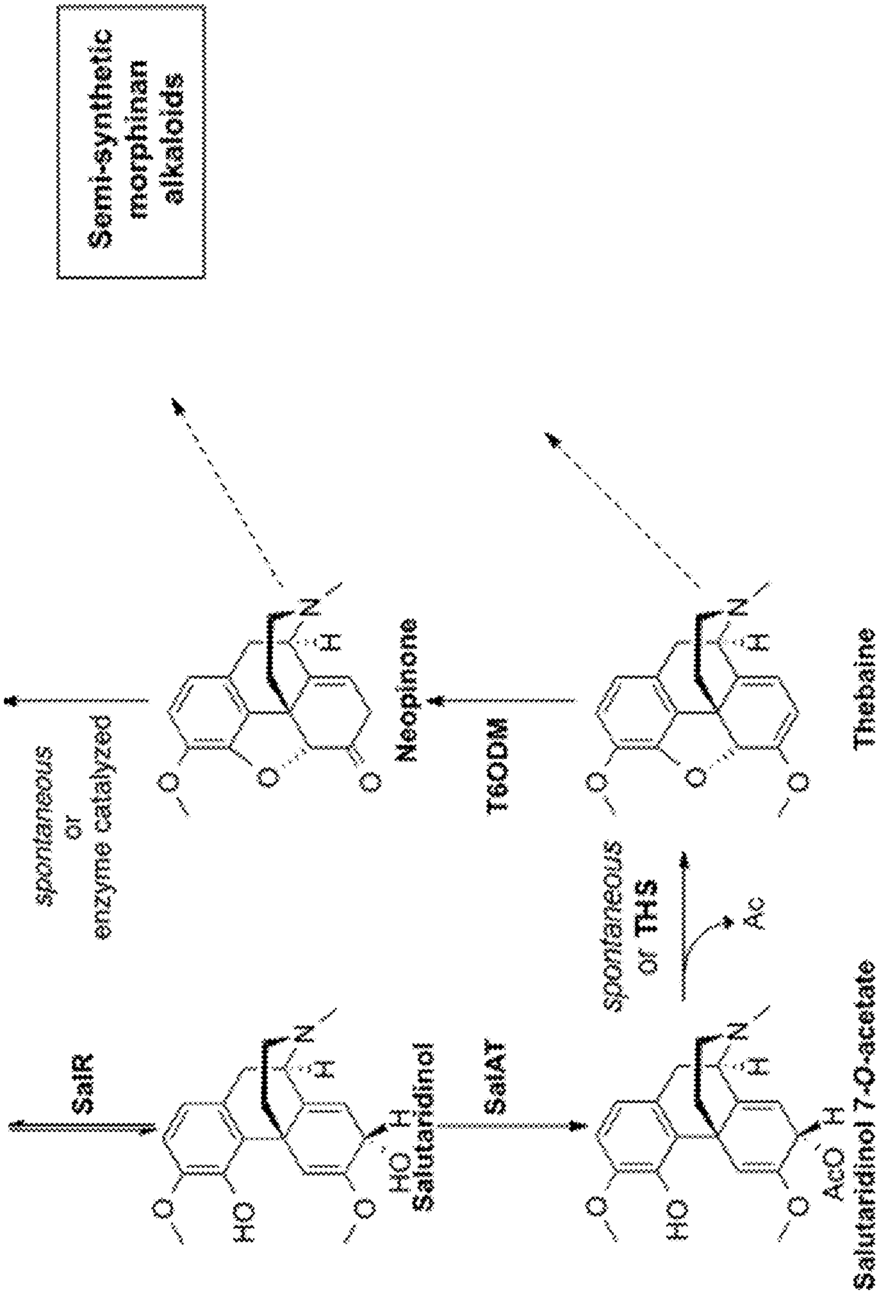

[DRS-DRR] As discussed above with regard to epimerizing 1-BIAs, the engineered host cell may modify the expression of a BIA epimerase. The BIA epimerase is encoded by the DRS-DRR gene. In some examples, DRS-DRR may also be referred to as CYP-COR. In some examples, the BIA epimerase, or an engineered split version or an engineered fused version of the BIA epimerase, catalyzes the conversion of (S)-1-BIA→(R)-1-BIA, as referenced in FIG. 14. In particular, FIG. 14 illustrates a biosynthetic scheme for conversion of L-tyrosine to morphinan alkaloids, in accordance with embodiments of the invention. FIG. 14 provides the use of the enzymes CPR, cytochrome P450 reductase; DRS-DRR, dehydroreticuline synthase and dehydroreticuline reductase; SalSyn, salutaridine synthase; SalR, salutaridine reductase; SalAT, salutaridinol 7-O-acetyltransferase; TS, thebaine synthase; T6ODM, thebaine 6-O-demethylase; COR, codeinone reductase; and CODM, codeine-O-demethylase.

The engineered host cell may be modified to include constitutive expression of the DRS-DRR gene or the engineered DRS-DRR gene in the engineered host cell. In some cases, the engineered DRS-DRR gene may encode an engineered fusion epimerase. In some cases, the engineered DRS-DRR gene may encode an engineered split epimerase. Additionally or alternatively, the engineered host cell may be modified to synthetically regulate the expression of the DRS-DRR gene in the engineered host cell. In examples, the engineered host cell may be modified to incorporate a copy, copies, or additional copies, of the DRS-DRR gene. Additionally or alternatively, the engineered host cell may be modified to incorporate the introduction of a strong promoter element for the overexpression of the DRS-DRR gene within the engineered host cell. The DRS-DRR gene may be derived from *Papaver bracteatum, Papaver somniferum, Papaver setigerum, Chelidonium majus*, or another species. In some examples, the DRS-DRR gene may be 77% similar to the naturally occurring gene.

[CPR] In some examples, the engineered host cell may modify the expression of the enzyme cytochrome P450 reductase. The cytochrome P450 reductase is encoded by the CPR gene. In some examples, the cytochrome P450 reductase catalyzes the reaction of (R)-reticuline salutaridine, as referenced in FIG. 14. Additionally, the cytochrome P450 reductase catalyzes other reactions such as those described in FIGS. throughout the application. The engineered host cell may be modified to include constitutive expression of the CPR gene in the engineered host cell. Additionally or alternatively, the engineered host cell may be modified to synthetically regulate the expression of the CPR gene in the engineered host cell. In examples, the engineered host cell may be modified to incorporate a copy, copies, or additional copies, of the CPR gene. Additionally or alternatively, the engineered host cell may be modified to incorporate the introduction of a strong promoter element for the overexpression of the CPR gene within the engineered host cell. The CPR gene may be derived from *E. californica, P. somniferum, Hsapiens, S. cerevisiae, A. thaliana*, or another species. In some examples, the CPR gene may be 100% similar to the naturally occurring gene.

[SalSyn] In some examples, the engineered host cell may modify the expression of the enzyme salutaridine synthase. The salutaridine synthase is encoded by the SalSyn gene. In some examples, the salutaridine synthase catalyzes the reaction of (R)-reticuline→salutaridine, as referenced in FIG. 14. The engineered host cell may be modified to include constitutive expression of the SalSyn gene in the engineered host cell. Additionally or alternatively, the engineered host cell may be modified to synthetically regulate the expression of the SalSyn gene in the engineered host cell. In examples, the engineered host cell may be modified to incorporate a copy, copies, or additional copies, of the SalSyn gene. Additionally or alternatively, the engineered host cell may be modified to incorporate the introduction of a strong promoter element for the overexpression of the SalSyn gene within the engineered host cell. In some cases, the SalSyn gene may be codon optimized for expression in *Saccharomyces cerevisiae*. In some examples the SalSyn may be modified at the N-terminus. The SalSyn gene may be derived from *Papaver somniferum, Papaver* spp, *Chelidonium majus*, or another species. In some examples, the SalSyn gene may be 78% similar to the naturally occurring gene.

[SalR] In some examples, the engineered host cell may modify the expression of the enzyme salutaridine reductase. Salutaridine reductase is encoded by the SalR gene. In some examples, salutaridine reductase reversibly catalyzes the reaction of salutaridinol→salutaridine, as referenced in FIG. 14. The engineered host cell may be modified to include constitutive expression of the SalR gene in the engineered host cell. Additionally or alternatively, the engineered host cell may be modified to synthetically regulate the expression of the SalR gene in the engineered host cell. In examples, the engineered host cell may be modified to incorporate a copy, copies, or additional copies, of the SalR gene. Additionally or alternatively, the engineered host cell may be modified to incorporate the introduction of a strong promoter element for the overexpression of the SalR gene within the engineered host cell. In some cases, the SalR gene may be codon optimized for expression in *Saccharomyces cerevisiae*. The SalR gene may be derived from *Papaver somniferum, Papaver bracteatum, Papaver* spp., *Chelidonium majus*, or another species. In some examples, the SalR gene may be 80-100% similar to the naturally occurring gene.

[SalAT] In some examples, the engineered host cell may modify the expression of the enzyme acetyl-CoA:salutaridinol 7-O-acetyltransferase. Acetyl-CoA:salutaridinol 7-O-acetyltransferase is encoded by the SalAT gene. In some examples, acetyl-CoA:salutaridinol 7-O-acetyltransferase catalyzes the reaction of acetyl-CoA+salutaridinol→CoA+7-O-acetylsalutaridinol, as referenced in FIG. 14. The engineered host cell may be modified to include constitutive expression of the SalAT gene in the engineered host cell. Additionally or alternatively, the engineered host cell may be modified to synthetically regulate the expression of the SalAT gene in the engineered host cell. In examples, the engineered host cell may be modified to incorporate a copy, copies, or additional copies, of the SalAT gene. Additionally or alternatively, the engineered host cell may be modified to incorporate the introduction of a strong promoter element for the overexpression of the SalAT gene within the engineered host cell. In some cases, the SalAT gene may be codon optimized for expression in *Saccharomyces cerevisiae*. The SalAT gene may be derived from *Papaver somniferum, Papaver bracteatum, Papaver orientale, Papaver* spp., or another species. In some examples, the SalAT gene may be 77-80% similar to the naturally occurring gene.

[TS] In some examples, the engineered host cell may modify the expression of the enzyme thebaine synthase. Thebaine synthase is encoded by the TS gene. In some examples, a thebaine synthase or an engineered thebaine synthase catalyzes the reaction of 7-O-acetylsalutaridinol→thebaine+acetate, as referenced in FIG. 14. In some examples, the reaction of 7-O-acetylsalutaridinol→thebaine+acetate occurs spontaneously, but thebaine synthase catalyzes some portion of this reaction. In particular, FIG. 14 illustrates a biosynthetic scheme for conversion of L-tyrosine to morphinan alkaloids, in accordance with embodiments of the invention. FIG. 14 provides the use of the enzymes CPR, cytochrome P450 reductase; DRS-DRR, dehydroreticuline synthase and dehydroreticuline reductase; SalSyn, salutaridine synthase; SalR, salutaridine reductase; SalAT, salutaridinol 7-O-acetyltransferase; TS, thebaine synthase; T6ODM, thebaine 6-O-demethylase; COR, codeinone reductase; and CODM, codeine-O-demethylase.

The engineered host cell may be modified to include constitutive expression of the TS gene or the engineering TS gene in the engineered host cell. In some cases, the engineered TS gene may encode an engineered fusion enzyme. Additionally or alternatively, the engineered host cell may be modified to synthetically regulate the expression of the TS gene in the engineered host cell. In examples, the engineered host cell may be modified to incorporate a copy, copies, or additional copies, of the TS gene. Additionally or alternatively, the engineered host cell may be modified to incorporate the introduction of a strong promoter element for the overexpression of the TS gene within the engineered host cell. In some cases, the TS gene may be codon optimized for expression in *Saccharomyces cerevisiae*. The TS gene may be derived from *Papaver somniferum, Papaver bracteatum, Papaver orientale, Papaver* spp., or another species. In some examples, the TS gene may be 75-80% similar to the naturally occurring gene.

[T6ODM] In some examples, the engineered host cell may modify the expression of the enzyme thebaine 6-O-demethylase. Thebaine 6-0 demethylase is encoded by the T6ODM gene. In some examples, thebaine 6-O-demethylase catalyzes the reaction of thebaine→neopinone, as referenced in FIGS. 14, 15, and 16. Once the neopinone has been produced, the neopinone may be converted to codeinone. The conversion of neopinone→codeinone may occur spontaneously. Alternatively, the conversion of neopinone→codeinone may occur as a result of a catalyzed reaction. In other examples, the T6ODM enzyme may catalyze the O-demethylation of substrates other than thebaine. For example, T6ODM may O-demethylate oripavine to produce morphinone. Alternatively, T6ODM may catalyze the O-demethylation of BIAs within the 1-benzylisoquinoline, protoberberine, or protopine classes such as papaverine, canadine, and allocryptopine, respectively. The engineered host cell may be modified to include constitutive expression of the T6ODM gene in the engineered host cell. Additionally or alternatively, the engineered host cell may be modified to synthetically regulate the expression of the T6ODM gene in the engineered host cell. In examples, the engineered host cell may be modified to incorporate a copy, copies, or additional copies, of the T6ODM gene. Additionally or alternatively, the engineered host cell may be modified to incorporate the introduction of a strong promoter element for the overexpression of the T6ODM gene within the engineered host cell. In some cases, the T6ODM gene may be codon optimized for expression in *Saccharomyces cerevisiae*. The T6ODM gene may be derived from *Papaver somniferum*, or another species. In some examples, the T6ODM gene may be 76.2% similar to the naturally occurring gene.

[COR] In some examples, the engineered host cell may modify the expression of the enzyme codeinone reductase. Codeinone reductase is encoded by the COR gene. In some examples, codeinone reductase catalyzes the reaction of codeinone to codeine, as referenced in FIGS. 14, 15, and 16. In some cases, codeinone reductase can catalyze the reaction of neopinone to neopine. In other examples, COR can catalyze the reduction of other morphinans including hydrocodone→dihydrocodeine, 14-hydroxycodeinone→14-hydroxycodeine, and hydromorphone→dihydromorphine. The engineered host cell may be modified to include constitutive expression of the COR gene in the engineered host cell. Additionally or alternatively, the engineered host cell may be modified to synthetically regulate the expression of the COR gene in the engineered host cell. In examples, the engineered host cell may be modified to incorporate a copy, copies, or additional copies, of the COR gene. Additionally or alternatively, the engineered host cell may be modified to incorporate the introduction of a strong promoter element for the overexpression of the COR gene within the engineered host cell. In some cases, the COR gene may be codon optimized for expression in *Saccharomyces cerevisiae*. Additionally or alternatively, the COR gene may be modified with the addition of targeting sequences for mitochondria, vacuole, endoplasmic reticulum, or a combination thereof. The COR gene may be derived from *Papaver somniferum*, or another species. In some examples, the COR gene may be 76-78% similar to the naturally occurring gene. In examples, the COR gene may be 76.8%, 77.0%, 77.3%, or 77.7% similar to the naturally occurring gene.

[CODM] In some examples, the engineered host cell may modify the expression of the enzyme codeine O-demethylase. Codeine O-demethylase is encoded by the CODM gene. In some examples, codeine O-demethylase catalyzes the reaction of codeine to morphine, as referenced in FIGS. 14, 15, and 16. Codeine O-demethylase can also catalyze the reaction of neopine to neomorphine. Codeine O-demethylase can also catalyze the reaction of thebaine to oripavine. In other examples, CODM may catalyze the O-demethylation of BIAs within the 1-benzylisoquinoline, aporphine, and protoberberine classes such as reticuline, isocorydine, and scoulerine, respectively. In other examples, the CODM enzyme may catalyze an O,O-demethylenation reaction to cleave the methylenedioxy bridge structures in protopines. The engineered host cell may be modified to include constitutive expression of the CODM gene in the engineered host cell. Additionally or alternatively, the engineered host cell may be modified to synthetically regulate the expression of the CODM gene in the engineered host cell. In examples, the engineered host cell may be modified to incorporate a copy, copies, or additional copies, of the CODM gene. Additionally or alternatively, the engineered host cell may be modified to incorporate the introduction of a strong promoter element for the overexpression of the CODM gene within the engineered host cell. In some cases, the CODM gene may be codon optimized for expression in *Saccharomyces cerevisiae*. Additionally or alternatively, the CODM gene may be modified with the addition of targeting sequences for mitochondria. The CODM gene may be derived from *Papaver somniferum, Papaver* spp., or another species. In some examples, the CODM gene may be 75% similar to the naturally occurring gene. In examples, the CODM gene may be 75.2% similar to the naturally occurring gene.

[BBE] In some examples, the engineered host cell may modify the expression of the enzyme berberine bridge enzyme. The berberine bridge enzyme is encoded by the BBE gene. In some examples, berberine bridge enzyme catalyzes the reaction of (S)-reticuline→(S)-scoulerine. The engineered host cell may be modified to include constitutive expression of the BBE gene in the engineered host cell. Additionally or alternatively, the engineered host cell may be modified to synthetically regulate the expression of the BBE gene in the engineered host cell. In examples, the engineered host cell may be modified to incorporate a copy, copies, or additional copies, of the BBE gene. Additionally or alternatively, the engineered host cell may be modified to incorporate the introduction of a strong promoter element for the overexpression of the BBE gene within the engineered host cell. The BBE gene may be derived from *Papaver somniferum, Argemone mexicana, Eschscholzia californica, Berberis stolonmfera, Thalictrum flavum* subsp. *glaucum, Coptis japonica, Papaver* spp., or another species. In some examples, the BBE gene may be 99% similar to the naturally occurring gene.

[S9OMT] In some examples, the engineered host cell may modify the expression of the enzyme S-adenosyl-L-methionine:(S)-scoulerine 9-O-methyltransferase. S-adenosyl-L-methionine:(S)-scoulerine 9-O-methyltransferase is encoded by the S9OMT gene. In some examples, S-adenosyl-L-methionine:(S)-scoulerine 9-O-methyltransferase catalyzes the reaction of S-adenosyl-L-methionine+(S)-scoulerine→S-adenosyl-L-homocysteine+(S)-tetrahydrocolumbamine. The engineered host cell may be modified to include constitutive expression of the S9OMT gene in the engineered host cell. Additionally or alternatively, the engineered host cell may be modified to synthetically regulate the expression of the S9OMT gene in the engineered host cell. In examples, the engineered host cell may be modified to incorporate a copy, copies, or additional copies, of the S9OMT gene. Additionally or alternatively, the engineered host cell may be modified to incorporate the introduction of a strong promoter element for the overexpression of the S9OMT gene within the engineered host cell. In some cases, the S9OMT gene may be codon optimized for expression in *Saccharomyces cerevisiae*. The S9OMT gene may be derived from *Thalictrum flavum* subsp. *glaucum, Coptis japonica, Coptis chinensis, Papaver somniferum, Thalictrum* spp., *Coptis* spp., *Papaver* spp., or another species. In some examples, the S9OMT gene may be 100% similar to the naturally occurring gene. In examples, the S9OMT gene may be 80% similar to the naturally occurring gene.

[CAS] In some examples, the engineered host cell may modify the expression of the enzyme (S)-canadine synthase. (S)-canadine synthase is encoded by the CAS gene. In some examples, (S)-canadine synthase catalyzes the reaction of (S)-tetrahydrocolumbamine→(S)-canadine. The engineered host cell may be modified to express the CAS gene in the engineered host cell. The engineered host cell may be modified to include constitutive expression of the CAS gene in the engineered host cell. Additionally or alternatively, the engineered host cell may be modified to synthetically regulate the expression of the CAS gene in the engineered host cell. In examples, the engineered host cell may be modified to incorporate a copy, copies, or additional copies, of the CAS gene. Additionally or alternatively, the engineered host cell may be modified to incorporate the introduction of a strong promoter element for the overexpression of the CAS gene within the engineered host cell. The CAS gene may be derived from *Thalictrum flavum* subsp. *glaucum, Coptis japonica, Thalictrum* spp., *Coptis* spp., or another species. In some examples, the CAS gene may be 100% similar to the naturally occurring gene.

[STOX] In some examples, the engineered host cell may modify the expression of the enzyme (S)-tetrahydroprotoberberine oxidase. (S)-tetrahydroprotoberberine oxidase is encoded by the STOX gene. In some examples, (S)-tetrahydroprotoberberine oxidase catalyzes the reaction of (S)-tetrahydroberberine+2 $O_2$→berberine+2 $H_2O_2$. The engineered host cell may be modified to include constitutive expression of the STOX gene in the engineered host cell. Additionally or alternatively, the engineered host cell may be modified to synthetically regulate the expression of the STOX gene in the engineered host cell. In examples, the engineered host cell may be modified to incorporate a copy, copies, or additional copies, of the STOX gene. Additionally or alternatively, the engineered host cell may be modified to incorporate the introduction of a strong promoter element for the overexpression of the STOX gene within the engineered host cell. In some examples the STOX may be modified at the N-terminus. In some cases, the STOX gene may be codon optimized for expression in *Saccharomyces cerevisiae*. The STOX gene may be derived from *Berberis wilsonae, Coptis japonica, Berberis* spp., *Coptis* spp., or another species. In some examples, the STOX gene may be 78% similar to the naturally occurring gene.

[TNMT] In some examples, the engineered host cell may modify the expression of the enzyme tetrahydroprotoberberine-N-methyltransferase. Tetrahydroprotoberberine-N-methyltransferase is encoded by the TNMT gene. In some examples, tetrahydroprotoberberine-N-methyltransferase catalyzes the reaction of canadine→N-methylcanadine. In some examples, tetrahydroprotoberberine-N-methyltransferase catalyzes the reaction of noroxymorphone→naloxone.

In other examples, tetrahydroprotoberberine-N-methyltransferase catalyzes the reaction of stylopine→cis-N-methylstylopine. The engineered host cell may be modified to include constitutive expression of the TNMT gene in the engineered host cell. Additionally or alternatively, the engineered host cell may be modified to synthetically regulate the expression of the TNMT gene in the engineered host cell. In examples, the engineered host cell may be modified to incorporate a copy, copies, or additional copies, of the TNMT gene. Additionally or alternatively, the engineered host cell may be modified to incorporate the introduction of a strong promoter element for the overexpression of the TNMT gene within the engineered host cell. In some cases, the TNMT gene may be codon optimized for expression in *Saccharomyces cerevisiae*. The TNMT gene may be derived from *Papaver somniferum, Eschscholzia californica, Papaver bracteatum, Argemone mexicana*, or another species. In some examples, the TNMT gene may be 100% similar to the naturally occurring gene. In examples, the TNMT gene may be 81% similar to the naturally occurring gene.

[CFS] In some examples, the engineered host cell may modify the expression of the enzyme cheilanthifoline synthase. Cheilanthifoline synthase is encoded by the CFS gene. In examples, cheilanthifoline synthase catalyzes the reaction of scoulerine→cheilanthifoline. An engineered host cell may be modified to include constitutive expression of the CFS gene in the engineered host cell. Additionally or alternatively, the engineered host cell may be modified to synthetically regulate the expression of the CFS gene in the engineered host cell. In examples, the engineered host cell may be modified to incorporate a copy, copies, or additional copies, of the CFS gene. Additionally or alternatively, the engineered host cell may be modified to incorporate the introduction of a strong promotor element for the overexpression of the CFS gene within the engineered host cell. The CFS gene may be derived from *P. somniferum, E. californica, A. mexicana*, or another species. In some examples, the CFS gene may be 77%, 78%, or 79% similar to the naturally occurring gene. Additionally, the CFS gene may be codon optimized for expression in *Saccharomyces cerevisiae.*

In some examples, the engineered host cell may modify the expression of the enzyme stylopine synthase. Stylopine synthase is encoded by the STS gene. In examples, stylopine synthase catalyzes the reaction of cheilanthifoline→stylopine. An engineered host cell may be modified to include constitutive expression of the STS gene in the engineered host cell. Additionally or alternatively, the engineered host cell may be modified to synthetically regulate the expression of the STS gene in the engineered host cell. In examples, the engineered host cell may be modified to incorporate a copy, copies, or additional copies, of the STS gene. Additionally or alternatively, the engineered host cell may be modified to incorporate the introduction of a strong promotor element for the overexpression of the STS gene within the engineered host cell. The STS gene may be derived from *P. somniferum, E. californica, A. mexicana*, or another species. In some examples, the STS gene may be 76%, 78%, or 79% similar to the naturally occurring gene. Additionally, the STS gene may be codon optimized for expression in *Saccharomyces cerevisiae.*

[MSH] In some examples, the engineered host cell may modify the expression of the enzyme cis-N-methylstylopine 14-hydroxylase. Cis-N-methylstylopine 14-hydroxylase is encoded by the MSH gene. In examples, cis-N-methylstylopine 14-hydroxylase catalyzes the reaction of cis-N-methylstylopine→protopine. An engineered host cell may be modified to include constitutive expression of the MSH gene in the engineered host cell. Additionally or alternatively, the engineered host cell may be modified to synthetically regulate the expression of the MSH gene in the engineered host cell. In examples, the engineered host cell may be modified to incorporate a copy, copies, or additional copies, of the MSH gene. Additionally or alternatively, the engineered host cell may be modified to incorporate the introduction of a strong promotor element for the overexpression of the MSH gene within the engineered host cell. The MSH gene may be derived from *P. somniferum* or another species. In some examples, the MSH gene may be 79% similar to the naturally occurring gene. Additionally, the MSH gene may be codon optimized for expression in *Saccharomyces cerevisiae.*

[P6H] In some examples, the engineered host cell may modify the expression of the enzyme protopine-6-hydroxylase. Protopine-6-hydroxylase is encoded by the P6H gene. In examples, protopine-6-hydroxylase catalyzes the reaction of Protopine→6-hydroxyprotopine. An engineered host cell may be modified to include constitutive expression of the P6H gene in the engineered host cell. Additionally or alternatively, the engineered host cell may be modified to synthetically regulate the expression of the P6H gene in the engineered host cell. In examples, the engineered host cell may be modified to incorporate a copy, copies, or additional copies, of the P6H gene. Additionally or alternatively, the engineered host cell may be modified to incorporate the introduction of a strong promotor element for the overexpression of the CFS gene within the engineered host cell. The P6H gene may be derived from *P. somniferum, E. californica*, or another species. In some examples, the P6H gene may be 79% similar to the naturally occurring gene. Additionally, the P6H gene may be codon optimized for expression in *Saccharomyces cerevisiae.*

[DBOX] In some examples, the engineered host cell may modify the expression of the enzyme dihydrobenzophenanthridine oxidase. Dihydrobenzophenanthridine oxidase is encoded by the DBOX gene. In examples, dihydrobenzophenanthridine oxidase catalyzes the reaction of dihydrosanguinarine→sanguinarine. An engineered host cell may be modified to include constitutive expression of the DBOX gene in the engineered host cell. Additionally or alternatively, the engineered host cell may be modified to synthetically regulate the expression of the DBOX gene in the engineered host cell. In examples, the engineered host cell may be modified to incorporate a copy, copies, or additional copies, of the DBOX gene. Additionally or alternatively, the engineered host cell may be modified to incorporate the introduction of a strong promotor element for the overexpression of the DBOX gene within the engineered host cell. The DBOX gene may be derived from *P. somniferum* or another species. In some examples, the DBOX gene may be 100% similar to the naturally occurring gene. Additionally, the DBOX gene may be codon optimized for expression in *Saccharomyces cerevisiae.*

Figure 15:
FIG. 15 illustrates a biosynthetic scheme for production of semi-synthetic opioids, in accordance with embodiments of the invention.
Figure 16:
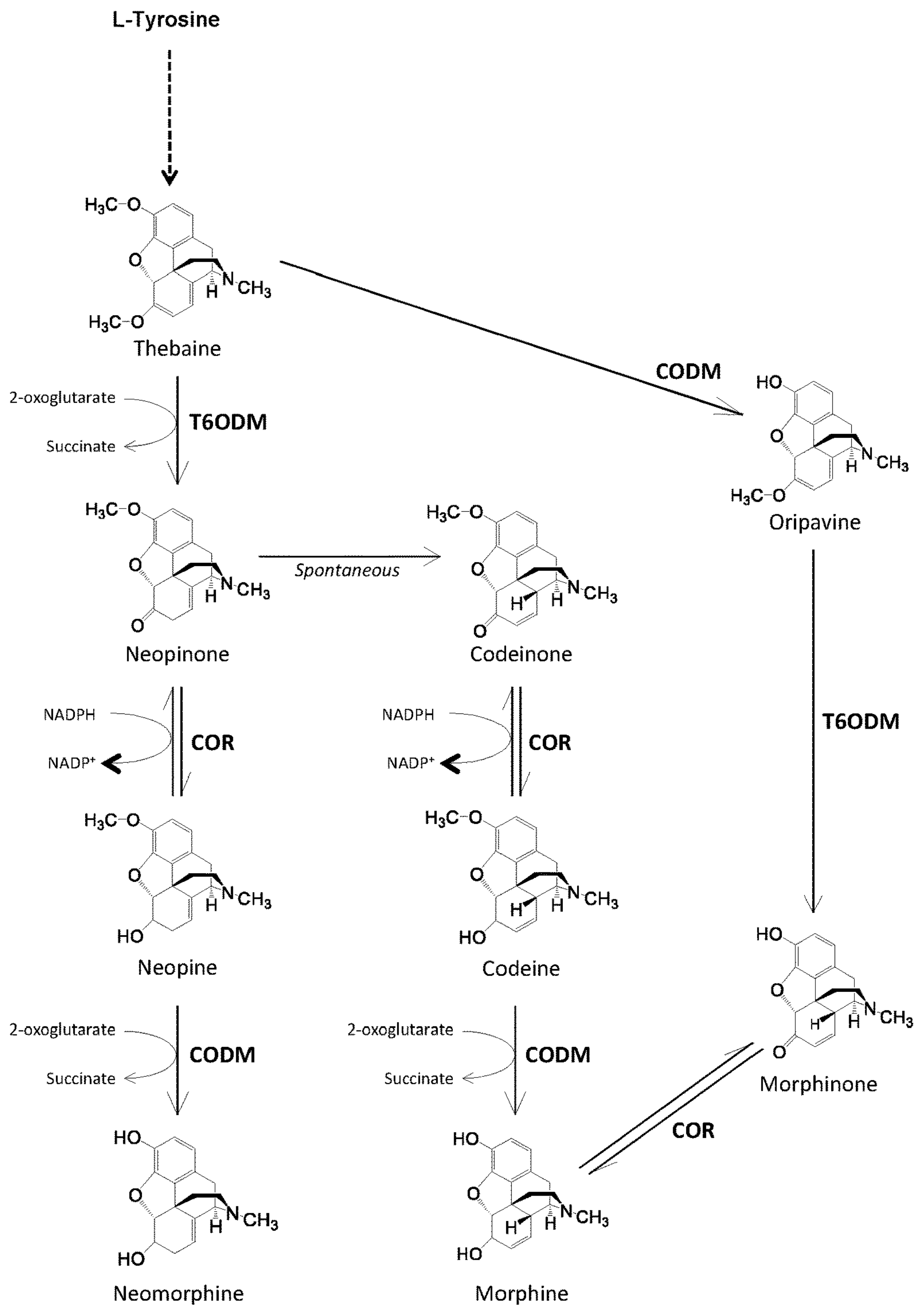
FIG. 16 illustrates a biosynthetic scheme for production of opioids, in accordance with embodiments of the invention.

[morA] In some examples, the engineered host cell may modify the expression of the enzyme morphine dehydrogenase. Morphine dehydrogenase is encoded by the morA gene. In some examples, morphine dehydrogenase catalyzes the reaction of morphine→morphinone, as referenced in FIG. 15. In other examples, morphine dehydrogenase catalyzes the reaction of codeinone-codeine, also as referenced in FIG. 15. FIG. 15 illustrates a biosynthetic scheme for production of semi-synthetic opioids, in accordance with embodiments of the invention. In particular, FIG. 15 illustrates extended transformations of thebaine in yeast by incorporating morA, morphine dehydrogenase; and morB, morphine reductase.

The engineered host cell may be modified to include constitutive expression of the morA gene in the engineered host cell. Additionally or alternatively, the engineered host cell may be modified to synthetically regulate the expression of the morA gene in the engineered host cell. In examples, the engineered host cell may be modified to incorporate a copy, copies, or additional copies, of the morA gene. Additionally or alternatively, the engineered host cell may be modified to incorporate the introduction of a strong promoter element for the overexpression of the morA gene within the engineered host cell. In some cases, the morA gene may be codon optimized for expression in *Saccharomyces cerevisiae*. The morA gene may be derived from *Pseudomonas putida* or another species. In some examples, the morA gene may be 73.7% similar to the naturally occurring gene.

[morB] In some examples, the engineered host cell may modify the expression of the enzyme morphinone reductase. Morphinone reductase is encoded by the morB gene. In some examples, morphinone reductase catalyzes the reaction of codeinone→hydrocodone, as referenced in FIG. 15. In other examples, morphinone reductase catalyzes the reaction of morphinone→hydromorphone, also as referenced in FIG. 15. In other examples, morphinone reductase catalyzes the reaction 14-hydroxycodeinone→oxycodone. The engineered host cell may be modified to include constitutive expression of the morB gene in the engineered host cell. Additionally or alternatively, the engineered host cell may be modified to synthetically regulate the expression of the morB gene in the engineered host cell. In examples, the engineered host cell may be modified to incorporate a copy, copies, or additional copies, of the morB gene. Additionally or alternatively, the engineered host cell may be modified to incorporate the introduction of a strong promoter element for the overexpression of the morB gene within the engineered host cell. In some cases, the morB gene may be codon optimized for expression in *Saccharomyces cerevisiae*. The morB gene may be derived from *Pseudomonas putida* or another species. In some examples, the morB gene may be 67.2% similar to the naturally occurring gene.

[CYP80A1] In some examples, the engineered host cell may express the enzyme berbamunine synthase. Berbamunine synthase is encoded by the gene for cytochrome P450 enzyme 80A1 (CYP80A1). In some examples, CYP80A1 catalyzes the reaction (S)—N-methylcoclaurine+(R)—N-methylcoclaurine→berbamunine. In other examples, CYP80A1 catalyzes the reaction (R)—N-methylcoclaurine+(R)—N-methylcoclaurine→guattegaumerine. In other examples, CYP80A1 catalyzes the reaction (R)—N-methylcoclaurine+(S)-coclaurine→2'norberbamunine. The engineered host cell may be modified to include constitutive expression of the CYP80A1 gene in the engineered host cell. Additionally or alternatively, the engineered host cell may be modified to synthetically regulate the expression of the CYP80A1 gene in the engineered host cell. In examples, the engineered host cell may be modified to incorporate a copy, copies, or additional copies, of the CYP80A1 gene. Additionally or alternatively, the engineered host cell may be modified to incorporate the introduction of a strong promoter element for the overexpression of the CYP80A1 gene within the engineered host cell. In some cases, the CYP80A1 gene may be codon optimized for expression in *Saccharomyces cerevisiae*. The CYP80A1 gene may be derived from Berber's stolonmfera or another species. In some examples, the CYP80A1 gene may be 76% similar to the naturally occurring gene.

[PODA] In some example, the engineered host cell may express the enzyme protopine O-dealkylase. Protopine O-dealkylase is encoded by the gene PODA. In some examples, PODA catalyzes the O,O-demethylenation of protoberberines and protopines such as canadine, stylopine, berberine, cryptopine, allocryptopine, and protopine. In some examples, PODA catalyzes the O-demethylation of BIAs including tetrahydropapaverine, tetrahydropalmatine, and cryptopine. The engineered host cell may be modified to include constitutive expression of the PODA gene in the engineered host cell. Additionally or alternatively, the engineered host cell may be modified to synthetically regulate the expression of the PODA gene in the engineered host cell. In examples, the engineered host cell may be modified to incorporate a copy, copies, or additional copies, of the PODA gene. Additionally or alternatively, the engineered host cell may be modified to incorporate the introduction of a strong promoter element for the overexpression of the PODA gene within the engineered host cell. In some cases, the PODA gene may be codon optimized for expression in *Saccharomyces cerevisiae*. The PODA gene may be derived from *Papaver somniferum* or other species. In some examples, the PODA gene may be 70-100% similar to the naturally occurring gene.

Figure 9:
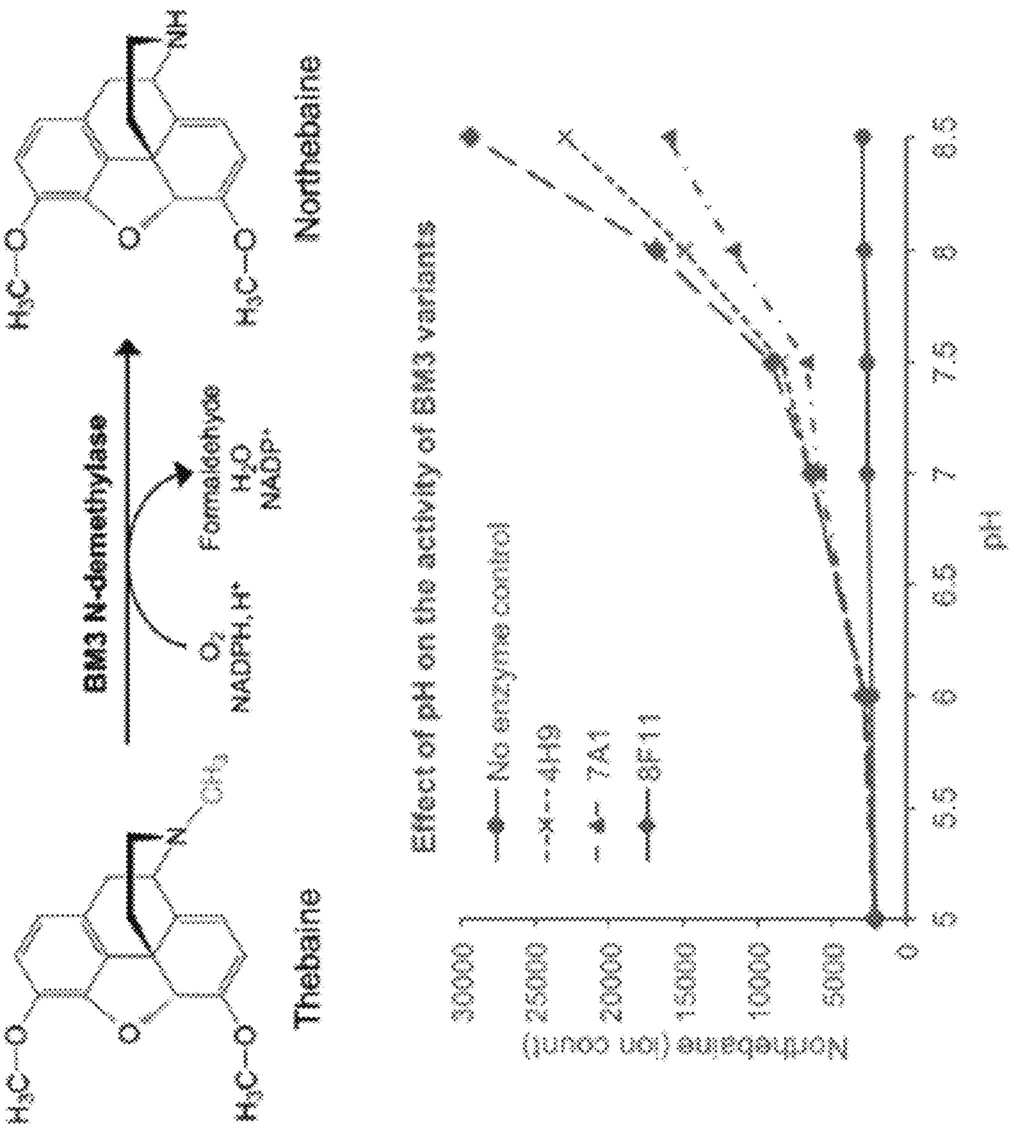
FIG. 9 illustrates the functional expression of BM3 variants, in accordance with embodiments of the invention.
Figure 9:
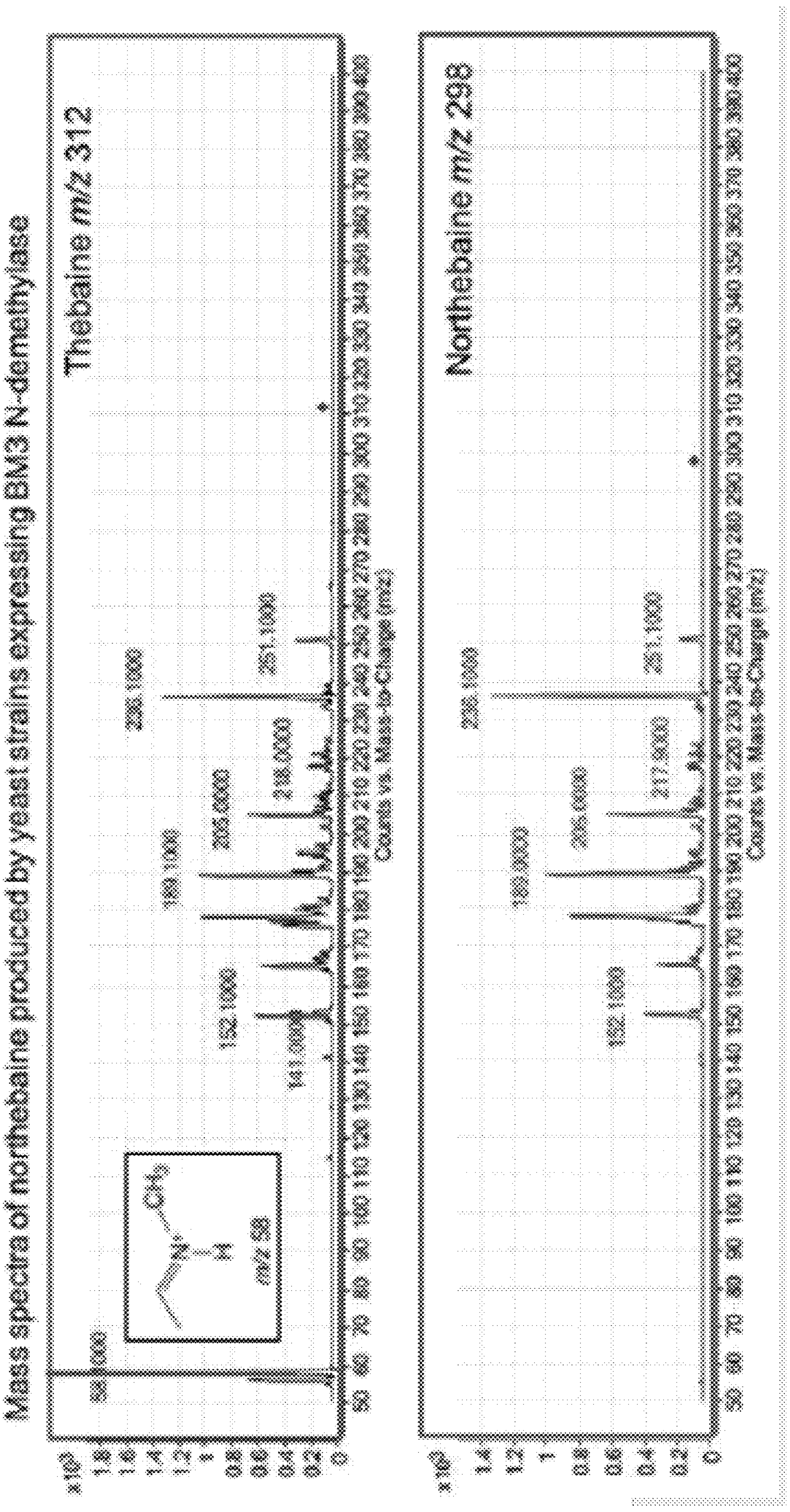

[BM3] In some examples, the engineered host cell may express the enzyme BM3. BM3 is a *Bacillus megaterium* cytochrome P450 involved in fatty acid monooxygenation in its native host. In some cases BM3 N-demethylates an opioid to produce a nor-opioid, as referenced in FIG. 9. In some cases the host cell is modified to express BM3 in addition to other heterologous enzymes for the production of a nal-opioid or nor-opioid, as referenced in FIG. 10. The engineered host cell may be modified to include constitutive expression of the BM3 gene in the engineered host cell. Additionally or alternatively, the engineered host cell may be modified to synthetically regulate the expression of the BM3 gene in the engineered host cell. In examples, the engineered host cell may be modified to incorporate a copy, copies, or additional copies, of the BM3 gene. Additionally or alternatively, the engineered host cell may be modified to incorporate the introduction of a strong promoter element for the overexpression of the BM3 gene within the engineered host cell. BM3 has several advantages as a biosynthetic enzyme including that it is soluble, comes with a fused reductase partner protein, and can readily be engineered to accept new substrates. Additionally, Table 8 illustrates variants of BM3 N-demethylase.

Examples of the aforementioned genes can be expressed from a number of different platforms in the host cell, including plasmid (2μ, ARS/CEN), YAC, or genome. In addition, examples of the aforementioned gene sequences can either be native or codon optimized for expression in the desired heterologous host (e.g., *Saccharomyces cerevisiae*).

EXAMPLES

The following examples are given for the purpose of illustrating various embodiments of the invention and are

126 not meant to limit the invention in any fashion. Where indicated, expression constructs are understood to incorporate a suitable promoter, gene, and terminator, even if the exact terminator sequence used is not specified. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Bioinformatic Identification of Enzymes for Morphinan Alkaloid Production The OneKP (Matasci N et al. 2014. Data access for the 1,000 Plants (1KP) project. Gigascience 3:17) and Phytometasyn (Xiao M et al. 2013. Transcriptome analysis based on next-generation sequencing of non-model plants producing specialized metabolites of biotechnological interest. *J Biotechnol* 166:122-34) plant transcriptome databases were queried with amino acid sequences of representative variants from each of the hypothesized classes of enzymes. In particular, the basal eudicot clade, which includes many plant species that produce benzylisoquinoline alkaloids of interest, were searched. A large number of sequences were identified from these searches and the list of candidate sequences were narrowed down by building phylogenetic trees. In building the trees, sequences were included from similar known and characterized enzymes from plant species that produce morphinan alkaloids. These reference sequences helped to develop an understanding of the relationships between sequences and further constrain the sequence space for identifying the candidates most likely to exhibit desired activities. An example of a phylogenetic tree generated for the Bet v 1/PR10/major latex protein class of enzymes using this approach is show in FIGS. 21-1-21-4.

Figure 17:
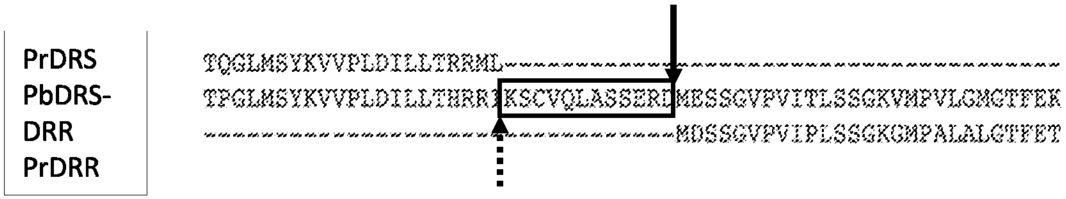
FIG. 17 illustrates an alignment between PbDRS-DRR, PrDRS, and PrDRR, in accordance with embodiments of the invention.

Example 2: The Amino Acid Positions at which DRS-DRR can be Truncated to Form Separate DRS and DRR Enzymes An alignment of the primary amino acid sequence of PbDRS-DRR versus dehydroreticuline synthase (DRS) and dehydroreticuline reductase (DRR) from *P. rhoeas* was generated using the Clustal Omega (http://www.ebi.ac.uk/Tools/msa/clustalo/). Based on the alignment with DRR from *P. rhoeas*, we identified a truncation point at which to separate PbDRS-DRR into DRS and DRR enzymes, where a conserved methionine residue at position M569 is found (SEQ ID NO. 16). This residue corresponds to position 1 of SEQ ID NO. 18. In FIG. 17, the black arrow, between residues D568 and M569, represents the site at which PbDRS-DRR was truncated. The separate DRS enzyme based on PbDRS-DRR was designed to end at position D568. The dashed arrow points to a region of PbDRS-DRR that is not conserved with or homologous to either DRS or DRR from *P. rhoeas*. Truncations after each of these non-conservative residues, the sequence starting at K557 and ending at D568 within the black box, were generated, and the activity of each successive truncation of DRS was assayed in a vector backbone identical to pDW21 (with DRR under the control of the TEF1 promoter). These plasmids were separately transformed in to the reporter yeast strain YA106 harboring PbSalSyn on a separate plasmid (DW24).

For propagation of yeast strains harboring engineered DRS-DRR (or separate DRS and DRR) enzymes, the reporter strain was transformed with expression plasmids using standard molecular biology techniques, and single colonies of yeast were isolated from solid agar medium plates under selective conditions (such as synthetic complete 2% dextrose without tryptophan). Colonies were inoculated into liquid culture medium and grown for 2 days at 30° C. Cultures were then subcultured into fresh medium of the same composition, or in some cases into synthetic complete liquid medium containing 8% maltodextrin. To release monosaccharide from the maltodextrin polymer, amyloglucosidase from *A. niger* (Sigma) was added at a concentration of approximately 3 U/L. Yeast strains were grown for an additional 3 or 4 days at 30° C., cultures were separated by centrifugation, and salutaridine concentration was measured directly in the supernatant by LC-MS.

Plasmids and Strains

| Plasmid/Strain | Genotype |
|---|---|
| pDW10 | Spec$^R$, TRP, P$_{TDH3}$-PbDRS-DRR-T$_{CYC1}$ |
| pDW18 | Spec$^R$, TRP, P$_{CYC1}$-PbDRS-DRR-T$_{CYC1}$ |
| pDW21 | Spec$^R$, TRP, P$_{CYC1}$-PbDRS-T$_{ADH1}$-P$_{TEF1}$-PbDRR-T$_{CYC1}$ |
| pJL29 | Spec$^R$, TRP, P$_{TDH3}$-PbDRS-T$_{ADH1}$-P$_{TEF1}$-PbDRR-T$_{CYC1}$ |
| pJL32 | Spec$^R$, TRP, P$_{CYC1}$-PbDRS-T$_{ADH1}$-P$_{TDH3}$-PbDRR-T$_{CYC1}$ |
| pJL35 | Spec$^R$, TRP, P$_{TDH3}$-PbDRS-T$_{ADH1}$-P$_{CYC1}$-PbDRR-T$_{CYC1}$ |
| YA106 | *S. cerevisiae* Cen. PK, BIA pathway = CjNCS, PsCNMT, Ps6OMT, PbCYP80B1, PsCPR, Ps4OMT (complete genotype in Galanie et al. 2015) |
| DW6 | YA106, PbSalSyn (LEU+) |
| DW24 | YA106, PbSalSyn (LEU+), ΔTRP(URA3+) |

Figure 18:
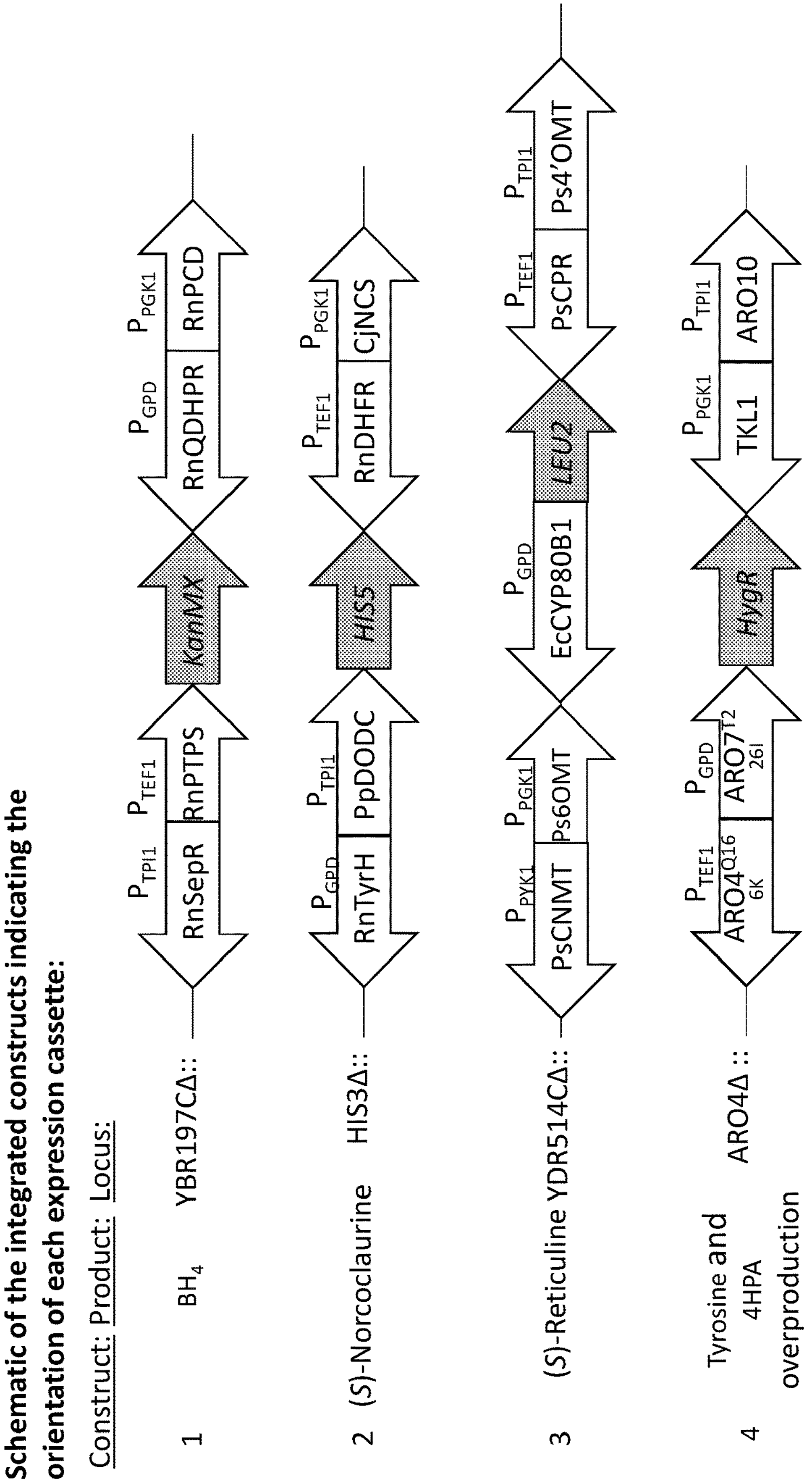
FIG. 18 illustrates yeast platform strains for the production of reticuline from L-tyrosine, in accordance with embodiments of the invention.

Example 3: Platform Yeast Strains Engineered to Produce (S)-Reticuline from Glucose and Simple Nitrogen Sources A platform yeast strain that produces the key branch point BIA intermediate (S)-reticuline from L-tyrosine was constructed (FIG. 12). Specifically, four multi-gene expression constructs were integrated into the genome of a yeast strain. The composition of the four constructs is indicated in FIG. 18. Each construct is comprised of 4 or 5 genes expressed from yeast promoters. Genes are positioned at each locus as complete expression cassettes comprising a promoter, gene open reading frame, and terminator as specified in the annotations above the schematic. The schematic shows the orientation of each expression cassette by the direction of the arrow representing a given gene. Selectable markers are italicized in the annotation and represented by grey arrows in the schematic. Each selection marker is flanked by loxP sites to allow removal of the marker from the locus. Additionally, each construct has a selectable marker flanked by loxP sites so that it can be removed by Cre recombinase.

In the first integration construct, four heterologous genes from *Rattus norvegicus* are integrated into the YBR197C locus together with a G418 selection marker (KanMX). RnPTPS, RnSepR, RnPCD, and RnQDHPR are required to synthesize and regenerate tetrahydrobiopterin (BH$_4$) from the yeast endogenous folate synthesis pathway as indicated in FIG. 1. Each gene is codon optimized for expression in yeast.

In the second integration construct, four heterologous genes are integrated into the HISS locus together with the HISS selection marker. *Rattus norvegicus* tyrosine hydroxylase (RnTyrH) converts tyrosine to L-DOPA using the cosubstrate $BH_4$ generated by the preceding integration construct. The RnTyrH gene can be any of the wild-type or improved mutants which confer enhanced activity (e.g., W166Y, R37E, and R38E). A second *Rattus norvegicus* gene, RnDHFR, encodes an enzyme that reduces dihydrobiopterin (an oxidation product of $BH_4$) to $BH_4$, in this way increasing the availability of this cosubstrate. Also included in the third construct is PpDODC from *Pseudomonas putida*, an enzyme that converts L-DOPA to dopamine. The fourth enzyme is CjNCS from *Coptis japonica*, which condenses 4-HPA and dopamine to make norcoclaurine. Each gene is codon optimized for expression in yeast.

In the third integration construct, five heterologous genes from plants and the LEU2 selection marker are integrated into the locus YDR514C. Ps6OMT, Ps4'OMT, and PsCNMT are methyltransferases from *Papaver somniferum* and are expressed as native plant nucleotide sequences. A fourth *P. somniferum* gene, yPsCPRv2, is codon optimized for yeast and encodes a reductase that supports the activity of a cytochrome P450 from *Eschscholzia* californica, EcCYP80A1. The enzymes encoded in this construct perform two O-methylations, an N-methylation, and a hydroxylation to produce reticuline from the norcoclaurine produced by the preceding integration construct. Each gene is codon optimized for expression in yeast.

In the final integration construct, additional copies of *Saccharomyces cerevisiae* endogenous genes $ARO4^{Q166K}$, $ARO7^{T226I}$, TYR1, and ARO10 are integrated into the ARO4 locus together with a hygromycin resistance selection marker. ARO42 and $ARO7^{7126}$ are feedback-resistant mutants of ARO4 and ARO10 which each encode a single base pair substitution relative to the wild-type sequence. TYR1 and ARO10 are identical to the native yeast genes, but are expressed behind strong promoters. Aro4p and Aro7p are enzymes in the biosynthesis of aromatic amino acids including tyrosine. Removing feedback inhibition from these enzymes results in upregulation of endogenous tyrosine biosynthesis. Overexpression of Tyrlp upregulates tyrosine biosynthesis and thus production of tyrosine. Overexpression of Aro10p increases the production of 4-HPA.

Platform yeast strains can be constructed with any number of the four expression cassettes. Specifically, platform yeast strains were constructed with integration constructs 1-4 and integration constructs 1-3. In the latter strain in which the tyrosine over-production construct (construct 4) is excluded, additional tyrosine may be supplied in the culture medium to support the biosynthesis of reticuline. Additional genetic modifications may be incorporated into the platform strains to support production of downstream BIAs and increased flux to BIA biosynthesis.

The yeast strains were grown in synthetic complete media with the appropriated amino acid drop out solution at 30° C. BIA metabolites in the media supernatant were analyzed after 48 and 96 hours of growth by LC-MS/MS analysis.

Example 4A: Platform Yeast Strains Engineered to Produce Thebaine from Glucose and Simple Nitrogen Sources Yeast strains can be engineered for the production of the morphinan alkaloid thebaine from early precursors such as tyrosine. As an example, the platform yeast strains described in Example 3 can be further engineered to produce the morphinan alkaloid products from L-tyrosine (FIG. 14).

Figure 19:
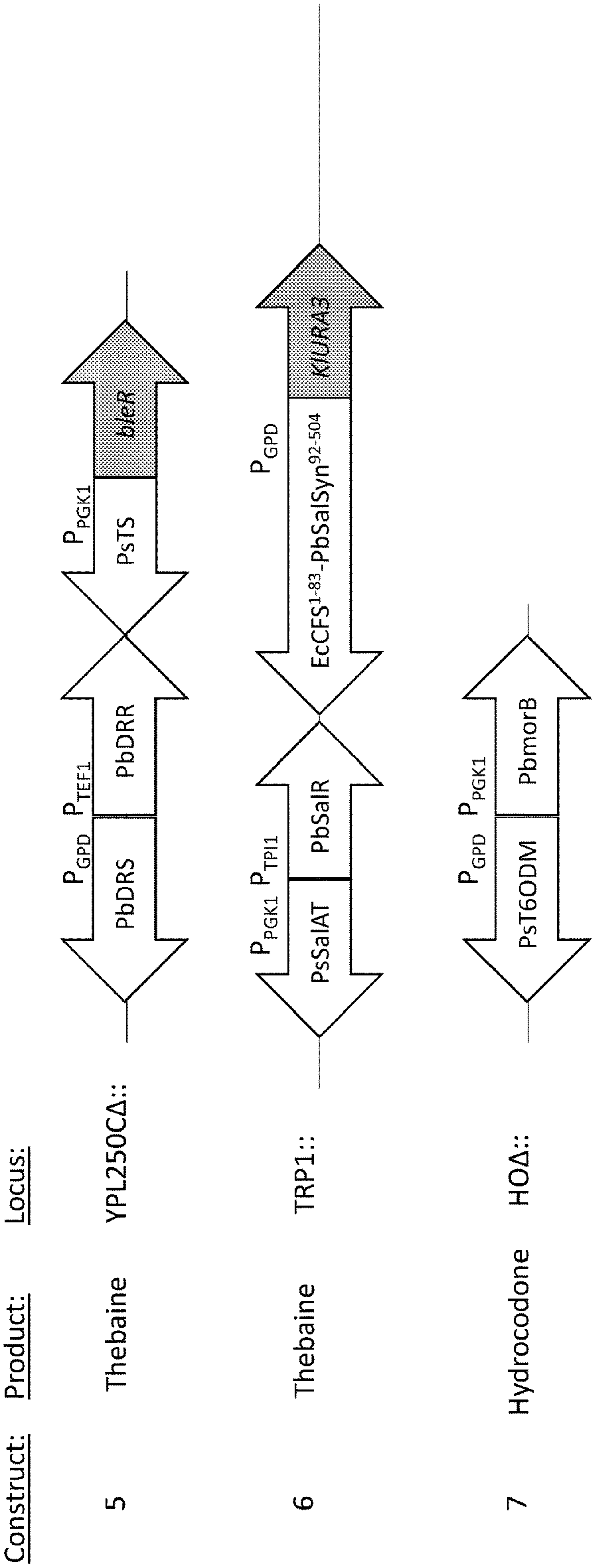
FIG. 19 illustrates yeast strains for the production of thebaine and hydrocodone from L-tyrosine, in accordance with embodiments of the invention.

The platform yeast strain producing (S)-reticuline from L-tyrosine (see description in Example 3) was further engineered to incorporate an engineered split epimerase DRS-DRR, an engineered salutaridine synthase, salutaridine reductase, salutaridinol acetyltransferase, and thebaine synthase to convert the biosynthesized (S)-reticuline to the first morphinan alkaloid thebaine (FIG. 14). Three expression cassettes ($P_{TDH3}$-yEcCFS$^{1-26}$-yPbSS$^{33-504}$, $P_{TP11}$-yPbSalR, $P_{TEF1}$-yPsSalAT) were assembled into an integration construct with a bMeR selective marker and integrated into the locus TRP1 in the platform yeast strain. An additional three expression cassettes ($P_{TDH3}$-yPbDRS, $P_{TEF1}$-yPbDRR, $P_{PGK1}$-yPsTS) were assembled into an integration construct with a URA3 selective marker and integrated into the locus YPL250CΔ in the platform yeast strain. The composition of the two constructs is indicated in FIG. 19.

The yeast strains harboring the integrated cassettes were grown in synthetic complete media with the appropriated drop out solution at 30° C. After 96 hours of growth, the media was analyzed for BIA metabolites by LC-MS/MS analysis.

Example 4B: Production of Thebaine from Glucose and Simple Nitrogen Sources Via Engineered Yeast Strains Yeast strains were engineered as described in Examples 3 and 4 to produce the pentacyclic morphinan alkaloid thebaine directly from simple sugars (e.g., glucose) and nitrogen sources present in standard growth media. Specifically, a CEN.PK strain of *Saccharomyces cerevisiae* was engineered to express the following heterologous enzymes via integration into the yeast chromosome: TyrH, DODC, PTPS, SepR, PCD, QDHPR, NCS, 6OMT, CNMT, CYP80B1, CPR, 4OMT, DRS, DRR, SalSyn, SalR, SalAT, and TS. In this example, the SalSyn enzyme is engineered to have its leader sequence replaced with 83 amino acids from the N-terminus of *Eschscholzia californica* chelanthifoline synthase (EcCFS). Additional modifications were made to the strain to increase BIA precursor accumulation, including: overexpression of ARO10, overexpression of TYR1, expression of a feedback resistant ARO4 ($ARO4^{Q166K}$), and expression of a feedback resistant ARO7 ($ARO7^{T226I}$). Separate engineered yeast strains were made as described, harboring different variants of enzymes encoding thebaine synthase activity (TS), including SEQ ID NOs. 35 (i.e., TS1), 37 (i.e., TS2), and a variant of 35 with a N-terminal truncation of the first 22 amino acids (i.e., tTS1), and no thebaine synthase enzyme (YA397). The sequences of the enzyme variants are provided in Table 2.

Figure 22:
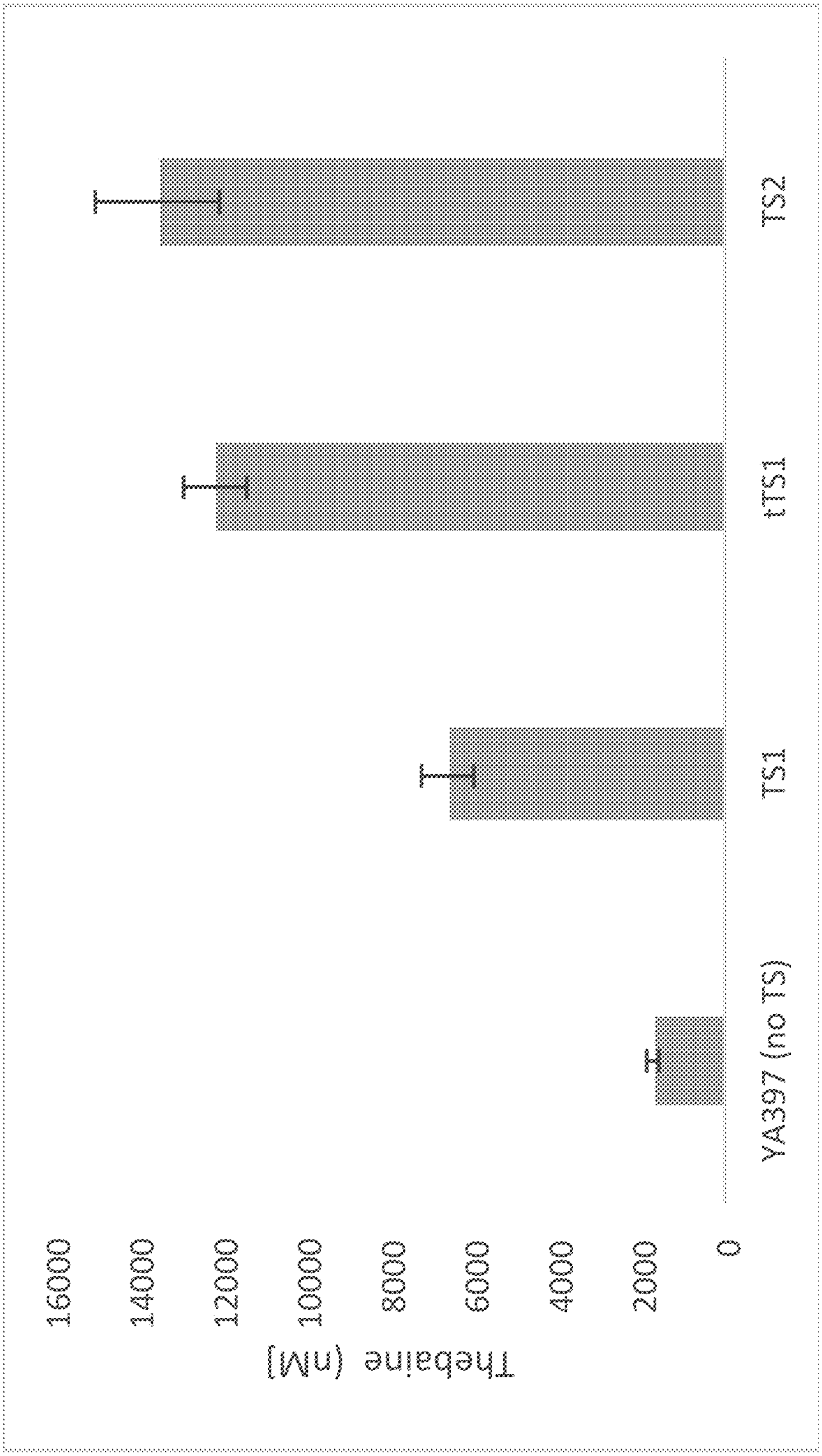
FIG. 22 illustrates the production of the morphinan alkaloid thebaine from sugar and L-tyrosine from an engineered yeast strain, in accordance with embodiments of the invention.
Figure 23:
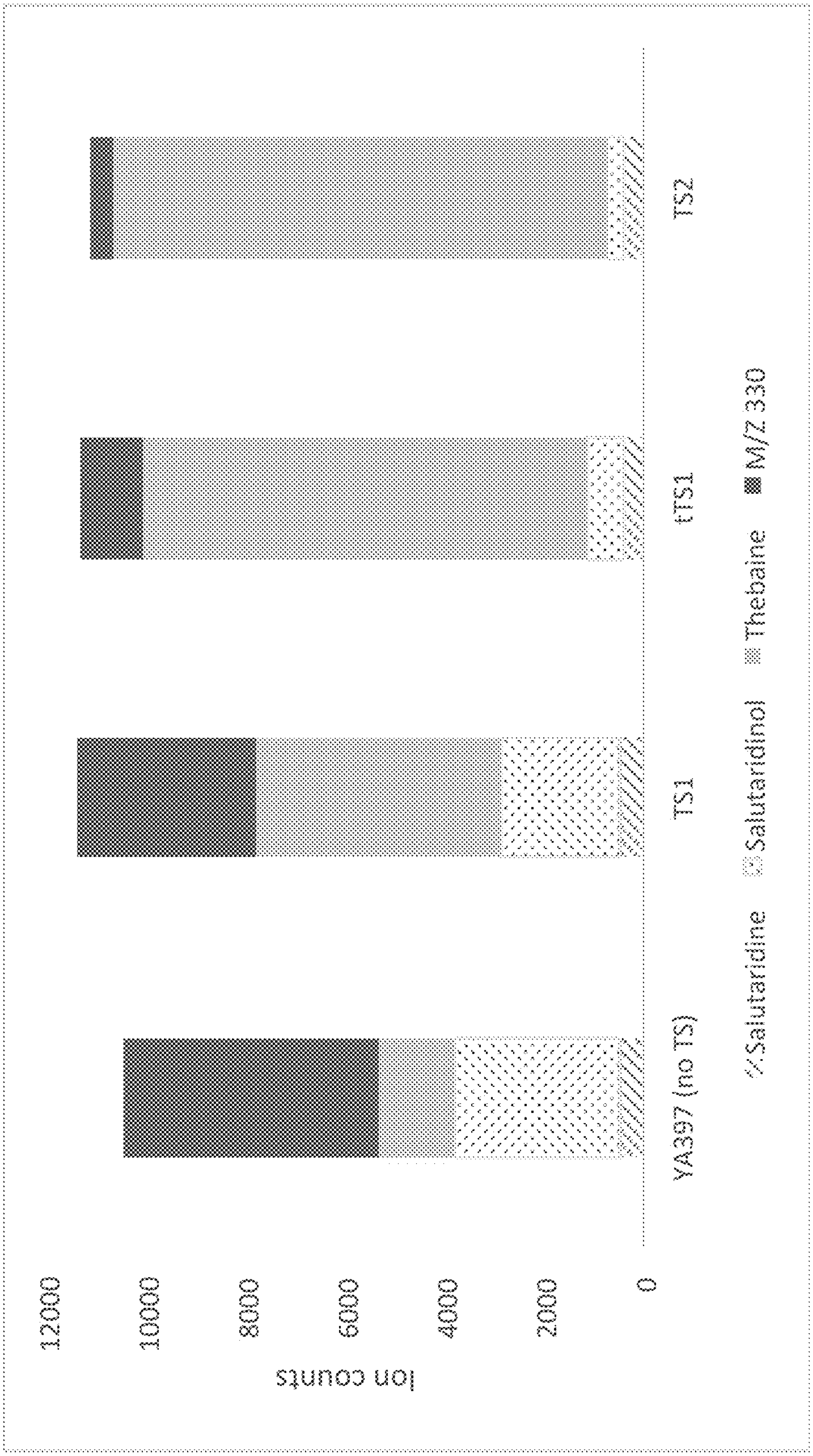
FIG. 23 illustrates the production of promorphinan alkaloids and a morphinan alkaloid thebaine from sugar and L-tyrosine from an engineered yeast strain, in accordance with embodiments of the invention.

The described yeast strains were inoculated into 2 ml of synthetic complete media (yeast nitrogen base and amino acids) with 2% glucose and grown for approximately 4 hours at 30° C. Then, 10 uL of each culture was transferred to 400 uL of fresh media in a 96-well plate in replicates of 4 and grown for an additional 48 hours at 30° C. The production media contains 1× yeast nitrogen broth and amino acids, 20 mM ascorbic acid, 300 mg/L tyrosine, 40 g/L maltodextrin, and 2 units/L amylase. The amylase is used to mimic a fed-batch process and gradually releases glucose from maltodextrin polymer so that the yeast can use it as a carbon source. The cells were separated from the media by centrifugation, and thebaine concentration was measured directly in the supernatant by LC-MS/MS analysis. All engineered yeast strains produced thebaine from glucose and simple nitrogen sources present in the growth media (FIGS. 22 and 23). Strains harboring a thebaine synthase activity produced higher levels of thebaine relative to strains not harboring this activity under the described fermentation conditions.

Example 5: Yeast Strains Engineered to Produce Downstream Morphinan Alkaloids from Glucose and Simple Nitrogen Sources Yeast strains can be engineered for the production of the downstream morphinan alkaloids from early precursors such as tyrosine. As an example, the platform yeast strains described in Example 4 can be further engineered to produce the downstream morphinan alkaloid products from L-tyrosine (FIG. 14).

The platform yeast strain producing thebaine from L-tyrosine (see description in Example 5) was further engineered to incorporate thebaine 6-O-demethylase, codeinone reductase, and codeinone-O-demethylase to convert the biosynthesized thebaine to the downstream morphinan alkaloids including morphine (FIG. 14). Three expression cassettes ($P_{ADH1}$-T6DM-$T_{ADH1}$, PH=7-COR-$T_{PGK1}$, $P_{TEF1}$-CODM-$T_{CYC1}$) were directly assembled with a TRP1 selective marker and integrated into the trpl locus in the thebaine platform yeast strain (Thodey et al., 2014).

The yeast strains harboring the integrated cassettes were grown in synthetic complete media with the appropriated drop out solution at 30° C. After 96 hours of growth, the media was analyzed for BIA metabolites by LC-MS/MS analysis.

Example 6: Yeast Strains Engineered to Produce Semi-Synthetic Opioids from Glucose and Simple Nitrogen Sources Yeast strains can be engineered for the production of the downstream morphinan alkaloids from early precursors such as tyrosine. As an example, the yeast strains described in Examples 4 and 5 can be further engineered to produce the semi-synthetic opioid products from L-tyrosine (FIG. 15).

The yeast strains producing downstream morphinan alkaloids from L-tyrosine (see description in Example 4) were further engineered to incorporate morphine dehydrogenase and morphinone reductase to convert the biosynthesized thebaine to the downstream morphinan alkaloids including morphine (FIG. 15). Two expression cassettes ($P_{GPD}$-morA-$T_{CYC1}$, $P_{PGK1}$-morB-$T_{PHO5}$) were directly assembled with a KanMX selective marker and integrated into the HO locus in the downstream morphinan alkaloids producing yeast strains (Thodey et al., 2014).

The yeast strains harboring the integrated cassettes were grown in synthetic complete media with the appropriated drop out solution at 30° C. After 96 hours of growth, the media was analyzed for BIA metabolites by LC-MS/MS analysis.

Example 7: Microbial Strains Engineered to Produce O-Demethylated Opioid Compounds from Glucose and Simple Nitrogen Sources Enzymes listed in Table 4 that displayed O-demethylase activity on morphinan alkaloids, were incorporated into a microbial strain (either *Saccharomyces cerevisiae* or *Escherichia coli*) which biosynthesizes morphinan alkaloids de novo (as described in Example 5). The complete BIA biosynthetic pathway uses L-tyrosine produced by the host cell and/or supplemented in the culture medium. Two molecules of tyrosine are modified and condensed to form the first benzylisoquinoline structure, which may be either norcoclaurine or norlaudanosoline. The benzylisoquinoline is further modified to form (S)-reticuline and then stereochemically inverted by the activity of an epimerase enzyme to yield (R)-reticuline. (R)-reticuline undergoes a carbon-carbon coupling reaction to form the first promorphinan, salutaridine, and is further modified before undergoing an oxygen-carbon coupling reaction catalyzed by a thebaine synthase to arrive at the first morphinan alkaloid structure, thebaine (see FIG. 14). Table 3 lists enzymes and activities in the complete pathway.

Figure 10:
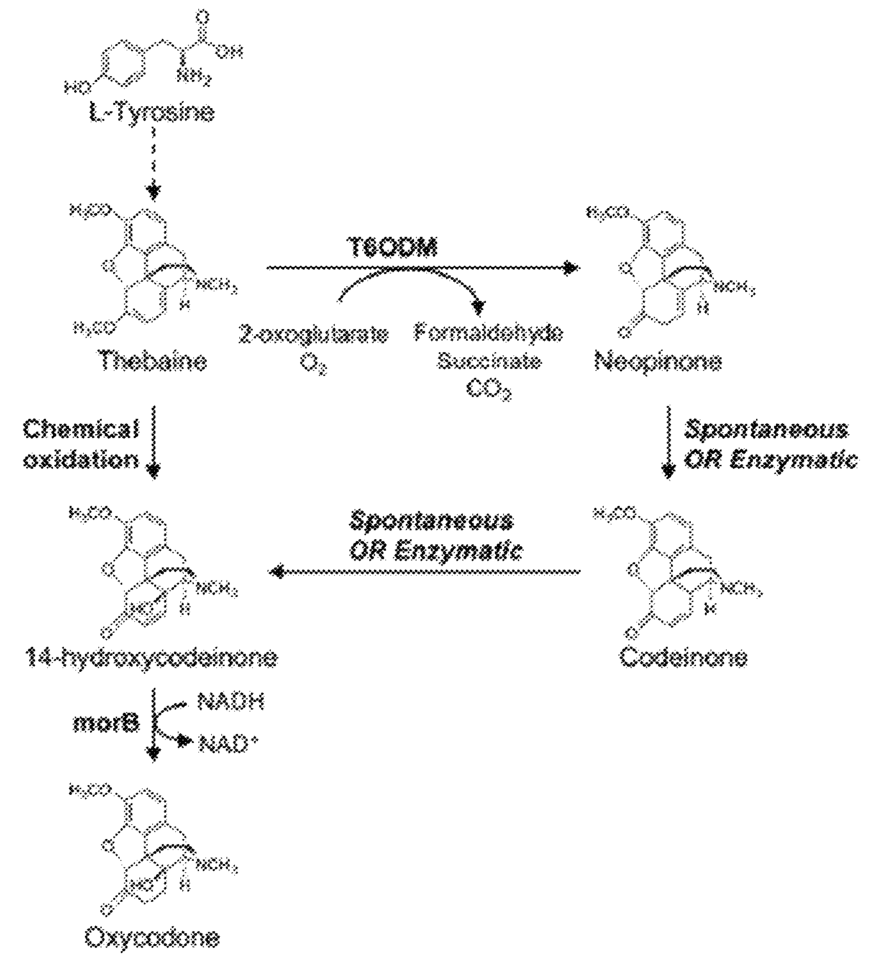
FIG. 10 illustrates a biosynthesis scheme for conversion of L-tyrosine to a nor-opioid or nal-opioid in a microbial cell, in accordance with embodiments of the invention.
Figure 10:
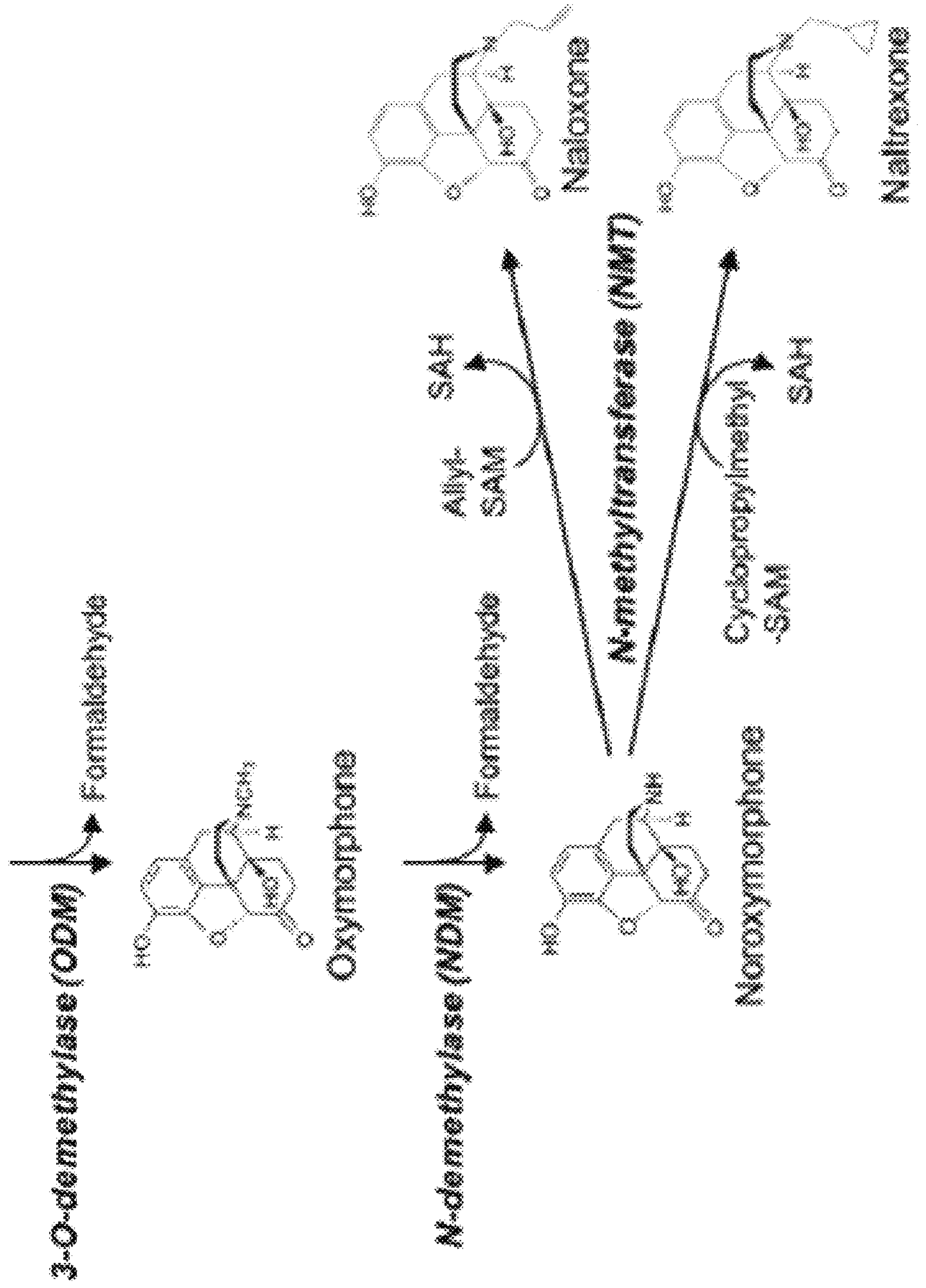

FIG. 10 illustrates a biosynthesis scheme in a microbial cell, in accordance with embodiments of the invention. Tyrosine produced endogenously by the cell and/or supplied in the culture medium is converted to oxycodone (broken arrows represent multiple enzymatic steps). The oxycodone is then 3-O-demethylated to oxymorphone and N-demethylated to noroxymorphone. Finally, an N-methyltransferase accepts allyl and cyclopropylmethyl carbon moieties from SAM analogues to produce naloxone and naltrexone, respectively.

To detect O-demethylase activity in strains producing morphinan alkaloid molecules, cells expressing candidate enzymes, either from plasmid vectors or chromosomally-integrated cassettes, were propagated by fermentation and cell supernatants were collected to analyze the total opioid profile (as described above). O-demethylation of opioid molecules in strains harboring the complete BIA pathway was detected by LC-MS (as described above). Specifically, the conversion of oxycodone to oxymorphone was detected. To detect O-demethylation activity via biocatalysis, strains were cultured in selective medium and then lysed by glass bead disruption. Cell lysates were supplied exogenously with opioid substrates (see FIG. 6), and other cofactors necessary for enzyme function. O-demethylation of opioid molecules was detected by LC-MS.

Example 8: Microbial Strains Engineered to Produce N-Demethylated Opioid Compounds from Glucose and Simple Nitrogen Sources Enzymes listed in Table 5, that displayed N-demethylase activity on morphinan alkaloids, were incorporated into a microbial strain (either *Saccharomyces cerevisiae* or *Escherichia coli*) which biosynthesizes morphinan alkaloids de novo (as described in Example 6). The complete BIA biosynthetic pathway uses L-tyrosine produced by the host cell and/or supplemented in the culture medium. Two molecules of tyrosine are modified and condensed to form the first benzylisoquinoline structure which may be either norcoclaurine or norlaudanosoline. The benzylisoquinoline is further modified to form (S)-reticuline and then stereochemically inverted by the activity of an epimerase enzyme to yield (R)-reticuline. (R)-reticuline undergoes a carbon-carbon coupling reaction to form the first promorphinan, salutaridine, and is further modified before undergoing an oxygen-carbon coupling reaction catalyzed by a thebaine synthase to arrive at the first morphinan alkaloid structure, thebaine (see FIG. 14). Table 3 lists enzymes and activities in the complete pathway.

To detect N-demethylase activity in strains producing morphinan alkaloid molecules, cells expressing candidate enzymes, either from plasmid vectors or chromosomally-integrated cassettes, were propagated by fermentation and cell supernatants were collected to analyze the total opioid profile (as described above). N-demethylation of opioid molecules in strains harboring the complete BIA pathway was detected by LC-MS (as described above). Specifically, the conversion of oxymorphone to noroxymorphone was detected. To detect N-demethylation activity via biocatalysis, strains were cultured in selective medium and then lysed by glass bead disruption. Cell lysates were supplied exogenously with opioid substrates (see FIG. 7), and other cofactors necessary for enzyme function. N-demethylation of opioid molecules was detected by LC-MS.

Example 9: Microbial Strains Engineered to Produce Nal-Opioid Compounds from Glucose and Simple Nitrogen Sources Enzymes listed in Table 6, that displayed N-methylase activity on morphinan alkaloids, were incorporated into a microbial strain (either *Saccharomyces cerevisiae* or *Escherichia coli*) which biosynthesizes morphinan alkaloids de novo (as described in Example 6). FIG. 10 shows an example of the complete reaction scheme from the precursor molecule thebaine to the final nal-opioid compounds naloxone and naltrexone. These strains additionally express enzymes from Examples 8 and 9 and Table 3, that are responsible for generating nor-opioid compounds from the complete BIA pathway. N-methylase enzymes were also expressed in a microbial strain (either Cen.PK2 for *S. cerevisiae* or BL21 for *E. coli*, for example) lacking the biosynthetic pathway, to generate a strain that is capable of biocatalysis of several different exogenously-supplied substrate molecules. The complete BIA biosynthetic pathway uses tyrosine produced by the host cell and/or supplemented in the culture medium. Two molecules of tyrosine are modified and condensed to form the first benzylisoquinoline structure which may be either norcoclaurine or norlaudanosoline. The benzylisoquinoline is further modified to form (S)-reticuline and then stereochemically inverted by the activity of an epimerase enzyme to yield (R)-reticuline. (R)-reticuline undergoes a carbon-carbon coupling reaction to form the first promorphinan, salutaridine, and is further modified before undergoing an oxygen-carbon coupling reaction catalyzed by a thebaine synthase to arrive at the first morphinan alkaloid structure, thebaine (see FIG. 14). Table 3 lists enzymes and activities in the complete pathway.

To detect N-modifying activity in strains with the complete BIA pathway to nor-opioids (see FIG. 10), cells expressing candidate enzymes were propagated by fermentation (as described above) and incubated with SAM or SAM analogs, such as those listed in FIG. 8. Enzymatic modification of nor-opioid or other BIA molecules in strains harboring the complete BIA pathway was detected in supernatants by LC-MS (as described above). To detect N-modifying activity via biocatalysis, strains were cultured in selective medium and then lysed by glass bead disruption. Cell lysates were supplied exogenously with SAM or SAM analogs, and other cofactors necessary for enzyme function. Specifically, the conversion of noroxymorphone to naloxone and naltrexone (using the SAM analogs allyl-SAM or cyclopropane-SAM, as shown in FIG. 8) was detected. Modification of nor-opioid or other BIA molecules was detected by LC-MS. To detect N-modifying activity by biocatalysis in a strain that does not have the complete BIA pathway, Cen.PK2 strains expressing the described heterologous enzymes were grown in selective medium and lysed by glass bead disruption. Cell lysates were supplied exogenously with SAM or SAM analogs, cofactors necessary for enzyme function, and nor-opioid molecules such as those listed in FIG. 8 and Table 3. Modification of these compounds was detected by LC-MS.

TABLE 3

Enzyme list

| Enzyme | Abbrev | Catalyzed Reactions | Source organisms | Genbank # |
|---|---|---|---|---|
| 3-deoxy-d-arabinose-heptulosonate-7-phosphate synthase | ARO4, DHAP synthase | erythrose-4-phosphate + PEP → DHAP (EC 2.5.1.54) | *Saccharomyces cerevisiae* | CAA85212.1 |
| Chorismate mutase | ARO7 | chorismate → prephenate (EC 5.4.99.5) | *Saccharomyces cerevisiae* | NP_015385.1 |
| Phenylpyruvate decarboxylase | ARO10 | hydroxyphenylpyruvate → 4HPA (EC 4.1.1.80) | *Saccharomyces cerevisiae* | NP_010668.3 |
| Aromatic aminotransferase | ARO9 | hydroxyphenylpyruvate + L-alanine ↔ tyrosine + pyruvate (EC 2.6.1.58) | *Saccharomyces cerevisiae* | AEC14313.1 |
| Aromatic aminotransferase | ARO8 | hydroxyphenylpyruvate + glutamate ↔ tyrosine + alpha-ketogluterate (EC 2.6.1.5) | *Saccharomyces cerevisiae* | KZV11.027.1 |
| Transketolase | TKL1 | fructose-6-phosphate + glyceraldehyde-3-phosphate ↔ xylulose-5-phosphate + erythrose-4-phosphate (EC 2.2.1.1) | *Saccharomyces cerevisiae* | NP_015399.1 |
| Glucose-6-phosphate dehydrogenase | ZWF1 | glucose-6-phosphate → 6-phosphogluconolactone (EC 1.1.1.49) | *Saccharomyces cerevisiae* | CAA96146.1 |
| Prephenate dehydrogenase | TYR1 | prephenate + $NADP^+$ → 4-hydroxyphenylpyruvate + $CO_2$ + NADPH (EC1.3.1.13) | *Saccharomyces cerevisiae* | CAA85127.1 |

TABLE 3-continued

| Enzyme list | | | | |
|---|---|---|---|---|
| Enzyme | Abbrev | Catalyzed Reactions | Source organisms | Genbank # |
| Alcohol dehydrogenase | ADH2-7, SFA1 | 4HPA → tyrosol (EC 1.1.1.90) | *Saccharomyces cerevisiae* | NP_014032.1, AAT93007.1, NP_011258.2, NP_009703.3, NP_014051.3, NP_010030.1, NP_010113.1 |
| Aldehyde oxidase | ALD2-6 | 4HPA → hydroxyphenylacetic acid (EC 1.2.1.39) | *Saccharomyces cerevisiae* | NP_013893.1, NP_013892.1, NP_015019.1, NP_010996.2, NP_015264.1 |
| Tyrosinase | TYR | tyrosine → L-DOPA, L-DOPA → dopaquinone (EC 1.14.18.1) | *Ralstonia solonacearum*, *Agaricus bisporus* | NP_518458.1, AJ223816, |
| Tyrosine hydroxylase | TyrH | tyrosine → L-DOPA (EC 1.14.16.2) | *Homo sapiens*, *Rattus norvegicus*, *Mus musculus* | NM 012740, NM 000240, |
| GTP cyclohydrolase | FOL2 | GTP → dihydroneopterin triphosphate (EC 3.5.4.16) | *Saccharomyces cerevisiae*, *Homo sapiens*, *Mus musculus* | CAA97297.1, NP_001019195.1, NP_032128.1 |
| 6-pyruvoyl tetrahydrobiopterin (PTP) synthase | PTPS | dihydroneopterin triphosphate → PTP (EC 4.2.3.12) | *Rattus norvegicus*, *Homo sapiens*, *Mus musculus* | AAH59140.1 BAA04224.1, AAH29013.1 |
| Sepiapterin reductase | SepR | PTP → BH4 (EC 1.1.1.153) | *Rattus norvegicus*, *Homo sapiens*, *Mus musculus* | NP_062054.1, NP_003115.1, NP_035597.2 |
| 4a-hydroxytetrahydrobiopterin (pterin-4α-carbinolamine) dehydratase | PCD | 4a-hydroxytetrahydrobiopterin → H2O + quinoiddihydropteridine (EC 4.2.1.96) | *Rattus norvegicus*, *Homo sapiens*, *Mus musculus* | NP_001007602.1, AAB25581.1, NP_079549.1 |
| Quinoid dihydropteridine reductase | QDHPR | quinoiddihydropteridine → BH4 (EC 1.5.1.34) | *Rattus norvegicus*, *Homo sapiens*, *Mus musculus* | AAH72536.1, NP_000311.2, AAH02107.1 |
| L-DOPA decarboxylase | DODC | L-DOPA → dopamine (EC 4.1.1.28) | *Pseudomonas putida*, *Rattus norvegicus* | AE015451.1, NP_001257782.1 |
| Tyrosine/DOPA decarboxylase | TYDC | L-DOPA → dopamine (EC 4.1.1.28) | *Papaver somniferum* | AAA97535.1, CAB56038.1 |
| Monoamine oxidase | MAO | dopamine → 3,4-DHPA (EC 1.4.3.4) | *E. coli*, *Homo sapiens*, *Micrococcus luteus* | 103792, D2367, AB010716.1 |
| Dihydrofolate reductase | DHFR | 7,8-Dihydrobiopterin → 5,6,7,8-Tetrahydrobiopterin (BH4) EC 1.5.1.3 | *Rattus norvegicus*, *Homo sapiens* | AF318150.1 |
| Norcoclaurine 6-O-methyltransferase | 6OMT | Norcoclaurine → coclaurine Norlaudanosoline → 3'hydroxycoclaurine EC 2.1.1.128 | *P. somniferum* *T. flovum* *Coptis japonica** | AY268894 AY610507 D29811 |
| Coclaurine-N-methyltransferase | CNMT | Coclaurine → N-methylcoclaurine 3'hydroxycoclaurine → 3'-hydroxy-N-methylcoclaurine EC 2.1.1.140 | *P. somniferum* *T. flovum* *Coptis japonica** | AY217336 AY610508 AB061863 |
| 4'-O-methyltransferase | 4'OMT | 3'-hydroxy-N-methylcoclaurine → Reticuline EC 2.1.1.116 | *P. somniferum* *T. flovum* *Coptis japonica** | AY217333, AY217334 AY610510 D29812 |
| Norcoclaurine synthase | NCS | 4HPA + dopamine → S-norcoclaurine (EC 4.2.1.78) 3,4-DHPA + dopamine → S-norlaudanosoline | *Coptis japonica*, *Papaver somniferum*, *Papver bracteatum*, *Thalicitum flavum*, *Corydalis saxicola* | BAF45337.1, ACI45396.1, AC090258.1, AC090247.1, AEB71889.1 |

TABLE 3-continued

| Enzyme list | | | | |
|---|---|---|---|---|
| Enzyme | Abbrev | Catalyzed Reactions | Source organisms | Genbank # |
| Cytochrome P450 80B1 | CYP80B1 | N-methylcoclaurine → 3'-hydroxy-N-methylcoclaurine (EC 1.14.13.71) | *P. somniferum*, *E. californica*, *T. flavum* | AAF61400.1, AAC39453.1, AAU20767.1 |
| Cheilanthifoline synthase | CFS | Scoulerine → cheilanthifoline EC1.14.21.2 | *P. somniferum* *E. californica* *A. mexicana* | GU325749 AB434654 EF451152 |
| Stylopine synthase | STS | Cheilanthifoline → stylopine EC1.14.21.1 | *P. somniferum* *E. californica* *A. mexicana* | GU325750 AB126257 EF451151 |
| Tetrahydroprotoberberine-N-methyltransferase | TNMT | Stylopine → cis-N-methylstylopine EC2.1.1.122 | *P. somniferum* *E. californica* *P. bracteatum* *A. mexicana* | DQ028579 EU882977 EU882994 HQ116698 |
| Cis-N-methylstylopine 14-hydroxylase | MSH | cis-N-methylstylopine → protopine EC1.14.13.37 | *P. somniferum* | KC154003 |
| Protopine-6-hydroxylase | P6H | Protopine → 6-hydroxyprotopine EC1.14.13.55 | *E. californica* *P. somniferum* | AB598834 AGC92397 |
| Dihydrobenzophenanthridine oxidase | DBOX | Dihydrosanguinarine → sanguinarine EC 1.5.3.12 | *P. somniferum* | [not in genbank] |
| (S)-tetrahydroprotoberberine oxidase | STOX | (S)-tetrahydroberberine + 2 $O_2$ → berberine + 2 $H_2O_2$ EC 1.3.3.8 | *Berberis wilsonae*, *Coptis japonica*, *Berberis* spp, *Coptis* spp | HQ116697, AB564543 |
| S-adenosyl-L-methionine: (S)-scoulerine 9-O-methyltransferase | S9OMT | S-adenosyl-L-methionine + (S)-scoulerine → S-adenosyl-L-homocysteine + (S)-tetrahydrocolumbamine EC 2.1.1.117 | *Thalictrum flavum* subsp. *glaucum*, *Coptis japonica*, *Coptis chinensis*, *Papaver somniferum*, *Thalictrum* spp, *Coptis* spp, *Papaver* spp | AY610512, D29809, EU980450, JN185323 |
| (S)-tetrahydrocolumbamine, NAD PH: oxygen oxidoreductase (methylenedioxy-bridge-forming), also known as (S)-canadine synthase | CAS | (S)-tetrahydrocolumbamine + NADPH + H+ + O2 → (S)-canadine + NADP+ + 2 H2O EC 1.14.21.5 | *Thalictrum flavum* subsp. *glaucum*, *Coptis japonica*, *Thalictrum* spp, *Coptis* spp | AY610513, AB026122, AB374407, AB374408 |
| (S)-reticuline: oxygen oxidoreductase (methylene-bridge-forming), also known as berberine bridge enzyme | BBE | (S)-reticuline + O2 → (S)-scoulerine + H2O2 EC 1.21.3.3 | *Papaver somniferum*, *Argemone mexicana*, *Eschscholzia californica*, *Berberis stolonifera*, *Thalictrum flavum* subsp. *glaucum*, *Coptis japonica*, *Papaver* spp, *Eschscholzia* spp, *Berberis* spp, *Thalictrum* spp, *Coptis* spp | AF025430, EU881889, EU881890, S65550 AF005655, AF049347, AY610511, AB747097 |
| NADPH: hemoprotein oxidoreductase, also known as cytochrome P450 reductase | ATR1, CPR | NADPH + H+ + n oxidized hemoprotein → NADP+ + n reduced hemoprotein EC 1.6.2.4 | *Arabidopsis thaliana*, *Eschscholzia californica*, *Papaver somniferum*, *Homo sapiens*, *Saccharomyces cerevisiae*, *Papaver bracteatum*, *Papaver* spp, all plants | CAB58576.1, CAB58575.1,AAC05021.1, AAC05022.1, NM118585, many others (Ref PMID 19931102) |

TABLE 3-continued

Enzyme list

| Enzyme | Abbrev | Catalyzed Reactions | Source organisms | Genbank # |
|---|---|---|---|---|
| salutaridinol: NADP+ 7-oxidoreductase, also known as salutaridine reductase | SalR | salutaridinol + NADP+ → salutaridine + NADPH + H+ EC 1.1.1.248 | *Papaver somniferum*, *Papaver bracteatum*, *Papaver* spp *Chelidonium majus* | DQ316261, EF184229 (Ref PMID 22424601) |
| acetyl-CoA: salutaridinol 7-O-acetyltransferase, also known as salutaridinol 7-O-acetyltransferase | SalAT | acetyl-CoA + salutaridinol → CoA + 7-O-acetylsalutaridinol EC 2.3.1.150 | *Papaver somniferum*, *Papaver bracteatum*, *Papaver orientale*, *Papaver* spp | AF339913, FJ200355, FJ200358, FJ200356, JQ659008 |
| thebaine synthase | TS | 7-O-acetylsalutaridinol → thebaine + acetate | *Papaver somniferum*, *Papaver bracteatum*, *Papaver orientale*, *Papaver* spp | [not in genebank] |
| (R)-reticuline, NADPH: oxygen oxidoreductase (C—C phenol- coupling), also known as salutaridine synthase | SalSyn | (R)-reticuline + NADPH + H+ + O2 → salutaridine + NADP+ + 2 H2O EC 1.14.21.4 | *Papaver somniferum*, *Papaver* spp *Chelidonium majus* | EF451150 (Ref PMID 22424601) |
| 1-benzylisoquinoline alkaloid epimerase (cytochrome P450 82Y1-like codeinone reductase-like) | DRS-DRR (or CYP-COR) | (S)-reticuline -> (R)-reticuline (S)-1-benzylisoquinoline -> (R)-1-benzylisoquinoline EC 1.5.1.27 | *Papaver bracteatum*, *Papaver somniferum*, *Papaver setigerum*, *Chelidonium majus* | P0DKI7.1, AK060175.1, AK060180.1, AK060179.1, AK060175.1 |
| Cytochrome P450, family 2, subfamily D, polypeptide 6 | CYP2D6 | Promiscuous oxidase, can perform (R)-reticuline + NADPH + H+ + O2 → salutaridine + NADP+ + 2 H2O among other reactions EC 1.14.14.1 | *Homo sapiens* | BC067432 |
| Thebaine 6-O demethylase | T6ODM | thebaine → [a]neopinone EC 1.14.11.31 | *Papaver somniferium*, *Papaver* spp. | GQ500139.1 |
| Codeinone reductase | COR | codeinone → [a]codeine EC 1.1.1.247, neopinone → [a]neopine | *Papaver somniferium*, *Papaver* spp. | AF108432.1 AF108433.1 AF108434.1 AF108435.1 |
| Codeine O-demethylase | CODM | codeine → [a]morphine EC 1.14.11.32, neopine → [a]neomorphine | *Papaver somniferium*, *Papaver* spp. | GQ500141.1 |
| Morphine dehydrogenase | morA | morphine → [a]morphinone EC 1.1.1.218, codeinone → [a]codeine EC 1.1.1.247 | *Pseudomonas putida* | M94775.1 |
| Morphinone reductase | morB | codeinone → [a]hydrocodone morphinone [aa]hydromorphone EC 1.3.1.- | *Pseudomonas putida* | U37350.1 |
| Reticuline N-methyltransferase | RNMT | reticuline → tembetarine | *Papaver somniferum*, *Papaver* spp. | KX369612.1 |
| Papaverine 7-O-demethylase | P7OMT | papaverine → pacodine | *Papaver somniferum*, *Papaver* spp. | KT159979.1 |

TABLE 3-continued

| Enzyme list | | | | |
|---|---|---|---|---|
| Enzyme | Abbrev | Catalyzed Reactions | Source organisms | Genbank # |
| 3-O-demethylase | 3ODM | oxycodone → oxymorphone<br>hydrocodone → hydromorphone<br>dihydrocodeine → dihydromorphine<br>14-hydroxycodeine → 14-hydroxymorphine<br>codeinone-morphinone<br>14-hydroxycodeinone → 14-hydroxymorphinone | *Papaver somniferum*, *Papaver bracteatum*, *Papaver rhoeas*, *Papaver* spp. | |
| N-demethylase | NDM | Codeine → Norcodeine<br>Morphine-Normorphine<br>Oxycodone → Noroxycodone<br>Oxymorphone → Noroxymorphone<br>Thebaine → Northebaine<br>Oripavine → Nororipavine<br>Hydrocodone → Norhydrocodone<br>Hydromorphone → Norhydromorphone<br>Dihydrocodeine → Nordihydrocodeine<br>Dihydromorphine → Nordihydromorphine<br>14-hydroxycodeine → Nor-14-hydroxycodeine<br>14-hydroxymorphine → Nor-14-hydroxymorphine<br>Codeinone → Norcodeinone<br>Morphinone → Normorphinone<br>14-hydroxycodeinone → Nor-14-hydroxycodeinone<br>14-hydroxymorphinone → Nor-14-hydroxymorphinone | *Bacillus megaterium*, *Homo sapiens*, *Papaver somniferum*, *Papaver* spp., *Chelidonium majus*, *Stylophorum diphyllum*, *Nigella sativa*, *Hydrastis canadensis*, *Glaucium flavum*, *Eschscholzia californica*, *Menispermum canadense*, *Papaver bracteatum* | |
| N-methyltransferase | NMT | Norcodeine → codeine<br>Normorphine → morphine<br>Noroxycodone → oxycodone<br>Noroxymorphone → noroxymorphone<br>Northebaine → thebaine<br>Nororipavine → oripavine<br>Norhydrocodone → hydrocodone<br>Norhydromorphone → Hydromorphone<br>Nordihydrocodeine → Dihydrocodeine<br>Nordihydromorphine → Dihydromorphine<br>Nor-14-hydroxycodeine → 14-hydroxycodeine<br>Nor-14-hydroxymorphine → 14-hydroxymorphine<br>Norcodeineone → Codeineone<br>Normorphinone → Morphinone<br>Nor-14-hydroxy-codeinone → 14-hydroxycodeinone<br>Nor-14-hydroxy-morphinone → 14-hydroxymorphinone | *Papaver* spp., *Chelidonium majus*, *Thalictrum flavum*, *Coptis japonica*, *Papaver somniferum*, *Eschscholzia californica*, *Papaver bracteatum*, *Argenome mexicana*, *Glaucium flavum*, *Sanguinaria canadensis*, *Corydalis chelanthifolia*, *Nigella saliva*, *Jeffersonia diphylla*, *Berberis thunbergii*, *Mahonia aquifolium*, *Menispermum canadense*, *Tinospora cordifolia*, *Cissampelos mucronata*, *Cocculus trilobus* | |
| N-allyltransferase | NAT | Norcodeine → N-allyl-norcodeine<br>Normorphine → N-allyl-normorphine | *Papaver* spp., *Chelidonium majus*, *Thalictrum* | |

TABLE 3-continued

Enzyme list

| Enzyme | Abbrev | Catalyzed Reactions | Source organisms | Genbank # |
|---|---|---|---|---|
| | | Noroxycodone → N-allyl-noroxycodone<br>Noroxymorphone → N-allyl-nornoroxymorphone<br>Northebaine → N-allyl-northebaine<br>Nororipavine → N-allyl-nororipavine<br>Norhydrocodone → N-allyl-norhydrocodone<br>Norhydromorphone → N-allyl-norhydromorphone<br>Nordihydrocodeine → N-allyl-nordihydrocodeine<br>Nordihydromorphine-N-allyl-nordihydromorphine<br>Nor-14-hydroxycodeine → N-allyl-nor-14-hydroxycodeine<br>Nor-14-hydroxymorphine → N-allyl-nor-14-hydroxymorphine<br>Norcodeineone → N-allyl-norcodeineone<br>Normorphinone → N-allyl-normorphinone<br>Nor-14-hydroxy-codeinone → N-allyl-nor-14-hydroxycodeinone<br>Nor-14-hydroxy-morphinone → N-allyl-nor-14-hydroxymorphinone | *flavum*, *Coptis japonica*, *Papaver somniferum*, *Eschscholzia californica*, *Papaver bracteatum*, *Argenome mexicana*, *Glaucium flavum*, *Sanguinaria canadensis*, *Corydalis chelanthifolia*, *Nigella sativa*, *Jeffersonia diphylla*, *Berberis thunbergii*, *Mahonia aquifolium*, *Menispermum canadense*, *Tinospora cordifolia*, *Cissampelos mucronata*, *Cocculus trilobus* | |
| N-cyclopropylmethyltransferase | NCPMT | Norcodeine-N-(Cyclopropylmethyl) norcodeine<br>Normorphine-N-(Cyclopropylmethyl) normorphine<br>Noroxycodone → N-(Cyclopropylmethyl) noroxycodone<br>Noroxymorphone → N-(Cyclopropylmethyl) nornoroxymorphone<br>Northebaine → N-(Cyclopropylmethyl) northebaine<br>Nororipavine → N-(Cyclopropylmethyl) nororipavine<br>Norhydrocodone → N-(Cyclopropylmethyl) norhydrocodone<br>Nordihydrocodeine → N-(Cyclopropylmethyl) nordihydrocodeine<br>Nordihydromorphine-N-(Cyclopropylmethyl) nordihydromorphine<br>Nor-14-hydroxycodeine → N-(Cyclopropylmethyl) nor-14-hydroxycodeine<br>Nor-14-hydroxymorphine → N-(Cyclopropylmethyl) nor-14-hydroxymorphine<br>Norcodeineone → N-(Cyclopropylmethyl) norcodeineone<br>Normorphinone → N-(Cyclopropylmethyl) normorphinone<br>Nor-14-hydroxy- | *Papaver* spp., *Chelidonium majus*, *Thalictrum flavum*, *Coptis japonica*, *Papaver somniferum*, *Eschscholzia californica*, *Papaver bracteatum*, *Argenome mexicana*, *Glaucium flavum*, *Sanguinaria canadensis*, *Corydalis chelanthifolia*, *Nigella sativa*, *Jeffersonia diphylla*, *Berberis thunbergii*, *Mahonia aquifolium*, *Menispermum canadense*, *Tinospora cordifolia*, *Cissampelos mucronata*, *Cocculus trilobus* | |

TABLE 3-continued

| Enzyme list | | | | |
|---|---|---|---|---|
| Enzyme | Abbrev | Catalyzed Reactions | Source organisms | Genbank # |
| | | codeinone → N-(Cyclopropylmethyl) nor-14-hydroxycodeinone Nor-14-hydroxy-morphinone → N-(Cyclopropylmethyl) nor-14-hydroxymorphinone | | |

TABLE 4

| O-demethylase candidate enzymes | |
|---|---|
| Name | Sequence |
| T6ODM | MEKAKLMKLGNGMEIPSVQELAKLTLAEIPSRYVCANENLLLPMGASVINDHETIPVIDIE NLLSPEPIIGKLELDRLHFACKEWGFFQVVNHGVDASLVDSVKSEIQGFFNLSMDEKTKY EQEDGDVEGFGQGFIESEDQTLDWADIFMMFTLPLHLRKPHLFSKLPVPLRETIESYSSEM KKLSMVLFNKMEKALQVQAAEIKGMSEVFIDGTQAMRMNYYPPCPQPNLAIGLTSHSDF GGLTILLQINEVEGLQIKREGTWISVKPLPNAFVVNVGDILEIMTNGIYHSVDHRAVVNST NERLSIATFHDPSLESVIGPISSLITPETPALFKSGSTYGDLVEECKTRKLDGKSFLDSMRI |
| CODM | METPILIKLGNGLSIPSVQELAKLTLAEIPSRYTCTGESPLNNIGASVTDDETVPVIDLQNLL SPEPVVGKLELDKLHSACKEWGFFQLVNHGVDALLMDNIKSEIKGFFNLPMNEKTKYGQ QDGDFEGFGQPYIESEDQRLDWTEVFSMLSLPLHLRKPHLFPELPLPFRETLESYLSKMKK LSTVVFEMLEKSLQLVEIKGMTDLFEDGLQTMRMNYYPPCPRPELVLGLTSHSDFSGLTIL LQLNEVEGLQIRKEERWISIKPLPDAFIVNVGDILEIMTNGIYRSVEHRAVVNSTKERLSIA TFHDSKLESEIGPISSLVTPETPALFKRGRYEDILKENLSRKLDGKSFLDYMRM |
| PsP7ODM | MEKAKLMKLGNGLSIPSVQELAELTFAEVPSRYVCTNDENLLLMTMGASEIDDETVPVID LQNLLSPEPAIGKSELDWLHYSCKEWGFFQLVNHGVDALLVDHVKSEIHSFFNLPLNEKT KYGQRDGDVEGFGQAFLVSENQKLDWADMFFINTLPLHLRKPHLFPNLPLPLRETIESYSS EMKKLSMVLFEMMGKAIEVIDIKEAITEMFEDGMQSMRMNYYPPCPQPERVIGITPHSDF DGLTILLQLNEVEGLQIRKEDKWISIKPLPDAFIVNVGDIWEIMTNGVHRSVDHRGVINST KERLSIATFHSPKLELEIGPISSLIRPETPAVFKSAGRFEDLLKEGLSRKLDGKSFLDCMRM |
| PsoDIOX1 | MEKAKLMKLGNGMEIPSVQELAKLTLAEIPSRYVCANENLLLPMGASVINDHETIPVIDIE NLLSPEPIIGKLELDRLHFACKEWGFFQVVNHGVDASLVDSVKSEIQGFFNLSMDEKTKY EQEDGDVEGFGQGFIESEDQTLDWADIFMMFTLPLHLRKPHLFSKLPVPLRETIESYSSEM KKLSMVLFNKMEKALQVQAAEIKGMSEVFIDGTQAMRMNYYPPCPQPNLAIGLTSHSDF GGLTILLQINEVEGLQIKREGTWISVKPLPNAFVVNVGDILEIMTNGIYHSVD |
| PsoDIOX2 | METAKLMKLGNGMSIPSVQELAKLTLAEIPSRYICTVENLQLPVGASVIDDHETVPVIDIE NLISSEPVIEKLELDRLHSACKEWGFFQVVNHGVDTSLVDNVKSDIQGFFNLSMNEKIKY GQKDGDVEGFGQAFVASEDQTLDWADIFMILTLPLHLRKPHLFSKLPLPLRETIESYSSEM KKLSMVLFEKMEKALQVQAVEIKEISEVFKDMTQVMRMNYYPPCPQPELAIGLTPHSDF GGLTILLQLNEVEGLQIKNEGRWISVKPLPNAFVVNVGDVLEIMTNGMYRSVDHRAVVN STKERLSIATFHDPNLESEIGPISSLITPNTPALFRSGSTYGELVEEFHSRKLDGKSFLDSMR M |
| PbrDIOX2 | METPKSIKLGGSLLVPSVQELAQQSFAEVPARYVRDDLEPLTDLSGVSMIDQTIPVIDLQK LQSPVPIIRELESEKLHSACKEWGFFQVVNHGVDILLVEKTKSEIKDFFNLPMDEKKKFWQ EEGDIQGFGQAFVQSEDQKLDWADIFLMVTLPRHTRNPRLFPKLPLPLRNTMDSYSSKLS KLASTLIEMMGKALHMETSVLAELFEDGRQTMRINYYPPCPQPKDVIGLTPHSDGGGLTI LLQLNEVDGLQIRKEKIWIPIKPLPNAFVVNIGNILEIMTNGIYRSVEHRATIHSTKERLSVA AFHNPKVGVEIGPIVSMITPESPALFRTIEYDDYGKKYFSRKLDGKSSLDFMRIGEGDEEN KAT |
| PbrDIOX3 | METPKLIKLGGSLLVPSVLELTKQSPAEVPARYIRNDLEPMTDLSSASLTDQTIPVIDLQNL LSPEPELELEKLHSGCKEWGFFQVMNHGVDILLVEKVKSEIQGFFNLPIDEKNKFWQEEG DLEGYGKAFVHSEDEKLDWADMFFILTQPQYMRKPRVFPKLPLRLRETIESYSLELSKLG LTLLDLMGKALQIETGVMSELFEDGRQTMRMNYYPPCPQPEHVIGLTPHSDGGALTILLQ LNQVDGLQIRKEEIWVPIKPLPNAFVVNIGDILEIMSNGVYRSVEHRATINSSKERLSVAIF QSPKHGTEIGPILSMITPEAPALFKTIPYEDYLRKFFSRKLGGKSFVDSMRIGESDEDNNTA |
| PbrDIOX4 | METQKQENFGASLSVPNVQELAKQSPEQVPDRYIRSDQDSSTNISCPSMTDQIPVIDLQSL LSPDPIIGELELERLHSACKEWGFFQVVNHGVDNLLVEKVKSEIQGFFNLPMDEKKKFWQ EEGDFEGFGQAFVFSEDQKLDWGDVFFILTQPQHMRKPRLFPKLPLPFRKTIESYSLETNK LSMTLLELMEKALKIETGVMTELFEGGIQRMRMTYYPPCPQPKHVIGLTPHSDPDALTILL QLNEVDGLQIRKEKIWVPIKPLSNAFVVNIGDILEIMSNGIYRSVEHRATVNSTKERLSVAT FHSPRKDTEIGPILITPETPALFRTSGFEDYFRKFFAHKLNGKSFLSSIRIGETDEGNNAT |

TABLE 4-continued

O-demethylase candidate enzymes

| Name | Sequence |
|---|---|
| PbrDIOX5 | MEAPKLIMLGGSLFVPSVQELAKQSLAEVPVRYVRDDQDTLGNNINITPMSMIDQSIPVID LEKLLSPEPIVGELELERLHSACKEWGFFQVVNHGVDSLLVEKVKSEIEGFFKLPMDEKTK FWQEEGDIEGFGQVFVHSQDQKLDWGDMFLMQTLPRHTRKPRLFPNLPLPLRQTIESYSS ELSKLVLTLVDLMGKALQMESGVLIELFENGIQRMRMNYYPPCPQPEQVIGLTPHSDVG GLTILLQLNEVDGLQIKKDKVWVPIKPLANAFVVNVGDALEIMSNGIYRSVEHRATINST KERLSIATFHNPRADREIGPIPSMISPETPALFKTTGYEEYFKKFFSRKLEGKSFLDSLRIREG DEHCGRLDVKGPCN |
| PbrDIOX6 | MEIPNPIKIGSSLLVPSVQELAKQSFAEVPARYIRNDVDPLITKLSDVSLIDQTVPVIDLQKL LSPEPIVGELELERLHSACKEWGFFQVVNHGVDNLLVEKVKSEIQGFFNLPMEEKKKFWQ EEGDFEGFGQMFVQSEEQKLDWGDMFFILTQPQHMRKPRLFSKLPLPLRETIESYSLELIK LGLTIIKLMEKALQIDAGVMAELFEDGIHTMRMNYYPPCPQPEHVIGLTPHSDGGGLTILL QLNEVDGLQIRRENIWVPIKPLPNAFVVNIGDILEILSNGIYRSVEHRSTVNATKERLSVAT FQNPKQESVIGPNMITPERPALFRKIVYKDYMKKLFSRKLDGKSFLDSLRIGEGDERP |
| PbrDIOX8 | METLKTVKPGGSLFIPNGQELAKQSLEEVYVGNDQDTMLLIGQTIPVIDLQKLLSPEPITG DMELDKLHSACKEWGFFQVVNHGVDILLVEKVKSEVHDFFNIPMDEKKPFWQEEGDLE GFGQVFITSEDQQLDWGDMFFMVTLPKHMRKPRLFLKLPLPLRETIESYSLKLSKLGVTL VELMGKALQMEDRIMSELFDDGRQTMRMNYYPPCPQPEQVIGLTPHSDPGGLTILLELNE VNGLIRKENIWVPIIPLPNAFIVNIGDILEIMSNGIYHSVEHRATINSTKERLSVAMFNSPKV DTEIGPIHSMITPETPALFRTIGYDEYLKIFFSRKLDGKSLLESMKI |
| PbrDIOX10 | MEAPKLIMLGGSLFVPSVQELAKQSLAEVPVRYVRDDQDTLGNNINITPMSMIDQSIPVID LEKLLSPEPIVGELELERLHSACKEWGFFQVVNHGVDSLLVEKVKSEIEGFFELPVDEKKK FWQEEGDIEGFGQIFVHSEDQKLDWADMFYMLTLPPNMRKPRLFPNLPLPLRQTIDSYSS ELSKLVLTLVDLMGKALQMESGVLTELFENGIQRMRMNYYPPCPQPEQVIGLTPHSDVG GLTILLQLNEVDGLQIKKDKIWVPIKPLRNAFVVNVGDALEIMSNGIYRSVEHRATINSTK ERLSIATFHNPRADREIGPIPSMISPETPALFKTTGYEEYFKKFFSRKLEGKSFLDSLRIGEG DEHCGRLXVKGXCN |
| PbrDIOX11 | METPKLMKLGGSLFVPSVQELAKQSLAEVPARYVRDDRDMVGNIINVTPMSMIDQSIPVI DLEKLLSPDLIVGELELERLHSACKEWGFFQVVNHGVDSLLVEKVKSEIEGFFELPMDEK KKFWQEEGDAEGFAQFFVQSEDQKLDYSGDMFFMLNLPQHMRKPRLFLKLPLPLRETIES YSLKLSKLGVTLVELMGKALQMEDRIMSELFDDGRQTMRMNYYPPCPQPEQVIGLTPHS DPGGLTILLELNEVNGLIRKENIWVPIIPLPNAFIVNIGDILEIMSNGIYHSVEHRATINSTKE RLSVAMFNSPKVDTEIGPIHSMITPETPALFRTIGYDEYLKIFFSRKLDGKSLLESMKI |
| PbrDIOX13 | METPKLRDFGSFLPVPSVQELAKQVLTEIPPRYIRTDLEALNKLSCASNTDQTVPIIDMQCL LSAEPEMELEKLHSACKEWGFFRVVNHGVDNLESVKSEIESFLNLPVNAKNKYGQKQGD DQGFGSRFVLSEEQKLDWGDFFYMVTRPLYLRKPHLFPELPLPLRETIESYSSEVSKLAMA LFEMMGKALKIETGVMTEIFEGGMQAMRMNYYPPCPRPDLVIGLNAHSDFGGLTILLQL NEVEGLEIRNKGEWVSVKPLANAFVVNVGDVMEILTNGIYHSVEHRATINSSKERLSVAT FHYPKLETGIGPLPCMITPKTPALFGRIERYELLLRKYYARKLNGKSTLDCMRIGNGFEDD NTA |
| PbrDIOX18 | MEAPKLIMLGGSLFVPSVQELAKQSLAEVPARYVRDDQDTLGNNINITPMSMIDQSIPVID LEKLLSPEPIVGELELERLHSACKEWGFFQVVNHGVDSLLVEKVKSEIEGFFELPVDEKKK FWQEEGDIEGFGQIFVHSEDQKLDWADMFYMLTLPPNMRKPRLFPNLPLPLRQTIDSYSS ELSKLVLTLVDLMGKALQMESGVLTELFENGIQRMRMNYYPPCPQPEQVIGLTPHSEVG GLTILLQLNEVDGLQIRKEKIWVPIKPLSNAFIVNIGDILEIMSNGIYRSVEHRATVNSTKER LSVATFHSPRKDTEIGPILITPETPALFRTSGFEDYFRKFFAHKLNGKSFLSSIRIGETDEGNN AT |
| PbrDIOX19 | MSMIDQSIPVIDLEKLLSPEPIVGELELERLHSACKEWGFFQVVNHGVDSLLVEKVKSEIE GFFELPVDEKKKFWQEEGDIEGFGQIFVHSEDQKLDWADMFYMLTLPPNMRKPRLFPNL PLPLRQTIDSYSSELSKLVLTLVDLMGKALQMESGVLTELFENGIQRMRMNYYPPCPQPE QVIGLTPHSDVGGLTILLQLNEVDGLQIRKEKIWVPIKPLSNAFIVNIGDILEIMSNGIYHSV EHRATINSTKERLSVAMFNSPKVDTEIGPIHSMITPETPALFRTIGYDEYLKIFFSRKLDGKS LLESMKI |
| PbrDIOX21 | METPKLVKSSGSSLFLSTSVQELAKQSLPEVPARYIRTNLEPLSNVSGDSQSVPVIDLQKLL SSEPIIGELELDKLHSACKEWGFFQVVNHGVDNLVMEKIKTIEIQGFFNLSLDEKQKFWKK EGDAEGFGQNFIESEDQKLDWGDTFGMFTLPIHMRNPRLFPELPLPLRETIESYSLDVRKL ALALIGLMEKALKIKTSAMSELFEDGGQAMRMNYYPPCPQPEHVIGLTPHSDAGGLTILL QLNEVDGLQIKKDKIWVPIKPLPNAFVVNIGDILEIMTNGIYRSVEHRATINSSKERLSVAA FHSPKGDTLIGPMVSLITPETPALFRTIGYQDYMKKFMSRKLDGKSLVNSMRIGEGDEDK |
| PbrDIOX-ZSNV-2004018 | METPTLMKLGNGLSVPSVQELAKATLAEIPSRYICTDENLLTMGASTTDNETVPVIDLQNL LSPEPVIGMLELDRLHSACKEWGFFQLVNHGVDALLVDNEVQGFFNLPMDEKTKYGQK DGDDEGFGQFFVISEDQKLDWADVFYMSTLPLHSRKPHLFPELPLPLRETMESYSSEMKK LSMVLFDMMGKALQVVEIKGITELFEDGAQQIRMNYYPPCPQPELVFGLTSHSDFDGLTI LLQLGEVEGLQIKKEERWISIKPLPDAFIVNVGDILEIMTNGIYRSVDHRAVVNSIKERLTIA TFHDPRLEAEIGPISSLITPETPALFKRGVFEDLLKEMFLRKLDGKSFLDCMRM |

TABLE 4-continued

| O-demethylase candidate enzymes | |
|---|---|
| Name | Sequence |
| PrhDIOX-<br>MVTX-<br>2001522 | GNGLSVPSVQELAKQTLAEIPSRYICTDENPLITGASVVDDETVPVINLQNLLSPEPVIGKL<br>ELDKLHSACKEWGFFQVVNHGVNDSLVDSVKSEIEGFFNLPANEKLKYGQKDGDVEGFG<br>QHFVVSEDQKLDWADVFYMVTLPVRLRKPHLFPELPLPLRDTLDSYSSELNKLSMVLLE<br>MMEKALKLVECKGITDFFEDGFQQMRMNYYPPCPRPELVTGLTSHSDFGGLTILLQLND<br>VEGLQIKKEERWISIKPLPNAFIVNIGDVLEIMSNGIYRSVDHRAVINSTKVRMSVATFHDP<br>RLEAVIGPISSLITPETPALFKRGVFEDLLKEMFLRKLDGKSFLDCMRI |
| PseDIOX-<br>JSVC-<br>2005842 | LMKLANGMSVPIVQELAKLTVGEIPSRYICTDGNLLTMGASVIDYETVPVIDLQNLQSREP<br>VIEKLELDRLHSACKEWGFFQLLNHGVDASLMDNVRSEIRGFFNLPISDKMKYGQKDGD<br>EEGFGQHFIVSEDQKLDWVDAFMMFTLPLHSRNPRLTPEFPQPLRETVESYSSEMKKLSV<br>LLFELMEKALQVKGITEMFEDGLQSIRMNYYPPCPRPELAIGLTSHSDFDGLTILLQLNEV<br>EGLQIKKEERWISIKPLPNAFIVNVGDVLEVMTNGIYRSVDHRAVVNSTKERLSIATFHDP<br>ELESEIGPIASLITPETPALFKRGRFKDLLKENLSTKLDGKSFLDCIRM |
| CYP2D6 | MGLEALVPLAVIVAIFLLLVDLMHRRQRWAARYSPGPLPLPGLGNLLHVDFQNTPYCFD<br>QLRRRFGDVFSLQLAWTPVVVLNGLAAVREALVTHGEDTADRPPVPITQILGFGPRSQGV<br>FLARYGPAWREQRRFSVSTLRNLGLGKKSLEQWVTEEAACLCAAFANHSGRPFRPNGLL<br>DKAVSNVIASLTCGRRFEYDDPRFLRLLDLAQEGLKEESGFLREVLNAVPVLLHIPALAG<br>KVLRFQKAFLTQLDELLTEHRMTWDPAQPPRDLTEAFLAEMEKAKGNPESSFNDENLRIV<br>VADLFSAGMVTTSTTLAWGLLLMILHPDVQRRVQQEIDDVIGQVRRPEMGDQAHMPYT<br>TAVIHEVQRFGDIVPLGVTHMTSRDIEVQGFRIPKGTTLITNLSSVLKDEAVWEKPFRFHPE<br>HFLDAQGHFVKPEAFLPFSAGRRACLGEPLARMELFLFFTSLLQHFSFSVPTGQPRPSHHG<br>VFAFLVTPSPYELCAVPR |

TABLE 5

| N-demethylase candidate enzymes | |
|---|---|
| Name | Sequence |
| BM3 | MTIKEMPQPKTFGELKNLPLLNTDKPVQALMKIADELGEIFKFEAPGRVTRYLSSQRLI<br>KEACDESRFDKNLSQAAKFARDFAGDGLVTSWTHEKNWKKAHNILLPSFSQQAMKG<br>YHAMMVDIAVQLVQKWERLNADEHIEVSEDMTRLTLDTIGLCGFNYRFNSFYRDQPH<br>PFIISMVRAADEVMNKLQRANPDDPAYDENKRQFQEDIKVMNDLVDKIIADRKARGEQ<br>SDDLLTQMLNGKDPETGEPLDDGNIRYQIITFLIAGHETTSGLLSFALYFLVKNPHVLQK<br>VAEEAARVLVDPVPSYKQVKQLKYVGMVLNEALRLWPTAPAFSLYAKEDTVLGGEY<br>PLEKGDEVMVLIPQLHRDKTVWGDDVEEFRPERFENPSAIPQHAFKPFGNGQRACIGQ<br>QFALHEATLVLGMMLKHFDFEDHTNYELDIKETLTLKPKGFVVKAKSKKIPLGGIPSPS<br>TEQSAKKVRKKAENAHNTPLLVLYGSNMGTAEGTARDLADIAMSKGFAPQVATLDSH<br>AGNLPREGAVLIVTASYNGHPPDNAKQFVDWLDQASADEVKGVRYSVFGCGDKNWA<br>TTYQKVPAFIDETLAAKGAENIADRGEADASDDFEGTYEEWREHMWSDVAAYFNLDI<br>ENSEDNKSTLSLQFVDSAADMPLAKMHGAFSTNVVASKELQQPGSARSTRHLEIELPK<br>EASYQEGDHLGVIPRNYEGIVNRVTARFGLDASQQIRLEAEEEKLAHLPLAKTVSVEEL<br>LQYVELQDPVTRTQLRAMAAKTVCPPHKVELEALLEKQAYKEQVLAKRLTMLELLEK<br>YPACEMKFSEFIALLPSIRPRYYSISSSPRVDEKQASITVSVVSGEAWSGYGEYKGIASN<br>YLAELQEGDTITCFISTPQSEFTLPKDPETPLIMVGPGTGVAPFRGFVQARKQLKEQGQS<br>LGEAHLYFGCRSPHEDYLYQEELENAQSEGIITLHTAFSRMPNQPKTYVQHVMEQDGK<br>KLIELLDQGAHFYICGDGSQMAPAVEATLMKSYADVHQVSEADARLWLQQLEEKGRY<br>AKDVWAG |
| CYP3A4-1 | MALIPDLAMETWLLLAVSLVLLYLYGTHSHGLFKKLGIPGPTPLPFLGNILSYHKGFCM<br>FDMECHKKYGKVWGFYDGQQPVLAITDPDMIKTVLVKECYSVFTNRRPFGPVGFMKS<br>AISIAEDEEWKRLRSLLSPTFTSGKLKEMVPIIAQYGDVLVRNLRREAETGKPVTLKDVF<br>GAYSMDVITSTSFGVNIDSLNNPQDPFVENTKKLLRFDFLDPFFLSITVFPFLIPILEVLNI<br>CVFPREVTNFLRKSVKRMKESRLEDTQKHRVDFLQLMIDSQNSKETESHKALSDLELV<br>AQSIIFIFAGYETTSSVLSFIMYELATHPDVQQKLQEEIDAVLPNKAPPTYDTVLQMEYL<br>DMVVNETLRLFPIAMRLERVCKKDVEINGMFIPKGVVVMIPSYALHRDPKYWTEPEKF<br>LPERFSKKNKDNIDPYIYTPFGSGPRNCIGMRFALMNMKLALIRVLQNFSFKPCKETQIP<br>LKLSLGGLLQPEKPVVLKVESRDGTVSGA |
| CYP3A4-2 | MALIPDLAMETWLLLAVSLVLLYLYGTHSHGLFKKLGIPGPTPLPFLGNILSYHKGFCM<br>FDMECHKKYGKVWGFYDGQQPVLAITDPDMIKTVLVKECYSVFTNRRPFGPVGFMKS<br>AISIAEDEEWKRLRSLLSPTFTSGKLKEMVPIIAQYGDVLVRNLRREAETGKPVTLKDVF<br>GAYSMDVITSTSFGVNIDSLNNPQDPFVENTKKLLRFDFLDPFFLSIIFPFLIPILEVLNICV<br>FPREVTNFLRKSVKRMKESRLEDTQKHRVDFLQLMIDSQNSKETESHKALSDLELVAQ<br>SIIFIFAGYETTSSVLSFIMYELATHPDVQQKLQEEIDAVLPNKAPPTYDTVLQMEYLDM<br>VVNETLRLFPIAMRLERVCKKDVEINGMFIPKGVVVMIPSYALHRDPKYWTEPEKFLPE<br>RFSKKNKDNIDPYIYTPFGSGPRNCIGMRFALMNMKLALIRVLQNFSFKPCKETQIPLKL<br>SLGGLLQPEKPVVLKVESRDGTVSGA |

TABLE 5-continued

| N-demethylase candidate enzymes | |
|---|---|
| Name | Sequence |
| McaCYP82-4 | MIMMFIDYYSSWLPQTLLLQSILLAVSLVIFINLFLTRRRSYSSKSHTNIIHPPKAAGALP<br>VIGHLYTLFRGLSAGVPLYRQLDAMADRYGPAFIIHLGVYPTLVVTCRELAKECFTTND<br>QTFATRPSTCAGKYIGYNYAFFGFAPYGPYWREARKIATVELLSNYRLDSLRHVREAE<br>VGRNVDELYALHASSSTNKQNMMKIDMKQWFDQVTLNVILMMVVGKRCVTTGGNE<br>EEVRVVKVLHEFFKHLGTLSVSDVVPYVEWMDLDGNIGRMKSTAKELDCILGRWLEE<br>HRRERRSDFMDAMLAMVEGIKIPYYDSDTVIKAICLNLLNAGSDTLGITMTWALSLLL<br>NNRHVLKKVKDELDVHVGKNRQVEELDVKNLVYLHAVVKETLRLFPPAPLGVPHEA<br>MEDCVVGGFHVAKGTRLVVNVWKLHRDPSVWSDPLAFKPERFLDNNTVDVRGQHFQ<br>LLPFGSGRRGCPGITFALQVAHLTLARLLHGFEWDTPDGAPVDMSEVSVLTTAKKNPV<br>EVLFTPRLPAEVYTQN |
| NsaCYP82-4 | MLSIHDSTMVFLQLQAICGIFGFIFIITWWTRWKSSNKMKAPEVAGAWPVIGHLHLLGG<br>GRPLYQLLGDMSDKYGPAFTLRMGIQKALVVSSWEVAKECLTTNDRALATRPSSAGG<br>KYMGYNNALIPFSPYGPYWRDMRKIATLELLSNHRLEELKHVREMEINTCISDMYKLC<br>QVEDGVEIKPISVDLSQWFADLTFNVVVMMITGKRYIGSTDAGDMNEIRHFQAALVKF<br>MRLLRISLLVDVFPVLQWINYGGFKGVMKSTARDIDSVLENWLQEHQRKRLSPDFNGN<br>HDFIDVMISTLEGTEFSDYDHNTIIKAISMAMVVGGTDTTTTTLIWAISLLLNNPNAMK<br>KVQEELEIHVGKERNVDGSDIQHLVYLQAVVKETLRLYPPVPLSVMHQAMEDCVIGSY<br>NIQAGTRVLFNLWKLHRDSSVWSDPLEFRPERFLTSHVDVDVRGQHFELIPFGSGRRSC<br>PGISFALQVIHLTIARLFHGFNLTTPGNSSVDMSEISGATLSKVTPLEVLVTPRLSSKLYN |
| HcaCYP82-10 | MDSLLQLQIIGALAALIFTYKLLKVICRSPMTDGMEAPEPPGAWPIIGHLHLLGGQDPIA<br>RTLGVMTDKYGPILKLRLGVHTGLVVSNWELAKECFTTNDRVLASRPMGAAGKYLG<br>YNYAIFGLAPHGPYWSEVRKIVLRELLSNQSLEKLKHVRISEINTCLKNLFSLNNGNTPI<br>KVDMKQWFERPMFNVVTMMIAGKRYFSMENDNEAMNFRKVATEFMYLTGVFVVSD<br>ALPYLEWLDLQGHVSAMKRTAKELDIHVGKWLEEHRRAKLLGETKNEDDFVDVLLTI<br>LPEDLKDNQTYIHDRDTIIKATALALFLAASDTTAITLTWALSLILNNPDVLKRAQDELD<br>KHVGKEKLVKESDIINLVYLQAIIKETLRLYPAAPLLLPHEAMEDCTVGGYHVPKGTRI<br>FVNIWKLQRDPRVWFDPNEFRPERFLTTHANVDFKGQHFEYIPFSSGRRVCPGITFSTQI<br>MHLTLAHLLHEFNIVTPTKSNAGVDMTESLGITMPKATPLEVLLTPRLPSNLYNQYRD |
| EcaCYP82-7 | MNLLIFFQFLLQFQVLVGLSVLLAFSYYLWVSKNPKINKFKGKGALLAPQAAGAWPIV<br>GHLPQLVGPKPLFRILGAMADNYGPIFMLRFGVHPTVVVSSWEMTKECFTTNDRHLAS<br>RPSNAASQYLIYEVYALFGFSLYGSSYWRDARKIATLELLSHRRLELLKHVPYTEIDTCI<br>KQLHRLWTKNNKNQNNPELKVEMNQFFTDLTMNVILKLVVGKRFFNVDDAADHEKE<br>EARKIQGTIFEFFKLTEGSVSAGALPLLNWLDLNGQKRAMKRTAKKMDSIAEKLLDEH<br>RQKRLSKEGVKGTHDHNDFMDVLLSILDADQGDYSHHPFNYSRDHVIKATTLSMILSS<br>MSISVSLSWALSLLLNNRHVLKKAQDELDMNVGKDRQVEEGDIKNLVYLQAIVKETF<br>RMYPANPLLLPHEAIEDCKIGGFNVPAGTRVVVNAWKLQHDPRVWSNPSEFKPERFLN<br>DQAAKVVDVRGQNFEYLPFGSGRRVCPGISFSLQTIHMSLARLVQAFELGTPSNERIDM<br>TEGSGLTMPKTTPLHVLLNPRLPLPLYE |
| GflCYP82-8 | MELINSLEIQPITISILALLTVSILLYKIIWNHGSRKNNKSNKNNRKTSSSAGVVEIPGAWP<br>IIGHLHLFNGSEQMFHKLGSLADQYGPAPFFIRFGSRKYVVVSNWELVKTCFTAQSQIF<br>VSRPPMLAMNILFFPKDSLSYIQHGDHWRELRKISSTKLLSSHRVETQKHLIASEVDYCF<br>KQLYKLSNNGEFTLVRLNTWCEDMALNVHVRMIAGMKNYVAAPGSGEYGGQARRY<br>RKALEEALDLLNQFTITDVVPWLGWLDHFRDVVGRMKRCGAELDSIFATWVEEHRVK<br>RASGKGGDVEPDFIDLCWESMEQLPGNDPATVIKLMCKEHIFNGSGTSSLTLAWILSLI<br>MNNPYVIKKAREELEKHVGNHRQVEESDLPNLLYIQAIIKEGMRLYTPGPFIDRNTTED<br>YEINGVHIPAGTCLYVNLWKIHRDPNVYEDPLEFKPERFLKNNSDLDLKGQNYQLLPF<br>GAGRRICPGVSLALPLMYLTVSRLIHGFDMKLPKGVEKADMTAHGGVINQRAYPLEVL<br>LKPRLTFQQA |
| SdiCYP82-3 | MTIGALALLSFIYFLRVSVIKRTKYTNTAVTATNKLENDEDEANHSKRVVAPPEVAGA<br>WPILGHLPQLVGLKQPLFRVLGDMADKYGPIFIVRFGMYPTLVVSSWEMAKECFTTND<br>RVLASRPASASGKYLTYNYAMFGFTNGPYWREIRKISMLELLSHRRVELLKHVPSTEID<br>SSIKQLYHLWVENQNQNKQGDHQVKVDMSQLLRDLTLNIVLKLVVGKRLFNNNDMD<br>HEQDEAARKLQKTMVELIKVAGASVASDALPFLGWLDVDGLKRTMKRIAKEIDVIAE<br>RWLQEHRQKKLTSNDKGGSNNIQGGGGDNDFMDVMLSILDDDSNFFINYNRDTVIKA<br>TSLTMILAGSDTTTLSLTWALTLLATNPGALRKAQDELDTKVGRDRQVDERDIKNLVY<br>LQAIVKETLRMYPAAPLAIPHEATQDCIVGGYHVTAGTRVWVNLWKLQRDPHAWPNP<br>SEFRPERFLAVENDCKQQGTCDGEAANMDFRGQHFEYMPFGSGRRMCPGINFAIQIIH<br>MTLARLLHSFELRVPEEEVIDMAEDSGLTISKVTPLELLLTPRLPLPLYI |
| SdiCYP82-6 | FCQFQGIVGILLAFLTFLYYLWRASITGLRTKPKHNDFKVTKAAPEADGAWPIVGHFAQ<br>FIGPRPLFRILGDMADKYGSIFMVRFGMYPTLVVSSWEMAKECFTTNDRFLASRPASAA<br>GKYLTYDFAMLSFSFYGPYWREIRKISMLELLSHRRVELLKHVPSTEIDSSIKQLYHLW<br>VENQNQNKQGDHQVKVDMSQLLRDLTLNIVLKLVVGKRLFNNNDMDHEQDEAARK<br>LQKTMVELIKVAGASVASDALPFLGWLDVDGLKRTMKRIAKEIDVIAERWLQEHRQK<br>KLTSNDKGGSNNIQGGGGDNDFMDVMLSILDDDSNFFINYNRDTVIKATSLTMILAGS<br>DTTTLSLTWALTLLATYPLCALRKAQDELDTKVGRDRQVDERDIKNLVYLQAIVKETL<br>RMYPAAPLAIPHEATQDCIVGGYHVTAGTRVWVNLWKLQRDPHAWPNPSEFRPERFL<br>AVENDCKQQGTCDGEAANMDFRGQHFEYMPFGSGRRMCPGINFAIQIIHMTLARLLHS<br>FELRVPEEEVIDMAEDSGLTISKVTPLELLLTPRLPLPLYI |

TABLE 5-continued

N-demethylase candidate enzymes

| Name | Sequence |
|---|---|
| CmaCYP82-6 | MDLFIFFSRFQYIVGLLAFLTFFYYLWRVSITGTRIKTNQNIMNGTNMMAPEAAGAWPI<br>VGHLPQLVGPQPLFKILGDMADKYGSIFMVRFGMHPTLVVSSWEMAKECFTTNDKFL<br>ASRPTSAGGKYLTYDFAMFGFSFYGPYWREIRKISTLELLSHRRVELLKHVPYIEIGGSI<br>KQLYKLWMETQNQNKQRDDHQVKVDMSQVFGYLTLNTVLKLVVGKGLFNNNDMN<br>HEQEEGRKLHETVLEFFKLAGVSVASDALPFLGWLDVDGQKRSMKRIAKEMDLIAER<br>WLQEHRQKRLTSNNKASSGHDDFMSVLLSILDDDSNFFNYNRDTVIKATSLNLILAASD<br>TTSVSLTWVLSLLVTNPGALKKVQDELDTKVGRNRHVEERDIEKLVYLQATVKETLR<br>MYPAGPLSVPHEATQDCTVGGYQVTAGTRLVVNVWKLQRDPRVWPNPSEFKPERFLP<br>DGCEVGCGEAANMDFRGQHFEYIPFGSGRRMCPGIDFAIQIIHMTLACLLHAFEFQVPS<br>SLDKHLVPAVIDMSEGSGLTMPKVTPLEVLLNPRLPLPLYEL |
| EcaCYP82-5 | MEKPILLQLQPGILGLLALMCFLYYVIKVSLSTRNCNQLVRHPPEAAGSWPIVGHLPQL<br>VGSGKPLFRVLGDMADKFGPIFMVRFGVHPTLVVSSWEMAKECFTSNDKFLASRPPSA<br>ASIYMAYDHAMLGFSSYGPYWREIRKISTLHLLSHRRLELLKHVPHLEIHNFIKGLYGI<br>WKDHQKQQQQPTARDDQDSVMLEMSQLFGYLTLNIVLSLVVGKRVCNYHADGHLDD<br>GEEAGQGQKLHQTITDFFKLSGVSVASDALPFLGLFDLDGQKKIMKRVAKEMDFVAER<br>WLQDKKSSLLLSSKSNNKQNEAGEGDVDDFMDVLMSTLPDDDDSFFTKYSRDTVIKA<br>NSLSMVVAGSDTTSVSLTWALSLLLNNIQVLRKAQDELDTKVGRDRHVEEKDIDNLV<br>YLQAIVKETLRMYPAGPLSVPHEAIEDCNVGGYHIKTGTRLLVNIWKLQRDPRVWSNP<br>SEFRPERFLDNQSNGTLLDFRGQHFEYIPFGSGRRMCPGVNLATPILHMTLARLLQSFDL<br>TTPSSSPVDMTEGSGLTMPKVTPLKVLLTPRLPLPLYDY |
| PbrCYP82-5 | MDVAIIVDHHYLQPFVSIAGLLALLSFFYCIWVFIIRPRIIKSNLDERKLSPSSPPEVAGA<br>WPIVGHLPQLIGSTPLFKILADMSNKYGPIFMVRFGMYPTLVVSSWEMSKECFTTNDRL<br>FATRPPSAAGKYLTKALFAFSVYGPYWREIRKISTIHLLSLRRLELLKHGRYLEIDKCMK<br>RLFEYWMEHHKNIISTTSSVKVNMSQVFAELSLNVVLKIIVGKTLFIKNGNEDYTKEEE<br>EGQKLHKTILKFMELAGVSVASDVLPFLGWLDVDGQKKQMKRVYKEMNLIASKWLG<br>EHRERKRLQIIQKRGAARGSNYDDGNDFMDVLMSILDEENDDLFFGYSRDTVIKSTCL<br>QLIVAASDTTSLAMTWALSLLLTNPNVLQKAQDELDTKVGRDRIIEEHDIECLVYLQAI<br>VKETLRLYPPAPLSLPHEAMEDCTVGGYQVKAGTRLVVNLWKLQRDPRVWSNPLEFK<br>PERFLPQSDGGFGGEEARMDFRGQHFEYTPFGSGRRICPGIDFFLQTVHMALARLLQAF<br>DFNTAGGLVIDMVEGPGLTMPKVTPLEVHLNP<br>RLPVTLY |
| PbrCYP82-6 | MQVDWPNILQKYYPIITCSLLTLLSFYYIWVSITKPSRNSKTKLPPPEVAGSWPIVGHLP<br>QLVGSTPLFKILANMSDKYGPIFMVRFGMHPTLVVSSWEMSKECFTTNDKFLASRPPSA<br>SAKYLGYDNAMFVFSDYGPYWREIRKISTLQLLTHKRLDSLKNIPYLEINSCVKTLYTR<br>WAKTQSQIKQNVGGAADDFVKVDMTEMFGHLNLNVVLRLVVGKPIFIQKDNADEDY<br>TKDGHNKEELGQKLHKTIIEFFELAGASVASDVLPYLGWLDVDGQKKRMKKIAMEMD<br>LFAQKWLEEHRQKGINHDNENDFMAVLISVLGEGKDDHIFGYSRDTVIKATCLTLIVA<br>ATDTTLVSLTWALSLLLTNPRVLSKAQDELDTVVGKERNVEDRDVNHLVYLQAVIKE<br>TLRLYPPSPLAVPHEAIENCNVGGYEVKARTRLLVNLWKIHRDPRVWSNPLEFKPERFL<br>PKLDGGTGEASKLDFKGQDFVYTPFGSGRRMCPGINFASQTLHMTLARLLHAFDFDIES<br>NGLVIDMTEGSGLTMPKVTPLQVHLRPRLPATLY |
| McaCYP82-4 | MIMMFIDYYSSWLPQTLLLQSILLAVSLVIFINLFLTRRRSYSSKSHTNIIHPPKAAGALP<br>VIGHLYTLFRGLSAGVPLYRQLDAMADRYGPAFIIHLGVYPTLVVTCRELAKECFTTND<br>QTFATRPSTCAGKYIGYNYAFFGFAPYGPYWREARKIATVELLSNYRLDSLRHVREAE<br>VGRNVDELYALHASSSTNKQNMMKIDMKQWFDQVTLNVILMMVVGKRCVTTGGNE<br>EEVRVVKVLHEFFKHLGTLSVSDVVPYVEWMDLDGNIGRMKSTAKELDCILGRWLEE<br>HRRERRSDFMDAMLAMVEGIKIPYYDSDTVIKAICLNLLNAGSDTLGITMTWALSLLL<br>NNRHVLKKVKDELDVHVGKNRQVEELDVKNLVYLHAVVKETLRLFPPAPLGVPHEA<br>MEDCVVGGFHVAKGTRLVVNVWKLHRDPSVWSDPLAFKPERFLDNNTVDVRGQHFQ<br>LLPFGSGRRGCPGITFALQVAHLTLARLLHGFEWDTPDGAPVDMSEVSVLTTAKKNPV<br>EVLFTPRLPAEVYTQN |
| NsaCYP82-4 | MLSIHDSTMVFLQLQAICGIFGFIFIITWWTRWKSSNKMKAPEVAGAWPVIGHLHLLGG<br>GRPLYQLLGDMSDKYGPAFTLRMGIQKALVVSSWEVAKECLTTNDRALATRPSSAGG<br>KYMGYNNALIPFSPYGPYWRDMRKIATLELLSNHRLEELKHVREMEINTCISDMYKLC<br>QVEDGVEIKPISVDLSQWFADLTFNVVVMMITGKRYIGSTDAGDMNEIRHFQAALVKF<br>MRLLRISLLVDVFPVLQWINYGGFKGVMKSTARDIDSVLENWLQEHQRKRLSPDFNGN<br>HDFIDVMISTLEGTEFSDYDHNTIIKAISMAMVVGGTDTTTTTLIWAISLLLNNPNAMK<br>KVQEELEIHVGKERNVDGSDIQHLVYLQAVVKETLRLYPPVPLSVMHQAMEDCVIGSY<br>NIQAGTRVLFNLWKLHRDSSVWSDPLEFRPERFLTSHVDVDVRGQHFELIPFGSGRRSC<br>PGISFALQVIHLTIARLFHGFNLTTPGNSSVDMSEISGATLSKVTPLEVLVTPRLSSKLYN |
| HcaCYP82-10 | MDSLLQLQIIGALAALIFTYKLLKVICRSPMTDGMEAPEPPGAWPIIGHLHLLGGQDPIA<br>RTLGVMTDKYGPILKLRLGVHTGLVVSNWELAKECFTTNDRVLASRPMGAAGKYLG<br>YNYAIFGLAPHGPYWSEVRKIVLRELLSNQSLEKLKHVRISEINTCLKNLFSLNNGNTPI<br>KVDMKQWFERPMFNVVTMMIAGKRYFSMENDNEAMNFRKVATEFMYLTGVFVVSD<br>ALPYLEWLDLQGHVSAMKRTAKELDIHVGKWLEEHRRAKLLGETKNEDDFVDVLLTI<br>LPEDLKDNQTYIHDRDTIIKATALALFLAASDTTAITLTWALSLILNNPDVLKRAQDELD<br>KHVGKEKLVKESDIINLVYLQAIIKETLRLYPAAPLLLPHEAMEDCTVGGYHVPKGTRI<br>FVNIWKLQRDPRVWFDPNEFRPERFLTTHANVDFKGQHFEYIPFSSGRRVCPGITFSTQI<br>MHLTLAHLLHEFNIVTPTKSNAGVDM1ESLGITMPKATPLEVLLTPRLPSNLYNQYRD |

TABLE 5-continued

N-demethylase candidate enzymes

| Name | Sequence |
|---|---|
| EcaCYP82-7 | MNLLIFFQFLLQFQVLVGLSVLLAFSYYLWVSKNPKINKFKGKGALLAPQAAGAWPIV<br>GHLPQLVGPKPLFRILGAMADNYGPIFMLRFGVHPTVVVSSWEMTKECFTTNDRHLAS<br>RPSNAASQYLIYEVYALFGFSLYGSSYWRDARKIATLELLSHRRLELLKHVPYTEIDTCI<br>KQLHRLWTKNNKNQNNPELKVEMNQFFTDLTMNVILKLVVGKRFFNVDDAADHEKE<br>EARKIQGTIFEFFKLTEGSVSAGALPLLNWLDLNGQKRAMKRTAKKMDSIAEKLLDEH<br>RQKRLSKEGVKGTHDHNDFMDVLLSILDADQGDYSHHPFNYSRDHVIKATTLSMILSS<br>MSISVSLSWALSLLLNNRHVLKKAQDELDMNVGKDRQVEEGDIKNLVYLQAIVKETF<br>RMYPANPLLLPHEAIEDCKIGGFNVPAGTRVVVNAWKLQHDPRVWSNPSEFKPERFLN<br>DQAAKVVDVRGQNFEYLPFGSGRRVCPGISFSLQTIHMSLARLVQAFELGTPSNERIDM<br>TEGSGLTMPKTTPLHVLLNPRLPLPLYE |
| GflCYP82-8 | MELINSLEIQPITISILALLTVSILLYKIIWNHGSRKNNKSNKNNRKTSSSAGVVEIPGAWP<br>IIGHLHLFNGSEQMFHKLGSLADQYGPAPFFIRFGSRKYVVVSNWELVKTCFTAQSQIF<br>VSRPPMLAMNILFFPKDSLSYIQHGDHWRELRKISSTKLLSSHRVETQKHLIASEVDYCF<br>KQLYKLSNNGEFTLVRLNTWCEDMALNVHVRMIAGMKNYVAAPGSGEYGGQARRY<br>RKALEEALDLLNQFTITDVVPWLGWLDHFRDVVGRMKRCGAELDSIFATWVEEHRVK<br>RASGKGGDVEPDFIDLCWESMEQLPGNDPATVIKLMCKEHIFNGSGTSSLTLAWILSLI<br>MNNPYVIKKAREELEKHVGNHRQVEESDLPNLLYIQAIIKEGMRLYTPGPFIDRNTTED<br>YEINGVHIPAGTCLYVNLWKIHRDPNVYEDPLEFKPERFLKNNSDLDLKGQNYQLLPF<br>GAGRRICPGVSLALPLMYLTVSRLIHGFDMKLPKGVEKADMTAHGGVINQRAYPLEVL<br>LKPRLTFQQA |
| SdiCYP82-3 | MTIGALALLSFIYFLRVSVIKRTKYTNTAVTATNKLENDEDEANHSKRVVAPPEVAGA<br>WPILGHLPQLVGLKQPLFRVLGDMADKYGPIFIVRFGMYPTLVVSSWEMAKECFTTND<br>RVLASRPASASGKYLTYNYAMFGFTNGPYWREIRKISMLELLSHRRVELLKHVPSTEID<br>SSIKQLYHLWVENQNQNKQGDHQVKVDMSQLLRDLTLNIVLKLVVGKRLFNNNDMD<br>HEQDEAARKLQKTMVELIKVAGASVASDALPFLGWLDVDGLKRTMKRIAKEIDVIAE<br>RWLQEHRQKKLTSNDKGGSNNIQGGGGDNDFMDVMLSILDDDSNFFINYNRDTVIKA<br>TSLTMILAGSDTTTLSLTWALTLLATNPGALRKAQDELDTKVGRDRQVDERDIKNLVY<br>LQAIVKETLRMYPAAPLAIPHEATQDCIVGGYHVTAGTRVWVNLWKLQRDPHAWPNP<br>SEFRPERFLAVENDCKQQGTCDGEAANMDFRGQHFEYMPFGSGRRMCPGINFAIQIIH<br>MTLARLLHSFELRVPEEEVIDMAEDSGLTISKVTPLELLLTPRLPLPLYI |
| SdiCYP82-6 | FCQFQGIVGILLAFLTFLYYLWRASITGLRTKPKHNDFKVTKAAPEADGAWPIVGHFAQ<br>FIGPRPLFRILGDMADKYGSIFMVRFGMYPTLVVSSWEMAKECFTTNDRFLASRPASAA<br>GKYLTYDFAMLSFSFYGPYWREIRKISMLELLSHRRVELLKHVPSTEIDSSIKQLYHLW<br>VENQNQNKQGDHQVKVDMSQLLRDLTLNIVLKLVVGKRLFNNNDMDHEQDEAARK<br>LQKTMVELIKVAGASVASDALPFLGWLDVDGLKRTMKRIAKEIDVIAERWLQEHRQK<br>KLTSNDKGGSNNIQGGGGDNDFMDVMLSILDDDSNFFINYNRDTVIKATSLTMILAGS<br>DTTTLSLTWALTLLATYPLCALRKAQDELDTKVGRDRQVDERDIKNLVYLQAIVKETL<br>RMYPAAPLAIPHEATQDCIVGGYHVTAGTRVWVNLWKLQRDPHAWPNPSEFRPERFL<br>AVENDCKQQGTCDGEAANMDFRGQHFEYMPFGSGRRMCPGINFAIQIIHMTLARLLHS<br>FELRVPEEEVIDMAEDSGLTISKVTPLELLLTPRLPLPLYI |
| CmaCYP82-6 | MDLFIFFSRFQYIVGLLAFLTFFYYLWRVSITGTRIKTNQNIMNGTNMMAPEAAGAWPI<br>VGHLPQLVGPQPLFKILGDMADKYGSIFMVRFGMHPTLVVSSWEMAKECFTTNDKFL<br>ASRPTSAGGKYLTYDFAMFGFSFYGPYWREIRKISTLELLSHRRVELLKHVPYIEIGGSI<br>KQLYKLWMETQNQNKQRDDHQVKVDMSQVFGYLTLNTVLKLVVGKGLFNNNDMN<br>HEQEEGRKLHETVLEFFKLAGVSVASDALPFLGWLDVDGQKRSMKRIAKEMDLIAER<br>WLQEHRQKRLTSNNKASSGHDDFMSVLLSILDDDSNFFNYNRDTVIKATSLNLILAASD<br>TTSVSLTWVLSLLVTNPGALKKVQDELDTKVGRNRHVEERDIEKLVYLQATVKETLR<br>MYPAGPLSVPHEATQDCTVGGYQVTAGTRLVVNVWKLQRDPRVWPNPSEFKPERFLP<br>DGCEVGCGEAANMDFRGQHFEYIPFGSGRRMCPGIDFAIQIIHMTLACLLHAFEFQVPS<br>SLDKHLVPAVIDMSEGSGLTMPKVTPLEVLLNPRLPLPLYEL |
| EcaCYP82-5 | MEKPILLQLQPGILGLLALMCFLYYVIKVSLSTRNCNQLVRHPPEAAGSWPIVGHLPQL<br>VGSGKPLFRVLGDMADKFGPIFMVRFGVHPTLVVSSWEMAKECFTSNDKFLASRPPSA<br>ASIYMAYDHAMLGFSSYGPYWREIRKISTLHLLSHRRLELLKHVPHLEIHNFIKGLYGI<br>WKDHQKQQQQPTARDDQDSVMLEMSQLFGYLTLNIVLSLVVGKRVCNYHADGHLDD<br>GEEAGQGQKLHQTITDFFKLSGVSVASDALPFLGLFDLDGQKKIMKRVAKEMDFVAER<br>WLQDKKSSLLLSSKSNNKQNEAGEGDVDDFMDVLMSTLPDDDDSFFTKYSRDTVIKA<br>NSLSMVVAGSDTTSVSLTWALSLLLNNIQVLRKAQDELDTKVGRDRHVEEKDIDNLV<br>YLQAIVKETLRMYPAGPLSVPHEAIEDCNVGGYHIKTGTRLLVNIWKLQRDPRVWSNP<br>SEFRPERFLDNQSNGTLLDFRGQHFEYIPFGSGRRMCPGVNLATPILHMTLARLLQSFDL<br>TTPSSSPVDMTEGSGLTMPKVTPLKVLLTPRLPLPLYDY |
| PbrCYP82-5 | MDVAIIVDHHYLQPFVSIAGLLALLSFFYCIWVFIIRPRIIKSNLDERKLSPSSPPEVAGA<br>WPIVGHLPQLIGSTPLFKILADMSNKYGPIFMVRFGMYPTLVVSSWEMSKECFTTNDRL<br>FATRPPSAAGKYLTKALFAFSVYGPYWREIRKISTIHLLSLRRLELLKHGRYLEIDKCMK<br>RLFEYWMEHHKNIISTTSSVKVNMSQVFAELSLNVVLKIIVGKTLFIKNGNEDYTKEEE<br>EGQKLHKTILKFMELAGVSVASDVLPFLGWLDVDGQKKQMKRVYKEMNLIASKWLG<br>EHRERKRLQIIQKRGAARGSNYDDGNDFMDVLMSILDEENDDLFFGYSRDTVIKSTCL<br>QLIVAASDTTSLAMTWALSLLLTNPNVLQKAQDELDTKVGRDRIIEEHDIECLVYLQAI<br>VKETLRLYPPAPLSLPHEAMEDCTVGGYQVKAGTRLVVNLWKLQRDPRVWSNPLEFK<br>PERFLPQSDGGFGGEEARMDFRGQHFEYTPFGSGRRICPGIDFFLQTVHMALARLLQAF<br>DFNTAGGLVIDMVEGPGLTMPKVTPLEVHLNPRLPVTLY |

TABLE 5-continued

| N-demethylase candidate enzymes | |
|---|---|
| Name | Sequence |
| PbrCYP82-6 | MQVDWPNILQKYYPIITCSLLTLLSFYYIWVSITKPSRNSKTKLPPPEVAGSWPIVGHLP<br>QLVGSTPLFKILANMSDKYGPIFMVRFGMHPTLVVSSWEMSKECFTTNDKFLASRPPSA<br>SAKYLGYDNAMFVFSDYGPYWREIRKISTLQLLTHKRLDSLKNIPYLEINSCVKTLYTR<br>WAKTQSQIKQNVGGAADDFVKVDMTEMFGHLNLNVVLRLVVGKPIFIQKDNADEDY<br>TKDGHNKEELGQKLHKTIIEFFELAGASVASDVLPYLGWLDVDGQKKRMKKIAMEMD<br>LFAQKWLEEHRQKGINHDNENDFMAVLISVLGEGKDDHIFGYSRDTVIKATCLTLIVA<br>ATDTTLVSLTWALSLLLTNPRVLSKAQDELDTVVGKERNVEDRDVNHLVYLQAVIKE<br>TLRLYPPSPLAVPHEAIENCNVGGYEVKARTRLLVNLWKIHRDPRVWSNPLEFKPERFL<br>PKLDGGTGEASKLDFKGQDFVYTPFGSGRRMCPGINFASQTLHMTLARLLHAFDFDIES<br>NGLVIDMIEGSGLTMPKVTPLQVHLRPRLPATLY |
| PbrCYP82-7 | MMDLAMFIDQYFSLAKIAGLLALLSFFYYLWISTLWSPRNPKLSSVSPPEVAGAWPILG<br>HLPQLLGSRPLFKILADMSDNYGPIFMVRFGMHPTLVVSSWEMAKECFTTNDRFLAGR<br>PSGAANKYLTFALFGFSTYGPYWREIRKIATLHLLSHRRLELLKHVPDLEVTNCMKHL<br>HRRWIDSQNQIKQNDAAAGSVKVDMGRVFGELTLNVVLKLVAGKSIFFKNDNTRQYD<br>SKDGHNKEEEEGKKLHKTIIDFYSLAGASVASDVLPFLGWLDVDGQKKRMKRVAKD<br>MDFIAAKWLEEHRHQKRQTVLSSSATLGSSNHDDAKDFMDVLMSILDGENDDLFFGY<br>SRDTVIKTTCLQLIAAAADTTSVTMTWALALLITNPTILRKAQDELDTKVGKDRNIEER<br>DINDLVYLQAIVKETLRMYPAGPLNVPHEAIADCNIGGYEVRAGTRLLVNLWKMHRD<br>PRVWSNPSEFKPERFLPQLDGGSGGEAANLDFRGQDFEYLPFSAGRRMCPGIDFSLQTL<br>HMTLARLLHGFDFNNDSAGIIIDMEEGSGLTMPKLTPLEIYLCPRLPAKLY |

TABLE 6

| N-methyltransferase and N-modifying candidate enzymes | |
|---|---|
| Name | Sequence |
| TfCNMT | MAVEGKQVAPKKAIIVELLKKLELGLVPDDEIKKLIRIQLGRRLQWGCKSTYEEQIAQLVNLTHSLRQMKIATEVE<br>TLDDQMYEVPIDFLKIMNGSNLKGSCCYFKNDSTTLDEAEIAMLELYCERAQIKDGHSVLDLGCGQGALTLYVA<br>QKYKNSRVTAVTNSVSQKEFIEEESRKRNLSNVEVLLADITTHKMPDTYDRILVVELFEHMKNYELLLRKIKEWM<br>AKDGLLFVEHICHKTFAYHYEPIDEDDWFTEYVFPAGTMIIPSASFFLYFQDDVSVVNHWTLSGKHFSRTNEEWL<br>KRLDANVELIKPMFVTITGQCRQEAMKLINYWRGFCLSGMEMFGYNNGEEWMASHVLFKKK |
| CjCNMT | MAVEAKQTKKAAIVELLKQLELGLVPYDDIKQLIRRELARRLQWGYKPTYEEQIAEIQNLTHSLRQMKIATEVETL<br>DSQLYEIPIEFLKIMNGSNLKGSCCYFKEDSTTLDEAEIAMLDLYCERAQIQDGQSVLDLGCGQGALTLHVAQKY<br>KNCRVTAVTNSVSQKEYIEEESRRRNLLNVEVKLADITTHEMAETYDRILVIELFEHMKNYELLLRKISEWISKDG<br>LLFLEHICHKTFAYHYEPLDDDDWFTEYVFPAGTMIIPSASFFLYFQDDVSVVNHWTLSGKHFSRTNEEWLKRLD<br>ANLDVIKPMFETLMGNEEEAVKLINYWRGFCLSGMEMFGYNNGEEWMASHVLFKKK |
| PsCNMT | MQLKAKEELLRNMELGLIPDQEIRQLIRVELEKRLQWGYKETHEEQLSQLLDLVHSLKGMKMATEMENLDLKLY<br>EAPMEFLKIQHGSNMKQSAGYYTDESTTLDEAEIAMLDLYMERAQIKDGQSVLDLGCGLGAVALFGANKFKKC<br>QFTGVTSSVEQKDYIEGKCKELKLTNVKVLLADITTYETEERFDRIFAVELIEHMKNYQLLLKKISEWMKDDGLLF<br>VEHVCHKTLAYHYEPVDAEDWYTNYIFPAGTLTLSSASMLLYFQDDVSVVNQWTLSGKHYSRSHEEWLKNMDK<br>NIVEFKEIMRSITKTEKEAIKLLNFWRIFCMCGAELFGYKNGEEWMLTHLLFKKK |
| PsTNMT | MGSIDEVKKESAGETLGRLLKGEIKDEELKKLIKFQFEKRLQWGYKSSHQEQLSFNLDFIKSLKKMEMSGEIETMN<br>KETYELPSEFLEAVFGKTVKQSMCYFTHESATIDEAEEAAHELYCERAQIKDGQTVLDIGCGQGGLVLYIAQKYKN<br>CHVTGLTNSKAQVNYLLKQAEKLGLTNVDAILADVTQYESDKTYDRLLMIEAIEHMKNLQLFMKKLSTWMTKES<br>LLFVDHVCHKTFAHFFEAVDEDDWYSGFIFPPGCATILAANSLLYFQDDVSVVDHWVVNGMHMARSVDIWRK<br>ALDKNMEAAKEILLPGLGGSHETVNGVVTHIRTFCMGGYEQFSMNNGDEWMVAQLLFKKK |
| EcTNMT | MGSSAGEIMGRLMKGEIEDEELKKLIRHQWDRRIEWGYKPTHEKQLAFNLDFIKGLKEMVMSGEIDTMNKETY<br>ELPTAFLEAVFGKTVKQSCCYFKDENSTIDEAEEAAHELYCERAQIKDGQTVLDIGCGQGGLVLYIAEKYKNCHVT<br>GLTNSKAQANYIEQQAEKLELTNVDVIFADVTKFDTDKTYDRILVVETIEHMKNIQLFMKKLSTWMTEDSLLFVD<br>HISHKTFNHNFEALDEDDWYSGFIFPKGCVTILSSSTLLYFQDDVSALDHWVVNGMHMARSVEAWRKKLDETI<br>EAAREILEPGLGSKEAVNQVITHIRTFCIGGYEQFSYNNGEEWMITQILFKKK |
| PsRNMT | MSTTMETTKISQQDDLWKNMELGQISDEEVRRLMKIGIEKRIKWGTKPTQQEQLAQLLDFNKSLRGMKMATE<br>IDTLENHKIYETPESFNQIIGGKESAGLFTDETTTTMEEANTKMMDLYCERAGLKDGHTILDLGCGAGLLVLHLAK<br>KYKKSKITGITNTSSHKEYILKQCKNLNLSNVEIILADVTKVDIESTFDRVFVIGLIEHMKNFELFLRKISKWMKD<br>DGLLLLEHLCHKSFSDHWEPLSEDDWYAKNFFPSGTLVIPSATCLLYFQEDVTVIDHWILSGNNFARSNEVILKRI<br>DGKIEEVKDIFMSFYGIGREEAVKLINWWRLLCITANELFKYNNGEEWLISQLLFKKKLMTCI |
| TfPNMT | METKQTKKEAVANLIKRIEHGEVSDEEIRGMMKIQVQKRLKWGYKPTHEQQLAQLVTFAQSLKGMEMAEEVD<br>TLDAELYEIPLPFLHIMCGKTLKFSPGYFKDESTTLDESEVYMMDLYCERAQIKDGQSILDLGCGHGSLTLHVAQK<br>YRGCKVTGITNSVSQKEFIMDQCKKLDLSNVEIILEDVTKFETEITYDRIFAVALIEHMKNYELFLKKVSTWIAQY<br>GLLFVEHHCHKVFAYQYEPLDEDDWYTEYIFPSGTLVMSSSSILLYFQEDVSVVNHWTLSGKHPSLGFKQWLKRLD<br>DNIDEVKEIFESFYGSKEKAMKFITYWRVFCIAHSQMYSTNNGEEWMLSQVLFKKK |

TABLE 6-continued

N-methyltransferase and N-modifying candidate enzymes

| Name | Sequence |
|---|---|
| PbrTNMT1 | MGSIDEVKKESAGETLGRLLKGEIKDEELKKLIKFQFEKRLQWGYKSSHQEQLSFNLDFIKSLKKMEMSGEIETMNKETYELPSEFLEAVFGKTVKQSMCYFKHESATIDEAEEAAHELYCERAQIKDGQTVLDIGCGQGGLVLYIARKYKKCHVTGLTNSKAQVNYLLKQAEKLGLTNVDAILADVTQYESDKTYDRLLMIEAIEHMKNLQLFMKKLSTWMTEESLLFVDHVCHKTFAHFFEAVDEDDWYSGFIFPPGCATILAANSLLYFQDDVSVVDHWVVNGMHMARSVDIWRKALDKNMEAAKEILLPGLGGSHEAVNGVVTHIRTFCMGGYEQFSMNDGDEWMVAQLLFKKK |
| PbrTNMT2 | MGSIEEVKKESAEETLGRLLRGEINDEELKKLIKYQLEKRLQWGYKSSHQEQLSFNLDFINSLKKMGMSGQVEAFTNEVYELPTECFEAAYGKSMKLSGCYFKHESSTIDEAEEASHELYCERAQIKDGQTVLDIGCGQGGLVLYVAQKYKNCHVTGLTNSKEQVNYILKQAEKLGLRNVDVILADVTQYESDKTYDRILVIGVVEHMKNMQLFIKKLSTWMAEDSLLFVDHSCHKTFNHFFEALDEDDWYSGYIFPPGCATFLSADSLLYFQDDVSVVDHWVVNGMHFARTVDAWRKKLDKNMEAVKEILLPGLGGNHEAVNGVITHIRTCCVGGYVQFSLNDGDEWMNAQLLFKKK |
| AmeNMT1 | MCLFFAEKMGLMAEANNQQQLKKEDLLKNMELGLIPDEEIRKLIRVQLEKRLNWGYKSTHEQQLSQLLHLVHSLKKMKIATEMENLDLKLYEAPFSFVQIQHGSTIKESSGLFKDESTTLDEAEIAMLDLYTKRAKIEDGQSVLDLGCGLGAVTLYVAQKFKNCYVTGITSSVEQKDFIEGRCKELKLSNVKVILADITTYETEEKYNRIFAVELIEHMKNYELLLRKISEWMKQDGLLFIEHVCHKTLAYHYEPLDEEDWYTNYIFPAGTLTLSSATLLLYFQDDVAVVDQWTLSGKHYSRSHEEWLKRIDGNIEEVKEIMKSITKSEEEAKKLLNFWRIFCMCGAELFGYKNGEEWMMTHILFKKK |
| GfINMT1 | MDLMATSKQVKKKEELLKNMELGLVPDEEIRRLIRIELEKRLKWGYKPTHQQQLAQLLDLVHSLKKMKIATEMESLDLKLYEAPFSFVQIKHGSTIKESSSYFKDESMTLDEAEIAMLDLYVERAQIEDGQSVLDLGCGLGAVTLHVAKKYKNCHVTGLTNSVEQKDFIEGKCKELNLSNVKVILADVTSHEMEDKFDRIFAVELIEHMKNYELLLRRISKWMKDDGLLFIEHVCHKTFAYHYEPIDEDDWYTEYIFPAGTLTLSSASLLLYFQDDVSVVNHWTLSGKHYSRSHEEWLKRIDGNMDAVKEIMKSITKTEEEAVKLINFWRIFCMCGAELFGYKDGEEWMMSHVLFKKKQLLQQC |
| EcaNMT1 | MVDLKVEKEELLKSMELGLVPDEDIRKHIRSQLEKRLKWGYKPNHEQQLAQLLDVIHSLKKMKISKEYESFDLRLYEAPFDFHKIQLGTHLKESCSYYKDESTTLDEAEGAMLDLYTQKAKIEDGQSILDLGCGVGAVTLFVANKYKNCKVTGITSCQWQKDFIENKCKELNLTNVRVIIGDVTAYEMEETFDRIFAIELIEHMKNYELLLRKISKWMKDDGLLFIEHVCHKILAYPYEPIDEEDWFTEYIFPGGTLTLSSASLLLYFQDDVSVVEHSSLNGKHYSRSHGEWLKNIDANIDEVKGIMRSITKTEEEAVRLVNFWRIFCMCGIELFGYNNGEEWMVSHILLKKK |
| EcaNMT2 | MAADLVVKKWNNKKELIDEMELGLVGDEEIRELIRNDLEKRLKWGYKSNHEQQLAQLLHFVHSLRGMKIAADEVESFNIKVYEAPFSFNKIQLGSSLKESSCYYKHDETTLDEGEIAMMELYTEKAQIKDGQSVLDLGCGLGSLTLYVANKYPNCKVTGTTASLWHKDFIESKCKEQELTNVKIVLGDATTHEMEERFDRILAIGLIEHLKNYGLLLGRISKWLKDDGFLFIQHVCHKTLAYPLVPVDEEDWIGEYIFPGGTLTMPSASLLLYFQDELSVVDHSTLNGKHFSRTHEEWLKNIDAKIDEVKEILKSVTKTEEEVVRLTNFWRIFCMFGVEMFGYNEGEEWMLSQILFKKK |
| CmaNMT4 | MASGKVVDLLKRLDSGLVSDEELRRVIRFELERRLKWGYKPTHEQQLAELLNLAHATKQMEIATKIDTLNSTMYEVPNSFLEIQLGSTLKESCLYFKDESTTVDEAEIAMMDLYLERAQIKDGQIILDLGCGLGALAFHIAQKYTNCNVTSVTNSVKQKEFIEEKCKILNVSNVKVILTDICTLEMEATFDRIFAIGLIEHMKNYELLLRKFSAWMKQDGLLFIEHLCHKTLGYHNEPIDEDDWYTAYFFPAGTLTFIPSSFLLYFQDDVSVVNHWTLSGKHFSRSNEEWLKRMDNKIDEVKEIYKAAASETKDDDIMKLIRLWRFLSISAAEMFGYKDGEEWMISQVLFKKK |
| EcNMT3 | MASLVEEGSFVNNKESVKERVSELVKRLKNGLVSDEELRKLMRVELEKRLEWGYKSTHEQQLSQLIDLAHSMKKMEIAMEIDALNSTVYEVPLSFLQIIHGTTIKESCLYFKDESTTVDEAEIAMMDLYLERAQIKDGQSILDLGCGLGGFSFHIASKFTGCNITAVTNSVKQKEFIEEKCKTLNVPNIKVILADICTTEIENVFDRIIAIGLIEHMKNYELLLKKFSKWMTQDGLLFIEHLCHKTFGYHNEPLDEDDWYTTYFFPAGTLTFIPSSFLLYFQDDVSVVDHWTLNGKHFARSNEEWLKRMDEKMDEVKQIFRSNLKSENEVTKTIGEWRFLSMSAAEMFGYNNGEEWMVSQLLFKKK |
| GflNMT5 | MGSNETNGELKTKEMVPDLLKRLESGLVADEELRKLIRFELERRLKWGYKPTHEQQLAELLKLAHSTKQMKIATETDSLNSTMYEVPIPFLQLQFGSAIKESCCYFKDESTTLDEAEVAMMDLYLERTQIKDGQSILDLGCGLGALAFHIVQKYPNCNVLAITNSVEQKEFIEEKCKIRKVENVKVSLADICTLEMKTTFDRIFAIGLLEHMKNYQLLLKKFSNWMKQDGLLFIEHLCHKTLAYHYEPLDEDDWYTEYFFPAGTLTIISSSFLLYFQDDVSIVNHWSLSGKHFSRSNEEWLKRMDMKIDEVKEILEAAFENKDHDITKLINHWRFLAINATEMFGYNNGEEWMVSQVLFKKK |
| ScaNMT1 | MASDHEVSNKELKKKKEVITELLKRLESGLVSDEELRGLIRFELERRLRWGYKPTHEQQLAQLLNLAHSMKQMKIATEIDALNSTMYEVPIPFLQIQLGSTLKESCCYFKDESTTVDEAEIAMMDLYLERAQIKDGQSILDLGCGLGALAFHIAQKYTNCNITAITNSVRQKEFIEEKCKILNVSNVKVSLADICTLEMEATFDRIFAIGLIEHMKNYELLLKKFSEWMKQDGLIFIEHLCHKTLAYHYEPLDEDDWYTEYFFPAGTLTLISSSFLLYFQDDVSVVDHWTLSGKHFSRSNEEWLKRMDEKIDEVKEIFESVSDSKDDDVTKLINHWRFFCISSAEMFGYNNGEEWMISQVLFKKK |
| CchNMT3 | MIKKSKIMAFSDHHHEVVKNHSKKEMIADLLKRLEAGLVPDEEMRNLFRFELERRLQWGYKSIHQEQLSQLLKLAHSTKEMTIVAEMDALNSSMYELPISFLQIQLGSNLKQSSLYFKDELTTVDEAEVAIMDLYLERAQIEDGQSILDLGCGLGAFSFHVARKYTNCNITAVTNSLTQKEFIEKKSKILNIQNVKVIFADVTTVEMETTFDRVFAIGLIEHMQNYELFLKKLSKWMKQDGLLFIEHFCHKTLAYHYKPIDEDDWFTNLLYPNGTVISSSLLLYFQDDVSVVDHWSLSGKHFSRASEESLKRMDAKMDEMKEIFESITDSKEEAMKLINQWRIFCISCAEMFGYNNGEEWMTSHFLFKKKL |
| CchNMT6 | MGSSTASDHEMVIMENDSKNKQVVIADLLKRLVGGLVPDEEMRNMFRFELEKRLKWGYKSTHQQQLSQLLNLVELNKGIAKIAPEMDALNSAMYEVPIPYLKLMLGSTLKQSCLYFKDESTTLDEAEIEMMDLYLERADIQDGQSILDLGCGLGGLGFHIAQKYISCNITALTNSLTQKEFIEEKCKTLNIPNVKVILADVTTVEIETTFDRLFAIGLVEHMENYELFLRKLSKWMKQDGLLFIEHLCHKTLAYHYKPIDEDDWYSNLLYPTGTLTSASFLLYFQDDLSVVDHWSLSGKHFSRATEEWLKMIDANMDKIREIYESVTESKEEATRSINQWRIFCISCAEMFGYNDGEEWMISHFLFKNKKQIE |
| CchNMT1 | MATSDQEVKTSKMEMIADLLKRLEAGLVPDDEIRSLIRVELERRLKWGYKSTHQEQLDQLLNLAHSIKKMKIASTEMDGLTSTMYEVPISLVQIQLGSHLKESCLYFKDETTTVDEAEIAMMDLYLERAQIKDGQSILDLGCGLGAVSFHIAQKYTSCNITAVTNSVRQKEFIEEKSKTLNVPNVKVLLADITTLEMEHTFDRLFAISLIEHMENYELLLRKLSEWM |

TABLE 6-continued

N-methyltransferase and N-modifying candidate enzymes

| Name | Sequence |
|---|---|
| | KQDGLLFIEHLCHKTLSYHFEPMDEDDWYTNLLFPAGTLTLVSASFLLYFQDDLSVVNQWVMSGKHFSRANEEW<br>LKNMDAKMDEMREIFESITDSEEEVVKLINHWRIFCISSAEMFAYNDGEEWMNSHVLFKKKKQIQ |
| CchNMT2 | MAGSGANKEMIADLLKRLEVGLVPDEEIRSLIRFQLKRRLKWGYKTTHQEQLEQLLSLAHSIRKMKIATEMDALN<br>STMYEVPISFMQIVFGSTLKESCLYFKDEATTVNEAEIAMMDLYLERAQIKDGQSILDLGCGMGSLCFHIARKYT<br>NCNITAVTNSVSQKEFIEEKSKTLNLPNVKVILADITTLEMDDTYDCLFAIGLIEHMKNYELLLRKLSNWMKQDSL<br>LFIDHVCHKTLAYHYEPIDEDDWYTNLLFPAGTLTLVSASFLLYFQDDLSLVDHWSMSGKHFSRTNKEWLKNID<br>GKMDKIREIVKSITDSEEEVVKLINHWRMLCINSSEMFGFNDGEEWMNSHVLFKKKKQI |
| ScaNMT2 | MEMIADLLKRLEAGLVPDDEIRSLIRVELERRLKWGYKSTHQEQLDQLLNLAHSIKKMKIASTEMDGLTSTMYEV<br>PISLVQIQLGSHLKESCLYFKDETTTVDEAEIAMMDLYLERAQIKDGQSILDLGCGLGSVCFHIARKYTSCNITAV<br>TNSVSQKEFIEEKSKTLNVPNVKVLLADITTLEMDDTFDCLFAIGLIEHMENYELLLRKLSDWMKQDGLLFIDHVC<br>HKTLSYHFEPMDEDDWYTNLLFPAGTLTLVSASFLLYFQDDLSLVDHWSMSGKHFSRTNKEWLKNIDGKMDKIR<br>EIVKSITDSEEEVVKLINHWRMLCINSSEMFGFNDGEEWMNSHVLFKKKKQI |
| PbrNMT2 | MCTTMDTTKISQQDDLWKNMELGLISDEEVRRLMKIETEKRIKWGTKPTQQEQLAQLLDFNKSLRGMKMATE<br>VHALENHKIYEIPDSFNQIIGGKESAGLFTDEATTTIEEANTKMMDLYCERAGLKDGQTILDIGCGAGLLVLHLAK<br>KYKNCKITGVTNTSWHKEHILEQCKNLNLSNVEVILADVTTVDIERTFDRVFVIGLIEHMKNFELFLRKISKWMKD<br>DGLLFLEHLCHKSFSDHWEPLSEDDWYAKNFFPSGTLVIPSATCLLYFQEDVTVKDHWLLSGNNFARSNEAILKR<br>IDSKIEEVKDIFMSFYGIGEEEAVKLINWWRLLCITANELFKYNNGEEWLISQLLFKKKLMTCI |
| PbrNMT1 | MVKGDQFQTTTMEETKISQENDLWTNMELGLIPDEEVRRLMKIEIEKRIEWGMKPTQHQQLAQLLDFTKSLR<br>GMKMATELDKLDSKLYETPHSFNQIVNGSTLKESSGLYTDVTTTMDEASIKMMDLYCERANIKDGQTILDLGCG<br>PGPLVLHIAKKYSNCKITGVTNAFSQREYILEECKKLSLSNVEIILADVTSLDLETTFDRVFVIGFIEHMKNFELF<br>LRKISKWMKDDAVLFLEHFCHKSFSYHGEPLSEDDWYAKNFFAPGTLVIPSATCLLYFQEDLAVIDHWFLSGNHFA<br>RTNEEMLKGIDGKIEEIKDIFMSFYGINEAEAVKLINWWRLFCITGAEMFSYNNGEEWFISQLLFKKK |
| EcaNMT4 | MALEQEDSMSVPERNEGVADLIKRMELGLVNDEEIRRLMRIQIENRLKWGYKPTHDQQLAQHLHFINSLKEMK<br>MATEMDSLDSQVYESPNSFQQIMCGRSMKESAGLFMDDVTTVEEAHIRMMDLYCDKATFEDGQKILDLGCG<br>HGSVVLHVAQKYKGCQVTGVTNSSAQKQYILEQCKKLDLSNVEIILADVTTLEMEEKFDRVIIIGLIEHMKNFKLF<br>FQKVSKWMKEGGLLFLENYFHKDFAYHCEKIDEDDWYDGYIFPPGSLLMPSASTLLYFQEDLTVADHWVLPGTH<br>FAKTFEEFLKKIDLRIEEVREIFEAFYGISKEEAMKLSNYWRNFCISAMEIFNYNNGQEWMISHLLYTKK |
| CmaNMT5 | METGKNNQNMKTTIDDLWNQMMLGIVPDKEIRRLMKIELKKRLDWGYRPTHQQQLSQLLDFAKGLCNYCW<br>TALRCMKMSAEFDTLDSKVYETPKSFQQ1MCGTTIKESSGLFMNESTTLDQAQISMLDLYFDKAKIKDGQSILDL<br>GCGHGALILYLAQKYQNCNITGVTNSLSQKEFIVEKCKKLGLSNVEILLADVTKLEMEDMFDRVFVIGLIEHMKNF<br>ELFLRKISEWMKPDGLLFLEHYCHKSFAHQWEPIDEEDWFSKYIFPPGTVIIPSASFLLYFQEDVKVIDHWTLSGN<br>HFARTQEEWLKGIDGHIDEVEKTFESFYGISKEEAVKLINFWRVFCLSGVEMFGYNNGEEWMISHLLFKKK |
| GflNMT4 | MTMEANNAKKEAIENLWEQMMMGLVPDHEITRLMKSELQKRLNWGYKPTHQQQISQLLDFAKSLRRMEM<br>SLDFDNLELDTKMYETPESFQLIMSGTTLKESSGLFTDETATLDQTQIRMMDLYLEKAKIKDGQSILDLGCGHGA<br>LILHVAQKYRNCNVTGVTNSIAQKEFIFKQCKKLGLSNVEMVLADVTKCEMKATFDHIFVIGLIEHMKNFELFLRK<br>VSEWMKSDGLLFMEHYCHKSFAYQWEPMDDDDLFSKYVFPPGSAIIPSASFLLYFQDDLTVVDHWTLSGNHF<br>ARTHQEWLKRIDSQSDEIKGIFESFYGISKEEAVKLINYWRVFCLFGVEMFGYNNGEEWMISHLLFKKK |
| CchNMT5 | MEVVATSSARNPKKEIVDLWKRMELGLIPDEEIRDLMKIGLEKRLKWGYKPTHEQQLSQLLHFAKSLRSMKMA<br>SEMETLDDQMYETPTAFQQLMCGSTIKESAGFFKDESTTLDEAEIKMLDLYCEKARIEDGQKILDLGCGHGAVM<br>LHIAQKYKNCNVTGVTNSISQQQFIVQRSKELNLSNVNMILADVTMLEMDATYDRIFIIGLIEHMKNFELFLRKIS<br>KWITKEGLLFLEHYCHKTFAYQCEPVDEDDWYNMFIFPPGTLILPSASFLLYFQDDLIVVDRWTLNGNHYARTQE<br>EWLKRIDANVDGVKQMFESVCDGNKEEAVKLMNFWRIFCISGAEMLAYNNGEEWMISHYLFKKRN |
| NsNMT2 | MEATQITKKQGVAELIKRIENGQVPDEEITRMMKIQIQKRLKLGYKSTHEQQLAQLLHFVHSLQKMEMAEEVD<br>TLDSELYEIPLPFLHIMCGKALKFSPGYFKDESTTLDESEVNMLDLYCERAQIEDGQTILDLGCGHGSLTLHVAKK<br>YRGCKVTGITNSVSQKDFIMEECKKLNLSNVEIILEDVTKFETGTTYDRIFAVALIEHMKNYELFLKKVSAWMAQD<br>GLLFVEHHCHKVFAYKYEPIDDDDWYTEYIFPTGTLVMSSSSILLYFQEDVSVVNHWTLSGKHPSLGFKQWLKRI<br>DDNIDEIKEIFESFYGSKEKATKFITYWRVFCIAHSEMYATNGGEEWMLSQVLFKRK |
| ScaNMT5 | MGGVADLLKKMELGLVPEEEIRRLMRIIIEKRLEWGYKPTHAEQLDHLTNFIQCLRGMKMADEIDALDAKMYEI<br>PLPFMQTICGSTLKFSPGYFKDESTTLDESEIHMMDLYCERAEVKDGHSILDLGCGHGGFVLHVAQKYKNSIVTG<br>VTNSVAEKEFIMTQCKKLCLSNVEIILADVTKFEPETTYDRVFAIALIEHMKNYELVLEKLSKWVAQDGFLFVEHH<br>CHKVFPYKYEPLDEDDWYTEYIFPGGTIVLPSASILLYFQKDVSVVNHWSLNGKHPARGFKEWLKRLDENMDAV<br>KAIFEPFYGSKEEAMKWITYWRVFCITHSEMYAYNNGEEWMLSQVLFKRK |
| JdiNMT1 | MSKGVAKLVERMELGLVSDDEVRRLMRILIEKRLKWGYKPTHEEQLTYLTNFIQGLKGMKIAEEIDALDAKMYEI<br>PIAFMQILCGYSLKFSPGFFEDESTTLDESETIMMDLYCERAQVQDGQSILDLGCGHGGFVLHVAQKYKNCKVT<br>GVTNSVSETEYIMEQCKKLGLSNVEIIIADVTKFEPEVTYDRVFAIALIEHMKNYELVLQKLSKWVAQDGFLFVDH<br>HCHKVFPYKYEPIDEDDWYTQYIFPGGTLVLPSASILLYFQEDVSIVNHWTLSGNHPARGFKEWLKRLDDNMDE<br>IKAIFEPFYGSKEEAMKWITYWRVFCITHSEMYAYNGGEEWMISQVLFKRK |
| BthNMT1 | MEVKQAGKEGVTELLVKRMELGLVPEEEIRRLMRIQIQKRLDWGYKPTHEEQLAHLTKFIQNIRGMKMADEID<br>ALDAKMYEIPLPFLQTICGKTLKFSPGYFKDESTTLDESETLMMDLYCERAQVKDGQSILDLGCGHGGFVLHLAQ<br>KYRNSVVTGVTNSVSETEYIKEQCKKLGLSNVEIIIADVTKFEPEVTYDRVFAIALIEHMKNYALVLNKISKWVAQ<br>DGYLFVEHHCHKVFPYKYEPLDEDDWYTNYIFPGGTLILPSASILLYFQEDVTVLNHWSLSGKHPSRGFIEWLKRL<br>DENIDVIMGIFEPFYGSKEEATKWINYWRVFCMTHSEMYAYGNGEEWMLSQVLLKRK |

TABLE 6-continued

| N-methyltransferase and N-modifying candidate enzymes | |
|---|---|
| Name | Sequence |
| MaqNMT3 | MELGLVPEKEIRRLMRIQIQKRLEWGYKPTHEEQLAHLTKFIQNIRGMKMADEIDALDAKMYEIPLPFLQTICGK TLKFSPGYFKDESTTLDESETLMMDLYCERAQVKDGQSILDLGCGHGGFVLHLAQKYRNSIVTGVTNSVSETEYI KEQCKKLGLSNVEIIIADVTKFEPEVTYDRVFAIALIEHMKNYALVLNKISKWVAQDGYLFVEHHCHKVFPYKYEP LDEDDWYTNYIFPGGTLILPSASILLYFQEDVTVLNHWSLSGKHPSRGFIEWLKRLDENIDVIMGIFEPFYGSKEE ATKWINYWRVFCITHSEMYAYGNGEEWMLSQVLLKRK |
| McaNMT4 | MDKANERELKRAELFKKLEDDLVTYDEIKQVMRTELAKRLEWGYKPTHQQQLAHLLDFAHALEGMKIANEVET LASEVYETPLPFXEIVLGPAKKXSSCLFEDESTTLEQAEIAMLDLYFERAQIRXGMSVLDLGCGXGSVGLHIARKY KNCXVTCITNSISQKQYIENQCKLYNLSNVKIILADIVAHDTDDTFDVVLVIGVIEHMKNYALLLNKISKWMAKDG LLFVEHLCHKTFPYHFEPLDEDDWYSNFVFPTGTLTMPSVSFLLYFQADVSILNHWILSGKNFSRTXEEFLKRIDA NVDAIKDGLKPSLGSEGVAKLISYWRGFCLTGMEMFGYNNGEEWMVSQVLFKNK |
| TcoNMT3 | MEDNNNLLQEEMNVVELLQRPELGLVPDEKIRKLTRLQLQKRLKWGYKPTHEAQLSHLFQFIHSLPSLNMESED ENPKSWLYETPTSFLQLLYGDCIKESDTYYKEDTATLEEAVINMLELYCERARITEGLSVLDLGCGYGALTLHVAQ KYKSCKVTGVTSSISQKQYIMEKCKKLNLTNVEIILADVATIEIEAASYDRIFALGIFEHVNDYKLFLGKLSKWMK QDGLLFVEYLCHKTFPYQNKPLDKGDKWYNEYVFPSGGLIIPSASFILYFQNDVSVVRQWTQGGQHSARTFEELLK RIDGNIDKIKEIFIESYGSKEDAVRFINYWRVFLITGVEMFSYNDGEEWMGAHFLFKKKFIMQE |
| CmuNMT4 | MEVKQSKGDELRSRVAELLERPELGLVPDEEIRRLAKARLEKRLKWGYKATHGEQLSSLLQFVESLPSLNMASED DSPKAWLYETPTSFLQLIYGDIIKESGSYYKDESTTLEEAMIHNMNLCCERANIKEGQSVVDLGCGYGAFILHVAQ KYKTCRVTGITSSISQKHYIMEQCKKLNLSNVEVILADVATIKLDATFDRVFAAGMFEHVNDYKSFLRKITNWMK PDGRLFVEHLCNKTFPYQNKPLDDGDNWGEYVFPSGGLIIPSASLLLYFQEDVSIVNHWTFSGKHAANKFEELLK RIDAKIDAIKRIFNECYGSKDSIRFINYWRVFLITAAEMFGYNNGEEWMGVHLLFKKK |
| CtrNMT2 | GLKSSVAELLERPELGLVPDGEIRKLTKTRLAKRLEWGYKATHEDQLSHLLRFIHSLPSLNMASEDDSPKAWLYET PTSFLQLIYGDIIKESGTYYKDESSTLEEAIIHNMDLCCERARIKEGQSVLDLGCGYGAFTLHVAQKYKSCSVTGI TSSISQKDYIMEQCKKLNLSNVEVILADVATIKMNTTFDRVFALGMFEHINDYKLFLRRISNWMKHDGLLFVEHLC NKTFAYQNKPLDDGDDWFNEYVFPSAGLIIPSASLLLYFQEDVSIVHHWTFSGKHAAYKFEELLERIDAKIEAIKE IFIECYGSKEDAIRFINYWRVFLITAAEMFAYRDGEEWMGSHVLFKKK |
| CmuNMT5 | MEAKQHESNNNIDEELKNRVNIGEQEERPGFEDEEIRRLAKAQLAKRLKWGYKPTHEQQLSHLLQFLQSLPSLN MASEDESSKAWLYETPTSFLQLLFGNVIKFSGYYYKHESSTFEESMIHNMDLCCERANIKEGQNVIDLGCGYGAF VLHVAQKYKSCSVTGITCSITQKHHIMEECKKLNLCNVKVILADVATIELGTAFDRVFAFGMFEEINDYKLILRKI SNWMKPDGLFFVEHLCHKTLAYQNKLIDDQDWYEEYIFPSGGLIVPSASLLLYFQDDLSVVYHWTYNGKHGARS FEKMLERTDANIDTIKDMFTEFYGSKEKAIKFINYWRVFFITAAEMFAYNDGEEWMCSQLLFKKK |
| CmuNMT8 | MEHKIEDIRKLKSRVEEQLERPELGLVKDEDIKTLAKAKLEKRLKWGYKPTYAEQLSNLLQFAQSLPSLKMENVDD QGSSKQWLYGVPSEFLQIIYGGIIKMSGSYYEDESTTLEESMIKDMDSCCEKANVKEGHSVLDIGCGYGSLIIHIA KKYRTCNVTGITNFVEQKQYIMEECKKLNLSNVEVIVGDGTTINLNTTTFDRVFVTGMLEEINDYKLFLKSVSDWM KPDGLLLVTHFCHKTFAYQNNKALDDEDWHNEYIFPSGNLIVPSASLLLYFQEDLSVVSHWATNGTHTGRTCKK LVERIDANIEKIKEIFSEFYGSKEDAIRMINYWRVLCITGAEMYTCKDGEEWMDVYYLFKKK |

TABLE 7

| Variants of BM3 N-demethylase | |
|---|---|
| BM3 variant | |
| | Genotype |
| 8F11 | L437A |
| 4H9 | L181A, T260A, L437A |
| 8C7 | L75A, L181A |
| 4H5 | L75A, M177A, L181A |
| 7A1 | L75A, M177A, L181A, T260A |
| | Amino Acid Sequence |
| 8F11 | MTIKEMPQPKTFGELKNLPLLNTDKPVQALMKIADELGEIFKFEAPGRVTRY LSSQRLIKEACDESRFDKNLSQALKFARDFAGDGLVTSWTHEKNWKKAHNI LLPSFSQQAMKGYHAMMVDIAVQLVQKWERLNADEHIEVSEDMTRLTLDT IGLCGFNYRFNSFYRDQPHPFIISMVRALDEVMNKLQRANPDDPAYDENKR QFQEDIKVMNDLVDKIIADRKARGEQSDDLLTQMLNGKDPETGEPLDDGNI RYQIITFLIAGHETTSGLLSFALYFLVKNPHVLQKVAEEAARVLVDPVPSYKQ VKQLKYVGMVLNEALRLWPTAPAFSLYAKEDTVLGGEYPLEKGDEVMVLI PQLHRDKTVWGDDVEEFRPERFENPSAIPQHAFKPFGNGQRACIGQQFALHE ATLVLGMMLKHFDFEDHTNYELDIKETATLKPKGFVVKAKSKKIPLGGIPSP STEQSAKKVRKKAENAHNTPLLVLYGSNMGTAEGTARDLADIAMSKGFAP |

TABLE 7-continued

| Variants of BM3 N-demethylase | |
|---|---|
| BM3 variant | |
| | QVATLDSHAGNLPREGAVLIVTASYNGHPPDNAKQFVDWLDQASADEVKG<br>VRYSVFGCGDKNWATTYQKVPAFIDETLAAKGAENIADRGEADASDDFEG<br>TYEEWREHMWSDVAAYFNLDIENSEDNKSTLSLQFVDSAADMPLAKMHGA<br>FSTNVVASKELQQPGSARSTRHLEIELPKEASYQEGDHLGVIPRNYEGIVNRV<br>TARFGLDASQQIRLEAEEEKLAHLPLAKTVSVEELLQYVELQDPVTRTQLRA<br>MAAKTVCPPHKVELEALLEKQAYKEQVLAKRLTMLELLEKYPACEMKFSE<br>FIALLPSIRPRYYSISSSPRVDEKQASITVSVVSGEAWSGYGEYKGIASNYLAE<br>LQEGDTITCFISTPQSEFTLPKDPETPLIMVGPGTGVAPFRGFVQARKQLKEQ<br>GQSLGEAHLYFGCRSPHEDYLYQEELENAQSEGIITLHTAFSRMPNQPKTYV<br>QHVMEQDGKKLIELLDQGAHFYICGDGSQMAPAVEATLMKSYADVHQVSE<br>ADARLWLQQLEEKGRYAKDVWAG |
| 4H9 | MTIKEMPQPKTFGELKNLPLLNTDKPVQALMKIADELGEIFKFEAPGRVTRY<br>LSSQRLIKEACDESRFDKNLSQALKFARDFAGDGLVTSWTHEKNWKKAHNI<br>LLPSFSQQAMKGYHAMMVDIAVQLVQKWERLNADEHIEVSEDMTRLTLDT<br>IGLCGFNYRFNSFYRDQPHPFIISMVRAADEVMNKLQRANPDDPAYDENKR<br>QFQEDIKVMNDLVDKIIADRKARGEQSDDLLTQMLNGKDPETGEPLDDGNI<br>RYQIIAFLIAGHETTSGLLSFALYFLVKNPHVLQKVAEEAARVLVDPVPSYK<br>QVKQLKYVGMVLNEALRLWPTAPAFSLYAKEDTVLGGEYPLEKGDEVMVL<br>IPQLHRDKTVWGDDVEEFRPERFENPSAIPQHAFKPFGNGQRACIGQQFALH<br>EATLVLGMMLKHFDFEDHTNYELDIKETATLKPKGFVVKAKSKKIPLGGIPS<br>PSTEQSAKKVRKKAENAHNTPLLVLYGSNMGTAEGTARDLADIAMSKGFA<br>PQVATLDSHAGNLPREGAVLIVTASYNGHPPDNAKQFVDWLDQASADEVK<br>GVRYSVFGCGDKNWATTYQKVPAFIDETLAAKGAENIADRGEADASDDFE<br>GTYEEWREHMWSDVAAYFNLDIENSEDNKSTLSLQFVDSAADMPLAKMHG<br>AFSTNVVASKELQQPGSARSTRHLEIELPKEASYQEGDHLGVIPRNYEGIVNR<br>VTARFGLDASQQIRLEAEEEKLAHLPLAKTVSVEELLQYVELQDPVTRTQLR<br>AMAAKTVCPPHKVELEALLEKQAYKEQVLAKRLTMLELLEKYPACEMKFS<br>EFIALLPSIRPRYYSISSSPRVDEKQASITVSVVSGEAWSGYGEYKGIASNYLA<br>ELQEGDTITCFISTPQSEFTLPKDPETPLIMVGPGTGVAPFRGFVQARKQLKE<br>QGQSLGEAHLYFGCRSPHEDYLYQEELENAQSEGIITLHTAFSRMPNQPKTY<br>VQHVMEQDGKKLIELLDQGAHFYICGDGSQMAPAVEATLMKSYADVHQVS<br>EADARLWLQQLEEKGRYAKDVWAG |
| 8C7 | MTIKEMPQPKTFGELKNLPLLNTDKPVQALMKIADELGEIFKFEAPGRVTRY<br>LSSQRLIKEACDESRFDKNLSQAAKFARDFAGDGLVTSWTHEKNWKKAHNI<br>LLPSFSQQAMKGYHAMMVDIAVQLVQKWERLNADEHIEVSEDMTRLTLDT<br>IGLCGFNYRFNSFYRDQPHPFIISMVRAADEVMNKLQRANPDDPAYDENKR<br>QFQEDIKVMNDLVDKIIADRKARGEQSDDLLTQMLNGKDPETGEPLDDGNI<br>RYQIITFLIAGHETTSGLLSFALYFLVKNPHVLQKVAEEAARVLVDPVPSYKQ<br>VKQLKYVGMVLNEALRLWPTAPAFSLYAKEDTVLGGEYPLEKGDEVMVLI<br>PQLHRDKTVWGDDVEEFRPERFENPSAIPQHAFKPFGNGQRACIGQQFALHE<br>ATLVLGMMLKHFDFEDHTNYELDIKETLTLKPKGFVVKAKSKKIPLGGIPSP<br>STEQSAKKVRKKAENAHNTPLLVLYGSNMGTAEGTARDLADIAMSKGFAP<br>QVATLDSHAGNLPREGAVLIVTASYNGHPPDNAKQFVDWLDQASADEVKG<br>VRYSVFGCGDKNWATTYQKVPAFIDETLAAKGAENIADRGEADASDDFEG<br>TYEEWREHMWSDVAAYFNLDIENSEDNKSTLSLQFVDSAADMPLAKMHGA<br>FSTNVVASKELQQPGSARSTRHLEIELPKEASYQEGDHLGVIPRNYEGIVNRV<br>TARFGLDASQQIRLEAEEEKLAHLPLAKTVSVEELLQYVELQDPVTRTQLRA<br>MAAKTVCPPHKVELEALLEKQAYKEQVLAKRLTMLELLEKYPACEMKFSE<br>FIALLPSIRPRYYSISSSPRVDEKQASITVSVVSGEAWSGYGEYKGIASNYLAE<br>LQEGDTITCFISTPQSEFTLPKDPETPLIMVGPGTGVAPFRGFVQARKQLKEQ<br>GQSLGEAHLYFGCRSPHEDYLYQEELENAQSEGIITLHTAFSRMPNQPKTYV<br>QHVMEQDGKKLIELLDQGAHFYICGDGSQMAPAVEATLMKSYADVHQVSE<br>ADARLWLQQLEEKGRYAKDVWAG |
| 4H5 | MTIKEMPQPKTFGELKNLPLLNTDKPVQALMKIADELGEIFKFEAPGRVTRY<br>LSSQRLIKEACDESRFDKNLSQAAKFARDFAGDGLVTSWTHEKNWKKAHNI<br>LLPSFSQQAMKGYHAMMVDIAVQLVQKWERLNADEHIEVSEDMTRLTLDT<br>IGLCGFNYRFNSFYRDQPHPFIISAVRAADEVMNKLQRANPDDPAYDENKR<br>QFQEDIKVMNDLVDKIIADRKARGEQSDDLLTQMLNGKDPETGEPLDDGNI<br>RYQIITFLIAGHETTSGLLSFALYFLVKNPHVLQKVAEEAARVLVDPVPSYKQ<br>VKQLKYVGMVLNEALRLWPTAPAFSLYAKEDTVLGGEYPLEKGDEVMVLI<br>PQLHRDKTVWGDDVEEFRPERFENPSAIPQHAFKPFGNGQRACIGQQFALHE<br>ATLVLGMMLKHFDFEDHTNYELDIKETLTLKPKGFVVKAKSKKIPLGGIPSP<br>STEQSAKKVRKKAENAHNTPLLVLYGSNMGTAEGTARDLADIAMSKGFAP<br>QVATLDSHAGNLPREGAVLIVTASYNGHPPDNAKQFVDWLDQASADEVKG<br>VRYSVFGCGDKNWATTYQKVPAFIDETLAAKGAENIADRGEADASDDFEG<br>TYEEWREHMWSDVAAYFNLDIENSEDNKSTLSLQFVDSAADMPLAKMHGA<br>FSTNVVASKELQQPGSARSTRHLEIELPKEASYQEGDHLGVIPRNYEGIVNRV<br>TARFGLDASQQIRLEAEEEKLAHLPLAKTVSVEELLQYVELQDPVTRTQLRA<br>MAAKTVCPPHKVELEALLEKQAYKEQVLAKRLTMLELLEKYPACEMKFSE<br>FIALLPSIRPRYYSISSSPRVDEKQASITVSVVSGEAWSGYGEYKGIASNYLAE<br>LQEGDTITCFISTPQSEFTLPKDPETPLIMVGPGTGVAPFRGFVQARKQLKEQ<br>GQSLGEAHLYFGCRSPHEDYLYQEELENAQSEGIITLHTAFSRMPNQPKTYV<br>QHVMEQDGKKLIELLDQGAHFYICGDGSQMAPAVEATLMKSYADVHQVSE |

TABLE 7-continued

Variants of BM3 N-demethylase

| BM3 variant | |
|---|---|
| | ADARLWLQQLEEKGRYAKDVWAG |
| 7A1 | MTIKEMPQPKTFGELKNLPLLNTDKPVQALMKIADELGEIFKFEAPGRVTRY<br>LSSQRLIKEACDESRFDKNLSQAAKFARDFAGDGLVTSWTHEKNWKKAHNI<br>LLPSFSQQAMKGYHAMMVDIAVQLVQKWERLNADEHIEVSEDMTRLTLDT<br>IGLCGFNYRFNSFYRDQPHPFIISAVRAADEVMNKLQRANPDDPAYDENKR<br>QFQEDIKVMNDLVDKIIADRKARGEQSDDLLTQMLNGKDPETGEPLDDGNI<br>RYQIIAFLIAGHETTSGLLSFALYFLVKNPHVLQKVAEEAARVLVDPVPSYK<br>QVKQLKYVGMVLNEALRLWPTAPAFSLYAKEDTVLGGEYPLEKGDEVMVL<br>IPQLHRDKTVWGDDVEEFRPERFENPSAIPQHAFKPFGNGQRACIGQQFALH<br>EATLVLGMMLKHFDFEDHTNYELDIKETLTLKPKGFVVKAKSKKIPLGGIPS<br>PSTEQSAKKVRKKAENAHNTPLLVLYGSNMGTAEGTARDLADIAMSKGFA<br>PQVATLDSHAGNLPREGAVLIVTASYNGHPPDNAKQFVDWLDQASADEVK<br>GVRYSVFGCGDKNWATTYQKVPAFIDETLAAKGAENIADRGEADASDDFE<br>GTYEEWREHMWSDVAAYFNLDIENSEDNKSTLSLQFVDSAADMPLAKMHG<br>AFSTNVVASKELQQPGSARSTRHLEIELPKEASYQEGDHLGVIPRNYEGIVNR<br>VTARFGLDASQQIRLEAEEEKLAHLPLAKTVSVEELLQYVELQDPVTRTQLR<br>AMAAKTVCPPHKVELEALLEKQAYKEQVLAKRLTMLELLEKYPACEMKFS<br>EFIALLPSIRPRYYSISSSPRVDEKQASITVSVVSGEAWSGYGEYKGIASNYLA<br>ELQEGDTITCFISTPQSEFTLPKDPETPLIMVGPGTGVAPFRGFVQARKQLKE<br>QGQSLGEAHLYFGCRSPHEDYLYQEELENAQSEGIITLHTAFSRMPNQPKTY<br>VQHVMEQDGKKLIELLDQGAHFYICGDGSQMAPAVEATLMKSYADVHQVS<br>EADARLWLQQLEEKGRYAKDVWAG |
| | Nucleotide Sequence |
| 8F11 | ATGACCATCAAAGAAATGCCACAACCTAAGACTTTCGGTGAATTGAAGA<br>ATTTGCCTTTGTTGAACACCGATAAGCCAGTTCAAGCTTTGATGAAGATT<br>GCTGATGAATTGGGTGAAATCTTCAAGTTTGAAGCTCCAGGTAGAGTCAC<br>TAGATACTTGTCATCTCAAAGATTGATCAAAGAAGCCTGCGACGAATCC<br>AGATTTGATAAGAATTTGTCTCAAGCTTTGAAGTTCGCTAGAGATTTTGC<br>TGGTGATGGTTTGGTTACTTCTTGGACTCACGAAAAGAATTGGAAGAAG<br>GCCCATAACATTTTGTTGCCATCTTTCTCACAACAAGCCATGAAGGGTTA<br>TCATGCTATGATGGTTGATATCGCCGTTCAATTGGTTCAAAAGTGGGAAA<br>GATTGAACGCCGATGAACATATCGAAGTCTCTGAAGATATGACCAGATT<br>GACCTTGGATACCATTGGTTTGTGTGGTTTCAACTACAGATTCAACTCCTT<br>CTACAGAGATCAACCACATCCATTCATCATCTCTATGGTTAGAGCTTTGG<br>ATGAAGTCATGAACAAATTGCAAAGAGCTAATCCAGACGATCCAGCTTA<br>TGACGAAAACAAGAGACAATTCCAAGAAGATATCAAGGTCATGAACGAT<br>TTGGTCGATAAGATTATCGCTGATAGAAAGGCTAGAGGTGAACAATCTG<br>ATGATTTGTTGACCCAAATGTTGAACGGTAAGGATCCAGAAACTGGTGA<br>ACCATTGGATGATGGTAACATCAGATACCAAATTATCACCTTCTTGATTG<br>CTGGTCACGAAACTACATCTGGTTTGTTGTCTTTTGCCTTGTACTTTTTGG<br>TTAAGAACCCACACGTCTTGCAAAAGGTTGCTGAAGAAGCTGCAAGAGT<br>TTTGGTTGATCCAGTTCCATCTTACAAGCAAGTCAAGCAATTGAAGTACG<br>TTGGTATGGTTTTGAACGAAGCTTTGAGATTGTGGCCAACTGCTCCAGCT<br>TTTTCATTATACGCTAAAGAAGATACCGTCTTGGGTGGTGAATATCCATT<br>GGAAAAAGGTGATGAAGTTATGGTCTTGATCCCACAATTGCATAGAGAT<br>AAGACTGTTTGGGGTGATGATGTCGAAGAATTCAGACCAGAAAGATTCG<br>AAAACCCATCTGCTATTCCACAACATGCTTTTAAGCCATTTGGTAACGGT<br>CAAAGAGCTTGCATTGGTCAACAATTCGCTTTACATGAAGCTACCTTGGT<br>TTTGGGTATGATGTTGAAACACTTCGACTTCGAAGATCACACCAACTACG<br>AATTGGATATCAAAGAAACCGCTACCTTGAAGCCAAAGGGTTTTGTTGTT<br>AAGGCTAAGTCCAAAAAGATTCCATTGGGTGGTATTCCATCTCCATCTAC<br>TGAACAATCCGCTAAGAAGGTTAGAAAGAAAGCTGAAAACGCTCATAAC<br>ACACCTTTGTTGGTCTTGTACGGTTCTAATATGGGTACTGCTGAAGGTAC<br>AGCAAGAGATTTGGCAGATATTGCTATGTCTAAAGGTTTCGCTCCACAAG<br>TTGCTACTTTGGATTCTCATGCTGGTAATTTGCCAAGAGAAGGTGCTGTT<br>TTGATAGTTACTGCTTCTTACAATGGTCACCCACCAGATAATGCTAAGCA<br>ATTCGTTGATTGGTTGGATCAAGCTTCAGCTGATGAAGTAAAAGGTGTTA<br>GATACTCTGTTTTCGGTTGCGGTGACAAAAATTGGGCTACTACTTATCAA<br>AAGGTTCCAGCCTTTATTGACGAAACTTTGGCTGCTAAAGGTGCTGAAAA<br>CATTGCTGACAGAGGTGAAGCTGATGCCTCCGACGACTTCGAAGGTACT<br>TACGAAGAATGGAGAGAACACATGTGGTCTGACGTTGCTGCTTACTTCA<br>ACTTGGACATCGAAAACTCTGAAGACAACAAGTCCACTTTGTCTTTGCAA<br>TTCGTTGACTCCGCTGCTGACATGCCATTGGCTAAGATGCACGGTGCTTT<br>CTCTACCAACGTCGTTGCCTCCAAGGAATTGCAACAACCAGGTTCTGCTA<br>GATCTACTAGACACTTGGAAATCGAATTGCCAAAGGAAGCTTCCTACCA<br>AGAAGGTGACCACTTGGGCGTTATTCCAAGAAACTACGAAGGTATCGTC<br>AACAGAGTTACTGCTAGATTCGGTTTGGATGCTTCTCAACAAATCAGATT<br>AGAAGCTGAAGAAGAAAAGTTGGCTCACTTGCCATTAGCTAAGACTGTC<br>TCCGTTGAAGAATTGTTGCAATACGTCGAATTGCAAGACCCAGTTACCAG<br>AACCCAATTGAGAGCCATGGCTGCCAAGACCGTCTGTCCACCACACAAG<br>GTTGAATTGGAAGCCTTGTTGGAAAAGCAAGCCTACAAGGAACAAGTTT<br>TGGCTAAGAGATTGACCATGTTGGAATTGTTGGAAAAGTACCCAGCCTG<br>CGAAATGAAGTTCTCTGAATTTATCGCCTTGTTGCCATCTATCAGACCAC |

TABLE 7-continued

| Variants of BM3 N-demethylase | |
|---|---|
| BM3 variant | |
| | GTTACTACTCTATTTCTTCCTCTCCACGTGTTGACGAAAAGCAAGCTTCTA |
| | TTACTGTTTCCGTTGTCTCCGGTGAAGCTTGGTCCGGTTACGGTGAATAC |
| | AAGGGTATTGCTTCTAACTACTTGGCTGAATTGCAAGAAGGTGACACCAT |
| | TACTTGTTTCATCTCTACTCCACAATCCGAATTTACTTTGCCAAAGGACCC |
| | AGAAACTCCATTGATCATGGTTGGTCCAGGTACTGGTGTCGCTCCATTCA |
| | GAGGTTTCGTTCAAGCTAGAAAACAATTGAAGGAACAAGGTCAATCTTT |
| | GGGTGAAGCTCACTTGTACTTCGGTTGTAGATCTCCACACGAAGACTACT |
| | TATACCAAGAAGAATTGGAAAACGCTCAATCCGAAGGTATTATCACTTT |
| | GCACACCGCTTTCTCCAGAATGCCAAACCAACCAAAGACTTACGTCCAA |
| | CACGTTATGGAACAAGACGGTAAGAAGTTGATTGAATTGTTGGACCAAG |
| | GTGCTCACTTCTACATTTGTGGTGATGGTTCTCAAATGGCTCCAGCCGTT |
| | GAAGCCACTTTGATGAAGTCTTACGCTGATGTTCACCAAGTTTCCGAAGC |
| | CGATGCTAGATTATGGTTGCAACAATTGGAAGAAAAAGGTCGTTACGCT |
| | AAGGATGTCTGGGCCGGTTGA |
| 4H9 | ATGACCATCAAAGAAATGCCACAACCTAAGACTTTCGGTGAATTGAAGA |
| | ATTTGCCTTTGTTGAACACCGATAAGCCAGTTCAAGCTTTGATGAAGATT |
| | GCTGATGAATTGGGTGAAATCTTCAAGTTTGAAGCTCCAGGTAGAGTCAC |
| | TAGATACTTGTCATCTCAAAGATTGATCAAAGAAGCCTGCGACGAATCC |
| | AGATTTGATAAGAATTTGTCTCAAGCTTTGAAGTTCGCTAGAGATTTTGC |
| | TGGTGATGGTTTGGTTACTTCTTGGACTCACGAAAAGAATTGGAAGAAG |
| | GCCCATAACATTTTGTTGCCATCTTTCTCACAACAAGCCATGAAGGGTTA |
| | TCATGCTATGATGGTTGATATCGCCGTTCAATTGGTTCAAAAGTGGGAAA |
| | GATTGAACGCCGATGAACATATCGAAGTCTCTGAAGATATGACCAGATT |
| | GACCTTGGATACCATTGGTTTGTGTGGTTTCAACTACAGATTCAACTCCTT |
| | CTACAGAGATCAACCACATCCATTCATCATCTCTATGGTTAGAGCTGCAG |
| | ATGAAGTCATGAACAAATTGCAAAGAGCTAATCCAGACGATCCAGCTTA |
| | TGACGAAAACAAGAGACAATTCCAAGAAGATATCAAGGTCATGAACGAT |
| | TTGGTCGATAAGATTATCGCTGATAGAAAGGCTAGAGGTGAACAATCTG |
| | ATGATTTGTTGACCCAAATGTTGAACGGTAAGGATCCAGAAACTGGTGA |
| | ACCATTGGATGATGGTAACATCAGATACCAAATTATCGCTTTCTTGATTG |
| | CTGGTCACGAAACTACATCTGGTTTGTTGTCTTTTGCCTTGTACTTTTTGG |
| | TTAAGAACCCACACGTCTTGCAAAAGGTTGCTGAAGAAGCTGCAAGAGT |
| | TTTGGTTGATCCAGTTCCATCTTACAAGCAAGTCAAGCAATTGAAGTACG |
| | TTGGTATGGTTTTGAACGAAGCTTTGAGATTGTGGCCAACTGCTCCAGCT |
| | TTTTCATTATACGCTAAAGAAGATACCGTCTTGGGTGGTGAATATCCATT |
| | GGAAAAAGGTGATGAAGTTATGGTCTTGATCCCACAATTGCATAGAGAT |
| | AAGACTGTTTGGGGTGATGATGTCGAAGAATTCAGACCAGAAAGATTCG |
| | AAAACCCATCTGCTATTCCACAACATGCTTTTAAGCCATTTGGTAACGGT |
| | CAAAGAGCTTGCATTGGTCAACAATTCGCTTTACATGAAGCTACCTTGGT |
| | TTTGGGTATGATGTTGAAACACTTCGACTTCGAAGATCACACCAACTACG |
| | AATTGGATATCAAAGAAACCGCTACCTTGAAGCCAAAGGGTTTTGTTGTT |
| | AAGGCTAAGTCCAAAAAGATTCCATTGGGTGGTATTCCATCTCCATCTAC |
| | TGAACAATCCGCTAAGAAGGTTAGAAAGAAAGCTGAAAACGCTCATAAC |
| | ACACCTTTGTTGGTCTTGTACGGTTCTAATATGGGTACTGCTGAAGGTAC |
| | AGCAAGAGATTTGGCAGATATTGCTATGTCTAAAGGTTTCGCTCCACAAG |
| | TTGCTACTTTGGATTCTCATGCTGGTAATTTGCCAAGAGAAGGTGCTGTT |
| | TTGATAGTTACTGCTTCTTACAATGGTCACCCACCAGATAATGCTAAGCA |
| | ATTCGTTGATTGGTTGGATCAAGCTTCAGCTGATGAAGTAAAAGGTGTTA |
| | GATACTCTGTTTTCGGTTGCGGTGACAAAAATTGGGCTACTACTTATCAA |
| | AAGGTTCCAGCCTTTATTGACGAAACTTTGGCTGCTAAAGGTGCTGAAAA |
| | CATTGCTGACAGAGGTGAAGCTGATGCCTCCGACGACTTCGAAGGTACT |
| | TACGAAGAATGGAGAGAACACATGTGGTCTGACGTTGCTGCTTACTTCA |
| | ACTTGGACATCGAAAACTCTGAAGACAACAAGTCCACTTTGTCTTTGCAA |
| | TTCGTTGACTCCGCTGCTGACATGCCATTGGCTAAGATGCACGGTGCTTT |
| | CTCTACCAACGTCGTTGCCTCCAAGGAATTGCAACAACCAGGTTCTGCTA |
| | GATCTACTAGACACTTGGAAATCGAATTGCCAAAGGAAGCTTCCTACCA |
| | AGAAGGTGACCACTTGGGCGTTATTCCAAGAAACTACGAAGGTATCGTC |
| | AACAGAGTTACTGCTAGATTCGGTTTGGATGCTTCTCAACAAATCAGATT |
| | AGAAGCTGAAGAAGAAAAGTTGGCTCACTTGCCATTAGCTAAGACTGTC |
| | TCCGTTGAAGAATTGTTGCAATACGTCGAATTGCAAGACCCAGTTACCAG |
| | AACCCAATTGAGAGCCATGGCTGCCAAGACCGTCTGTCCACCACACAAG |
| | GTTGAATTGGAAGCCTTGTTGGAAAAGCAAGCCTACAAGGAACAAGTTT |
| | TGGCTAAGAGATTGACCATGTTGGAATTGTTGGAAAAGTACCCAGCCTG |
| | CGAAATGAAGTTCTCTGAATTTATCGCCTTGTTGCCATCTATCAGACCAC |
| | GTTACTACTCTATTTCTTCCTCTCCACGTGTTGACGAAAAGCAAGCTTCTA |
| | TTACTGTTTCCGTTGTCTCCGGTGAAGCTTGGTCCGGTTACGGTGAATAC |
| | AAGGGTATTGCTTCTAACTACTTGGCTGAATTGCAAGAAGGTGACACCAT |
| | TACTTGTTTCATCTCTACTCCACAATCCGAATTTACTTTGCCAAAGGACCC |
| | AGAAACTCCATTGATCATGGTTGGTCCAGGTACTGGTGTCGCTCCATTCA |
| | GAGGTTTCGTTCAAGCTAGAAAACAATTGAAGGAACAAGGTCAATCTTT |
| | GGGTGAAGCTCACTTGTACTTCGGTTGTAGATCTCCACACGAAGACTACT |
| | TATACCAAGAAGAATTGGAAAACGCTCAATCCGAAGGTATTATCACTTT |
| | GCACACCGCTTTCTCCAGAATGCCAAACCAACCAAAGACTTACGTCCAA |
| | CACGTTATGGAACAAGACGGTAAGAAGTTGATTGAATTGTTGGACCAAG |
| | GTGCTCACTTCTACATTTGTGGTGATGGTTCTCAAATGGCTCCAGCCGTT |

TABLE 7-continued

| Variants of BM3 N-demethylase | |
|---|---|
| BM3 variant | |
| | GAAGCCACTTTGATGAAGTCTTACGCTGATGTTCACCAAGTTTCCGAAGC<br>CGATGCTAGATTATGGTTGCAACAATTGGAAGAAAAAGGTCGTTACGCT<br>AAGGATGTCTGGGCCGGTTGA |
| 8C7 | ATGACCATCAAAGAAATGCCACAACCTAAGACTTTCGGTGAATTGAAGA<br>ATTTGCCTTTGTTGAACACCGATAAGCCAGTTCAAGCTTTGATGAAGATT<br>GCTGATGAATTGGGTGAAATCTTCAAGTTTGAAGCTCCAGGTAGAGTCAC<br>TAGATACTTGTCATCTCAAAGATTGATCAAAGAAGCCTGCGACGAATCC<br>AGATTTGATAAGAATTTGTCTCAAGCTGCTAAGTTCGCTAGAGATTTTGC<br>TGGTGATGGTTTGGTTACTTCTTGGACTCACGAAAAGAATTGGAAGAAG<br>GCCCATAACATTTTGTTGCCATCTTTCTCACAACAAGCCATGAAGGGTTA<br>TCATGCTATGATGGTTGATATCGCCGTTCAATTGGTTCAAAAGTGGGAAA<br>GATTGAACGCCGATGAACATATCGAAGTCTCTGAAGATATGACCAGATT<br>GACCTTGGATACCATTGGTTTGTGTGGTTTCAACTACAGATTCAACTCCTT<br>CTACAGAGATCAACCACATCCATTCATCATCTCTATGGTTAGAGCTGCAG<br>ATGAAGTCATGAACAAATTGCAAAGAGCTAATCCAGACGATCCAGCTTA<br>TGACGAAAACAAGAGACAATTCCAAGAAGATATCAAGGTCATGAACGAT<br>TTGGTCGATAAGATTATCGCTGATAGAAAGGCTAGAGGTGAACAATCTG<br>ATGATTTGTTGACCCAAATGTTGAACGGTAAGGATCCAGAAACTGGTGA<br>ACCATTGGATGATGGTAACATCAGATACCAAATTATCACCTTCTTGATTG<br>CTGGTCACGAAACTACATCTGGTTTGTTGTCTTTTGCCTTGTACTTTTTGG<br>TTAAGAACCCACACGTCTTGCAAAAGGTTGCTGAAGAAGCTGCAAGAGT<br>TTTGGTTGATCCAGTTCCATCTTACAAGCAAGTCAAGCAATTGAAGTACG<br>TTGGTATGGTTTTGAACGAAGCTTTGAGATTGTGGCCAACTGCTCCAGCT<br>TTTTCATTATACGCTAAAGAAGATACCGTCTTGGGTGGTGAATATCCATT<br>GGAAAAAGGTGATGAAGTTATGGTCTTGATCCCACAATTGCATAGAGAT<br>AAGACTGTTTGGGGTGATGATGTCGAAGAATTCAGACCAGAAAGATTCG<br>AAAACCCATCTGCTATTCCACAACATGCTTTTAAGCCATTTGGTAACGGT<br>CAAAGAGCTTGCATTGGTCAACAATTCGCTTTACATGAAGCTACCTTGGT<br>TTTGGGTATGATGTTGAAACACTTCGACTTCGAAGATCACACCAACTACG<br>AATTGGATATCAAAGAAACCTTGACCTTGAAGCCAAAGGGTTTTGTTGTT<br>AAGGCTAAGTCCAAAAAGATTCCATTGGGTGGTATTCCATCTCCATCTAC<br>TGAACAATCCGCTAAGAAGGTTAGAAAGAAAGCTGAAAACGCTCATAAC<br>ACACCTTTGTTGGTCTTGTACGGTTCTAATATGGGTACTGCTGAAGGTAC<br>AGCAAGAGATTTGGCAGATATTGCTATGTCTAAAGGTTTCGCTCCACAAG<br>TTGCTACTTTGGATTCTCATGCTGGTAATTTGCCAAGAGAAGGTGCTGTT<br>TTGATAGTTACTGCTTCTTACAATGGTCACCCACCAGATAATGCTAAGCA<br>ATTCGTTGATTGGTTGGATCAAGCTTCAGCTGATGAAGTAAAAGGTGTTA<br>GATACTCTGTTTTCGGTTGCGGTGACAAAAATTGGGCTACTACTTATCAA<br>AAGGTTCCAGCCTTTATTGACGAAACTTTGGCTGCTAAAGGTGCTGAAAA<br>CATTGCTGACAGAGGTGAAGCTGATGCCTCCGACGACTTCGAAGGTACT<br>TACGAAGAATGGAGAGAACACATGTGGTCTGACGTTGCTGCTTACTTCA<br>ACTTGGACATCGAAAACTCTGAAGACAACAAGTCCACTTTGTCTTTGCAA<br>TTCGTTGACTCCGCTGCTGACATGCCATTGGCTAAGATGCACGGTGCTTT<br>CTCTACCAACGTCGTTGCCTCCAAGGAATTGCAACAACCAGGTTCTGCTA<br>GATCTACTAGACACTTGGAAATCGAATTGCCAAAGGAAGCTTCCTACCA<br>AGAAGGTGACCACTTGGGCGTTATTCCAAGAAACTACGAAGGTATCGTC<br>AACAGAGTTACTGCTAGATTCGGTTTGGATGCTTCTCAACAAATCAGATT<br>AGAAGCTGAAGAAGAAAAGTTGGCTCACTTGCCATTAGCTAAGACTGTC<br>TCCGTTGAAGAATTGTTGCAATACGTCGAATTGCAAGACCCAGTTACCAG<br>AACCCAATTGAGAGCCATGGCTGCCAAGACCGTCTGTCCACCACACAAG<br>GTTGAATTGGAAGCCTTGTTGGAAAAGCAAGCCTACAAGGAACAAGTTT<br>TGGCTAAGAGATTGACCATGTTGGAATTGTTGGAAAAGTACCCAGCCTG<br>CGAAATGAAGTTCTCTGAATTTATCGCCTTGTTGCCATCTATCAGACCAC<br>GTTACTACTCTATTTCTTCCTCTCCACGTGTTGACGAAAAGCAAGCTTCTA<br>TTACTGTTTCCGTTGTCTCCGGTGAAGCTTGGTCCGGTTACGGTGAATAC<br>AAGGGTATTGCTTCTAACTACTTGGCTGAATTGCAAGAAGGTGACACCAT<br>TACTTGTTTCATCTCTACTCCACAATCCGAATTTACTTTGCCAAAGGACCC<br>AGAAACTCCATTGATCATGGTTGGTCCAGGTACTGGTGTCGCTCCATTCA<br>GAGGTTTCGTTCAAGCTAGAAAACAATTGAAGGAACAAGGTCAATCTTT<br>GGGTGAAGCTCACTTGTACTTCGGTTGTAGATCTCCACACGAAGACTACT<br>TATACCAAGAAGAATTGGAAAACGCTCAATCCGAAGGTATTATCACTTT<br>GCACACCGCTTTCTCCAGAATGCCAAACCAACCAAAGACTTACGTCCAA<br>CACGTTATGGAACAAGACGGTAAGAAGTTGATTGAATTGTTGGACCAAG<br>GTGCTCACTTCTACATTTGTGGTGATGGTTCTCAAATGGCTCCAGCCGTT<br>GAAGCCACTTTGATGAAGTCTTACGCTGATGTTCACCAAGTTTCCGAAGC<br>CGATGCTAGATTATGGTTGCAACAATTGGAAGAAAAAGGTCGTTACGCT<br>AAGGATGTCTGGGCCGGTTGA |
| 4H5 | ATGACCATCAAAGAAATGCCACAACCTAAGACTTTCGGTGAATTGAAGA<br>ATTTGCCTTTGTTGAACACCGATAAGCCAGTTCAAGCTTTGATGAAGATT<br>GCTGATGAATTGGGTGAAATCTTCAAGTTTGAAGCTCCAGGTAGAGTCAC<br>TAGATACTTGTCATCTCAAAGATTGATCAAAGAAGCCTGCGACGAATCC<br>AGATTTGATAAGAATTTGTCTCAAGCTGCTAAGTTCGCTAGAGATTTTGC<br>TGGTGATGGTTTGGTTACTTCTTGGACTCACGAAAAGAATTGGAAGAAG<br>GCCCATAACATTTTGTTGCCATCTTTCTCACAACAAGCCATGAAGGGTTA |

TABLE 7-continued

| Variants of BM3 N-demethylase | |
|---|---|
| BM3 variant | |
| | TCATGCTATGATGGTTGATATCGCCGTTCAATTGGTTCAAAAGTGGGAAA<br>GATTGAACGCCGATGAACATATCGAAGTCTCTGAAGATATGACCAGATT<br>GACCTTGGATACCATTGGTTTGTGTGGTTTCAACTACAGATTCAACTCCTT<br>CTACAGAGATCAACCACATCCATTCATCATCTCTGCTGTTAGAGCTGCAG<br>ATGAAGTCATGAACAAATTGCAAAGAGCTAATCCAGACGATCCAGCTTA<br>TGACGAAAACAAGAGACAATTCCAAGAAGATATCAAGGTCATGAACGAT<br>TTGGTCGATAAGATTATCGCTGATAGAAAGGCTAGAGGTGAACAATCTG<br>ATGATTTGTTGACCCAAATGTTGAACGGTAAGGATCCAGAAACTGGTGA<br>ACCATTGGATGATGGTAACATCAGATACCAAATTATCACCTTCTTGATTG<br>CTGGTCACGAAACTACATCTGGTTTGTTGTCTTTTGCCTTGTACTTTTTGG<br>TTAAGAACCCACACGTCTTGCAAAAGGTTGCTGAAGAAGCTGCAAGAGT<br>TTTGGTTGATCCAGTTCCATCTTACAAGCAAGTCAAGCAATTGAAGTACG<br>TTGGTATGGTTTTGAACGAAGCTTTGAGATTGTGGCCAACTGCTCCAGCT<br>TTTTCATTATACGCTAAAGAAGATACCGTCTTGGGTGGTGAATATCCATT<br>GGAAAAAGGTGATGAAGTTATGGTCTTGATCCCACAATTGCATAGAGAT<br>AAGACTGTTTGGGGTGATGATGTCGAAGAATTCAGACCAGAAAGATTCG<br>AAAACCCATCTGCTATTCCACAACATGCTTTTAAGCCATTTGGTAACGGT<br>CAAAGAGCTTGCATTGGTCAACAATTCGCTTTACATGAAGCTACCTTGGT<br>TTTGGGTATGATGTTGAAACACTTCGACTTCGAAGATCACACCAACTACG<br>AATTGGATATCAAAGAAACCTTGACCTTGAAGCCAAAGGGTTTTGTTGTT<br>AAGGCTAAGTCCAAAAAGATTCCATTGGGTGGTATTCCATCTCCATCTAC<br>TGAACAATCCGCTAAGAAGGTTAGAAAGAAAGCTGAAAACGCTCATAAC<br>ACACCTTTGTTGGTCTTGTACGGTTCTAATATGGGTACTGCTGAAGGTAC<br>AGCAAGAGATTTGGCAGATATTGCTATGTCTAAAGGTTTCGCTCCACAAG<br>TTGCTACTTTGGATTCTCATGCTGGTAATTTGCCAAGAGAAGGTGCTGTT<br>TTGATAGTTACTGCTTCTTACAATGGTCACCCACCAGATAATGCTAAGCA<br>ATTCGTTGATTGGTTGGATCAAGCTTCAGCTGATGAAGTAAAAGGTGTTA<br>GATACTCTGTTTTCGGTTGCGGTGACAAAAATTGGGCTACTACTTATCAA<br>AAGGTTCCAGCCTTTATTGACGAAACTTTGGCTGCTAAAGGTGCTGAAAA<br>CATTGCTGACAGAGGTGAAGCTGATGCCTCCGACGACTTCGAAGGTACT<br>TACGAAGAATGGAGAGAACACATGTGGTCTGACGTTGCTGCTTACTTCA<br>ACTTGGACATCGAAAACTCTGAAGACAACAAGTCCACTTTGTCTTTGCAA<br>TTCGTTGACTCCGCTGCTGACATGCCATTGGCTAAGATGCACGGTGCTTT<br>CTCTACCAACGTCGTTGCCTCCAAGGAATTGCAACAACCAGGTTCTGCTA<br>GATCTACTAGACACTTGGAAATCGAATTGCCAAAGGAAGCTTCCTACCA<br>AGAAGGTGACCACTTGGGCGTTATTCCAAGAAACTACGAAGGTATCGTC<br>AACAGAGTTACTGCTAGATTCGGTTTGGATGCTTCTCAACAAATCAGATT<br>AGAAGCTGAAGAAGAAAAGTTGGCTCACTTGCCATTAGCTAAGACTGTC<br>TCCGTTGAAGAATTGTTGCAATACGTCGAATTGCAAGACCCAGTTACCAG<br>AACCCAATTGAGAGCCATGGCTGCCAAGACCGTCTGTCCACCACACAAG<br>GTTGAATTGGAAGCCTTGTTGGAAAAGCAAGCCTACAAGGAACAAGTTT<br>TGGCTAAGAGATTGACCATGTTGGAATTGTTGGAAAAGTACCCAGCCTG<br>CGAAATGAAGTTCTCTGAATTTATCGCCTTGTTGCCATCTATCAGACCAC<br>GTTACTACTCTATTTCTTCCTCTCCACGTGTTGACGAAAAGCAAGCTTCTA<br>TTACTGTTTCCGTTGTCTCCGGTGAAGCTTGGTCCGGTTACGGTGAATAC<br>AAGGGTATTGCTTCTAACTACTTGGCTGAATTGCAAGAAGGTGACACCAT<br>TACTTGTTTCATCTCTACTCCACAATCCGAATTTACTTTGCCAAAGGACCC<br>AGAAACTCCATTGATCATGGTTGGTCCAGGTACTGGTGTCGCTCCATTCA<br>GAGGTTTCGTTCAAGCTAGAAAACAATTGAAGGAACAAGGTCAATCTTT<br>GGGTGAAGCTCACTTGTACTTCGGTTGTAGATCTCCACACGAAGACTACT<br>TATACCAAGAAGAATTGGAAAACGCTCAATCCGAAGGTATTATCACTTT<br>GCACACCGCTTTCTCCAGAATGCCAAACCAACCAAAGACTTACGTCCAA<br>CACGTTATGGAACAAGACGGTAAGAAGTTGATTGAATTGTTGGACCAAG<br>GTGCTCACTTCTACATTTGTGGTGATGGTTCTCAAATGGCTCCAGCCGTT<br>GAAGCCACTTTGATGAAGTCTTACGCTGATGTTCACCAAGTTTCCGAAGC<br>CGATGCTAGATTATGGTTGCAACAATTGGAAGAAAAAGGTCGTTACGCT<br>AAGGATGTCTGGGCCGGTTGA |
| 7A1 | ATGACCATCAAAGAAATGCCACAACCTAAGACTTTCGGTGAATTGAAGA<br>ATTTGCCTTTGTTGAACACCGATAAGCCAGTTCAAGCTTTGATGAAGATT<br>GCTGATGAATTGGGTGAAATCTTCAAGTTTGAAGCTCCAGGTAGAGTCAC<br>TAGATACTTGTCATCTCAAAGATTGATCAAAGAAGCCTGCGACGAATCC<br>AGATTTGATAAGAATTTGTCTCAAGCTGCTAAGTTCGCTAGAGATTTTGC<br>TGGTGATGGTTTGGTTACTTCTTGGACTCACGAAAAGAATTGGAAGAAG<br>GCCCATAACATTTTGTTGCCATCTTTCTCACAACAAGCCATGAAGGGTTA<br>TCATGCTATGATGGTTGATATCGCCGTTCAATTGGTTCAAAAGTGGGAAA<br>GATTGAACGCCGATGAACATATCGAAGTCTCTGAAGATATGACCAGATT<br>GACCTTGGATACCATTGGTTTGTGTGGTTTCAACTACAGATTCAACTCCTT<br>CTACAGAGATCAACCACATCCATTCATCATCTCTGCTGTTAGAGCTGCAG<br>ATGAAGTCATGAACAAATTGCAAAGAGCTAATCCAGACGATCCAGCTTA<br>TGACGAAAACAAGAGACAATTCCAAGAAGATATCAAGGTCATGAACGAT<br>TTGGTCGATAAGATTATCGCTGATAGAAAGGCTAGAGGTGAACAATCTG<br>ATGATTTGTTGACCCAAATGTTGAACGGTAAGGATCCAGAAACTGGTGA<br>ACCATTGGATGATGGTAACATCAGATACCAAATTATCGCTTTCTTGATTG<br>CTGGTCACGAAACTACATCTGGTTTGTTGTCTTTTGCCTTGTACTTTTTGG<br>TTAAGAACCCACACGTCTTGCAAAAGGTTGCTGAAGAAGCTGCAAGAGT |

TABLE 7-continued

| Variants of BM3 N-demethylase | |
|---|---|
| BM3 variant | |
| | TTTGGTTGATCCAGTTCCATCTTACAAGCAAGTCAAGCAATTGAAGTACG<br>TTGGTATGGTTTTGAACGAAGCTTTGAGATTGTGGCCAACTGCTCCAGCT<br>TTTTCATTATACGCTAAAGAAGATACCGTCTTGGGTGGTGAATATCCATT<br>GGAAAAAGGTGATGAAGTTATGGTCTTGATCCCACAATTGCATAGAGAT<br>AAGACTGTTTGGGGTGATGATGTCGAAGAATTCAGACCAGAAAGATTCG<br>AAAACCCATCTGCTATTCCACAACATGCTTTTAAGCCATTTGGTAACGGT<br>CAAAGAGCTTGCATTGGTCAACAATTCGCTTTACATGAAGCTACCTTGGT<br>TTTGGGTATGATGTTGAAACACTTCGACTTCGAAGATCACACCAACTACG<br>AATTGGATATCAAAGAAACCTTGACCTTGAAGCCAAAGGGTTTTGTTGTT<br>AAGGCTAAGTCCAAAAAGATTCCATTGGGTGGTATTCCATCTCCATCTAC<br>TGAACAATCCGCTAAGAAGGTTAGAAAGAAAGCTGAAAACGCTCATAAC<br>ACACCTTTGTTGGTCTTGTACGGTTCTAATATGGGTACTGCTGAAGGTAC<br>AGCAAGAGATTTGGCAGATATTGCTATGTCTAAAGGTTTCGCTCCACAAG<br>TTGCTACTTTGGATTCTCATGCTGGTAATTTGCCAAGAGAAGGTGCTGTT<br>TTGATAGTTACTGCTTCTTACAATGGTCACCCACCAGATAATGCTAAGCA<br>ATTCGTTGATTGGTTGGATCAAGCTTCAGCTGATGAAGTAAAAGGTGTTA<br>GATACTCTGTTTTCGGTTGCGGTGACAAAAATTGGGCTACTACTTATCAA<br>AAGGTTCCAGCCTTTATTGACGAAACTTTGGCTGCTAAAGGTGCTGAAAA<br>CATTGCTGACAGAGGTGAAGCTGATGCCTCCGACGACTTCGAAGGTACT<br>TACGAAGAATGGAGAGAACACATGTGGTCTGACGTTGCTGCTTACTTCA<br>ACTTGGACATCGAAAACTCTGAAGACAACAAGTCCACTTTGTCTTTGCAA<br>TTCGTTGACTCCGCTGCTGACATGCCATTGGCTAAGATGCACGGTGCTTT<br>CTCTACCAACGTCGTTGCCTCCAAGGAATTGCAACAACCAGGTTCTGCTA<br>GATCTACTAGACACTTGGAAATCGAATTGCCAAAGGAAGCTTCCTACCA<br>AGAAGGTGACCACTTGGGCGTTATTCCAAGAAACTACGAAGGTATCGTC<br>AACAGAGTTACTGCTAGATTCGGTTTGGATGCTTCTCAACAAATCAGATT<br>AGAAGCTGAAGAAGAAAAGTTGGCTCACTTGCCATTAGCTAAGACTGTC<br>TCCGTTGAAGAATTGTTGCAATACGTCGAATTGCAAGACCCAGTTACCAG<br>AACCCAATTGAGAGCCATGGCTGCCAAGACCGTCTGTCCACCACACAAG<br>GTTGAATTGGAAGCCTTGTTGGAAAAGCAAGCCTACAAGGAACAAGTTT<br>TGGCTAAGAGATTGACCATGTTGGAATTGTTGGAAAAGTACCCAGCCTG<br>CGAAATGAAGTTCTCTGAATTTATCGCCTTGTTGCCATCTATCAGACCAC<br>GTTACTACTCTATTTCTTCCTCTCCACGTGTTGACGAAAAGCAAGCTTCTA<br>TTACTGTTTCCGTTGTCTCCGGTGAAGCTTGGTCCGGTTACGGTGAATAC<br>AAGGGTATTGCTTCTAACTACTTGGCTGAATTGCAAGAAGGTGACACCAT<br>TACTTGTTTCATCTCTACTCCACAATCCGAATTTACTTTGCCAAAGGACCC<br>AGAAACTCCATTGATCATGGTTGGTCCAGGTACTGGTGTCGCTCCATTCA<br>GAGGTTTCGTTCAAGCTAGAAAACAATTGAAGGAACAAGGTCAATCTTT<br>GGGTGAAGCTCACTTGTACTTCGGTTGTAGATCTCCACACGAAGACTACT<br>TATACCAAGAAGAATTGGAAAACGCTCAATCCGAAGGTATTATCACTTT<br>GCACACCGCTTTCTCCAGAATGCCAAACCAACCAAAGACTTACGTCCAA<br>CACGTTATGGAACAAGACGGTAAGAAGTTGATTGAATTGTTGGACCAAG<br>GTGCTCACTTCTACATTTGTGGTGATGGTTCTCAAATGGCTCCAGCCGTT<br>GAAGCCACTTTGATGAAGTCTTACGCTGATGTTCACCAAGTTTCCGAAGC<br>CGATGCTAGATTATGGTTGCAACAATTGGAAGAAAAAGGTCGTTACGCT<br>AAGGATGTCTGGGCCGGTTGA |

TABLE 8

| pA24, pA25, and pA26 sequences | |
|---|---|
| pA24 Sequence | cctcgccgcagttaattaaagtcagtgagcgaggaagcgcgtaactataacggtcctaaggtagcgaatcct<br>gatgcggtattttctccttacgcatctgtgcggtatttcacaccgcatagatcggcaagtgcacaaacaata<br>cttaaataaatactactcagtaataacctatttcttagcattttgacgaaatttgctattttgttagagtc<br>ttttacaccatttgtctccacacctccgcttacatcaacaccaataacgccatttaatctaagcgcatcacc<br>aacattttctggcgtcagtccaccagctaacataaaatgtaagctttcggggctctcttgccttccaaccca<br>gtcagaaatcgagttccaatccaaaagttcacctgtcccacctgcttctgaatcaaacaagggaataaacga<br>atgaggtttctgtgaagctgcactgagtagtatgttgcagtcttttggaaatacgagtcttttaataactgg<br>caaaccgaggaactcttggtattcttgccacgactcatctccatgcagtggagccaatcaattcttgcggtc<br>aactttggacgatatcaatgccgtaatcattgaccagagccaaaacatcctccttaagttgattacgaaaca<br>cgccaaccaagtatttcggagtgcctgaactatttttatatgcttttacaagacttgaaattttccttgcaa<br>taaccgggtcaattgttctctttctattgggcacacatataatacccagcaagtcagcatcggaatctagag<br>cacattctgcggcctctgtgctctgcaagccgcaaactttcaccaatggaccagaactacctgtgaaattaa<br>taacagacatactccaagctgcctttgtgtgcttaatcacgtatactcacgtgctcaatagtcaccaatgcc<br>ctccctcttggccctctcctttttcttttttcgaccgaattaattcttaatcggcaaaaaaagaaaagctccg<br>gatcaagattgtacgtaaggtgacaagctatttttcaataaagaatatcttccactactgccatctggcgtc<br>ataactgcaaagtacacatatattacgatgctgttctattaaatgcttcctatattatatatatagtaatgt<br>cgtgatctatggtgcactctcagtacaatctgctctgatgccgcatagttaagccagccccgacacccgcca<br>acacccgctgacgcgccctgacgggcttgtctgctcccggcatccgcttacagacaagctgtgaccgtctcc<br>gggagctgcatgtgtcagaggttttcaccgtcatcaccgaaacgcgcgagacgaaagggcctcgtgatacgc<br>ctatttttataggttaatgtcatgataataatggtttcttagacggatcgcttgcctgtaacttacacgcgc<br>ctcgtatcttttaatgatggaataatttgggaatttactctgtgtttatttatttttatgttttgtatttgg<br>attttagaaagtaaataaagaaggtagaagagttacggaatgaagaaaaaaaaataaacaaaggtttaaaaa |

TABLE 8-continued

| pA24, pA25, and pA26 sequences | |
|---|---|
| | atttcaacaaaaagcgtactttacatatatatttattagacaagaaaagcagattaaatagatatacattcg<br>attaacgataagtaaaatgtaaaatcacaggattttcgtgtgtggtcttctacacagacaaggtgaaacaat<br>tcggcattaatacctgagagcaggaagagcaagataaaaggtagtatttgttggcgatcccctagagtctt<br>ttacatcttcggaaaacaaaaactattttttctttaatttctttttttactttctatttttaatttatatat<br>ttatattaaaaaatttaaattataattatttttatagcacgtgatgaaaaggacccaggtggcacttttcgg<br>ggaaatgtgcgcggaacccctatttgtttatttttctaaatacattcaaatatgtatccgctcatgagacaa<br>taaccctgataaatgcttcaataatattgaaaaaggaagagtatgagtattcaacatttccgtgtcgccctt<br>attcccttttttgcggcattttgccttcctgtttttgctcacccagaaacgctggtgaaagtaaaagatgct<br>gaagatcagttgggacgcgtagtctagaccagccaggacagaaatgcctcgacttcgctgctacccaaggtt<br>gccgggtgacgcacaccgtggaaacggatgaaggcacgaacccagtggacataagcctgttcggttcgtaag<br>ctgtaatgcaagtagcgtatgcgctcacgcaactggtccagaaccttgaccgaacgcagcggtggtaacggc<br>gcagtggcggttttcatggcttgttatgactgtttttttggggtacagtctatgcctcgggcatccaagcag<br>caagcgcgttacgccgtgggtcgatgtttgatgttatggagcagcaacgatgttacgcagcagggcagtcgc<br>cctaaaacaaagttaaacattatgagggaagcggtgatcgccgaagtatcgactcaactatcagaggtagtt<br>ggcgccatcgagcgccatctcgaaccgacgttgctggccgtacatttgtacggctccgcagtggatggcggc<br>ctgaagccacacagtgatattgatttgctggttacggtgaccgtaaggcttgatgaaacaacgcggcgagct<br>ttgatcaacgaccttttggaaacttcggcttcccctggagagagcgagattctccgcgctgtagaagtcacc<br>attgttgtgcacgacgacatcattccgtggcgttatccagctaagcgcgaactgcaatttggagaatggcag<br>cgcaatgacattcttgcaggtatcttcgagccagccacgatcgacattgatctggctatcttgctgacaaaa<br>gcaagagaacatagcgttgccttggtaggtccagcggcggaggaactctttgatccggttcctgaacaggat<br>ctatttgaggcgctaaatgaaaccttaacgctatggaactcgccgcccgactgggctggcgatgagcgaaat<br>gtagtgcttacgttgtcccgcatttggtacagcgcagtaaccggcaaaatcgcgccgaaggatgtcgctgcc<br>ggctgggcaatggagcgcctgccggcccagtatcagcccgtcatacttgaagctagacaggcttatcttgga<br>caagaagaagatcgcttggcctcgcgcgcagatcagttggaagaatttgtccactacgtgaaaggcgagatc<br>accaaggtagtcggcaaataaccctcgagcattcaaggcgccttgattatttgacgtggtttgatggcctcc<br>acgcacgttgtgatatgtagatgattcagttcgagtttatcattatcaatactgccatttcaaagaatacgt<br>aaataattaatagtagtgattttcctaactttatttagtcaaaaaattagccttttaattctgctgtaaccc<br>gtacatgcccaaaatagggggcgggttacacagaatatataacatcgtaggtgtctgggtgaacagtttatt<br>cctggcatccactaaatataatggagcccgctttttaagctggcatccagaaaaaaaaagaatcccagcacc<br>aaaatattgttttcttcaccaaccatcagttcataggtccattctcttagcgcaactacagagaacaggggc<br>acaaacaggcaaaaaacgggcacaacctcaatggagtgatgcaacctgcctggagtaaatgatgacacaagg<br>caattgacccacgcatgtatctatctcattttcttacaccttctattaccttctgctctctctgatttggaa<br>aaagctgaaaaaaaaggttgaaaccagttccctgaaattattcccctacttgactaataagtatataaagac<br>ggtaggtattgattgtaattctgtaaatctatttcttaaacttcttaaattctacttttatagttagtcttt<br>tttttagttttaaaacaccaagaacttagtttcgaataaacacacataaacaaacaaaacaggcccctttttc<br>ctttgtcgatatcatgtaattagttatgtcacgcttacattcacgccctcctcccacatccgctctaaccga<br>aaaggaaggagttagacaacctgaagtctaggtccctatttattttttttaatagttatgttagtattaaga<br>acgttatttatatttcaaatttttcttttttttctgtacaaacgcgtgtacgcatgtaacattatactgaaa<br>accttgcttgagaaggttttgggacgctcgaaggctttaatttgtaatcattatcactttacgggtcctttc<br>cggtgatccgacaggttacggggcggcgacctcgcgggttttcgctatttatgaaaattttccggtttaagg<br>cgtttccgttcttcttcgtcataacttaatgtttttatttaaaatacctcgcgagtggcaacactgaaaata<br>cccatggagcggcgtaaccgtcgcacaggatctaggtgaagatcctttttgataatctcatgaccaaaatcc<br>cttaacgtgagttttcgttccactgagcgtcagaccccgtagaaaagatcaaaggatcttcttgagatcctt<br>tttttctgcgcgtaatctgctgcttgcaaacaaaaaaaccaccgctaccagcggtggtttgtttgccggatc<br>aagagctaccaactctttttccgaaggtaactggcttcagcagagcgcagataccaaatactgtccttctagt<br>gtagccgtagttaggccaccacttcaagaactctgtagcaccgcctacatacctcgctctgctaatcctgtt<br>accagtggctgctgccagtggcgataagtcgtgtcttaccgggttggactcaagacgatagttaccggataa<br>ggcgcagcggtcgggctgaacggggggttcgtgcacacagcccagcttggagcgaacgacctacaccgaact<br>gagatacctacagcgtgagctatgagaaagcgccacgcttcccgaagggagaaaggcggacaggtatccggt<br>aagcggcagggtcggaacaggagagcgcacgagggagcttccagggggaaacgcctggtatctttatagtcc<br>tgtcgggtttcgccacctctgacttgagcgtcgatttttgtgatgctcgtcaggggggcggagcctatggaa<br>aaacgccagcaacgcggcagtggaacgtgcattatgaattagttacgctagggataacagggtaatatagaa<br>cccgaacgaccgagcgcagcggcggccgcgctgataccgccgc |
| pA25 sequence | aacgacctacaccgaactgagatacctacagcgtgagctatgagaaagcgccacgcttcccgaagggagaaa<br>ggcggacaggtatccggtaagcggcagggtcggaacaggagagcgcacgagggagcttccagggggaaacgc<br>ctggtatctttatagtcctgtcgggtttcgccacctctgacttgagcgtcgatttttgtgatgctcgtcagg<br>ggggcggagcctatggaaaaacgccagcaacgcggcagtggaacgtgcattatgaattagttacgctaggga<br>taacagggtaatatagaacccgaacgaccgagcgcagcggcggccgcgctgataccgccgccctcgccgcag<br>ttaattaaagtcagtgagcgaggaagcgcgtaactataacggtcctaaggtagcgaatcctgatgcggtatt<br>ttctccttacgcatctgtgcggtatttcacaccgcatagatcggcaagtgcacaaacaatacttaaataaat<br>actactcagtaataacctatttcttagcatttttgacgaaatttgctattttgttagagtcttttacaccat<br>ttgtctccacacctccgcttacatcaacaccaataacgccatttaatctaagcgcatcaccaacattttctg<br>gcgtcagtccaccagctaacataaaatgtaagattcggggctctcttgccttccaacccagtcagaaatcga<br>gttccaatccaaaagttcacctgtcccacctgcttctgaatcaaacaagggaataaacgaatgaggtttctg<br>tgaagctgcactgagtagtatgttgcagtcttttggaaatacgagtcttttaataactggcaaaccgaggaa<br>ctcttggtattcttgccacgactcatctccatgcagtggagccaatcaattcttgcggtcaactttggacga<br>tatcaatgccgtaatcattgaccagagccaaaacatcctccttaagttgattacgaaacacgccaaccaagt<br>atttcggagtgcctgaactatttttatatgcttttacaagacttgaaattttccttgcaataaccgggtcaa<br>ttgttctctttctattgggcacacatataatacccagcaagtcagcatcggaatctagagcacattctgcgg<br>cctctgtgctctgcaagccgcaaactttcaccaatggaccagaactacctgtgaaattaataacagacatac<br>tccaagctgcctttgtgtgcttaatcacgtatactcacgtgctcaatagtcaccaatgccctccctcttggc<br>cctctcctttttctttttttcgaccgaattaattcttaatcggcaaaaaaagaaaagctccggatcaagattgt<br>acgtaaggtgacaagctattttttcaataaagaatatcttccactactgccatctggcgtcataactgcaaag<br>tacacatatattacgatgctgttctattaaatgcttcctatattatatatatagtaatgtcgtgatctatgg<br>tgcactctcagtacaatctgctctgatgccgcatagttaagccagccccgacacccgccaacacccgctgac<br>gcgccctgacgggcttgtctgctcccggcatccgcttacagacaagctgtgaccgtctccgggagctgcatg<br>tgtcagaggttttcaccgtcatcaccgaaacgcgcgagacgaaagggcctcgtgatacgcctatttttatag |

TABLE 8-continued

| pA24, pA25, and pA26 sequences | |
|---|---|
| | gttaatgtcatgataataatggtttcttagacggatcgcttgcctgtaacttacacgcgcctcgtatctttt<br>aatgatggaataatttgggaatttactctgtgtttatttatttttatgttttgtatttggattttagaaagt<br>aaataaagaaggtagaagagttacggaatgaagaaaaaaaaataaacaaaggtttaaaaaatttcaacaaaa<br>agcgtactttacatatatatttattagacaagaaaagcagattaaatagatatacattcgattaacgataag<br>taaaatgtaaaatcacaggattttcgtgtgtggtcttctacacagacaaggtgaaacaattcggcattaata<br>cctgagagcaggaagagcaagataaaaggtagtatttgttggcgatcccccctagagtcttttacatcttcgg<br>aaaacaaaaactatttttttctttaatttctttttttactttctatttttaatttatatatttatattaaaaa<br>atttaaattataattatttttatagcacgtgatgaaaaggacccaggtggcacttttcggggaaatgtgcgc<br>ggaacccctatttgtttatttttctaaatacattcaaatatgtatccgctcatgagacaataaccctgataa<br>atgcttcaataatattgaaaaaggaagagtatgagtattcaacatttccgtgtcgcccttattcccttttt<br>gcggcattttgccttcctgtttttgctcacccagaaacgctggtgaaagtaaaagatgctgaagatcagttg<br>ggacgcgtagtctagaccagccaggacagaaatgcctcgacttcgctgctacccaaggttgccgggtgacgc<br>acaccgtggaaacggatgaaggcacgaacccagtggacataagcctgttcggttcgtaagctgtaatgcaag<br>tagcgtatgcgctcacgcaactggtccagaaccttgaccgaacgcagcggtggtaacggcgcagtggcggtt<br>ttcatggcttgttatgactgtttttttggggtacagtctatgcctcgggcatccaagcagcaagcgcgttac<br>gccgtgggtcgatgtttgatgttatggagcagcaacgatgttacgcagcagggcagtcgccctaaaacaaag<br>ttaaacattatgagggaagcggtgatcgccgaagtatcgactcaactatcagaggtagttggcgccatcgag<br>cgccatctcgaaccgacgttgctggccgtacatttgtacggctccgcagtggatggcggcctgaagccacac<br>agtgatattgatttgctggttacggtgaccgtaaggcttgatgaaacaacgcggcgagctttgatcaacgac<br>cttttggaaacttcggcttcccctggagagagcgagattctccgcgctgtagaagtcaccattgttgtgcac<br>gacgacatcattccgtggcgttatccagctaagcgcgaactgcaatttggagaatggcagcgcaatgacatt<br>cttgcaggtatcttcgagccagccacgatcgacattgatctggctatcttgctgacaaaagcaagagaacat<br>agcgttgccttggtaggtccagcggcggaggaactctttgatccggttcctgaacaggatctatttgaggcg<br>ctaaatgaaaccttaacgctatggaactcgccgcccgactgggctggcgatgagcgaaatgtagtgcttacg<br>ttgtcccgcatttggtacagcgcagtaaccggcaaaatcgcgccgaaggatgtcgctgccggctgggcaatg<br>gagcgcctgccggcccagtatcagcccgtcatacttgaagctagacaggcttatcttggacaagaagaagat<br>cgcttggcctcgcgcgcagatcagttggaagaatttgtccactacgtgaaaggcgagatcaccaaggtagtc<br>ggcaaataaccctcgagcattcaaggcgccttgattatttgacgtggtttgatggcctccacgcacgttgtg<br>atatgtagatgagagcgttggttggtggatcaagcccacgcgtaggcaatcctcgagcagatccgccaggcg<br>tgtatatatagcgtggatggccaggcaactttagtgctgacacatacaggcatatatatatgtgtgcgacaa<br>cacatgatcatatggcatgcatgtgctctgtatgtatataaaactcttgttttcttcttttctctaaatatt<br>ctttccttatacattaggacctttgcagcataaattactatacttctatagacacacaaacacaaatacaca<br>cactaaattaataacaggccccttttcctttgtcgatatcatgtaattagttatgtcacgcttacattcacg<br>ccctcccccacatccgctctaaccgaaaaggaaggagttagacaacctgaagtctaggtccctatttattt<br>ttttatagttatgttagtattaagaacgttatttatatttcaaatttttctttttttttctgtacaaacgcgt<br>gtacgcatgtaacattatactgaaaaccttgcttgagaaggttttgggacgctcgaaggctttaatttgtaa<br>tcattatcactttacgggtcctttccggtgatccgacaggttacggggcggcgacctcgcgggttttcgcta<br>tttatgaaaatttccggtttaaggcgtttccgttcttcttcgtcataacttaatgtttttatttaaaatac<br>ctcgcgagtggcaacactgaaaatacccatggagcggcgtaaccgtcgcacaggatctaggtgaagatcctt<br>tttgataatctcatgaccaaaatcccttaacgtgagttttcgttccactgagcgtcagaccccgtagaaaag<br>atcaaaggatcttcttgagatcctttttttctgcgcgtaatctgctgcttgcaaacaaaaaaaccaccgcta<br>ccagcggtggtttgtttgccggatcaagagctaccaactctttttccgaaggtaactggcttcagcagagcg<br>cagataccaaatactgtccttctagtgtagccgtagttaggccaccacttcaagaactctgtagcaccgcct<br>acatacctcgctctgctaatcctgttaccagtggctgctgccagtggcgataagtcgtgtcttaccgggttg<br>gactcaagacgatagttaccggataaggcgcagcggtcgggctgaacggggggttcgtgcacacagcccagc<br>ttggagcg |
| pA26 sequence | acgacctacaccgaactgagatacctacagcgtgagctatgagaaagcgccacgcttcccgaagggagaaag<br>gcggacaggtatccggtaagcggcagggtcggaacaggagagcgcacgagggagcttccagggggaaacgcc<br>tggtatctttatagtcctgtcgggtttcgccacctctgacttgagcgtcgatttttgtgatgctcgtcaggg<br>gggcggagcctatggaaaaacgccagcaacgcggcagtggaacgtgcattatgaattagttacgctagggat<br>aacagggtaatatagaacccgaacgaccgagcgcagcggcggccgcgctgataccgccgccctcgccgcagt<br>taattaaagtcagtgagcgaggaagcgcgtaactataacggtcctaaggtagcgaatcctgatgcggtattt<br>tctccttacgcatctgtgcggtatttcacaccgcatagatcggcaagtgcacaaacaatacttaaataaata<br>ctactcagtaataacctatttcttagcatttttgacgaaatttgctattttgttagagtcttttacaccatt<br>tgtctccacacctccgcttacatcaacaccaataacgccatttaatctaagcgcatcaccaacatttttctgg<br>cgtcagtccaccagctaacataaaatgtaagctttcggggctctcttgccttccaacccagtcagaaatcga<br>gttccaatccaaaagttcacctgtcccacctgcttctgaatcaaacaagggaataaacgaatgaggtttctg<br>tgaagctgcactgagtagtatgttgcagtcttttggaaatacgagtcttttaataactggcaaaccgaggaa<br>ctcttggtattcttgccacgactcatctccatgcagtggagccaatcaattcttgcggtcaactttggacga<br>tatcaatgccgtaatcattgaccagagccaaaacatcctccttaagttgattacgaaacacgccaaccaagt<br>atttcggagtgcctgaactatttttatatgcttttacaagacttgaaattttccttgcaataaccgggtcaa<br>ttgttctctttctattgggcacacatataatacccagcaagtcagcatcggaatctagagcacattctgcgg<br>cctctgtgctctgcaagccgcaaactttcaccaatggaccagaactacctgtgaaattaataacagacatac<br>tccaagctgcctttgtgtgcttaatcacgtatactcacgtgctcaatagtcaccaatgccctccctcttggc<br>cctctccttttctttttcgaccgaattaattcttaatcggcaaaaaaagaaaagctccggatcaagattgt<br>acgtaaggtgacaagctatttttcaataaagaatatcttccactactgccatctggcgtcataactgcaaag<br>tacacatatattacgatgctgttctattaaatgcttcctatattatatatatagtaatgtcgtgatctatgg<br>tgcactctcagtacaatctgctctgatgccgcatagttaagccagccccgacacccgccaacacccgctgac<br>gcgccctgacgggcttgtctgctcccggcatccgcttacagacaagctgtgaccgtctccgggagctgcatg<br>tgtcagaggttttcaccgtcatcaccgaaacgcgcgagacgaaagggcctcgtgatacgcctatttttatag<br>gttaatgtcatgataataatggtttcttagacggatcgcttgcctgtaacttacacgcgcctcgtatctttt<br>aatgatggaataatttgggaatttactctgtgtttatttatttttatgttttgtatttggattttagaaagt<br>aaataaagaaggtagaagagttacggaatgaagaaaaaaaaataaacaaaggtttaaaaaatttcaacaaaa<br>agcgtactttacatatatatttattagacaagaaaagcagattaaatagatatacattcgattaacgataag<br>taaaatgtaaaatcacaggattttcgtgtgtggtcttctacacagacaaggtgaaacaattcggcattaata<br>cctgagagcaggaagagcaagataaaaggtagtatttgttggcgatcccccctagagtcttttacatcttcgg<br>aaaacaaaaactatttttttctttaatttctttttttactttctatttttaatttatatatttatattaaaaa |

TABLE 8-continued

| pA24, pA25, and pA26 sequences |
|---|
| atttaaattataattatttttatagcacgtgatgaaaaggacccaggtggcacttttcggggaaatgtgcgc<br>ggaacccctatttgtttatttttctaaatacattcaaatatgtatccgctcatgagacaataaccctgataa<br>atgcttcaataatattgaaaaaggaagagtatgagtattcaacatttccgtgtcgcccttattcccttttt<br>gcggcattttgccttcctgtttttgctcacccagaaacgctggtgaaagtaaaagatgctgaagatcagttg<br>ggacgcgtagtctagaccagccaggacagaaatgcctcgacttcgctgctacccaaggttgccgggtgacgc<br>acaccgtggaaacggatgaaggcacgaacccagtggacataagcctgttcggttcgtaagctgtaatgcaag<br>tagcgtatgcgctcacgcaactggtccagaaccttgaccgaacgcagcggtggtaacggcgcagtggcggtt<br>ttcatggcttgttatgactgtttttttggggtacagtctatgcctcgggcatccaagcagcaagcgcgttac<br>gccgtgggtcgatgtttgatgttatggagcagcaacgatgttacgcagcagggcagtcgccctaaaacaaag<br>ttaaacattatgagggaagcggtgatcgccgaagtatcgactcaactatcagaggtagttggcgccatcgag<br>cgccatctcgaaccgacgttgctggccgtacatttgtacggctccgcagtggatggcggcctgaagccacac<br>agtgatattgatttgctggttacggtgaccgtaaggcttgatgaaacaacgcggcgagctttgatcaacgac<br>cttttggaaacttcggcttcccctggagagagcgagattctccgcgctgtagaagtcaccattgttgtgcac<br>gacgacatcattccgtggcgttatccagctaagcgcgaactgcaatttggagaatggcagcgcaatgacatt<br>cttgcaggtatcttcgagccagccacgatcgacattgatctggctatcttgctgacaaaagcaagagaacat<br>agcgttgccttggtaggtccagcggcggaggaactctttgatccggttcctgaacaggatctatttgaggcg<br>ctaaatgaaaccttaacgctatggaactcgccgcccgactgggctggcgatgagcgaaatgtagtgcttacg<br>ttgtcccgcatttggtacagcgcagtaaccggcaaaatcgcgccgaaggatgtcgctgccggctgggcaatg<br>gagcgcctgccggcccagtatcagcccgtcatacttgaagctagacaggcttatcttggacaagaagaagat<br>cgcttggcctcgcgcgcagatcagttggaagaatttgtccactacgtgaaaggcgagatcaccaaggtagtc<br>ggcaaataaccctcgagcattcaaggcgccttgattatttgacgtggtttgatggcctccacgcacgttgtg<br>atatgtagatgactcgtaggaacaatttcgggcccctgcgtgttcttctgaggttcatcttttacatttgct<br>tctgctggataattttcagaggcaacaaggaaaaattagatggcaaaaagtcgtctttcaaggaaaaatccc<br>caccatctttcgagatcccctgtaacttattggcaactgaaagaatgaaaaggaggaaaatacaaaatatac<br>tagaactgaaaaaaaaaaagtataaatagagacgatatatgccaatacttcacaatgttcgaatctattctt<br>catttgcagctattgtaaaataataaaacatcaagaacaaacaagctcaacttgtcttttctaagaacaaag<br>aataaacacaaaaacaaaaagtttttttaattttaatcaaaaaacaggcccctttttcctttgtcgatatcat<br>gtaattagttatgtcacgcttacattcacgccctccccccacatccgctctaaccgaaaaggaaggagttag<br>acaacctgaagtctaggtccctatttatttttttatagttatgttagtattaagaacgttatttatatttca<br>aatttttcttttttttctgtacaaacgcgtgtacgcatgtaacattatactgaaaaccttgcttgagaaggt<br>tttgggacgctcgaaggctttaatttgtaatcattatcactttacgggtcctttccggtgatccgacaggtt<br>acggggcggcgacctcgcgggttttcgctatttatgaaaattttccggtttaaggcgtttccgttcttcttc<br>gtcataacttaatgttttatttaaaatacctcgcgagtggcaacactgaaaatacccatggagcggcgtaa<br>ccgtcgcacaggatctaggtgaagatcctttttgataatctcatgaccaaaatcccttaacgtgagttttcg<br>ttccactgagcgtcagaccccgtagaaaagatcaaaggatcttcttgagatcctttttttctgcgcgtaatc<br>tgctgcttgcaaacaaaaaaaccaccgctaccagcggtggtttgtttgccggatcaagagctaccaactctt<br>tttccgaaggtaactggcttcagcagagcgcagataccaaatactgtccttctagtgtagccgtagttaggc<br>caccacttcaagaactctgtagcaccgcctacatacctcgctctgctaatcctgttaccagtggctgctgcc<br>agtggcgataagtcgtgtcttaccgggttggactcaagacgatagttaccggataaggcgcagcggtcgggc<br>tgaacggggggttcgtgcacacagcccagcttggagcga |

TABLE 9

| Tailoring enzymes | | |
|---|---|---|
| Reaction Catalyzed | Enzyme | Species |
| Carbon-carbon coupling | Berberine bridge enzyme (BBE) | Ps, Ec, Cj, Bs, Tf |
| | Salutaridine synthase (SalSyn) | Ps |
| | Corytuberine synthase (CorSyn) | Cj |
| Oxidation | Tetrahydroprotoberberine oxidase (STOX) | Cj, Am, Bw |
| | Dihydrobenzophenanthridine oxidase (DBOX) | Ps |
| | Methylistylopine hydroxylase (MSH) | Ps |
| | Protopine 6-hydroxylase (P6H) | Ps, Ec |
| Methylenedioxy bridge formation | Stylopine synthase (StySyn) | Ps, Ec, Am |
| | Cheilanthifoline synthase (CheSyn) | Ps, Ec, Am |
| | Canadine synthase (CAS) | Tf, Cc |
| O-methylation | Norcoclaurine 6-O-methyltransferase (6OMT) | Ps, Tf, Cj, Pb |
| | 3'hydroxy-N-methylcoclaurine 4'-O-methyltransferase (4'OMT) | Ps, Tf, Cj, Cc |
| | Reticuline 7-O-methyltransferase (7OMT) | Ps, Ec |
| | Scoulerine 9-O-methyltransferase (9OMT) | Ps, Tf, Cj, Cc |
| N-methylation | Coclaruine N-methyltransferase (CNMT) | Ps, Tf, Cj |
| | Tetrahydroprotoberberine N-methyltransferase (TMNT) | Ps, Ec, Pb |
| O-demethylation | Thebaine demthylase (T6ODM) | Ps |
| | Codeine demthylase (CODM) | Ps, Ga |
| Reduction | Salutaridine reductase (SalR) | Ps, Pb, Ga |
| | Codeinone reductase (COR) | Ps |
| | Sanguinarine reductase (SanR) | Ec |
| Acetylation | Salutaridine acetyltransferase (SalAT) | Ps |

TABLE 10 comparison of impurities that may be present in concentrate of poppy straw and clarified yeast culture medium.

| Impurities: | | Concentrate of Poppy Straw | Clarified Yeast Culture Medium |
|---|---|---|---|
| Inorganic | Sodium | ✓ | ✓ |
| | Magnesium | ✓ | ✓ |
| | Silicon | ✓ | |
| | Phosphorus | ✓ | ✓ |
| | Sulfur | ✓ | ✓ |
| | Chloride | ✓ | ✓ |
| | Potassium | ✓ | ✓ |
| | Calcium | ✓ | ✓ |
| | Copper | ✓ | ✓ |
| | Zinc | ✓ | ✓ |
| | Molybdenum | ✓ | |
| | Iron | ✓ | ✓ |
| | Manganese | ✓ | ✓ |
| | Ammonium | ✓ | ✓ |
| | Boron | ✓ | ✓ |
| Organic | Polysaccharide (starch, cellulose, xylan) | ✓ | |
| | Lignin (p-courmaryl, coniferyl, sinapyl alcohols) | ✓ | |
| | Pigments (chlorophyll, anthocyanins, carotenoids) | ✓ | |
| | Flavonoids | ✓ | |
| | Phenantheroids | ✓ | |
| | Latex, gum and wax | ✓ | |
| | Rubisco | ✓ | |
| | Meconic acid | ✓ | |
| | Pseudomorphine | ✓ | |
| | Narceine | ✓ | |
| | Thebaol | ✓ | |
| Other | Pesticides | ✓ | |
| | Pollen | ✓ | |

TABLE 11

Distinct groups of molecules present in clarified yeast culture medium (CYCM). Unlike concentrate of poppy straw (CPS), yeast host strains may be engineered to produce molecules of a predetermined class of alkaloids (i.e., only one biosynthesis pathway per strain) such that other classes of alkaloids are not present. Therefore, the CYCM may contain molecules within a single biosynthesis pathway including a subset of molecules spanning one or two columns, whereas the CPS may contain a subset of molecules across many columns.

| 1-Benzylisoquinoline | Protoberberine and Phihalideisoquinoline | Morphinan | Isopavine | Aporphine | BisBIA |
|---|---|---|---|---|---|
| Tetrahydropapaverine | Scoulene | Saluterdine | | Magnolonine | Daurince |
| Dihydropapaverine | Chelanthiloline | Salutaridinol | Caryachine | Corytuberine | Berbamonine |
| Papavierine | Styopine | Salutaridine-7-O-acetate | Biso | Apimorphine | |
| | Cis-N-methylstylopine | Thebane | Isonaremonine | Boldine | Fang |
| | Protopine | Codeinone | | | Tetracrine |
| | Dihydrosanguinrine | Oripavine | | | Curine |
| | Sanguinarine | Morphinone | | | Cepharanthine |
| | Tetrahydro | Neopinone | | | Berbamine |
| | Canadine | Neopine | | | |
| | N-methylcandine | Codeine | | | |
| | Noscapine | Morphine | | | |
| | Berberine | Neomorphine | | | |
| | | Hydrocodone | | | |
| | | Oxycodone | | | |
| | | 14-hydroxycodenone | | | |
| | | 14-hydroxycodeine | | | |
| | | Dihydromorphine | | | |
| | | Dihydrocodeine | | | |

TABLE 12

| Impurities that may be present in chemical synthesis preparations of compounds | |
|---|---|
| Compound | Impurities |
| Buprenorphine | 15,16-Dehydrobuprenolphine, 17,18-Dehydrobuprenmphine, 18,19-demethylbuprenolphine, 19,19'-Ethylbuprenotphine, 2,2'-Bisbuprenorphine, 3-Deshydroxybuprenorphine, 3-O-Methylbuprenorphine, 3-O-Methyl-N-cyanonorbuprenorphine, 3-O-Methyl-N-methylnorbuprenolphine, 6-O-Desmethylbuprenorphine, Buprenorphine N-oxide, N-But-3-enylnorbuprenorphine, N-But-3-enylnormethylbuprenorphine, N-Butylnorbuprenorphine, N-Methylbuprenorphine, Norbuprenorphine, Tetramethylfuran buprenorphine |
| Oxymorphone | 1-Bromooxymorphone, 6-Beta oxymorphol, 10-Alpha-hydroxyoxymorphone, 10-Ketooxymorphone, 2,2-Bisoxymorphone, Noroxymorphone, Oxymorphone N-oxide, 10-Hydroxyoxymorphone, 4-Hydroxyoxymorphone, 8-Hydroxyoxymolphone, Hydromorphinol. |
| Naltrexone | 10-Hydroxynaltrexone, 10-Ketonaltrexone, 14-Hydroxy-17-cyclopropylmethylnormorphinone, 2,2'-Bisnaltrexone, 3-Cyclopropylmethylnaltrexone, 3-O-Methylnaltrexone, 8-Hydroxynaltrexone, N-(3-Butenyl)-noroxymolphone, Naltrexone aldol dimer, N-Formyl-noroxymorphone |
| Naloxone | 10-Alpha-hydroxynaloxone, 10-Beta-hydroxynaloxone, 10-Ketonaloxone, 3-O-Allylnaloxone, 7,8-Didehydronaloxone, 2,2'-Bisnaloxone, Naloxone N-oxide |
| Nalbuphine | Beta-epimer of nalbuphine, 2,2'-Bisnalbuphine, 6-Ketonalbuphine, 10-Ketonalbuphine, Alpha-noroxymorphol, N-(Cyclobutylcarbonyl)-alpha-noroxymorphol, N-Formyl-6-alpha-noroxymophol. |

While preferred embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An engineered non-plant cell, comprising:

i) an epimerase, ii) a thebaine synthase; and iii) at least one modification selected from the group consisting of: a) a substrate inhibition alleviating mutation, b) a product inhibition alleviating mutation, c) a cofactor recovery promoting mechanism, d) a feedback inhibition alleviating mutation, e) transcriptional modulation modification, and f) an inactivating mutation; and iv) wherein the cell further comprises three or more of the enzymes of:

(a) tyrosinase or tyrosine hydroxylase (TYR or TyrH), L-DOPA decarboxylase (DODC), 6-O-methyltransferase (6OMT), coclaurine-N-methyltransferase (CNMT), N-methylcoclaurine 3'-hydroxylase (CYP80B1), 4'-O-methyltransferase (4'OMT), salutaridine synthase (SalSyn), salutaridine reductase (SalR), salutaridinol 7-O-acetyltransferase (SalAT), and norcoclaurine synthase (NCS); or (b) TYR or TyrH, DODC, monoamine oxidase (maoA), 6OMT, CNMT, 4'OMT, DRS-DRR, SalSyn, SalR, SalAT, and norcoclaurine synthase (NCS), and wherein, within the engineered non-plant cell, the engineered non-plant cell converts a precursor of a promorphinan molecule to an alkaloid product selected from the group consisting of: i) a morphinan alkaloid, ii) a nal-opioid alkaloid, and iii) a nor-opioid alkaloid.

2. The engineered non-plant cell of claim 1, wherein the epimerase is an engineered epimerase.

3. The engineered non-plant cell of claim 2, wherein the engineered epimerase is a split epimerase.

4. The engineered non-plant cell of claim 2, wherein the engineered epimerase converts an (S)-l-benzylisoquinoline precursor to an (R)-l-benzylisoquinoline product.

5. The engineered non-plant cell of claim 4, wherein the engineered epimerase converts(S)-reticuline to (R)-reticuline.

6. The engineered non-plant cell of claim 4, wherein at least 50% of the (S)-l-benzylisoquinoline alkaloid molecules within the engineered non-plant cell are converted to the (R)-l-benzylisoquinoline product.

7. The engineered non-plant cell of claim 1, wherein the thebaine synthase is an engineered thebaine synthase.

8. The engineered non-plant cell of claim 1, wherein the precursor of a promorphinan molecule is fed to the engineered non-plant cell.

9. The engineered non-plant cell of claim 1, wherein the precursor of a promorphinan molecule is produced within the engineered non-plant cell.

10. The engineered non-plant cell of claim 1, wherein the precursor of a promorphinan molecule is selected from the group consisting of reticuline, 3'hydroxy-N-methylcoclaurine, coclaurine, norcoclaurine, norlaudanosoline, methylnorlaudanosoline, laudanosoline, methylnorlaudanosoline, norreticuline, 3'hydroxy-N-methylcoclaurine, 4'-0'-methylaudanosoline, L-Dopa, tyrosine, dopamine, 3,4-dihydroxyphenylacetaldehyde (3,4-DHPA), hydroxyphenylpyruvate, prephenate, chorismate, 5-enolpyruvylshikimate-3-phosphate (EPSP), 3-deoxy-D-arabinoheptulosonate-7-phosphate (DAHP), erythrose-4-phosphate (E4P), phosphoenolpyruvate (PEP), and glucose.

11. The engineered non-plant cell of claim 1, wherein at least 50% of tetracyclic promorphinan precursor molecules within the engineered non-plant cell are converted to thebaine.

12. The engineered non-plant cell of claim 1, wherein the precursor of a promorphinan molecule is an (S)-substrate of Formula I:

Formula I

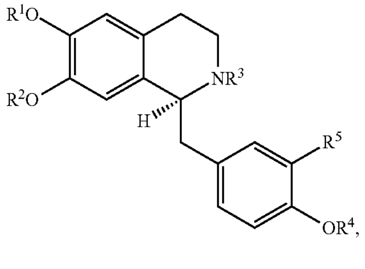

or a salt thereof, wherein:

$R^1$, $R^2$, $R^3$, and $R^4$ are independently selected from hydrogen and methyl; and $R^5$ is selected from hydrogen, hydroxy, and methoxy.

13. The engineered non-plant cell of claim 12, wherein at least one of $R^1$, $R^2$, $R^3$, $R^4$, and $R^5$ is hydrogen.

14. The engineered non-plant cell of claim 1, wherein the precursor of a promorphinan molecule is (S)-substrate is a compound of Formula II:

Formula II

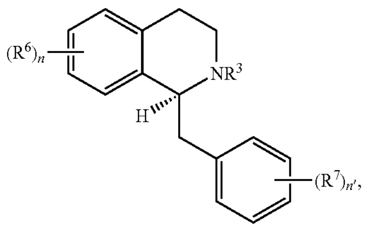

or a salt thereof, wherein:

$R^3$ is selected from hydrogen and $C_1$-$C_4$ alkyl;

$R^6$ and $R^7$ are independently selected at each occurrence from hydroxy, fluoro, chloro, bromo, carboxaldehyde, $C_1$-$C_4$ acyl, $C_1$-$C_4$ alkyl, and $C_1$-$C_4$ alkoxy;

n is 0, 1, 2, 3, or 4; and n' is 0, 1, 2, 3, 4 or 5.

15. The engineered non-plant cell of claim 1, wherein the precursor of a promorphinan molecule is selected from tyrosine and sugar.

16. The engineered non-plant cell of claim 1, further comprising at least one modification selected from the group consisting of: i) a BIA-generating modification, ii) an O-demethylation modification, iii) an N-demethylation modification, and iv) an N-linked modification.

17. The engineered non-plant cell of claim 1, wherein the morphinan alkaloid product is a thebaine, codeinone, codeine, morphine, morphinone, oripavine, neopinone, neopine, neomorphine, hydrocodone, dihydrocodeine, 14-hydroxycodeinone, oxycodone, 14-hydroxycodeine, morphinone, hydromorphone, dihydromorphine, dihydro-etorphine, ethylmorphine, etorphine, metopon, buprenorphine, pholcodine, heterocodeine, or oxymorphone.

18. The engineered non-plant cell of claim 1, wherein (i) the nal-opioid alkaloid product is a naltrexone, naloxone, nalmefene, nalorphine, nalorphine, nalodeine, naldemedine, naloxegol, 6b-naltrexol, naltrindole, methylnaltrexone, methylsamidorphan, alvimopan, axelopran, bevenpran, dinicotinate, levallorphan, samidorphan, buprenorphine, dezocine, eptazocine, butorphanol, levorphanol, nalbuphine, pentazocine, phenazocine, norbinaltorphimine, or diprenorphine or (ii) the nor-opioid alkaloid product is a norcodeine, noroxycodone, northebaine, norhydrocodone, nordihydrocodeine, nor-14-hydroxy-codeine, norcodeinone, nor-14-hydroxy-codeinone, normorphine, noroxymorphone, nororipavine, norhydro-morphone, nordihydro-morphine, nor-14-hydroxy-morphine, normorphinone, or nor-14-hydroxy-morphinone.

19. The engineered non-plant cell of claim 1, wherein the engineered non-plant cell is a bacterial cell or a fungal cell.

20. A method of converting a precursor of a promorphinan molecule to a thebaine, or a derivative thereof, comprising:

contacting the precursor of a promorphinan molecule with an epimerase and a thebaine synthase, wherein at least one precursor of promorphinan molecule is produced within an engineered non-plant cell where the conversion occurs, wherein the cell further comprises three or more of the enzymes of:

(a) tyrosinase or tyrosine hydroxylase (TYR or TyrH), L-DOPA decarboxylase (DODC), 6-O-methyltransferase (6OMT), coclaurine-N-methyltransferase (CNMT), N-methylcoclaurine 3'-hydroxylase (CYP80B1), (4'-O-methyltransferase) (4'OMT), salutaridine synthase (SalSyn), salutaridine reductase (SalR), salutaridinol 7-O-acetyltransferase (SalAT), and norcoclaurine synthase (NCS); or (b) TYR or TyrH, DODC, monoamine oxidase (maoA), 6OMT, CNMT, 4'OMT, DRS-DRR, SalSyn, SalR, SalAT, and norcoclaurine synthase (NCS) and wherein contacting the precursor of a promorphinan molecule with the epimerase and thebaine synthase converts the precursor of a promorphinan molecule to a thebaine, or a derivative thereof, within the engineered non-plant cell.

* * * * *